United States Patent
Leveau et al.

(10) Patent No.: US 11,820,989 B2
(45) Date of Patent: Nov. 21, 2023

(54) PHAGE-DERIVED PARTICLES FOR IN SITU DELIVERY OF DNA PAYLOAD INTO C. ACNES POPULATION

(71) Applicant: Eligo Bioscience, Paris (FR)

(72) Inventors: Aymeric Leveau, Paris (FR); Inès Canadas Blasco, Paris (FR); Aurélie Mathieu, Paris (FR); Antoine Decrulle, Paris (FR)

(73) Assignee: Eligo Bioscience, Paris (FR)

( * ) Notice: Subject to any disclaimer, the term of this patent is extended or adjusted under 35 U.S.C. 154(b) by 14 days.

(21) Appl. No.: 17/518,936

(22) Filed: Nov. 4, 2021

(65) Prior Publication Data

US 2022/0135986 A1 May 5, 2022

Related U.S. Application Data

(60) Provisional application No. 63/145,969, filed on Feb. 4, 2021, provisional application No. 63/145,967, filed on Feb. 4, 2021, provisional application No. 63/109,832, filed on Nov. 4, 2020, provisional application No. 63/109,834, filed on Nov. 4, 2020.

(51) Int. Cl.
| | |
|---|---|
| C12N 7/00 | (2006.01) |
| C12N 15/76 | (2006.01) |
| A61P 17/10 | (2006.01) |
| A61K 39/05 | (2006.01) |
| C12N 9/22 | (2006.01) |
| C12N 15/11 | (2006.01) |
| A61K 39/02 | (2006.01) |
| A61K 39/00 | (2006.01) |
| C12N 9/64 | (2006.01) |

(52) U.S. Cl.
CPC .............. *C12N 15/76* (2013.01); *A61K 39/02* (2013.01); *A61K 39/05* (2013.01); *A61P 17/10* (2018.01); *C12N 9/22* (2013.01); *C12N 15/11* (2013.01); *A61K 2039/53* (2013.01); *C12N 9/64* (2013.01); *C12N 2310/20* (2017.05); *C12N 2795/10343* (2013.01); *C12N 2800/101* (2013.01); *C12N 2800/80* (2013.01)

(58) Field of Classification Search
None
See application file for complete search history.

(56) References Cited

U.S. PATENT DOCUMENTS

| | | | | |
|---|---|---|---|---|
| 2019/0030090 | A1* | 1/2019 | Li | A61K 8/606 |
| 2021/0252081 | A1* | 8/2021 | Feron | C07K 14/33 |

FOREIGN PATENT DOCUMENTS

| | | | | | |
|---|---|---|---|---|---|
| WO | WO-2007007055 | A1 * | 1/2007 | ............. | A61K 35/76 |
| WO | WO-2017185018 | A1 * | 10/2017 | ............. | A61K 35/74 |
| WO | WO-2019113066 | A1 * | 6/2019 | ............. | A61K 35/76 |
| WO | 2020181178 | A1 | 9/2020 | | |
| WO | 2020181180 | A1 | 9/2020 | | |
| WO | 2020181193 | A1 | 9/2020 | | |
| WO | 2020181195 | A1 | 9/2020 | | |
| WO | 2020181202 | A1 | 9/2020 | | |

OTHER PUBLICATIONS

Brede et al. (Enzymology and Protein Engineering, 2005, vol. 71, No. 12, pp. 8077-8084). (Year: 2005).*
Simon et al. Survey and Summary. Retrons and their applications in genome engineering. Nucleic Acids Research, 2019, vol. 47, No. 21 11007-11019.
Abudayyeh et al. RNA targeting with CRISPR-Cas13a. Nature. Oct. 12, 2017; 550(7675): 280-284.
Adachi et al. Hair follicle-derived IL-7 and IL-15 mediate skin-resident memory T cell homeostasis and lymphoma. Nat Med. Nov. 2015 ; 21(11): 1272-1279.
Allhorn, M. et al. A novel enzyme with antioxidant capacity produced by the ubiquitous skin colonizer Propionibacterium acnes. Sci. Rep. 6, 36412.
Anzalone, A. et al. Search-and-replace genome editing without double-strand breaks or donor DNA. Nature. Dec. 2019 ; 576(7785): 149-157.
Aoki et al., Journal of Medical Microbiology 2019;68:26-30.
Aoki et al., Transferable Multidrug-Resistance Plasmid Carrying a Novel Macrolide-Clindamycin Resistance Gene, erm (50), in Cutibacterium acnes. Antimicrob Agents Chemother. Feb. 21, 2020;64(3):e01810-19.
Arazoe et al. Site-specific DNA double-strand break generated by I-SceI endonuclease enhances ectopic homologous recombination in Pyricularia oryzae. FEMS Microbiol Lett 352 (2014) 221-229.
Armenteros, et al. SignalP 5.0 improves signal peptide predictions using deep neural networks. Nat Biotechnol 37, 420-423 (2019).
Barnard, E. et al. Strains of the Propionibacterium acnes type III lineage are associated with the skin condition progressive macular hypomelanosis. Sci. Rep. 6, 31968.
Barnard, E. et al. The balance of metagenomic elements shapes the skin microbiome in acne and health. Sci. Rep. 6, 39491.
Bay L, et al. 2020. Universal dermal microbiome in human skin. mBio 11:e02945-19.
Brown et al. (2016) The Formulation of Bacteriophage in a Semi Solid Preparation for Control of Propionibacterium acnes Growth. PLoS ONE 11(3): e0151184.

(Continued)

*Primary Examiner* — Celine X Qian
(74) *Attorney, Agent, or Firm* — Arrigo, Lee, Guttman & Mouta-Bellum LLP

(57) ABSTRACT

The invention relates to C. acnes carrying DNA vectors with a C. acnes phage packaging signal and a gene of interest. The invention encompasses a C. acnes producer cell carrying DNA vectors, with a C. acnes phage packaging signal and a gene of interest, for the production of phage-derived particles that can robustly transduce C. acnes receiver cell allowing transgene expression. The invention encompasses C. acnes phage-derived particles carrying these vectors, C. acnes containing these vectors or modified by transduction of these phage-derived particles, and methods of using these phage-derived particles.

18 Claims, 12 Drawing Sheets

Specification includes a Sequence Listing.

(56) References Cited

OTHER PUBLICATIONS

Chen et al. Skin microbiota-host interactions. Nature. Jan. 24, 2018; 553(7689): 427-436.
Chen et al. Decoding commensal-host communication through genetic engineering of Staphylococcus 5 epidermidis. Jun. 10, 2019. bioRxiv 664656.
Chen et al. Precise and programmable C:G to G:C base editing in genomic DNA. bioRxiv 2020.07.21.213827.
Davidsson S, et al. (2017) Prevalence of Flp Pili-Encoding Plasmids in Cutibacterium acnes Isolates Obtained from Prostatic Tissue. Front. Microbiol. 8:2241.
Dréno, et al. (2018), Cutibacterium acnes (Propionibacterium acnes) and acne vulgaris: a brief look at the latest updates. J Eur Acad Dermatol Venereol, 32: 5-14.
Fitz-Gibbon et al. Propionibacterium acnes Strain Populations in the Human Skin Microbiome Associated with Acne. Journal of Investigative Dermatology (2013) 133, 2152-2160.
Fonfara et al. Phylogeny of Cas9 determines functional exchangeability of dual-RNA and Cas9 among orthologous type II CRISPR-Cas systems .Nucleic Acids Research, 2014, vol. 42, No. 4 2577-2590.
Gaudelli et al. Programmable base editing of A•T to G•C in genomic DNA without DNA cleavage. Nature. Nov. 23, 2017; 551(7681): 464-471.
Di Girolamo, et al. Characterization of the housekeeping sortase from the human pathogen Propionibacterium acnes: first investigation of a class F sortase. Biochem J Feb. 28, 2019; 476 (4): 665-682.
Grünewald et al. A dual-deaminase CRISPR base editor enables concurrent adenine and cytosine editing. Nat Biotechnol. Jul. 2020 ; 38(7): 861-864.
Karberg, et al. Group II introns as controllable gene targeting vectors for genetic manipulation of bacteria. Nat Biotechnol 19, 1162-1167 (2001).
Kasimatis et al. Analysis of Complete Genomes of Propionibacterium acnes Reveals a Novel Plasmid and Increased Pseudogenes in an Acne Associated Strain. Hindawi Publishing Corporation: BioMed Research International. 2013. 1-11.
Komor et al. Programmable editing of a target base in genomic DNA without double stranded DNA cleavage. Nature. ; 533(7603): 420-424.
Koonin, et al. Diversity, classification and evolution of CRISPR-Cas systems. Current Opinion in Microbiology. vol. 37, 2017, pp. 67-78.
Kurt et al. CRISPR C-to-G base editors for inducing targeted DNA transversions in human cells. Nat Biotechnol. Jan. 2021 ; 39(1): 41-46.
Li et al. Targeted, random mutagenesis of plant genes with dual cytosine and adenine base editors. Nature Biotechnology. 38, 875-882 (2020).
Liu et al. The diversity and host interactions of Propionibacterium acnes bacteriophages on human skin. The ISME Journal (2015) 9, 2078-2093.
Lood et al. Characterization and genome sequencing of two Propionibacterium acnes phages displaying pseudolysogeny. BMC Genomics 2011, 12:198.
McDowell, et al. (2021), Is Cutibacterium (previously Propionibacterium) acnes a potential pathogenic factor in the aetiology of the skin disease progressive macular hypomelanosis?. J Eur Acad Dermatol Venereol, 35: 338-344.
McLaughlin et al. Propionibacterium acnes and Acne Vulgaris: New Insights from the Integration of Population Genetic, Multi-Omic, Biochemical and Host-Microbe Studies. Microorganisms 2019, 7(5), 128.
Nagao et al. Stress-induced production of chemokines by hair follicles regulates the trafficking of dendritic cells in skin. Nat Immunol. ; 13(8): 744-752.
Naik et al. Commensal-dendritic-cell interaction specifies a unique protective skin immune signature. Nature. Apr. 2, 2015; 520(7545): 104-108.
Nakatsuji et al. The microbiome extends to subepidermal compartments of normal skin. Nat Commun. 2013 ; 4: 1431.
Nazipi et al. The Skin Bacterium Propionibacterium acnes Employs Two Variants of Hyaluronate Lyase with Distinct Properties. Microorganisms 2017, 5, 57.
Oh et al. Biogeography and individuality shape function in the human skin metagenome. Nature. Oct. 2, 2014; 514 (7520): 59-64.
Pasparakis et al. Mechanisms regulating skin immunity and inflammation. Nature Reviews: Immunology. vol. 14. 289-301.
Paus et al. The Hair Follicle and Immune Privilege. JID Symposium Proceedings. 2003. 1087-0024.
Petersen et al. Propionibacterium Acnes Phylogenetic Type III is Associated with Progressive Macular Hypomelanosis. Eur J Microbiol Immunol (Bp). Feb. 27, 2017;7(1):37-45.
Rouet et al. Expression of a site-specific endonuclease stimulates homologous recombination in mammalian cells. Jun. 1994. Proc. Nati. Acad. Sci. USA. vol. 91, pp. 6064-6068.
Scharschmidt et al. A Wave of Regulatory T Cells into Neonatal Skin Mediates Tolerance to Commensal Microbes. Immunity, vol. 43, Issue 5, 1011-1021.
Scholz et al. The natural history of cutaneous propionibacteria, and reclassification of selected species within the genus Propionibacterium to the proposed novel genera Acidipropionibacterium gen. nov., Cutibacterium gen. nov. and Pseudopropionibacterium gen. nov. International Journal of Systematic and Evolutionary Microbiology (2016), 66, 4422-4432.
Sharon et al. Functional genetic variants revealed by massively parallel precise genome editing. Cell. Oct. 4, 2018; 175(2): 544-557.e16.
Sievers et al. Fast, scalable generation of high-quality protein multiple sequence alignments using Clustal Omega. Molecular Systems Biology 7; 539.
Sörensen et al. Mutagenesis of Propionibacterium acnes and analysis of two CAMP factor knock-out mutants. Journal of Microbiological Methods 83 (2010) 211-216.
Wannier et al. Improved bacterial recombineering by parallelized protein discovery. PNAS. Jun. 16, 2020. 117: 24. 13689-13698.
Yu. Different Propionibacterium acnes Phylotypes Induce Distinct Immune Responses and Express Unique Surface and Secreted Proteomes. Society for Investigative Dermatology. 2016. 2221-2228.
Zhao et al. New base editors change C to A in bacteria and C to G in mammalian cells. Nature Biotechnology. Jul. 20, 2020.

\* cited by examiner

FIGURE 2 (beginning)

| C. acnes strains | 19 | 26 | 2 | 22 | 9 | 13 | 10 | 20 | 4 | 7 | ATCC29399 | 1 |
|---|---|---|---|---|---|---|---|---|---|---|---|---|
| Bacteriophage titer (PFU/μL) | ? | 4.00E+06 | 2.20E+07 | 2.00E+07 | 1.60E+07 | 4.00E+06 | 1.00E+07 | 4.00E+04 | 1.60E+07 | 4.00E+06 | 2.00E+06 | 8.00E+06 |
| Ca0s2345-001 | 1 | 1 | 1 | 1 | 1 | 1 | 1 | 1 | 1 | 1 | 1 | 1 |
| Ca0s2341-001 | 1 | 1 | 1 | 1 | 1 | 1 | 1 | 1 | 1 | 1 | 1 | 1 |
| Ca0s2343-001 | 1 | 1 | 1 | 1 | 1 | 1 | 1 | 1 | 1 | 1 | 1 | 1 |
| Ca0s2329-001 | 1 | 1 | 1 | 1 | 1 | 1 | 1 | 1 | 1 | 1 | 1 | 1 |
| Ca0s2334-001 | 1 | 1 | 1 | 1 | 1 | 1 | 1 | 1 | 1 | 1 | 1 | 1 |
| Ca0s2328-001 | 1 | 1 | 1 | 1 | 1 | 1 | 1 | 1 | 1 | 1 | 1 | 1 |
| Ca0s2306-001 | 1 | 1 | 1 | 1 | 1 | 1 | 1 | 1 | 1 | 1 | 1 | 1 |
| Ca0s2277-001 | 1 | 1 | 1 | 1 | 1 | 1 | 1 | 1 | 1 | 1 | 1 | 1 |
| Ca0s2272-001 | 1 | 1 | 1 | 1 | 1 | 1 | 1 | 1 | 1 | 1 | 1 | 1 |
| Ca0s2391-001 | 1 | 1 | 1 | 1 | 1 | 1 | 1 | 1 | 1 | 1 | 1 | 1 |
| Ca0s2373-001 | 1 | 1 | 1 | 1 | 1 | 1 | 1 | 1 | 1 | 1 | 1 | 1 |
| Ca0s2327-001 | 1 | 1 | 1 | 1 | 1 | 1 | 1 | 1 | 1 | 1 | 1 | 1 |
| Ca0s2312-001 | 1 | 1 | 1 | 1 | 1 | 1 | 1 | 1 | 1 | 1 | 1 | 1 |
| Ca0s2289-001 | 1 | 1 | 0.5 | 1 | 1 | 1 | 1 | 1 | 1 | 1 | 1 | 1 |
| Ca0s2333-001 | 1 | 1 | 0.5 | 0.5 | 1 | 1 | 1 | 1 | 1 | 1 | 1 | 1 |
| Ca0s2262-001 | 1 | 1 | 1 | 1 | 1 | 1 | 1 | 1 | 1 | 1 | 1 | 1 |
| Ca0s2258-001 | 1 | 1 | 1 | 0.5 | 0.5 | 1 | 1 | 1 | 1 | 1 | 1 | 1 |
| Ca0s2260-001 | 1 | 1 | 1 | 0.5 | 0.5 | 1 | 1 | 1 | 1 | 1 | 1 | 1 |
| Ca0s2261-001 | 1 | 1 | 1 | 1 | 1 | 1 | 1 | 1 | 1 | 1 | 1 | 1 |
| Ca0s2265-001 | 0.5 | 0.5 | 1 | 1 | 1 | 1 | 1 | 0.5 | 1 | 1 | 1 | 1 |
| Ca0s2259-001 | 0.5 | 0.5 | 0.5 | 0.5 | 0.5 | 0.5 | 0.5 | 0.5 | 1 | 1 | 1 | 1 |
| Ca0s2263-001 | 0.5 | 0.5 | 0.5 | 0.5 | 0.5 | 0.5 | 0.5 | 0.5 | 1 | 1 | 1 | 1 |
| Ca0s2264-001 | 0.5 | 1 | 1 | 1 | 1 | 1 | 1 | 1 | 1 | 1 | 1 | 1 |
| Ca0s2550-002 | 1 | 1 | 1 | 1 | 1 | 1 | 1 | 1 | 1 | 1 | 1 | 1 |
| Ca0s2549-002 | 1 | 1 | 1 | 1 | 1 | 1 | 1 | 1 | 1 | 1 | 1 | 1 |
| Ca0s2552-002 | 1 | 1 | 1 | 1 | 1 | 1 | 1 | 1 | 1 | 1 | 1 | 1 |
| Ca0s2508-002 | 1 | 1 | 1 | 1 | 1 | 1 | 1 | 1 | 1 | 1 | 1 | 1 |
| Ca0s2548-002 | 1 | 1 | 1 | 1 | 1 | 1 | 1 | 1 | 1 | 1 | 1 | 1 |
| Ca0s2504-002 | 1 | 1 | 1 | 1 | 1 | 1 | 1 | 1 | 1 | 1 | 1 | 1 |
| Ca0s2506-002 | 1 | 1 | 1 | 1 | 1 | 1 | 1 | 1 | 1 | 1 | 1 | 1 |
| Ca0s2553-002 | 1 | 1 | 1 | 1 | 1 | 1 | 1 | 1 | 1 | 1 | 1 | 1 |
| Ca0s2507-002 | 1 | 1 | 1 | 1 | 1 | 1 | 1 | 1 | 1 | 1 | 1 | 1 |
| Ca0s2509-002 | 1 | 1 | 1 | 1 | 1 | 1 | 1 | 1 | 1 | 1 | 1 | 1 |

| C. acnes strains | C. acnes bacteriophage | | | | | | | | | | | |
|---|---|---|---|---|---|---|---|---|---|---|---|---|
| | 19 | 26 | 2 | 22 | 9 | 13 | 10 | 20 | 4 | 7 | ATCC29399 | 1 |
| Ca0s2247-002 | 1 | 1 | 1 | 1 | 1 | 1 | 1 | 1 | 1 | 1 | 1 | 1 |
| Ca0s2243-002 | 1 | 1 | 1 | 1 | 1 | 1 | 1 | 1 | 1 | 1 | 1 | 1 |
| Ca0s2228-002 | 1 | 1 | 1 | 1 | 1 | 1 | 1 | 1 | 1 | 1 | 1 | 1 |
| Ca0s2225-002 | 1 | 1 | 1 | 1 | 1 | 1 | 1 | 1 | 1 | 1 | 1 | 1 |
| Ca0s2220-002 | 1 | 1 | 1 | 1 | 1 | 1 | 1 | 1 | 1 | 1 | 1 | 1 |
| Ca0s2218-002 | 1 | 1 | 1 | 1 | 1 | 1 | 1 | 1 | 1 | 1 | 1 | 1 |
| Ca0s2255-002 | 1 | 1 | 1 | 1 | 1 | 1 | 1 | 1 | 1 | 1 | 1 | 1 |
| Ca0s2227-002 | 1 | 1 | 1 | 1 | 1 | 1 | 1 | 1 | 1 | 1 | 1 | 1 |
| Ca0s2211-002 | 1 | 1 | 1 | 1 | 1 | 1 | 1 | 1 | 1 | 1 | 1 | 1 |
| Ca0s2219-002 | 1 | 1 | 1 | 1 | 1 | 1 | 1 | 1 | 1 | 1 | 1 | 1 |
| Ca0s2209-002 | 1 | 1 | 1 | 1 | 1 | 1 | 1 | 1 | 1 | 1 | 1 | 1 |
| Ca0s2208-002 | 1 | 1 | 1 | 1 | 1 | 1 | 1 | 1 | 1 | 1 | 1 | 1 |
| Ca0s2233-002 | 1 | 1 | 1 | 1 | 1 | 1 | 1 | 1 | 1 | 1 | 1 | 1 |
| Ca0s2232-002 | 1 | 1 | 1 | 1 | 1 | 1 | 1 | 1 | 1 | 1 | 1 | 1 |
| Ca0s2239-002 | 1 | 1 | 1 | 1 | 1 | 1 | 1 | 1 | 1 | 1 | 1 | 1 |
| Ca0s2235-002 | 1 | 1 | 1 | 1 | 1 | 1 | 1 | 1 | 1 | 1 | 1 | 1 |

FIGURE 2 (end)

PHAGE-DERIVED PARTICLES FOR IN SITU DELIVERY OF DNA PAYLOAD INTO C. ACNES POPULATION

CROSS REFERENCE TO RELATED APPLICATIONS

This application claims the benefit of U.S. patent application Ser. No. 63/109,832 filed Nov. 4, 2020, U.S. patent application Ser. No. 63/145,967 filed Feb. 4, 2021, U.S. patent application Ser. No. 63/109,834 filed Nov. 4, 2020, and U.S. patent application Ser. No. 63/145,969 filed Feb. 4, 2021, all of which are herein incorporated by reference in their entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Nov. 4, 2021, is named EB2020-04b_SequenceListing_ST25.txt and is 473,763 bytes in size.

FIELD OF THE INVENTION

The present invention concerns *Cutibacterium acnes* phagemids and production method thereof.

BACKGROUND OF THE INVENTION

The skin is the largest organ of the human body and the biggest interface between our body and our environment. As such it also acts as a barrier protecting us from physical (e.g., UV, wounds), chemical (e.g., acid, base) and microbial (virus, bacteria, fungi) threats. This protection is not only the result of its passive physical isolating nature made from successive layers of dense and interconnected dead cells (stratum corneum) surrounded by a lipidic matrix. It is also thanks to active mechanisms orchestrated by diverse types of skin and immune cells that secrete antimicrobial peptides (AMP), produce cytokine and chemokine to recruit lymphoid immune cells, sense skin injuries and trigger wound healing mechanisms among other processes[1].

Skin is the first organ in contact with microorganisms after our birth, it is populated with a vast amount of immune cells in close contact with a great diversity of microorganisms and thus, the skin immune system need to develop abilities to recognize beneficial microorganisms from pathogenic ones to avoid constant immune response and inflammation. Part of this education is happening early in life when specific bacterial species are colonizing the skin and modulate immune responses in order for them to be tolerated[2]. These specific bacterial species are then able to stably colonize the skin establishing communities and becoming commensal strains.

Skin is not physiologically and spatially homogeneous throughout the body: oily (e.g cheek, back), moist (e.g., inguinal crease, interdigital web space, antecubital crease) and dry skin (e.g, volar forearm, hypothenar palm) exist depending on the body sites[3]. These different body sites are associated with different physiological conditions and carry distinct microbiomes with oily sites being mostly colonized with *Cutibacterium acnes* (formerly known as *Propionibacterium acnes*), whereas *Staphylococcus* and *Corynebacterium* species are more abundant in moist sites[4]. In addition to these physiological characteristics skin is also heterogeneous in space with different appendages: the sweat glands, the hair follicle, the sebaceous gland. The colonization of these appendages is only recently studied but show differences compared to skin surface (stratum corneum)[4-6].

These skin appendages are specific anatomical places because they do not have stratum corneum. As a consequence, micro-organism inside these appendages are in contact with living keratinocytes and have access to a higher diversity of immune cells due to the dermis proximity. The hair follicle has specific immunological properties. It is able to recruit specific immune cells such as monocyte-derived Langerhans Cells precursors[7] and actively maintain resident memory T cells (TRM)[8] making it a potential essential place for antigen presentation. The hair follicle is also deprived of effector T cells and has a strong immunosuppressive environment making it an immune privileged area[9].

Examples in the published literature indicate that skin-resident bacteria actively engage host immunity through an intact skin barrier, and activate specific immune cells in a species- and strain-dependent manner (Chen et al, Nature 2018; 555(7697):543). For instance, some but not all strains of *S. epidermidis* induce activation of *S. epidermidis*-specific IL-17$^+$CD8$^+$ T cells that protect against cutaneous infection (Naik et al, Nature 2015, 520(7545):104-108).

Due to the absence of stratum corneum, the skin appendages are also more permeable to chemicals as these will only need to cross the tight-junction barrier and not the stratum corneum which normally prevents water exchange and as a result all water-soluble substances are able to diffuse.

The pilosebaceous subunit comprising the fair follicle and the sebaceous gland is mostly colonized by *C. acnes* that thrive in this sebum rich and anaerobic environment. *Cutibacterium acnes* (formerly *Propionibacterium acnes*) is a gram-positive rod-shaped aerotolerant bacteria, first isolated from skin in 1897. It belongs to the order Actinomycetales, it is part of the Propionibacteriaceae family and it belongs to the genus *Cutibacterium*. This genus includes other human skin species such as *Cutibacterium avidum*, *Cutibacterium granulosum* and *Cutibacterium humerusii*[10]. *C. acnes* is one of the most prevalent and abundant bacteria on human skin where it can be found both on the skin surface (stratum corneum) and in the hair follicle. Inside the hair follicle, it is in direct contact with a large diversity of living cells such as keratinocytes, stem cells, sebaceous cells and immune cells, unlike on the stratum corneum where it is mostly in contact with the dead corneocyte. *C. acnes* is a commensal bacterium but has also been associated with several skin diseases such as acne vulgaris[11] or progressive macular hypomelanosis[12-14].

In particular, new findings on *C. acnes* reveal that specific phylotypes might play a critical role in acne development[11]. Precisely, the role of *C. acnes* phylotype IA1 in acne is being widely underscored. Fitz-Gibbon and colleagues demonstrated that chromosomal regions, loci 1, 2 and 3, characteristic of ribotypes RT4 and RT5 (classified within the phylogroup IA1), are strongly associated with acne[15]. Since these chromosomal regions are absent in ribotypes that are associated with healthy skin (i.e., RT6), they represent a potential target to eliminate acne-associated *C. acnes* strains.

Being able to edit *Cutibacterium acnes* population by removing specific proinflammatory strains to prevent or cure disease such as acne vulgaris or leverage their privilege location into the pilosebaceous unit to modulate host immune response or improve wound healing are attractive therapeutic approaches. To implement such approaches, one can either genetically modify *C. acnes* strains in situ or provide in vitro genetically modified *C. acnes*. Because of the large intra-individual and inter-individual microbiome diversity both at the species and at the strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-establish strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[16-18]. This in vitro process has been shown to be of very low efficiency and rely on the use of an antibiotic selection marker to select such events. Moreover, these genetic modifications have been restricted to a few specific strains (KPA17202, one RT6 *C. acnes*) and might not be generalizable to all *C. acnes* strains. Second, in order to perform in situ genetic modification of *C. acnes* we need to deliver DNA into *C. acnes*. The only described method for introducing DNA into *C. acnes* is the use of electroporation[19,20], a method that can only be performed in vitro.

The present invention solves both the lack of replicative and stable DNA vectors and their delivery into *C. acnes* using phage-derived particles.

BRIEF SUMMARY OF INVENTION

The invention encompasses *Cutibacterium acnes* phagemids, bacterial cells comprising these phagemids, methods for making phage-derived particles comprising these phagemids, phage-derived particles comprising these phagemids, and methods for using these phagemids, particles, and cells, particularly in treatments of *Cutibacterium acnes* related disorders and/or diseases.

The invention encompasses a recombinant DNA phagemid vector, phage-derived particles comprising these vectors, and *Cutibacterium acnes* carrying the vector, wherein the vector comprises:
a phage packaging signal allowing packaging of the DNA vector in a *Cutibacterium acnes* phage capsid; and
a gene of interest.
In one embodiment, the DNA vector comprises:
a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 66; and
a gene of interest.
In one embodiment, the DNA vector comprises:
a phage packaging signal allowing packaging of the DNA vector in a *Cutibacterium acnes* phage capsid;
a gene of interest; and
a selection marker allowing for selection of the DNA vector in *Cutibacterium acnes*.
In one embodiment, the DNA vector comprises:
a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 66;
a gene of interest; and
a selection marker allowing for selection of the DNA vector in *Cutibacterium acnes*.

In one embodiment, the DNA vector comprises:
a phage packaging signal allowing packaging of the DNA vector in a *Cutibacterium acnes* phage capsid;
a gene of interest;
an origin of replication allowing replication in *Cutibacterium acnes*; and
optionally a selection marker allowing for selection of the DNA vector in *Cutibacterium acnes*.
In one embodiment, the DNA vector comprises:
a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 66;
a gene of interest;
an origin of replication allowing replication in *Cutibacterium acnes*; and
optionally a selection marker allowing for selection of the DNA vector in *Cutibacterium acnes*.
In one embodiment, the phage packaging signal sequence is at least 80, 83, 85, 87, 90, 93, 95, 97, 98, 99, or 100% identical to a phage packaging signal sequence selected from the group consisting of the sequences SEQ ID NO: 76, SEQ ID NO: 77, SEQ ID NO: 78, SEQ ID NO: 79, SEQ ID NO: 80 and SEQ ID NO: 81.
In one embodiment, the DNA vector further comprises a *C. acnes* phage origin of replication.
In one embodiment, the DNA vector further comprises a *C. acnes* phage origin of replication, wherein the phage origin of replication sequence is identical at least 75, 77, 80, 83, 85, 87, 90, 93, 95, 96, 97, 98, 99 or 100% identical to the sequence SEQ ID NO: 67.
In one embodiment, the gene of interest is a DNA encoding an antigen.

The invention encompasses a *Cutibacterium acnes* producer cell carrying a recombinant DNA vector for the production of *Cutibacterium acnes* phage-derived particles that contain the recombinant DNA vector.

The DNA vector is typically packaged into proteins produced from a *Cutibacterium acnes* phage genome or a helper phage. The *C. acnes* phage genome can be introduced into the *C. acnes* producer cell, for instance, by transformation or transduction with a *C. acnes* phage whereas the helper phage can be introduced into the *C. acnes* producer cell, for instance, by transformation or conjugation before or after introduction of the DNA vector into the *C. acnes* producer cell (FIG. 1).

The *Cutibacterium acnes* producer cell carrying a recombinant DNA vector typically comprises a *Cutibacterium acnes* phage genome leading to the production of phage-derived particles carrying the DNA vector.

In one embodiment, the *Cutibacterium acnes* phage genome is a non-engineered/wild-type genome.

In another embodiment, the *Cutibacterium acnes* phage genome is engineered.

In one embodiment, the DNA vector comprises an origin of replication able to replicate only in the *Cutibacterium acnes* producer cell and not in the *Cutibacterium acnes* receiver cell.

In one embodiment, the DNA vector comprises:
a phage packaging signal allowing packaging of the DNA vector in a *Cutibacterium acnes* phage capsid;
at least one gene of interest;
an origin of replication allowing replication only in *Cutibacterium acnes* producer cell; and
optionally a selection marker allowing for selection of the DNA vector in *Cutibacterium acnes*.

In one embodiment, the selection marker is an auxotrophic marker and the *Cutibacterium acnes* producer cell growth is dependent on this auxotrophic marker.

In one embodiment, the selection marker is an antibiotic resistance marker.

In one embodiment, the DNA vector further comprises a CRISPR-Cas system.

In one embodiment, the CRISPR-Cas system targets a *C. acnes* chromosome locus. Preferably, the targeted locus is not present in the *C. acnes* producer cell. Preferably, the CRISPR array is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus. Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in *C. acnes* producer cell. Preferably the CRISPR-Cas system is repressed in *C. acnes* producer cell.

In one embodiment, the CRISPR-Cas system targets a proinflammatory sequence related to host disease.

In one embodiment, the CRISPR-Cas system targets a proinflammatory sequence related to acne vulgaris.

In one embodiment, the DNA vector comprises a CRISPR-Cas system targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allow for the integration of the DNA vector inside the chromosome.

In one embodiment, the DNA vector comprises a prime editor gene expression cassette and one or multiple pegRNAs.

In one embodiment, the DNA vector comprises a base editor gene expression cassette and one or multiple crRNAs or sgRNAs.

In one embodiment, the selection marker is catA.
In one embodiment, the selection marker is ermE.
In one embodiment, the selection marker is hygB.

The invention encompasses a *C. acnes* phage-derived particle comprising any of the DNA vectors of the invention.

The invention encompasses a *C. acnes*, in particular an engineered *C. acnes*, comprising any of the DNA vectors of the invention.

In a particular embodiment, the engineered *C. acnes* comprises at least one, two, three or more DNA vectors, in particular DNA vectors of the invention.

In a particular embodiment, the engineered *C. acnes* comprises a DNA vector of the invention which comprises a DNA encoding an antigen.

The invention encompasses a *C. acnes* engineered following transduction of any of the vectors of the invention by phage-derived particles.

The invention encompasses an engineered *C. acnes* whose genome is altered following the transduction by a phage-derived particle containing any of the vectors of the invention.

The invention encompasses an engineered *C. acnes* produced by transducing *C. acnes* with any of the vectors of the invention, modifying the *C. acnes* with a gene of interest carried by the vector, selecting for the modification.

The invention encompasses an engineered *C. acnes* produced by transducing *C. acnes* with any of the vectors of the invention, modifying the *C. acnes* with a gene of interest carried by the vector, selecting for the modification, and curing the engineered *C. acnes* of the vector.

In one embodiment, the engineered *C. acnes* has been modified by a CRISPR-Cas system carried by the vector and transduced by a phage-derived particle containing any vectors from the invention.

In one embodiment, the engineered *C. acnes* has been modified by insertion of an exogenous gene into the *C. acnes* chromosome.

In one embodiment, the engineered *C. acnes* has been modified by insertion of an exogenous gene into the *C. acnes* plasmid.

In one embodiment, the engineered *C. acnes* has been modified by deletion or mutation of an endogenous genetic sequence in the *C. acnes* chromosome.

In one embodiment, the engineered *C. acnes* has been modified by deletion, insertion or substitution of one or several nucleotides into the *C. acnes* chromosome.

In one embodiment, the engineered *C. acnes* has been modified by deletion, insertion or substitution of one or several nucleotides into the *C. acnes* plasmid.

The invention encompasses a method for producing *C. acnes* phage-derived particles that contain any vector of the inventions, comprising the introduction of any of the DNA vectors of the invention into a *C. acnes* producer cell and contacting the producer cell with *C. acnes* phage genome.

The invention encompasses a method for engineering *C. acnes* comprising the introduction of any of the DNA vectors of the invention into a *C. acnes*. The method can further comprise selecting a modified *C. acnes*. The method can further comprise selecting a modified *C. acnes* that has an insertion of an exogenous gene into the *C. acnes* chromosome or into an endogenous plasmid. The method can further comprise selecting a modified *C. acnes* that has one or several deletions, insertions or substitutions of one or several nucleotides into *C. acnes* chromosome or endogenous plasmids.

The invention encompasses a phage-derived particle produced by any of the methods of the invention.

The invention encompasses methods for treating a *C. acnes*-related disorder or disease. In one embodiment, the method comprises administering a phage-derived particle of the invention or a bacterium producing such a phage-derived particle to a subject. The invention further concerns a phage-derived particle of the invention or a bacterium producing such a phage derived particle for use in a method for treating a *C. acnes*-related disorder or disease.

The invention encompasses methods for modifying a *C. acnes* to treat a disorder or disease or skin condition or for cosmetic applications. In one embodiment, the method comprises administering a phage-derived particle of the invention or a bacterium producing such a phage-derived particle to a subject. The invention further concerns a phage-derived particle of the invention or a bacterium producing such a phage-derived particle for use in a method for treating a disorder or disease or skin condition.

In one embodiment, the method is performed ex-situ.

In one embodiment, the method is performed in-situ.

In one embodiment, the method is performed ex-situ with a *C. acnes* strain isolated from the subject.

BRIEF DESCRIPTION OF DRAWINGS

In order to better understand the subject matter that is disclosed herein and to exemplify how it may be carried out in practice, embodiments will be described, by way of non-limiting example, with reference to the accompanying drawings. With specific reference to the drawings, it is stressed that the particulars shown are by way of example and for purposes of illustrative discussion of embodiments of the invention.

FIG. 2 depicts host range determination of isolated *C. acnes* bacteriophages. 1 indicates strain infection with full spot lysis; 0.5 indicates lower efficiency in strain infection with single plaques observed instead of full spot lysis.

FIG. 4A depicts a vector (pEB_HR01) containing a single homology arm (HA) to *C. acnes* chromosome which is conjugated into *C. acnes*. Because the vector is not replicative in *C. acnes*, only *C. acnes* cells that perform a single recombination event stably maintain the antibiotic marker and are able to grow on antibiotic plate. Cells that do not perform the first recombination event or cells that perform the first and the second recombination events are not able to grow on antibiotic plates (erythromycin). FIG. 4B depicts a vector (pEB_HR02) containing two homology arms to *C. acnes* chromosome which is conjugated into *C. acnes*. Selection of the final recombinant is performed using an antibiotic selection (ErmE) and a counter selection (SacB).

FIG. 6A depicts a vector, containing an antibiotic selection marker flanked by two homology arms and a CRISPR-Cas system targeting the vector outside the homology regions, which is conjugated into *C. acnes*. The CRISPR-Cas system cuts the vector leading to linearization of the template and plasmid loss. Thus, only recombinant cells are able to grow in presence of antibiotic. FIG. 6B depicts a vector, containing a mutant allele flanked by two homology arms and a CRISPR-Cas system targeting the vector outside the homology regions as well as the non mutated allele of *C. acnes* chromosome, which is conjugated into *C. acnes*. The CRISPR-Cas system cuts the vector leading to linearization of the template and plasmid loss as well as the *C. acnes* chromosome. Thus, only recombinant cells are able to grow in the presence of erythromycin.

FIGS. 9 (A and B) depicts absorbance values from ELISAs for the presence of chicken ovalbumin (OVA) protein in different *C. acnes* culture supernatant diluted 1/10.

Figure 1:
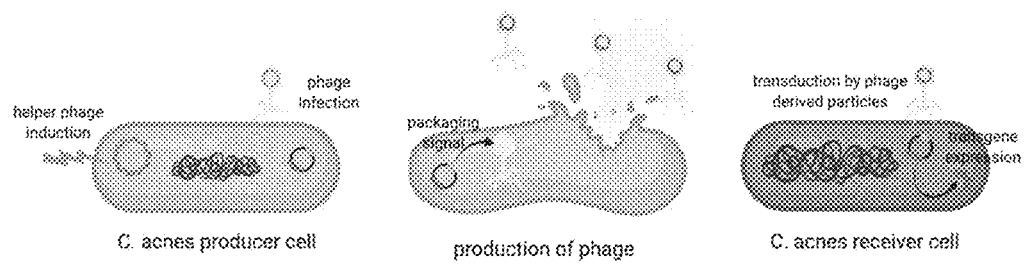
FIG. 1 depicts a *C. acnes* producer cell carrying a DNA vector with a packaging signal and a transgene which is infected by a *C. acnes* phage, phage-derived particles carrying the DNA vector are then produced and upon binding to *C. acnes* receiver cell transduce the DNA vector that replicates and leads to transgene expression. Alternatively, the *C. acnes* producer is not infected by a phage but carries also a helper phage that is induced to trigger phage-derived particle production.

supernatant from strain Ca0s22130, (7) supernatant from strain Ca0s22132, (8) supernatant from strain Ca0s16973, (9) ovalbumin.

DETAILED DESCRIPTION OF INVENTION

The inventors demonstrated, for the first time, the introduction of a recombinant replicative DNA in *C. acnes* by transduction, of a phage-derived particle.

The inventors also demonstrated, for the first time, the production of *C. acnes* phage-derived particles from a *C. acnes* strain, carrying a recombinant self-replicative DNA vector.

The invention relates to a *C. acnes* strain carrying a DNA vector comprising a phage packaging signal and a gene of interest, the production of phage-derived particles containing the DNA vector and the use of this phage-derived particles to transduce *C. acnes* in vitro or in situ and the subsequent expression of the gene of interest in the transduced *C. acnes* cell. The invention also relates to the modified *C. acnes* strains obtained by transduction of a DNA vector by the phage-derived particle, the modified *C. acnes* strains containing or not the DNA vector.

*C. acnes* phages are naturally present in the human skin and have been isolated numerous times since the first isolation in 1964. More recently, sequencing of *C. acnes* phages has revealed an unusual high level of nucleotide conservation with ~85% identity. All *C. acnes* phages described so far are siphoviridae with a genome size constraint around 30 kb and a similar genome architecture. Despite their small genetic diversity, most *C. acnes* phages have the capacity to infect several *C. acnes* phylotypes and thus are considered as broad-host range. Their in-situ infectivity and their broad host range make them a relevant platform to be engineered for transgene delivery into the *C. acnes* population.

The inventors show for the first time that phage-derived particles can be produced from the co-occurrence of a wild-type or engineered *C. acnes* phage genome and a recombinant DNA vector with a packaging signal in a *C. acnes* cell ("producer cell"). The phage-derived particles are able to transduce the DNA vector into a "receiver" *C. acnes* cell and express a transgene such as an antibiotic resistance gene allowing the selection of the transductants. This widely expands the possibility to engineer *C. acnes* population directly on the skin, paving the way for many applications (industrial, therapeutic, cosmetic, environmental). The invention encompasses a *C. acnes* "producer" cell carrying DNA vectors, particularly phagemids, and methods for generating phage-derived particles and their use to modify or kill *C. acnes*.

DNA Vectors

The invention encompasses recombinant DNA vectors for use in *Cutibacterium acnes*. Preferably, the DNA vector is a recombinant DNA vector, which is not integrated into the *C. acnes* chromosome. The vector allows transfer to progeny cells. The vector is preferably a phagemid. The DNA vector preferably comprises an origin of replication allowing replication in *C. acnes* and a phage packaging signal.

In various embodiments, the DNA vector comprises any combination of a phage packaging signal, an origin of replication allowing replication in *C. acnes*, a selection marker allowing for selection of the DNA vector in *C. acnes*, a gene of interest, and an origin of replication allowing replication in *C. acnes* producer cell but no replication in *C. acnes* receiver cell.

In one embodiment, the DNA vector comprises a phage packaging signal, an origin of replication allowing replication in *C. acnes*, a first selection marker allowing for selection of the DNA vector in *C. acnes* and a gene of interest.

In one embodiment, the DNA vector comprises a phage packaging signal, an origin of replication allowing replication in *C. acnes* producer cell but no replication in *C. acnes* receiver cell, a first selection marker allowing for selection of the DNA vector in *C. acnes* and a gene of interest.

Preferably, the gene of interest is exogenous to *C. acnes*, that is, one that is not found naturally in *C. acnes*.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 66; an origin of replication allowing replication in *C. acnes*; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 66; an origin of replication allowing replication in *C. acnes*; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 66; an origin of replication allowing replication in *C. acnes*; a selection marker allowing for selection of the DNA vector in *C. acnes*; a selection marker allowing for selection in a first bacteria wherein the first bacteria is *E. coli*; an origin of replication allowing replication in a first bacteria wherein the first bacteria is *E. coli*; and a gene of interest.

In one embodiment, the DNA vector can be efficiently introduced into and stably replicated in *C. acnes* producer cell using electroporation, using protoplast electroporation, using chemical transformation, using conjugation, using natural competency or using transduction.

In one embodiment, the DNA vector can be efficiently transformed into and stably replicated in *C. acnes* producer cell using physical methods such as electroporation of *C. acnes* cells or electroporation of *C. acnes* protoplast.

In one embodiment, the *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, the DNA vector can be efficiently transformed into and stably replicated in *C. acnes* producer cell using *C. acnes* protoplast mix with DNA vector or DNA vector+glass beads.

In one embodiment, delivery of the DNA vector into *C. acnes* is by transduction. In one embodiment, the DNA vector comprises one packaging signal of a *C. acnes* phage selected from the group consisting of: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75), and is packaged into proteins expressed from the genome of a *C. acnes* phage selected from the group consisting of the phages: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75) allowing transduction of the DNA vector into *C. acnes*.

In one embodiment, the DNA vector comprises a packaging signal, the sequence of which is at least 80, 83, 85, 87, 90, 93, 95, 97, 98, 99, or 100% identical to the sequence of any of the above packaging signals.

In one embodiment, the phage packaging signal is of sequence at least 80, 83, 85, 87, 90, 93, 95, 97, 98, 99, or 100% identical to a phage packaging signal sequence selected from the group consisting of: SEQ ID NO: 76, SEQ ID NO: 77, SEQ ID NO: 78, SEQ ID NO: 79, SEQ ID NO: 80 and SEQ ID NO: 81.

In one embodiment, delivery of the DNA vector into *C. acnes* is by conjugation.

In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_pTiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29); oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40); and oriT_pIP501 (typically of sequence SEQ ID NO: 41).

In one embodiment, the DNA vector comprises the origin of transfer oriT_pMRC01 (typically of sequence SEQ ID NO: 1). In one embodiment, the DNA vector comprises the origin of transfer oriT_RSF1010 (typically of sequence SEQ ID NO: 2). In one embodiment, the DNA vector comprises the origin of transfer oriT_pRS01 (typically of sequence SEQ ID NO: 3). In one embodiment, the DNA vector comprises the origin of transfer oriT_pMV158 (typically of sequence SEQ ID NO: 4). In one embodiment, the DNA vector comprises the origin of transfer oriT_pTF1 (typically of sequence SEQ ID NO: 5). In one embodiment, the DNA vector comprises the origin of transfer oriT_pSC101 (typically of sequence SEQ ID NO: 6). In one embodiment, the DNA vector comprises the origin of transfer oriT_pBTK445 (typically of sequence SEQ ID NO: 7). In one embodiment, the DNA vector comprises the origin of transfer oriT_pBBR1 (typically of sequence SEQ ID NO: 8). In one embodiment, the DNA vector comprises the origin of transfer oriT_R721 (typically of sequence SEQ ID NO: 9). In one embodiment, the DNA vector comprises the origin of transfer oriT_pRmeGR4a (typically of sequence SEQ ID NO: 10). In one embodiment, the DNA vector comprises the origin of transfer oriT_ColE1 (typically of sequence SEQ ID NO: 11). In one embodiment, the DNA vector comprises the origin of transfer oriT_pTiC58 (typically of sequence SEQ ID NO: 12). In one embodiment, the DNA vector comprises the origin of transfer oriT_pMdT1 (typically of sequence SEQ ID NO: 13). In one embodiment, the DNA vector comprises the origin of transfer oriT_R1 (typically of sequence SEQ ID NO: 14). In one embodiment, the DNA vector comprises the origin of transfer oriT_Tn5520 (typically of sequence SEQ ID NO: 15). In one embodiment, the DNA vector comprises the origin of transfer oriT_QKH54 (typically of sequence SEQ ID NO: 16). In one embodiment, the DNA vector comprises the origin of transfer oriT_R64 (typically of sequence SEQ ID NO: 17). In one embodiment, the DNA vector comprises the origin of transfer oriT_R751 (typically of sequence SEQ ID NO: 18). In one embodiment, the DNA vector comprises the origin of transfer oriT_RP4 (typically of sequence SEQ ID NO: 19). In one embodiment, the DNA vector comprises the origin of transfer oriT_pKL1 (typically of sequence SEQ ID NO: 20). In one embodiment, the DNA vector comprises the origin of transfer oriT_RK2 (typically of sequence SEQ ID NO: 21). In one embodiment, the DNA vector comprises the origin of transfer oriT_R1162 (typically of sequence SEQ ID NO: 22). In one embodiment, the DNA vector comprises the origin of transfer oriT_Tn4555 (typically of sequence SEQ ID NO: 23). In one embodiment, the DNA vector comprises the origin of transfer oriT_pHT (typically of sequence SEQ ID NO: 24). In one embodiment, the DNA vector comprises the origin of transfer oriT_Tn4399 (typically of sequence SEQ ID NO: 25). In one embodiment, the DNA vector comprises the origin of transfer oriT_Tn916 (typically of sequence SEQ ID NO: 26). In one embodiment, the DNA vector comprises the origin of transfer oriT_pST12 (typically of sequence SEQ ID NO: 27). In one embodiment, the DNA vector comprises the origin of transfer oriT_pCU1 (typically of sequence SEQ ID NO: 28). In one embodiment, the DNA vector comprises the origin of transfer oriT_pSU233 (typically of sequence SEQ ID NO: 29). In one embodiment, the DNA vector comprises the origin of transfer oriT_F (typically of sequence SEQ ID NO: 30). In one embodiment, the DNA vector comprises the origin of transfer oriT_pMAB01 (typically of sequence SEQ ID NO: 31). In one embodiment, the DNA vector comprises the origin of transfer oriT_R388 (typically of sequence SEQ ID NO: 32). In one embodiment, the DNA vector comprises the origin of transfer oriT_pS7a (typically of sequence SEQ ID NO: 33). In one embodiment, the DNA vector comprises the origin of transfer oriT_pS7b (typically of sequence SEQ ID NO: 34). In one embodiment, the DNA vector comprises the origin of transfer oriT_R702 (typically of sequence SEQ ID NO: 35). In one embodiment, the DNA vector comprises the origin of transfer oriT_pMUR274 (typically of sequence SEQ ID NO: 36). In one embodiment, the DNA vector comprises the origin of transfer oriT_R100 (typically of sequence SEQ ID NO: 37). In one embodiment, the DNA vector comprises the origin of transfer oriT_pVCR94deltaX (typically of sequence SEQ ID NO: 38). In one embodiment, the DNA vector comprises the origin of transfer oriT_R46 (typically of sequence SEQ ID NO: 39). In one embodiment, the DNA vector comprises the origin of transfer oriT_pGO1 (typically of sequence SEQ ID NO: 40). In one embodiment, the DNA vector comprises the origin of transfer oriT_pIP501 (typically of sequence SEQ ID NO: 41).

In one embodiment, the DNA vector comprises an origin of transfer (oriT), the sequence of which is at least 80, 83, 85, 87, 90, 93, 95, 97, 98, 99, or 100% identical to the sequence of any of the above oriT.

In one embodiment, a donor bacterium, such as E. coli, carry a conjugative plasmid, a conjugative transposon, or an integrative and conjugative element (ICE) selected from the group consisting of: pMRC01, RSF1010, pRS01, pMV158, pTF1, pSC101, pBTK445, pBBR1, R721, pRmeGR4a, ColE1, pTiC58, pMdT1, R1, Tn5520, QKH54, R64, R751, RP4, pKL1, RK2, R1162, Tn4555, pHT, Tn4399, Tn916, pST12, pCU1, pSU233, F, pMAB01, R388, pS7a, pS7b, R702, pMUR274, R100, pVCR94deltaX, R46, pGO1 and pIP501; and is used to efficiently transfer the DNA vector into C. acnes recipient cells. In one embodiment the DNA vector contains an origin of transfer and the associated relaxase of the conjugative plasmid, conjugative transposon and integrative and conjugative element (ICE) selected from the group consisting of pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises an origin of transfer and the relaxase of the following conjugative plasmid, conjugative transposon and integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises an origin of transfer selected from the group consisting of: oriT_pMRC01 (SEQ ID NO: 1); oriT_RSF1010 (SEQ ID NO: 2); oriT_pRS01 (SEQ ID NO: 3); oriT_pMV158 (SEQ ID NO: 4); oriT_pTF1 (SEQ ID NO: 5); oriT_pSC101 (SEQ ID NO: 6); oriT_pBTK445 (SEQ ID NO: 7); oriT_pBBR1 (SEQ ID NO: 8); oriT_R721 (SEQ ID NO: 9); oriT_pRmeGR4a (SEQ ID NO: 10); oriT_ColE1 (SEQ ID NO: 11); oriT_pTiC58 (SEQ ID NO: 12); oriT_pMdT1 (SEQ ID NO: 13); oriT_R1 (SEQ ID NO: 14); oriT_Tn5520 (SEQ ID NO: 15); oriT_QKH54 (SEQ ID NO: 16); oriT_R64 (SEQ ID NO: 17); oriT_R751 (SEQ ID NO: 18); oriT_RP4 (SEQ ID NO: 19); oriT_pKL1 (SEQ ID NO: 20); oriT_RK2 (SEQ ID NO: 21); oriT_R1162 (SEQ ID NO: 22); oriT_Tn4555 (SEQ ID NO: 23); oriT_pHT (SEQ ID NO: 24); oriT_Tn4399 (SEQ ID NO: 25); oriT_Tn916 (SEQ ID NO: 26); oriT_pST12 (SEQ ID NO: 27); oriT_pCU1 (SEQ ID NO: 28); oriT_pSU233 (SEQ ID NO: 29); oriT_F (SEQ ID NO: 30); oriT_pMAB01 (SEQ ID NO: 31); oriT_R388 (SEQ ID NO: 32); oriT_pS7a (SEQ ID NO: 33); oriT_pS7b (SEQ ID NO: 34); oriT_R702 (SEQ ID NO: 35); oriT_pMUR274 (SEQ ID NO: 36); oriT_R100 (SEQ ID NO: 37); oriT_pVCR94deltaX (SEQ ID NO: 38); oriT_R46 (SEQ ID NO: 39); oriT_pGO1 (SEQ ID NO: 40) and oriT_pIP501 (SEQ ID NO: 41).

In one embodiment, the DNA vector comprises an origin of transfer (oriT) that is at least 80, 83, 85, 87, 90, 93, 95, 97, 98, 99, or 100% identical to any of these ICE.

In one embodiment, the invention encompasses a DNA vector comprising an origin of replication allowing replication in C. acnes, an oriT allowing conjugation into C. acnes, a selection marker allowing for selection in the transconjugant C. acnes, and a selection marker allowing for selection in the donor bacteria. In another embodiment, the invention encompasses a DNA vector comprising an origin of replication allowing replication in C. acnes and an oriT allowing conjugation into C. acnes as defined above.

In one embodiment, origin of replication allowing replication in C. acnes is selected from the group consisting of: R6K (typically of sequence SEQ ID NO: 42); RK2 (typically of sequence SEQ ID NO: 43); pBBR1 (typically of sequence SEQ ID NO: 44); pRO1600 (typically of sequence SEQ ID NO: 45); RSF1010 (typically of sequence SEQ ID NO: 46); pAMβ1 (typically of sequence SEQ ID NO: 47); pLME106 (typically of sequence SEQ ID NO: 48); pTZC1 (typically of sequence SEQ ID NO: 49); pBC1 (typically of sequence SEQ ID NO: 50); pEP2 (typically of sequence SEQ ID NO: 51); pWVO1 (typically of sequence SEQ ID NO: 52); pAP1 (typically of sequence SEQ ID NO: 53); pWKS1 (typically of sequence SEQ ID NO: 54); pLME108 (typically of sequence SEQ ID NO: 55); pLS1 (typically of sequence SEQ ID NO: 56); pUB6060 (typically of sequence SEQ ID NO: 57); p545 (typically of sequence SEQ ID NO: 58); pJD4 (typically of sequence SEQ ID NO: 59); pIJ101 (typically of sequence SEQ ID NO: 60); pSN22 (typically of sequence SEQ ID NO: 61); pGP01 (typically of sequence SEQ ID NO: 62); pIP501 (typically of sequence SEQ ID NO: 63); pCU1 (typically of sequence SEQ ID NO: 64); and pBAV1K-T5 (typically of sequence SEQ ID NO: 65). In one embodiment, the origin of replication allowing replication in C. acnes is R6K (typically of sequence SEQ ID NO: 42). In one embodiment, the origin of replication allowing replication in C. acnes is RK2 (typically of sequence SEQ ID NO: 43). In one embodiment, the origin of replication allowing replication in C. acnes is pBBR1 (typically of sequence SEQ ID NO: 44). In one embodiment, the origin of replication allowing replication in C. acnes is pRO1600 (typically of sequence SEQ ID NO: 45). In one embodiment, the origin of replication allowing replication in C. acnes is RSF1010 (typically of sequence SEQ ID NO: 46). In one embodiment, the origin of replication allowing replication in C. acnes is pAMβ1 (typically of sequence SEQ ID NO: 47). In one embodiment, the origin of replication allowing replication in C. acnes is pLME106 (typically of sequence SEQ ID NO: 48). In one embodiment, the origin of replication allowing replication in C. acnes is pTZC1 (typically of sequence SEQ ID NO: 49). In one embodiment, the origin of replication allowing replication in C. acnes is pBC1 (typically of sequence SEQ ID NO: 50). In one embodiment, the origin of replication allowing replication in C. acnes is pEP2 (typically of sequence SEQ ID NO: 51). In one embodiment, the origin of replication allowing replication in C. acnes is pWVO1 (typically of sequence SEQ ID NO: 52). In one embodiment, the origin of replication allowing replication in C. acnes is pAP1 (typically of sequence SEQ ID NO: 53). In one embodiment, the origin of replication allowing replication in *C. acnes* is pWKS1 (typically of sequence SEQ ID NO: 54). In one embodiment, the origin of replication allowing replication in *C. acnes* is pLME108 (typically of sequence SEQ ID NO: 55). In one embodiment, the origin of replication allowing replication in *C. acnes* is pLS1 (typically of sequence SEQ ID NO: 56). In one embodiment, the origin of replication allowing replication in *C. acnes* is pUB6060 (typically of sequence SEQ ID NO: 57). In one embodiment, the origin of replication allowing replication in *C. acnes* is p545 (typically of sequence SEQ ID NO: 58). In one embodiment, the origin of replication allowing replication in *C. acnes* is pJD4 (typically of sequence SEQ ID NO: 59). In one embodiment, the origin of replication allowing replication in *C. acnes* is pIJ101 (typically of sequence SEQ ID NO: 60). In one embodiment, the origin of replication allowing replication in *C. acnes* is pSN22 (typically of sequence SEQ ID NO: 61). In one embodiment, the origin of replication allowing replication in *C. acnes* is pGP01 (typically of sequence SEQ ID NO: 62). In one embodiment, the origin of replication allowing replication in *C. acnes* is pIP501 (typically of sequence SEQ ID NO: 63). In one embodiment, the origin of replication allowing replication in *C. acnes* is pCU1 (typically of sequence SEQ ID NO: 64). In one embodiment, the origin of replication allowing replication in *C. acnes* is pBAV1K-T5 (typically of sequence SEQ ID NO: 65).

In one embodiment, the DNA vector comprises an origin of replication allowing replication in *C. acnes*. In one embodiment, the DNA vector comprises an origin of replication selected from the group consisting of: R6K (SEQ ID NO: 42); RK2 (SEQ ID NO: 43); pBBR1 (SEQ ID NO: 44); pRO1600 (SEQ ID NO: 45); RSF1010 (SEQ ID NO: 46); pAMβ1 (SEQ ID NO: 47); pLME106 (SEQ ID NO: 48); pTZC1 (SEQ ID NO: 49); pBC1 (SEQ ID NO: 50); pEP2 (SEQ ID NO: 51); pWVO1 (SEQ ID NO: 52); pAP1 (SEQ ID NO: 53); pWKS1 (SEQ ID NO: 54); pLME108 (SEQ ID NO: 55); pLS1 (SEQ ID NO: 56); pUB6060 (SEQ ID NO: 57); p545 (SEQ ID NO: 58); pJD4 (SEQ ID NO: 59); pIJ101 (SEQ ID NO: 60); pSN22 (SEQ ID NO: 61); pGP01 (SEQ ID NO: 62); pIP501 (SEQ ID NO: 63); pCU1 (SEQ ID NO: 64); and pBAV1K-T5 (SEQ ID NO: 65).

Preferably, the origin of replication is of sequence at least 80, 83, 85, 87, 90, 93, 95, 97, 98, 99, or 100% identical to the sequence of any of the above origins of replication.

In various embodiments, the selection marker is selected from ermE, catA, hygB, ermX, tetW, erm(50) and other high GC antibiotic resistance genes. In one embodiment, the selection marker is not ermE. In one embodiment, the selection marker is catA. In one embodiment, the selection marker is hygB.

In one embodiment, the DNA vector further comprises a CRISPR-Cas system. Typically, the CRISPR-Cas system comprises a CRISPR array. Typically, the CRISPR-Cas system comprises a RNA guide (crRNA or sgRNA).

In one embodiment, the CRISPR-Cas system targets a *C. acnes* chromosome locus. Preferably, the targeted locus is not present in the *C. acnes* producer cell. Preferably, the CRISPR array from the CRISPR-Cas system is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus. Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in *C. acnes* producer cell. Preferably the CRISPR-Cas system is repressed in *C. acnes* producer cell.

In one embodiment, the CRISPR-Cas system targets a proinflammatory sequence related to a host disease.

In one embodiment, the CRISPR-Cas system targets a proinflammatory sequence related to acne vulgaris.

In one embodiment, the DNA vector comprises a template for homologous recombination and the CRISPR-Cas system is targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allow for the integration of the DNA vector inside the chromosome.

In one embodiment, the DNA vector comprises a base editor gene expression cassette and one or multiple crRNAs or sgRNAs.

In one embodiment, the base editor is used to inactivate the expression of a gene by editing one or several nucleotides involved in transcription or translation of said gene. More specifically the base editor is targeting one or several nucleotides of a promoter, a RBS or a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation of said genes. More specifically the base editor is targeting one or several nucleotides of a promoter, a RBS or a start codon, leading to an increase or decrease of gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site or post translational modification site (phosphorylation, glycosylation, acetylation, pupylation . . . ).

In one embodiment, the DNA vector comprises a prime editor gene expression cassette and one or multiple pegRNAs.

In one embodiment, the prime editor is used to introduce one or several premature stop codon.

In one embodiment, the prime editor is used to introduce one or several rare codons.

In one embodiment, the prime editor is used to introduce or delete a nucleotide inducing a frameshift in the reading frame.

In another embodiment, the prime editor is used to modulate the expression of genes by replacing, deleting or inserting one or several nucleotides involved in transcription or translation of said genes. More specifically the prime editor is replacing, deleting or inserting one or several nucleotides in a promoter, a RBS or a start codon. leading to an increase or decrease of gene expression.

In another embodiment, the prime editor is used to revert a mutation that leads to the inactivation or decrease in activity of a gene or pathway.

In another embodiment, the prime editor is used to revert a mutation that leads to an increase of pathogenicity.

In one embodiment, the vector is a plasmid which comprises an *E. coli* replicon and an *E. coli* resistance marker allowing extraction of the plasmid from *C. acnes* and transformation and replication in *E. coli*.

In one embodiment, the vector is a plasmid which comprises an *E. coli* replicon and an *E. coli* resistance marker allowing extraction of the plasmid from *E. coli* and transformation and replication in *C. acnes*.

In one embodiment, the vector comprises 2 origins or replication, one allowing replication in *C. acnes* or *C. acnes* producer cell only, the second origin of replication allowing replication in another bacteria.

In one embodiment, the vector comprising the template DNA for homologous recombination allows expression of genes increasing recombination rate.

In one embodiment, the template for homologous recombination contains homology arms upstream and downstream of recombination points. These homology arms can be at least 50, 100, 500 or at least 1000 bp in size.

In one embodiment, the gene of interest comprised by the DNA vector can be a transgene that is exogenous to the *C. acnes*. Transgenes include but are not limited to:
- a DNA encoding a fluorescent protein (e.g., UnaG) that leads to fluorescent *C. acnes* cells once a specific substrate is added;
- a DNA encoding an enzymatic reporter (e.g., LacZ) that leads to the production of a chromogenic compound by *C. acnes* colonies;
- a DNA encoding a human protein (e.g., an interleukin);
- a DNA encoding an antigen (e.g. a tumor antigen, a viral antigen, a bacterial antigen, a fungal antigen, a self-antigen, an allergen or a graft-specific antigen);
- a CRISPR-Cas system;
- a prime-editing system; or
- a base-editor system.

In a particular embodiment, the gene of interest encoded by the DNA vector is a DNA encoding an antigen, more particularly a DNA encoding an antigen selected from the group consisting of tumor antigens, viral antigens, bacterial antigens, fungal antigens, self-antigens, allergens and graft-specific antigens, as defined below.

*C. acnes* Strains Comprising DNA Vectors and Engineered *C. acnes* Strains

The invention encompasses *C. acnes* comprising any of the DNA vectors of the invention. The invention further encompasses *C. acnes* produced by any of the methods of the invention. Thus, the invention encompasses *C. acnes* that have been modified following transduction of any of the DNA vectors of the invention by a phage-derived particle, whether retaining the DNA vector or subsequently having that DNA vector removed (i.e., cured) from *C. acnes*.

Thus, the invention encompasses *C. acnes* produced by a method comprising producing a phage-derived particle from a *C. acnes* producer cell containing a DNA vector of the invention; contacting these phage-derived particles with *C. acnes* receiver cells leading to transduction of the DNA vector into the *C. acnes* receiver cell and modification of the *C. acnes* receiver cell with a gene of interest carried by the vector (e.g., a CRISPR-Cas system) and/or an exogenous gene inserted into the *C. acnes* chromosome; selecting for the modification; and curing *C. acnes* of the vector.

The invention encompasses an engineered *C. acnes* that has been modified by a CRISPR-Cas system transduced by a phage or phage-derived particle carrying a vector of the invention.

The invention encompasses an engineered *C. acnes* that has been modified by transduction of DNA vector and subsequent insertion of an exogenous gene into the *C. acnes* chromosome.

The invention encompasses an engineered *C. acnes* that has been modified by transduction of DNA vector and subsequent deletion or mutation of an endogenous gene into the *C. acnes* chromosome or *C. acnes* endogenous plasmid.

The invention encompasses *C. acnes* produced by transduction of a DNA vector of the invention.

The invention encompasses an engineered *C. acnes* that has been modified by delivery of a plasmid, in particular by conjugation. In a particular embodiment, said plasmid comprises a CRISPR-Cas system. In another particular embodiment, said plasmid comprises an exogenous gene. In another particular embodiment, said plasmid enables the insertion of an exogenous gene into the *C. acnes* chromosome. In another particular embodiment, said plasmid enables the deletion or mutation of an endogenous gene into the *C. acnes* chromosome or *C. acnes* endogenous plasmid. In a particular embodiment, said plasmid comprises an origin of replication allowing replication in *C. acnes*, as defined above and/or an origin of transfer as defined above.

*Cutibacterium acnes*, previously named *Propionibacterium acnes*, has been historically classified in three major phylotypes based on recA and tly sequencing: IA, IB, II and III. These phylotypes have been further subdivided using different multi-locus sequence typing (MLST) schemes into IA1, IA2, IB, II and III. More recently, Fitz-Gibbon et al (Fitz-Gibbon, S. et al. (2013) *J Invest Dermatol* 133, 2152-2160) have introduced a new classification based on sequence diversity of 16S rRNA gene (ribotyping) as well as a refined classification of phylotypes: IA-1, IA-2, IB-1, IB-2, IB-3, IC, II, III. The present disclosure refers to this classification but concordance between this classification and others is well-known from the skilled person and can be obtained from the following review (1. Dréno, B. et al. (2018). *Journal of the European Academy of Dermatologyand Venereology* 32, 5-14). In a particular embodiment, *C. acnes* may thus be from a phylotype selected from the group consisting of phylotypes IA-1, IA-2, IB-1, IB-2, IB-3, IC, II and III.

By comparing whole genome sequences of strains isolated from acne and healthy volunteers, Fitz-Gibbon and colleagues could identify acne-associated strains (IA-2 and IB-1) and healthy-associated strains (II) in accordance with previous studies. More interestingly, they found specific loci (locus 1, locus 2 and locus 3) present in acne associated strains and absent of neutral and healthy strains. Similar loci were found in a subsequent metagenomic analysis confirming the association between the presence of these loci and acne vulgaris (Barnard, E. et al. (2016) *Scientific Reports* 6, srep39491).

The ability of specific strain phylotypes to induce immune response has been recently investigated (Yu et al. (2016) Journal of Investigative Dermatology 136:2221-2228). Yu et al. demonstrated that the different *C. acnes* phylotypes induced different cytokine profiles when incubated with peripheral blood mononuclear cells (PBMC). More particularly, they showed that acne-associated phylotypes IA-2 p+ (i.e. with a large plasmid associated with acne), IB-1, and IC induced high levels of inflammatory IFN-γ and IL-17 but low levels of IL-10, suggesting that these specific phylotypes could induce both Th1 and Th17 responses. They also showed that phylotypes IB-3, II and III induced lower levels of IL-17 (and of IFN-γ for phylotype III) but higher levels of IL-10, suggesting induction of Treg responses. They further showed that phylotypes IA-1, IA-2 p– (i.e. without the large plasmid associated with acne) and IB-2 induced lower levels of IFN-γ and IL-10 and higher levels of IL-17, suggesting induction of mainly Th17 responses.

Therefore, depending on the particular immune response that is desired when using the engineered *C. acnes* of the invention for a particular indication, the use of a given *C. acnes* phylotype or strain may be advantageous. Accordingly, in a particular embodiment, *C. acnes* is from a phylotype selected from the group consisting of phylotypes IA-2 p+, IB-1 and IC. In another embodiment, *C. acnes* is from a phylotype selected from the group consisting of phylotypes IA-1, IA-2 p– and IB-2. In still another embodiment, *C. acnes* is from a phylotype selected from the group consisting of phylotypes IB-3, II and III.

Furthermore, a previous study showed that it was possible, in *S. epidermidis*, to induce different T cell responses with different strains within the same species by engineering said strains (Chen et al. (2019) "Decoding commensal-host communication through genetic engineering of *Staphylococcus epidermidis*" bioRxiv https://doi.org/10.1101/664656).

Therefore, in a particular embodiment, the *C. acnes* is a strain inducing, or engineered to induce, a given T cell response. In a particular embodiment, more particularly when the *C. acnes* cell is intended to be used in the prevention and/or treatment of cancer, said *C. acnes* is a strain inducing, or engineered to induce, increased levels of IFN-γ and/or IL-17a. In a particular embodiment, more particularly when the *C. acnes* cell is intended to be used in the prevention and/or treatment of an infection, said *C. acnes* is a strain inducing, or engineered to induce, increased levels of IFN-γ and/or IL-17. In a particular embodiment, more particularly when the *C. acnes* cell is intended to be used in the prevention and/or treatment of an autoimmune disease, said *C. acnes* is a strain inducing, or engineered to induce, increased levels of IL-10. In a particular embodiment, more particularly when the *C. acnes* cell is intended to be used in the prevention and/or treatment of an allergy, such as asthma, said *C. acnes* is a strain inducing, or engineered to induce, increased levels of IFN-g and/or IL-10. In a particular embodiment, more particularly when the *C. acnes* cell is intended to be used in the prevention and/or treatment of a graft rejection, said *C. acnes* is a strain inducing, or engineered to induce, increased levels of IL-10.

*C. acnes* comprising a recombinant self-replicative DNA vector of the invention (or comprising a plasmid, in particular a conjugative plasmid as defined above) can be generated for the expression of molecules of interest and modulation of *C. acnes*-host interaction. The molecule of interest can be carried on a self-replicative DNA vector in the *C. acnes* (or on a plasmid, in particular a conjugative plasmid) or can be inserted into the chromosome of the *C. acnes* through the action of the self-replicative DNA vector (or of the plasmid, in particular the conjugative plasmid, as defined above).

In one embodiment, the DNA vector is used for *C. acnes* chromosome engineering.

In one embodiment, the DNA vector is used for *C. acnes* plasmid engineering.

In one embodiment, the DNA vector is used for *C. acnes* phage engineering.

In one embodiment, the DNA vector (or the plasmid, in particular the conjugative plasmid, as defined above) is used for the expression of molecules of interest and modulation of *C. acnes*-host interaction. In one embodiment, the DNA vector (or the plasmid, in particular the conjugative plasmid, as defined above) is used for the expression of transgenes in *C. acnes*. A transgene can be cloned into the recombinant autonomously-replicating DNA vector (or in the plasmid, in particular the conjugative plasmid) under the control of a given promoter (constitutive or inducible) and followed by a given terminator. The transfer of this vector into *C. acnes* allows the expression of the transgene. The transgene can be, for example, a CRISPR/Cas system or can encode a human protein, such as an interleukin. In one embodiment the DNA vector (or the plasmid, in particular the conjugative plasmid) encodes several transgenes under the control of a single promoter or under the control of different promoters. The promoters can be endogenous or exogenous, inducible or constitutive.

In one embodiment, the DNA vector (or the plasmid, in particular the conjugative plasmid) is used for the modification of *C. acnes* genome. In one embodiment, the transfer of the vector (or of the plasmid, in particular the conjugative plasmid) into *C. acnes* allows the expression of a CRISPR/Cas system that cleaves the *C. acnes* genome (plasmid or chromosome) at a specific site, leading to modification of the *C. acnes* genome. In one embodiment, the vector (or the plasmid, in particular the conjugative plasmid) further comprises a gene of interest and homology with the site of cleavage to facilitate integration of the gene of interest into the *C. acnes* genome.

Delivery of DNA Vectors into *C. acnes* Strains

In one embodiment, delivery of any DNA vector of the invention into *C. acnes* producer cell is performed by contacting *C. acnes* with any DNA vector of the invention.

In one embodiment, delivery of any DNA vector of the invention into *C. acnes* producer cell is performed by transfection (e.g., electroporation) into *C. acnes* cells, where it stably replicates. In one embodiment the DNA vector transfected is purified from dam(–) *E. coli* cells such as ET12567 and electroporated into *C. acnes* cells made competent at 24° C.

In one embodiment, delivery of any DNA vector of the invention into *C. acnes* producer cell is performed by transfection (e.g., electroporation) into *C. acnes* protoplasts. In one embodiment *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, delivery of any DNA vector of the invention into *C. acnes* producer cell is performed by mixing *C. acnes* protoplasts with the DNA vector. In one embodiment glass beads are added with the DNA vector and bead beating is performed to introduce the DNA into *C. acnes* protoplasts.

In one embodiment, delivery of DNA vectors of the invention into *C. acnes* is by transduction. In one embodiment, the DNA vector comprises one packaging signal of a *C. acnes* phage selected from the group consisting of the phages: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75) and is packaged into proteins expressed from the genome of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75), allowing transduction of the DNA vector into *C. acnes*.

In one embodiment, delivery of any DNA vector of the invention into *C. acnes* producer cell is by conjugation. In one embodiment, the DNA vector comprises an origin of transfer. In one embodiment, a donor bacterium, such as *E. coli*, is used to efficiently transfer the DNA vector into *C. acnes* recipient cells, where it stably replicates. In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_pTiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29); oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40) and oriT_pIP501 (typically of sequence SEQ ID NO: 41). In one embodiment, a donor bacterium, such as *E. coli*, carries a conjugative plasmid, a conjugative transposon or an integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501, and is used to efficiently transfer the DNA vector into *C. acnes* recipient cells. In one embodiment the DNA vector contains an origin of transfer and the associated relaxase of a conjugative plasmid, conjugative transposon or integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises the origin of transfer oriT_pMRC01 (typically of sequence SEQ ID NO: 1). In a preferred embodiment, the DNA vector comprises the origin of transfer oriT_RSF1010 (typically of sequence SEQ ID NO: 2). In a preferred embodiment, the DNA vector comprises the origin of transfer oriT_pRS01 (typically of sequence SEQ ID NO: 3). In a preferred embodiment, the DNA vector comprises the origin of transfer oriT_pMV158 (typically of sequence SEQ ID NO: 4). In a preferred embodiment, the DNA vector comprises the origin of transfer oriT_pTF1 (typically of sequence SEQ ID NO: 5). In a preferred embodiment, the DNA vector comprises the origin of transfer oriT_pSC101 (typically of sequence SEQ ID NO: 6). In a preferred embodiment, the DNA vector comprises the origin of transfer oriT_pBTK445 (typically of sequence SEQ ID NO: 7). In a preferred embodiment, the DNA vector comprises the origin of transfer oriT_pBBR1 (typically of sequence SEQ ID NO: 8). In a preferred embodiment, the DNA vector comprises the origin of transfer oriT_R721 (typically of sequence SEQ ID NO: 9). In a preferred embodiment, the DNA vector comprises the origin of transfer oriT_pRmeGR4a (typically of sequence SEQ ID NO: 10). In a preferred embodiment, the DNA vector comprises the origin of transfer oriT_ColE1 (typically of sequence SEQ ID NO: 11). In a preferred embodiment, the DNA vector comprises the origin of transfer oriT_pTiC58 (typically of sequence SEQ ID NO: 12). In a preferred embodiment, the DNA vector comprises the origin of transfer oriT_pMdT1 (typically of sequence SEQ ID NO: 13). In a preferred embodiment, the DNA vector comprises the origin of transfer oriT_R1 (typically of sequence SEQ ID NO: 14). In a preferred embodiment, the DNA vector comprises the origin of transfer oriT_Tn5520 (typically of sequence SEQ ID NO: 15). In a preferred embodiment, the DNA vector comprises the origin of transfer oriT_QKH54 (typically of sequence SEQ ID NO: 16). In a preferred embodiment, the DNA vector comprises the origin of transfer oriT_R64 (typically of sequence SEQ ID NO: 17). In a preferred embodiment, the DNA vector comprises the origin of transfer oriT_R751 (typically of sequence SEQ ID NO: 18). In a preferred embodiment, the DNA vector comprises the origin of transfer oriT_RP4 (typically of sequence SEQ ID NO: 19). In a preferred embodiment, the DNA vector comprises the origin of transfer oriT_pKL1 (typically of sequence SEQ ID NO: 20). In a preferred embodiment, the DNA vector comprises the origin of transfer oriT_RK2 (typically of sequence SEQ ID NO: 21). In a preferred embodiment, the DNA vector comprises the origin of transfer oriT_R1162 (typically of sequence SEQ ID NO: 22). In a preferred embodiment, the DNA vector comprises the origin of transfer oriT_Tn4555 (typically of sequence SEQ ID NO: 23). In a preferred embodiment, the DNA vector comprises the origin of transfer oriT_pHT (typically of sequence SEQ ID NO: 24). In a preferred embodiment, the DNA vector comprises the origin of transfer oriT_Tn4399 (typically of sequence SEQ ID NO: 25). In a preferred embodiment, the DNA vector comprises the origin of transfer oriT_Tn916 (typically of sequence SEQ ID NO: 26). In a preferred embodiment, the DNA vector comprises the origin of transfer oriT_pST12 (typically of sequence SEQ ID NO: 27). In a preferred embodiment, the DNA vector comprises the origin of transfer oriT_pCU1 (typically of sequence SEQ ID NO: 28). In a preferred embodiment, the DNA vector comprises the origin of transfer oriT_pSU233 (typically of sequence SEQ ID NO: 29). In a preferred embodiment, the DNA vector comprises the origin of transfer oriT_F (typically of sequence SEQ ID NO: 30). In a preferred embodiment, the DNA vector comprises the origin of transfer oriT_pMAB01 (typically of sequence SEQ ID NO: 31). In a preferred embodiment, the DNA vector comprises the origin of transfer oriT_R388 (typically of sequence SEQ ID NO: 32). In a preferred embodiment, the DNA vector comprises the origin of transfer oriT_pS7a (typically of sequence SEQ ID NO: 33). In a preferred embodiment, the DNA vector comprises the origin of transfer oriT_pS7b (typically of sequence SEQ ID NO: 34). In a preferred embodiment, the DNA vector comprises the origin of transfer oriT_R702 (typically of sequence SEQ ID NO: 35). In a preferred embodiment, the DNA vector comprises the origin of transfer oriT_pMUR274 (typically of sequence SEQ ID NO: 36). In a preferred embodiment, the DNA vector comprises the origin of transfer oriT_R100 (typically of sequence SEQ ID NO: 37). In a preferred embodiment, the DNA vector comprises the origin of transfer oriT_pVCR94deltaX (typically of sequence SEQ ID NO: 38). In a preferred embodiment, the DNA vector comprises the origin of transfer oriT_R46 (typically of sequence SEQ ID NO: 39). In a preferred embodiment, the DNA vector comprises the origin of transfer oriT_pGO1 (typically of sequence SEQ ID NO: 40). In a preferred embodiment, the DNA vector comprises the origin of transfer oriT_pIP501 (typically of sequence SEQ ID NO: 41).

In one embodiment, a donor bacterium is selected from the group consisting of: *Escherichia coli, Pseudomonas aeruginosa, Lactococcus lactis, Lactobacillus casei, Lactobacillus fermentum, Lactobacillus rhamnosus, Propionibacterium freudenreichii, Lactobacillus brevis, Staphylococcus epidermidis, Staphylococcus aureus, Cutibacterium granulosum, Cutibacterium humerusii, Enterococcus faecalis* and *Bacillus subtilis*, carrying a conjugative plasmid, a conjugative transposon or an integrative and conjugative element (ICE).

In one embodiment the conjugation is performed growing at high density the donor bacteria, such as *E. coli*, harboring the mobilizable DNA vector and the conjugative machinery (ICE, plasmid, conjugative transposon). Donor cells are pelleted by centrifugation, and washed to remove antibiotics added during growth to maintain mobilizable and conjugative DNA vectors. Donor cells are then mixed in presence of *C. acnes* cells. The mixture donor cells—*C. acnes* is spotted onto *Brucella agar* plates and allowed to mate at 37° C. under anaerobic conditions. After mating, cells are harvested from the mating plate, re-suspended in BHI broth and plated onto *Brucella agar* plates that are supplemented with:
  a compound killing donor cells but not *C. acnes*, or
  an antibiotic selecting the mobilizable DNA vector.

After several days of incubation, *C. acnes* colonies are streaked on *Brucella agar* plates supplemented with the appropriate selection and the presence of the conjugated plasmid is confirmed via specific PCRs. The identity of *C. acnes* as well as the absence of donor cells is also confirmed by PCR analyses.

In one embodiment the conjugation is performed according to the following protocol: 2 mL of overnight cultures of *E. coli* donor cells harboring a mobilizable DNA vector and a conjugative machinery (ICE, plasmid, conjugative transposon) is grown in LB broth and pelleted at 6,000×g for 1 min. Supernatants are discarded and pellets are washed with 500 μL of pre-sterilized LB medium, centrifuged again using the same conditions. Pellet is then re-suspended in 200 μL of exponentially growing (OD600=0.5) *C. acnes* receptor BHI culture concentrated 10×. The mixture *E. coli-C. acnes* is spotted (50 μL/spot) onto *Brucella agar* plates and allowed to mate at 37° C. under anaerobic conditions for 24 hours. After that time, cells are harvested from the mating plate, re-suspended in 300 μL of BHI broth and plated onto *Brucella agar* plates that had been supplemented with 50 μg/mL polymyxin B and 5 μg/mL erythromycin or 3.5 μg/mL chloramphenicol depending on the selection marker present in the mobilizable DNA vector. After 7 days, *C. acnes* cells that grow in the presence of selection are streaked on *Brucella agar* plates supplemented with the appropriate selection and the presence of the conjugated plasmid confirmed via specific PCRs. The identity of *C. acnes* as well as the absence of *E. coli* donor strain are also confirmed by PCR analyses.

Methods to Modify Endogenous *C. acnes* Plasmids

Naturally occurring *C. acnes* plasmids have been described[21,22] and some of them are able to be transferred from one *C. acnes* to another by conjugation[20]. Being able to modify such plasmids is of interest to study their effect notably their pro-inflammatory role in acne vulgaris or to use them for further genetic manipulation of *C. acnes*. The inventors have developed methods to modify *C. acnes* plasmids.

In one embodiment, the method comprises, in a first step, introducing into *C. acnes* a replicative vector comprising:
  a selection marker for *C. acnes* as defined above,
  an origin of replication for *C. acnes* as defined above,
  a phage packaging signal as defined above, and
  a template for homologous recombination in the *C. acnes* endogenous plasmid.

In one embodiment, the method comprises, in a first step, introducing in *C. acnes* a replicative vector comprising:
  a selection marker for *C. acnes* as defined above,
  an origin of replication for *C. acnes* as defined above,
  a phage packaging signal as defined above, and
  a CRISPR-Cas system
  a template for homologous recombination with the *C. acnes* endogenous plasmid.

Introduction can be achieved with electroporation, electroporation of protoplast, conjugation, chemical transformation or transduction. *C. acnes* recombinants are then preferably grown in presence of an antibiotic.

Recombinants are then typically infected with *C. acnes* phage to produce phage-derived particles carrying the DNA vectors.

Phage-derived particles are then typically mixed with *C. acnes* receiver cells containing an endogenous plasmid such as pIMPLE-HL096PA1. *C. acnes* transductants are then typically selected on the appropriate antibiotic.

In a second step, *C. acnes* transductants are grown in the presence of an antibiotic A to a high density to increase chances of a homologous recombination event occurring. Homologous recombination typically leads to introduction of a selection marker, giving resistance to an antibiotic B. In the dense culture, *C. acnes* strains carrying wild-type endogenous plasmid and recombinant endogenous plasmid carrying a resistance marker are typically present. The high-density culture is then preferably washed and typically put in the presence of a receiver *C. acnes* strain that is resistant to a third antibiotic C. Selection of transconjugant with antibiotics C and B typically leads to selection of receiver cells with the recombinant plasmid.

Other modifications enabled by the methods of the invention include the insertion of an *E. coli* replicon and an *E. coli* resistant marker on the plasmid allowing extraction of the plasmid from *C. acnes* and transformation and replication in *E. coli*.

Additionally, the plasmid carrying the template DNA for homologous recombination preferably allows the expression of genes that increase recombination rate.

The template for homologous recombination typically contains homology arms upstream and downstream recombination points. These homology arms are preferably 50, 100, 500, 1000 bp long or more.

*C. acnes* Genome Engineering and Engineered *C. acnes* Strains

The invention encompasses methods of *C. acnes* genome engineering and engineered *C. acnes* strains that have been engineered by any of the methods of the invention. An "engineered strain" is a strain that has been obtained by any of the methods of the invention to contain an alteration either found or not found in nature. For example, the engineered *C. acnes* strain can comprise any of the vectors or DNAs of the invention.

The invention encompasses methods for delivering DNA of interest into *C. acnes* strains by conjugation. The invention also encompasses methods for delivering DNA of interest into *C. acnes* strains via phage-derived particles. The invention encompasses methods to engineer the *C. acnes* chromosome with replicative and non-replicative vector methods.

In one embodiment, delivery of the DNA vector into *C. acnes* is by transduction. In one embodiment, the DNA vector comprises a phage packaging signal (cos) originating from *C. acnes* phages. In one embodiment, phage-derived particles containing the DNA vector can be generated and allow the DNA vector to be transduced into *C. acnes* cells.

In one embodiment, the invention encompasses replicative and non-replicative vector methods using a vector comprising at least a recombination template with one or two homology arms.

To engineer the *C. acnes* genome, the inventors have developed methods using replicative and non-replicative vectors.

Non-Replicative Vector Methods

In one embodiment, non replicative vector methods use a vector comprising at least:
a phage packaging signal, as defined above;
a selection marker for *C. acnes*, as defined above;
a recombination template with one or two homology arms;
an origin of replication allowing replication only in *Cutibacterium acnes* producer cell; and
optionally a counter selection marker such as SacB.

Non replicative vector methods use vectors that carry a *C. acnes* replicon that replicate only in a *C. acnes* producer cell but not in other *C. acnes* cells. Thus, such vectors are able to replicate in *C. acnes* producer cell, get packaged into phage capsid upon contacting with phage genome leading to a phage-derived particle, and get transduced by the phage-derived particle into *C. acnes* receiver cell where they do not replicate.

Figure 4A:
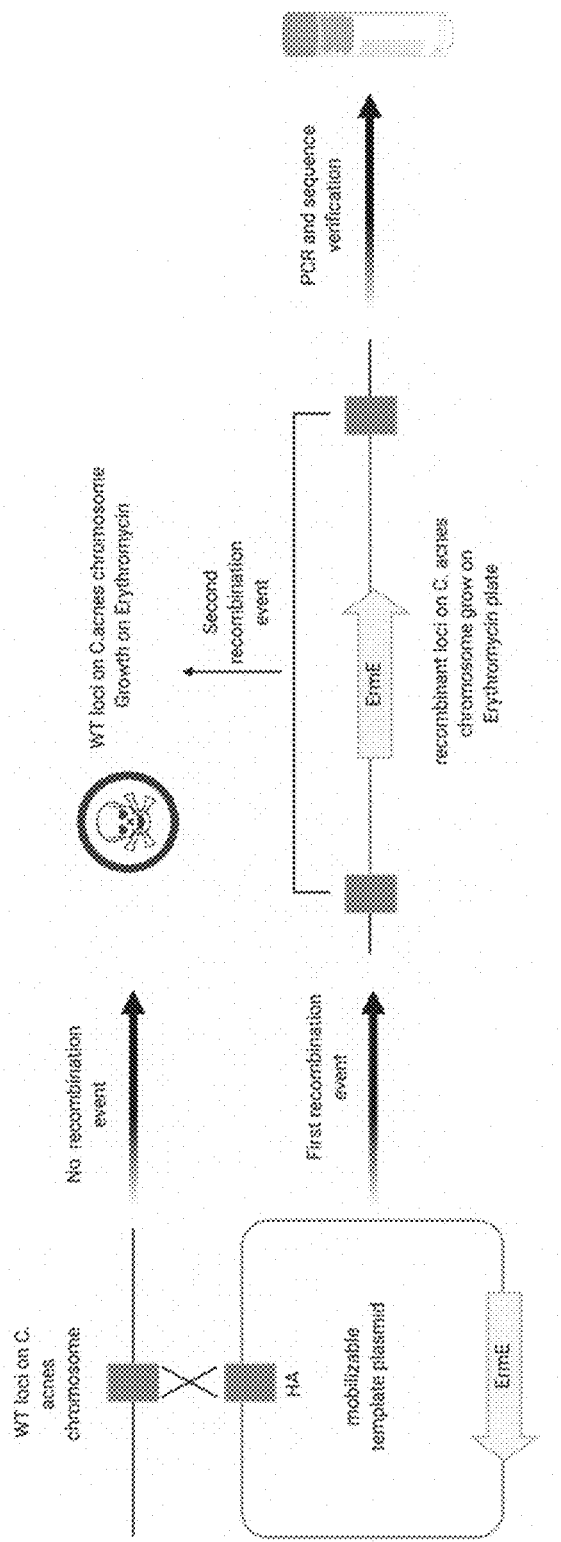
FIGS. 4A and 4B depict a method for *C. acnes* genome engineering using non-replicative vector carrying recombination template.
Figure 4B:
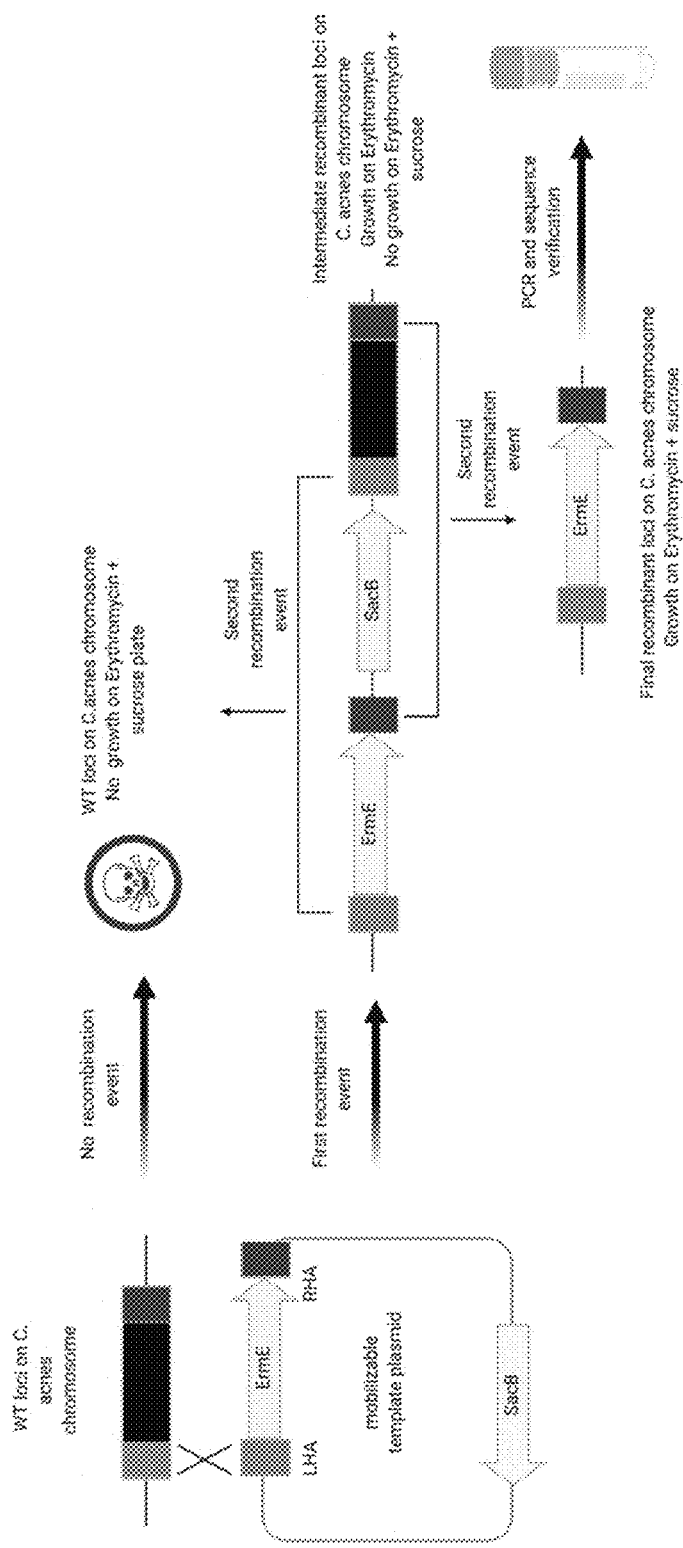

The methods comprise introducing into a *C. acnes* producer cell a plasmid containing a template for homologous DNA recombination inside the genome. The template can contain one (FIG. 4A) or two homologous regions (FIG. 4B) leading to homologous recombination.

In one embodiment, the method comprises a *C. acnes* producer cell, carrying a plasmid containing a template for homologous DNA recombination inside the chromosome where the homologous DNA is not present in the *C. acnes* producer cell, a phage packaging signal (cos) originating from *C. acnes* phages, a selection marker for *C. acnes*, as defined above, and an origin of replication for *C. acnes* producer cell but not replicating in *C. acnes* receiver cell. The template can contain one (FIG. 4A) or two homologous regions (FIG. 4B), leading to homologous recombination. The producer cell is typically infected by a *C. acnes* phage leading to production of phage-derived particles containing the DNA vector with homology arm(s). Phage-derived particles are preferably mixed with *C. acnes* receiver cells (e.g., ATCC 11828). Transductants can be selected on antibiotic plates, streaked on antibiotic plates and plasmid integration screened by PCR. Because the plasmid is not replicative in *C. acnes*, only recombinant cells that stably maintain the antibiotic marker are able to grow on antibiotic plates.

In the case where there are two homology arms present on the template DNA, a first recombination event (also called cross-over) typically leads to the full integration of the plasmid. This is typically followed by a second recombination event that removes the plasmid backbone and leads to either the modification of the chromosome or to the reconstitution of wild-type wt locus.

In one embodiment, the *C. acnes* producer cell carries a vector containing a left homology arm (LHA) and a right homology arm (RHA) flanking a *C. acnes* selection marker, for example, ermE (pEB_HR02). The two homology arms typically do not match the *C. acnes* producer cell chromosome. In one embodiment, the vector also contains a phage packaging signal (cos) originating from *C. acnes* phages, a selection marker for *C. acnes* and an origin of replication for *C. acnes* producer cell but not replicating in *C. acnes* receiver cell. In one embodiment the DNA vector also contains a *C. acnes* counter-selection marker, such as sacB, on the plasmid backbone allowing selection of the second recombination event. The *C. acnes* producer cell carrying pEB_HR02 is typically infected by a phage leading to production of phage-derived particles comprising pEB_HR02. The phage-derived particles are typically put in presence of *C. acnes* receiver cells (e.g., ATCC 11828). Transductants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence. In one embodiment the DNA vector contains only one homology arm (pEB_HR01). In one embodiment, both pEB_HR01 and pEB_HR02 phage-derived particles are applied on the skin and no antibiotic selection is applied.

In one embodiment, the *C. acnes* producer cell carries a plasmid (vector) containing a left homology arm (LHA) and a right homology arm (RHA) flanking *C. acnes* selection marker ErmE (pEB_HR02). The vector also preferably contains an *E. coli* origin of replication, an *E. coli* selection marker, an oriT and relaxase from a conjugative plasmid and a *C. acnes* counter-selection marker, such as sacB. pEB_HR02 can be transformed into an *E. coli* donor strain (e.g. EcOs2862). Transformants are typically selected, grown and mixed with *C. acnes* receiver cells (e.g., ATCC 11828). Transconjugants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence Replicative CRISPR-Cas System Selection Vector Methods The invention encompasses replicative vectors comprising an origin of replication for *C. acnes*.

In one embodiment, a replicative CRISPR-Cas selection vector method uses vector with at least:
- a phage packaging signal (cos) originating from *C. acnes* phages, as defined above;
- a selection marker for *C. acnes*, as defined above;
- an origin of replication for *C. acnes*;
- a recombination template with two homology arms; and
- a CRISPR-Cas system for expression in *C. acnes*.

In one embodiment, a replicative CRISPR-Cas selection vector method uses a vector with at least:
- a selection marker for *E. coli*, as defined above;
- an origin of replication for *E. coli*;
- a selection marker for *C. acnes*, as defined above;
- a recombination template with two homology arms;
- an origin of replication for *C. acnes*; and
- a CRISPR-Cas system that is expressed in *C. acnes*.

Thus, such vectors are able to replicate in *E. coli* and are able to replicate in *C. acnes*. They also carry a CRISPR-Cas system able to induce double stranded breaks at the wild-type loci where recombination is wanted, leading to death of *C. acnes* receiver cell.

Figure 5:
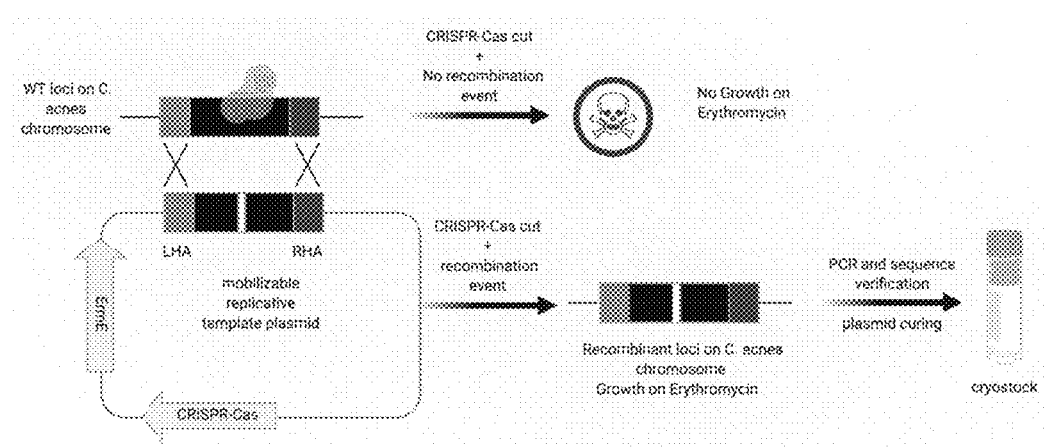
FIG. 5 depicts a method for *C. acnes* genome engineering using replicative CRISPR-Cas system selection vector carrying recombination template. A replicative CRISPR-Cas system selection vector containing a template for homologous DNA recombination with the chromosome is conjugated into *C. acnes*. The template contains two homology arms (LHA and RHA) leading to homologous recombination in *C. acnes* chromosome and removal of the target sequence of the CRISPR-Cas system. Thus only recombinants *C. acnes* are able to grow in the presence of erythromycin when selected for the presence of the vector expressing CRISPR-Cas system.

In one embodiment, the method comprises the use of a *C. acnes* producer cell, for example strain ATCC 6919, carrying a replicative CRISPR-Cas system selection vector containing a template for homologous DNA recombination inside the chromosome and a phage packaging signal (cos) originating from *C. acnes* phages. In one embodiment, the template contains two homologous regions (FIG. 5), leading to homologous recombination. The producer cell preferably does not contain the wild-type loci targeted by the CRISPR-Cas system. The *C. acnes* producer cell is typically infected by a *C. acnes* phage leading to production of phage-derived particles carrying the DNA vector. Phage-derived particles are typically put in contact with *C. acnes* receiver cell. After transduction into *C. acnes* receiver cell, cells that have recombined with the DNA template vector are not targeted by the CRISPR-Cas system because, for example, they do not have the associated PAM sequence anymore. Plating on antibiotic-containing media, e.g., erythromycin plates, typically ensures that the cells that survive have been transduced and still carry the DNA vector (e.g. plasmid) expressing the CRISPR-Cas system. Single colonies are typically streaked on antibiotic-containing media, e.g., erythromycin plates, and recombinant loci are typically confirmed by PCR and sequencing.

In one embodiment, a step of plasmid curing is performed to eliminate the plasmid.

In one embodiment, the *C. acnes* producer cell contains the DNA target of the CRISPR-Cas system but the CRISPR-Cas system is not expressed in the *C. acnes* producer cell but is expressed in *C. acnes* receiver cell. More preferably the CRISPR-Cas system is repressed in the *C. acnes* producer cell but not in *C. acnes* receiver cell.

Such methods can be used for scarless editing such as substitution, deletion or insertion because there is no need to introduce a selection marker to select for recombinants, the selection being done by CRISPR-Cas killing.

Self-Targeted Replicative Vector Methods

In one embodiment, the invention encompasses self-targeted replicative vector methods. In one embodiment, the invention encompasses the use of a CRISPR-Cas system to program cutting of the DNA vector (e.g. plasmid) in one or several target sequences, leading to linearization of the recombination template that have been shown to increase recombination efficiency[9]. To be able to clone a self-targeting vector, an inducible CRISPR-Cas system can be used, for example, using an inducible promoter upstream of the gene encoding the Cas nuclease. By combining this inducible promoter with a riboswitch, even tighter inhibition of CRISPR-Cas system expression can be assured. Another strategy to generate self-targeting CRISPR-Cas system relies on promoters that are repressed in the *C. acnes* producer cell and not in *C. acnes* receiver cell. In this way, the CRISPR-Cas system will only be active once transduced in a *C. acnes* receiver cell.

Figure 6A:
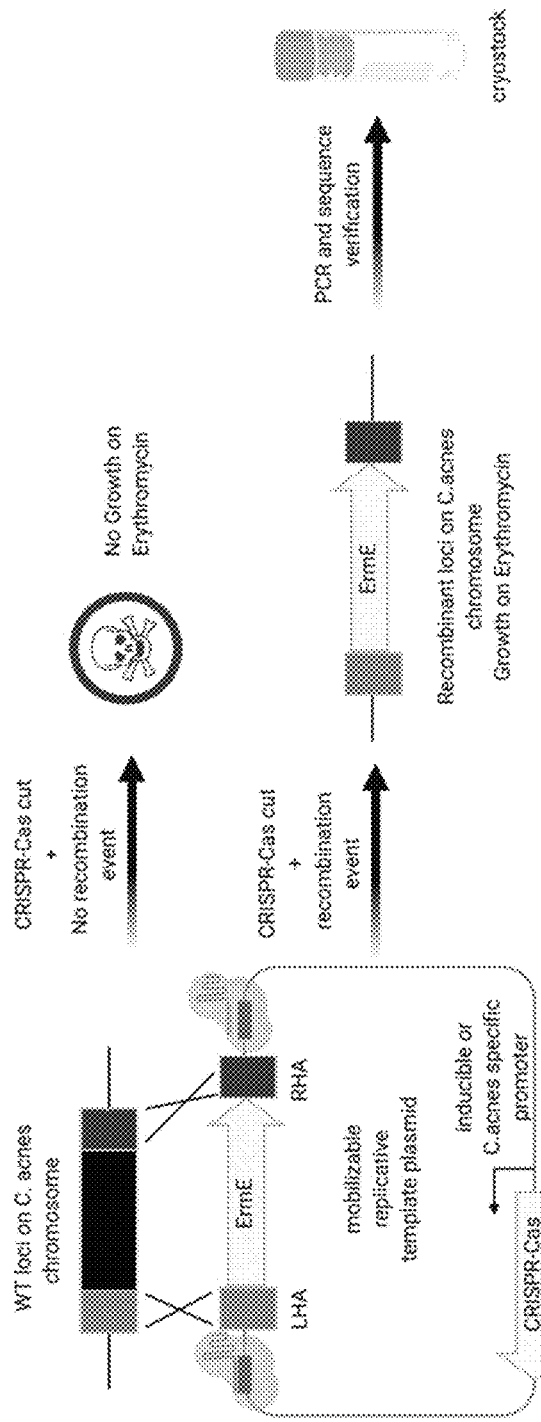
FIGS. 6A and 6B depict a method for *C. acnes* genome engineering using self-targeted replicative vector carrying CRISPR-Cas system and recombination template.
Figure 6B:
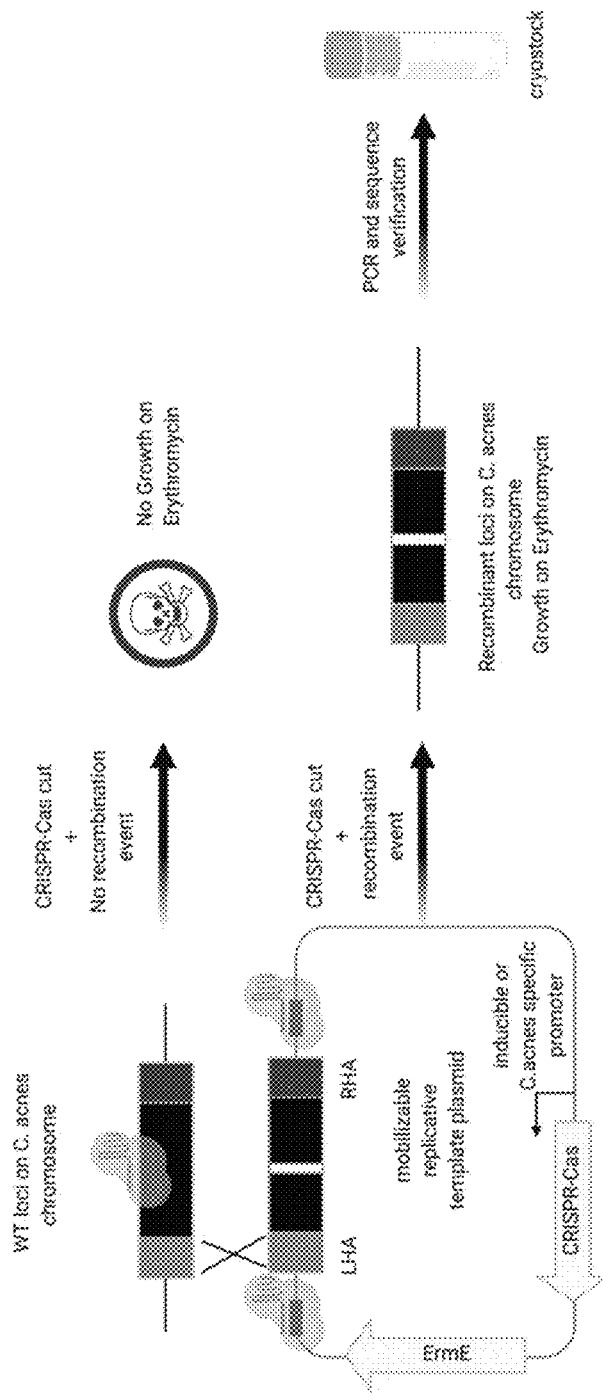
Figure 7:
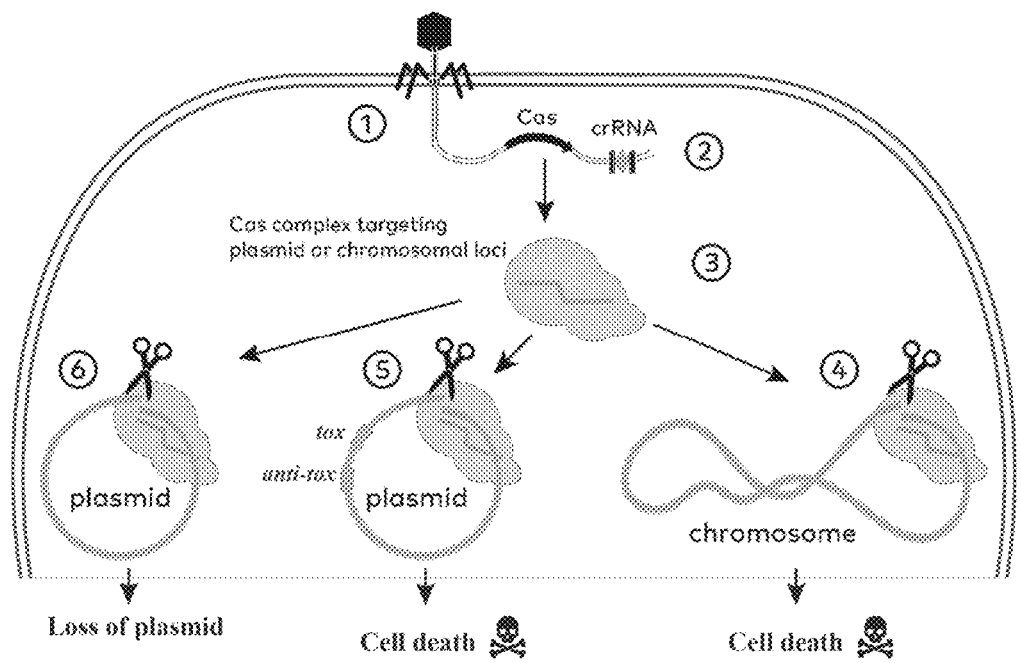
FIG. 7 depicts a method for sequence specific killing or plasmid curing using phage-derived particles. *C. acnes* phage-derived particles bind a *C. acnes* cell (1) allowing injection of a DNA vector encoding a CRISPR-Cas system (2). The CRISPR-Cas system is expressed (3) and cuts the chromosome (4) and/or a plasmid (5 and 6) in a sequence specific manner. Cutting of the chromosome leads to cell death (4) whereas cutting of the plasmid leads to either the plasmid loss (6) or cell death if the plasmid encodes a toxin-antitoxin system (5).

Using such strategy, for example, a gene replacement can be performed using an antibiotic marker flanked by homology arms (FIG. 6A) or by performing scarless recombination using the CRISPR-Cas system ability to kill the bacteria when targeting *C. acnes* chromosome (FIG. 6B).

After introduction and selection of the DNA vector (e.g. plasmid), a homologous event typically takes place leading to removal of a PAM sequence.

Additionally, the DNA vector (e.g. plasmid) carrying the template DNA for homologous recombination typically allows expression of genes increasing recombination rate.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the invention encompasses replicative vector methods using a vector with at least:
- a phage packaging signal (cos) originating from C. acnes phages, as defined above;
- a selection marker for C. acnes, as defined above;
- an origin of replication for C. acnes, as defined above; and
- a CRISPR-Cas system for expression in C. acnes.

In one embodiment, vectors carry a CRISPR-Cas system able to induce double stranded break leading to death of most C. acnes receiver cells except C. acnes receiver cells that by spontaneous mutation or recombination do not carry anymore the CRISPR-Cas system target sequence.

Expression of Proteins by Engineered C. acnes Strains

The invention encompasses the expression of proteins by engineered C. acnes strains. By incorporating an expression cassette into the DNA vector, the protein can be expressed by the transduced C. acnes. The promoter within the expression cassette can be inducible or constitutive, allowing inducible or constitutive expression of proteins by engineered C. acnes strains. Expression of several proteins can be performed as single transcriptional unit (operon) or as separated transcriptional units. In a particular embodiment, said protein is an antigen, such as a tumor antigen, a viral antigen, a bacterial antigen, a fungal antigen, a self-antigen, an allergen or a graft-specific antigen, as defined below.

C. acnes Phage

The invention encompasses the C. acnes phage and related engineered phages, methods for producing these phages, and methods for using these phages to transduce C. acnes.

Phage-Derived Particles in C. acnes

The invention encompasses phage-derived particles comprising any DNA vector of the invention and the methods for the production of these phage-derived particles.

In one embodiment a C. acnes strain carrying any DNA vector of the invention is contacted with a C. acnes phage leading to introduction of the phage genome into the C. acnes strain and the expression of the phage proteins necessary for the assembly of a phage capsid and the packaging of the DNA vector inside the phage capsid.

In one embodiment a C. acnes strain carrying any DNA vector comprising: a selection marker for C. acnes as defined above, a C. acnes phage packaging signal (cos site) as defined above, and an origin of replication for C. acnes as defined above, is contacted with a C. acnes phage leading to introduction of the phage genome into the C. acnes strain and the expression of the phage proteins necessary for the assembly of a phage capsid and the packaging of the DNA vector inside the phage capsid.

In one embodiment, the phage genome is a wild type phage genome.

In one embodiment, the C. acnes phage is PAC7 (typically of sequence SEQ ID NO: 68).

In one embodiment, the phage genome is an engineered phage genome.

The phage-derived particles can be purified by methods known in the art. The invention encompasses purified phage-derived particles comprising a DNA vector of the invention. In one embodiment, the purified phage-derived particles are in an isolated composition or pharmaceutical composition. The composition can comprise at least $10^4$, $10^5$, $10^6$, $10^7$, $10^8$, $10^9$, $10^{10}$, $10^{11}$, $10^{12}$, $10^{13}$, $10^{14}$, or more purified phage-derived particles.

Sequence Specific Killing of C. acnes by Phage-Derived Particles

In one embodiment, the invention comprises specific killing of C. acnes by phage-derived particles carrying CRISPR-Cas system.

Phage-derived particles carrying a vector (e.g. plasmid) encoding CRISPR-Cas system have been recently used to perform in situ sequence specific killing of bacteria[10,11]. The inventors have developed a method for the production of such phage-derived particles to target C. acnes, which is encompassed by the invention.

In said method, a C. acnes producer strain comprising a DNA vector of the invention is contacted with a C. acnes phage, such as PAC7 (typically of sequence SEQ ID NO: 68) to produce a high titer phage suspension.

In one embodiment, the C. acnes comprises a DNA vector comprising:
- a selection marker for C. acnes, as defined above,
- a C. acnes phage packaging signal (cos site), as defined above,
- an origin of replication for C. acnes, as defined above, and
- a CRISPR-Cas system targeting a specific C. acnes receiver cell chromosomal locus (pTarget).

High titer C. acnes phage suspensions are typically added to C. acnes. The suspensions typically contain a mix of wild-type phages and phage-derived particles carrying the plasmid. Contacting of C. acnes cells carrying the locus targeted by the pTarget CRISPR-Cas system is typically performed with phage-derived particles containing pTarget. This can be performed in vivo or in vitro. Sequence specific killing is typically observed for lysate containing phage-derived particles comprising pTarget.

In one embodiment, the phage-derived particles comprising the pTarget vector (e.g. plasmid) are not mixed with phage and allow sequence specific killing of cells carrying the DNA targeted by the CRISPR-Cas system.

C. acnes Plasmid Curing

Naturally occurring C. acnes plasmids have been described and some of them have been associated with pro-inflammatory phenotypes[15,23] and acne vulgaris[16-18]. Being able to cure such plasmids is of interest to study their effect, notably, their pro-inflammatory role in acne vulgaris. The inventors have developed a method to cure C. acnes plasmid.

In a first step, a C. acnes producer cell carrying the DNA vector comprising:
- a C. acnes phage packaging signal as defined above,
- optionally a selection marker for C. acnes, as defined above,
- an origin of replication that allows replication only in C. acnes producer cell, as defined above, and
- a transgene, such as a CRISPR-Cas system targeting a genetic sequence of an endogenous plasmid to be cured in a target C. acnes receiver cell, the sequence being preferably in a conserved region such as the origin of replication or in loci associated with acne vulgaris, is infected by a C. acnes phage leading to production of phage-derived particles carrying the DNA vector.

Contacting C. acnes phage-derived particles with C. acnes receiver cell carrying an endogenous plasmid to be cured, such as pIMPLE-HL096PA1 is performed. This can be performed in vivo or in vitro.

In some embodiments, C. acnes transductants can be selected on the appropriate antibiotic. Single colonies are typically streaked on plates with media containing the antibiotic and the presence of the plasmid is typically screened by PCR. Single colonies where no positive PCR for the plasmid pIMPLE-HL096PA1 is obtained, are then cured from the vector (e.g. plasmid) comprising the CRISPR-Cas system, and typically cryostocked.

Treatment Methods

The invention encompasses methods to treat a *C. acnes* related disorder or disease.

The invention encompasses the use of engineered *C. acnes* strains for the treatment and/or prevention of a wide range of skin diseases and disorders.

The invention encompasses methods to treat a decrease in sebum production, follicular hyperkeratinization, colonization of skin bacteria, and inflammation using engineered *C. acnes* strains as defined above.

The invention encompasses the use of engineered *C. acnes* as defined above in cosmetics and other compositions.

In one embodiment, the invention encompasses expression of therapeutic molecules by engineered *C. acnes*.

In one embodiment, the invention encompasses expression of non-therapeutic molecules by engineered *C. acnes*.

*Cutibacterium acnes* is one of the most prevalent and abundant bacteria on human skin, where it can be found both on the skin surface (stratum corneum) and in the hair follicle[12]. Inside the hair follicle, it is in direct contact with a large diversity of living cells such as keratinocytes, stem cells, sebaceous cells and immune cells. This is not the case on the stratum corneum, where it is mostly in contact with the dead corneocyte[13]. Thus, it appears interesting to use *C. acnes* as a bacterial chassis for the production and delivery of therapeutic molecules in situ inside and outside the hair follicle.

Phage-derived particles and/or bacteria producing them can be delivered to the skin by dermal or other appropriate administration method to a subject.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with an engineered *C. acnes* bacteria according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of engineered *C. acnes* bacteria according to the invention, can be adjusted by the man skilled in the art according to the type and severity of the disease, disorder and/or infection (e.g. depending on the bacteria species involved in the disease, disorder and/or infection and its localization in the patient's or subject's body), and to the patient or subject, in particular its age, weight, sex, and general physical condition.

Particularly, the amount of engineered *C. acnes* bacteria according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

Preferably, total amount of an engineered *C. acnes* bacteria according to the invention, for each administration is comprised between $10^4$ and $10^{15}$ bacteria.

The invention encompasses plasmids for the expression of toxins such as nuclease, more preferably CRISPR-Cas systems to kill transduced *C. acnes* population.

The invention encompasses plasmids for the expression of CRISPR-Cas systems where the CRISPR-Cas systems is targeted towards sequences present only in specific strains and not present in others allowing strain specific killing among the *C. acnes* population.

The invention encompasses modifications of *C. acnes* chromosome or *C. acnes* endogenous plasmid. Modifications such as deletion, substitution and/or insertion leading to alteration in the *C. acnes*-host relation are for example contemplated.

The invention encompasses vectors, e.g. plasmids, for the expression of therapeutic molecules containing one or several genes involved in the production of the therapeutic molecule.

In the case where the therapeutic molecule is not freely diffusing from *C. acnes* cells, such as in the case of a therapeutic protein, a fusion with a signal peptide allowing secretion or export on the cell membrane or wall of *C. acnes* cells is preferably encoded on the vector, e.g. plasmid. Examples of secretion systems or signal peptides include: TAT, SEC and type VII/WXG100 secretion systems. More specifically, the signal peptide can be extracted from proteins selected from the group consisting of the proteins PPA0532 (typically referenced as Q6AAD1 in the UniprotKB database as of Nov. 4, 2020); PPA0533 (typically referenced as Q6AAD0 in the UniprotKB database as of Nov. 4, 2020); PPA0534 (typically referenced as Q6AAC9 in the UniprotKB database as of Nov. 4, 2020); PPA0598 (typically referenced as Q6AA63 in the UniprotKB database as of Nov. 4, 2020); PPA0644 (typically referenced as Q6AA16 in the UniprotKB database as of Nov. 4, 2020); PPA0687 (typically referenced as Q6A9X2 in the UniprotKB database as of Nov. 4, 2020); PPA0721 (typically referenced as Q6A9T8 in the UniprotKB database as of Nov. 4, 2020); PPA0816 (typically referenced as Q6A9J4 in the UniprotKB database as of Nov. 4, 2020); PPA1310 (typically referenced as Q6A856 in the UniprotKB database as of Nov. 4, 2020); PPA1498 (typically referenced as Q6A7M0 in the UniprotKB database as of Nov. 4, 2020); PPA1662 (typically referenced as Q6A771 in the UniprotKB database as of Nov. 4, 2020); PPA1715 (typically referenced as Q6A720 in the UniprotKB database as of Nov. 4, 2020); PPA1939 (typically referenced as Q6A6F6 in the UniprotKB database as of Nov. 4, 2020); PPA2097 (typically referenced as Q6A608 in the UniprotKB database as of Nov. 4, 2020); PPA2105 (typically referenced as Q6A601 in the UniprotKB database as of Nov. 4, 2020); PPA2106 (typically referenced as Q6A600 in the UniprotKB database as of Nov. 4, 2020); PPA2142 (typically referenced as Q6A5W4 in the UniprotKB database as of Nov. 4, 2020); PPA2164

(typically referenced as Q6A5U3 in the UniprotKB database as of Nov. 4, 2020); PPA2175 (typically referenced as Q6A5T2 in the UniprotKB database as of Nov. 4, 2020), PPA2152 (typically referenced as Q6A5V4 in the UniprotKB database as of Nov. 4, 2020); PPA1340 (typically referenced as Q6A826 in the UniprotKB database as of Nov. 4, 2020) and PPA2239 (typically referenced as Q6A5M0 in the UniprotKB database as of Nov. 4, 2020).

In the case where secretion is not wanted or functional, a lysing module can be added to the vector, e.g. plasmid, in order to lyse the cell and release the therapeutic molecule.

In a particular embodiment, said therapeutic molecule may be displayed on the cell membrane or wall of *C. acnes* cells. To be displayed, a protein of interest typically requires a N-terminal secretion signal peptide such as the ones described above as well as a C-terminal LPXTG motif allowing the class F sortase from *C. acnes* (Girolamo, S. D. et al. *Biochem J* 476, 665-682 (2019)) to covalently link the protein of interest to the cell wall. Additionally a PT rich region might be integrated upstream of the LPXTG motif. Alternatively a more classical cell wall sorting sequence (CWSS) combining a LPxTG motif followed by hydrophobic amino acids and a positively charged C-terminus can be used.

In order to control expression of the therapeutic molecule, one or several of the genes, as an operon or as single isolated genes, can be put under the control of an inducible system, such as an inducible promoter, a riboswitch, a RNA-based induction method or a combination thereof. Several promoters of several transcriptional strengths might be tested and combined with different RBS strengths to optimize for in situ production of the therapeutic molecule. An RBS library approach might be used to select the best RBS variant for in vitro or in situ expression.

Examples of therapeutic molecules include but are not limited to antibodies, antibody-based drugs, Fc fusion proteins, anticoagulants, blood factors, bone morphogenetic proteins, engineered protein scaffolds, enzymes, growth factors, hormones, interferons, interleukins, and thrombolytics. Other examples include those that bind non-covalently to target (e.g., monoclonal antibodies), those that affect covalent bonds (e.g., enzymes), and those that exert activity without specific interactions (e.g., serum albumin).

Also contemplated herein are therapeutic molecules (e.g., recombinant therapeutic proteins) used to treat, for example, cancers, immune disorders, infections and/or other diseases. Engineered proteins, including bispecific mAbs and multi-specific fusion proteins, and proteins with optimized pharmacokinetics are also contemplated by the present disclosure.

In some embodiments, the therapeutic proteins is Etanercept, Bevacizumab, Rituximab, Adalimumab, Infliximab, Trastuzumab, Insulin glargine, Epoetin alfa, Pegfilgrastim, Ranibizumab, Darbepoetin alfa, Interferon beta-Ia, Interferon beta-Ia. Insulin aspart, Rhu insulin, Octocog alfa, Insulin lispro, Cetuximab, Peginterferon alfa-2a, Interferon beta-Ib, Eptacog alfa, Insulin aspart, OnabotulinumtoxinA, Epoetin beta, Rec antihemophilic factor, Filgrastin, Insulin detemir, Natalizumab, Insulin (humulin) or Palivizumab.

Examples of antibodies, antibody fragments, and/or Fc fusion proteins that may be expressed in the context of the present disclosure include, without limitation, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anifrolumab, Anrukinzumab, Apolizumab, Arcitumomab, Aselizumab, Atinumab, Atlizumab (or tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab (or tremelimumab), Tildrakizumab, Tigatuzumab, TNX-, Tocilizumab (or atlizumab), Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

Other examples of Fc fusion proteins that may be expressed in the context of the present disclosure include, without limitation, Etanercept, Alefacept, Abatacept, Rilonacept, Romiplostim, Belatacept and Aflibercept.

Examples of anticoagulants and/or blood factors that may be expressed in the context of the present disclosure include, without limitation, Protein C, Protein S, and antithrombin, Factors I-VIII, prothrombinase, prothrombin, thrombin von Willebrand Factor (vWF), fibrinogen, fibrin and fibrinopeptides.

Examples of bone morphogenetic proteins (BMPs) that may be expressed in the context of the present disclosure include, without limitation, BMP1-BMP7, BMP8a, BMP8b, BMP 10, and BMP15.

Examples of enzymes that may be expressed in the context of the present disclosure include, without limitation, any of the enzymes assigned an Enzyme Commission Number (EC) number (e.g., EC1-EC6) by the International Union of Biochemistry and Molecular Biology (IUBMB) (Webb, Edwin C. Enzyme nomenclature 1992: recommendations of the Nomenclature Committee of the International Union of Biochemistry and Molecular Biology on the nomenclature and classification of enzymes. San Diego: Published for the International Union of Biochemistry and Molecular Biology by Academic Press. ISBN 0-12-227164-5 (1992), incorporated by reference herein). Other examples include: styrene monooxygenase (StyAB), toluene dioxygenase (TODC1C2AB), luciferase and lactase. In some embodiments, the enzyme is toluene dioxygenase. In some embodiments, the enzyme is styrene monoxygenase.

Examples of growth factors that may be expressed in the context of the present disclosure include, without limitation, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-a), Transforming growth factor beta (TGF-P), Tumor necrosis factor-alpha (TNF-), Vascular endothelial growth factor (VEGF), placental growth factor (P1GF), Foetal Bovine Somatotrophin (FBS) and IL-1-IL7.

Examples of peptide hormones that may be expressed in the context of the present disclosure include, without limitation, Amylin (or Islet Amyloid Polypeptide), Antimullerian hormone (or Miillerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Brain natriuretic peptide, Calcitonin, Cholecystokinin, Corticotropin-releasing hormone, Enkephalin, Endothelin, Erythropoietin, Follicle-stimulating hormone, Galanin, Gastrin, Ghrelin, Glucagon, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Lipotropin, Luteinizing hormone, Melanocyte stimulating hormone, Motilin, Orexin, Oxytocin, Pancreatic polypeptide, Parathyroid hormone, Prolactin, Prolactin releasing hormone, Relaxin, Renin, Secretin, Somatostatin, Thrombopoietin, Thyroid-stimulating hormone (or thyrotropin), and Thyrotropin-releasing hormone.

Examples of interferons (IFNs) that may be expressed in the context of the present disclosure include, without limitation, IFN-α, IFN-β, IFN-ω and IFN-γ.

Examples of interleukins that may be expressed in the context of the present disclosure include, without limitation, interleukin 1-17. In some embodiments, the interleukin is Interleukin-4, Interleukin-6, Interleukin-10, Interleukin-11 or Interleukin-13.

Other examples of therapeutic proteins that may be expressed in the context of the invention present disclosure include, without limitation, Insulin (blood glucose regulator), Pramlintide acetate (glucose control), Growth hormone GH (growth failure), Pegvisoman (growth hormone receptor antagonist), Mecasermin (IGFI, growth failure), Factor VIII (coagulation factor), Factor IX (coagulation factor, Protein C concentrate (anti-coagulation), al-proteinase inhibitor (anti-trypsin inhibitor), Erythropoietin (stimulates erythropoiesis), Filgrastim (granulocyte colony-stimulating factor, G-CSF; stimulates neutrophil proliferation), Sargramostim[36, 37] (granulocytemacrophage colony-stimulating factor, GM-CSF), Oprelvekin (interleukin II, IL11), Human follicle-stimulating hormone (FSH), Human chorionic gonadotropin (HCG), Lutropin-a (human luteinizing hormone), Interleukin 2 (IL2), Interleukin-1 Receptor Agonist, Denileukin diftitox (fusion of IL2 and Diphtheria toxin), Interferon alfacon 1 (consensus interferon), Interferon-2a (IFNa2a), Interferon-2b (IFNa2b), Interferon-n3 (IFNan3), Interferon-pia (rIFN-β), Interferon-β Ib (rIFN-β), Interferon-yIb (IFNy, Salmon calcitonin (32-amino acid linear polypeptide hormone), Teriparatide (part of human parathyroid hormone 1-34 residues), Exenatide (Incretin mimetic with actions similar to glucagon-like peptide 1), Octreotide (octapeptide that mimics natural somatostatin), Dibotermin-a (recombinant human bone morphogenic protein 2), Recombinant human bone morphogenic protein 7, Histrelin acetate (gonadotropin-releasing hormone; GnRH), Palifermin (Keratinocyte growth factor, KGF), Becaplermin (platelet-derived growth factor, PDGF), Nesiritide (recombinant human B-type natriuretic peptide), Lepirudin (recombinant variant of hirudin, another variant is Bivalirudin), Anakinra (interleukin 1 (IL1) receptor antagonist), Enfuviritide (an HIV-1 gp41-derived peptide), β-Glucocerebrosidase (hydrolyzes to glucose and ceramide), Alglucosidase-a (degrades glycogen), Laronidase (digests glycosaminoglycans within lysosomes), Idursulfase (cleaves O-sulfate preventing GAGs accumulation), Galsulfase (cleave terminal sulphate from GAGs), Agalsidase-β (human a-galactosidase A, hydrolyzes glycosphingolipids), Lactase (digest lactose), Pancreatic enzymes (lipase, amylase, protease; digest food), Adenosine deaminase (metabolizes adenosine), Tissue plasminogen activator (tPA, serine protease involved in the breakdown of blood clots), Factor Vila (serine protease, causes blood to clot), Drotrecogin-a (serine protease, human activated protein C), Trypsin (serine protease, hydrolyzes proteins), *Botulinum* toxin type A (protease, inactivates SNAP-25 which is involved in synaptic vesicle fusion), *Botulinum* toxin type B (protease that inactivates SNAP-25 which is involved in synaptic vesicle fusion), Collagenase (endopeptidase, digest native collagen), Human deoxyribonuclease I (endonuclease, DNase I, cleaves DNA), Hyaluronidase (hydrolyzes hyaluronan), Papain (cysteine protease, hydrolyzes proteins), L-Asparaginase (catalyzes the conversion of L-asparagine to aspartic acid and ammonia), Rasburicase (urate oxidase, catalyzes the conversion of uric acid to allantoin), Streptokinase (Anistreplase is anisoylated plasminogen streptokinase activator complex (APSAC)), and Antithrombin III (serine protease inhibitor).

Other examples of therapeutic proteins that may be expressed in the context of the present disclosure include antigens, as defined below.

The invention further encompasses engineered *C. acnes* comprising vectors (e.g. plasmids) for the expression of antigens, such as a tumor antigen, a viral antigen, a bacterial antigen, a fungal antigen, a self-antigen, an allergen or a graft-specific antigen.

As used herein, an "antigen" refers to a molecule containing one or more epitopes (e.g., linear, conformational or both) that elicit an immunological response. The antigen may be of any type. In particular, it can be a protein, a polypeptide or a peptide, a carbohydrate, a lipid, a nucleic acid, such as DNA or RNA. In a particular embodiment, it is a protein, a polypeptide or a peptide. As intended herein, "protein" will be understood to encompass protein, polypeptide and peptide. Furthermore, for purposes of the present invention, an "antigen" encompasses a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

In a particular embodiment, said antigen induces the activation or enhancement of an immune response, in particular specific to said antigen. In an alternative embodiment, said antigen results in tolerization or suppression of an immune response, in particular towards said antigen.

In a particular embodiment, said antigen decreases the subject inflammatory response.

In a particular embodiment, said antigen is a tumor antigen.

By "tumor antigen" is meant herein an antigenic substance produced in tumor cells. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen.

Tumor antigens include, but are not limited to, (a) polypeptide-containing tumor antigens, including polypeptides (which can range, for example, from about 8 to about 20 amino acids in length, although lengths outside this range are also common), lipopolypeptides and glycoproteins, and (b) saccharide-containing tumor antigens, including polysaccharides, mucins, gangliosides, glycolipids and glycoproteins. Moreover, tumor antigens can be (a) full length molecules associated with cancer cells, (b) homologs and modified forms of the same, including molecules with deleted, added and/or substituted portions, and (c) fragments of the same. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CD 4 (associated with, e.g., melanoma), MUM 1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkin's lymphoma), BCR-abl (associated with, e.g., chronic myelogenous leukemia), triosephosphate isomerase, IA 0205, CDC-27, and LDLR-FUT, (c) overexpressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), SA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-I/Melan A, gpIOO, MC1R, melanocyte-stimulating hormone receptor, tyrosinase, tyrosinase related protein-1/TRPI and tyrosinase related protein-2/TRP2 (associated with, e.g., melanoma), (e) prostate associated antigens such as PAP, PSA, PSMA, PSH-P1, PSM-P1, PSM-P2 (associated with e.g., prostate cancer), (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins may be coupled to a carrier protein (e.g., MUC-1 may be coupled to LH); (ii) lipopolypeptides (e.g., MUC-1 linked to a lipid moiety); (iii) polysaccharides (e.g., Globo H synthetic hexasaccharide), which may be coupled to a carrier protein (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pI80erbB-3, c-met, mn-23H I, TAG-72-4, CA 19-9, CA 72-4, CAM 17.1, NuMa, K-ras, p 16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV 18, NB/70K, NY-CO-1, RCAS1, SDCCAG16, TA-90 (Mac-2 binding protein\cyclophilin C-associated protein), TAAL6, TAG72, TLP, TPS, and the like.

In another embodiment, said antigen is a viral antigen.

By "viral antigen" is meant herein a protein encoded by a viral genome.

In certain embodiments, viral antigens preferably include epitopes which are exposed on the surface of the virus during at least one stage of its life cycle. Viral antigens are preferably conserved across multiple serotypes or isolates. Viral antigens suitable for use in the context of the invention include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (MI), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In other embodiments, the Paramyxovirus is Nipahvirus or Henipavirus and the antigens are selected from one or more of the following proteins: Fusion (F) protein, Glycoprotein (G) protein, Matrix (M) protein, Nucleocapsid (N) protein, Large (L) protein and Phosphoprotein (P).

Poxviridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses.

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus. Rhinovirus: Viral antigens include, but are not limited to, those derived from rhinovirus. In certain embodiments, the rhinovirus antigens are selected from one or more of the following Capsid proteins: VP0, VP1, VP2, VP2 and VP4.

Heparnavirus: Viral antigens include, but are not limited to, those derived from a Heparnavirus, such as, by way of example only, Hepatitis A virus (HAV).

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3.

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E.

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe).

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the non-structural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity.

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS).

Caliciviridae; Viral antigens include, but are not limited to, those derived from Caliciviridae, such as Norwalk virus, and Norwalk-like Viruses, such as Hawaii Virus and Snow Mountain Virus.

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J. K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: HIVIIIb, HIVSF2, HIVLAV, HIVLAI, HIVMN, HIV-1CM235, HIV-1US4, HIV-1 SF162, HIV-1TV1, HIV-1MJ4. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins λ1, λ2, λ3, μ1, μ2, σ1, σ2, or σ3, or nonstructural proteins σNS, μNS, or ols. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2.

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (α), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp65/IE1 (Reap et al., Vaccine (2007) 25:7441-7449).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

In another embodiment, said antigen is a bacterial antigen.

Examples of bacterial antigens suitable for use in the context of the invention include, but are not limited to, proteins, polysaccharides and lipopolysaccharides, which are derived from a bacteria. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis*: *N. meningitidis* antigens include, but are not limited to, proteins, saccharides (including a polysaccharide, or lipooligosaccharide), derived from *N. meningitidis* serogroup such as A, C, W135, Y, X or B. A useful combination of *N. meningitidis* protein antigens includes one, two or three of a NHBA, a fHbp, and/or a NadA immunogen.

*Streptococcus pneumoniae*: *Streptococcus pneumoniae* antigens include, but are not limited to, a saccharide (including a polysaccharide or an oligosaccharide) and/or protein from *Streptococcus pneumoniae*. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. A vaccine or immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. Nos. 6,699,703, 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm. (2006) 74:2453-2456, Hoskins et al., J. Bacteriol. (2001) 183:5709-5717, Adamou et al., Infect. Immun. (2001) 69(2):949-958, Briles et al., J. Infect. Dis. (2000) 182:1694-1701, Talkington et al., Microb. Pathog. (1996) 21(1):17-22, Bethe et al., FEMS Microbiol. Lett. (2001) 205(1):99-104, Brown et al., Infect. Immun. (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Spl28, SplOI, Spl30, Spl25, Spl33, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (SfbI), Streptococcal heme-associated protein (Shp), and Streptolysin S (SagA).

*Moraxella catarrhalis*: *Moraxella* antigens include, but are not limited to, antigens identified in WO 02/18595 and WO 99/58562, outer membrane protein antigens (HMW-OMP), C-antigen, and/or LPS.

*Bordetella pertussis*: pertussis antigens include, but are not limited to, pertussis toxoid (PT) and filamentous haemagglutinin (FHA) from *B. pertussis*, optionally also combination with pertactin and/or agglutinogens 2 and 3.

*Burkholderia*: *Burkholderia* antigens include, but are not limited to *Burkholderia mallei*, *Burkholderia pseudomallei* and *Burkholderia cepacia*.

*Staphylococcus aureus*: *S. aureus* antigens include, but are not limited to, a polysaccharide and/or protein from *S. aureus*. *S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis*: *S. epidermidis* antigens include, but are not limited to, slime-associated antigen (SAA).

*Clostridium tetani* (*tetanus*): tetanus antigens include, but are not limited to, tetanus toxoid (TT).

*Clostridium perfringens*: Antigens include, but are not limited to, Epsilon toxin from *Clostridium perfringens*.

*Clostridium botulinum* (Botulism): Botulism antigens include, but are not limited to, those derived from *C. botulinum*.

*Corynebacterium diphtheriae* (Diphtheria): Diphtheria antigens include, but are not limited to, diphtheria toxin, preferably detoxified, such as CRM 197. In certain embodiments, the diphtheria toxoids are used as carrier proteins.

*Haemophilus influenzae* B (Hib): Hib antigens include, but are not limited to, a Hib saccharide antigen. The Hib antigens may be conjugated.

*Pseudomonas aeruginosa: Pseudomonas* antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Brucella*: Bacterial antigens derived from *Brucella*, including but not limited to, *B. abortus, B. canis, B. melitensis, B. neotomae, B. ovis, B. suis* and *B. pinnipediae.*

*Francisella*: Bacterial antigens derived from *Francisella*, including but not limited to, *F. novicida, F. philomiragia* and *F. tularensis.*

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae*: gonorrhoeae antigens include, but are not limited to, Por (or porin) protein, such as PorB (see Zhu et al., Vaccine (2004) 22:660-669), a transferrin binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis: Chlamydia trachomatis* antigens include, but are not limited to, antigens derived from serotypes A, B, Ba and C (agents of trachoma, a cause of blindness), serotypes L1, L2 & L3 (associated with Lymphogranuloma venereum), and serotypes, D-K. In certain embodiments, *Chlamydia trachomatis* antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori: H. pylori* antigens include, but are not limited to, CagA, VacA, NAP, HopX, HopY and/or urease antigen.

*Staphylococcus saprophyticus*: Antigens include, but are not limited to, the 160 kDa hemagglutinin of *S. saprophyticus* antigen.

*Yersinia enterocolitica*: Antigens include, but are not limited to, LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orfl767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (*anthrax*): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein), VIsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to *tetanus* toxoid.

Other bacterial antigens used in the context of the invention include, but are not limited to, capsular antigens, polysaccharide antigens, or protein antigens of any of the above. In certain embodiments, the bacterial antigens used in the context of the invention are derived from gram-negative bacteria, while in other embodiments they are derived from gram-positive bacteria. In certain embodiments, the bacterial antigens used in the context of the invention are derived from aerobic bacteria, while in other embodiments they are derived from anaerobic bacteria.

In another embodiment, said antigen is a fungal antigen.

Examples of fungal antigens used in the context of the invention include, but are not limited to, those derived from one or more of the fungi set forth below.

Fungal antigens may be derived from Dermatophytes, including: *Epidermophyton floccosum, Microsporum audouini, Microsporum canis, Microsporum distortum, Microsporum equinum, Microsporum gypsum, Micrspo-*

*rum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleinii, Trichophyton tonsurans, Trichophyton verrucosum, T. verrucosum* var. *album,* var. *discoides,* var. *ochraceum, Trichophyton violaceum,* and/or *Trichophyton faviforme.*

Fungal antigens may also be derived from *Aspergillus fumigatus, Aspergillus flavus, Aspergillus niger, Aspergillus nidulans, Aspergillus terreus, Aspergillus sydowii, Aspergillus flavarus, Aspergillus glaucus, Blastoschizomyces capitatus, Candida albicans, Candida enolase, Candida tropicalis, Candida glabrata, Candida krusei, Candida parapsilosis, Candida stellatoidea, Candida krusei, Candida parakwsei, Candida lusitaniae, Candida pseudotropicalis, Candida guilliermondii, Cladosporium carrionii, Coccidioides immitis, Blastomyces dermatitidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microspiridium* spp., *Nosema* spp., *Pleistophora* spp., *Trachipleistophora* spp., *Vittaforma* spp *Paracoccidioides brasiliensis, Pneumocystis carinii, Pythium insidiosum, Pityrosporum ovale, Saccharomyces cerevisiae, Saccharomyces boulardii, Saccharomyces pombe, Scedosporium apiospermum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monilinia* spp, *Rhizoctonia* spp, *Paecilomyces* spp, *Pithomyces* spp, and *Cladosporium* spp.

For example, the fungal antigen may elicit an immune response against a *Candida* fungus such as *C. albicans*.

In another embodiment, said antigen is a self-antigen.

In the context of the invention, the term "self-antigen" refers to an immunogenic antigen or epitope which is native to the subject and which may be involved in the pathogenesis of an autoimmune disease.

In some embodiments, the self-antigen is a central nervous system (CNS) antigen. In some embodiments, the self-antigen is a multiple sclerosis-associated antigen, a diabetes mellitus-associated antigen, a rheumatoid arthritis associated antigen, a myocarditis associated self-antigen, or a thyroiditis associated antigen.

Exemplary self-antigens are disclosed, for example, in US Patent Application Publication 2016/0022788, which is incorporated herein by reference in its entirety.

In some embodiments, the self-antigen is a multiple sclerosis-associated antigen. In some embodiments, the self-antigen is an antigenic peptide of or derived from myelin oligodendrocyte glycoprotein (MOG), myelin basic protein (MBP), myelin associated glycoprotein (MAG), alphaB-crystallin, S100beta, or proteolipid protein (PLP).

In some embodiments, the self-antigen is a diabetes mellitus-associated antigen. In some embodiments, the self-antigen is selected from insulin, chromogranin A, glutamic acid decarboxylase (GAD1; GAD67), glutamate decarboxylase 2 (GAD2; GAD65) and islet-specific glucose-6-phosphatase catalytic subunit-related protein and combinations thereof. Antigenic fragments and antigenic derivatives of these antigens are also contemplated. In some embodiments, the antigen can be proinsulin.

In some embodiments, the self-antigen is a rheumatoid arthritis associated antigen. In some embodiments, the rheumatoid arthritis associated self-antigen can be the peptide (Q/R)(K/R)RAA. In some embodiments, the arthritis associated self-antigen can be type II collagen or a fragment thereof.

In some embodiments, the self-antigen is a myocarditis associated self-antigen. In some embodiments, the myocarditis associated self-antigen is myosin or an antigenic fragment or antigenic derivative. In some embodiments, the antigen can be a peptide contained in human myosin. In some embodiments, the antigen can be a peptide contained within a-myosin.

In some embodiments, the self-antigen is a thyroiditis associated antigen. In some embodiments, the self-antigen is selected from thyroid peroxidase (TPO), thyroglobulin, or Pendrin.

In another embodiment, said antigen is an allergen.

An "allergen" is defined as a substance, usually a protein, which elicits the production of IgE antibodies in predisposed individuals. Similar definitions are presented in the following references: Clin. Exp. Allergy, No. 26, pp. 494-516 (1996); Mol. Biol. of Allergy and Immunology, ed. R. Bush, Immunology and Allergy Clinics of North American Series (August 1996). In a particular embodiment, the antigen is a protein allergen, i.e. any amino acid chain likely to trigger an allergic response, including short peptides of about 6 to 20 amino acids, polypeptides, or full proteins.

Non limitative examples of allergens include pollen allergens (such as tree-, herb, weed-, and grass pollen allergens), insect allergens (such as inhalant, saliva and venom allergens, e.g., cockroach and midges allergens, hymenoptera venom allergens), mite allergens, animal hair and dandruff allergens (from e.g. dog, cat, horse, rat, mouse etc.), and food allergens.

For instance, the protein allergen may be selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*; a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

Examples of various known protein allergens derived from some of the above-identified genus include: *Betula* (*verrucosa*) Bet v I; Bet v II; *Blomia* Blo t I; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (*artemiisfolia*) Amb a I.1; Amb a I.2; Amb a I.3; Amb a I.4; Amb a II; *Lollium* (*perenne*) Lol p I; Lot p II; Lol p III; Lot p IV; Lol p IX (Lol p V or Lol p Ib); *Cryptomeria* (*japonica*) Cry j I; Cry j II; *Canis* (*familiaris*) Can f I; Can f II; *Juniperus* (*sabinoides* or *virginiana*) Jun s I; Jun v I; *Juniperus* (*ashei*) Jun a I; Jun a II; *Dactylis* (*glomerata*) Dac g I; Dac g V; *Poa* (*pretensis*) Poa p I; Phl p I; Phl p V; Phl p VI and *Sorghum* (*halepensis*) Sor h I.

Food allergens may originate from milk and milk products, eggs, legumes (peanuts and soy), tree nuts, cereals (such as wheat), brassicaceae (such as mustard), crustaceans, fish, and mollusks. In particular, food allergens may be ovalbumin or gluten.

The invention also encompasses vaccine and/or immunogenic and/or immunotherapeutic compositions comprising a DNA vector, as defined above, comprising a nucleic acid encoding an antigen, such as a tumor antigen, a viral antigen, a bacterial antigen, a fungal antigen, a self-antigen, an allergen or a graft-specific antigen, as defined above, or an engineered *C. acnes* comprising said DNA vector; and optionally an adjuvant.

Any conventional or exploratory, synthetic or biological adjuvant for vaccination, including heat-labile enterotoxin (LT), cholera-toxin (CT), cholera toxin B subunit (CTB), polymerised liposomes, mutant toxins, probiotic bacteria, oligonucleotides, RNA, siRNA, DNA, lipids can be used.

The invention also encompasses methods to prevent and/or a treat cancer in a subject in need thereof, comprising administering to said subject a therapeutically or prophylactically efficient amount of a DNA vector comprising a nucleic acid encoding a tumor antigen, as defined above, or of an engineered *C. acnes* comprising said DNA vector. The invention also concerns a DNA vector comprising a nucleic acid encoding a tumor antigen, as defined above, or an engineered *C. acnes* comprising said DNA vector for use in a method to prevent and/or treat cancer in a subject.

As used herein, the term "cancer" means a type of hyperproliferative disease that includes a malignancy characterized by deregulated or uncontrolled cell growth. Cancers of virtually every tissue are known. Examples of cancer include, but are not limited to, carcinoma, lymphoma, blastema, sarcoma, and leukemia or lymphoid malignancies. More particular examples of such cancers are noted below and include squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer, uterine carcinoma, salivary gland carcinoma, kidney or renal cancer, prostate cancer, thyroid cancer, hepatic carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

The term "cancer," is encompassed within the scope of the broader term "abnormal cellular proliferation", which can also be referred to as "excessive cellular proliferation or "cellular proliferative disease". Examples of diseases associated abnormal cellular proliferation include metastatic tumors, malignant tumors, benign tumors, cancers, precancers, hyperplasias, warts, and polyps, as well as non-cancerous conditions such as benign melanomas, benign chondroma, benign prostatic hyperplasia, moles, dysplastic nevi, dysplasia, hyperplasias, and other cellular growths occurring within the epidermal layers. Classes of precancers include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (high grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma.

The invention also encompasses methods to prevent and/or treat a viral infection in a subject in need thereof, comprising administering to said subject a therapeutically or prophylactically efficient amount of a DNA vector comprising a nucleic acid encoding a viral antigen, as defined above, or of an engineered *C. acnes* comprising said DNA vector. The invention also concerns a DNA vector comprising a nucleic acid encoding a viral antigen, as defined above, or an engineered *C. acnes* comprising said DNA vector for use in a method to prevent and/or treat a viral infection in a subject.

In said embodiment, said antigen preferably induces the activation or enhancement of an immune response, in particular specific to said antigen.

Particular examples of viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C. Additional examples of viral infections include infections caused by Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arenaviridae (hemorrhagic fever viruses); Reoviridae (e.g., reoviruses, orbiviruses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e., Hepatitis C)); Norwalk and related viruses, and astroviruses.

The invention also encompasses methods to prevent and/or treat a bacterial infection in a subject in need thereof, comprising administering to said subject a therapeutically or prophylactically efficient amount of a DNA vector comprising a nucleic acid encoding a bacterial antigen, as defined above, or of an engineered *C. acnes* comprising said DNA vector. The invention also concerns a DNA vector comprising a nucleic acid encoding a bacterial antigen, as defined above, or an engineered *C. acnes* comprising said DNA vector for use in a method to prevent and/or treat a bacterial infection in a subject.

In said embodiment, said antigen preferably induces the activation or enhancement of an immune response, in particular specific to said antigen.

Examples of bacterial infections include, but are not limited to, infections caused by *Helicobacter pyloris, Borrelia burgdorferi, Legionella pneumophila, Mycobacteria* sp. (such as *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira*, and *Actinomyces israelii*.

The invention also encompasses methods to prevent and/or treat a fungal infection in a subject in need thereof, comprising administering to said subject a therapeutically or prophylactically efficient amount of a DNA vector comprising a nucleic acid encoding a fungal antigen, as defined above, or of an engineered *C. acnes* comprising said DNA vector. The invention also concerns a DNA vector comprising a nucleic acid encoding a fungal antigen, as defined above, or an engineered *C. acnes* comprising said DNA vector for use in a method to prevent and/or treat a fungal infection in a subject.

In said embodiment, said antigen preferably induces the activation or enhancement of an immune response, in particular specific to said antigen.

Examples of fungal infections include but are not limited to: aspergillosis; thrush (caused by *Candida albicans*); cryptococcosis (caused by *Cryptococcus*); and histoplasmosis. Thus, examples of fungal infections include, but are not limited to, infections caused by *Cryptococcus neoformans, Histoplasma capsulatum, Coccidioides immitis, Blastomyces dermatitidis, Chlamydia trachomatis*, or *Candida albicans*.

The invention also encompasses methods to prevent and/or treat an auto-immune disease in a subject in need thereof, comprising administering to said subject a therapeutically or prophylactically efficient amount of a DNA vector comprising a nucleic acid encoding a self-antigen, as defined above, or of an engineered *C. acnes* comprising said DNA vector.

The invention also concerns a DNA vector comprising a nucleic acid encoding a self-antigen, as defined above, or an engineered *C. acnes* comprising said DNA vector for use in a method to prevent and/or treat an auto-immune disease in a subject.

In said embodiment, said antigen preferably results in tolerization or suppression of an immune response, in particular towards said antigen.

Autoimmune diseases include, but are not limited to, multiple sclerosis, rheumatoid arthritis, myasthenia gravis, psoriasis, systemic lupus erythematosus, autoimmune thyroiditis (Hashimoto's thyroiditis), Graves' disease, inflammatory bowel disease, autoimmune uveoretinitis, myocarditis, polymyositis, and certain types of diabetes, including Type 1 diabetes.

The invention also encompasses methods to prevent and/or treat allergy, such as asthma in a subject in need thereof, comprising administering to said subject a therapeutically or prophylactically efficient amount of a DNA vector comprising a nucleic acid encoding an allergen, as defined above, or of an engineered *C. acnes* comprising said DNA vector. The invention also concerns a DNA vector comprising a nucleic acid encoding an allergen, as defined above, or an engineered *C. acnes* comprising said DNA vector for use in a method to prevent and/or treat allergy, such as asthma in a subject.

In said embodiment, said antigen preferably results in tolerization or suppression of an immune response, in particular towards said antigen.

In the context of the disclosure allergy relates to asthma or to the allergies due to the above-defined allergens.

The invention also encompasses methods to prevent and/or treat graft rejection in a subject in need thereof, comprising administering to said subject a therapeutically or prophylactically efficient amount of a DNA vector comprising a nucleic acid encoding a graft-specific antigen, as defined above, or of an engineered *C. acnes* comprising said DNA vector. The invention also concerns a DNA vector comprising a nucleic acid encoding a graft-specific antigen, as defined above, or an engineered *C. acnes* comprising said DNA vector for use in a method to prevent and/or treat graft rejection in a subject.

In said embodiment, said antigen preferably results in tolerization or suppression of an immune response, in particular towards said antigen.

Unless defined otherwise, all technical and scientific terms used herein have the same meaning as commonly understood by one of ordinary skill in the art to which this invention belongs.

All publications mentioned herein are incorporated herein by reference. It is understood that the present disclosure supersedes any disclosure of an incorporated publication to the extent there is a contradiction.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

Definitions

«Delivery Vehicle»

As used herein, the term «delivery vehicle» refers to any mean that allows the transfer of a payload into a bacterium.

There are several types of delivery vehicle encompassed by the present invention including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention.

The delivery vehicle can refer to a bacteriophage derived scaffold and can be obtained from a natural, evolved or engineered capsid.

In some embodiment, the delivery vehicle is the payload as bacteria are naturally competent to take up a payload from the environment on their own.

«Conjugation»

Conjugation is a process by which a donor bacteria actively transfers DNA to a recipient bacteria. DNA transfer involves recognition of an origin of transfer (oriT) by a protein known as the relaxase which nicks and covalently binds to the oriT DNA. The relaxase and single stranded DNA are then typically injected into a recipient cell through a type IV secretion system. During conjugation of a plasmid or ICE (Integrative and Conjugative Elements), transfer of the relaxase is coupled with rolling circle replication of the plasmid or ICE. Once in the recipient, the relaxase will recircularize the transferred strand at the oriT. Smillie et al, Microbiology and Molecular Biology Rev, 2010, P. 434-452.

Examples of conjugative plasmids are F, R388, RP4, RK2, R6K. Plasmids of the following groups are frequently conjugative and carry a type IV secretion system: IncA, IncB/O (Ind O), IncC, IncD, IncE, IncFI, IncF2, IncG, IncHM, IncHl2, Inch, Incl2, IncJ, IncK, IncL/M, IncN, IncP, IncQI, IncQ2, IncR, IncS, IncT, IncU, IncV, IncW, IncXI, IncX2, IncY, IncZ, ColE1, ColE2, ColE3, p15A, pSC101, IncP-2, IncP-5, IncP-7, IncP-8, IncP-9, Ind, Inc4, Inc7, Inc8, Inc9, Inc11, Inc13, Ind 4 or Ind 8.

List of type IV secretion systems can be found in public databases such as AtlasT4SS.

Conjugation is not limited to plasmids but can also occur from the chromosome of bacteria when an oriT is present. This can happen naturally through the recombination of conjugative plasmids in the chromosome or artificially by introducing an oriT at a position of interest in the chromosome. A particular class of conjugative elements are known as Integrative and Conjugative Elements (ICEs). These are not maintained in a circular plasmidic form but integrate in the host chromosome. Upon transfer, the ICE excises from the chromosome and is then transferred in a manner akin to a conjugative plasmid. Once in a recipient cell, the ICE integrates in the recipient's chromosome. Lists of ICE elements can be found in public databases such as ICEberg.

ICEs or plasmids which carry both an origin of transfer and the type IV secretion system genes are commonly referred to as mobile elements, while ICEs or plasmids that only carry the oriT can be referred to as mobilizable plasmids. Mobilizable elements can only be transferred from the donor cell to a recipient cell if a type IV secretion system is expressed in trans, either by another plasmid or from the chromosome of the host cell.

«Payload»

As used herein, the term «payload» refers to any nucleic acid sequence or amino acid sequence, or a combination of both (such as, without limitation, peptide nucleic acid or peptide-oligonucleotide conjugate) transferred into a bacterium with a delivery vehicle.

The term «payload» may also refer to a plasmid, a vector or a cargo.

The payload can be a phagemid or phasmid obtained from natural, evolved or engineered bacteriophage genome. The payload can also be composed only in part of phagemid or phasmid obtained from natural, evolved or engineered bacteriophage genome.

In some embodiment, the payload is the delivery vehicle as bacteria are naturally competent to take up a payload from the environment on their own.

«Nucleic Acid»

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

«Vector»

As used herein, the term "vector" refers to any construct of sequences that are capable of expression of a polypeptide in a given host cell. If a vector is used then the choice of vector is dependent upon the method that will be used to transform host bacteria as is well known to those skilled in the art. Vectors can include, without limitation, plasmid vectors and recombinant phage vectors, or any other vector known in that art suitable for delivering a polypeptide of the invention to target bacteria. The skilled artisan is well aware of the genetic elements that must be present on the vector in order to successfully transform, select and propagate host cells comprising any of the isolated nucleotides or nucleic acid sequences of the invention.

«Phagemid»

As used herein the term "phagemid" or "phasmid" are equivalent and refer to a recombinant DNA vector comprising at least one sequence of a bacteriophage genome. A phagemid of the disclosure comprises a phage packaging site and optionally an origin of replication (ori), in particular a bacterial and/or phage origin of replication. In one embodiment, the phagemid of the disclosure does not comprise a bacterial origin of replication and thus cannot replicate by itself once injected into a bacterium. Alternatively, the phagemid comprises a plasmid origin of replication, in particular a bacterial and/or phage origin of replication.

«Packaged Phagemid»

As used herein, the term "packaged phagemid" or "phage-derived particle" refers to a phagemid which is encapsidated in a bacteriophage scaffold, bacterial virus particle or capsid. Particularly, it refers to a bacteriophage scaffold, bacterial virus particle or capsid devoid of a bacteriophage genome. The packaged phagemid or phage-derived particle may be produced with a helper phage strategy, well known from the man skilled in the art. The helper phage comprises all the genes coding for the structural and functional proteins that are indispensable for the phagemid according to the invention to be encapsidated. The packaged phagemid or phage-derived particle may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

«Peptide»

As used herein, the term "peptide" refers both to a short chain of at least 2 amino acids linked between each other and to a part of, a subset of, or a fragment of a protein which part, subset or fragment being not expressed independently from the rest of the protein. In some instances, a peptide is a protein. In some other instances, a peptide is not a protein and peptide only refers to a part, a subset or a fragment of a protein. Preferably, the peptide is from 4, 5, 6, 7, 8, 9, 10, 11, 12, 13, 14, 15 amino acids to 4, 5, 6, 7, 8, 9, 10, 11, 12, 13, 14, 15, 20, 25, 30, 40, 50, 100, 200 amino acids in size.

"Engineered"

[01] As used herein, the term "engineered" means that the bacterial cells, phages, phage-derived particles, phagemids or vectors of the invention have been modified by molecular biology techniques. As will be understood by the skilled person, engineering of bacterial cells, phages, phage-derived particles, phagemids or vectors implies a deliberate action to introduce or modify a nucleic acid sequence and does not cover introduction or modification of a nucleic acid sequence through natural evolution of the bacterial cell, phage, phage-derived particle, phagemid or vector.

"Percent of Identity"

[02] As used herein, the percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

[03] The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

CRISPR-Cas System

A CRISPR-Cas system refers to DNA encoding two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al., Science 2012). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR-Cas system includes two main classes depending on the nuclease mechanism of action:
   Class 1 is made of multi-subunit effector complexes and includes type I, III and IV
   Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, VI-C, VI-D)

The sequence of interest according to the present invention comprises a nucleic acid sequence encoding Cas protein. A variety of CRISPR enzymes are available for use as a sequence of interest on the plasmid according to the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type III CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Fonfara et al., 2014; Koonin et al., 2017). Examples of Cas9 proteins useful in the present invention include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al., 2017). Examples of Cpf1 (Cas12a) proteins useful in the present invention include, but are not limited to, Cpf1 (Cas12a) proteins of *Acidaminococcus* sp, *Lachnospiraceae bacteriu* and *Francisella novicida*.

The sequence encoding Cas13a (the entire protein or a fragment thereof) as used in the context of the invention can be obtained from any known Cas13a (C2c2) protein (Abudayyeh et al., 2017). Examples of Cas13a (C2c2) proteins useful in the present invention include, but are not limited to, Cas13a (C2c2) proteins of *Leptotrichia wadei* (LwaCas13a).

The sequence encoding Cas13d (the entire protein or a fragment thereof) as used in the context of the invention can be obtained from any known Cas13d protein (Yan et al., 2018). Examples of Cas13d proteins useful in the present invention include, but are not limited to, Cas13d proteins of *Eubacterium siraeum* and *Ruminococcus* sp.

In a particular embodiment, the nucleic sequence of interest is a CRISPR/Cas9 system for the reduction of gene expression or inactivation a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host.

In one embodiment, the CRISPR-Cas system is used to target and inactivate a virulence factor. A virulence factor can be any substance produced by a pathogen that alter host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, scavenging factors and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (*Anthrax* toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be *Cutibacterium acnes* porphyrins genes, CAMP-factors (CAMP1, CAMP2, CAMP3, CAMP4), Hyaluronate lyase (HYL-IB/II, HYL-IA), Lipases (GehA, GehB), Haemolysins, Sialidases, Endo-glycoceramidases, Endo-β-N-acetylglucosaminidase, Dermatan sulphate adhesin (DsA1, DsA2), Proline-Threonine Repeats (PTRs) or any virulence factors included on the acne associated genomic loci 1, 2, 3 (plasmid), 4 such as a tight adhesion locus (tad), Streptolysin S-associated genes (sag), nonribosomal peptide synthetases (NRPS) as described in Tomida et al.

In another embodiment, the CRISPR/Cas9 system is used to target and inactivate an antibiotic resistance gene such as, without limitation, GyrB, ParE, ParY, AAC(1), AAC(2'), AAC(3), AAC(6'), ANT(2''), ANT(3''), ANT(4'), ANT(6), ANT(9), APH(2''), APH(3''), APH(3'), APH(4), APH(6), APH(7''), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-TolC, MsbA, MsrA, VgaB, EmrD, EmrAB-TolC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example *Botulinum* neurotoxin, *tetanus* toxin, *Staphylococcus* toxins, Diphtheria toxin, *Anthrax* toxin, *Alpha* toxin, *pertussis* toxin, *Shiga* toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

Base Editing

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

One of the main challenges for base editing is how to restrict activity of the enzyme performing the nucleotide conversion to the target nucleotide, for example a SNP involved in pathogenicity. This spatial restriction has been achieved recently repurposing the CRISPR-Cas system. Indeed, fusing catalytically impaired or inactive Cas nuclease to base modification enzymes that are active only on single stranded DNA, it's possible to achieve high efficiency base editing. This is possible thanks to the CRISPR-Cas ability to generate locally ssDNA bubble in an 'R loop' when the complex is annealed to its DNA target strand by RNA-DNA base pairing.

So far there are seven types of DNA base editors described:
- Cytosine Base Editor (CBE) that convert C:G into T:A (Komor, A et al. Programmable editing of a target base in genomic DNA without double-stranded DNA cleavage. Nature 533:420-4. (2016).
- Adenine Base Editor (ABE) that convert A:T into G:C (Programmable base editing of A•T to G•C in genomic DNA without DNA cleavage. Nature 551(7681) 464-471 (2017).
- Cytosine Guanine Base Editor (CGBE) that convert C:G into G:C Chen, L et al. Precise and programmable C:G to G:C base editing in genomic DNA. Biorxiv (2020); Kurt, I et al. CRISPR C-to-G base editors for inducing targeted DNA transversions in human cells. Nature Biotechnology (2020).
- Cytosine Adenine Base Editor (CABE) that convert C:G into A:T Zhao, D et al. New base editors change C to A in bacteria and C to G in mammalian cells. Nature Biotechnology (2020).
- Adenine Cytosine Base Editor (ACBE) that convert A:T into C:G (Liu, D et al. A:T to C:G base editors and uses thereof. Patent application WO2020181180 (2020).
- Adenine Thymine Base Editor (ATBE) that convert A:T into T:A (Liu, D et al. A:T to C:G base editors and uses thereof. Patent application WO2020181180 (2020).
- Thymine Adenine Base Editor (TABE) that convert T:A into A:T (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY. ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA.TadA* include TadA-8a-e and TadA-7.10.

Except from base modification enzyme there has been also modifications implemented to base editor to increase editing efficacy, precision and modularity:
- the addition of one or two uracil DNA glycosylase inhibitor domain (UGI) to prevent base excision repair mechanism to revert base edition
- the addition of Mu-GAM that decrease insertion-deletion rate by inhibiting Non-homologous end joining mechanism in the cell (NHEJ)
- the use of nickase active Cas9 (nCas9 D10A) that, by creating nicks on the non-edited strand favor its repair and consequently the fixation of the edited base
- the use of divers Cas proteins from for example different organisms, mutants with different PAM motifs or different fidelity or different family (e.g. Cas12a)

Non-limiting examples of DNA based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:
- A cytosine deaminase (rAPOBEC) and base excision repair proteins (e.g. rXRCC1). (Precise and programmable C:G to G:C base editing in genomic DNA. Biorxiv (2020).
- A rat APOBEC1 variant (R33A) protein and an E. coli-derived uracil DNA N-glycosylase (eUNG). (Kurt, I et al. CRISPR C-to-G base editors for inducing targeted DNA transversions in human cells. Nature Biotechnology (2020).

Cytosine Adenine Base Editors (CABE) consist of a Cas9 nickase, a cytidine deaminase (e.g. AID), and a uracil-DNA glycosylase (Ung). Zhao, D et al. New base editors change C to A in bacteria and C to G in mammalian cells. Nature Biotechnology (2020).

ACBE include a nucleic acid programmable DNA-binding protein and an adenine oxidase. Liu, D et al. A:T to C:G base editors and uses thereof. Patent application WO2020181180 (2020).

ATBE consist of a Cas9 nickase and one or more adenosine deaminase or an oxidase domain. Liu, D et al. A:T to T:A base editing through adenine deamination and oxidation. Patent application WO2020181202 (2020).

TABE consist of a Cas9 nickase and an adenosine methyltransferase, a thymine alkyltransferase, or an adenosine deaminase domain. (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editor molecules can also consist of two or more of the above listed editor enzymes fused to a Cas protein (e.g. combination of an ABE and CBE). These biomolecules are named dual base editors and enable the editing of two different bases. (Grunewald, J et al. A dual-deaminase CRISPR base editor enables concurrent adenine and cytosine editing, Nature Biotechnology (2020); Li, C et al. Targeted, random mutagenesis of plant genes with dual cytosine and adenine base editors, Nature Biotechnology (2020).

In one embodiment, the base editor is used to inactivate the expression of a gene by editing one or several nucleotides involved in transcription or translation. More specifically the base editor is targeting one or several nucleotides of a promoter, a RBS, a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation. More specifically the base editor is targeting one or several nucleotides of a promoter, a RBS, a start codon. leading to an increase or decrease of gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

RNA Based Editing

RNA base editing is based on the same principle as DNA base editing: an enzyme catalysing the conversion of a RNA base into another has to be brought close to the target base to perform its conversion locally. So far the only enzyme used for RNA editing is an adenosine deaminase from ADAR family that converts Adenosine into Inosine in dsRNA structure. Several seminal studies used this specificity for dsRNA and fused the ADAR deaminase domain (ADARDD) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to an hyperactive mutant of ADAR2 deaminase domain (ADAR2DD-E488Q for REPAIRv1 and ADAR2DD-E488Q-T375G for REPAIRv2) Cox et al improved specificity and efficiency compare to previous RNA editing strategies.

Non-limiting examples of RNA based editor proteins include REPAIRv1, REPAIRv2

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

Prime Editing

Prime editors (PE), as described in Anzalone et al. (Anzalone, A. V. et al. Search-and-replace genome editing without double-strand breaks or donor DNA. Nature 576, 149-157 (2019) which is hereby incorporated by reference, consist of a nCas9 fused to a reverse transcriptase used in combination with a prime editing RNA (pegRNA; a guide RNA that includes a template region for reverse transcription).

Prime Editing allows introduction of insertions, deletions (indels) and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
- a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
- a prime editing guide RNA (pegRNA)

To favor editing the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b, Cas9 Retron preclSe Parallel Editing via homologY ('CRISPEY'), a retron RNA fused to the sgRNA and expressed together with Cas9 and the retron proteins including at least the reverse transcriptase (Sharon, E. et al. Functional Genetic Variants Revealed by Massively Parallel Precise Genome Editing. Cell 175, 544-557.e16 (2018).) The SCRIBE strategy: a retron system expressed in combination with a recombinase promoting the recombination of single stranded DNA, also known as single stranded annealing proteins (SSAPs)12. Such recombinases include but are not limited to phage recombinases such as lambda red, recET, Sak, Sak4, and newly described SSAPs described in Wannier et al (Wannier, T. M. et al. Improved bacterial recombineering by parallelized protein discovery. Biorxiv 2020.01.14.906594 (2020) doi:10.1101/2020.01.14.906594), the targetron system based on group II introns described in Karberg et al. (Karberg, M. et al. Group II introns as controllable gene targeting vectors for genetic manipulation of bacteria. Nat Biotechnol 19, 1162-7 (2001) and which has been adapted to many bacterial species, Other retron based gene targeting approaches, as described in Simon et al (Simon, A. J., Ellington, A. D. & Finkelstein, I. J. Retrons and their applications in genome engineering. Nucleic Acids Res 47, 11007-11019 (2019)).

In one embodiment, the prime editing system is used to inactivate the expression of a gene by replacing, deleting, inserting one or several nucleotides involved in transcription or translation. More specifically the prime editing system is replacing, deleting, inserting one or several nucleotides in a promoter, a RBS, a coding sequence.

In one embodiment, the prime editing system is used to introduce one or several premature stop codon.

In one embodiment, the prime editing system is used to introduce one or several rare codons.

In one embodiment, the prime editing system is used to introduce, delete a nucleotide inducing a frameshift in the reading frame.

In another embodiment, the prime editing system is used to modulate the expression of genes by replacing, deleting, inserting one or several nucleotides involved in transcription or translation. More specifically the prime editing system is replacing, deleting, inserting one or several nucleotides in a promoter, a RBS, a start codon. leading to an increase or decrease of gene expression.

In another embodiment, the prime editing system is used to revert a mutation that leads to the inactivation or a decrease in activity of a gene or pathway.

In another embodiment, the prime editing system is used to revert a mutation that leads to an increase of pathogenicity.

The invention encompasses the following embodiments:
1. A *C. acnes* cell carrying a recombinant DNA vector comprising:
   - a phage packaging signal allowing packaging of the DNA vector in a *Cutibacterium acnes* phage capsid, and
   - a gene of interest.
2. A *C. acnes* producer cell carrying a recombinant DNA vector comprising:
   - a phage packaging signal allowing packaging of the DNA vector in a *Cutibacterium acnes* phage capsid
   - a gene of interest
   - an origin of replication allowing replication in the producer cell, and
   - a selection marker for *C. acnes*.
3. The DNA vector of embodiment 1, further comprising an origin of replication for *C. acnes* and a selection marker for *C. acnes*.
4. The DNA vector of any of embodiments 1-3, wherein the phage packaging signal is at least 90, 93, 95, 97, 98, 99, or 100% identical to SEQ ID NO: 66.
5. The DNA vector of any of embodiments 1-3, wherein the phage packaging signal is at least 90, 93, 95, 97, 98, 99, or 100% identical to phage packaging signal selected from the group consisting of: SEQ ID NO: 76, SEQ ID NO: 77, SEQ ID NO: 78, SEQ ID NO: 79, SEQ ID NO: 80, SEQ ID NO: 81.
6. The DNA vector of any of embodiments 1-5, wherein the DNA vector also comprises a CRISPR-Cas system.
7. The DNA vector of any of embodiments 1-6, comprising a CRISPR-Cas system targeting a *C. acnes* chromosome locus not present in the *C. acnes* producer cell strain.
8. The DNA vector of embodiment 7, wherein the targeted locus is a proinflammatory sequence related to acne vulgaris.
9. The DNA vector of any of embodiments 1-8, wherein the DNA vector comprises a template for homologous recombination in *C. acnes* phages.
10. The DNA vector of any of embodiments 1-9, wherein the DNA vector comprises a template for homologous recombination in *C. acnes* plasmids.
11. The DNA vector of embodiment 6, wherein the DNA vector comprises a template for homologous recombination and wherein the CRISPR-Cas system targets the DNA vector itself.
12. The DNA vector of any of embodiments 1-11, wherein first selection marker and second selection marker are the same.
13. The DNA vector of any of embodiments 1-11, wherein neither the first nor second selection marker is ermE.
14. The DNA vector of any of embodiments 1-11, wherein first selection marker and second selection marker is catA.
15. The DNA vector of any of embodiments 1-11, wherein first selection marker or second selection marker is catA.
16. An engineered *C. acnes* comprising any of the DNA vectors of embodiments 1-15.
17. An engineered *C. acnes* produced by modification with any of the vectors of embodiments 1-15.
18. An engineered *C. acnes* produced by contacting *C. acnes* with any of the vectors of embodiments 1-15, modifying the *C. acnes* with a gene of interest carried by the vector, selecting for the modification, and curing the *C. acnes* of the plasmid.

19. The engineered *C. acnes* of any of embodiments 16-18, wherein the *C. acnes* has been modified by a CRISPR-Cas system carried by the vector.

20. The engineered *C. acnes* of any of embodiments 16-19, wherein the *C. acnes* has been modified by insertion of an exogenous gene into the *C. acnes* chromosome.

21. A method for engineering a *C. acnes* comprising introducing the DNA vector of any of embodiments 1-15 into a *C. acnes*.

22. The method of embodiment 21, further comprising selecting a modified *C. acnes*.

23. The method of embodiment 22, comprising selecting a modified *C. acnes* that has an insertion of an exogenous gene into the *C. acnes* chromosome.

24. A method for the production of phage-derived particles comprising the transformation or the transduction of a *C. acnes* phage genome into the producer cell of embodiment 2.

25. A method for the production of phage-derived particles comprising the introduction of a helper phage into the producer cell of embodiment 2.

26. A phage-derived particle produced by the method of any of embodiments 24-25.

27. A recombinant DNA vector comprising:
   an origin of replication allowing replication in *C. acnes*;
   optionally a first selection marker allowing for selection of the DNA vector in *C. acnes*; and
   a gene of interest.

28. The DNA vector of embodiment 27 further comprising an oriT allowing conjugation into *C. acnes*; an origin of replication allowing replication in a donor bacteria and a second selection marker allowing for selection in a donor bacteria.

29. The DNA vector of embodiment 27 or 28, wherein the origin of replication allowing replication in *C. acnes* is R6K (typically of sequence SEQ ID NO: 42).

30. The DNA vector of embodiment 27 or 28, wherein the origin of replication allowing replication in *C. acnes* is RK2 (typically of sequence SEQ ID NO: 43).

31. The DNA vector of embodiment 27 or 28, wherein the origin of replication allowing replication in *C. acnes* is pBBR1 (typically of sequence SEQ ID NO: 44).

32. The DNA vector of embodiment 27 or 28, wherein the origin of replication allowing replication in *C. acnes* is pRO1600 (typically of sequence SEQ ID NO: 45).

33. The DNA vector of embodiment 27 or 28, wherein the origin of replication allowing replication in *C. acnes* is RSF1010 (typically of sequence SEQ ID NO: 46).

34. The DNA vector of embodiment 27 or 28, wherein the origin of replication allowing replication in *C. acnes* is pAMβ1 (typically of sequence SEQ ID NO: 47).

35. The DNA vector of embodiment 27 or 28, wherein the origin of replication allowing replication in *C. acnes* is pLME106 (typically of sequence SEQ ID NO: 48).

36. The DNA vector of embodiment 27 or 28, wherein the origin of replication allowing replication in *C. acnes* is pTZC1 (typically of sequence SEQ ID NO: 49).

37. The DNA vector of embodiment 27 or 28, wherein the origin of replication allowing replication in *C. acnes* is pBC1 (typically of sequence SEQ ID NO: 50).

38. The DNA vector of embodiment 27 or 28, wherein the origin of replication allowing replication in *C. acnes* is pEP2 (typically of sequence SEQ ID NO: 51).

39. The DNA vector of embodiment 27 or 28, wherein the origin of replication allowing replication in *C. acnes* is pWVO1 (typically of sequence SEQ ID NO: 52).

40. The DNA vector of embodiment 27 or 28, wherein the origin of replication allowing replication in *C. acnes* is pAP1 (typically of sequence SEQ ID NO: 53).

41. The DNA vector of embodiment 27 or 28, wherein the origin of replication allowing replication in *C. acnes* is pWKS1 (typically of sequence SEQ ID NO: 54).

42. The DNA vector of embodiment 27 or 28, wherein the origin of replication allowing replication in *C. acnes* is pLME108 (typically of sequence SEQ ID NO: 55).

43. The DNA vector of embodiment 27 or 28, wherein the origin of replication allowing replication in *C. acnes* is pLS1 (typically of sequence SEQ ID NO: 56).

44. The DNA vector of embodiment 27 or 28, wherein the origin of replication allowing replication in *C. acnes* is pUB6060 (typically of sequence SEQ ID NO: 57).

45. The DNA vector of embodiment 27 or 28, wherein the origin of replication allowing replication in *C. acnes* is p545 (typically of sequence SEQ ID NO: 58).

46. The DNA vector of embodiment 27 or 28, wherein the origin of replication allowing replication in *C. acnes* is pJD4 (typically of sequence SEQ ID NO: 59).

47. The DNA vector of embodiment 27 or 28, wherein the origin of replication allowing replication in *C. acnes* is pIJ101 (typically of sequence SEQ ID NO: 60).

48. The DNA vector of embodiment 27 or 28, wherein the origin of replication allowing replication in *C. acnes* is pSN22 (typically of sequence SEQ ID NO: 61).

49. The DNA vector of embodiment 27 or 28, wherein the origin of replication allowing replication in *C. acnes* is pGP01 (typically of sequence SEQ ID NO: 62).

50. The DNA vector of embodiment 27 or 28, wherein the origin of replication allowing replication in *C. acnes* is pIP501 (typically of sequence SEQ ID NO: 63).

51. The DNA vector of embodiment 27 or 28, wherein the origin of replication allowing replication in *C. acnes* is pCU1 (typically of sequence SEQ ID NO: 64).

52. The DNA vector of embodiment 27 or 28, wherein the origin of replication allowing replication in *C. acnes* is pBAV1K-T5 (typically of sequence SEQ ID NO: 65).

53. The DNA vector of any one of embodiments 28 to 52, wherein the oriT is oriT_pMRC01 (typically of sequence SEQ ID NO: 1).

54. The DNA vector of any one of embodiments 28 to 52, wherein the oriT is oriT_RSF1010 (typically of sequence SEQ ID NO: 2).

55. The DNA vector of any one of embodiments 28 to 52, wherein the oriT is oriT_pRS01 (typically of sequence SEQ ID NO: 3).

56. The DNA vector of any one of embodiments 28 to 52, wherein the oriT is oriT_pMV158 (typically of sequence SEQ ID NO: 4).

57. The DNA vector of any one of embodiments 28 to 52, wherein the oriT is oriT_pTF1 (typically of sequence SEQ ID NO: 5).

58. The DNA vector of any one of embodiments 28 to 52, wherein the oriT is oriT_pSC101 (typically of sequence SEQ ID NO: 6).

59. The DNA vector of any one of embodiments 28 to 52, wherein the oriT is oriT_pBTK445 (typically of sequence SEQ ID NO: 7).

60. The DNA vector of any one of embodiments 28 to 52, wherein the oriT is oriT_pBBR1 (typically of sequence SEQ ID NO: 8).

61. The DNA vector of any one of embodiments 28 to 52, wherein the oriT is oriT_R721 (typically of sequence SEQ ID NO: 9).

62. The DNA vector of any one of embodiments 28 to 52, wherein the oriT is oriT_pRmeGR4a (typically of sequence SEQ ID NO: 10).

63. The DNA vector of any one of embodiments 28 to 52, wherein the oriT is oriT_ColE1 (typically of sequence SEQ ID NO: 11).

64. The DNA vector of any one of embodiments 28 to 52, wherein the oriT is oriT_pTiC58 (typically of sequence SEQ ID NO: 12).

65. The DNA vector of any one of embodiments 28 to 52, wherein the oriT is oriT_pMdT1 (typically of sequence SEQ ID NO: 13).

66. The DNA vector of any one of embodiments 28 to 52, wherein the oriT is oriT_R1 (typically of sequence SEQ ID NO: 14).

67. The DNA vector of any one of embodiments 28 to 52, wherein the oriT is oriT_Tn5520 (typically of sequence SEQ ID NO: 15).

68. The DNA vector of any one of embodiments 28 to 52, wherein the oriT is oriT_QKH54 (typically of sequence SEQ ID NO: 16).

69. The DNA vector of any one of embodiments 28 to 52, wherein the oriT is oriT_R64 (typically of sequence SEQ ID NO: 17).

70. The DNA vector of any one of embodiments 28 to 52, wherein the oriT is oriT_R751 (typically of sequence SEQ ID NO: 18).

71. The DNA vector of any one of embodiments 28 to 52, wherein the oriT is oriT_RP4 (typically of sequence SEQ ID NO: 19).

72. The DNA vector of any one of embodiments 28 to 52, wherein the oriT is oriT_pKL1 (typically of sequence SEQ ID NO: 20).

73. The DNA vector of any one of embodiments 28 to 52, wherein the oriT is oriT_RK2 (typically of sequence SEQ ID NO: 21).

74. The DNA vector of any one of embodiments 28 to 52, wherein the oriT is oriT_R1162 (typically of sequence SEQ ID NO: 22).

75. The DNA vector of any one of embodiments 28 to 52, wherein the oriT is oriT_Tn4555 (typically of sequence SEQ ID NO: 23).

76. The DNA vector of any one of embodiments 28 to 52, wherein the oriT is oriT_pHT (typically of sequence SEQ ID NO: 24).

77. The DNA vector of any one of embodiments 28 to 52, wherein the oriT is oriT_Tn4399 (typically of sequence SEQ ID NO: 25).

78. The DNA vector of any one of embodiments 28 to 52, wherein the oriT is oriT_Tn916 (typically of sequence SEQ ID NO: 26).

79. The DNA vector of any one of embodiments 28 to 52, wherein the oriT is oriT_pST12 (typically of sequence SEQ ID NO: 27).

80. The DNA vector of any one of embodiments 28 to 52, wherein the oriT is oriT_pCU1 (typically of sequence SEQ ID NO: 28).

81. The DNA vector of any one of embodiments 28 to 52, wherein the oriT is oriT_pSU233 (typically of sequence SEQ ID NO: 29).

82. The DNA vector of any one of embodiments 28 to 52, wherein the oriT is oriT_F (typically of sequence SEQ ID NO: 30).

83. The DNA vector of any one of embodiments 28 to 52, wherein the oriT is oriT_pMAB01 (typically of sequence SEQ ID NO: 31).

84. The DNA vector of any one of embodiments 28 to 52, wherein the oriT is oriT_R388 (typically of sequence SEQ ID NO: 32).

85. The DNA vector of any one of embodiments 28 to 52, wherein the oriT is oriT_pS7a (typically of sequence SEQ ID NO: 33).

86. The DNA vector of any one of embodiments 28 to 52, wherein the oriT is oriT_pS7b (typically of sequence SEQ ID NO: 34).

87. The DNA vector of any one of embodiments 28 to 52, wherein the oriT is oriT_R702 (typically of sequence SEQ ID NO: 35).

88. The DNA vector of any one of embodiments 28 to 52, wherein the oriT is oriT_pMUR274 (typically of sequence SEQ ID NO: 36).

89. The DNA vector of any one of embodiments 28 to 52, wherein the oriT is oriT_R100 (typically of sequence SEQ ID NO: 37).

90. The DNA vector of any one of embodiments 28 to 52, wherein the oriT is oriT_pVCR94deltaX (typically of sequence SEQ ID NO: 38).

91. The DNA vector of any one of embodiments 28 to 52, wherein the oriT is oriT_R46 (typically of sequence SEQ ID NO: 39).

92. The DNA vector of any one of embodiments 28 to 52, wherein the oriT is oriT_pGO1 (typically of sequence SEQ ID NO: 40).

93. The DNA vector of any one of embodiments 28 to 52, wherein the oriT is oriT_pIP501 (typically of sequence SEQ ID NO: 41).

94. The DNA vector of any one of embodiments 27 to 93, further comprising:
   a relaxase gene;
   a selection marker allowing for selection in the transconjugant *C. acnes*; and
   a selection marker allowing for selection in the donor bacteria wherein the donor bacteria is an *E. coli* strain carrying a conjugative plasmid, conjugative transposon, or integrative and conjugative element (ICE), expressing a conjugative machinery.

95. The DNA vector of embodiment 94, wherein the donor bacteria is an *E. coli* strain carrying the conjugative plasmid, conjugative transposon or ICE pMRC01.

96. The DNA vector of embodiment 94, wherein the donor bacteria is an *E. coli* strain carrying the conjugative plasmid, conjugative transposon or ICE RSF1010.

97. The DNA vector of embodiment 94, wherein the donor bacteria is an *E. coli* strain carrying the conjugative plasmid, conjugative transposon or ICE pRS01.

98. The DNA vector of embodiment 94, wherein the donor bacteria is an *E. coli* strain carrying the conjugative plasmid, conjugative transposon or ICE pMV158.

99. The DNA vector of embodiment 94, wherein the donor bacteria is an *E. coli* strain carrying the conjugative plasmid, conjugative transposon or ICE pTF1.

100. The DNA vector of embodiment 94, wherein the donor bacteria is an *E. coli* strain carrying the conjugative plasmid, conjugative transposon or ICE pSC101.

101. The DNA vector of embodiment 94, wherein the donor bacteria is an *E. coli* strain carrying the conjugative plasmid, conjugative transposon or ICE pBTK445.

102. The DNA vector of embodiment 94, wherein the donor bacteria is an *E. coli* strain carrying the conjugative plasmid, conjugative transposon or ICE pBBR1.

103. The DNA vector of embodiment 94, wherein the donor bacteria is an *E. coli* strain carrying the conjugative plasmid, conjugative transposon or ICE R721.

104. The DNA vector of embodiment 94, wherein the donor bacteria is an *E. coli* strain carrying the conjugative plasmid, conjugative transposon or ICE pRmeGR4a.

105. The DNA vector of embodiment 94, wherein the donor bacteria is an *E. coli* strain carrying the conjugative plasmid, conjugative transposon or ICE ColE1.

106. The DNA vector of embodiment 94, wherein the donor bacteria is an *E. coli* strain carrying the conjugative plasmid, conjugative transposon or ICE pTiC58.

107. The DNA vector of embodiment 94, wherein the donor bacteria is an *E. coli* strain carrying the conjugative plasmid, conjugative transposon or ICE pMdT1.

108. The DNA vector of embodiment 94, wherein the donor bacteria is an *E. coli* strain carrying the conjugative plasmid, conjugative transposon or ICE R1.

109. The DNA vector of embodiment 94, wherein the donor bacteria is an *E. coli* strain carrying the conjugative plasmid, conjugative transposon or ICE Tn5520.

110. The DNA vector of embodiment 94, wherein the donor bacteria is an *E. coli* strain carrying the conjugative plasmid, conjugative transposon or ICE QKH54.

111. The DNA vector of embodiment 94, wherein the donor bacteria is an *E. coli* strain carrying the conjugative plasmid, conjugative transposon or ICE R64.

112. The DNA vector of embodiment 94, wherein the donor bacteria is an *E. coli* strain carrying the conjugative plasmid, conjugative transposon or ICE R751.

113. The DNA vector of embodiment 94, wherein the donor bacteria is an *E. coli* strain carrying the conjugative plasmid, conjugative transposon or ICE RP4.

114. The DNA vector of embodiment 94, wherein the donor bacteria is an *E. coli* strain carrying the conjugative plasmid, conjugative transposon or ICE pKL1.

115. The DNA vector of embodiment 94, wherein the donor bacteria is an *E. coli* strain carrying the conjugative plasmid, conjugative transposon or ICE RK2.

116. The DNA vector of embodiment 94, wherein the donor bacteria is an *E. coli* strain carrying the conjugative plasmid, conjugative transposon or ICE R1162.

117. The DNA vector of embodiment 94, wherein the donor bacteria is an *E. coli* strain carrying the conjugative plasmid, conjugative transposon or ICE Tn4555.

118. The DNA vector of embodiment 94, wherein the donor bacteria is an *E. coli* strain carrying the conjugative plasmid, conjugative transposon or ICE pHT.

119. The DNA vector of embodiment 94, wherein the donor bacteria is an *E. coli* strain carrying the conjugative plasmid, conjugative transposon or ICE Tn4399.

120. The DNA vector of embodiment 94, wherein the donor bacteria is an *E. coli* strain carrying the conjugative plasmid, conjugative transposon or ICE Tn916.

121. The DNA vector of embodiment 94, wherein the donor bacteria is an *E. coli* strain carrying the conjugative plasmid, conjugative transposon or ICE pST12.

122. The DNA vector of embodiment 94, wherein the donor bacteria is an *E. coli* strain carrying the conjugative plasmid, conjugative transposon or ICE pCU1.

123. The DNA vector of embodiment 94, wherein the donor bacteria is an *E. coli* strain carrying the conjugative plasmid, conjugative transposon or ICE pSU233.

124. The DNA vector of embodiment 94, wherein the donor bacteria is an *E. coli* strain carrying the conjugative plasmid, conjugative transposon or ICE F.

125. The DNA vector of embodiment 94, wherein the donor bacteria is an *E. coli* strain carrying the conjugative plasmid, conjugative transposon or ICE pMAB01.

126. The DNA vector of embodiment 94, wherein the donor bacteria is an *E. coli* strain carrying the conjugative plasmid, conjugative transposon or ICE R388.

127. The DNA vector of embodiment 94, wherein the donor bacteria is an *E. coli* strain carrying the conjugative plasmid, conjugative transposon or ICE pS7a.

128. The DNA vector of embodiment 94, wherein the donor bacteria is an *E. coli* strain carrying the conjugative plasmid, conjugative transposon or ICE pS7b.

129. The DNA vector of embodiment 94, wherein the donor bacteria is an *E. coli* strain carrying the conjugative plasmid, conjugative transposon or ICE R702.

130. The DNA vector of embodiment 94, wherein the donor bacteria is an *E. coli* strain carrying the conjugative plasmid, conjugative transposon or ICE pMUR274.

131. The DNA vector of embodiment 94, wherein the donor bacteria is an *E. coli* strain carrying the conjugative plasmid, conjugative transposon or ICE R100.

132. The DNA vector of embodiment 94, wherein the donor bacteria is an *E. coli* strain carrying the conjugative plasmid, conjugative transposon or ICE pVCR94deltaX.

133. The DNA vector of embodiment 94, wherein the donor bacteria is an *E. coli* strain carrying the conjugative plasmid, conjugative transposon or ICE R46.

134. The DNA vector of embodiment 94, wherein the donor bacteria is an *E. coli* strain carrying the conjugative plasmid, conjugative transposon or ICE pGO1.

135. The DNA vector of embodiment 94, wherein the donor bacteria is an *E. coli* strain carrying the conjugative plasmid, conjugative transposon or ICE pIP501.

136. An engineered *C. acnes* comprising any of the DNA vectors of any one of embodiments 27 to 135.

137. An engineered *C. acnes* produced by contacting *C. acnes* with any of the vectors of any one of embodiments 27 to 135.

138. A method for engineering a *C. acnes* comprising introducing the DNA vector of any one of embodiments 27 to 135 into a *C. acnes*.

139. A recombinant DNA vector comprising:
a phage packaging signal allowing packaging of the DNA vector in a *Cutibacterium acnes* phage capsid, and
a gene of interest.

140. A *C. acnes* producer cell carrying a recombinant DNA vector comprising:
a phage packaging signal allowing packaging of the DNA vector in a *Cutibacterium acnes* phage capsid
a gene of interest
an origin of replication allowing replication in the producer cell, and
a selection marker for *C. acnes*.

141. The DNA vector of embodiment 139 further comprising an origin of replication for *C. acnes* and a selection marker for *C. acnes*.

142. The DNA vector of any of embodiments 139-141, wherein the phage packaging signal is at least 90, 93, 95, 97, 98, 99, or 100% identical to (SEQ ID NO: 66).

143. The DNA vector of any of embodiments 139-141, wherein the phage packaging signal is at least 90, 93, 95, 97, 98, 99, or 100% identical to phage packaging signal selected from the group consisting of: SEQ ID NO: 76, SEQ ID NO: 77, SEQ ID NO: 78, SEQ ID NO: 79, SEQ ID NO: 80, SEQ ID NO: 81.

144. The DNA vector of any of embodiments 139-143, wherein the DNA vector also comprises a CRISPR-Cas system.

145. The DNA vector of any of embodiments 139-144, comprising a CRISPR-Cas system targeting a *C. acnes* chromosome locus not present in the *C. acnes* producer cell strain.

146. The DNA vector of embodiment 145, wherein the targeted locus is a proinflammatory sequence related to acne vulgaris.

147. The DNA vector of any of embodiments 139-146, wherein the DNA vector comprises a template for homologous recombination in *C. acnes* phages.

148. The DNA vector of any of embodiments 139-147, wherein the DNA vector comprises a template for homologous recombination in *C. acnes* plasmids.

149. The DNA vector of embodiment 144, wherein the DNA vector comprises a template for homologous recombination and wherein the CRISPR-Cas system targets the DNA vector itself.

150. The DNA vector of any of embodiments 139-149, wherein first selection marker and second selection marker are the same.

151. The DNA vector of any of embodiments 139-149, wherein neither the first nor second selection marker is ermE.

152. The DNA vector of any of embodiments 139-149, wherein first selection marker and second selection marker is catA.

153. The DNA vector of any of embodiments 139-149, wherein first selection marker or second selection marker is catA.

154. The DNA vector of embodiment 139, which comprises a DNA encoding an antigen.

155. An engineered *C. acnes* comprising any of the DNA vectors of embodiments 139-154.

156. The engineered *C. acnes* according to embodiment 155, which comprises a DNA vector as defined in claim 1 which comprises a DNA encoding an antigen.

157. An engineered *C. acnes* produced by modification with any of the vectors of embodiments 139-154.

158. An engineered *C. acnes* produced by contacting *C. acnes* with any of the vectors of embodiments 139-154, modifying the *C. acnes* with a gene of interest carried by the vector, selecting for the modification, and curing the *C. acnes* of the plasmid.

159. The engineered *C. acnes* of any of embodiments 155-158, wherein the *C. acnes* has been modified by a CRISPR-Cas system carried by the vector.

160. The engineered *C. acnes* of any of embodiments 155-158, wherein the *C. acnes* has been modified by insertion of an exogenous gene into the *C. acnes* chromosome.

161. A method for engineering a *C. acnes* comprising introducing the DNA vector of any of embodiments 139-154 into a *C. acnes*.

162. The method of embodiment 161, further comprising selecting a modified *C. acnes*.

163. The method of embodiment 161, comprising selecting a modified *C. acnes* that has an insertion of an exogenous gene into the *C. acnes* chromosome.

164. A method for the production of phage-derived particles comprising the transformation or the transduction of a *C. acnes* phage genome into the producer cell of embodiment 140.

165. A method for the production of phage-derived particles comprising the introduction of a helper phage into the producer cell of embodiment 140.

166. A phage-derived particle produced by the method of any of embodiments 164-165.

167. A vaccine and/or immunogenic compositions comprising engineered *C. acnes* of embodiment 155 comprising a DNA vector comprising a nucleic acid encoding an antigen.

168. A method to prevent and/or treat cancer in a subject in need thereof, comprising administering to said subject a therapeutically or prophylactically efficient amount of an engineered *C. acnes* of embodiment 155 comprising a DNA vector comprising a nucleic acid encoding a tumor antigen.

169. A method to prevent and/or treat a viral infection in a subject in need thereof, comprising administering to said subject a therapeutically or prophylactically efficient amount of an engineered *C. acnes* of embodiment 155 comprising a DNA vector comprising a nucleic acid encoding a viral antigen.

170. A method to prevent and/or treat a bacterial infection in a subject in need thereof, comprising administering to said subject a therapeutically or prophylactically efficient amount of an engineered *C. acnes* of embodiment 155 comprising a DNA vector comprising a nucleic acid encoding a bacterial antigen.

171. A method to prevent and/or treat a fungal infection in a subject in need thereof, comprising administering to said subject a therapeutically or prophylactically efficient amount of an engineered *C. acnes* of embodiment 155 comprising a DNA vector comprising a nucleic acid encoding a fungal antigen.

172. A method to prevent and/or treat an autoimmune disease in a subject in need thereof, comprising administering to said subject a therapeutically or prophylactically efficient amount of an engineered *C. acnes* of embodiment 155 comprising a DNA vector comprising a nucleic acid encoding a self-antigen.

173. A method to prevent and/or treat an allergy in a subject in need thereof, comprising administering to said subject a therapeutically or prophylactically efficient amount of an engineered *C. acnes* of embodiment 155 comprising a DNA vector comprising a nucleic acid encoding an allergen.

174. A method to prevent and/or treat graft rejection in a subject in need thereof, comprising administering to said subject a therapeutically or prophylactically efficient amount of an engineered *C. acnes* of embodiment 155 comprising a DNA vector comprising a nucleic acid encoding a graft-specific antigen.

EXAMPLES

Example 1. Phage-Derived Particles for Delivery of DNA Payload into *C. acnes*

*C. acnes* phage-derived particles containing a synthetic DNA payload and able to inject it inside *C. acnes* were developed. It is demonstrated for the first time the stable and autonomous replication of a recombinant DNA vector that allows for transgene expression. These phage-derived particles are produced upon the co-occurrence of a *C. acnes* phage genome and a DNA payload inside a *C. acnes* producer cell. The DNA payload is introduced into the *C. acnes* producer cell by different methods such as electroporation, electroporation of protoplast, conjugation, chemical transformation, transduction into the *C. acnes* producer cell. Such phage-derived particles open possibilities to deliver DNA encoding a therapeutic molecule into all *C. acnes* strains in situ with high efficiency and specificity, allowing, for example, sequence specific killing due to CRISPR-Cas expression or modulation of the immune system by secretion of immunomodulators.

Being able to edit *Cutibacterium acnes* population by removing specific proinflammatory strains to prevent or cure disease such as acne vulgaris or leverage their privilege location into the pilosebaceous unit to modulate the immune system or improve wound healing are attractive therapeutic approaches. To implement such approaches, one can either genetically modify *C. acnes* strains in situ or provide in vitro genetically modified *C. acnes*. Because of the large intra and inter-individual microbiome diversity both at the species and strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-establish strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[26]. This in vitro process has been shown to be very low efficiency and rely on the use of an antibiotic selection marker to select such events. Moreover, these genetic modifications have been restricted to a few specific strains (KPA17202) and might not be generalizable to all *C. acnes* strains. Second, in order to perform in situ genetic modification of *C. acnes* we need to deliver DNA. The only described method for introducing DNA into *C. acnes* is the use of electroporation[26,27], a method that can only be performed in vitro.

The present invention solves both delivery and maintenance of synthetic DNA inside *C. acnes* population in situ. Phage-derived particles composed of a synthetic DNA vector/payload packaged inside the phage capsid at the expense of the phage genome are used. By hijacking the phage-capsid, it was taken advantage of the ability of the phage to transduce DNA into the bacterial host. These phage-derived particles, when put in the presence of the natural bacterial host of the phage, are able to bind to the bacteria and inject the DNA vector/payload inside the bacterial cytoplasm where it can replicate and lead to expression of a protein of interest.

*C. acnes* phage are naturally present on the skin where they infect and replicate using *C. acnes* as a host. *C. acnes* phages have a broad host range, meaning that they can infect most of the *C. acnes* strain diversity isolated so far. This makes the capsid of these phages a really efficient vehicle to deliver DNA in situ into all *C. acnes* strains regardless of their genetic diversity. To develop phage-derived particles from *C. acnes* phages, several phages from the skin of volunteer individuals were first isolated by sampling nose microcomedones using Biore Deep Cleansing Pore Strips (Kao Brands Company), following manufacturer's instructions. After being removed from the nose, microcomedones were collected, homogenized in sterile water and spread onto an RCM *agar* plate. After incubation under anaerobic conditions at 37° C. for 7 days, plaques could be observed on the lawn of *C. acnes* growth. Plaques were then isolated and the phages amplified on an indicator strain. Phage DNA was extracted using the Promega wizard DNA clean-up System and sent for library preparation by mechanical random fragmentation and sequenced with an Illumina MiSeq platform. Sequencing reads were assembled using Spades. As expected from previous publications, isolated phages were genetically similar to other sequenced phages.

A host-range determination was performed with the different isolated phages against a collection of *C. acnes* strains, covering the known phylogenetic diversity. All phages were able to infect most of the *C. acnes* strains showing, as previously reported, a broad host-range (FIG. 2). PAC7 phage was selected for further experiments.

Genome of phage PAC7 was purified, mechanically sheared to allow for random DNA fragmentation and a PCR-free library preparation was performed prior to paired-end sequencing using illumina Mi-seq. DNA reads were assembled using Spades, a single contig was obtained and annotated. After annotation, cohesive-ends were identified and DNA fragments of different sizes, containing cohesive ends, were cloned in order to identify the packaging sequence (called cos site for phages with cohesive ends) that allow recognition by the small terminase and packaging of the phage genome into the phage capsid. Potential packaging signals from PAC7 were cloned into the pIC086 vector in two different orientations. The pIC086 vector contains:
an origin of replication allowing replication into *C. acnes*, and
a selection marker functional in *C. acnes* (here giving resistance to erythromycin).

Cos containing vectors (cosmids) were cloned into the *E. coli* DH10B cloning strain, sequence verified. The DNA vectors (Table 1) were introduced into the *C. acnes* strain ATCC 11828, and recombinants were selected on *agar* plates with erythromycin.

To produce phage-derived particles, a liquid culture of the different *C. acnes* strains carrying the DNA vector (Table 2) were grown and infected by PAC7. A strain containing a plasmid without cos PAC7 (Ca0s16973) was used as control. After infection, the supernatant was filtered and collected. Because both phage genomes and DNA vectors contain a packaging signal, they compete for packaging into the capsid, giving rise to a phage/phage-derived particle mixture.

Figure 8:
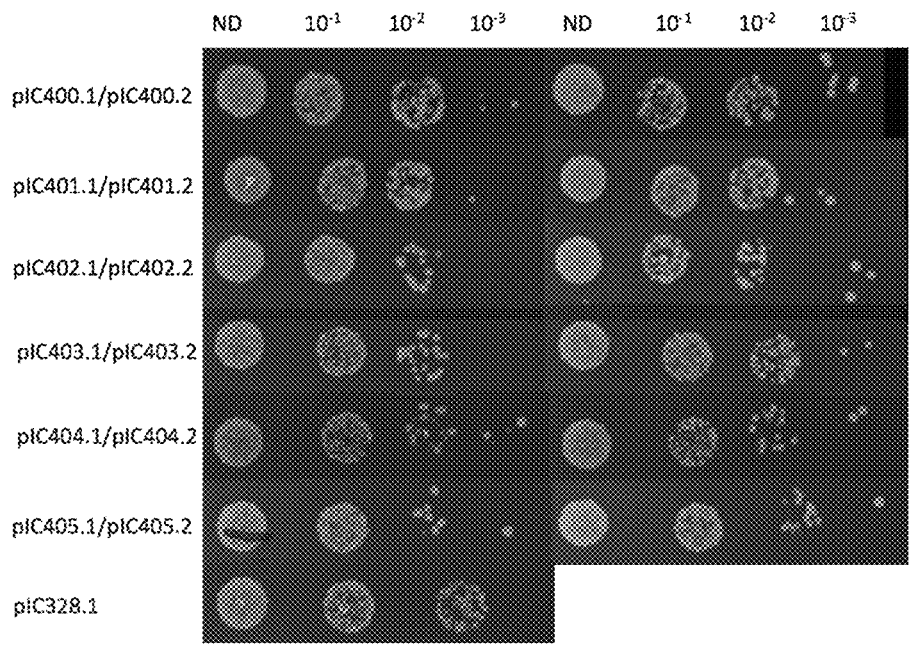
FIG. 8 depicts *C. acnes* transductants of phage-derived particles carrying DNA vector with phage packaging signal (cos) of different sizes. Each suspension of phage-derived particles, also containing phages, was mixed with *C. acnes* ATCC 11828 pseudolysogene, the mixture was incubated for 1 hour at room temperature, diluted and 4 µL of each dilution was plated on *Brucella* plates in presence of erythromycin (5 µg/mL). For each phage-derived particle containing a same DNA vector, two suspensions from independent productions were used (e.g pIC400.1 and pIC400.2).

To quantify the number of phages and phage-derived particles in the suspension, phage and phage-derived particles titration was performed. Titration of phage-derived particles was first performed with *C. acnes* ATCC 6919, showing high efficiency killing due to phage infection but no transductants could be observed. In these conditions, transductants are co-infected with the phage, leading to death of transduced cells and to the underestimation of phage-derived particle titers. To circumvent this, it was decided to perform titration with a *C. acnes* ATCC 11828 pseudolysogene strain. Indeed, *C. acnes* phages are not strictly temperate nor strictly lytic phages in laboratory conditions. They are able to inject their genome into cells and stay dormant in the cell without integrating into the genome. These cells carrying the phage in pseudolysogeny state are immune to phage killing. Using a pseudolysogene culture for phage/phage-derived particles titration, a higher amount of transductants were observed. However due to some residual killing of *C. acnes* by phages, a large variability in phage-derived particle titers can be observed in different productions from infection of the same producer cell (FIG. 8). The concentration of phage was determined by plaque assay and showed a high concentration of phage for all phage/phage-derived particle suspension with a titer of approximatively $10^7$ PFU/µL for each suspension. (Table 3). Several colonies were confirmed to be *C. acnes* harbouring the cosmid by PCR. Phage suspension from infection of Ca0s16973 carrying pIC086 plasmid without cos did not show any transductant, confirming that packaging, and thus, the production of phage-derived particles, was specific to cos carrying plasmids.

Titration of the phage-derived particles carrying the DNA vectors comprising phage packaging signal of different sizes shows (FIG. 8) no significant difference in number of transductants. The phage-derived particles titer was similar between all the different cosmids indicating that they are all functional and allow packaging of the DNA vector inside the phage capsid to produce phage-derived particles.

The results show, for the first time:
transduction by a phage-derived particle of a synthetic DNA vector in *C. acnes*
replication of the DNA vector in *C. acnes*
expression of a transgene (erythromycin resistance gene) carried by the replicative DNA vector.

This is a key milestone for the development of in situ DNA delivery, genetic modification and transgene expression in *C. acnes*.

Materials and Methods:

Cosmids construction: Cos fragments were extracted by PCR on diluted phage PAC7 suspension, gel purified and cloned using SapI golden gate reaction and the pIC086 vector.

Introduction of cosmids in *C. acnes* can be performed by methods such as electroporation, protoplast electroporation, chemical transformation, using conjugation, natural competency, transduction.

*C. acnes* conjugation: 2 mL of overnight cultures of *E. coli* donor harboring the different mobilizable shuttle plasmids, grown in LB broth (Fisher Scientific), were pelleted in a benchtop centrifuged at 6,000×g for 1 min. Supernatants were discarded and pellets were washed with 500 µL of pre-sterilized LB medium and centrifuged again using the same conditions. Each pellet was then re-suspended in 200 µL of exponentially growing ($OD_{600}$=0.5) *C. acnes* receptor BHI culture concentrated 10× (BHI broth, Oxoid). The mixture *E. coli*-*C. acnes* was spotted (50 µL/spot) onto *Brucella agar* plates (Sigma-Aldrich) and allowed to mate at 37° C. under anaerobic conditions for 24 hours. After that time, cells were harvested from the mating plate, re-suspended in 300 µL of BHI broth and plated onto *Brucella agar* plates that had been supplemented with 50 µg/mL polymyxin B (Sigma-Aldrich) and 5 µg/mL erythromycin (Sigma-Aldrich) or 5 µg/mL chloramphenicol (Sigma-Aldrich). After 7 days, *C. acnes* cells that grew in the presence of selection were streaked on *Brucella agar* plates supplemented with the appropriate selection and the presence of the conjugated plasmid was confirmed via specific PCRs. The identity of *C. acnes* as well as the absence of *E. coli* donor strain were also confirmed by PCR analyses.

Phage/phage-derived particles production: Overnight cultures of *C. acnes* ATCC 11828 harbouring the different vectors (two clones per construct) were set in 10 mL BHI cultures supplemented with 5 µg/mL erythromycin. Production from phagemid pIC328 was used as a positive control. After overnight culture, once the OD600 had reached 0.8-1, 15 mL of each culture were taken and spin down at 3,000×g for 5 min. The supernatant was discarded and the pellet was re-suspended in 200 µL of PAC7 phage suspension and left on the bench at room temperature for 30 min so phages infect the cells. After one hour, 15 mL of BHI medium were added to each culture and allowed to grow/infect overnight under anaerobic conditions at 37° C. After overnight incubation, cultures were very clear, indicating that infection had taken place. Cultures were spun down at 3,000×g for 5 min, and the supernatant was filtered through a 0.45 µm filter.

Phage titration: Serial dilutions of the phage/packaged phagemid mixture were made in $MgSO_4$ 5 mM and 4 µL of each dilution were spotted onto *Brucella* plates containing a top layer of agarose 4.5 g/L and the strain ATCC 11828. After overnight incubation under anaerobic conditions at 37° C., lysis plaques were counted.

Phage-derived particles titration: 90 µL of an overnight culture ($OD_{600}$ approx 0.8-1, concentrated×10) of *C. acnes* ATCC 11828 pseudolysogene cells were mixed with 10 µL of Phage/Phage-derived particles from non-diluted to dilution $10^{-4}$ (dilution in $MgSO_4$ 5 mM). A control of cells with no phage was included in the assay. The cultures were incubated at room temperature for 1 hour. After this first incubation period, the cultures (bacteria+phages/phage-derived particles at different dilutions) were serially diluted up to $10^{-7}$ in BHI and incubated for 3-4 hours under anaerobic conditions at 37° C. After incubation, 4 µL of each dilution were spotted onto *Brucella* plates in the presence and absence of erythromycin (5 µg/mL). After 5 days of incubation at 37° C. under anaerobic conditions, colonies on BHI plates and BHI+erythromycin 5 µg/mL plates were scanned (FIG. 8).

Pseudolysogene production: strains were freshly made prior to the transduction test. PAC7 phage was added to a suspension of *C. acnes* ATCC 11828 cells and plated onto BHI *agar* plates. After 3 to 4 incubation days, cells growing on plates were recovered and either plated again to have more cells or used for titration. If successive growth on plates is needed, *C. acnes* phages are added to the culture in order to maintain strains in the pseudolysogene state.

Figure 3:
FIG. 3 depicts a gel. Individual colonies from phage-derived particles titration were streaked and a PCR on an individual colony was performed with primers IC208 (SEQ ID NO: 82)/IC310 (SEQ ID NO: 83) to confirm the presence of the phagemid. 1 and 2 refer to transductants coming from the independent production and titration of phage-derived particles carrying the same phagemid. B and W are respectively PCR on the phagemid extraction (positive control) and the ATCC 11828 strain (negative control). Presence of the plasmid after restreak confirms that transductants carry the replicative phagemid.

Confirmation of the phagemid transduction into *C. acnes* cells: colonies observed on BHI plates supplemented with erythromycin were re-isolated on BHI+erythromycin plates. Individual erythromycin resistant colonies obtained after streaking were then tested by PCR to confirm the presence of the phagemid (FIG. 3).

PCR verification of the transductant: colony PCR to check the presence of the phagemid was performed with primers IC208/IC310. A PCR performed with primers AD1261/AD1262 was also included to confirm *C. acnes* identity.

TABLE 1

Mobilizable DNA vectors including packaging signal of PAC7 phage

| DNA vector Name | Cos region | Primers for cloning | Mobilisable vector |
| --- | --- | --- | --- |
| pIC328 | PAC7 Cos region 1 in orientation 1 (383 bp) | AD1542/AD1541 | pIC086 |
| pIC400 | PAC7 Cos region 1 in orientation 1 (317 bp) | IC511/AD1542 | pIC086 |
| pIC401 | PAC7 Cos region 1 in orientation 2 (317 bp) | AD1541/IC512 | pIC086 |
| pIC402 | PAC7 Cos region 2 in orientation 1 (217 bp) | IC511/IC512 | pIC086 |
| pIC403 | PAC7 Cos region 2 in orientation 2 (167 bp) | IC513/IC512 | pIC086 |
| pIC404 | PAC7 Cos region 3 in orientation 1 (167 bp) | IC511/IC514 | pIC086 |
| pIC405 | PAC7 Cos region 3 in orientation 2 (83 bp) | IC513/IC514 | pIC086 |

TABLE 2

List of C. acnes strains generated

| name | Strain description | plasmid |
|---|---|---|
| Ca0s16973 | *Cutibacterium acnes* ATCC 11828 | pIC086 |
| Ca0s18253 | *Cutibacterium acnes* ATCC 11828 | pIC328 |
| Ca0s19443 | *Cutibacterium acnes* ATCC 11828 | pIC400 |
| Ca0s19444 | *Cutibacterium acnes* ATCC 11828 | pIC401 |
| Ca0s19445 | *Cutibacterium acnes* ATCC 11828 | pIC402 |
| Ca0s19446 | *Cutibacterium acnes* ATCC 11828 | pIC403 |
| Ca0s19447 | *Cutibacterium acnes* ATCC 11828 | pIC404 |
| Ca0s19448 | *Cutibacterium acnes* ATCC 11828 | pIC405 |

TABLE 3

Results of phage titration

| strain infected | DNA payload | Phage used for infection | Phage titer (PFU/μL) on *C. acnes* ATCC 11828 indicator strain |
|---|---|---|---|
| Ca0s16973 | pIC086 | PAC7 | ~1E+8 |
| Ca0s18253 | pIC328 | PAC7 | ~1E+7 |
| Ca0s19443 | pIC400 | PAC7 | ~1E+7 |
| Ca0s19444 | pIC401 | PAC7 | ~1E+7 |
| Ca0s19445 | pIC402 | PAC7 | ~1E+7 |
| Ca0s19446 | pIC403 | PAC7 | ~1E+7 |
| Ca0s19447 | pIC404 | PAC7 | ~1E+7 |
| Ca0s19448 | pIC405 | PAC7 | ~1E+7 |

TABLE 4

Primers sequences

| Primers name | Primers sequence |
|---|---|
| AD1541 | GTTCCAGCTCTTCCGAGGACCACATCACACCCGTC (SEQ ID NO: 84) |
| AD1542 | GTTCCAGCTCTTCCTGCCCACTCCTCATCAGACAC (SEQ ID NO: 85) |
| IC511 | GTTCCAGCTCTTCCGAGAGGCAACAGAACACAACCAAA (SEQ ID NO: 86) |
| IC512 | GTTCCAGCTCTTCCTGCGACTATCAGGAAGCTCAGGC (SEQ ID NO: 87) |
| IC513 | GTTCCAGCTCTTCCGAGAAAACCCGCCAACCCCCACC (SEQ ID NO: 88) |
| IC514 | GTTCCAGCTCTTCCTGCACAAAAGGGAGGTATTTCACT (SEQ ID NO: 89) |
| AD1261 | CAGCGGCGCTGCTAAGAACTT (SEQ ID NO: 90) |
| AD1262 | CCGGCTGGCAAATGAGGCAT (SEQ ID NO: 91) |
| IC208 | GCTTCCTTAGCTTGCGAAATCTCGA (SEQ ID NO: 82) |
| IC310 | GTTCGGCTAAACCCAAAAGTAAAAAC (SEQ ID NO: 83) |

Example 2

Effects of genetically modified *C. acnes* strains are tested in vitro for their effects on immune cells, in particular for their ability to induce specific cytokines or immune profiles, according to previously described protocols.

In particular, the protocol disclosed in Yu et al. (2016) Journal of Investigative Dermatology 136:2221-2228, with optional modifications and/or adaptations if needed, is implemented on said strains.

Example 3: Secretion of Antigens by Engineered *C. acnes* Strains

The pilosebaceous unit (PSU) is a complex skin appendage containing a diverse set of cells such as immune cells, sebaceous cells and stem cells. It is also a highly vascularized area making it an entry point for systemic delivery of molecules. The PSU microbiota is dominated by *C. acnes*, therefore the ability to engineer *C. acnes* to secrete recombinant proteins in situ is of great interest to both modulate the activity of the cells present as well as for the delivery of molecules in the blood. The present example demonstrates the use of DNA vectors that once introduced into *C. acnes* lead to the secretion of recombinant proteins, here the chicken ovalbumin antigen protein. This invention opens possibilities to use engineered *C. acnes* strains secreting specific proteins of interest such as antigens as skin probiotics. Alternatively engineered phages or phage-derived particles can be used to deliver DNA vectors, encoding for the secretion of protein of interest, in the *C. acnes* population already present in the PSU.

*C. acnes* is one of the, if not the, most abundant and prevalent bacterial commensal of the human skin. It resides mostly in the PSU even if it can also be isolated from the skin surface. Specific strains belonging to specific phylotypes have been associated with acne vulgaris disease and are considered to be "pro-inflammatory". In order to characterize the difference between the different *C. acnes* phylotypes, a few studies have been characterizing the secretome in order to identify potential proteins specific to the pro-inflammatory phenotypes. Using a subset of the identified secreted proteins, the present inventors were able to identify putative secretion signal peptides (Table 5) using signalP (Armenteros, J. et al. SignalP 5.0 improves signal peptide predictions using deep neural networks. *Nat Biotechnol* 37, 420-423 (2019)).

To test the ability of these secretion signal peptides to drive secretion of a recombinant protein in *C. acnes*, the present inventors built several replicative plasmids comprising:
- a promoter driving the expression of the recombinant protein,
- a signal peptide addressing the proteins to secretion systems fused to the N-terminal of a chicken ovalbumin CDS codon optimized for *C. acnes*,
- an erythromycin selection marker for *C. acnes*, and
- an origin of replication functional in *C. acnes*.

Figure 9A:
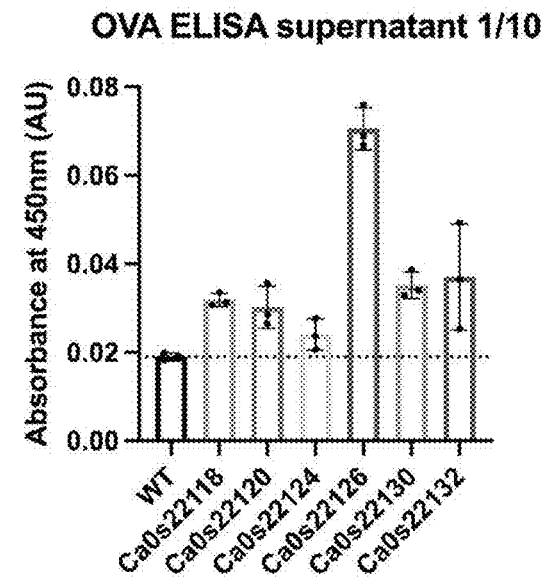
FIG. 9A and FIG. 9B represent two independent replicas. Bar graphs represent the mean of three technical replicates of the same supernatant culture. *C. acnes* strains ATCC 11828 (WT) was used as negative control.
Figure 9B:
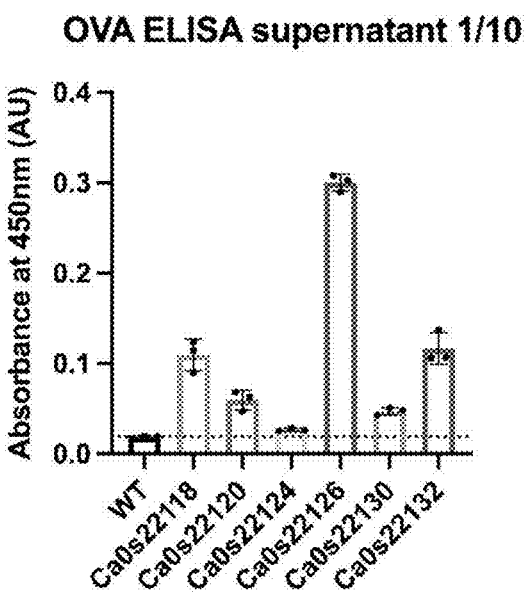
Figure 10:
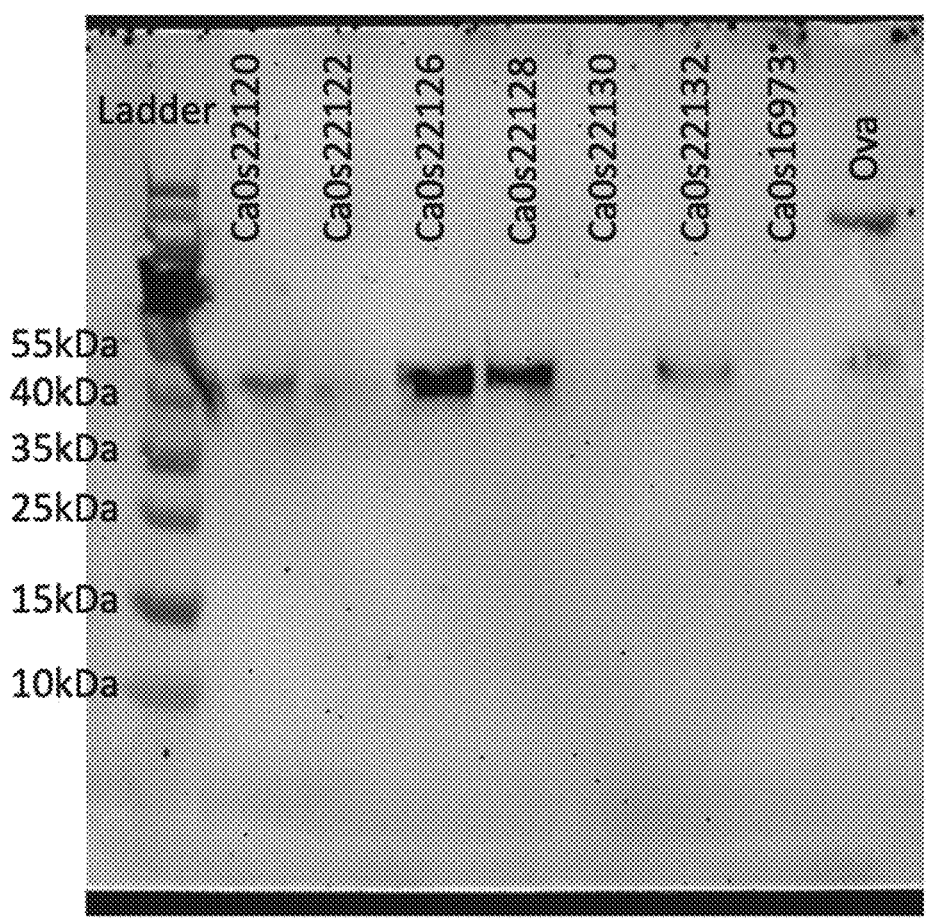
FIG. 10 depicts an ovalbumin specific western blot on culture supernatant from different *C. acnes* strains engineered to secrete ovalbumin. From left to right: (1) Pageruler ladder, (2) supernatant from strain Ca0s22120, (3) supernatant from strain Ca0s22122, (4) supernatant from strain Ca0s22126, (5) supernatant from strain Ca0s22128, (6)

The different DNA vectors (Table 6) were introduced into *C. acnes* ATCC 11828 (Table 7). Introduction into *C. acnes* cells can be performed by different methods such as electroporation, electroporation of protoplast, conjugation, chemical transformation, transduction into the *C. acnes*. Presence of the DNA vectors into *C. acnes* was confirmed, after streaking on selective plates, by colony PCR. Secretion of chicken ovalbumin protein in the different *C. acnes* culture supernatants was monitored using ELISA (FIG. 9) and Western Blot (FIG. 10). As shown in FIG. 9, both replicas of ELISA experiment show a significantly higher absorbance for most engineered *C. acnes* strains, except Ca0s22124, compared to wild-type *C. acnes* (*C. acnes* ATCC 11828). Strain Ca0s22126 was repeatedly giving the highest signal indicating higher level of secreted ovalbumin in culture supernatant. Secretion was further confirmed by Western blot (FIG. 10). A single band just above 40 kDa was observed for culture supernatant from strains Ca0s22120, Ca0s22122, Ca0s22126, Ca0s22128 and Ca0s22132. This band corresponds to ovalbumin size (43 kDa) and to the faint band from the ovalbumin control well. No band was observed for control strain Ca0s16973 that carries the empty plasmid used for cloning the different secretion plasmids. More intense band was found for Ca0s22126 confirming the results of the ELISA.

In conclusion, the present inventors describe for the first time the use of endogenous *C. acnes* secretion peptide for the secretion of recombinant protein by *C. acnes* using replicative DNA plasmids.

Materials and Methods:

Plasmids construction: Synthetic DNA fragments were ordered and assembled using SapI golden gate cloning in the p1047 plasmid (pIC086).

Conjugation: As described in Materials and methods of Example 1.

ELISA: The different *C. acnes* strains were streaked from cryostock into BHI+erythromycin plate, except for the control strain without plasmid that was streaked on BHI without antibiotic, and plates were incubated at 37° C. in anaerobic conditions for 4-7 days. When fully grown, 10 mL cultures of BHI+5 µg/mL erythromycin were inoculated with an inoculum from the corresponding streak and incubated one overnight at 37° C. in anaerobic conditions. After incubation, $OD_{600\ nm}$ was measured to control for difference in growth. 1 mL of culture was dispensed into a 1.5 mL tube and centrifuged 6 min at 6000 g. 10 µL of the supernatant was transferred to a high-binding 96 well-plate (Greiner 655061) prefiled with 90 µL of 1×PBS. Incubation of the covered plate during 2 hours at 37° C. was performed. After incubation, samples were discarded from the plate, 100 µL of PBS+5% bovine serum albumin (BSA) was added and the covered plate was incubated for 1 hour at 37° C. Three consecutive washing steps with 100 µL of PBS+0.05% Tween 20 were performed prior to the addition of 100 µL of primary antibody solution (Anti-OVA innovagen PA-O323-100 diluted 1/1000 in PBS 1×+1% BSA+0.05% Tween 20). The covered plate was incubated at RT for 1 hour. Following incubation, three consecutive washing steps with 100 µL of PBS+0.05% Tween 20 were performed prior to the addition of 100 µL of secondary antibody solution (Anti-rabbit Invitrogen A16035 antibody diluted 1/5000 in PBS 1×+1% BSA+0.05% Tween 20) and incubation at RT for 1 hour. After incubation, samples were discarded from the plate and final three consecutive washing steps with 100 µL of PBS+0.05% Tween 20 were performed. 100 µL of TMB-ELISA substrate (Thermo Scientific 34028) was added to each well and incubation was performed under light protection for 10 to 12 min at RT. 100 µL of 1 M sulfuric acid was added to each well to stop the reaction. Absorbance measurement at 450 nm was performed using an infinite reader (Tecan).

Western blot: The different *C. acnes* strains were streaked from cryostock into BHI+erythromycin plate, except for the control strain without plasmid that was streaked on BHI without antibiotic, and plates were incubated at 37° C. in anaerobic conditions for 4-7 days. When fully grown, 10 mL cultures of BHI+5 µg/mL erythromycin were inoculated with an inoculum from the corresponding streak and incubated one overnight at 37° C. in anaerobic conditions. After incubation, $OD_{600}$ was measured to control for difference in growth. 1 mL of culture was dispensed into a 1.5 mL tube and centrifuged 6 min at 6000 g. Filtration of the supernatant using 0.2 µm filter. 30 µL of the filtered supernatant was supplemented with 7.5 µL of LDS sample buffer (B0008 Invitrogen™) and 3 µL of Bolt™ antioxidant (BT0005 Invitrogen™) before boiling at 100° C. for 10 min. 30 µL of the mixture was loaded into a Bolt™ 4 to 12% Bis-Tris gel (NW04120 Invitrogen™). After migration, transfer on nitrocellulose membrane was performed. After the transfer, the membrane was: soaked first in 5% skim milk solution in PBS+0.05% Tween 20 for 1 h, then soaked in 20 mL 5% skim milk solution in PBS+0.05% Tween 20 containing the primary antibody (Anti-OVA innovagen PA-O323-100) diluted 1:1000 overnight at 4° C., washed three times with PBS+Tween 0.05%, soaked 1 h in 20 mL 5% skim milk solution in PBS+0.05% Tween 20 containing the secondary antibody (Anti-rabbit Invitrogen A16035 antibody) diluted 1:5000, washed three times with PBS+Tween 0.05%. Final step of revelation was performed using chemiluminescent substrate (34580 Thermofisher). Imaging was done using iBright CL1000 (Invitrogen™).

TABLE 5

Secreted proteins used to extract secretion signals

| Protein id | SignalP 5.0 prediction |
|---|---|
| YP_056615.1 | Prediction: Signal peptide (Sec/SPI) Cleavage site between pos. 23 and 24: GAA-TP. Probability: 0.4339 |
| YP_056817.1 | Prediction: Lipoprotein signal peptide (Sec/SPII) Cleavage site between pos. 20 and 21: LSA-CG. Probability: 0.9859 |
| YP_055402.1 | Prediction: Signal peptide (Sec/SPI) Cleavage site between pos. 28 and 29: AHA-VE. Probability: 0.9710 |
| YP_056047 | Prediction: Signal peptide (Sec/SPI) Cleavage site between pos. 28 and 29: AHA-AP. Probability: 0.8551 |

TABLE 6

DNA vectors encoding secretion of ovalbumin

| DNA vector Name | Promoter | signal peptide from | protein |
|---|---|---|---|
| p2152 | P138 | YP_056047 | chicken ovalbumin |
| p2154 | P138 | YP_055402.1 | chicken ovalbumin |
| p2156 | P138 | YP_056817.1 | chicken ovalbumin |
| p2158 | P138 | YP_056615.1 | chicken ovalbumin |
| p2160 | ProxP | YP_056047 | chicken ovalbumin |
| p2162 | ProxP | YP_055402.1 | chicken ovalbumin |
| p2164 | ProxP | YP_056817.1 | chicken ovalbumin |
| p2166 | ProxP | YP_056615.1 | chicken ovalbumin |

TABLE 7

List of *C. acnes* strains generated

| name | Strain description | plasmid |
|---|---|---|
| Ca0s22118 | *Cutibacterium acnes* ATCC 11828 | p2152 |
| Ca0s22120 | *Cutibacterium acnes* ATCC 11828 | p2154 |
| Ca0s22122 | *Cutibacterium acnes* ATCC 11828 | p2156 |
| Ca0s22124 | *Cutibacterium acnes* ATCC 11828 | p2158 |
| Ca0s22126 | *Cutibacterium acnes* ATCC 11828 | p2160 |
| Ca0s22128 | *Cutibacterium acnes* ATCC 11828 | p2162 |
| Ca0s22130 | *Cutibacterium acnes* ATCC 11828 | p2164 |
| Ca0s22132 | *Cutibacterium acnes* ATCC 11828 | p2166 |
| Ca0s16973 | *Cutibacterium acnes* ATCC 11828 | p1047 (pIC86) |

REFERENCES

1. Pasparakis, M., Haase, I. & Nestle, F. O. Mechanisms regulating skin immunity and inflammation. *Nature Reviews Immunology* 14, 289-301 (2014).

2. Scharschmidt, T. C. et al. A Wave of Regulatory T Cells into Neonatal Skin Mediates Tolerance to Commensal Microbes. *Immunity* 43, 1011-1021 (2015).
3. Oh, J. et al. Biogeography and individuality shape function in the human skin metagenome. *Nature* 514, 59-64 (2014).
4. Oh, J. et al. Biogeography and individuality shape function in the human skin metagenome. Nature 514, 59-64 (2014).
5. Nakatsuji, T. et al. The microbiome extends to subepidermal compartments of normal skin. *Nat Commun* 4, 1431 (2013).
6. Bay, L. et al. Universal Dermal Microbiome in Human Skin. *Mbio* 11, (2020).
7. Nagao, K. et al. Stress-induced production of chemokines by hair follicles regulates the trafficking of dendritic cells in skin. *Nat Immunol* 13, 744-752 (2012).
8. Adachi, T. et al. Hair follicle-derived IL-7 and IL-15 mediate skin-resident memory T cell homeostasis and lymphoma. *Nat Med* 21, 1272-1279 (2015).
9. Paus, R., Ito, N., Takigawa, M. & Ito, T. The Hair Follicle and Immune Privilege. *J Invest Derm Symp P* 8, 188-194 (2003).
10. Scholz, C. F. & Kilian, M. The natural history of cutaneous propionibacteria, and reclassification of selected species within the genus Propionibacterium to the proposed novel genera *Acidipropionibacterium* gen. nov., *Cutibacterium* gen. nov. and *Pseudopropionibacterium* gen. nov. *International Journal of Systematic and Evolutionary Microbiology* 66, 4422-4432 (2016).
11. McLaughlin, J. et al. *Propionibacterium acnes* and Acne Vulgaris: New Insights from the Integration of Population Genetic, Multi-Omic, Biochemical and Host-Microbe Studies. *Microorganisms* 7, 128 (2019).
12. Barnard, E. et al. Strains of the *Propionibacterium acnes* type III lineage are associated with the skin condition progressive macular hypomelanosis. *Scientific reports* 6, 31968 (2016).
13. Petersen, R. L. W., Scholz, C. F. P., Jensen, A., Brüggemann, H. & Lomholt, H. B. *Propionibacterium acnes* phylogenetic type III is associated with progressive macular hypomelanosis. *European J Microbiol Immunol* 7, 37-45 (2017).
14. McDowell, A., McLaughlin, J. & Layton, A. M. Is *Cutibacterium* (previously *Propionibacterium*) acnes a potential pathogenic factor in the aetiology of the skin disease progressive macular hypomelanosis? *J European Acad Dermatology Venereol Jeadv* (2020) doi:10.1111/jdv.16789.
15. Fitz-Gibbon, S. et al. *Propionibacterium acnes* Strain Populations in the Human Skin Microbiome Associated with Acne. *J Invest Dermatol* 133, 2152-2160 (2013).
16. Sörensen, M. et al. Mutagenesis of *Propionibacterium acnes* and analysis of two CAMP factor knock-out mutants. *Journal of Microbiological Methods* 83, 211-216 (2010).
17. Allhorn, M., Arve, S., Brüggemann, H. & Lood, R. A novel enzyme with antioxidant capacity produced by the ubiquitous skin colonizer Propionibacterium acnes. *Sci Rep-uk* 6, 36412 (2016).
18. Nazipi, S., Stødkilde, K., Scavenius, C. & Brüggemann, H. The Skin Bacterium *Propionibacterium acnes* Employs Two Variants of Hyaluronate Lyase with Distinct Properties. Microorg 5, 57 (2017).
19. Kasimatis, G., Fitz-Gibbon, S., Tomida, S., Wong, M. & Li, H. Analysis of Complete Genomes of *Propionibacterium acnes* Reveals a Novel Plasmid and Increased Pseudogenes in an Acne Associated Strain. *BioMed Research International* 2013, 1-11 (2013).
20. Davidsson, S. et al. Prevalence of Flp Pili-Encoding Plasmids in *Cutibacterium acnes* Isolates Obtained from Prostatic Tissue. *Frontiers in microbiology* 8, 2241 (2017).
21. Aoki, S., Nakase, K., Hayashi, N. & Noguchi, N. Transconjugation of erm(X) conferring high-level resistance of clindamycin for *Cutibacterium acnes*. *Journal of Medical Microbiology* (2018) doi:10.1099/jmm.0.000875.
22. Aoki, S. et al. Transferable Multidrug-Resistance Plasmid Carrying a Novel Macrolide-Clindamycin Resistance Gene, erm (50), in *Cutibacterium acnes*. *Antimicrob Agents Ch* 64, (2019).
23. Barnard, E., Shi, B., Kang, D., Craft, N. & Li, H. The balance of metagenomic elements shapes the skin microbiome in acne and health. *Scientific Reports* 6, srep39491 (2016).
24. Rouet, P., Smih, F. & Jasin, M. Expression of a site-specific endonuclease stimulates homologous recombination in mammalian cells. *Proc National Acad Sci* 91, 6064-6068 (1994).
25. Arazoe, T. et al. Site-specific DNA double-strand break generated by I-SceI endonuclease enhances ectopic homologous recombination in *Pyricularia oryzae*. *Ferns Microbiol Lett* 352, 221-229 (2014).
26. Liu, J. et al. The diversity and host interactions of Propionibacterium acnes bacteriophages on human skin. *The ISME Journal* 9, 2078 (2015).
27. Lood, R. & Collin, M. Characterization and genome sequencing of two *Propionibacterium acnes* phages displaying pseudolysogeny. *BMC Genomics* 12, 198 (2011).

We claim:

1. A phagemid lacking genes encoding phage structural proteins comprising:

a phage packaging signal allowing packaging of the phagemid in a *Cutibacterium acnes* phage capsid, wherein the phage packaging signal is at least 87% identical to SEQ ID NO: 76, and a gene of interest that is a transgene that is exogenous to *C. acnes*;

wherein said phagemid is packaged in a *C. acnes* phage capsid.

2. The phagemid of claim 1 further comprising an origin of replication for *C. acnes* and a selection marker for *C. acnes*.

3. The phagemid of claim 1, wherein the phagemid also comprises a CRISPR-Cas system.

4. The phagemid of claim 1, wherein the phagemid comprises a template for homologous recombination with *C. acnes* phages.

5. The phagemid DNA vector of claim 1, wherein the phagemid comprises a template for homologous recombination with *C. acnes* plasmids.

6. The phagemid of claim 3, wherein the phagemid comprises a template for homologous recombination and wherein the CRISPR-Cas system targets the phagemid itself.

7. The phagemid of claim 2, wherein the selection marker is not ermE.

8. The phagemid of claim 2, wherein the selection marker is catA.

9. The phagemid of claim 1, which comprises a DNA encoding an antigen.

10. An engineered *C. acnes* comprising the phagemid of claim 1.

11. The engineered *C. acnes* according to claim 10, wherein the phagemid comprises a DNA encoding an antigen.

12. An engineered *C. acnes* produced by contacting *C. acnes* with the phagemid of claim 1, modifying the *C. acnes* with a gene of interest carried by the phagemid, selecting for the modification, and curing the *C. acnes* of the phagemid.

13. The engineered *C. acnes* of claim 10, wherein the *C. acnes* has been modified by a CRISPR-Cas system carried by the phagemid.

14. The engineered *C. acnes* of claim 10, wherein the *C. acnes* has been modified by insertion of an exogenous gene into the *C. acnes* chromosome.

15. A method for engineering a *C. acnes* comprising introducing the phagemid of claim 1 into a *C. acnes*.

16. The method of claim 15, further comprising selecting a modified *C. acnes*.

17. The method of claim 16, comprising selecting a modified *C. acnes* that has an insertion of an exogenous gene into the *C. acnes* chromosome.

18. A vaccine and/or immunogenic composition comprising the engineered *C. acnes* of claim 10 comprising a phagemid comprising a nucleic acid encoding an antigen.

* * * * *

SEQUENCE LISTING

<160> NUMBER OF SEQ ID NOS: 91

<210> SEQ ID NO 1
<211> LENGTH: 38
<212> TYPE: DNA
<213> ORGANISM: Artificial Sequence
<220> FEATURE:
<223> OTHER INFORMATION: oriT_pMRC01

<400> SEQUENCE: 1
acaccaccca attttggagt ggtgtgtaag tgcgcatt                          38

<210> SEQ ID NO 2

```
<211> LENGTH: 38
<212> TYPE: DNA
<213> ORGANISM: Artificial Sequence
<220> FEATURE:
<223> OTHER INFORMATION: oriT_RSF1010

<400> SEQUENCE: 2
ccagtttctc gaagagaaac cggtaagtgc gccctccc                              38

<210> SEQ ID NO 3
<211> LENGTH: 40
<212> TYPE: DNA
<213> ORGANISM: Artificial Sequence
<220> FEATURE:
<223> OTHER INFORMATION: oriT_pRS01

<400> SEQUENCE: 3
tccgtaagat gctatcatct tactatgctt gcaaaaggtc                            40

<210> SEQ ID NO 4
<211> LENGTH: 41
<212> TYPE: DNA
<213> ORGANISM: Artificial Sequence
<220> FEATURE:
<223> OTHER INFORMATION: oriT_pMV158

<400> SEQUENCE: 4
cactttatga atataaagta tagtgtgtta tactttacat g                          41

<210> SEQ ID NO 5
<211> LENGTH: 42
<212> TYPE: DNA
<213> ORGANISM: Artificial Sequence
<220> FEATURE:
<223> OTHER INFORMATION: oriT_pTF1

<400> SEQUENCE: 5
gcacgggtaa tctcgaagag attactctaa gtgcgccctt gc                         42

<210> SEQ ID NO 6
<211> LENGTH: 45
<212> TYPE: DNA
<213> ORGANISM: Artificial Sequence
<220> FEATURE:
<223> OTHER INFORMATION: oriT_pSC101

<400> SEQUENCE: 6
gggcgcacgt ttctgaacga agtgaagaaa gtctaagtgc gccct                      45

<210> SEQ ID NO 7
<211> LENGTH: 51
<212> TYPE: DNA
<213> ORGANISM: Artificial Sequence
<220> FEATURE:
<223> OTHER INFORMATION: oriT_pBTK445

<400> SEQUENCE: 7
agcctttaaa gcgaaaatag ggtactccat gctcgctata tcatcctgac a               51

<210> SEQ ID NO 8
<211> LENGTH: 52
<212> TYPE: DNA
<213> ORGANISM: Artificial Sequence
<220> FEATURE:
<223> OTHER INFORMATION: oriT_pBBR1

<400> SEQUENCE: 8
```

```
ggtcacgact ttgcgaagca aagtctagtg agtatactca agcattgagt gg              52

<210> SEQ ID NO 9
<211> LENGTH: 53
<212> TYPE: DNA
<213> ORGANISM: Artificial Sequence
<220> FEATURE:
<223> OTHER INFORMATION: oriT_R721

<400> SEQUENCE: 9
cacacgattg taacatgacc ggaacggtct tgtgtacaat cggtatcgtg cct             53

<210> SEQ ID NO 10
<211> LENGTH: 59
<212> TYPE: DNA
<213> ORGANISM: Artificial Sequence
<220> FEATURE:
<223> OTHER INFORMATION: oriT_pRmeGR4a

<400> SEQUENCE: 10
gcaggaaaac ggcgtagcac attttttccgt atcctgcccc tccacattgt aagggatt       59

<210> SEQ ID NO 11
<211> LENGTH: 60
<212> TYPE: DNA
<213> ORGANISM: Artificial Sequence
<220> FEATURE:
<223> OTHER INFORMATION: oriT_ColE1

<400> SEQUENCE: 11
gggtgtcggg gcgcagccct gacccagtca cgtagcgata gcggagtgta tactggctta     60

<210> SEQ ID NO 12
<211> LENGTH: 61
<212> TYPE: DNA
<213> ORGANISM: Artificial Sequence
<220> FEATURE:
<223> OTHER INFORMATION: oriT_pTiC58

<400> SEQUENCE: 12
ggatccaagg gcgcaattat acgtcgctga cgcgacgcct tgcgtagggg gccaaacagg     60
g                                                                    61

<210> SEQ ID NO 13
<211> LENGTH: 64
<212> TYPE: DNA
<213> ORGANISM: Artificial Sequence
<220> FEATURE:
<223> OTHER INFORMATION: oriT_pMdT1

<400> SEQUENCE: 13
aggtttcggg gcgcagccct gaaccagtca cctagcgcta gcggagtgta tactggctta     60
gtat                                                                 64

<210> SEQ ID NO 14
<211> LENGTH: 71
<212> TYPE: DNA
<213> ORGANISM: Artificial Sequence
<220> FEATURE:
<223> OTHER INFORMATION: oriT_R1

<400> SEQUENCE: 14
agcaaatcag caaaaacttg tttttgcgtg gggtgtggtg cttttggtgg tgagaaccac     60
```
caacctgttg a    71

<210> SEQ ID NO 15
<211> LENGTH: 71
<212> TYPE: DNA
<213> ORGANISM: Artificial Sequence
<220> FEATURE:
<223> OTHER INFORMATION: oriT_Tn5520

<400> SEQUENCE: 15
cttattgggg aattttcagc gatacggagt attgcggctc ggaaaattcc ctaataagct    60 acggtattttt c    71

<210> SEQ ID NO 16
<211> LENGTH: 90
<212> TYPE: DNA
<213> ORGANISM: Artificial Sequence
<220> FEATURE:
<223> OTHER INFORMATION: oriT_QKH54

<400> SEQUENCE: 16
gtgaagatag ttaaccggct tgccggttag ctaacttcac ctatcttgcc cggctcttcg    60
agccgtttaa cgccaggtga gtatcgcata    90

<210> SEQ ID NO 17
<211> LENGTH: 92
<212> TYPE: DNA
<213> ORGANISM: Artificial Sequence
<220> FEATURE:
<223> OTHER INFORMATION: oriT_R64

<400> SEQUENCE: 17
ggggtgtcgg ggcgaagccc tgaccagatg gcaattgtaa tagcgtcgcg tgtgacggta    60
ttacaattgc acatcctgtc ccgttttttcg gg    92

<210> SEQ ID NO 18
<211> LENGTH: 99
<212> TYPE: DNA
<213> ORGANISM: Artificial Sequence
<220> FEATURE:
<223> OTHER INFORMATION: oriT_R751

<400> SEQUENCE: 18
gaataaggga cagtgaagat agataaccgg ctcgccggtt agctaacttc acacatcctg    60
cccgccttac ggcgttaata acaccaagga aagtctaca    99

<210> SEQ ID NO 19
<211> LENGTH: 814
<212> TYPE: DNA
<213> ORGANISM: Artificial Sequence
<220> FEATURE:
<223> OTHER INFORMATION: oriT_RP4

<400> SEQUENCE: 19
cgacaggctc atgccggccg ccgccgcctt ttcctcaatc gctcttcgtt cgtctggaag    60
gcagtacacc ttgataggtg ggctgcccct cctggttggc ttggtttcat cagccatccg    120
cttgccctca tctgttacgc cggcggtagc cggccagcct cgcagagcag gattcccgtt    180
gagcaccgcc aggtgcgaat aagggacagt gaagaaggaa cacccgctcg cgggtgggcc    240
tacttcacct atcctgcccg gctgacgccg ttggatacac caaggaaagt ctacacgaac    300
cctttggcaa aatcctgtat atcgtgcgaa aaaggatgga tataccgaaa aaatcgctat    360

```
aatgaccccg aagcagggtt atgcagcgga aaagcgctgc ttccctgctg ttttgtggaa    420
tatctaccga ctggaaacag gcaaatgcag gaaattactg aactgagggg acaggcgaga    480
gacgatgcca aagagctaca ccgacgagct ggccgagtgg gttgaatccc gcgcggccaa    540
gaagcgccgg cgtgatgagg ctgccggttgc gttcctggcg gtgagggcgg atgtcgaggc    600
ggcgttagcg tccggctatg cgctcgtcac catttgggag cacatgcggg aaacggggaa    660
ggtcaagttc tcctacgaga cgttccgctc gcacgccagg cggcacatca aggccaagcc    720
cgccgatgtg cccgcaccgc aggccaaggc tgcggaaccc gcgccggcac ccaagacgcc    780
ggagccacgg cggccgaagc aggggggcaa ggct                                814

<210> SEQ ID NO 20
<211> LENGTH: 100
<212> TYPE: DNA
<213> ORGANISM: Artificial Sequence
<220> FEATURE:
<223> OTHER INFORMATION: oriT_pKL1

<400> SEQUENCE: 20
cggggtgtcg gggtgaagcc ctgaccaagt ggtaatcgta tcggcgtgca tgcgcggtta     60
tacgattaca catcctgtcc cgatttctga ggcgttttaa                          100

<210> SEQ ID NO 21
<211> LENGTH: 112
<212> TYPE: DNA
<213> ORGANISM: Artificial Sequence
<220> FEATURE:
<223> OTHER INFORMATION: oriT_RK2

<400> SEQUENCE: 21
ccggccagcc tcgcagagca ggattcccgt tgagcaccgc caggtgcgaa taagggacag     60
tgaagaagga acaccgctc gcgggtgggc ctacttcacc tatcctgccc gg             112

<210> SEQ ID NO 22
<211> LENGTH: 160
<212> TYPE: DNA
<213> ORGANISM: Artificial Sequence
<220> FEATURE:
<223> OTHER INFORMATION: oriT_R1162

<400> SEQUENCE: 22
ggccagtttc tcgaagagaa accggtaaat gcgccctccc ctacaaagta gggtcgggat     60
tgccgccgct gtgcctccat gatagcctac gagacagcac attaacaatg gggtgtcaag   120
atggttaagg ggagcaacaa ggcggcggat cggctggcca                         160

<210> SEQ ID NO 23
<211> LENGTH: 174
<212> TYPE: DNA
<213> ORGANISM: Artificial Sequence
<220> FEATURE:
<223> OTHER INFORMATION: oriT_Tn4555

<400> SEQUENCE: 23
ccctcgggag agcccacaac tacgtaagcg gagcgtgtag ttatagtggg ctatatcaat     60
ggcaagccat tgtctgcaaa ctccagccta cggcttccgc tctcctccgt cagggaggtt   120
tttcatcatc gttgccgatt ggagatgcac cgaccagcac aaggtctaaa tcgt         174

<210> SEQ ID NO 24
```

<211> LENGTH: 192
<212> TYPE: DNA
<213> ORGANISM: Artificial Sequence
<220> FEATURE:
<223> OTHER INFORMATION: oriT_pHT

<400> SEQUENCE: 24

| | |
|---|---:|
| ccaaagaatt aatgcaaaga gcataaggga aaactaatag caccttccta aaggaaggtg | 60 |
| gctaagttgg ctgtgccaac tggttttctt tcaaaatcac ttcatatttt ttgctatcac | 120 |
| aaaaaaatcc attttcgacc tattttcggt cataatatag tacctacttt tggtcatagt | 180 |
| ttcgtccgta gt | 192 |

<210> SEQ ID NO 25
<211> LENGTH: 199
<212> TYPE: DNA
<213> ORGANISM: Artificial Sequence
<220> FEATURE:
<223> OTHER INFORMATION: oriT_Tn4399

<400> SEQUENCE: 25

| | |
|---|---:|
| taaggtgatt atgttgtttt tcttcatctg ttctatctgt ttttagtga ataatccgat | 60 |
| tgatgtaatc tgaaaagtcc gtgaccatcg ggagccgttc ccctcatctt tttgaggggc | 120 |
| aagtggtcgg ggaatgtaat acgccgacat taacttgcta tcctaaaaaa gatgtgattt | 180 |
| acggcttaga tgccgaatc | 199 |

<210> SEQ ID NO 26
<211> LENGTH: 216
<212> TYPE: DNA
<213> ORGANISM: Artificial Sequence
<220> FEATURE:
<223> OTHER INFORMATION: oriT_Tn916

<400> SEQUENCE: 26

| | |
|---|---:|
| aagcggaagt cgcaggtgtg gactgatctt gctggctggt gtggcaatag ccacgccagc | 60 |
| acttaacccc ccgtatctaa caggggggta caaatcgaca ggaaacagtc aaaaaaacat | 120 |
| tagaaaatcc tttggttaca agggatttac aaaatttcag cgtatgtcaa atgggcttta | 180 |
| aaagttgaca tacggccttt ttgattggag ggattt | 216 |

<210> SEQ ID NO 27
<211> LENGTH: 242
<212> TYPE: DNA
<213> ORGANISM: Artificial Sequence
<220> FEATURE:
<223> OTHER INFORMATION: oriT_pST12

<400> SEQUENCE: 27

| | |
|---|---:|
| ttgtgtgatt atatcgcgta ccacttttcg actgttttac cgccggtatt ctgccgtctg | 60 |
| acgctttgac gggtatttct gcctgacaat actgtcactg ccaaaaaact gccgtgcctt | 120 |
| tgtcggtaat tcgagcttgc tgacaggaca ggatgtgcaa ttgttatacc gcgcatacat | 180 |
| gcacgctatt acaattaccc tggtcagggc ttcgccccga caccccatgt cagatacgga | 240 |
| gc | 242 |

<210> SEQ ID NO 28
<211> LENGTH: 268
<212> TYPE: DNA
<213> ORGANISM: Artificial Sequence
<220> FEATURE:
<223> OTHER INFORMATION: oriT_pCU1

<400> SEQUENCE: 28

```
gtattaccaa agtaataaag caaactcatt ataaaacaat gagttattag gtgtttttaa      60
tacctaatta ttaccgaata ttgacgctat ttatttttt attttttaaa tcagtgtgat      120
agcgtgattt atgccgctgc gttaggtgta tagcaggtta agggataaaa aatcatctttt   180 tttggtagga gcgatctacg taggttaagg actaactgac taaaaagcgt tcaatattcc    240
gtattcatgc ttgcatgaat accagtac                                       268
```

<210> SEQ ID NO 29
<211> LENGTH: 279
<212> TYPE: DNA
<213> ORGANISM: Artificial Sequence
<220> FEATURE:
<223> OTHER INFORMATION: oriT_pSU233
<220> FEATURE:
<221> NAME/KEY: misc_feature
<222> LOCATION: (199)..(199)
<223> OTHER INFORMATION: n is a, c, g, or t

<400> SEQUENCE: 29

```
cgctagcagc gcccctgacg gtatcctata aaaaaacaca ccgcgccgct agcagcaccc     60
ctaatataaa ataatgtttt ttataaaaat agtcagtacc accctacaa agcggtgtcg    120 gcgcgttgct gtagctgcgt taacgacgct gctttaaata aatcagattt aaacaatata   180
aatccacaaa tacaactcna tgatattaaa gataaatcag caaaaacttg tttttgcgtg   240
gggtgtggtg cttttggtgg tgagaaccac caacctgtt                           279
```

<210> SEQ ID NO 30
<211> LENGTH: 290
<212> TYPE: DNA
<213> ORGANISM: Artificial Sequence
<220> FEATURE:
<223> OTHER INFORMATION: oriT_F

<400> SEQUENCE: 30

```
cgcaccgcta gcagcgcccc tagcggtatc ctataaaaaa acacaccgcg ccgctagcag     60 caccctaat ataaaataat gttttttata aaaatagtca gtaccacccc tacaaaacgg   120
tgtcggcgcg ttgttgtagc cgcgccgaca ccgcttttt aaatatcata agagagtaa    180 gagaaactaa ttttcataa cactctattt ataagaaaa atcagcaaaa acttgttttt    240
gcgtggggtg tggtgctttt ggtggtgaga accaccaacc tgttgagcct              290
```

<210> SEQ ID NO 31
<211> LENGTH: 304
<212> TYPE: DNA
<213> ORGANISM: Artificial Sequence
<220> FEATURE:
<223> OTHER INFORMATION: oriT_pMAB01

<400> SEQUENCE: 31

```
tgcctcgcag agcaggatga cccgttgagc gccccggcg cgaataaggg acagtgaaga      60
tagataaccg gctcgccggt tagctaactt cacacatcct gcccgcccta cggcgttaat   120
aacaccaagg aaagtctaca ccagccatta cgatttatcc gcaactatcg cgctatcagg   180
ccgcaaaagc agcaacggat atagcgaaaa ccgccacaat ggcccataat gccgctatcg   240
aagcgtgcca atgcacgccg atagcggact ttttgcgttt ccgtagcgcc gcttagtagc   300
gtta                                                                 304
```

<210> SEQ ID NO 32
<211> LENGTH: 402
<212> TYPE: DNA
<213> ORGANISM: Artificial Sequence
<220> FEATURE:
<223> OTHER INFORMATION: oriT_R388

<400> SEQUENCE: 32

```
ccgcctcgtc ctccaaaagt gcctgctttt ccgggcttag ccgtacttgg atggggtcgc      60
ctagtgccat gtcctctccc gtagtgttac tgtagtggtt caatcctagc atttacaagg     120
ggttgcggca atattgtagt ggcataacac tacacaggtt ttcgtccttg gcgtggaagt     180
cattgtaaat caatgactta cgcgcaccga aggtgcgta ttgtctatag cccagattta      240
aggataccaa cccggctttt aaggacggaa accatgcgat aacgccagcg tgaccctaaa     300
gagggtcaaa actgctccca atgcgctatg cgcattgggt tatcgtgcag caatgatgca     360
actataatgc tatgatggtg ctacaatgat gcagaaaatg ag                         402
```

<210> SEQ ID NO 33
<211> LENGTH: 456
<212> TYPE: DNA
<213> ORGANISM: Artificial Sequence
<220> FEATURE:
<223> OTHER INFORMATION: oriT_pS7a

<400> SEQUENCE: 33

```
ggatgatcaa acaaaatacg agagattttt tgttcgttca tccatggttt tagaaaaaag      60
agggacgatt tcggaagaag aaaatcgtct cttttttttc ttcttttgt atgacaaaaa      120
gaaagatctt tgcccatttt tattttta taaatgggc aggtggcgtt tgcgtaaagc        180
aaatcgacac aatccaaagg ggataaaagg ggaaagtgaa acttcccct tttcaagcca      240
cattgtaata caagaacgaa gtgctttgta ttacaatgtg atagcttgca gtatttatgg     300
ttttatatgg tctattttgt tgtgaggatt gtaaccgaat agggcgcaat acttattaca     360
aaatcaatga caaagggcga ttgagaaatg agcgctgggg cattttatct ttgaggaagt     420
tcttgatgga tcagaaaaat gtatcacaaa tttaaa                                456
```

<210> SEQ ID NO 34
<211> LENGTH: 456
<212> TYPE: DNA
<213> ORGANISM: Artificial Sequence
<220> FEATURE:
<223> OTHER INFORMATION: oriT_pS7b

<400> SEQUENCE: 34

```
tggatgatca acaaaatac gagagatttt ttgttcgttc atccatggtt ttagaaaaaa        60
gagggacgat tcggaagaa gaaaatcgtc tcttttttt cttctttttg tatgacaaaa       120
agaaagatct tttgcccatt tttattttt ataaatggg caggtggcgt tgcgtaaag        180
caaatcgaca caatccaaag gggataaaag gggaaagtga acttccccc ttttcaagcc      240
acattgtaat acaagaacga agtgctttgt attacaatgt gatagcttgc agtatttatg     300
gttttatatt tccatttttg ttgtgaggat tgtaaccgaa tagggcgcaa tgcttattac     360
aaaatcaatg acaaagggcg agtgaggaat gagcgctgag gcattttatc tttgaggaag     420
ttcttgatgg atcagaaaaa tgtatcacaa atttaa                                456
```

<210> SEQ ID NO 35
<211> LENGTH: 697

<212> TYPE: DNA
<213> ORGANISM: Artificial Sequence
<220> FEATURE:
<223> OTHER INFORMATION: oriT_R702

<400> SEQUENCE: 35

| | | | | | |
|---|---|---|---|---|---|
| ccctgcttcg | gggtcattat | agcgattttt | tcggtatatc | catccttttt | cgcacgatat | 60 |
| acaggatttt | gccaaagggt | tcgtgtagac | tttccttggt | gtatccaacg | gcgtcagccg | 120 |
| ggcaggatag | gtgaagtagg | cccacccgcg | agcgggtgtt | ccttcttcac | tgtcccttat | 180 |
| tcgcacctgg | cggtgctcaa | cgggaatcct | gctctgcgag | gctggccggc | taccgccggc | 240 |
| gtaacagatg | agggcaagcg | gatggctgat | gaaaccaagc | caaccaggaa | gggcagccca | 300 |
| cctatcaagg | tgtactgcct | tccagacgaa | cgacgagcga | ttgaggaaaa | ggcggcggcg | 360 |
| gccggcatga | gcctgtcggc | ctacctgctg | gccgtcggcc | agggctacaa | aatcacgggc | 420 |
| gtcgtggact | atgagcacgt | ccgcgagctg | gcccgcatca | atggcgacct | gggccgcctg | 480 |
| ggcggcctgc | tgaaactctg | gctcaccgac | gacccgcgca | cggcgcggtt | cggtgatgcc | 540 |
| acgatcctcg | ccctgctggc | gaagatcgaa | gagaagcagg | acgagcttgg | caaggtcatg | 600 |
| atgggcgtgg | tccgcccgag | ggcagagcca | tgactttttt | agccgctaaa | acggccgggg | 660 |
| ggtgcgcgtg | attgccaagc | acgtccccat | gcgctcc | | | 697 |

<210> SEQ ID NO 36
<211> LENGTH: 475
<212> TYPE: DNA
<213> ORGANISM: Artificial Sequence
<220> FEATURE:
<223> OTHER INFORMATION: oriT_pMUR274

<400> SEQUENCE: 36

| | | | | | |
|---|---|---|---|---|---|
| actccgatac | gttgccctcc | gaacggtatt | caaggtcgat | ttttgcgct | tcggtcactc | 60 |
| ttaaactgat | agatggcata | ggtttccttt | gtgtaatacc | gatgtaatac | atacaaatct | 120 |
| agcatagatg | cggcttaatt | ccacatatgt | aatacgttgt | gtattacata | ttaaaacaca | 180 |
| aattagaata | atttgttttg | ttttcaagca | tttacgatga | aaatcgtaat | tgcgtatggt | 240 |
| gtatagccgt | taagggatac | cataccacgc | cttttttaag | ggagaaaccg | gtgttacgtg | 300 |
| caagtgaatc | gctcaaaaag | cgttcacatt | cacacctttc | atgcttgcat | gaaaggaaac | 360 |
| ggacgggaat | tagacaaaaa | taagacacga | tgagtaagtt | attgagacaa | gaaaggaca | 420 |
| caaataagac | attttttaga | aaaaaacatt | gacttgagac | tagaaatgga | caata | 475 |

<210> SEQ ID NO 37
<211> LENGTH: 550
<212> TYPE: DNA
<213> ORGANISM: Artificial Sequence
<220> FEATURE:
<223> OTHER INFORMATION: oriT_R100

<400> SEQUENCE: 37

| | | | | | |
|---|---|---|---|---|---|
| ttactctggc | cataagataa | aaccttcat | tattaagcaa | cgaacttttc | actataaata | 60 |
| tgcatatagt | gtttacaagt | aagaaagaca | ctcctagcag | cgcctctagg | atcatcctat | 120 |
| aaaaaaatgc | gatccggcgc | tagggcgtc | cctaatatat | atcaatgttt | ttcgtgaaaa | 180 |
| ttgtcagtac | tgatcctaat | aagagtcgct | ataggtcgt | aacaggatcg | ccaacgactc | 240 |
| tctatttaat | aattcagaat | tattaaatat | aaatagcgtt | tgttaattac | atgatttaaa | 300 |
| acgtaaatca | gcaaaaactt | gttttgcgt | agtgtgtggt | gctttggtg | gtgagaacca | 360 |

```
ccaacctgtt gagcctttt gtggagtggg ttaaattatt tacggataaa gtcaccagag    420
gtggaaaaat gaaaaaatgg atgttagcaa tctgcctgat gttttataaat gggatctgcg    480 aagccgccga ttgctttgat cttgcaggtc gggattacaa aatagacccg gatttactaa    540
gaatgatatc                                                            550
```

```
<210> SEQ ID NO 38
<211> LENGTH: 551
<212> TYPE: DNA
<213> ORGANISM: Artificial Sequence
<220> FEATURE:
<223> OTHER INFORMATION: oriT_pVCR94deltaX

<400> SEQUENCE: 38
gagcagagct atgtgtgaca agaagtatag agattacgag gtagccatca tggtcgatgt     60 gaacccttc gacagggtta tgaatgaatt gaaaagtcgt ggccgcaaga acgctcacat    120
cctgagcatc ctccaattcg actggcctgc atcggaggcc atcatcgaga agctgagctg    180
ctacatcaca gacgggatta aggctaatca ggagcctgtg atttacccga tcattgaaga    240
agctctgcat cgctacagcc agctcgtgtt tcatgagcag agagagaaat atgaagaccc    300
ggccagaatt ggggcatttc tggaaaccct gatcaccgaa acctgccggg cgttggaagt    360
gcaaattgtc gatagtggcg gtgattcatg gtctgtcgat tcaggagagt cgttctcact    420
gtggctttct tcccatccag gagaactatc cattaacccg cagcccatg aggatgagac    480 ctctttgcgt ggcttgctgt atgagctcat cacctgtgag agcgtgaaaa ctgttttaag    540
gagaaccgac t                                                        551
```

```
<210> SEQ ID NO 39
<211> LENGTH: 650
<212> TYPE: DNA
<213> ORGANISM: Artificial Sequence
<220> FEATURE:
<223> OTHER INFORMATION: oriT_R46

<400> SEQUENCE: 39
agcgccgcag ataatctgac cgattacctc ctgaaaccag gtctatatag gccaaaaagt     60
tcatctgata cttttgcggt tattattggc attcagtcct cacattgtgc atttcttaaa    120
caaaagattg ggatctaaca agctgaaatc ttagtattac caaagtaata aagcaaactc    180
attataaaac aatgagttat taggtgtttt taatacctaa ttattaccga atattgacgc    240 tatttattt tttatttttt aaatcagtgt gatagcgtga tttatgccgc tgcgttaggt    300
gtatagcagg ttaagggata aaaaatcatc tttttggta ggagcgatct acgtaggtta    360
aggactaact gactaaaaag cgttcaatat tccgtattca tgcttgcatg aataccagta    420
caacactatt acaacaaaag tacatcaaaa ttacatcaaa agtacatcac ttgaaggttg    480
acagtacaac agaattacat cattatctgg tactgaggta gccagtacaa caaaagtaca    540
tcaaaaatac atcataaata catcagaaat acatcaaaat tacatcattc taaatgaggg    600
tactatgaag cccaaaagta tcagggcggc acttcagttg atgttgccgg                650
```

```
<210> SEQ ID NO 40
<211> LENGTH: 36
<212> TYPE: DNA
<213> ORGANISM: Artificial Sequence
<220> FEATURE:
<223> OTHER INFORMATION: oriT_pGO1

<400> SEQUENCE: 40
```

```
cacgcgaacg gaacgttcgc ataagtgcgc ccttac                                36
```

<210> SEQ ID NO 41
<211> LENGTH: 38
<212> TYPE: DNA
<213> ORGANISM: Artificial Sequence
<220> FEATURE:
<223> OTHER INFORMATION: oriT_pIP501

<400> SEQUENCE: 41

```
atacgaagta acgaagttac tgcgtataag tgcgccct                              38
```

<210> SEQ ID NO 42
<211> LENGTH: 392
<212> TYPE: DNA
<213> ORGANISM: Artificial Sequence
<220> FEATURE:
<223> OTHER INFORMATION: R6K

<400> SEQUENCE: 42

```
gatctgaaga tcagcagttc aacctgttga tagtacgtac taagctctca tgtttcacgt      60
actaagctct catgtttaac gtactaagct ctcatgttta acgaactaaa ccctcatggc     120
taacgtacta agctctcatg gctaacgtac taagctctca tgtttcacgt actaagctct     180
catgtttgaa caataaaatt aatataaatc agcaacttaa atagcctcta aggttttaag     240
ttttataaga aaaaaagaa tatataaggc ttttaaagcc tttaaggttt aacggttgtg      300
gacaacaagc cagggatgta acgcactgag aagcccttag agcctctcaa agcaattttg     360
agtgacacag gaacacttaa cggctgacat gg                                   392
```

<210> SEQ ID NO 43
<211> LENGTH: 2222
<212> TYPE: DNA
<213> ORGANISM: Artificial Sequence
<220> FEATURE:
<223> OTHER INFORMATION: RK2

<400> SEQUENCE: 43

```
gcgatgcagg tggctgctga acccccagcc ggaactgacc ccacaaggcc ctagcgtttg      60
caatgcacca ggtcatcatt gacccaggcg tgttccacca ggccgctgcc tcgcaactct     120
tcgcaggctt cgccgacctg ctcgcgccac ttcttcacgc gggtggaatc cgatccgcac     180
atgaggcgga aggtttccag cttgagcggg tacggctccc ggtgcgagct gaaatagtcg     240
aacatccgtc gggccgtcgg cgacagcttg cggtacttct cccatatgaa tttcgtgtag     300
tggtcgccag caaacagcac gacgatttcc tcgtcgatca ggacctggca acgggacgtt     360
ttcttgccac ggtccaggac gcggaagcgg tgcagcagcg acaccgattc caggtgccca     420
acgcggtcgg acgtgaagcc catcgccgtc gcctgtaggc gcgacaggca ttcctcggcc     480
ttcgtgtaat accggccatt gatcgaccag cccaggtcct ggcaaagctc gtagaacgtg     540
aaggtgatcg gctcgccgat aggggtgcgc ttcgcgtact ccaacacctg ctgccacacc     600
agttcgtcat cgtcggcccg cagctcgacg ccggtgtagg tgatcttcac gtccttgttg     660
acgtggaaaa tgaccttgtt ttgcagcgcc tcgcgcggga ttttcttgtt gcgcgtggtg     720
aacagggcag agcgggccgt gtcgtttggc atcgctcgca tcgtgtccgg ccacggcgca     780
atatcgaaca ggaaagctg catttccttg atctgctgct tcgtgtgttt cagcaacgcg     840
gcctgcttgg cttcgctgac ctgttttgcc aggtcctcgc cggcggtttt tcgcttcttg     900
```

| | |
|---|---|
| gtcgtcatag ttcctcgcgt gtcgatggtc atcgacttcg ccaaacctgc cgcctcctgt | 960 |
| tcgagacgac gcgaacgctc cacggcggcc gatggcgcgg gcagggcagg gggagccagt | 1020 |
| tgcacgctgt cgcgctcgat cttggccgta gcttgctgga ctatcgagcc gacggactgg | 1080 |
| aaggtttcgc ggggcgcacg catgacggtg cggcttgcga tggtttcggc atcctcggcg | 1140 |
| gaaaaccccg cgtcgatcag ttcttgcctg tatgccttcc ggtcaaacgt ccgattcatt | 1200 |
| caccctcctt gcgggattgc cccggaatta attccccgga tcgatccgtc gatcttgatc | 1260 |
| ccctgcgcca tcagatcctt ggcggcaaga aagccatcca gtttactttg cagggcttcc | 1320 |
| caaccttacc agagggcgcc ccagctgca attccggttc gcttgctgtc cataaaaccg | 1380 |
| cccagtctag ctatcgccat gtaagcccac tgcaagctac ctgctttctc tttgcgcttg | 1440 |
| cgttttccct tgtccagata gcccagtagc tgacattcat ccggggtcag caccgttttct | 1500 |
| gcggactggc tttctacgtg gctgccattt ttggggtgag gccgttcgcg gccgaggggc | 1560 |
| gcagcccctg gggggatggg aggcccgcgt tagcgggccg ggagggttcg agaaggggggg | 1620 |
| gcacccccct tcggcgtgcg cggtcacgcg cacagggcga gccctggtt aaaaacaagg | 1680 |
| tttataaata ttggtttaaa agcaggttaa aagacaggtt agcggtggcc gaaaaacggg | 1740 |
| cggaaaccct tgcaaatgct ggattttctg cctgtggaca gccctcaaa tgtcaatagg | 1800 |
| tgcgcccctc atctgtcagc actctgcccc tcaagtgtca aggatcgcgc ccctcatctg | 1860 |
| tcagtagtcg cgcccctcaa gtgtcaatac cgcagggcac ttatcccag gcttgtccac | 1920 |
| atcatctgtg ggaaactcgc gtaaaatcag gcgttttcgc cgatttgcga ggctggccag | 1980 |
| ctccacgtcg ccgccgaaa tcgagcctgc ccctcatctg tcaacgccgc gccgggtgag | 2040 |
| tcggcccctc aagtgtcaac gtccgcccct catctgtcag tgagggccaa gttttccgcg | 2100 |
| aggtatccac aacgccggcg gccctacatg gctctgctgt agtgagtggg ttgcgctccg | 2160 |
| gcagcggtcc tgatcccccg cagaaaaaaa ggatctcaag aagatccttt gatcttttct | 2220 |
| ac | 2222 |

```
<210> SEQ ID NO 44
<211> LENGTH: 1522
<212> TYPE: DNA
<213> ORGANISM: Artificial Sequence
<220> FEATURE:
<223> OTHER INFORMATION: pBBR1

<400> SEQUENCE: 44
```

| | |
|---|---|
| ctaccggcgc ggcagcgtta cccgtgtcgg cggctccaac ggctcgccat cgtccagaaa | 60 |
| acacggctca tcgggcatcg gcaggcgctg ctgcccgcgc cgttcccatt cctccgtttc | 120 |
| ggtcaaggct ggcaggtctg gttccatgcc cggaatgccg ggctggctgg gcggctcctc | 180 |
| gccggggccg gtcggtagtt gctgctcgcc cggatacagg gtcgggatgc ggcgcaggtc | 240 |
| gccatgcccc aacagcgatt cgtcctggtc gtcgtgatca accaccacgg cggcactgaa | 300 |
| caccgacagg cgcaactggt cgcggggctg gcccacgcc acgcggtcat tgaccacgta | 360 |
| ggccgacacg gtgccggggc cgttgagctt cacgacggag atccagcgct cggccaccaa | 420 |
| gtccttgact gcgtattgga ccgtccgcaa agaacgtccg atgagcttgg aaagtgtctt | 480 |
| ctggctgacc accacggcgt tctggtggcc catctgcgcc acgaggtgat gcagcagcat | 540 |
| tgccgccgtg ggtttcctcg caataagccc ggcccacgcc tcatgcgctt tgcgttccgt | 600 |
| ttgcacccag tgaccgggct tgttcttggc ttgaatgccg atttctctgg actgcgtggc | 660 |
| catgcttatc tccatgcggt aggggtgccg cacggttgcg gcaccatgcg caatcagctg | 720 |

-continued

```
caacttttcg gcagcgcgac aacaattatg cgttgcgtaa aagtggcagt caattacaga      780
ttttctttaa cctacgcaat gagctattgc gggggggtgcc gcaatgagct gttgcgtacc      840
cccctttttt aagttgttga tttttaagtc tttcgcattt cgccctatat ctagttcttt      900
ggtgcccaaa gaagggcacc cctgcggggt tcccccacgc cttcggcgcg ctccccctc       960 cggcaaaaag tggcccctcc ggggcttgtt gatcgactgc gcggccttcg gccttgccca     1020
aggtggcgct gccccttgg aaccccgca ctcgccgccg tgaggctcgg ggggcaggcg      1080
ggcgggcttc gcccttcgac tgcccccact cgcataggct gggtcgttc caggcgcgtc     1140 aaggccaagc cgctgcgcgg tcgctgcgcg agccttgacc cgccttccac ttggtgtcca     1200
accggcaagc gaagcgcgca ggccgcaggc cggaggcttt tccccagaga aaattaaaaa     1260
aattgatggg gcaaggccgc aggccgcgca gttggagccg gtgggtatgt ggtcgaaggc     1320
tgggtagccg gtgggcaatc cctgtggtca agctcgtggg caggcgcagc ctgtccatca     1380
gcttgtccag cagggttgtc cacgggccga gcgaagcgag ccagccggtg gccgctcgcg     1440
gccatcgtcc acatatccac gggctggcaa gggagcgcag cgaccgcgca gggcgaagcc     1500
cggagagcaa gcccgtaggg gg                                              1522
```

<210> SEQ ID NO 45
<211> LENGTH: 1969
<212> TYPE: DNA
<213> ORGANISM: Artificial Sequence
<220> FEATURE:
<223> OTHER INFORMATION: pRO1600

<400> SEQUENCE: 45

```
gataatctca tgaccaaaat cccttaacgt gagttttcgt tccactgagc gtcagacccc       60
gtagaaaaga tcaaaggatc ttcttgagat cctttttttc tgcgcgtaat ctgctgcttg      120
caaacaaaaa aaccaccgct accagcggtg gtttgtttgc cggatcaaga gctaccaact      180 cttttttccga aggtaactgg cttcagcaga gcgcagatac caaatactgt tcttctagtg      240
tagccgtagt taggccacca cttcaagaac tctgtagcac cgcctacata cctcgctctg      300
ctaatcctgt taccagtggc tgctgccagt ggcgataagt cgtgtcttac cgggttggac      360
tcaagacgat agttaccgga taaggcgcag cggtcgggct gaacggggg ttcgtgcaca      420 cagcccagct tggagcgaac gacctacacc gaactgagat acctacagcg tgagctatga      480
gaaagcgcca cgcttcccga agggagaaag gcggacaggc atccggtaag cggcagggtc      540
ggaacaggag agcgcacgag ggagcttcca gggggaaacg cctggtatct ttatagtcct      600
gtcgggtttc gccacctctg acttgagcgt cgatttttgt gatgctcgtc agggggggcgg      660 agcctatgga aaaacgccag caacgcggcc gtgaaaggca ggccggtccg tggtggccac      720
ggcctctagg ccagatccag cggcatctgg gttagtcgag cgcgggccgc ttcccatgtc      780
tcaccagggc gagcctgttt cgcgatctca gcatctgaaa tcttcccggc cttgcgcttc      840 gctgggggcct tacccaccgc cttggcgggc ttcttcggtc caaaactgaa caacagatgt      900
gtgaccttgc gccggtctt tcgctgcgcc cactccacct gtagcgggct gtgctcgttg      960
atctgcgtca cggctggatc aagcactcgc aacttgaagt ccttgatcga gggataccgg     1020
ccttccagtt gaaaccactt tcgcagctgg tcaatttcta tttcgcgctg gccgatgctg     1080
tcccattgca tgagcagctc gtaaagcctg atcgcgtggg tgctgtccat cttggccacg     1140
tcagccaagg cgtatttggt gaactgtttg gtgagttccg tcaggtacgg cagcatgtct     1200
```

```
ttggtgaacc tgagttctac acggccctca ccctcccggt agatgattgt ttgcacccag    1260
ccggtaatca tcacactcgg tcttttcccc ttgccattgg gctcttgggt taaccggact    1320
tcccgccgtt tcaggcgcag ggccgcttct ttgagctggt tgtaggaaga ttcgataggg    1380
acacccgcca tcgtcgctat gtcctccgcc gtcactgaat acatcacttc atcggtgaca    1440
ggctcgctcc tcttcacctg gctaatacag gccagaacga tccgctgttc ctgaacactg    1500
aggcgatacg cggcctcgac cagggcattg cttttgtaaa ccattggggg tgaggccacg    1560
ttcgacattc cttgtgtata aggggacact gtatctgcgt cccacaatac aacaaatccg    1620
tccctttaca acaacaaatc cgtcccttct taacaacaaa tccgtccctt aatggcaaca    1680
aatccgtccc tttttaaact ctacaggcca cggattacgt ggcctgtaga cgtcctaaaa    1740
ggtttaaaag gaaaaggaa  gaaagggtg  gaaacgcaaa aaacgcacca ctacgtggcc    1800
ccgttggggc cgcatttgtg cccctgaagg ggcggggag  gcgtctgggc aatcccgtt    1860
ttaccagtcc cctatcgccg cctgagaggg cgcaggaagc gagtaatcag ggtatcgagg    1920
cggattcacc cttggcgtcc aaccagcggc accagcggcg cctgagagg              1969

<210> SEQ ID NO 46
<211> LENGTH: 3674
<212> TYPE: DNA
<213> ORGANISM: Artificial Sequence
<220> FEATURE:
<223> OTHER INFORMATION: RSF1010

<400> SEQUENCE: 46
tcagcctgcc gccttgggcc gggtgatgtc gtacttgccc gccgcgaact cggttaccgt      60
ccagcccagc gcgaccagct ccggcaacgc ctcgcgcacc cgctggcggc gcttgcgcat     120
ggtcgaacca ctggcctctg acggccagac atagccgcac aaggtatcta tggaagcctt     180
gccggttttg ccggggtcga tccagccaca cagccgctgg tgcagcaggc gggcggtttc     240
gctgtccagc gcccgcacct cgtccatgct gatgcgcaca tgctggccgc cacccatgac     300
ggcctgcgcg atcaagggt  tcagggccac gtacaggcgc ccgtccgcct cgtcgctggc     360
gtactccgac agcagccgaa acccctgccg cttgcgccaa ttctgggcga tgatggatac     420
cttccaaagg cgctcgatgc agtcctgtat gtgcttgagc gccccaccac tatcgacctc     480
tgccccgatt ccttttgcca cgcccgata  gctacctttg accacatggc attcagcggt     540
gacggcctcc cacttgggtt ccaggaacag ccggagctgc cgtccgcctt cggtcttggg     600
ttccgggcca agcactaggc cattaggccc agccatggcc accagccctt gcaggatgcg     660
cagatcatca gcgcccagcg gctccgggcc gctgaactcg atccgcttgc cgtcgccgta     720
gtcatacgtc acgtccagct tgctgcgctt gcgctcgccc gcttgagggc cacggaacag     780
gccggggggcc agacagtgcg ccgggtcgtg ccggacgtgg ctgaggctgt gcttgttctt     840
aggcttcacc acggggcacc cccttgctct tgcgctgcct ctccagcacg gcgggcttga     900
gcaccccgcc gtcatgccgc ctgaaccacc gatcagcgaa cggtgcgcca tagttggcct     960
tgctcacacc gaagcggacg aagaaccggc gctggtcgtc gtccacaccc cattcctcgg    1020
cctcggcgct ggtcatgctc gacaggtagg actgccagcg gatgttatcg accagtaccg    1080
agctgccccg gctggcctgc tgctggtcgc ctgcgcccat catggccgcg cccttgctgg    1140
catggtgcag gaacacgata gagcacccgg tatcggcggc gatggcctcc atgcgaccga    1200
tgacctgggc catggggccg ctggcgtttt cttcctcgat gtggaaccgg cgcagcgtgt    1260
ccagcaccat caggcggcgg ccctcggcgg cgcgcttgag gccgtcgaac cactccgggg    1320
```

```
ccatgatgtt gggcaggctg ccgatcagcg gctggatcag caggccgtca gccacggctt    1380
gccgttcctc ggcgctgagg tgcgcccaa gggcgtgcag gcggtgatga atggcggtgg    1440
gcgggtcttc ggcgggcagg tagatcaccg ggccggtggg cagttcgccc acctccagca    1500
gatccggccc gcctgcaatc tgtgcggcca gttgcagggc cagcatggat ttaccggcac    1560
caccgggcga caccagcgcc ccgaccgtac cggccaccat gttgggcaaa acgtagtcca    1620
gcggtggcgg cgctgctgcg aacgcctcca gaatattgat aggcttatgg gtagccattg    1680
attgcctcct ttgcaggcag ttggtggtta ggcgctggcg gggtcactac ccccgccctg    1740
cgccgctctg agttcttcca ggcactcgcg cagcgcctcg tattcgtcgt cggtcagcca    1800
gaacttgcgc tgacgcatcc ctttggcctt catgcgctcg gcatatcgcg cttggcgtac    1860
agcgtcaggc ctggccagca ggtcgccggt ctgcttgtcc ttttggtctt tcatatcagt    1920
caccgagaaa cttgccgggg ccgaaaggct tgtcttcgcg gaacaaggac aaggtgcagc    1980
cgtcaaggtt aaggctggcc atatcagcga ctgaaaagcg gccagcctcg gccttgtttg    2040
acgtataacc aaagccaccg gcaaccaat agcccttgtc acttttgatc aggtagaccg    2100
accctgaagc gctttttcg tattccataa acccccttc tgtgcgtgag tactcatagt    2160
ataacaggcg tgagtaccaa cgcaagcact acatgctgaa atctggcccg ccctgtcca    2220
tgcctcgctg gcggggtgcc ggtgccgtg ccagctcggc ccgcgcaagc tggacgctgg    2280
gcagacccat gaccttgctg acggtgcgct cgatgtaatc cgcttcgtgg ccgggcttgc    2340
gctctgccag cgctgggctg gcctcggcca tggccttgcc gatttcctcg gcactgcggc    2400
cccggctggc cagcttctgc gcggcgataa agtcgcactt gctgaggtca tcaccgaagc    2460
gcttgaccag cccggccatc tcgctgcggt actcgtccag cgccgtgcgc cggtggcggc    2520
taagctgccg ctcgggcagt tcgaggctgg ccagcctgcg ggccttctcc tgctgccgct    2580
gggcctgctc gatctgctgg ccagcctgct gcaccagcgc cgggccagcg gtggcggtct    2640
tgcccttgga ttcacgcagc agcacccacg gctgataacc ggcgcgggtg gtgtgcttgt    2700
ccttgcggtt ggtgaagccc gccaagcggc catagtggcg gctgtcggcg ctggccgggt    2760
cggcgtcgta ctcgctggcc agcgtccggg caatctgccc ccgaagttca ccgcctgcgg    2820
cgtcggccac cttgacccat gcctgatagt tcttcgggct ggtttccact accagggcag    2880
gctcccggcc ctcggctttc atgtcatcca ggtcaaactc gctgaggtcg tccaccagca    2940
ccagaccatg ccgctcctgc tcggcgggcc tgatatacac gtcattgccc tgggcattca    3000
tccgcttgag ccatggcgtg ttctggagca cttcggcggc tgaccattcc cggttcatca    3060
tctggccggt ggtggcgtcc ctgacgccga tatcgaagcg ctcacagccc atggccttga    3120
gctgtcggcc tatggcctgc aaagtcctgt cgttcttcat cgggccacca agcgattccc    3180
acacattata cgagccggaa gcataaagtg taaagcctag atccgaagga tgagccgggc    3240
tgaatgatcg accgagacag gccctgcggg gctgcacacg cgcccccacc cttcgggtag    3300
ggggaaaggc cgctaaagcg gctaaaagcg ctccagcgta tttctgcggg gtttggtgtg    3360
gggtttagcg ggctttgccc gccttttcccc ctgccgcgca gcggtggggc ggtgtgtagc    3420
ctagcgcagc gaatagacca gctatccggc ctctggccgg gcatattggg caagggcagc    3480
agcgccccac aagggcgctg ataaccgcgc ctagtggatt attcttagat aatcatggat    3540
ggatttttcc aacaccccgc cagccccgc ccctgctggg tttgcaggtt tggggcgtg    3600
acagttattg caggggttcg tgacagttat tgcagggggg cgtgacagtt attgcagggg    3660
```
ttcgtgacag ttag                                                    3674

<210> SEQ ID NO 47
<211> LENGTH: 2982
<212> TYPE: DNA
<213> ORGANISM: Artificial Sequence
<220> FEATURE:
<223> OTHER INFORMATION: pAMbeta1

<400> SEQUENCE: 47

| | | | | | | |
|---|---|---|---|---|---|---|
| attctcccaa | gaattagaaa | tgagtagatc | aaattattca | cgaatagaat | caggaaaatc | 60 |
| agatccaacc | ataaaaacac | tagaacaaat | tgcaaagtta | actaactcaa | cgctagtagt | 120 |
| ggattttaat | cccaaatgag | ccaacagaac | cagagccaga | aacagaatca | gaacaagtaa | 180 |
| cattggattt | agaaatggaa | gaagaaaaaa | gcaatgactt | cgtgtgaata | atgcacgaaa | 240 |
| tcgttgctta | ttttttttaa | agcggtata | ctagatataa | cgaaacaacg | aactgaatag | 300 |
| aaacgaaaaa | agagccatga | cacatttata | aaatgtttga | cgacatttta | taaatgcata | 360 |
| gcccgataag | attgccaaac | caacgcttat | cagttagtca | gatgaactct | tccctcgtaa | 420 |
| gaagttattt | aattaacttt | gtttgaagac | ggtatataac | cgtactatca | ttatataggg | 480 |
| aaatcagaga | gttttcaagt | atctaagcta | ctgaatttaa | gaattgttaa | gcaatcaatc | 540 |
| ggaaatcgtt | tgattgcttt | ttttgtattc | atttatagaa | ggtggagttt | gtatgaatca | 600 |
| tgatgaatgt | aaaacttata | taaaaaatag | tttattggag | ataagaaaat | tagcaaatat | 660 |
| ctatacacta | gaaacgttta | agaaagagtt | agaaagaga | aatatctact | tagaaacaaa | 720 |
| atcagataag | tattttttctt | cggagggga | agattatata | tataagttaa | tagaaaataa | 780 |
| caaaataatt | tattcgatta | gtggaaaaaa | attgacttat | aaaggaaaaa | aatctttttc | 840 |
| aaaacatgca | atattgaaac | agttgaatga | aaaagcaaac | caagttaatt | aaacaaccta | 900 |
| ttttatagga | tttataggaa | aggagaacag | ctgaatgaat | atccctttg | ttgtagaaac | 960 |
| tgtgcttcat | gacggcttgt | taaagtacaa | atttaaaaat | agtaaaattc | gctcaatcac | 1020 |
| taccaagcca | ggtaaaagca | aggggctat | ttttgcgtat | cgctcaaaat | caagcatgat | 1080 |
| tggcggtcgt | ggtgttgttc | tgacttccga | ggaagcgatt | caagaaaatc | aagatacatt | 1140 |
| tacacattgg | acacccaacg | tttatcgtta | tggaacgtat | gcagacgaaa | accgttcata | 1200 |
| cacgaaagga | cattctgaaa | acaatttaag | acaaatcaat | accttcttta | ttgatttga | 1260 |
| tattcacacg | gcaaaagaaa | ctatttcagc | aagcgatatt | ttaacaaccg | ctattgattt | 1320 |
| aggttttatg | cctactatga | ttatcaaatc | tgataaaggt | tatcaagcat | attttgtttt | 1380 |
| agaaacgcca | gtctatgtga | cttcaaaatc | agaatttaaa | tctgtcaaag | cagccaaaat | 1440 |
| aatttcgcaa | aatatccgag | aatattttgg | aaagtctttg | ccagttgatc | taacgtgtaa | 1500 |
| tcattttggt | attgctcgca | taccaagaac | ggacaatgta | gaatttttg | atcctaatta | 1560 |
| ccgttattct | ttcaaagaat | ggcaagattg | gtctttcaaa | caaacagata | taagggctt | 1620 |
| tactcgttca | agtctaacgg | ttttaagcgg | tacagaaggc | aaaaaacaag | tagatgaacc | 1680 |
| ctggtttaat | ctcttattgc | acgaaacgaa | attttcagga | gaaagggtt | taatagggcg | 1740 |
| taataacgtc | atgtttaccc | tctctttagc | ctacttagt | tcaggctatt | caatcgaaac | 1800 |
| gtgcgaatat | aatatgtttg | agtttaataa | tcgattagat | caacccttag | aagaaaaga | 1860 |
| agtaatcaaa | attgttagaa | gtgcctattc | agaaaactat | caaggggcta | atagggaata | 1920 |
| cattaccatt | ctttgcaaag | cttgggtatc | aagtgattta | accagtaaag | atttatttgt | 1980 |
| ccgtcaaggg | tggtttaaat | tcaagaaaaa | aagaagcgaa | cgtcaacgtg | ttcatttgtc | 2040 |

```
agaatggaaa gaagatttaa tggcttatat tagcgaaaaa agcgatgtat acaagcctta    2100
tttagtgacg accaaaaaag agattagaga agtgctaggc attcctgaac ggacattaga    2160
taaattgctg aaggtactga aggcgaatca ggaaattttc tttaagatta aaccaggaag    2220
aaatggtggc attcaacttg ctagtgttaa atcattgttg ctatcgatca ttaaagtaaa    2280
aaaagaagaa aaagaaagct atataaaggc gctgacaaat tcttttgact tagagcatac    2340
attcattcaa gagactttaa acaagctagc agaacgccct aaaacggaca cacaactcga    2400
tttgtttagc tatgatacag gctgaaaata aaacccgcac tatgccatta catttatatc    2460
tatgatacgt gtttgttttt tctttgctgt ttagcgaatg attagcagaa atatacagag    2520
taagatttta attaattatt aggggagaa ggagagagta gcccgaaaac ttttagttgg    2580
cttggactga acgaagtgag ggaaaggcta ctaaaacgtc gaggggcagt gagagcgaag    2640
cgaacacttg atttttttaat tttctatctt ttataggtca ttagagtata cttatttgtc    2700
ctataaacta tttagcagca taatagattt attgaatagg tcatttaagt tgagcatatt    2760
agaggaggaa aatcttggag aaatatttga agaacccgat tacatggatt ggattagttc    2820
ttgtggttac gtggttttta actaaaagta gtgaattttt gattttggt gtgtgtgtct    2880 tgttgttagt atttgctagt caaagtgatt aaatagaatt ctcatgtttg acagcttatc    2940
atcggagctc cgatgataag ctgtcaaaca tgagaattcc cg                      2982

<210> SEQ ID NO 48
<211> LENGTH: 4154
<212> TYPE: DNA
<213> ORGANISM: Artificial Sequence
<220> FEATURE:
<223> OTHER INFORMATION: pLME106

<400> SEQUENCE: 48
gatccggcgg aacttcacgt cctggcggtg gagttggcgg gcgcgttcca gccgttcctc      60
cagcacggtg atccgggcct ccagacgctc acgctcaccc tgctccaggt gccgggtcac     120
cgtcaccgtc cgcaccggcc gggcctcggc ctgggcggcc cggcgttcct cactggcccg     180
cttccggcaa tcgtcggaac accacacccg gggccgaccc cgcccaccgt gggcctccac     240
cggcgccccg cagtggggac acgcccgcag cgccgacgca tcctcatcca aggccatcac     300
cgggtcggaa tccatacccg aaaccatatc gtccggacga tgaactgcgc cagacagcta     360
agaatgcacg aggtgtgtct ccgattctca ggaaacgctc agcattttcc gagacgttcg     420
gcgcacgcac acaccccac aagaaccgac ccgcccagca tccgccgaca cgtcgatccg     480
cacccgcgat gggctggccg aggccgacta cgaccgctag tcagcacctg cgctgatcta     540
ccgtcgccct gaccgactct cccgtcggga ttgtcgccgg ccgctgccag catggacctg     600
cggccccgcc ccctcgccct gcaactcgag ggaggcgggg ccgtccaccc cccacaccac     660
cccgacaccg tgatgcgccc atgtcgccta acgggttgcc cgacctcccc gacatcaaga     720
aaacctgaca ccgtcgccgc aagcgctaca ctgactacta gtagtcagga ggtgcgtgat     780
gaccatcgcc acatcggtga aactctccga agagaccggc cgcaaactcg atgaactagc     840
ccgggccacc gggcgatcca agtcctacta cctgcgcgag gccatcgagg accacatcga     900
ccagatggtc cacgactacg ccatcgcccg actcgccgac gacgtgcgag ccggccgggc     960
cgccacctac agcgccgacg aagtggacca gatccttggc ctggacgatt gagtacaccg    1020
accccgccgt caaagcactg cgcaaactcg accgagccca ggcccgccgc atcaccgcct    1080
```

-continued

```
acatacgtga gctcaccggc ctggacgatc cccaccaacg cgggaaaggc ctcaccgggc   1140
ccctggccgg actctggcgc taccgcgtcg gggactaccg gatcatctgc gacctgaacg   1200
ccgaccgcct ggccatcatc gccctgacca tcgagcaccg atcccaggcc taccgctgac   1260
acgcaacccc gcaccctcgg ccaagacgtc acacaccacc cgccccaccg agcactgagg   1320
atgtcaactc gcccgagccg gcctgccggc cgtcttacgg gttgtcttgg cgggcgggt    1380 gtctttgccc tggcccagca gccccacgat ctcccgcagc gtgtcggcgg tggcggcgtc   1440
ccgggccgcc tgacgctccg cctccgccct ggcctgctcg gctgcctgcg cccgatcctc   1500
cgcggcggcg gcctgctccc tcgcctcggc cagctcgccg gtcagggcct cgacccgggc   1560
ctgcacctgc cccaggcgcg cctccgcctc ctgctgcacc tgctcggccc gggcctccgc   1620
ctggtcccgg gccgcctcgg cctcggcccg gtgctgatcc gccagggccg cctcggccac   1680
cgcttcggcc tgcccatcca ccgcctgctc ggcccgagcc ccgaactcct cgcgggccgc   1740
atcactcgcc tgacgccacg ccgccgccca ccagaccccc aacggctccg acagatccgg   1800
cggggccggc gtctggaccg acgccgagac gtcgcgcagg aaccccgccg cagcgtcggt   1860
ggagcacccc gcctccgcct tcaacgaccg caccgtcacc cgccgacccg caccgctcaa   1920
ccgcgcatag gccgccgcca accttgaccc attcgactcc atgacccacc ctcccattct   1980
gtaccctgta cctgttccta ggtacgttcc taatgtacct caccggatgc agaacccgca   2040
acccccctca cactccccct gcacggggcc cgccccctgc accccgctg ccgcgcccgc    2100 tcctgcgtcg cggccttgcc cctgcccaac gccgggccgg cgggcagccc accagaggct   2160
ctgtgagacg tcgcgcccc cgtccaccta ccctaaagac caaccggccg tggaaacgtc    2220
tgtgaggagc cttgtaggag ttcccaggac aagccagcaa ggccgggcct gacggcccgg   2280
aaaggaagtc gctgcgctcc tacgaagaag cccctctggg gaccccagaa ccccggaact   2340
atctgatttg gtttagcggc gtacttccgt cataccggaa tttatggcat gctgtggtca   2400
tggcgacgac gacggtcgat gagcagtggg agcaggtgtg gctgccccgc tggcccctgg   2460
cctccgacga cctggcagcg ggcatctacc ggatggcccg cccctcggcg ctggggtcc    2520 gatacatcga ggtcaacccc caagccatca gcaacctcct cgtggtcgac tgcgaccacc   2580
ccgacgctgc catgcgcgcc gtctgggacc gccacgactg gctgcccaac gccatcgtcg   2640
agaaccccga caacggccac gcccacgccg tgtgggccct ggaagcagcc atcccgcgca   2700
ccgagtacgc ccaccgcaag cccatcgcct acgccgccgc cgtcaccgag ggcctgcgcc   2760
gatccgtcga cggagacgcc tcctacgccg gcctgatcac caagaacccc gaacaccccg   2820
cctggaacac cacctggtgc accgaccacc tctaccggct ggccgagctc gacacccacc   2880
tggatgccgc cggcctcatg cccgccccct cctggcgacg cacccgccgg cgcaaccccg   2940
tcggcctggg ccgcaactgc gccatcttcg agaccgcccg cacctgggcc taccgcgacg   3000
cccgccgcat ccgacaacgc cacgaatacc cgaccgccga ggactcggcc gacctgcacg   3060
ccgtcatcgc ctccaccgtc gaggcgctca acgccggcta cagcgaaccc ctgccggccc   3120
gcgaggccgc cggcatcgcc gccagcatcc accgatggat cacccaccgt ttctacggct   3180
ggatcgactc ccacaccgtc aacgaggcca ctttctccac catccagagc tacagaggac   3240
acaagggagc cggcaaggct cgtcctcgtg cccgccgtgc tgcttctatc accgattggg   3300
aggcatgatg gctgacgtcc agcaccgcgt gaagcgtcgg ggcacggccc gcgaggccgc   3360
agaacgtgta ggggcctcca tccgaaccgc ccagcggtgg acctccatcc cccgtgagga   3420
atggatcact cagaaggccg tcgagcgtga ggagatccgg gcctacaagt acgacgaggg   3480
```

| | |
|---|---|
| gcacacgtgg ggcgagacct cgcgccactt cgggatcgcg aagaccaccg cccaggagcg | 3540 |
| ggcccggcgg gctcgaaggg agcgggcggc cgaagcggag aaggctgccg aggaggccga | 3600 |
| ggccgcgctg cgtccgacac tcttcgaggg ccaggagcaa ggttctgcat gagcaacccc | 3660 |
| gagtcctcgg gtagaccgtc tggcccgacg ttaagcatgg ctgaagcggc ccgtgcctgt | 3720 |
| ggggtttcag tgtccacggt gaggcgtcac cgtgatgccc tggtggccca cggtgctacc | 3780 |
| cgtcatgacg cgtcatgggt gatacccta tcagcgttga tttcatgcgg tttgatgccc | 3840 |
| cgggtgacac cccctgatgc cccgtcaccc aataacgtgg cgcctgccat gacgtcccac | 3900 |
| ggtgacgccc ccctgacggg ggaagtccaa gagctgcgcg agcgactggc caacgctgag | 3960 |
| catcgagccg agctagcagt agaggttggg gacgacgtct cggcgactcc ggagaacacc | 4020 |
| aagtcagggt ctcatgagtg tgcgatagct tgagctgtct accaatctgg atatagctat | 4080 |
| atcggtcgtt tgtgtctgat tcgccagtga gccaacggcg ggggcgacac gcggtggcga | 4140 |
| aaccccctgg caga | 4154 |

<210> SEQ ID NO 49
<211> LENGTH: 22046
<212> TYPE: DNA
<213> ORGANISM: Artificial Sequence
<220> FEATURE:
<223> OTHER INFORMATION: pTZC1

<400> SEQUENCE: 49

| | |
|---|---|
| gcgagcacac ttccctcacg ctgactcgtc actccgacac gctcgctcgt gtccgtgaac | 60 |
| tggcgggcga cggcccgcca gtcacccgga tcgatgaccg ccgcattagt cgaaacccac | 120 |
| acgccatcct gggtcgcatc gggccgcgtg atgtacgcca gcgccttcgc cggcgtcgtc | 180 |
| ttgatctgcc ccatcttcac aacagccatc actccgcccc cgcttccgtt gcggcgtcga | 240 |
| tggcccgttg gacttgtccc agcagctccc gcgtggcacg catctgctca accgtcacca | 300 |
| catcatcagt gttcacctgc cgagcgatct ggttgatgtt gttcccgatc ctcgacaact | 360 |
| cggcgcgcag cggagccgga tcgaacgcca cgcgacgcac gacgatcttc ccctcagtga | 420 |
| gagcgcgccg cgcatagtcg gcgaacgtcc tcgcctccgc aagttccata cgccgttcca | 480 |
| cccgcttcca ttcagcatca ctgagccaca agcccttgaa gacccctcgc gaccgcttcg | 540 |
| cgccctgctc agccatgcat ccactcctac cgggtttggg cagagcccat agtgcccagg | 600 |
| ggccacgca actgtgtaac agttgctatg cttgctaccc cgtcagggtc agtctacaac | 660 |
| ctacggtcta catggcgcta gaatgagaaa cggatcgtcc ggctaaccgg acgatccgag | 720 |
| atcggaaggg ccgcccaggg gcggcccacg atgatccttg tacggggtgt cccgcgctgc | 780 |
| ccgcgcggga caccctaggg gtcgccgtcg cggccccgc accaagatga aggagggcgt | 840 |
| atggccacca gtccgacccc gatctaatc gacgacctgc tgcgccaaga cgaggcggag | 900 |
| ctgcgggcga agaagaagcg gctgcgcgcc tttcagacgg ctctggatga gcttcggcac | 960 |
| gccagcgagg cagtggccac ggccggtgcc gccctcatcg ctgccggcga tgtctcccgc | 1020 |
| gccgaggcga gcaaggtctt caagctctcc aagggagaac gcgccgccgc gttccctacc | 1080 |
| cggcctcgct cagagtcgag cgtcgcggat cggtcgatg agccgccgaa ccccgtagac | 1140 |
| gatccatccg atgagtcgga tgaacagcac accgatctgg gtcagtagcc acaccgcgac | 1200 |
| gtggaagatc gcgctcagtc cgtacatcgc gatgatgagg atgagcgcga gcacggcgat | 1260 |
| cacgccggcg atcatcaacc acgcgagccc catcgctcat cctcccttca actctcggtg | 1320 |

-continued

```
tctccatggt gccacttcgg gatgactctt gtcccgatgc catcaggatg gtgcgctcca    1380
ggtcgccgtc aagggcgctg cgcgtcgctg cgcgatgccg caagcggcac ccttgaccgc    1440
gaccctccac acaccgattg gcagttatcg gaacgaaggg gcgctctggg ctcggacgag    1500
ggctcggcgt accgacgacg tgctcacacc gagcacggtg gcgatatgcg cgttgctctg    1560
accctgcgcc ttcatgcgca aggcggcgtc ggtccgctcc ggacccatga cggtgggacg    1620
gccaccgact ctgccctggg cccgcgcgta ggccaggccc cgccgggtgt tctcccggat    1680
cgtgtccacg cgcagctggg cgaacacggc catgatcccc acaatggcct ggcccatcgg    1740
gctcgacgtg tcgatgctca acgccggctc cgtcaggctc ctgatactca ctccctgccc    1800
gatcaggtca tggacgatct cgatggccat gacctcgctt ccggccagcc ggtccagcgc    1860
ccggaacacc agcgtgtcgc ccggacgcag atagtcgcgg cacgccaacc actgcggccg    1920
gtcggccgca cggctggact cgccgtggtc cacgaacaca cgctcggccc cggccgcgcg    1980
cagctcggcc tcctgcgcgg ccgggttctg ctcgcgcgtg gacacgcgcg cgtacccgac    2040
gatggtcatc ttctccccg ccccacaggg ccgcctcggt gcggctcgtc gtcgccgcgc    2100
tccgctcgac gacgttccac ctcccgctcg atgcgctcgt gcaggccgct gcgggtactc    2160
tcccgccggg ctaggccgcg aatgctcgcc gcccacgcct tggtgcgcgt cttcacgtcg    2220
tcgagctgac tggccgtcag accgtagacg cgcacctctt cgggctggat gcgctccacg    2280
ttgtcgaggt tctgggcgaa ccgtcctagg tcgaagccgg catcagcgtt gcgggccaag    2340
ttcagcagtt ccttgtcgct gtacctgccg gaacgccgga tcgcgtccac atcgagatag    2400
tcgcgggtct cggcccgcga gaacagggca cccaccttgt tccctaccgc gtcctcgatg    2460
gcaagcacgg gcccgacctc cagccgcacg ggcgggtgag cccgccagtc cacgcccagg    2520
tccatgtcgg tactgcgccc ttgcgcactg acgatggtga gctgggcgaa cgtgtcctgg    2580
cggcggcggg tctccacggt gtagccggcc gcacgcagcg cggcgataat ccggtcgagc    2640
gacgtgccga atcgggcctg ggcctgctgg acggtgaaca ggtccacgtc ctctgtgggc    2700
cggtcgatca gccatgctc acggatcgcg cccgagccgg ccagggcgaa gccggcatcg    2760
tcgccgacgg cctccagggc caggcgcgtg atgcgccgct gctcctcctg gtcaccgctc    2820
acacgggcac ccgaagccgg gggaaccgtc cctcccacaa gacgcggacg tgcgggtcca    2880
tgttcaggat cggccacgtc tcgatgagcc gatctcggtt catcaagcgg ccctgctcgt    2940
caaccgtccc ctcggcgagc agcgcctggt aggccatacg acgccaaccc aggttcgaca    3000
cgtccacacc gagccgatca gcctgccagc gcacagagtg aggcaggtcg atgggcccgt    3060
cataggccc acgcagctcg tcgagcgaag cgggcgcgtc atagggcttg acatcgcgga    3120
accgcacacg agtcgctgcc acctcagcca tggcccgcct ccttccatct catcccagtt    3180
taccccggcca ggtcgaaaac ggtctatcac tggtttcggt ttcggtgggg gtttttgaccg    3240
cccttccacc gccaacctac gcggattgtg aatgtgatcg ctatatgtcg tggattcttg    3300
atcactctat ggcgtgctgg tctggtggac cgggaagaca ttgctcttcg catggcaaac    3360
ggtgccgtct ttaggatttc tctgcgccag gatccggaag ggatggcact tcttctcctg    3420
ccgacatcgg tcggagcggc tgatggtatc gcgatcagct tgcctttagc accccacggc    3480
cgtaaacagt gtggcccact gccccgcgtc caactgtttc ggcagtgcgt gtgccggaac    3540
accggcctca cgcaagacct gggcacaccg tcgcgcacgc cgacgcccca caacccggga    3600
cacgatgtcg gcgacgccac ggcccttgcc ggtgaacacg tcatgacgga aggacgcgta    3660
ccgcgcacgc tccgaccagt ccacgagagg ttcctcccgg cgacgtatca ccaggacacc    3720
```

```
ggcgtcgacg gtggggcggg gacggaaatg cgtggacggc acccgcccgt actgttcgaa    3780
gtcgacccac ggccaccact gggcagtcat catcgtggca ccaccgacac cggcgcggcg    3840
gcgcgcgacc tcccactgca ccaggagcac cgcgtgggtc caccccggtg agtgaaggac    3900
gtgccgcagg atcgcggtgg tcaggtgaa cggcaggttc cccaccagga cgtgcgggcc    3960
gtccggaagc acaaaatcaa ggacatcctg ctcgtacagg tggacctccg ggcgcagccg    4020
cttctccaac caccggacag aggccgggtc gatctcgacg gcggtcaacg atccaccggc    4080
agccaagaca cgatcctgaa ggggaaaggt cagcgccccg tgtcccgggc cgatctcgat    4140
gaccgggacg gaggcgttga cggggacgag gtcgacgatc cgtctgatcg tcgcctcatt    4200
gacgaggtag ttctggccgt tctcgtgacg gcccttgttc ggcctgtagg taggcatgga    4260
aagacactcc gcagcagata tcgtgctccg ggcatgccga aaaggccgcc cggctggaca    4320
agctgagcgg tgggtgtctc tacctccgtg gaacgtcccc cgttagcgca cacacccacc    4380
ggcggctccg ggttccgga gccgaccgaa ggtggtgaaa attgcattca ttgcacccat    4440
ggggtgaacc ataccacagc acgcggatgc ctgacctgcc ctgtcccggt catccaaaac    4500
tgtcatgtgg acctgacccg gtcggtctgc cgactggtgc tggatacgcc gccggggtca    4560
gattggtggg tgagtaccta cgcctccacg gaggtacggc agcaagcaac gtgcatgcgc    4620
tggcagaaac aattctgtct gatgttctcc ctcggctcgg gctaggtaat gagtagtagt    4680
acaaaactgt actgcccgtt ctctcttgta ttgaaatgct aaaggtttac aagacatcta    4740
cggcgaacgc actgaaacag ggcgctcctg cgagaatcga cccgaaaact gtctcgtata    4800
cctgtctcac cgtaatgtgt tccaccttct tccaatctgg ggtttggtga ggcatgatgg    4860
tggtcatgag actgttgggc tacacccggg tgtccaccgt cggtcaggat ccgactcttc    4920
aacacgacgc cttggtcacc gccggggttc aggaccgtga tgtcttcagc gatgtcacct    4980
ccggggcgaa aaacgccact gagcgtccgg ggatgaagaa gctcctcgcc tacgctcaac    5040
ccggtgacac ggtggtggtg tggcgcatcg accggctggg ccggtcccta ctcgatgtac    5100
tcaacacggt gaacctgtta cgcgaacgag acgtgaaaat caagtccgtc tccgacggca    5160
tcgacccgga gacctcctcg ggccggttga tgctcggcat gctgggcacc ctggctgagt    5220
acgaacgaga actgatcacc gaacgcgtca acgccggcat cgccgcagca aagtccaacg    5280
gcacccgctt cggccgacca cctgtggatc cagaggtggt cgaccgcaaa ctcgccatcg    5340
tcgccgagga acgagccaaa ggccgcagtg ccgaagacgc cgcgagcatg gtcggctggt    5400
cacgggcgac actgtaccgc catctgcagg gcgccaaacg acgacagtca gcactgcccg    5460
cctgacacgg acacaatgac cagcgcgtga ggtgacggtg atggacgaga tgcaacgctg    5520
ggagatcctc cggctccaca tcgaagacga catcaccctg accgacctgg cacaggccac    5580
cgacatcagc acccgaaccc tatcccggtg ggtagcccga taccgcgccg acggaatccg    5640
cgggctacgc aacaccacac gatccgacgc cggagcccat cgcatatccg cggaactcgt    5700
cgcctacatc gaacaccttg gtctcaccaa gccacgccca tcgatcgccg ccctgcatcg    5760
cctcgtgagc tgtcgagcac aacaactatc gctgaaacca cccagctacg ccaccgtgcg    5820
cagcatcatc caagcccttg acccggcgat ggtcacccctc gcattggagg gcccgacgtc    5880
ctaccgagat cgacacgaac tggtctaccg gcacccggct gaacaccccca acgccatctg    5940 gcaggccgat cacacccaac tcgacatcct catccagaac ccggacggca ccccgactcg    6000
cccctggctc accatcatca tcgacgacta ctcccgggca gtgtgcggct acatggtcac    6060
```

-continued

```
caccaccgca ccctcggcaa tgaacaccgc cctggcacta cgccaggcga tctggcgaaa    6120
aacagacccc acctgggcga tgtgcggtat tcccgacgtc ctctacgtcg atcacggctc    6180
cgacttcacc agtggccata tcacgtacac cacgacagca ctgaagatcc ggatcatcca    6240
ctcgaccatc gcccgtccgc agggccgcgg caagatcgag cggttcttca gcaccgtcaa    6300
caccgaactt ctcaccaccc tgcccggcca cctcgccccc ggcgtccgca acccacaccc    6360
cgtactagac ctgacgagcc tggataccgc cgtcggcgag ttcatcagca gctacaacca    6420
gcgcacgcat tcttcaatca acaccagccc gaaagccgcg tggatcgggc aggggtggat    6480
ccccagaatg ccggagaacc ttgaagaact cgacggactc ctgctgcggg tctccaccca    6540
ccgccgagtc cagcgagacg gcatccactt ccaaggccag cgctacatca gcccgaccct    6600
ggcaccttt t gtcggccatg acgtcaccat ccgctacgac ccgcgggatc tctccgagat    6660
ccgggtctac gaccacgaca cgttgctgtg cgtcgctgtc gatgaagacc accccaacca    6720
gcgctacagc ctggccgata tccaggccgc tcgtcgacgc cgacggcgtc aactacgtgc    6780
cgggatcaac gagcgcatcc ccatccacga gccacgccca tcagaccttg ccctgtgaa    6840
ccccgatgtg agcgccgaag cgccacggcc gcgtggtcgt acgtctcgcc tgcggaccta    6900
tgaagaggac ctgtcaccat gaaccgcgac ttcatcgtca ccaaagagca ccgccgcttc    6960
gtcgagttcg ccaacgcgat ccgcaaagac gccaccatcg gcatctgcca cggtgatgca    7020
ggagtcggca aaacacagtc cgccagacgc tatgcccact gggatgctct gggctcgttc    7080
attgacgact ggggtccacg cagtgaatct gacctggcca tctacgcgac ggctcatcgg    7140
gcgcgcaccg tgttctacac ccctgaggtg caaccgaagt accggacgtt gatccgtgac    7200
atcgaattt t accggggcaa actcgacgtc tgcatcatgg agcatctgat ggccaccgga    7260
cagcgggaca ggctccacat gcgcagatcc agtggcgaga agctcaccca actgatcatt    7320
attgatgagg cagaacgtct gcctcccacc gccctggaga tgctgcgcga catccacgat    7380
cgtgacggtg tggcgatcat gttcatcggc atgcccggta ttgaccagcg cttccggcac    7440
taccctcagt tgttcagccg gctggggttc tcgcatcgct accgtgccct gggcaaagac    7500
gagctgctgt tcgtgctgaa ccggcactgg aggcgcctgg gtagagaatt gaacccggag    7560
gatttcacgg atgcgcaggc catcgccgcg atcgagcggc tgacccgcgg caatttccgt    7620
gtggtggagc gattgttccc acagatcaag cgagtgttga agatcaacga gttggagacc    7680
atcaccgacg atgtgattga agctgccgcc agcaccctgg tactcggcca ctgaccaggt    7740
cagtacgaca catagtgatc aaaaaagcag gccacatagc gatcacattc acagcggatc    7800
acacgacata ccgccaaccg gtgcaaaaac gatcgttttt gagacgcacc gcgagagcgg    7860
agccgttagc cgctcccgga gcgtccacaa cgcgtctcaa aaccggtcgt gtcgcaccct    7920
ggttttacgc ccgggcagtc tgcttatgtg tgataaagaa gcaatagaag tgcaaaaaat    7980
tttgccgttc ctatccgaca cttggccatt gtgtcggata ggtcgggcgg ttattcgggc    8040
aagtcaatct tgccgacaaa gctgtaataa atctcaatgt cctgcctgcg ggtgccgttc    8100
tcatcatagc tgcactcatg caccacaatt ttctcgatca tttcccgcaa gagagtgggg    8160
gtcagttctt caaaggcaag gtgcttgcgg acaatgccca taaatttctc ggcgttgacg    8220
gtagttgcct gtgacttgtc cagttcggct tgcagggcgg cggctctctt tttcagctcc    8280
gcttgctcgg cttcgtagtc agccgacagt tccatgaaac gctcatcgct gattttgccg    8340
tttacattgt cctcatacag ccgcttgata atgcggctga tttcagaaat gcgttcctgc    8400
gcctgttcaa gctgcttgat ggctgcggcg gtctttcgct tgccgccgat ctcgttctgc    8460
```

```
tggacaaaat gtaatccgca ggattaggag atagaagttc cgttactttg ggacgcacta   8520
cctctctgtg aaattcatta gattcgtcac ccattgcatt atcccaaaat tgtgcgttct   8580
cctcccagat ttttttactt tcctctgttc ccatgttctc tcccactccc caaatttgct   8640
tttttgcttc cattaaatct tccttactat attccattgt taccctccat aacttctgat   8700
tgttgccgtc ttgacgatta tgtatcttta cattaccttc tgaaacatat ggcgcacctt   8760
gtccaggcgg ctgtttggac ggcggggctg atgaccggc tgaccgacag cggcctgata    8820 tccttttcagc tctgtaaggc atacgctccg cccgttggtg taaaaggcca gatcagtacg  8880
gtatgcctgt atacagcggg cgggaatctc gccagtaaag acaacttcat ccttttttac   8940
ctgggccgtt tcgatggtgg cacagtattt cggtgcatca tgataagccc tggaaaggta   9000
ttcctggggc gcatagagga tgaaggagag ataaggttcc agcagctgcg tcccgattc    9060 cttcaatgcc tgttccaata caatcggggc caatgagcgg aagtccgccg gcgtgctgac   9120
cggactgtaa taaagcccgt attcaaagca aatcttacag tccgttacgt tccagccgaa   9180
caagccctgc tccagcccgt aacggatacc atccctgaca gcgttttgaa aactctggtt   9240
caagtatccc agcgaaaccc ggctctcgta ttgtacaccg gagccaagcg agagtggtgt   9300
aacagacagt cctatggatg cccaaaacgg gttgggcggc acctcgatat ggatggtgtg   9360
gctggctgct ttgagcggcc gctccatata aatgacggag ggttccttta ccactgtttc   9420
aagcttgtat ttttccgaca gcaaagcgga acaacctcc aactgcaccc ggcccaaaaa    9480
agaaagaatg atctcatggg tgatggaatc cacttcgcaa cgcaaaagcg ggtcagtatc   9540
cgcaagttgc gtaagagcgt ccagcagccg ttctctttgc gctgccgttt tcggcgcaat   9600
cgtcgtccgc agcatgggga gggggtcctc gcgccacctt ttacgaggga gccgggtttg   9660 gtccctaat acatcgttta acctcacgct gtcgctggga aggataacaa tttcaccctg    9720
ataagcggtg tctgtccgaa caatttcccc tttggatgga atacgcatct ctgtgatttt   9780
cagcttttct ctcccggcca gggccaccgt atcccgcagg cgcagcgttc cgctgtataa   9840
ccgtagatag acacgccgct ggccgcaatc ggtgtactca accttgaaaa cgctgccgca   9900
tagggcggcg ccccccctgtt ccccaatcgg ttggaacagc cctgtcaccg catccatcaa  9960
cggttgaatg ccaaggccat ttttggcgct gccatgatag actgggaaca gggaggcgtc   10020
ttgaacccgc tgctgttcct cccgcgcaag ttttcccgg ctgattggtt ctcctgcgat    10080
atacttttcc aataattcat cgttattttc gatgaccgca tcccatgctt ctatgtcggt   10140
attttcctcc aggactattt ccggggacag cgacaccgtc tgcttgatga taatatcggc   10200
ggagagctta tcccgaacag actgaaccac gctctgcaaa tcaacgccag cctggtcgat   10260
cttgttgata aagataacgg tgggaatgtt cattttccgc agggcatgga acagaatacg   10320
ggtctgggcc tgcacgccat ctttagcgga gatcaccaag atggccccat ctaaaacagc   10380
caaagagcgg tacacctccg ccaaaaaatc catgtggccg ggcgtatcca caatgttaac   10440
tttacatctg tgccactgga aggaagtgac tgccgcttga atggtaatcc cacgctgccg   10500
ctccaaaaac atggtgtccg tcctcgttgt ccctttttcg acgctccccg gttctgaaat   10560
ggctccgctg gcatatagca ggctctccgt caaggtcgtc tttccagcgt ctacatgggc   10620
aagaattcca atattgatta ttttcatgtg attgtcctcc ctttacagcc ccaaagggca   10680
taaaaatccc cagcagtaaa atactttttac cactgggggat tataagttgc ggacatacac  10740
atatacagca tacacctgtt tgtgattgct gttttttgggg atatgtcaaa attgataagg   10800
```

-continued

```
caaaagtatt cttaaattgg gtacaaaaaa ctaagcccct acaaaaggag ctatcataat    10860
cctttgttcc cactatttga ttatagtttt atttaagaat accttgccgc atattttta    10920 ctccttttct ggattaaatc attgtatcac atcagtttta ggaaagcaag tacctaaaag    10980
aaatttttct tccccttata tgtaacaatc ataccggctt cctagcgttc agaatgtttt    11040
ctgctgtctg ctgtggtgtt tggttggaat tgtccaacca aaagccgatc cgtggtgttg    11100
tctgcatttt actaaataca aattcaatgt atacagaaag atataaggag tgggagggat    11160
tccgccgtag ttggcattgt aggaaaatcc aaaagtttag attttcccac aatgcttatc    11220
ttttggtctt tggttcggaa tagtgtagtg ctggcggtct atctcttgtt ttcggttgct    11280
tgcttcctta ccgtacatga gcattcgcgc agtgcattcc cgaccacgtc cggcacggca    11340
cctcgaccgt ctgcgccgcg ctgaacattg cgacccgctt cgacaaactc gccatcacgt    11400
accgcgccgg cgtcaccctc tgcgccatcc tcacctgggt ccgactattg ggagacacga    11460
cctaggagaa gaccggctcc cacatccgct accgcttcgt ggggaggccgt ggccggctc    11520 ccgccgggca tgaagaaggg tccgctgaag gtttggttga cctcctacgg cagcagctca    11580
gccagttctc gcagctgctc aaggatccgc tcggcctggt cgggagcgac attcttgtcc    11640
agctgcttga gctgacgctg catcttctcg atgactgcgt cggaaccagc ggactcgctg    11700
tggagcttca ggaagtgtac ccaagcacgc gtctcgatac cgaggatggg cacacgcatc    11760
gtcgactcaa cgaacgaatc catgaggggg cgacaccgag gcagtcgtcc gaagttgcca    11820
ccgccatcgt tcaccggatg caccgtcacg cggtcagcct tcgacgggta cggcgtcgcg    11880
tcggccgggt actccagctc cgcactgcca tcggtctcct tgatgttggt ccaccagtag    11940
tcgcgccact cggcggcgta cttggcggac tcgacccacg gctcggccac caccggcacg    12000
ccgctgacgg cgctgtcgag gtgccacggc acgcagcaca ccaggtccca gtcggtcag    12060 gcatcggggg agacctggta ccgcagcgaa gggaccttct ccttggccag catccaccag    12120
cccttgagct cgatgccgat cgcgatgggc tcaccctcgg ttccacgatt caccagacgc    12180
acgtcgggga aggcctgcgc cgaccgctcg aaccggtagg tcgaccactc ggagtccggg    12240
tcccagatct gccgaaggct gttcagcgtg cgcacgacct ccagtcgat gcccgagccc    12300 aagaagctgt tgaggctgaa caggtcggtg gcgttgaccc cgctgatctc gttcttcgac    12360
tcgaactcgc ccggaagggc ttggaggggc gcggagaccc ccttctggag cttggtatgc    12420
ggatcgttgg gatccagcac cgggcgggca ggacccgcac ccacctgggc gctcgtcgcc    12480
actgcatcaa ccgacattgc tctcctcctc ggggttggcg tcgaagaggg ccacgagctc    12540
gtcgttggtc tcggcctcct cggcggcgac gtcaagccgc tcgtgcgcaa gctccgcgaa    12600
gtaggggtca cgctcggcaa ggaaagcctg ccgacgcagg gccaccgcag ccacggagcc    12660
cgtgccaagc ccgccgaagg gctcccatac gacgtcgccc tccttcgtga cggcgtgcac    12720
caggcgctcc atgagctcca gtggcttctg gttcagatgg gtcgtgctgg ccttcgtggg    12780
cttgtacacg cgcggcgccg accgacgcat cgagcccttc atacgctcgc cgtcgtgcag    12840 cgggggggcgg ctccacacgt tggtcaggcc atggacgtgg tgccactggt ggcgcatccg    12900
gtcccactgc ttcgcggtga ccgacgtcac accgtcgagc gagaagtacg ggcggccgct    12960
ctccaggccg tgctgattgc agtacgcggc catgcggcc acggcgactc ccggcggcca    13020
gtaccagagc cagtcgttcg tcaggtactt gcgcgtggcg gcgttcttca cgccgcaggc    13080
ctcattggcc aggtacatcg gcagaccaga gcggcgccac tcgtgccgca gccactgctg    13140
ggcatcgaga atgcccgcgt cggtcgccgc ctcgaagcgg cgctggtaga ggacgcagac    13200
```

```
ctccgtgacg acggggaagc ggcggatggt gttgccgttg acgttgcccg cgatgtggct  13260
cagaccottg tcccagacca cggtctggac gtagtcccag ccctgacgct tcaactcagg  13320
atgcaccgtg gcccagccca cctccgtacc ccagaaccac agcgccgtgc ccggggcggc  13380
agccttcgtc cactgctcga tgtgcggggc gtaccagtca acgagccctt cctcgtcggt  13440
ggtgtccccg taaaaaccgc ggacgccgta ggcgccgtcg ctgatgatgc acgtcggcga  13500
cggccaggac gcgtaggcgt ccgccacatc ccccacgtgc aggtcgtagg gcctcttctt  13560
ctcggccatg ctcccagcct ctcataatcg atggttactg gtcattcgcc cggtccaggt  13620
acgtcaggcc ggcgcggcgt agcgcgtcgg ccggcgtgcc gccgctccag tcggggcgg  13680
tcccggtcat cggcaggggc gtggccgacc gggctgtgtt ctccagctcg tcggccagtt  13740
cgtcccactc gggcacgtcg aggacctggt tgaccgagac ctcgacgacg acgctcaccc  13800
cgcgctcggc cagcagccgg cccacggtct ccttgtacgc ctcggcgtag tcggcctggt  13860
cctgctccca ccgggcctct acagcgtcag cggcgcgccg cgcctcgatg agggtggccg  13920
ccagcggatg ggcactctcg gctgctcgct cctccacggc cttgatgatc tttccggcct  13980
cctcatacat cgcggtcacc cggtcggggt cactgtccca ctcgggtccc ccagctgggg  14040
gcatgtcggc ctggagcgcg gccagccggt cgcgctcctc ggccgtggcc acggcctccc  14100
agagtgcatc ggccgccgcg tcgacgcggc ggccgagttc ttcggccgcg tcctcgtaga  14160
gctggtagag cccgaagtcc tcgaagacgg cctccacgtc gagcgcgagg cgcaccggct  14220
cggtgcgcca ggccagcagg tcccgatcat cggtgccggc tgtcccctcg acgacctggc  14280
ggatgagggc ggcctcccac gatccgggcc ggccggccag cagctcgtcg acgctgccga  14340
tgttcgcggc cacggccgtg agcacgtggc acgcgatccc cgcgaagtcg tccggctccg  14400
tgtgctcgct tggggtgccc gctccgacga cgcgacgccg gcgcgccgcg tcggtcaggg  14460
ccgtgatcgc ctgggcgatc gggtccggga ctgtctcggt catgtctggc tccttcagtg  14520
ggtggtgatg ccgggcttgg ggcctggcgt cacggcgtcg aggtcgggga acgggcggcc  14580
gtcgttgtac tcggcttcca gccgggcgac tttctcgttg acggcttctt ggacgaactg  14640
ccagtagggg cggatgccga gcttcgcctg cgtgtagaac cacgctcccc tggcacgccg  14700
gccttcctcg atggtgtgct tgaagctggt gcgcgtccat ccttcgccgg tcccggtctt  14760
tttcgcggcc tcgtgccggg cctcgtcaac gttgggcggc tgcgccgcct cgacggcctg  14820
gggcacgagg gggttgctca ggttggtggt gcgccgctcg ggccgcttgc tcatttgatc  14880
gctcctttag tgatggtgtc gaggtgctgg cggtagaggt cggccagctc ggcggcgtcc  14940
ttgccgcccc actggtccag gccggtggca gcctccagcg cgtcggcgat gacggcgcgc  15000
ttcgggatgg gcggatcaag gatggtcagg ccctcgatct tctccaggtc ttccagagcg  15060
cttcgcgcgc cgatggtttg cgcctcgtac tggttgacga tcaccccggc cacggccaac  15120
tgcgggttgt agtacttgcg cacgatgcg atcgtctgaa gcagccgacc gagcccggcg  15180
atcgagtaga ccttggcctg ggtgacgatg gccacccgct cggcggccac taggccgttg  15240
agggtgaggt gatccagcga tggcgggcag tcgatgagca ccaggtcgta gcggtccgcg  15300
acgctggcca cggcctcgct cagccggtgc tcgacgccgg gggtctgcgt ggtcagcagt  15360
tcgttgcgaa cgctggtcag cgcctcgttg ggcggcgtcg gggccacgtc gaggccatcc  15420
cacacgccgg ggacgatgac gctctccagc gtctcggtac tgcgttcact cagcgcgtcg  15480
gccacgccga cgtcctcggg cgtgggcgtg tctttcgcgg ccgacatggt ggcgttaccc  15540
```

| | | |
|---|---|---|
| tgcgggtcga ggtcgatcag gagggtccgc cggccctcgg tgacggcggc gcgcgcgaag | 15600 |
| ttgacggcgg tggtcgtctt cccgacaccg cccttctggt tgctgattgc gagggtcatg | 15660 |
| ctcatgctgt tggttccgtt cgtgcgattg gtgcggttcg tggtgttagt gccattcgtt | 15720 |
| ctgttcgcac taactagtgt agtcgcttcc cgcctcgctg tcacgcgtc gaggacagtc | 15780 |
| gggagatcaa gtccggccgg aggccggcgc accgtggggg ctccggccgg acttgttctc | 15840 |
| actgttcatt ctattcgttc ctttcgttct aatggtgcga atcgcaccat tagaactagt | 15900 |
| cggtgatggc ttcgatgatc cggtgcgcgg cggccagcac acggctggcg ctcttgcgga | 15960 |
| tgaggtcggc gtctcccttg gaccatccgg cgacgtagcc gacgtgtag gcgctggtgt | 16020 |
| cgagtccaac gatgccggcg accacgtggg cgacgctttc ggcctcgacc tcgcattgtc | 16080 |
| cccggtgctc gtggtactcg gtggggtga tgtcggcgtg catgagcgcg tgggcggcct | 16140 |
| cgtgaagggt cgtcttggcg gcttgggcgg gggagatatc ggccgcgatc acgattcgct | 16200 |
| tgtcgtcgtg gctggtgtag ccgttgagtc cggccccgag ctggtcgtgc tcgatggtcc | 16260 |
| agccctggcc ggtgagccag tcggtcacgg cctcggcgat gccggcgggg tcgtcgccgc | 16320 |
| tgagctggtg ggcgtcggcg gggttctcgg ggatcggctc ggctccctcg atggggtcgg | 16380 |
| tctgggcgag gtcgaagacg gacacgggga agaatcgcgt gcggcgtcgc tcggtctcct | 16440 |
| ctccggtggt ctcgtcctcg atcgtttcgg tgacctcgcg gccgccgaag attctgattc | 16500 |
| cgcgctcacc tttgcggacc tgccggccga gcttctgcca ggtgcggtac cccgcgacct | 16560 |
| gcgtcgcgtt ctcgcgctgg gcgaggatca ggagcaagtt gttcaggctg tagcggtgga | 16620 |
| acttcccggc gaaggcgagg aactgggccc atgcttccga ggtggccagg gcctcaacct | 16680 |
| gctgggcgat ggtctcgtgc agttcggccg cttcggtgcg gcgctgctcg ggggtcttgt | 16740 |
| gggtcttgat cttccgggcc atgatgttgg ttccttctcgt gtgattggtg cggttcgtgc | 16800 |
| gaactgcctg tcttccctca cgttttttg ccattgaagg cactggaagt gccgccaggg | 16860 |
| agggagcccg gagtgcaagg gaccgtggaa taccggactg agcgcagcga gggaggatat | 16920 |
| gccgcgaaag cccttgcgcg tagggcggac gaccgtatgc tgccgaaggc ttcaatggca | 16980 |
| aaaacgtgcg ccgtaggcgc atgctgccgg ccgcgcagcg gccgtcctta tgatgacggt | 17040 |
| ccgccagggc cgcctgggga gggtcggcct gggggccggc tcgttgtggt cggctgtcca | 17100 |
| cctgtgggcg ggccagccgg tcgggagctg ggccgtccac aggtgcgtca ggcggtcccc | 17160 |
| tctacggagc ggccctgtgg ggcgttctgc gggccgtgac cccttccgc gtgtggttgc | 17220 |
| ctgggtgggg ttgagttcgg ccgtttcggg gcgttatg gcgtcgtttt tcgtggtcga | 17280 |
| tcatggctgc cgcctgtgga cggcccttcg gcccgccac agttgccttc gaaaccgggt | 17340 |
| ggccgggttc cggcgtggtt gggacgaggg ttgccccggg cggtcaggcg gcagtgacga | 17400 |
| ggctctgatg aaggtggtcg agtgctccgg cggcgatcgc ttcgcgggcc gctcgatggt | 17460 |
| cagcgcggcc gtctggtcgg cgcgggtagg gggtagat gtcccagggt cggccgaacg | 17520 |
| tgagcgcaat ctgtcccgtg ggctggtggc gtcgtttgtg gcggcctggt gtggtcatcc | 17580 |
| attccagttc ggcctgccac cattcccaca gatcgcgctc ggccttgtag cggccttctc | 17640 |
| gtgcgtcgag acgcccctcg acgcgagcc gtcgggccgc gaggtcgcgc agctcgggcc | 17700 |
| gggttcgccg ccagccggtg ggcgtggcca cgatgagacc ggcgtaggcg agtcggtcga | 17760 |
| gtagggggt gatctccgta gtggtgacct ggggtgatt gagcctggcg tagaggtttc | 17820 |
| ctgcggcgag gccagggcg tgggggttgg tgaaggtgtc gtggcgggcg aggtctaggc | 17880 |
| ggtgggtgag ttcgtccagg aggaggtttc tccatcggct gcccgcccct gcggggcgtg | 17940 |

```
cagcccctcg tgaccgggca tggtctgcat ccatgtggat agcggtctgg ggctcgattg    18000
tccaggtggt ggcgtgcctg ccggtgcccg cctgggcctg gctgatccac ccgtcgccgg    18060
ccaggcgcag gagggcggtg cgggcggtct ctcggccgat ccggcgagc agggcgaggc     18120 ggcgcacgtc tgcttcgacg gctgcgctga cggcttggag ggcgagcagg cacagggcgt    18180
cgagcacgcg ccggtcggcc ggccctcctc cgcgtgtcca gcgccctggt gccgcatcgg    18240
cgcggcgctg cacctggtcg acggtggcgg cgatcgcttc ggctcggggg tcgaaggtgg    18300
gatcgtcgcc tgcctggcgc gcgtgggtgg ccacgaacct gacggcggcc tgccacactc    18360
ggccgagcgc ggcttcgctg ctttgggctc cgtgtgtggg gcgcgcctgg cgtgcacggc    18420
ctccgtggcg tgcgcgctgg gtgcgggcgt gctccatgcc gggtgccgtg gacacgaggg    18480
cggccgcgtc gcggtagtgc cagtgggcgg cggctgcacc gagcaggatc acgtagagga    18540
cgcgggaggc gtcctcactg gcggcggcgt cttcgtcgac ggcagcgcgg ctcttggcgg    18600
gcatggcacg gcgggtccg ggcagccacg gccgcccgtc ctcgtcgacg gcacgcgca     18660 gctcggctgc gtggggagc gaggtcaccg tggccacgtc gccgaactcc tcattgagtc     18720
gggtcgccag ggccacgagc tgggctggtg tggtggtcgg gtgtgtgagg gtggcgagat    18780
ttccggcgat cacgcgggat gctccaccgt ggcggtgggg cgtgccgggg gggcgcaagc    18840
atccggtggt cgggttgagc aggggagtgg ggtccaggct ggtggcgaga ccctggaggg    18900
agtgcgtcag gtggtgcacg agctgcgggt cggccgtctc ggccagggcg atccacacgt    18960
ggcggccgcc ggtggggccg gactcgcaga tgacgtgctc gatgccggcc tggtcgagca    19020
ccgtggcgat cgccgtggca tcccgctctg cttgggcggc tccgccctcg tgggcgtcga    19080
ggtcgaggcc gatgtagcgg tagcggcgct gcgcgtccgt caggtacatg cccacgggc     19140 cggccggggc cggccccgcg acgggcacct gcgtcgggta ggcgttcacc tggtcgccgc    19200
tggcggcgcg cacctgcggg cgcgggctca acgtgcgtgt gagacgccac gccgcgcga    19260 tatgcgtagc gtcacggtta tcggcatctg ttgctatcat gtacgtgttc cttcggggga    19320
aagacgcaac gatccctcct tcggttggtg ggccctgcc aagggcccta ggtgtttggg     19380
tgttgcatcg ggtgccgact gccaaaccgg cttccgtact tggttcgctt gatctggttg    19440
tgttggggaa ctcagcagat caggcgctta ctcttctgac ccccgccctg ccaagggcgg    19500
gggtctgttc atgtctatgc ggtgcccgta gggtcctcct cgatgctcag ttccggttgg    19560
gtgctatctg gggttggaag ctcccatccc tgtggccagc cgtccgggcc tgggacacca    19620
gagcggatcg cagcttcaag gactgcccac tggggggcac ccttggcgcg cgcgtaggcg    19680
tcgagcttgg ccttgacgtc cggcgcaacg aagatgtgaa gcgctacggt aggcgctcca    19740
cggtcgcgac ggaatcggct ggtcatgaca gtcatcatat aagggcggct gtacatgtac    19800
acgggccgac acgccggcgt gtcgcgactt cttttcagat atcagagtcc tcgggcgacg    19860
gcggcggctg cgcgcagcca tgcgcgttgt gtgctgggc gcaggctgtc ccattggagg     19920
atgccgtcca cgatggcggg gtcgtggggg atcgtgacga cttcgcgggc gaggtcctgg    19980
tagccggtga cgatgttggt gatgtcggtc ttgctggcgc gcgggtcggc ttgggtgacc    20040
acggcgacgg cgttgtccgc gagctggcgt gagtgttggt cgcggccgcg cagcgcgtcg    20100
aggaggagcg cgccggcttc ggcgtggtct gcgcgggtgg tggtgggcac gacgatctgg    20160
tcggcgtgtt cgatggcttc cagccacaca ggatcggatt cgtcgttgcc ggtgtcgatg    20220
aagatgaggc ggtagtactt gccgacgacg ttccagatga ggtcgacgtc gtgagggggtg    20280
```

```
acgcgctggt cggcggcgag ctggatgggc tggctgcgca gcacgtcgaa ccggtcggcg    20340
gtctggtggt gaacgtagtg cgccagatcg gccgactggg ctccggtgcc caacagtcgt    20400
tcggtttggg gaaggaggtc gaggacggtg gcctcgtggg gtccctgttc ggtccgccat    20460
cccagggtgc ccctggtttg gttggcgtcc caggcgacca cgcccgcgcc gccataacgc    20520
gcgaacacag cactgagtag caccgtggtg ggggttttgc ctgccccgcc cttcccgttg    20580
gccacgatga tcgtcctggg gccgggccag tgctgggaga cggcgtgcac gtcgtcccgt    20640
tccgcgcgct cctgctggct cgggttcatg cgcagcccga gccgggtggc aacgccgcgc    20700
cagccctgcg tggcgggctg ctcgatctcg gtggctttga ggaatgaatg cggctctgg    20760 acctcgcgcc tgctgggcag gtgcgcgatg gggctgtcgg ccgagcgtgg gagagtgtgt    20820
gcctgggtgt gagggctgtc ctggcgtggg gttgggctgt catagaccgg ggccgccgtg    20880
gcggccgcgg cctcggcggg atcgtggagt tcgccgtcgg gggtgacgat gacggtccac    20940
acgccgtcgg ggtcggaggc ggtgagcgtg gcgctttcgc cggcggtggc tgcgcgctcc    21000
tgggcgatcg cgacgacctg ggcgcgggcg tcttcgaggc tggtggcggt gatcttctgc    21060
ggcgtgccgt cgatcgtgac gatggcgctg ccgtcgcggg ctgtggtggc ctctatgtcc    21120
atggggatgc tccttcgttc agctttgggt ggcctgggtc tgcatggctg tgatcgccca    21180
ctggccgttc tcttgggtcg cggtgaccca tgcgtcccag gccacgtcgt cggggggcgtc    21240 tgagccgtct cggggcgtgg tcttgacgag gtagtggacg atccggtgcg cgtcgccgtc    21300
ttggtcgggg tcgagtcctt cctcgacaat ctcgcggatg gtgacggtgg tgtaggagtc    21360
atgctgcgcg gcctgtgtga actgggcctg gcccttcgcg gtgtcggggt cgtagtcggc    21420
ggccgcttgg cgtagcgcgt cggttaggta gatcgccgcc cgttgggtgg cgtaggcgct    21480
ggtcttgtcg accgtggtgt cccaggtggc ggccgtggcc acgtaggcgc ggatgacggc    21540
ctcggggtcg gtgcggtcga cggtgctggg gttgggcagg tcggcgagcc aggtgggctt    21600
gcccccgggg atgggtgtgc cgtcgggtgc ctgcccgatt gtggggctgg tcgtggccgg    21660
cgtgctggtg gcgctcgtct gatccggtgc cggggtgtcg ttggctgtcg tgtgggcgca    21720
gccggtgatg gcgccagag tgatggtgcc gatgacgagg gcggcggcac gccggtgggt    21780
gcgcctcatt ggattctcct gtagttgctc ggtgagccgt agatgggctc gaagttgatg    21840
ccatcaatgt ggttgtcggc gctgaccatc cagccgttgc cggcgtagat ggcgacgtgg    21900
taggccggcg tgccgtagaa gatgaggtcg ccgaccttga gttcgccgcg ctcgatgccg    21960
gtgccgacct gctgctgctg gcggctgtg cggggcaggc tgatgccgag gcggcggtag    22020
acggcgctgg tgagcccgga gcagtc                                          22046
```

<210> SEQ ID NO 50
<211> LENGTH: 1615
<212> TYPE: DNA
<213> ORGANISM: Artificial Sequence
<220> FEATURE:
<223> OTHER INFORMATION: pBC1

<400> SEQUENCE: 50

```
ccccgatggt ttttcccccg acggctcgcc tttgggaagt ttgaagggcg caggttccac       60
acgaaaaacc acaaggcttt ttttgagtaa taaaaaagcg gacggcgagg gcgtgaaaaa      120
aacccgatga acccttgaaa ataaagggcg ggacgggttt tttcttatct tgataatata      180
tagaaacaat gagattttaa aaaaagcccct caaacccttg ataatactgg gtttgtggcg      240 ttttttttggg gtggataaat aaaaaccctc tgtgttatgg ttatgttgac tagacaaaac      300
```

-continued

```
catacagagg gctttacgcc tttctgtatc cagaaaggag ttattaaatt ttatgcacgt    360
taatcatagc attaaaacgt caaatctatc aaatatcgaa tttttgcaag ataaaacgaa    420
aacaggaaaa gagagagatt ggaaaggcaa gaaacaacgg tctttgctga cagcggaaca    480
cttcgaggta gcagggctga ctagcaaagc ggaacagtgc gagagtgtgc tgacacgttg    540
gtgtttaagc gaactgccga agggttaaaa ctatatcaag catggttctg taaagtgagg    600
ttatgcccga tgtgcaattg gcgaagatcg ctgaaaatag cttaccagaa taaagggtt     660 gtagaggcgg ttaatcaacg tgagaacgtt cagtggctat tcctaaccct taccgtccgc    720
aacacgagcc ctgagagcct tccagagacg atttcagcca tgtttgaggg gtttaatagg    780
ctgacgaagt acaaagcctt taaaacgtct gtaagggct attttagggc tttagaggtc     840
acaaagaata gagaccctca tagtgaatgg tttggcacgt atcaccctca ttttcacgtt    900
ctgctgtgtg ttccatccag ctatttcaag aaaaagaat tatacataac cgaacaagaa     960
tggactgacc tttggaaaaa ggctatgaag ttggattaca cgccgattgt ccacgtgcaa    1020
agggtaaaac ccaaagaaca gcttgaggac atggaaacct atgaagaaca gcttaaaaac    1080
gccattaggg aacaaaatgc gattttagaa gtctctaaat atccggtcaa agatacggac    1140
gtcattaaag ggaataaggt cacggccgaa aatgtggaaa ccgttttggc gttagacaac    1200
gccttggcaa ataagcggtt aatcgggtat ggcggtcttt tgaaacaggt tcacaaggaa    1260
ttaaaccttg gagatccgga agatggagat ttagttcatg tttcggaaga ggatgaaatc    1320
gctaatggtg catttgaggt catggcgaaa tggcatatcg gttttagaga ttattggatt    1380
caaaaatagc aggagagaaa actcctgctt tttatttttt tccgaagtta ttggcgaaag    1440
caaacttttt atcgagcgaa gcgaacccta ttgaatacct gcatggcaag gtatgtaaat    1500
gggcactctg tgatttttgg atacaaaata gactctagcg agccgatttt atgacgcagc    1560
aaaaaacgta gtcttttgc gttggagagc ccttcaagta aactgaccaa ggtgg          1615
```

<210> SEQ ID NO 51
<211> LENGTH: 1854
<212> TYPE: DNA
<213> ORGANISM: Artificial Sequence
<220> FEATURE:
<223> OTHER INFORMATION: pEP2

<400> SEQUENCE: 51

```
atggtaaatc tgcgcagaca gccctgtgca gctgaaacgc ggttacgtat agcttgccat     60
atgtctagcc atacgtaacc gcaggtaaaa ggcatatttt tcgcgtgtca tggctagtaa    120
ataacaccgg tgtcatttag agtcagggaa agacaatgaa aaacgaagaa agccaccggg    180
cggcaacccg atgactttcg cttatcaccc agcacacacc tgggagaaat cacggtcatg    240
agtttacaga ctcatgcgca gaatgcgcac actaaaacac ctaccgcgt cgagcgcgac     300 cgtggtggac tggacaacac cccagcatct gccagtgacc gcgacctttt acgcgatcat    360
ctaggccgcg atgtactcca cggttcagtc acacgagact ttaaaaaggc ctatcgacgc    420
aacgctgacg gcacgaactc gccgcgtatg tatcgcttcg agactgatgc tttaggacgg    480
tgcgagtacg ccatgctcac caccaagcag tacgccgccg tcctggtcgt agacgttgac    540
caagtaggta ccgcaggcgg tgaccccgca gacttaaacc cgtacgtccg cgacgtggtg    600
cgctcactga ttactcatag cgtcgggcca gcctgggtgg gtattaaccc aactaacggc    660
aaagcccagt tcatatggct tattgaccct gtctacgctg accgtaacgg taaatctgcg    720
```

```
cagatgaagc ttcttgcagc aaccacgcgt gtgctgggtg agcttttaga ccatgacccg    780 cactttccc accgctttag ccgcaacccg ttctacacag gcaaagcccc taccgcttat     840
cgttggtata ggcagcacaa ccgggtgatg cgccttggag acttgataaa gcaggtaagg    900
gatatggcag gacacgacca gttcaacccc accccacgcc agcaattcag ctctggccgc    960
gaacttatca acgcggtcaa gacccgccgt gaagaagccc aagcattcaa agcactcgcc   1020
caggacgtag acgcggaaat cgccggtggt ctcgaccagt atgacccgga acttatcgac   1080
ggtgtgcgtg tgctctggat tgtccaagga accgcagcac gcgacgaaac agcctttaga   1140
catgcgctta agactggcca ccgcttgcgc cagcaaggcc aacgcctgac agacgcagca   1200
atcatcgacg cctatgagca cgcctacaac gtcgcacaca cccacggcgg tgcaggccgc   1260
gacaacgaga tgccacccat gcgcgaccgc caaaccatgg caaggcgcgt gcgcgggtat   1320
gtcgcccaat ccaagagcga gacctacagc ggctctaacg caccaggtaa agccaccagc   1380
agcgagcgga aagccttggc cacgatggga cgcagaggcg gacaaaaagc cgcacaacgc   1440
tggaaaacag accccgaggg caaatatgcg caagcacaaa ggtcgaagct tgaaaagacg   1500
caccgtaaga aaaggctca aggacgatct acgaagtccc gtattagcca aatggtgaac    1560
gatcagtatt tccagacagg gacagttccc acgtgggctg aaatagggc agaggtagga    1620 gtctctcgcg ccacggttgc taggcatgtc gcggagctaa agaagagcgg tgactatccg   1680
gacgtttaag gggtctcata ccgtaagcaa tatacggttc ccctgccgtt aggcagttag   1740
ataaaacctc acttgaagaa aaccttgagg ggcagggcag cttatatgct tcaaagcatg   1800
acttcctctg ttctcctaga cctcgcaacc ctccgccata acctcaccga attc          1854
```

<210> SEQ ID NO 52
<211> LENGTH: 2178
<212> TYPE: DNA
<213> ORGANISM: Artificial Sequence
<220> FEATURE:
<223> OTHER INFORMATION: pWV01

<400> SEQUENCE: 52

```
cgatttttta ttaaaacgtc tcaaaatcgt ttctgagacg ttttagcgtt tatttcgttt     60
agttatcggc ataatcgtta aaacaggcgt tatcgtagcg taaaagccct tgagcgtagc    120 gtggcttttgc agcgaagatg ttgtctgtta gattatgaaa gccgatgact gaatgaaata   180
ataagcgcag cgcccttcta tttcggttgg aggaggctca agggagtatg agggaatgaa   240
attccctcat gggtttgatt ttaaaaattg cttgcaattt tgccgagcgg tagcgctgga   300 aaattttga aaaaaatttg gaatttggaa aaaatgggg ggaaggaag cgaattttgc      360 ttccgtacta cgaccccca ttaagtgccg agtgccaatt tttgtgccaa aaacgctcta    420
tcccaactgg ctcaagggtt taaggggttt ttcaatcgcc aacgaatcgc caacgttttc   480
gccaacgttt tttataaatc tatatttaag tagctttatt gttgttttta tgattacaaa   540
gtgatacact aactttataa aattatttga ttggagtttt taaatggtg atttcagaat    600 cgaaaaaaag agttatgatt tctctgacaa aagagcaaga taaaaaatta acagatatgg   660
cgaaacaaaa aggttttca aaatctgcgg ttgcggcgtt agctatagaa gaatatgcaa    720
gaaaggaatc agaacaaaaa aataagcga aagctcgcgt ttttagaagg atacgagttt    780
tcgctacttg ttttttgataa ggtaattata tcatggctat taaaaatact aaagctagaa    840 atttggatt tttattatat cctgactcaa ttcctaatga ttggaagaa aaattagaga      900 gttttgggcgt atctatggct gtcagtcctt tacacgatat ggacgaaaaa aaagataaag   960
```

| | | | | |
|---|---|---|---|---|
| atacatggaa | tagtagtgat | gttatacgaa | atggaaagca | ctataaaaaa ccacactatc | 1020 |
| acgttatata | tattgcacga | aatcctgtaa | caatagaaag | cgttaggaac aagattaagc | 1080 |
| gaaaattggg | gaatagttca | gttgctcatg | ttgagatact | tgattatatc aaaggttcat | 1140 |
| atgaatattt | gactcatgaa | tcaaaggacg | ctattgctaa | gaataaacat atatacgaca | 1200 |
| aaaaagatat | tttgaacatt | aatgattttg | atattgaccg | ctatataaca cttgatgaaa | 1260 |
| gccaaaaaag | agaattgaag | aatttacttt | tagatatagt | ggatgactat aatttggtaa | 1320 |
| atacaaaaga | tttaatggct | tttattcgcc | ttaggggagc | ggagtttgga attttaaata | 1380 |
| cgaatgatgt | aaaagatatt | gtttcaacaa | actctagcgc | ctttagatta tggtttgagg | 1440 |
| gcaattatca | gtgtggatat | agagcaagtt | atgcaaaggt | tcttgatgct gaaacggggg | 1500 |
| aaataaaatg | acaaacaaag | aaaaagagtt | atttgctgaa | aatgaggaat taaaaaaaga | 1560 |
| aattaaggac | ttaaaagagc | gtattgaaag | atacagagaa | atggaagttg aattaagtac | 1620 |
| aacaatagat | ttattgagag | gagggattat | tgaataaaata | aaagcccccct gacgaaagtc | 1680 |
| gaagggggtt | tttatttttgg | tttgatgttg | cgattaatag | caatacaatt gcaataaaca | 1740 |
| aaatgatcga | tgctgtttgg | caaaaaaaga | aaaagtgatt | aatttatatt ttatttatgg | 1800 |
| cgctaattta | ttacggcttt | ttttgttgtc | ggctagccga | ttctgataca ttttttttaag | 1860 |
| cacaaaaacc | acccaatttt | ggagtggtgt | gtaagtgcgc | attgtcatga aaaaatggca | 1920 |
| cgcaatttca | tcactttttta | aagtgatgtg | taagtgcgca | ttgtcatgaa aaaatggcac | 1980 |
| gcaatttcat | cacttttttaa | agtgatgtgt | aagtgcgcat | tgttcgaaaa atcgaactat | 2040 |
| gatttatttt | tgctgttgta | tttatttttc | atcttttggg | ttttggtttt gttttttgtt | 2100 |
| gctatcgtag | tttatttgct | ttttaagggc | tctattttc | gttctacggc attttttataa | 2160 |
| tttgccaata | taatttat | | | | 2178 |

<210> SEQ ID NO 53
<211> LENGTH: 2439
<212> TYPE: DNA
<213> ORGANISM: Artificial Sequence
<220> FEATURE:
<223> OTHER INFORMATION: pAP1

<400> SEQUENCE: 53

| | | | | |
|---|---|---|---|---|
| aacaagggtt | gttcgcgggg | acaaaactag | ccccaagctc | gcgtttccgc gaacaatccg | 60 |
| cgttagtacc | ttgacgcggc | tttacccagc | gcgcctacgc | gccgagattt cgcagttcct | 120 |
| gcatacttta | accagacagt | tttaacacta | cgagacaaga | aagcgccccc ggcagtccgg | 180 |
| caagactccg | agggcaactg | gaagattggt | ccttcctcta | atgaatagat tatctgaaag | 240 |
| aacggcgtta | agccttccgg | ctcgccagat | tcaaaaagtt | atccccgccg caggcggaag | 300 |
| gtcgctgaag | tccttcgaag | ggatgacggc | gacgtggtcg | gcgcgaggag gagcctccag | 360 |
| cgacgaacgc | agcagagaca | agcgaagcca | aatcccttcg | aaccggaggg aaggacgctc | 420 |
| agcgacccat | ccccttggca | atacggtatt | aacttttcca | gtatcaaacg agagcaagaa | 480 |
| aacagctaaa | tctcgccgtt | ctgagagata | cgaactcaga | gacggattag ccgaaatctc | 540 |
| gaccattgag | tccgtccgga | agtgtggccg | cgtgcccgtg | gcacctctcg tctcgttgcg | 600 |
| agcaaaatct | gacggtaaag | gcgccggata | tggtggtttg | cacacttgtg gaagcgtctg | 660 |
| ggcgtgccca | gtctgtagcg | cgaaaatcgc | cgctcgccga | aaaaccgacc tccaacaggt | 720 |
| cgttgaccac | gccgtaaaac | acggaatgac | cgtctcaatg | cttacgctca cccagcgtca | 780 |

```
ccacaaggga caagggctaa aacacctctg ggacgccttg tcgacggcat ggaatcgcgt    840
tacctctggt cgtcgttgga ttgagttcaa ggagcaattt ggtttagtcg gttatgttcg    900
agccaatgaa attactcatg gaaagcacgg ctggcatgtg cattcccatg ttctgattat    960
ttccgagaaa gacccgctga ccagcacgtt tgtctatcaa cgcaaacaag gacgccgccg   1020
ccttccctac ccccagaga tttatatgtc atccgatttc attgctgaac ggtgggaagc    1080
tggccttgcg aagcacggcg ttgattttct ccgcgattcc ggaggcttgg actgaccgt    1140 tgcgaaagac gcgcgagcca tcggcaacta tgtcagcaag atgcagacgt ccacagacgc   1200
gattagctcg gaagtcacgt tgggcggctt caaaaaagcc cgaaacggga acaggacgcc   1260
cttccagata ctcgcggata tcctttcgct cggcgatgtc gacgacctca agctctggaa   1320
agaatatgag aaagcttcgt tcggacgccg tgcacttaca tggtcgaaag ggctcagaga   1380
ttgggcaaat ctcggcgttg aacagtccga cgaagagatt gcctctgagg aaatcgggga   1440
cgaagcaata gcgctattta cgcatgacgc ttggcgtcag gtgcgacgtt ttggagccgc   1500
tgaactactc gatgtgaccg aatccggagg tcgtgcggcc gcttaccgct ggttggattt   1560
tagggaaatt gattggtcat tgcctccgaa aatcgagtga agtcgtcaaa ccatacttta   1620
agtagaggtc gagaagtccg tggaaaagtc gcggcgcctc tactgcgaaa gtaggtattt   1680
atcgatgttt ttcatcggaa aatatagaac taaattccag cccatcgcgc catgcaaacc   1740
ctccccgatt tttgacggca acggcaaacg cacaggtgaa ttttcttcgg agaagatgcg   1800
gactcaagca atcaccgaag acggccgcct cgtcgagctc acctcgattc ctccccagtt   1860
cgtccagttg attgatgacg ctgtgaagag tcgggaactt cttgaattcg agaaggtcaa   1920
tcttgccgta ttgccgcgca acggaggcgg aatttccacc tacctgacac taggggaagc   1980
cgtccacgtc cccgctccgg tcgtcgtgga ggtctcggaa tgatgagcga accctacgga   2040
atcagttcga acgctgaact gcaactcgtt tttagccgtc cagctaaacg agaagcccgt   2100
ctgtatatgt ctcggattct caagaaagaa ctggaatcag ggaagcactc gacgccgacg   2160
gaggccttgg aatcatgcga aaagctctac tggagcgttt ttgaaccgcg acttgttgat   2220
gttgttttgc acgaggtcgg agaatgccgg tgcgcgggta caaattccgc ggttgcccgc   2280
tcgctctcct ctcgcgcatt cattcctgca aggttcgttc aatctcttga aaatggggga   2340
cgcaacccag cccagctcct gacccaagac caagttgcag gtatgcggaa aactttagga   2400
acaaggtgac cacagcgtca cctgaccacc ctttcgtt                          2439
```

<210> SEQ ID NO 54
<211> LENGTH: 2697
<212> TYPE: DNA
<213> ORGANISM: Artificial Sequence
<220> FEATURE:
<223> OTHER INFORMATION: pWKS1

<400> SEQUENCE: 54

```
gaattcatgg tgttccagga tgatgacgag ttgcgtttcg ggcgcaccat cggcggcagg     60
gtccagaccg ccccaggccg acgctttgca atcctgcgct gcgccaagat caagaccctc    120
ggcaacatgg gcgccagcct tcaacacacc ttccgggaac gcgaaacccc gaacgccgat    180
cctgcccgcc ggaccgacaa cacggttctg atcggcggaa cagacagcgc tgcggtcctc    240
gatgcatggc gcgcccgtgc gccggaaaaa atccgcgcca atgccgtgca tgggctggaa    300
tacttcgttg gcggatcacc cgaggccctg aaggccatga gccgggatca gcaggacgcc    360
tatttccgcg atgccctgaa ctggctcaag acccggcatg gagccgaaaa catcctctca    420
```

```
gccgtcatcc accgcgacga gaccaccccg cacatgacgg ttatgaccat cccgctggac    480
caacagggca agctcaatgc ccgcgctttg gtcggcagcc gtcagcagct ctcggctatg    540
cagaccgact tcgcaaaggt tgtgggacag gcgcatggcc ttcagcgcgg tctggaaggc    600
tccagagcca cccacgagcg ggtgaagcgg gtctatgccc atatcagcga cccggaagcc    660
tctgtgagcc tcccagagcg ccgcagaggc ggtttcatgg gtcggggtgg ggaaacggag    720
gcagaatggc gggaaagggc cacagaagcc gtcacagagg cgctggcggg ggtccagcac    780
gccttgcggc gggaacgccg cgacagggct gcagagaccg aggcactgcg tcagcgcctt    840
cagggcagtc cagatcagca gcaggtgaac cagagactgg aacggcaggt tgcccggctg    900
aaggccgaaa cggcccgcct gcacgacagg ctggccaagg tcaaagacga agccgatgca    960
tatcacctca atgcgctcaa gctggacgcg gcccgcgagg ttatcctgac ccatgcgatt   1020
gccttcgtcc gcgatcacgg cctagacgag gccgacatgc tggcgcggat ggaggccggt   1080
ctgaacgaag ctctggcgga gtttaagccg gtgcagcagg agcaggtcgg gacagaacac   1140
gatgccgtgc aaaaaacccg ccagcgcgat gaggggctgg atcacggaga ctaagccgat   1200
ccgccgccag ttcaggccgt ccggcccgg attctgacca taatttcatc gaaaaaaggg    1260
gcgcagccct tcttgttcta atagttctat aagttcaggc gaaaatcgtg cagcaattac   1320
aaaaggttgc gcgtctataa gtggggaatc cagccgcaaa agtggggaat ccagccgcaa   1380
aagtggggaa tccagccgaa atcgcggatt gacgagtggg atttcccgcc aataaatcc    1440 accatgggaa agacactcga cgttgcccgc gaccgggcct ttgaccagac cgcgaccgtg   1500
ctgcccgccg aaatggcgcg gggggtctat atgcgcaacg cccccagcct cgcggccctg   1560
aagctgatgc atctgatgat cgccacggcg ggcgggcgca tggccgatga cgtgcgccac   1620
gaaatgcggc tggccgacat ccgcaagatc gacggtatgg ataaccacac ccgggccagc   1680 ctgacccccgc tctttgcgga actgcgcgcg gcggtgctga cccacgacga cccggaaaag   1740
cgggtcgtga ccatcggtgg cctgctggac gaagcccgga tcgattaccg gcacgaggtc   1800
agcggcgatc ttctggtgtc gtggaccttc cgcagcatgt tccgccgcat ggcggcggaa   1860
tcgaaccatt gggcgattct cgaccggcag accgtgttcc acctcggcag caagtattcc   1920
gtgctgttgt tccagcacat cgccagcttc aaggaatacg accacattac cggcaagacc   1980
tttaccgtgc cggagttgcg ggctgtgttt ggtatcccg agggcaaaat caagcgtttc    2040
gcagacctca acagagacgt gctgacgccc gccattgccg aaatcaacca gctttcccgc   2100
ctgactctga ccgccacgcc gaacaagatc gggcgcaccg tggccagcgt gacgattgct   2160
tgggaagaaa agcccctcga aggcaagcgc tcgaccaagg ccgaactgga ccgcccgaag   2220
gtgggccgga aggcccggcg cgacggcacc gccgagacgt ggcacgggc cttcccggca   2280 tcgggcggga tcgagttcga ccagcattgg cgcgacctca gcgggcggc gggctgcaac   2340 atggacaaca ccatgatcgc cgacaaattc cgggcatggt gcgccgggaa gggcctcgct   2400
ctcgatgccc ggaacatcga acaggcgttc agcagcttct gcaccaaggt gggccgggtc   2460
tgagacccgc cgcgccggtc gctcgatacc tgtggtctcg ctccctctgc ggctaccgtc   2520
agcgcctcgc ctgcatcgcc gcccttccg atcctcatcc cgcccagcc ttatgggggg    2580 atgaggatcg ggccgggact gaaacccgaa gggtaatgaa tgtgtctttc cctgcttggc   2640
agggcgaacg acattcggca gaatgtctag tgagtacaca ttcattaccc ttcaggt      2697
```

<210> SEQ ID NO 55

<211> LENGTH: 1952
<212> TYPE: DNA
<213> ORGANISM: Artificial Sequence
<220> FEATURE:
<223> OTHER INFORMATION: pLME108

<400> SEQUENCE: 55

| | | | | | |
|---|---|---|---|---|---|
| gcagctcaag | cgcctggtcg | atccgttctc | gcacaacgat | gaagcgctcg | aaaacatctt | 60 |
| cttcttcccc | cggttctgac | atcgctcccc | cagtcatcgt | gccgtgctag | tgctaccggt | 120 |
| tcgggtgtgg | cgggcgggct | cgccaccccc | aagggtccc | gcgcctcccc | gtccgccgca | 180 |
| cccgaaccca | tcagcccgag | catcgccgca | acgtccgcag | aagatcatc | aggagtcggg | 240 |
| agaccgcaac | agcacccacc | cgacaaacag | acctccacag | ccacgagacg | gcccccaggg | 300 |
| cggccagctg | cccgacgatc | agccctgttc | atccgagacc | ccctcagaag | accgcagacg | 360 |
| cgccgcaacg | tccgcacccc | agacgtccac | gtcctgcccg | aacacccgcc | gaaactcgtt | 420 |
| gacctggcgg | tacatcgtgc | tctcagccat | gaccccggcc | cccagcaggc | cggagcgtcc | 480 |
| gccgtagatg | tgccacatca | gccagaaccc | aagcagccgt | tgcaccgtgc | tccgagcaac | 540 |
| accgagggag | agcgccgaca | caccggggat | catgccgctg | atcagcgcca | gcacgtccca | 600 |
| cggacccaca | ttcttttccg | acttcttctt | cgccatttta | gtccacctcc | accaattcgt | 660 |
| gttcgattcc | gtgctcttgc | agccaccgcg | ccaagccagc | ttgaccgccc | aattcgcaac | 720 |
| ttcgcagaca | ctcgtagagc | ttctgctgcc | cgacgaggcg | acgccatccg | tcacccgtga | 780 |
| tcaaagcgac | agtgtcagcg | accgagccga | cctcctcagc | cgcgatcacg | tcgtcagatt | 840 |
| cctcaaccat | gaggccgagg | cggtccctca | ggcccgcaga | ccagccaatc | tgtctgcgtc | 900 |
| cccggctacc | cttctcccac | tcgaaccaca | ggccaacctc | tttcgccaag | ccgttggccg | 960 |
| cgtcgcccag | cacctcccaa | gtcgatcgag | tcgagcgc | agaacgcgcc | gtcttgctct | 1020 |
| gggagttcgt | caactcgtgg | ccgatcttac | cttgaaattg | tgctttgctc | aggtagcgcg | 1080 |
| cgaggtggtc | gaggccagtt | gctgcgctca | tctgctgaac | gtcttgcgcg | cgagcaaggg | 1140 |
| gagtcccgag | gcccgccgcg | agcacgccgc | gttcccaacg | gccgaacatg | accggtgca | 1200 |
| gcgccagagc | gtcgccgaag | tcgcccacga | ggaacacgag | cacatgcaga | tgcacatgcc | 1260 |
| acccattgcg | cccgtgcgta | acctcgacca | cacgcacgaa | gccctcgacc | ccgtgacgga | 1320 |
| gctggtccga | ggtccagccc | ttgcccgaag | tgactcgccg | ccaccccgaa | gcgacaccat | 1380 |
| cccaaacagc | cgtcaaggaa | tccttacgag | agtgccgaac | cgtgaacgtc | atgaacgcca | 1440 |
| cacgaccacc | gtgcttagtc | cacgtttcga | ccgccgcgcc | gagttcaagg | ccacgccgag | 1500 |
| ccatgatctt | cgcgttacac | accgggcagg | cccagaccga | tccgcagctc | tgcaacccag | 1560 |
| cgaaaccggc | ccggccgtcg | ctgcaccgca | caccaaccga | agcgaccgcc | gaggcggcaa | 1620 |
| cacgaccgca | gaacgcaacg | cgcttgagcg | acgtatgacg | ccacaaccaa | taacggaccg | 1680 |
| aaaaccggtg | tttgcgcttg | tcggcggcca | cttcaccagc | ggcgggcacg | gccgaaggtg | 1740 |
| aaacattgtt | cgcatgatta | tctagggcgc | ccccctagcgg | ggccaccgcc | gggctgccgc | 1800 |
| ccccacaccc | ccggacgcca | cgacttcggg | cgcgggcatc | gaccaccatt | ggtcgcgtac | 1860 |
| tctgggacaa | ggaagacccc | ctgctagttg | atgctgattc | gacaccagac | acgctagcag | 1920 |
| gggttctctc | agtttggga | gttctcagtt | ct | | | 1952 |

<210> SEQ ID NO 56
<211> LENGTH: 4408
<212> TYPE: DNA
<213> ORGANISM: Artificial Sequence
<220> FEATURE:
<223> OTHER INFORMATION: pLS1

<400> SEQUENCE: 56

```
ctgcagaagt agtcgctgat tggctaattc agcgtatcaa agacaaaggc gaccaaaaat      60
agcttgagtt cttttagaac aaaaaagaaa gacagtagtt gcacctactg tctttctttt     120
gcgttgtgct tttagttcct cgaacttttta gcgtcaagca tattatatca tggggcgaga    180
aattctgtca aaataatgct ataatgcttt tgaggcacct cagcgatacg gtcgtggtg      240
tgaatctcat ttacgtaggg cgactggaaa cggatagctc aaagggcgcg tttgagtgtc     300
gggtgtggga ctgccttcag cttcgggctg taaagacccc tgatactttt gaatgagatg     360
acccttgggg gtcttttttg ttttttttagg gagatgttgt gggggatttt ttctccgaaa    420
aaatctaaaa tatgggggggg ctactacgac cccccctata gtgccgagtg ccaaaatcaa    480
aaaaaaaacg cctttagcct tagagctgca agggtttgag gctcgtcaaa tctcggcgac     540
ttttcggcga cttttcggcg acttttttaga gattttttttgg gaaaaatacg aaaaagattg  600
cattgagtgc acggttatgc tactatagtt ttataaaatt ttgagaggtg acgcatgaaa     660
aaaagattga cgataacatt aagtgaatcg gtacttgaaa atcttgaaaa aatggcaaga    720
gagatggggt tatcaaaatc tgcaatgatt tctgttgcct tggaaaatta caagaaaggt     780
caagaaaaat aaaaaaagcc gtgctggcag gcactggcta aagtcaaaca tttcttgggt     840
atattatact ttatggctaa agaaaaagca agatacttca ctttttttact ttatcctgaa    900
tcaattccaa gcgactggga gctgaaactt gaacgcttg gagtgccgat ggcaattagt      960
ccattgcatg ataaggataa gagtagtatc aaaggacaaa aatataagaa agctcattat    1020
catgtgcttt atatagctaa aaatccagtt actgcagata gtgtacgtaa aaagattaaa    1080
ttattgcttg gtgaaaaaag tcttgcaatg gtgcaggttg ttctcaatgt cgaaaatatg    1140
tatttgtatt taacgcacga gagcaaggac gctattgcta agaagaaaca tgtttatgat    1200
aaggctgata taaagctaat caataatttt gatattgacc gttatgtgac gttagatgtc    1260
gaggaaaaga ccgaaccttttt caatgtggtt gtatcgctta ttcgtgcgta cactctccaa   1320
aatatttttg atttgtatga tttcattgac gaaaatggag aaacttatgg gttgactata   1380
aatttggtta acgaagttat tgcagggaaa actggttttta tgaaattgtt gtttgacgga   1440
gcttatcaac gtagtaagcg tggaacaaag aacgaagaga gataaaaagt tgatctttgt   1500
gaaaactaca gaaagtaaag aatgaaaaga gtaatgctaa catagcatta cggattttat   1560
gaccgatgat gaagaaaaga atttgaaact tagtttatat gtggtaaaat gtttttaatca  1620
agtttaggag gaattaatta tgaagtgtaa ttaatgtaac agggttcaat taaaagaggg    1680
aagcgtatca ttaaccctat aaactacgtc tgccctcatt attggagggt gaaatgtgaa    1740
tacatcctat tcacaatcga atttacgaca caaccaaatt ttaatttggc tttgcatttt    1800
atcttttttt agcgtattaa atgaaatggt tttgaacgtc tcattacctg atattgcaaa    1860
tgattttaat aaaccacctg cgagtacaaa ctgggtgaac acagccttta tgttaacctt    1920
ttccattgga acagctgtat atggaaaagct atctgatcaa ttaggcatca aaaggttact   1980
cctatttgga attataataa attgtttcgg gtcggtaatt gggtttgttg gccattcttt    2040
cttttcctta cttattatgg ctcgttttat tcaagggggct ggtgcagctg catttccagc   2100
actcgtaatg gttgtagttg cgcgctatat tccaaaggaa aatagggta aagcatttgg    2160
tcttattgga tcgatagtag ccatgggaga aggagtcggt ccagcgattg gtggaatgat  2220
```

```
agcccattat attcattggt cctatcttct actcattcct atgataacaa ttatcactgt    2280
tccgtttctt atgaaattat taaagaaaga agtaaggata aaaggtcatt ttgatatcaa    2340
aggaattata ctaatgtctg taggcattgt atttttatg ttgtttacaa catcatatag    2400
catttctttt cttatcgtta gcgtgctgtc attcctgata tttgtaaaac atatcaggaa    2460
agtaacagat cctttgttg atcccggatt agggaaaaat ataccttta tgattggagt    2520 tctttgtggg ggaattatat ttggaacagt agcagggttt gtctctatgg ttccttatat    2580
gatgaaagat gttcaccagc taagtactgc cgaaatcgga agtgtaatta ttttccctgg    2640
aacaatgagt gtcattattt tcggctacat tggtgggata cttgttgata gaagaggtcc    2700
tttatacgtg ttaaacatcg gagttacatt tcttttctgtt agcttttaa ctgcttcctt    2760 tcttttagaa acaacatcat ggttcatgac aattataatc gtatttgttt taggtgggct    2820
ttcgttcacc aaaacagtta tatcaacaat tgtttcaagt agcttgaaac agcaggaagc    2880
tggtgctgga atgagtttgc ttaacttac cagctttta tcagagggaa caggtattgc    2940
aattgtaggt ggtttattat ccatacccttt acttgatcaa aggttgttac ctatggaagt    3000
tgatcagtca acttatctgt atagtaattt gttattactt ttttcaggaa tcattgtcat    3060
tagttggctg gttaccttga atgtatataa acattctcaa agggatttct aaatcgttaa    3120
gggatcaact ttgggagaga gttcaaaatt gatccttttt ttataacagg aattcaagag    3180
ggcaatggct gatatggaac tcaaagagga acttcttgaa aaatatcatg caccgctttt    3240
tgttgatgag agaacaggcg agttgaacaa tgacacggaa gcttttggc atgaaaaaga    3300 gtttgctgat atgtttgaag ttcaatctcc gatacgtgaa acaactaacc aagaaaaaat    3360
ggactggtta agaaaacagt accaagaaga gctgaaaaaa ctagaatcgt ctaaaaagcc    3420
cctagaagac gatttaagcc atttagaaga gttgcttgat aaaaagacca aggaatatat    3480
taaaatcgat tctgaggcct ctgagagggc ctcagagcta tctaaagccg agggatatat    3540
aaatacccta gaaaatcatt cgaagagctt agaagcgaaa atagagtgtt tagagagtga    3600
taatctacaa ttggaaaaac aaaaggcgac aaaactcgaa gcgaaagcgt tgaacgagag    3660
tgagttgcga gaactaaagc ctaagaagaa ttttctagga aaagagcatt atgagttaag    3720
tcctgaacaa tttgaagggt tgaaggcaga agtttatcgt agtagaactc tattgcacca    3780
caaagatatt gaactggagg aagcaaaacg tcaagtatct ctgagagcct ctaaaaacta    3840
ttttacagct agtttagagc gagctaagga aaaagctaaa ggtgagagta tagaccgtct    3900
taaaagcgaa ataaagcgac taaaaaacga aaattcaatt ttacgtcagc aaaatgacaa    3960
gatgctaggg aaattaagag agttaatgcc tgataaagcc tttaagaatt tgttatcaga    4020
acttaaggcg attaagccaa tcgtgaatat aattaaaaag gctattgaaa agagcttgtt    4080
ctgagcgatt tatgccgtga agctatttg acaataagca gtgacagagt acgctaggac    4140
gtgccgagcc gaaaggcttt agcgtttcgg acggacacgg acaaaggacg gcagtcactg    4200
gttacttgtt gtcaaataga ccatggaata aaaagcgtca aaagtcttga gtggatgata    4260
ccctatggta ctctattcgc cttttgactt ttttgctata atttaagtgt cgccagttct    4320
tccgtcaggt aatgcgaact tagactggag gtgagcgttg tgaagacatt cctcgagctt    4380
gtctttgtcc cttttgtggt tggcgttg                                        4408

<210> SEQ ID NO 57
<211> LENGTH: 5804
<212> TYPE: DNA
<213> ORGANISM: Artificial Sequence
```

<220> FEATURE:
<223> OTHER INFORMATION: pUB6060

<400> SEQUENCE: 57

| | | | | |
|---|---|---|---|---|
| actgcgatgt | acgatagatg | ctgtattaag | caagtacaca | cagcgtcccc | tctgcgaggt | 60 |
| gccgtctgtg | actggttcag | ggggctcgcc | gcccccgaa | acccctagca | tccactgcga | 120 |
| aaattcgcac | gttgggtgcg | aaactttctc | agcggattct | catggaaaag | cgcaccaaag | 180 |
| agatcaaaat | cagactcacc | gaagcggagc | atcagcggtt | acttgaacgc | tgtgaccgaa | 240 |
| cgcatttggc | cgagtggtta | cgtgccgttg | gtttaggcga | atcgcggaca | gctcgtcgtc | 300 |
| gtccgctacc | taccgtagac | ccgatcttgt | tacgtcaggt | cagcgggatc | ggtaataacc | 360 |
| tcaatcaaat | agcccgttac | ttgaatcagc | atggcttacc | gccgcaagaa | cgggtgtcgt | 420 |
| tgttagatgt | gctcaatagc | attgaccaac | atcttgccga | actgctggag | caacatcatg | 480 |
| atcgttaaga | ttcatggtcg | tggtgccggt | ggcgggagtg | gccctgtcga | ttaccttctg | 540 |
| ggccctgatc | gtcagcgtga | acaagcgacg | gtgttacggg | gtaaccctga | gcacgtcaaa | 600 |
| gagctgattg | atggctgcga | atttgcccga | acctataccct | ctggcgtgct | ctcttttcag | 660 |
| gagagcgact | tacccgcagg | cgaaaaaaca | gcgtttgatg | gagaatggga | gcagacattg | 720 |
| atgaccggtc | tagataaaga | ccagtatgcc | tgcctctggg | ttcaacatca | ggacaaaggg | 780 |
| cgtcttgaat | tgaattttgt | tatcccgaac | atcgaattgc | agagcggaaa | acggctgcaa | 840 |
| ccttactttg | atcgggctga | ccggcctcgc | gttaacgcat | ggcaaaccct | caccaatgac | 900 |
| cggcttggat | tacgcgaccc | gaatgacccc | gccaatcgcc | gagcattaac | cccctcgaat | 960 |
| gaccttcctc | gcaacaaaca | gcaggcagcg | gaagccatta | ccaaagggct | aatcagcttg | 1020 |
| attgagcagg | gagaaattac | ggatcgtaaa | ggggtgattt | cccaccttac | cgatgccgga | 1080 |
| ttgtcggtcg | tacgggaaac | caaatccagt | atcagtattg | ctgatccggc | aggtggcccg | 1140 |
| aatattcgct | taaaggagt | gctgtatgag | cgagattta | aatttagcgc | gggagttcga | 1200 |
| gagcaaatcg | aagcagcaag | ccaagactac | cgcaacgagc | gtcgcgagcg | cattcgagaa | 1260 |
| gcacgagaaa | cgtatcaccg | aggccttgaa | attaagctca | gggaacatac | agaccgctat | 1320 |
| ccaagaagag | aacgacaacc | agctaaaaca | gatacaccgc | ttagtcggaa | tgacatggct | 1380 |
| gtacagcctg | gcattaagcg | cgatcctgtt | tgcgacattg | attggagtag | cttggtatct | 1440 |
| cgggactatc | gtggtcgaac | gccagaacga | aatcagcgag | cagagccaga | tcctgcagga | 1500 |
| cttaaagagc | cagaccggag | ccggcgtatc | gataattcac | gattccaaga | caagagcgt | 1560 |
| gtattacctg | atccttccgc | aggggcgaa | gcagatcgac | gagtacaaga | acgctcaaca | 1620 |
| tcgtcaggtc | atcaagtaca | gcgccaaata | acctcatcag | acgccacaga | atcgattctg | 1680 |
| ggcggtttta | tctatcaggg | tgaagagatt | catgccgaaa | tggcagcagc | agcttctgag | 1740 |
| cgcattagag | agcttacaga | ggcactacga | acaacagcag | caagcgtggc | aggacagcta | 1800 |
| cgccaactta | cagcgcatgt | tcgaggttac | ctcgcaggag | ttggcgaaaa | acgacagggt | 1860 |
| ttgtcaggcc | ttgagcatgc | aagtcaccgg | cttggcgcag | caagtcgaga | gcttaaacag | 1920 |
| aacagtgcgc | cgcttgagca | attagccaag | cggcacgaac | agcggcattc | tcggcggtca | 1980 |
| cggcatgagt | ttataagcgt | ttatcggcag | catcataagc | ggcagaacgc | tcgcgcttac | 2040 |
| cgaccgccac | cacgaatacc | gtaatggttt | gatcgcgaac | ctgatagacc | aaacgataac | 2100 |
| cggatgctcg | tagcttgatt | ttgtagcaat | ccggcagctc | tcgcaggcga | tttttatcga | 2160 |
| tccgcgggtg | ctgtagaacc | tgctcgagtt | ttttcttgaa | ctgcagacgg | acatcatccc | 2220 |

```
cgagcttgcg ccattccttc agggctcggg gatcaaactc aaggttatag ctcatccagt    2280
gacaccttta cgcccgcctg tgggttttcc agacgatccc gaacgatagc catcaaatcg    2340
gcatcatcct cggtcagcaa cacctgctgg aacggcaagc gtccgctttg gccacatac     2400
tccagtgttt ggcgcagaac ctcggacggc gttacgccca gcttttccag tgcggcataa    2460
gagcggcttt tcagctcgtc atcgatccga atattaatcg tggccatcat ctcacctctt    2520
gatgtagtga caagtgtatc tacaagaagt agtatgagcg taaagccgtg cgagaacaag    2580
caggaataac ggattgtcgg ggatgacaaa aaccgttgtt gaggtgtaac ttagcggcag    2640
aaaaaacaaa gccccgaatt catgtgctca acttggcgga agactcatga aattcagggc    2700
taggtcgaaa cctagaaagg atattagcac atgcagcgtg caaaacaaca gccccgccat    2760
aaggctggga gccatggcta atcaggcttt aacgcttttt aacgaccggt taccccacaa    2820
gccgtacttc tccgatgatt tacagtttgg tgtccgcatt gccggtaaag agcgtgctct    2880
cctcgcaaaa tacatccagt ttaaccagcc ccacgccatg tactggcttt gctttgacgt    2940
ggacagggcc ggagccgcga ttgattgggc cgatctgggt gcacctgcgc cgacactcac    3000
catcaaaaac cccgataacg gacatgctca cctgttgtat gccttgaaca ttgcggtacg    3060
caccgcgccg gatggtcgag gccgcctcct caaatatgcc gccgcattg agaatgcgct     3120
gcgtaaaaaa ttgggcgccg atgcggggta ttcagggcta atttgcaaga atccgaacca    3180
cctgcactgg cagatcaccg tctggcagcc tgagctctac accctcgact ggctagccga    3240
ctatctcgac cttggcgctg ccaatgaccg agaaatcctg cccgactacg gtttaggccg    3300
taactgcacc ctattcgata aaacccgcaa gtgggcttac cgcgctatcc gccaaggctg    3360
gccggagtat agccaatggc tacaagcctg cattgaacgc gctaaagcct acaacctgca    3420
gttctccgca cctttagacg agaacgaagt catgggaatt gctaaaagca tttccaagtg    3480
gacaatggtc acttatcgca gtctggggtt tgatgagtat gtgaagttaa ctcattcacc    3540
cgaggtacaa gcatatcgcg gtcggcgaag taaaggcggt ggtagaccta gtattgggga    3600
accatggtta gctttaggta ttagtcgtcg aagttatttt agatggaaaa agctaggtaa    3660
attatgaaaa taattagttt tatcaatatg aaaggtggtg ttggtaagtc tacggttgct    3720
attaatgttg ctcattgctt agcggagcga aatcaaaaaa aggtattgat aattgatatt    3780
gatcctcagt ttaatgcaac tcagtgcgtt atgaaggcag aggattacat agagcatatg    3840
cgtacgggta aggatactat ttgttctttg tttaactctg accgagttgc agctaaaagc    3900
gttagtggac catcttttga aaaatgcaaa gatatcagta gcatatctcc tgttgaaatg    3960
tctgagtatt tgcatatttt acctggtgac cttggtttgc atcgaattga ggttacagct    4020
gggagcgggc aggagttcaa gttaaaacga tacttggatt ctatcagtga caagtatgat    4080
tatgtgattg tggatactcc gccaacacca tcaatatgga tgtctagcgc attgatagct    4140
tctgactatt atataatacc ggttaaacca gatccgttat caaggacggg gattgattgc    4200
ttgatagtat aatagcagat aaaaaggaa actttgattt aaaaataaaa tgtgctggag    4260
tggtgtttaa tatggttgaa gaaaactgtg tttagagaga ctaagagttt ttttaataac    4320
agtgatactt ggcgcaatta catttttaga tcttttcctgc ctaagaaagt tgcgatagct    4380
aaaaggcaga catcaggaga acatatatta aagacaaaag attcctcttt gcacatgaaa    4440
cttgtcagag tggtcgatga aatcgaagag agaatacagt aataggataa cgtatggata    4500
agttaacaac taaagaaata aagacgttat tgaatttcat tgaagagttc tcttggattt    4560
caaataaata taaaaatttg gataccaata agttatatga ggctcttaat aattgcgagt    4620
```

```
ctcgtcgtca aaatgaatat aatgattata tttcgtactc aaaaagtgta ggtaagaata    4680
atcatgtgtc atataggaat agccttaaag ataagacatt tctaattggt aagctcccat    4740
ctcttttgat ggataaagaa ttgttctcta aaaataagga gctatctgac tttgctcgac    4800
tacttggtgt tgaggtcaga ttccctgaga acgttctag agatgagata tcggcacta     4860 ttatttgctc attacaagag gaaagtagtg ttaaaagaat tcatgagatt ggtgagttta    4920
tctatgcttt aactagcgat gaaaaactaa tgaataacat taaggttgag aagaaaatat    4980
ataatgatga gtatgattgg aataatgtaa ttagactttt atttatgggt aaatgatgtc    5040
tagattgata gggaaagact ttgatttatt tttaggcttc tttttaaatt acagccttaa    5100
agatttggca tctaatggtg attttaaaaa gaagctgcgt gaggcacaca aaaaatacta    5160
tccgttactc actcttagcg ctgagcttga tctcatgttt agggggatg tgggagagga     5220 ttgtgctgat agggttaaag aaacttgctc tgatataggt tcgtctattt ttttattagc    5280
ccatggaatg tataagcaat ccaacatgtc attgcgtagt tctattgaga acttttaaa     5340 atcaataggt tgcaatcatt gccctgacat attaacagat aagagtgttt tttctgtttt    5400
tgaaaaggct gggcaattag agttattttt agatcctgtg ttcaaatgca gtttgatga     5460 gttgcaatct atttactcat cgttgtgctt atatactcat accgcaagtg ctgaacacat    5520
ggctaaaatt agtgctatgg gcagtattcc aaaacgatga aaagcgaaaa gcgctattct    5580
tgttaatgac ctcactaggc ttgttcgaat ttatcttttc atttacacga agttgtttag    5640
gtgtgaattc ttcaaattta accatgacaa ccgagatgtc attctcagcg cattaaccaa    5700
gtcgcaacga cgttcgttaa tggaaccatc ctgatgtggc actaaacaac ctatatcaga    5760
taacagccct gcttttgcgg ggcttttgt ttgtgcgtga tgtg                      5804
```

<210> SEQ ID NO 58
<211> LENGTH: 1711
<212> TYPE: DNA
<213> ORGANISM: Artificial Sequence
<220> FEATURE:
<223> OTHER INFORMATION: p545

<400> SEQUENCE: 58

```
ggtgccatga gggttctcac tgatacctga atgagtttga cggtggggcc gcatgcacga     60
ctgccatacc gtcaatccga gcgccgcaga ctgggcatgt cccctgagt aacacttgcc     120 caccgggttc aacgtccgtt gctgatgccc cccattggct gtagccacaa tggccgcagg    180
ataagaacgt ggcgcgcact gtgcaaccgc acgcgaacgt agtgccaagc ggtgcacgat    240
caagaaaatg ctcatcgtgc ggcgttacgg tcatgcgtca gttcgattct tgttcagcgc    300
gtagtgcacg gtgcccacgg aaaccccgac ctcggcagca atcgcacgca tgctctgacc    360
ctccgagcgg agctcacgaa tccgcgcgtg gcgtgcggca acgcgggcca cgaactcctc    420
gcgtggctcg gaagtccacc gcttgacggt ggactcggag acaccgagct ttttcgcagc    480
agcggcgatg ctgtagccgt tgcggggag acgttcacgt gtggtcatga gagaccctcc    540
aagaactgtt gacgggtatg ggcgcgccgt gatgcgccac tggcaatgcc gcctttgtgg    600
ccgccttctt tgccgccttt ggatgctcca cggaggctga tcgctttctg gcgtgcgcgg    660
aaggtttcgg gggtgaagtt gcgccagacc catcgggaaa tggatcgaga taagtgctta    720
agttcgttca agccgagggg gcctgtgcg aattcgtcgg cgatgatcgt ctcgttcagt     780
aggtggatgt gctcgaatac ggtgtgctcc cattcggcga ccgggccgcc ccaggagtgc    840
```

```
cggacggccc ggtatgccca catgcggtg gtgtcgaaca gggtgacgtt gcggccgacc    900
gttgatcggg tgacgttgcg acgcgggttc cctgcctccg gcagtgcgtg gatctcgtcg    960
agggtgtgtg cgagggcgcg cagctcgtag agcgcgtctg cggggcccca gagggtcgca   1020
tgggcggtgc tgagcgggtt ctttgtgatc cggtgcccgt aggatgcatc gccgccgaga   1080
acgtcgcata ggccctgctc gacgcgggcg agcaggttga taggccgtcg ccgcgcggca   1140
tcggtcagac acacagggtt cttcaaggca tagacgatgt gtccggtggt cgtgacacgg   1200
ttcatggaca cgtaggacgg tgaaggcagc ccagcgaggt ctgcggccca gtcagcatcc   1260
gaagcatctc gatcggtgat gaccaaggac tgcatgacca acgggttcgc ttcgatgtaa   1320
ggcagctcca gcgccctctg ccgagtcacg tgccggtacg ccccagactt ctcggctgac   1380
gccagcggct tgcgtggcag ccagctctca gggaacaacg tctcgaacga atccatacat   1440
gcagtgaagc atgcgagtca cgttcagcgt ggtccattcc tcggcgtgtt caaagtgggc   1500
gacgaagacc ccatatcagt tagttacccg gttgagccat gtgagcaaag cgaactctct   1560
ttccacatcc cctgccaaac atcccccgac tcccctgacg ctgccacctg ctccaaggga   1620
tggctggggc gtgttcgggc attgcggcta gttcctcgcg cagctgtgcg atcttcgcct   1680
gaactgctcg ccggctgtca gggtcgacgg c                                  1711
```

<210> SEQ ID NO 59
<211> LENGTH: 7426
<212> TYPE: DNA
<213> ORGANISM: Artificial Sequence
<220> FEATURE:
<223> OTHER INFORMATION: pJD4

<400> SEQUENCE: 59

```
ctgcagcaat ggcaacaacg ttgcgcaaac tattaactgg cgaactactt actctagctt     60
cccggcaaca attaatagac tggatggagg cggataaagt tgcaggacca cttctgcgct    120
cggccccttcc ggctggctgg tttattgctg ataaatctgg agccggtgag cgtgggtctc    180
gcggtatcat tgcagcactg gggccagatg gtaagccctc ccgtatcgta gttatctaca    240
cgacggggag tcaggcaact atggatgaac gaaatagaca gatcgctgag ataggtgcct    300
cactgattaa gcattggtaa ctgtcagacc aagtttactc atatatactt tagattgatt    360
taaaacttca ttttttaattt aaaaggatct aggtgaagat cctttttgat aatctcatga    420
ccaaaatccc ttaacgtgag ttttcgttcc actgagcgtc agaccccttat ctataaactc    480
ttggcttggt tctaatccct ctaaacgatt attatcaata gccgctctaa ccgcttttttc    540
tcggcttaat ttttctgtct ctgttataaa attgctattc atcttgttct tcttcaaaaa    600
aaagttaagt aaaatacctta cctaaatttt tactagttcg caatctacga gcttataacc    660
tcgttttttc aattcattta aaaaatcaga ttttgagcct aattttgatc tattgctatc    720
gttacccgct agaaataccc agtaattacg caaatcttca ttggtaactt tcgtaatatc    780
ggtgtaatga tcttcgagta tttttaagca atctctagcc cataaaccgt actcgtgatt    840
gctcatctta gggttttgct tatcgagttt gacgaacttc ccatacttgt tttatgtgg    900
aaatactggc cgttttgcaa cttcttcaat tttttgagct gttcgttttt tactaccaat    960
cacaaaattt aaagagtgaa tagtacgccc acgcttgatt tgttcaacct caacgactaa   1020
atcagatttc tcgttaatct cagttattgc aggttccaaa acacgttgat ttaatgaatt   1080
aaatctaggg tatttatttt caacctgaag ccattctttt agttttttcta ctgtaatttc   1140
acgactacca acagagcgat attgtgtaat tagctcataa attcgaattg aatgtacact   1200
```

```
gttgaaataa gcgatatgtt tgagttgata ttgcgtgaat tgcccttta  gttgcgttag    1260 gtatggcata acttcatcag tcattgcaat tctaaaacgc ccctctttct tgaaatatgt    1320
tctagaggaa acccaacgaa attcagttac acggtcttta tcttcagttt taacacttcg    1380
gtcataaatc cgttttatag ccgcctgaat ttgcttatag gcgttatctt ggcttatttc    1440
tggaaactca cggacaaaat cagccaccgt aaaatcaaaa atcttttgat tagatttcgg    1500
atccatagtc ccaatagtta aagctaaaat tctgatttca tcaatactca atcggtaatt    1560
ggcttcaata aggctattag cctttacaac aactaaatca tttggcataa gacaacaaat    1620
ttcctgttta aaacaacaag caaaatatac ctgttgttta tatataaaac aacaagtatt    1680
ttcttaaaag ttgtctataa caggaaattt gttgtcttat aacaggaaat tgttgtcgt     1740 ataacaggaa atttgttgtc gtataacagg aaatttgttg tcgtataagt ttgtaactta    1800
ttgattttac tggttttaaa aacgccgaaa acaagtaaaa aacaaaaata taaaaatata    1860
gggactttcg tccctttttt gggctttcag ccctaatttt ttcttttttc aggattaaaa    1920
attacaaaac ccttacagag caagtaaact tgtttgcttg ttctgcaagg gttcagcaac    1980
cgaagccgtt aggcgtaggc ggtagcctat aaaagccatt taattttatc tttaaatttc    2040
cgtttaaatg ctttgagtgg gtgtcttta   tcgtactcat caatccttt   ttgcattctt    2100 tcgtttgctt tgtgatcggc aaatttttgaa taagatttt  ccatctcatc taacattcta    2160
tcaatccgtt ttttatgttg ccatttcagg taaacataaa cacttatagc aataaaagac    2220
aatatcaata cattgtaaaa aatgattgtt acaatttcgc tcacagttat tttttacctt    2280
tttcaatttc ttcattgata aatgcactca attcatcaaa tttcttgtca tcattgataa    2340
atttacgcaa cttagggaag tttctatcta catctaaaag agggttaaac gattattatc    2400
aatagccgct ctaaccgctt tttctcggct taatttttct gtctctgtta taaaattgct    2460
attcatcttg ttcttctctc cactttaac  taattcacag ttcacaatct tatacccctcg    2520 attttgcaac tcgtttaaaa aatctgaccg cttaccaagt tttgatctaa aactagcatt    2580
gctagtcaaa aaaacccaat aatgccgtaa atcttctgtt gtaacatcgg caagatcaga    2640
ataaaaatct tcaaggattt ttaggcaatc tctcgcatag tttccatatt cagcattact    2700 catttggga ttttgagtat ccaatttcac aaacttcccg tacttgtttt tatgcggaaa      2760
tgcagggcgt ttctgttcga ttttaccgc acttttctta ctcttgatcg tgaattttaa     2820
tgctacgatt gttcgcccac gcttgatagg ttcaacatca acaagcagat cggatttagc    2880
attaatttca tttatggatg gagttaatac tcgcttttta aaatccttaa acagtgggta    2940
cttatcagag atacttaacc aacttttaat atcttctacg cttgtttgtc gccaacctgt    3000
atcacgatat tgagaacaca attcataaag gcgaatagcg tgcgtactac ccaaagcccc    3060
aatattgatc aatttatatt ttgtgtagtt atcgtgtaat tcagaaatgt aaggaattag    3120
ctcatcgtgg aactcgatat aaaatcgccc ttctttttta aaataggaac gcttatgaat    3180
taaagctact tctgttaatt cgtgttcgtt atcaaccagt gtaacccaac gctttgagat    3240
ttttaaaacg gcatttctaa cttgtgtgta agctatatca ggatttacat cggggaagct    3300
tttacaaaaa tctgccaccg tgaaatcaaa tccacgctta gacggatttt taggattaaa    3360
aacccccaaa gttaaagcca gaatccgcat ttcatcaagt gtcattgaat agctggcttg    3420
tacaaaattg ttagctttat ggactgtaa  atcatttgtc atatcatcaa ggtggacata    3480
aaataaagat tgtcccatta taaccataca gttaaatggt ggtcaataaa aaacaaagac    3540
```

```
cactataaca ataaatttgt ccacctataa caataaattt gtccacctat aacaataaat   3600
ttgtccacct ataaatctcg caagccttgt gtaacaaggg gagccagagc ctacaaacaa   3660
gaatacaaac aagaatacaa aaaaatagag cctaaaggct cttttggggg ctttcagccc   3720
taattttttc ttttttttcag gatttaaaat tacaaaaccc ttacagagca agtaaacttg   3780
tttgcttgtt ctgcaagggt tcagcaaccg tagccgtcag gcgtagggcg gtagcctata   3840
aaagccattt aattttatct ttaaacttcc ttttaaatgc tttgagtggg tgtcttttat   3900
cgtactcatc aatccttttt tgcattcttt cgtttgcttt gtgatcggca aattttgaat   3960 aagattttc catctcatct aacattctat caatccgttt tttatgttgc catttcaggt   4020
aaacataaac acttatagca attaaagaca atatcaatac attgtaaaaa atgattgtta   4080
caatttcgct cacagttatt ttttacccttt tcaatttct tcattgataa atgcactcaa   4140
ttcatcaaat ttcttgtcat cattgataaa tttacgcaac ttagggaagt ttctatctac   4200
atctaaaaga gggttatta ttatttcatt tagccaaaaa gccctaata aaaccttgta   4260 atgcgtagct ttcttacgct tttctgcttg ttcttttgac ttaatcgcac gaattttcgc   4320
tttgatttcg tcctgcttgc gttgtaaatc tgcttgttgc tgttccaatc ttgtaagttt   4380
ttcgcttgcc atactagccc ctttatatag ttagaaatta tcgttatttt attcagtagg   4440
tgctaggctt gcaagtgttc tgttcattac gttaaaataa cgtaatgccc acttatcagt   4500
ttctcttcga gaaactggtg ggcaagcgta ccgcttgacc gtttcgcaat actcaacact   4560
atggcaatct atcatttaaa cgttcgctat tgcagtaaaa gcaaagggca atcagctcaa   4620
gccaaaaacg actacatcaa ccgcaatgat aaatattcaa agcggttaga tgatttacag   4680
ttttcaggct atggtaatat gccaaaattt gccgaagata atccgcaaga attttggcga   4740
ttgtcagata tttacgagcg agctaatgcc cgagtttgta ctgaaattga atttgcttta   4800
cctagagaat taaccctaga acaacagcaa aaattagtaa gttcgtttat agaaaatacg   4860
gttgatagcg gtagcaataa actaccctac tctttcgcta tccataccga taaaaataat   4920
cataatcccc attgtcattt gatattttca gaacgccaac ttgacggcat agaccgtaca   4980
gccgagcagt tttttaaacg tgctaatact aaatccccag aaaagggcgg agcgatgaaa   5040
acggcagatt ttcgagatcg tgagtttatc caatctgtcc gaaaaacgtg gagagagcaa   5100
gctaatcaag ccttagagca atacggatat gccgcacgaa ttgacgaacg tagctacaag   5160
gaacaaggca tagagcaagc cccaagagca agaattgaca gggtaacgtg gcaagaattg   5220
aaccgattag agcaagaaga acgccaaatc gtgcaagagc ttgcacttaa aggacaagaa   5280
attaacaaag aaaaatccta cttgcagaaa atcgaagaaa aacaggctca aggaatgggc   5340
aaatatgaat ccaaattcgc agctgcgttt tctaaattat cggaaagtgc cctaaaacac   5400
gatttaagca acgaaaaaga aaaagacagt aaaatacaca ctcaagaaga aaagtgcct   5460 caaaatcgca ttcaggggct ttctcaagca gattttgatc agttttttaat tgatgaatgg   5520 ctacctcaaa tagaaaaata cgttaaagcc caagaaaagc gggacggaat ggaagtagag   5580
atcacgcaat acgacaagga tttacagcgt attcagggag actataacaa gctcacagat   5640
aaaaatcagg gttttctcgg tttatgggaa actaagagac aaaaagcaaa gaaaaaagag   5700
cttgaagatg aatacaaaca tacagcagag caacggaacg ctaaaagcca agaattagcc   5760
gagtatagcc aaaaaataaa agcatacgaa cagaaaacgc tagagccaat caacgagaag   5820
attgccaaat atcaagctga caaccctgaa ataaaaatgc ggagcttagg atttgtgaaa   5880
aaaattaagg ctcaaggggc atataaagcg gctcaagagc gaatggagcg agaaaaacag   5940
```

```
caccaacagg aaaaacaaca gagacattta gagcgagaga gtggtttgag cttgtagcta    6000
acgccctacg cctacggctt cggttgttca acccttaaag aactcgcaac aagttgcaaa    6060
ttctttaagg gttcgcaata aaaacaaccg ctaaacattt ctgcccagcg gttgaaaatt    6120
tacctattca ccattacaat gatcaagcag gaaattttt tgattgccgt aaatgtccgt    6180
atatctagtt gaggcacaac ccgccaaagt cattgcccca accagaacgg cgataaaccg    6240
tatatttacc gataaggcat ccggcagttc aacagaccgg gaagggctgg atttgctgag    6300
gatgaaggtg gaggaaggtg atgtcattct ggttaagaag ctcgaccgtc ttggccgcga    6360
cactgccgat atgatccaac tgataaagga atttgacgct cagggcgtgg cagtccggtt    6420
cattgatgac gggatcagta ccgacggtga tatggggcaa atggtggtca ccatcctgtc    6480
ggctgtggca caggctgaac gccggaggat cctagaacgc acgaatgagg ccgacagga    6540 agcaaagctg aaaggaatca aatttggccg caggcgtacc gtggacagga acgtcgtgct    6600
gacgcttcat cagaagggca ctggtgcaac ggaaattgct catcagctca gtattgcccg    6660
ctccacggtt tataaaattc ttgaagacga aagggcctcg tgatacgctt attttatag    6720 gttaatgtca tgataataat ggtttcttag acgtcaggtg gcactttcg gggaaatgtg    6780 cgcggaaccc ctatttgttt attttctaa atacattcaa atatgtatcc gctcatgaga    6840
caataaccct ggtaaatgct tcaataatat tgaaaaagga agagtatgag tattcaacat    6900
tttcgtgtcg cccttattcc cttttttgcg gcattttgcc ttcctgtttt tgctcaccca    6960
gaaacgctgg tgaaagtaaa agatgctgaa gatcagttgg gtgcacgagt gggttacatc    7020
gaactggatc tcaacagcgg taagatcctt gagagttttc gccccgaaga acgttttcca    7080
atgatgagca cttttaaagt tctgctatgt ggtgcggtat tatcccgtgt tgacgccggg    7140
caagagcaac tcggtcgccg catacactat tctcagaatg acttggttga gtactcacca    7200
gtcacagaaa agcatcttac ggatggcatg acagtaagag aattatgcag tgctgccata    7260
accatgagtg ataacactgc tgccaactta cttctgacaa cgatcggagg accgaaggag    7320
ctaaccgctt ttttgcacaa catgggggat catgtaactc gccttgatcg ttgggaaccg    7380
gagctgaatg aagccatacc aaacgacgag cgtgacacca cgatgc                  7426

<210> SEQ ID NO 60
<211> LENGTH: 8830
<212> TYPE: DNA
<213> ORGANISM: Artificial Sequence
<220> FEATURE:
<223> OTHER INFORMATION: pIJ101

<400> SEQUENCE: 60
ggatcctcgt tgccgtcctt gccttcggcg gcccgggtcg cctcgaggtc gagggcgcgg      60
cgggtgaccg cgtgccatcc gtcctcggtc acggcgaccc cggcccgcag ctccccgccg     120
tcggcgtcgg ccgccaggag cagatcgagg tcgtcggcct cggtgtcgcc gccgtcgagc     180
ccgagcatct gccgcaggta gcgggtccat tcgatggccc ggcgtccccg ggttgcccgc     240
tcgtactcgt gccagcgcga gaggttccac tccagcgagc cgaccccggc ggcgtcgtcc     300
tcggtcatgc cgccggtcag gtccccgatc cgtccgagga gttcgaacgg ggcgacgttc     360
ccgccggtcg ccgtcttgag gtcggcgcgg gcgagttcga gggcgggcgc cttcccgtcc     420
tgggtcttgg cgatgtactc ggcgaggtcg ttggcgtcgc gctcggtctc cagccgcttg     480
aagtcgacgc cgtgccggtc gtcgggcgtg aaggcggggt tgaccttgcg cagggcggcg     540
```

-continued

```
gtccacacgg accgccagtg cccctgccac tcgtcgagcg cggcgccggt cggctcgaag    600
gtggcgacga tctgcttcgc ggaccgctcc ccctcggtcc ggccgccgac caggacgatc    660
gcgtggatgt gcgggtgcca gccgttgatc tgccccacgg tgacttcggt cgcgcggatc    720
atgccgacgt acccgatccg gtctcggatg ccctcgcgt cggcggcccg gtgcccgtcc     780
ttggcccggc gtccggccca cgtgccgccc gtgatcagtc gctggtaggc gcccggccgc    840 cggggggctgt ccggcgtctt ccgggtgccc tggaggggcgt ccatgaggtc cgcgagccgg  900
tccgtgtgcc catggcgggc cgtgaaggtg accaggtagg cggtccccc gcgcttgatc     960 cactcgacca cggcggcggt gatctcctcg gcccgcttgt gccggatcgt ggcggcgcag   1020
accgggcaga gccagatccg cccgcaccgc atcaggccca ggaccacgga cgttccggcc   1080
gccgtctggg cgacgatcac gccggaggca gggtccatca gggcgcggcc gcagcccttg   1140
cacgcggcgt ccccgctgat ccgccacagc gtccggcggc ggctgtaccg gcggcttttc   1200
cgcagtcggg cagcctcggt ccgcgacgtg cttcctactt cccagaggct gtcgcctctc   1260
gggctctccc catccacccc gtccggagaa accgcaggtc ggaggggtgc gggaaactct   1320
gttgtttctt tcccaaggtg ttcgcttttg cctcgggcgg catctcgcgt cacacgcgcg   1380
atcgcccgct tcgctgccat ccggcagcgg tctgagcagt agatacgcgg ccgtttgccc   1440
ggtgtgtggg caattgcggt cccgcagtgg cagcggggcc cggcgggccg atctggcaat   1500
gcctcggcat cgctccgtac tctgggcacg agcaacgttc ctgtctcgcc cggctaaggg   1560
gcgcgagtct gggagcggac gggtcggagg tgcgaagtcc ggcccgttgc tctttggtct   1620
ggtgggaatc ctggcaccaa tcgggccaga ggttccctcc gccactcccg acgcccttg    1680 gggctggtgt gacttggagg gccgaagaga gccccgccgg gtatccggcg gggctttgac   1740
gtgcggtcag tgcgtgtgtc ggcgagcgat ggccacgagg ccctggaagc cgagcggtcc   1800
ggcgaagtcg gcccagtcgc aaccgggctc agcgcagtgg gcggaccagc caccgccgtt   1860
ggggtcctgg accaggttca cggtcccctc ggtcaggcgt ccgtcgaagt cggtcatggt   1920
cggtctcctg gtgggtgggg gcggggcgcc agcacgaagt gccggcgccc cgcgggggtt   1980
ggtcgggtca ggcgccgaac cggcgggcgg cggcggcgac caggccgtcg gcggcggcca   2040
tggcgcggtc gcggtcggtg gtgagggcgg tgcggtcggc ggcggcccgc aggtcgtagg   2100
ccgcttgggc ggcggcggtc gctgcggggg cgagggcggg ggcgagcacc gacacggtgg   2160
tgaggggcgc ggtgatcgcg gagcgggtgg cgtgggactc ggtgcgggcc gcctcgtacg   2220
cctcggggga ggcgccggtc aggcgcaggt cctcgcgcac ccacatggcg cggcggtggt   2280
cggcgagggc ggcggcgagg gcggcgacgg cctggacggc cgcgtcgcgg cgggagtcgt   2340
cgcgggtggt gcggcggtg cggtgctgga ggagtccggc gaggccggtc ccggcgagcg    2400
tgccgatcac ggcaatgagc gtggtcacca tgtgagcccc ctggcgtcgt gtccgtctgc   2460
ctacgtgtat cagtctgaca cgcacgtgtc aggttgcgca atgggtaggc cccgccggtt   2520
tccggcgggg ccatccgtca tgcggcggtg ctgagtcggg cggcgagctg gtgggtggcg   2580
gcgaggatga cgcggatctc cgcgccgccg tcgaccgccg cgagggcggg ggccggggcg   2640
ggtgccggcg gattggtcgg ggtcgggcgg cggcggaggg cgacgccag gaccatggcg    2700 gcgatcgcca cggtggcgag gtaggcgagg gcgatcacgc ggccacctcc ctcgtgacgc   2760
ggcgccagga cgcctgcagc cgtgcctccc cggcggagta gcccatgtcc cggaagcgtc   2820
cggcggcgac ccggtacgac ccggagtcga ccaggccgga catgatcccg tcgatctcct   2880
cgttgctgag cgggaccacg tcggccgacc cctcgatggc ggccgggacg ggctccgtgg   2940
```

```
gtccccagac gggcaggcgc caggagggcg gagacgtggg cgtgacacga gaggtgacgc    3000
aggtcagagc gcgtgccgtg ccctcgccct cgcgggcctc ctccagcgtc gaccaggccg    3060
acgccagctc cccggcggtc tcggcctgga cccgggcgac ccgggccccg cgccggtca     3120 cggcctccag ccgggtgacc tccgtaccgg cctcggcccg gagctgagcg cgggccacgg    3180
ccgccctgtc gcgggcgtcc tgctggatgt cgcggatctg gtccagggcg gtcggggtga    3240
gcgcggtccg ctcccagagc ccgtgcacga gccagagcgc cttggcggcg agggggagcc    3300
aggcgaccgc gagccaggcc ccggccgact cctcacccag cgcgtgcgcg accaggacgc    3360
cggtcgccac ggcgccgaat ccccacccga cgccggtgat cgcgcggctg tggtcgcccc    3420
gcgcggcgag gcgccgctcg tacgcgaggg tggccagcca tccgccgtcg agcccgaggc    3480
cgacgaccaa ggcaacggcc cacggcatgg cctccccgag ccacatcacg atcacgacca    3540
cggtcaggac catggacacc gccgtcatgg cgacggccgg ggcggcggtc atcgaacgct    3600
tcttctccat gatcacttcc ccttccgggc cttgagcgag atggacaggc cgaccccggc    3660
gggggcggcg gcggcgagcg cggtcgccgt ggtggcggcg gtctggagca ggaggcagag    3720
cgtcatgacg acgccgaccg agccgccagc ggcgaccagc gccaggagga tcgggccggt    3780
ccagtcgcgg gcctcggcct ggtggtggac gacgacgacc gtgcgggggt cggtgccgtc    3840
cgggatcagg tgggccggaa tgtgaccggc cctcatctgc gcgtcggggg tgcgcatcag    3900
gccgacacct ccccgacctg cgtcacgacg gacagggagc cgtcctcgga ccgcaggacc    3960
tcgcccgcgt cgagcagctg cttgaccgcc ttcgacacgg agcccttgtt gatgccggtc    4020
acggtggcga cgtcggcgac ggtcgtagcg cccgtgccga tcgcggctgc gaccttctcc    4080
cggttggtcg gcgccttggt cggctgggcc gggacctcag ccgcggggc ggtctccttc     4140 accagccgga gcggggccgg ggcggaggcg ccggcacttc gtgcaggcga ctcctggcga    4200
cgccagaccg gccggtcggg gagcgcgatc acgtcggccg gggagaacgc gcgggtgttg    4260
atcgggtgag gctgcaccct cgggccggac cggagcatcg caaccccggg catgggcagc    4320
tcgtgcgcgt gccagcccct tctccgtcgc tcctcgccga acaccacgcg ggactccccg    4380
gaggtgctga gcgcgagggc ggcccggtag gtgatctgcg cgctgatctg cgggtcgatg    4440
ccgcccttgg cgtccatggt cggcttctgc gtggcccaga tcaggatgat ctcggccgcc    4500
cgtgccatcc gggccagcgt gctcaggttc tccatgatcc gggaccagtc cgggtcaccc    4560
ggctcttcct tcgacccctt cgcccgggtc ttcttggcca tggcgatgac ctcggcgccc    4620
tcgtcgatga acaccgtgat ccggggccgc tccgggctga tctggatcac gtcctggccg    4680
cgcgggatca gttcaagccg ctcgtgcatc tcctcgacca gctcgtcggt cacgtccagg    4740
acgtcttcga tcgagatggc cgtgcgagcc cggtgctgcc agttgatcgc ctcgacccgc    4800
ttggggtcga cgacgaccag gcggtgatcg gcgtactccg agccttccgc cagcagggcg    4860
cgggtggacc aggacttgcc cgagccggac gtaccggcga tcagcatccg cgcccgagc    4920 ggcacctgca ccggctcgcc ggtcaccgtg tcgactcccc acggggcgcc gggcgtccag    4980
ccggtcaggt cgatcccgtc ggccgcgctg cgggtccgca gcgtgatcac ggcgcggtcg    5040
ccgtgcgatc cggccttgat ctccatgcgg aggtcggtcc gggctccgag cagggcgcgg    5100
atctcctcgt gcttggcctt gaaggcggac ggcttccacc ggccgtccag gcgcaccgtg    5160
gtgaccagcc cggccggggt gacctgaacc ggcgtcgtca ccgtgcctac gaggccgcgc    5220
tcgtcggcgt gctgagccca gtacgacggg tcgagccgct cgaccaggcg ccgctcctcc    5280
```

```
gctgacagtt cgtccgcgac cgcgaccgcg accttgcggc ggccgatcac cagcgcggcg   5340
acgttggccg cgatgagtgc gagcgagccc gcgaccggcc aggccccggc ctggtcccag   5400
ccgagagcgg agatgccggc gcccggcacc gcgtgcatgg cgtgcgcctg aacggctcgc   5460
gcccggaggt tcgccgggta gtccttgcgc gcggccttga gcttggtctt cgcctggtcg   5520
cggtgcgtgc gggccgcctt gtccgccgtg cgagccgccc gacgcacggt cgacagcggg   5580
ttcttggacg ccgcccgcgc ggccgtccgc tggctcttgg ccgtggccgc cgtcgaccgc   5640
gcggagttgt agcccttctg ggcgtccatc agcgccttca ggtgctccgg ggtccggagc   5700
gccatgcggc ggtcggcctc ggcgtcccag cgggccgcga acggcgcgag ggtcggggcc   5760
atggcgtcga gcgcgttcgt gatcgctccg gcggcgttct tggagccggt tgcgatcttc   5820
gtagagactg ccttcgggtc cacggtttgt cctttcgcga gggacgtgga tctagggccg   5880
gagaccgttc acgcggtctc cggtccgccc cgtttccggg gctgtgtgtg gcgtcgaaca   5940
aggtccatac tgtggtcgca cagttgctgt gtcaaggcat acactgtgct agacagctac   6000
acaccgcgca ccacactcga aggagtcgtc atgtccctgg agcgcacgcc cccgtacctc   6060
caagtcgtcg ccgcgctgaa ggcaaagatc gtcagcgggg agctgaagca cggggacacg   6120
ctgccgtccg tgcgggacct cgcggcgcag tacgagatct cgaccgccac ggcccagaag   6180
gtccaccgga cgctgaaggc ggaagggctg gcggaggcga agcagggcag cgcgaccacg   6240
gtcagcacgc gacggaccct gcaccggacc gcagccgacc ggctggagtc ggcgctcagc   6300
acgggccgga tctacgcgga cggggagtac gcggtcatca ccagcgccgc ccttgccgag   6360
ccgcccgagt gggtggccga tctcctcggc accgagagcg gccaggccgt gcgacgcgag   6420
cgcgtcaccc actcagccga cgaccagccg gtgagcgcca gcgtgagctg gttctccgca   6480
gacctcgcgg agaccgtgcc cgccctcctg gtccgcgacc ggatcatcgg cggcaccccg   6540
tccgcgatcg aggcagccac cggccgccgg gccgtcgcca ccgaggaagc caccacggcg   6600
gccgccgcga ccgaggacca ggccgcgctt ctgggcgtag ccgcaggcgc cccagtcctg   6660
ctctcacgca acgtctacgt ggacgctcag ggcgacacga tcgaggtcgg ggagtccgtc   6720
gctccggcgg gccgctggcg cgtccaccgg gactgatcac tcgcccattg agaagccccg   6780
tcaggcaccg cccgacgggg cttcttcacg tccagacgac gtggtttccg ggggttgccc   6840
acccggttga gccgttgcac cccggttgac cccccgcaac cgggtctgac ctgcgaagtt   6900
gcaaggttgc gacggtttcc aggaggggggc cctacgcgtg cgcgcgcgag gaagccattt   6960
ttgatctagc ttccggagcc cttctcggcc tccgccttgg cccacgcccg ggccgtgttc   7020
ggagcgaccg ccgtcacctc gttgatgcgg cggtagggga cctccatccg gaccgcctcc   7080
gcgatcagcg ggcgcagctc cttctcaatc tcgtccagct ccgcgaggag cttgatccgc   7140
tgctgcccca acggcttcag cgccgcctct gcctcggccc ggatctcgcc cggtgtcttt   7200
tgcgtcatga agtcatcctg accgactgtg tcagtctgcg caactagttc aggctgcgtt   7260
ttttgcggta caactttccc tacgtcatca aggcggcccg cgagcgggcc gcgcggcccg   7320
gcccacggcc cggccgacgc tcctgtcttc gccccgctcc ggcccggccg ccgaccggcc   7380
cgcgcacacg acggggcgg catcggtggg cggtttacgt ggcgcctgct ccgccgactg   7440
cgggcatcgc cgttgtgctc gccgacaggg cagcggggag gggtggggga ctcgcggccc   7500
tacgcggccg tctgagcgcc tgtcagcctc ccggagcgcc gtaccccgc cgtcgcggtg   7560 ctgagccgcg tgaggcgacc ctgagccccg tcgtggggttg ctggggagca cctgctgccg   7620
cgatgaggtg gcggccgtcg agctggtcag ccgtgcggct ccgtcgtggc cggtcatccg   7680
```

```
gctgcccgat cgtggtgggc aagatgccgg cggaaccggc ggacctcgac cgcgacggct    7740
atccggcggg ccgcgggcgg gcctccgtag agggcgaggg cgggcgccat gccgaccgcc    7800
acggcgggcc acaggcccag gagctcccgc acgatcagcg tcccgccgac caggagcagt    7860
gcggccagca ctgccgctaa cgcctggtcc tggtcccggt cctggtggtg catcagtcct    7920
ccccgtgatc acttcggcac ccaccgtagt gatcacccec gacagcggat caaggggttt    7980
gcgggtcccg gtcggcgccg ggcggggggag gcaggagccg ccgacgctgc ctctgggacg    8040
ggccggacgg caggggggacc ggcggccggg cgagctgcag ccgggggtcc ggcagggccg    8100
gagcgggcgg aaccgtgctc tgacctgcgg cccgagtttc gtcacgtgac ggaatggaag    8160
gctgctgcat ttcgtcacgt gacgtatctc ggcgagcgac tgccgacgcc acggcggaca    8220
cgatcgcctc gcgctggcgc cgggcctcgt acgcccgctg gcggcaggag cggcggcagt    8280
agtcccggct ccggccgacg ccggattgct tgatctccga gccgcaccag gcgcagagct    8340
tcgcgccgtc ggcgtccctg ggggtggtgg tgctcatggc cgacgaccgt acgcggcacg    8400
tctcgtagcg aggcgagtcg ggcgcgaggt accgcctgca cgaagtgccg gcggggccga    8460
ccccgggcga gtaatcccag gattactccc gcggcttcga ccccgccgc cgtcgccgcg    8520 tacgtcaccg acccccgccg tacgtcaccg ggatgacgta cggcggggggg gagcgagtta    8580 gtgcgaagtg ggcccacttg cgagccgggc gatgtgccgg gcggcccgct cctggcggtc    8640
gtcggcgtcg tcgtcctggt cgtcgtcctg ctctcgccgt cggcgtgcag ttgcttcctc    8700
gcggcgctgg gcgagggcgg cgagcatgtc ggcgtacgcc tcggccacct ccccccgccgt    8760 gagcaccacc actgtgtcgg ccgcgtcggc cagcgccagg acctcccgca cccgttcgcc    8820
cacggccgcc                                                           8830
```

<210> SEQ ID NO 61  
<211> LENGTH: 11046  
<212> TYPE: DNA  
<213> ORGANISM: Artificial Sequence  
<220> FEATURE:  
<223> OTHER INFORMATION: pSN22

<400> SEQUENCE: 61

```
ctgcaggccg gtgactccag agaagggttg aagcggagtt gcggggctag ccccccgagc      60
ctccatcgtt ccgaccgccc ggcctgtccg ggacgggagg acttttcgag cacctggagg     120
agcacgtgac caaccagcag caggaccagg agcagccgca gcgcccggcg gaccgtggcc     180
gccgcgagtt cgcgaagaag ggagccgtga ccgtgctcgc cgctctcgtc tccggagctg     240
ctcgggcggt ggtagcccac ctcctcacgg gaggtggcga gtgacgcggc tcggcagccg     300
ggccggccgc cggacggagg caggagcggc ccggccggaa ccgggccgc cgggccgct     360 cgcgggccgc cttgatggag tagggaaagt tctaccgcgc ccactcgcca cgccacgaga     420
cgtgccgcgt acggtcgtcg gtcatgagca cagagacacc cacgaacggc gacggcgaga     480
cgctgtgcgc ctggtgcggc cgtggcccecg tgccacccag ccggggaacc aagccgcggg     540
cctactgctc gcgcagctgc gtccagcgag cccacgagtc gcgaaagctc gcaagaagc     600 tgctcggcgc gtacatgaag ggccgggccg aggaggctga gctgcgcgga ggaaagtcac     660
gtgacgatgc aggaaagtca cgtgactttc ccggtcggca ggcccagca aagtcacgtg     720 actttccaaa accccaggtc aaccctgggg ttccgcgtcc ccgggtcccg gtgacgtccg     780
cgccccggtc gaaaggccgg cgcccgctgc tgccccccgc gccgggcgtg acgcgggaga     840
```

```
cgctcccgct gttcggcgac gacgacacgc agcccggccc cctcgatggc cgcgccgaca    900
cggagtgacc acgacggccg tcaccccatc gcggcagcag cccgctcccc atcgacccga    960
gacgggcggt gcggtcgcct cacgcagccc agccccgcga cggcggggt acggggggtc   1020
cggcgactcc tggcccgcca gacggccgca cagagccgcc gacccccac ccctccccgc   1080
cagccgtcgg cgacgcgcac aacgacgatg cccggcggcc gggtgacggc cgccatgta   1140
aaccgctcag ggatgccgct cgtgggcagc agaaagcccc cgccgggtct cggacggggg   1200
ctcaatgggg aggtagggcg ggggcctggg gtcactcgcc catgggcacc cgggcgccgg   1260
gggcgtagac gtcttcccag tagccgagcg cctgttcgtc gtcgtggaac gtgacggtgg   1320
tgaccatgac ggcgatggct gagtgggccg ggggcgtcga tctcagagcg ttgagttcgt   1380
cctgggacgc ctgccgtgcg tgggcggccc gctgtcccct caccacttcg cgaccggtgc   1440
gctcgctgta gagcttgtcg aactgcttca ccatccgtac gtcctccccc agctcgggga   1500
cggcggccac cgtgtgggc gggtagacgg agacgccgac cgacgtcggc ttgtcgtcct   1560
ggcggaagac gcgaatgcgg atcacggctt cgtcgccggg ctccagggtg agagccgtgc   1620
agatctcggg atcgtggacc gaccgggtca tcacgcggtg gccggaggag gtctcgccgg   1680
gcgcgtagcg catcccgttc ttctccatgc gcttcaagcg gtccgcgcca gtgatgacga   1740
tggggttctt ctccacgacc gtacccagcg ccccgcgcga gctgaccagg ccctcgctct   1800
tcagcacggc caaggcccgg ctcacggtct tggccgccac gccgaactgg gcacggatgt   1860
cagcgacgga cggcagcgtg tcgcccggtg cgagttcccc gctcttgatc agcgtgcgga   1920
agtgggtggc cacgtcggca tagcccttcc cctccggtgc cttgtatggc atggcttctc   1980
cctgtttgtc ggagcgcggt acaccccga aggtacatca atgacccccc caaggtacat   2040
ccttgcttcg aatcggtgct tgatgtacct tcgtggcgtc ggcaaggtac gttaagtacc   2100
tcccgctgac tgatgcgtac cttcggcaag agagggtctg tcgtggccac gaggaacgtt   2160
ccgccccccg gggcgaacaa cagcaggaac aacaagttcg ccgacatggg ggcggcggcc   2220
ggcggtttcg tcggtgcgat gggcggctcg ttcgtcccgc ccgtgaacgt cacggtcaac   2280
cgcacgacca acaagggcgg tggcggacag cagtccggcg gccgccagtc gcatttcatc   2340
ctcggggagc cggagttcaa ctcggctgag gacgtgcgca actactgcaa ccacgtccgc   2400
gccctgatgc tccaggccgc gatcgagctg gccatggccg ccaagatcct ggaggcccgc   2460
ctcgcccagg cgcagacgct gcccggtgac aatccgatcc agggccggat gcgggcgcgg   2520
aaggtcggcc ggagcctcaa gaaggccgcc gacggcgcca cgtccgccgc gaagggcgcg   2580
gtcaccacct acggcgcctt cacccgcgag tacgccgacc tgatgcgccc cgcgccccag   2640
cgtcaggcgc ccaccaaccc cttcaagttc tgagaggcgg taccgagatg gcaaggacg   2700
ttcagcagca gcaggaagac cgcctcaact ccggcggcac gggaatgggt gcctggctgt   2760
ggcaccgggc caagccgtac acccccgccgt ggatcgtcac gggcgcggtc ggcgcggcgg   2820
gcgccggcgc ccacgagctg tggggcaact cgccctgggc cggagtcggc ctcaccctcg   2880
cgggggtcgg cctgacggcc gcgacctggt gggcgggcaa gtccaccggg cagcagcgcc   2940
gcctccactc cgccatcacc gtggcggccg ggcgacctg gttcaccgcc tccgccctct   3000
ccggcccgct caccggcccg ctgcccgacc tgtacctgat gggcggcacg agcctcgccc   3060
tgacctggaa catccgccag gtcatgcgct cgtcgacgcc cgagggcgcc ggatccgact   3120
cggacaaggg actcctggag aaggtcgggc tcgcccggac caagctcaag gacgtcaagg   3180
tcgagcccaa ccgcgtcacg gtcccctacg agctgcctgc cggggagctg accaacgacg   3240
```

```
acatcaacaa ggccatcccg cgcatcgcgt cggctctcga cgtgccgacc acggccatcc   3300
gtgtccagca cgaccccgac tccgcgagga agggccagtt cgtgatcgtg cccgaggaca   3360
tgctgaagca gcccacgatc tggcccggcc cgttcgcgcc cggcgagtcc gtggccgtgc   3420
gctgcggatc gcgtctacga cgacgcagcg acctggttct cccgctcctc gacgcgatcc   3480
acctgctcgt catggggatg accggctcgg gcaagaccga gggcgccgtg gacctcctgc   3540
tggagatcct gacccgcaac gacgtgaccg tgtggctcgc cgacgcggcc aaggccgggc   3600
aggacttcca gcccctcgtg cccgccctcg actgggcagc cctggacacg cgtcggccg    3660
gagcgatggt cgacgcggtc caggccgtca tccccgcccg caccgcctgg ctgcgggacc   3720
acagctaccg ggcctgggag cccgcggccg ccaagacgca gaccaacccc gcgcactcct   3780
gcgcgtcggc cggcgcctgc ggctgccccg ggatgccgta cctgctcacc tggttcgagg   3840
aggcggccaa gctcctgcgc gagctgggcg acgacgtgtt caccggcatc gcccaggagg   3900
cccggtcggc gggcgtctcc ctggtcgtct ccatgcagcg cgcctccggc taccagctct   3960
cgacggacac gagggcctcg ctcccggccg ccatgtgctt cggcgtccgg ggcgacgacg   4020
ccgggttcgc cctccccgag gaggtcctgg acgcaggtgc caacccggcc gcgtggggca   4080
acaagcgcaa gggctacgtg tacctggtgt ccgccggggt cgaggaggac ctgtacgcca   4140
accccgcccg gacgttctgg acgggccccc cggccgaggg cagctacgag cggatggccc   4200
gctacgtcgt cgagcacttc gcctcggttc gtgccgagct ggaccccggtg accggcgccg   4260
ccgccgagca ggctgccgga ccgctgttca ccaaccgccg tgcccgcgcg ggcgccgcct   4320
ccgccccggc ccgcccggtc caggagcaga tgctcctcga cgacgacggc caggaggacg   4380
gcgacctcgt ggagatggag cacgacggca tcgacctgag cgccgacctc ccgcccgtgg   4440
agaacgacgc ggaactcccg ccggccaagc cgtcgaccga ggaggccgc gagctcctcg    4500
acgaaatggt cgccacgctc gcctcggtcg gccccggcac ggtcgctgtc cgcgacctca   4560
agccgtacct ggagcagatc ggccgtgacc gctcctgggt ctcccgcgag atgaagcgga   4620
tggccgagga gggccgcctg gccgccacgg gcgaggaggg cgtctaccgc ctcatcccca   4680
cgctcgccgg ggtctgagac ggcccgcaca gccgcacagc cgcacagcgc gaatccccac   4740
gtcacacggc gtgtgaagag ggccgcacac cgcctcgcac accgtgcgca cagccggacc   4800
gcacacccccc gcacaccga acgacgacgg accgccccgc agcaaccggg gcggcccgcc   4860
cgatgaccac ggaggtagag cccgtgacca ccgacccgaa gcatctcacc gactccgagg   4920
cttccgccga agctgcccgc ctgatccgcg aggcgtacca gccgacccgg agccgcgcc    4980
ccatgacctt ccgcgacacc acccggtcac agcgttcggc ccgacccgcc cgtgccccag   5040
cccgagaccc ggatcgtccc cgagtgggcc gccggggtcg ccgtcgcctc catcggcatc   5100
ggcgccggcg tcaccggcct cggctgcgga gcctggctca tcttccaggg cctgtcctcc   5160
gtgaccctgc tcggagtcat cgctatcgcc gccccgttcg tcggcgtcgc cacggtggcc   5220
acggccatcg gcgccgccat ctccaaggcc aagcgctcgt cgaccacgaa cgtctaccag   5280
gggaccgtga tcaagcggac cgacatcacg tcgaccgccc gcggcatcgg cgcccgctcc   5340
cggatcgagg gctgagcgcc atgcagatga acactcagga gcaggtcgag caggcggaga   5400
aggtgctccg gctgagctgg atcatcgtct tcggcgtgat cctgttctcc gtcttcacgg   5460
tgacgccccct ggtagagcgg tccactccgg agggctggga gtggtcggcg ccgatcctgc   5520
cgctcgtggt cgacgtcgcc gtcgtcatct cgatccgggt cgacgcgatc gtgtcccggc   5580
```

```
tcggagggtc gaccaccggg tggccgctcg ccctgcgggt gctcaccggc ggcgcctccg    5640
tggcgctcaa cgtcgggcac tccgtactcc agggcgacct ggtgggcgcg ctcgtgcaca    5700
cggccgcccc ggcggtgctc atcgtcgtcg ccgaagcgtc gctcaagtgg cgcaaggaga    5760
tcgccgccgc cacggcccgg atcgaggctg agcaccgtga gcgcgaggac gcccgccgcc    5820
gtgagcagcg tgagcgcgag gagaaggcgc gggccgaccg cgagcgtgag caggaggccc    5880
ggcgcctgga gcgtgagcgg caggaggccg ccgaccgtga gcgccgccgc gaggaactcg    5940
ccgaccgtga gcgggagcgt gagcacgccg cccggctcgc caacaggag cgtgagacga    6000 ggcccggctg gaggccgagc gcgaggaccg gccgacgcc cgccgccgcg aggagcagga    6060
ccgccaggag cgtgaacgcg agaaggagcg ggagcgcagg agcaggagcg ccgtgagcag    6120
gaggctgccc gcaaggccaa ggaggccgtg cagaaggccg aacggaccg gaaggcagcc    6180 gaggcccgca agcccgccct cgcgcccgtg agcgctgctg tgagcacccc ccgcccggcc    6240
gtgagcgccg ccgtgagcac tcccgctcac gagactgctc acgacgccaa gcccgtccag    6300
aagatgagcg aggccgacgc ccgccaggcc gtcgccgacg cggtccgtga gggccgctca    6360
cagcgtcagg tggccacgct caccggctgg tcgaccggct gggtcgccgc ccgcttcaag    6420
gagcttgagg gggccgccgc atgagccgcg ccctgatgta cgcgctcatc ctgccgctgt    6480
tcgcggcgga gtgctgggcc cagttcgtgg tccatgacca cgctggacg acgtcttcg    6540 ccctcctcgc cggggccgtg ctccgcgtcc gctacgccct cggtccgcgc acggacgacg    6600
aggaatgcct gcccgactgc ccgaagtgcc gcgaatccag gggggacctg tgagcaccac    6660
cgaccagcac ctgaccgcac agcacgccga agtgaaggcc gagatcaccc gcaccgacac    6720
gaagaccgcg ctcttgctcg ccttcgtcgg cgcggtcttg gccggcgcct ggtccctcgc    6780
ccgagacctc cacctcaacc ccgtcgcgta cctggtcggc gtcctcggac tcgccgccct    6840
cctcgccgcg gccggcctcc tgctccggtc ggtccgcccg aacctcaacg gcgggcacgg    6900
cttcccgctg tgggccaccc tcacccccgca gcagctcacc gccgccgccg agacccgcga    6960
cctggccgcc gacgtcgtcg cctgtcccgc ctcgccgttg ccaagttcac ctgcctgcgc    7020
ctggccgtcg acctgacctg cacagggacg gcgtcctcct cgtcctggcc gccgtgatcg    7080
ccctcggagg tgccgcatga cccgcaagcc cgccatccac gacgccgagg cccacgtcgt    7140
cacctcccac ggcagccgac ttcttcaggc gaggaccgcc acccgctcaa ccgggtcgcc    7200
tccctcgccg ggtacgccga gggctgcctg ccgtacgccg aacagccgcc cgctggtcct    7260
gctgctgacc aaccccggcg acggcgggac catgacgctg ctcaggccgg agagatggcc    7320 acgtcctgc ggaagctcgc ccgccaccgg ttcgtcaaga ccagcgccgc cgcccacgcc    7380
cgcgcactgg gcgacgccgc cgcccgcgcc gccgccgacg cgagccctgg gaatggcgga    7440
tcgaagccgc tgcctgaaca ccgaagcccc gccggccttt cggctggcgg gcttccttc    7500 ggcccgtcaa atcacatctg ccccacgggc cgtgtcgcgt gccgggggga acctccggca    7560
caaaaagtgc caggatcacc cccagcaaag cgaaacggcc agggattagg gcccctgacc    7620
gcttctgacg tccgcccgga taccaaccaa gggactcgtc tgttgaacag ggtaagggac    7680
gctgaggcgt ccgcaagagc actcccggct cgcgccgtcc gtccgcgctg ccactgcggc    7740
actgcgatcg agcacacgcc cggcaaacgg ccgcgcgtgt actgctcgaa cgcctgcaag    7800
cagcgggcga agcgcgctct tgccaagatc gcccgggaag ccgccgacgc gcgtccgcga    7860
cccaaaacgt gtcgcgcctt gggaaagaaa caacagagtt tcccgcaccc ctccgacctg    7920
cggaaacgtc ggcgggggca aaaccggtcg cggacagccg ggacgacgcc gcccgcgccc    7980
```

-continued

```
ggaaggctcg ccggtacgcg aaccgccgga cgctgtggcg gatcaccggg gacgccgcgt    8040
gcaagggctg cggccgggcc ctgatggacc ccgcctccgg cgtgatcgtc gcccagacgg    8100
cggccggaac gtccgtggtc cttgggctga tgcggtgcgg gcggatctgg ctctgcccgg    8160
tctgcgccgc cacgatccgg cacaagcggg ccgaggagat caccgccgcc gtggtcgagt    8220
ggatcaagcg cgggggggacc gcctacctgg tcaccttcac cgcccggcac gggcacacgg    8280
accggctcgc ggacctcatg gacgccttgc agggcacgcg gaagacggcc gacgctcccc    8340
ggcggccggg tgcctaccaa cggctgatca cgggcggcac atgggccgga cgccgggcca    8400
aggacgggca ccgggccgct gaccgcgaag gcatccgcga ccggatcggc tacgtcggca    8460
tgatccgcgc gaccgaagtc accgtgggcc agatcaacgg ctggcacccg cacatccacg    8520
cgatcgtcct ggtcggcggc cggaccgagg gcgagaggtc cgcgaagcag atcgtcggca    8580
ccttcgagcc gtccgaggcc gcgctcgacg agtggcaagg ccagtggcga gccgtgtgga    8640
ccgctgccct gcgcaaggtc aacccgcagt tcacgcccga cgaccggcac ggcgttgact    8700
tcaagcggct ggagaccgaa cgcgacgcca acgacctcgc cgagtacatc gccaagaccc    8760
aggacgggaa agcgccggca ctcgaactcg cccgcgccga cctcaagacg gcgaacggcg    8820
ggaacgtcgc cccgttcgaa ctcctcggac ggatcgggga cctgaccggc ggcatgaccg    8880
aggacgacgc cgccggggtc ggctcgctgg aatggaacct ggcccgctgg cacgagtacg    8940
agcgggcgac caaggggcgc cggggccatcg aatggacccg ctacctgcgg cagatgctcg    9000
ggctcgacgg cggcgacacc gaggccgacg acctcgacct gctcctggcg gccgacgccg    9060
acggcggcga actccgcgcc ggggtcgccg tgaccgagga cggatggcac gcggtcaccc    9120
gtcgcgccct cgaccttgcc gccacgcagg ccgccgaggg aaccgacggc aacaccgatc    9180
cggccgccat gggcgagagg gtgcgcgagg tcctggcgca cgccgacgcc gccgacgccg    9240
tggtggtgct cacctccggc gaggtcgccg aggcgtacgc cgacatgctc gccgccctcg    9300
ccctgcgccg cgaggaagca gctgcacgcc gccgccggga gcaggacgac gaccaggacg    9360
acgacgccga cgaccgccag gagcgggccg cccggcacat cgcccgactg cggaactgat    9420
atcgatccgc actaactcgc tgcccgcccc tactcccgcg ccgacctctc cgtgaccgc    9480 acggagaggt gtcggcggcg gtcggaggct tgcccacgag gcgcgacctg cgaggcagcc    9540
gcaggcttgc ccacggggcc tcccaccctc ggtcccaccc tcggtccac cttcggtcc    9600 acggtggacg cgacggtggg agcaacggcc gagcccctg ctgaagcaac cccgcccggc    9660
gggcgtcact gatatcagtg acccacaact cgctctgcct gtggttactg cctccgaggc    9720
accgccatcg ggtccgccag cccaccgcca tacgcccgcc cacgaccgcc atccgaccgg    9780
aatgcatggc ggtccatgg cggtcggatc ggaccccatg gcggaccctt ggcggtgcca    9840
tggcggaccc agcggagcga gcaagttatc gcgagagcaa tgctctcgcg ggcgctcgtt    9900
ggggcgagca agttatccgc ttggagactc cagcggtgcc ccgaccgagg gcggtcgggg    9960
ttccccgggg aggggaaccc cctttgtcct caccccggtt ttgatcacgt cggcctacgc    10020
cgacggaccc gcgcggcgcg agccgtgcgg aacggaaaac ccggctgccg atccctcgc    10080 ccgccgcccg cgttcccgcc ccacctccct ctcctcctgg tgctcgtggc ggtcgtgggt    10140
ggcgtagagg ggatgtctgc ccaagcggaa gcccccgacc atgcgcggtg acgtgggacg    10200
ccgcgaagcc cggaaccgga tccccgcaac acccagcgca acccatggcg caacccatgg    10260
cgcaacaccc agcgcaaccc cgaccaagga cggccgggaa cccgctacga cacccccctcg    10320
```

```
acgggcagcg cgtcgactcc cggtccgagc gtccgccggc ctttccgggc ggccacgtcc    10380
tggtgctcga tgtcccccag gagtgcgtcc ggctccactc gctcgacggg cagcagccgc    10440
ggactcgcgt ccgccgtcgg cgtgctcctg gtggtgctcg ggccggtgcc gaggtgacgg    10500
cgcggggtgc tcatgacggg agtctcccgt gccgttcccg gagctcccgc agcggccctg    10560
atcgagccgt gcggcttgtg cgttcgtgaa tgcaagaggt gtgaccgttc ttcgcgtgca    10620
cgcgtgtgct cgtgcacctg tgcacgcggt acggcttcgc cgccgacttc gtcgtgaccg    10680
gagcggtcac acctcaggca ttacgaatga cctcggctgg tcgcgccctg cgttgtgccc    10740
tgggtcgcgt cctggattcc ggcctgagtc acgtcctggg tcgcaccgga cgggtccccg    10800
gccgcgcccg gttcggcgcc gtgacctggt ggacaagggg gcggtcggct gccgttccgc    10860
gcgccgactt cttgctggga gcggtgtcgg cgggcgcctt cggatcggaa tgcaagggtg    10920
tgcggcttgc tgctgccgta cgtcatctcg aagacgtacg cgggccgtcg gtgacgtact    10980
cgaggaacga ggccgggctc ggctcggctt ggtcgacccc aggggctttt tcgtctgcgg    11040
tcctgt                                                              11046
```

<210> SEQ ID NO 62
<211> LENGTH: 3539
<212> TYPE: DNA
<213> ORGANISM: Artificial Sequence
<220> FEATURE:
<223> OTHER INFORMATION: pGP01

<400> SEQUENCE: 62

```
ccacggtgtt ggatgacagt cctttgttgc cactgtcgca gttttctctt tcgcgaagtg      60
cttgagatcc ttgatgggtg gacagtacgg tatcctcaac cgtggattct acaacggaag     120
ccacaacgaa atcataggag gatatcccat gaacggacga gtgattgttt ggcctgatcc     180
tgcgctcttg tctgccatgc ctttaagttc cggattttcc ccggtcatgt cgtggaaccg     240
cgagctgaag tgtttcaccg atgtgcagac cacgactgac gacggactgc ctgtctgggg     300
ggcagatgcg tggttgagga tgggatggca accgcacgct gacacagtcc aactgcgcat     360
cgctgcacct cgaaagcctg cggtccagcc tgatcctgcg agaatcgctg attttttgc      420 gcctcgacgt agtgaggctg agcactgatg gcaggcgaac gaacgactgt tctgaccggc     480
gtctactggt ggctccgtat cttgccggtc ttattactcg gcgttgcctt cgcgtgctgg     540
tgtttctcgg tgcatctggt ctacgtgatc ggcttcgctg ttgcggcctt ggcggtggag     600
gcttttccgc cgtctgtatg gcaggtgccc aagaacatgc aggtgccagc acgatacgtc     660
tatcgctggt ggtggtcctt ggcgaaagcg ttcaagccga ttgaatccta tggcggcgac     720
agaatttact atcgacccgg cttgcagtgg atccgctctg accgacatgt actgcatctg     780
gtgcttcgcg ttcctgcagg tcttgccgac tcggcggcat atctggagaa aggtgcagca     840
gagatccaac gacagctacg tggcaagaag tcttggagga cctgcatcgt caaacctgcc     900
gagcatggcc tggacatcat tcctcgcgac gcgacagctg gtgatgagtt acttcctgct     960
ccgtccacgt cgtcgtggaa cgtgccagtc ggggttaaac ctgacgggtc cgaggtcgtc    1020
ttggatctct cccatccatc ccacatcctc gtctccggaa agactcgttc cggcaagtca    1080
tcgttcgtct acggcctgct cgatcagatg cgtcatcttc ctgtcactgt ggctggtgtc    1140
gacccgaccg gaatcctctt taatgagctg ggcgacggct ggggcggtga tgctctgcgt    1200
tccaagcgca tcacgaatga cgctgatgct gcagcagttg tccaggtcct ctccatgatc    1260
accgatgaaa tggatcggcg tatctatctt cttaactgtg agcatcgcga caagtggagc    1320
```

```
cgcaacgatt tcgagtccga cccgggacgt cgactcatca tcgtcatcct cgaggaatat    1380
ccgggcttga ttgagcggct gcagaacttc gattccgccc gcggcgctcg ctccagtgat    1440
cgttttgcct cgaaggcagc tggcctcgtt ggccgcatcg cgtacgaagg cgccaaggtc    1500
ggggttgtcc tcctccttgt cacacagcga cctgacgcca aaattatcgg cggtccactg    1560
cgagcccagc tcactacgcg ggtgacgttc gcccaagact cagacggatt gcgtatgtcg    1620
catcctgagc tctcatctga gcaggtcaaa cagaattcat gggcctcagg tgtcgggttc    1680
atcgaagcag atggcgtgat tccgctcact cggttccggt cctatcgagc ggaactcacc    1740
gacctgcatc ggcccggggc gtcggtcggc cagatcgatc tgatccagtg aggagctgct    1800
gccgaccgat gccgcggaac tctgagatcg acacgaccac agatgccgta gtcacggaga    1860
cgctcgagga agagatagga ttcagtacca gataaaaaat gcctcccac agcgccaact     1920 gcggggaggc gagtaagacc ttttctccc gggtcatgac cgccaaggag gcgatcggtg     1980
ttaaacatag taacactatc caaggcgcag ccacatgatc ggttgtgctc tgagcatgag    2040
ccgtgtgcgg ctcgccgcag cgagcgtcag cgagcggcgg gcgaccgcct tggtaccacg    2100
cgagcaactt ttccggtatc agattccccc tgtagaaagc cgaatgaggg ccgtcgccat    2160
cgctatgaga tgagggatgg tctacgaaat ccgcaggtca tgccgctgga gcgcgttcgc    2220
aagtgcgggg cagtgccggt ttcgcaacgg atcgcgttga tggcgggtca tggtggtgcc    2280
ggttatgccg gtttggcgac gtgcggaagt gtgtgggctt gccctgtctg tgcggcaaag    2340
atttccgcgc accgtcgtga tgagctggcc cgtgttgtcc aggttgcggt tggactcggc    2400
ttcaaggtgt cgatgctgac gcttactcaa cgtcatcatg ctggtcagga tctcgccgag    2460
ctgtgggcgt cgctccagtc gggttggaat gctgtcacga gtggtcgacg gtggcaggaa    2520
ttttgcgctc agctcggcgt ccagggatgg gtcaaggcag ttgaagtcac ccatgggtcg    2580
catgggtggc acgttcacgt gcacgtgctc gtcatctcta agcaggatcc gactagcgtt    2640
gacactaaga ttcggcatcg ccgcaaacaa ggtcggcgcc ggaccccgta tccagaagag    2700
gtacagaggc ccgaagactt catcgctgaa cggtggtcgc gaggtttgag gaagcgcggc    2760
gtcgacttca tcgccggtag tggtggcctc gattggcaga ctgctgattc tggagacgag    2820
gaagctctcg gtcggtacgt cgcgaagatg aactcgtccg tcgatggcct agcgaacgag    2880
gccacgttgg gcgggttcaa gaaggctcgt agaggtaatc ggacgccgtt ccagatcctc    2940
gaagatttcc tggatacggg ctcggagact gacctgagac tctggcgtac ctatgtttct    3000
gcaagtcatg gccgtaaggc attgacgtgg tccaagggtt tgcgtgactg ggctggcatg    3060
gaatctgaga tgagcgatga gcaggtcgcc gcccaagacc agtgcgggga agcggtcgcc    3120 cttttttgacc atgacgcgtg gcggcagatc cgcactgccg gtgccgcttt cctcctcgac    3180
gagctggagc tccacggatc cgagggcgtc tacgcctggc tgaagaagcg aagaatccat    3240
tatgagatac ctctagttcc ttggagtacg agtacctagg agccagtcgg ggtctgtcaa    3300
ttttttagct cctccatttc atcacactct ttctatgatg aagtcatcac aattcggtat    3360
tctttgactc ccctgagaag ccgataatca ggccagtaga gctatcttat gtgcctaggt    3420
ggatactatt tattcttcac ctatcaggga ctctggtcga tcacagcctc cgtcgacgat    3480
gacacatctg actaggtact atgatgactt catcatagac agaggtggag cacagacga    3539
```

<210> SEQ ID NO 63
<211> LENGTH: 8136
<212> TYPE: DNA

<213> ORGANISM: Artificial Sequence
<220> FEATURE:
<223> OTHER INFORMATION: pIP501

<400> SEQUENCE: 63

```
cctgctcggg accccccta gaatttcgtt attcaccaaa aaaatacgca tggtataaag      60
caccaagcga ttataaaaaa cgtagtcgaa aaaattatga tatggacaca ataaggggaa    120
tgtatggaag ccaaaaaatt aaagaagaaa agcagaaaa aaaatactta caagcccgat     180
agggtttgta agtttatcag aaaggaagtt ttaaagtgga tattaaaata aaaaaaataa    240
attttgaagg taatatttta aaagttataa agcgacagt aacagaaatg agaggaataa     300
ataatcatca aaaatatgat tttgatttat atcaaataga agcacgttcg ccaatgtcaa    360
caagagaaat aactttaaca gttgacttta tagaaaaaaa gtatcaggtg atattatcgc    420
ttttggtgat tggtacgatt tggatataga atcagtaaat gaaatattaa agcaattaaa    480
aaaggaagaa caaacattaa gaacaatcaa ttttatttaa aaaagtatca aaaaaaggaa    540
aattattttt cctttttttg atactttta ggtttatttg ctttaatata ttcagaaaaa     600
attttttaaaa attcttccgt ttcttctaca gttaaatagt caatttcaaa atactttct    660
aacaaagcac ctttttcaat tagacgcttt gttcttcttt ttctgttaat attttgctcg    720
ctattcgctc gcaaaatatt tttttgaatt tttagttttt ctattctttt gttgatgtca    780
tttaaatcat tatttgccat aactatttaa gtaattcaga aaaattttga ctattcgcat    840
ttaataaagt ttctaattcg tcatagaata attctttgtt ttcttcaatt gattcaatag    900
aaatattatt ttttgaaagg gtagaaagaa caaagtcacc aatatctgct ttagacttta    960
gaattaattc ttctttttc ttttgtaatt ctttaatttg aagttcaata tcagaaacag   1020
ttttcttctt tcttttttt ggcttcgttt tagaattaaa attaccatta attgcattaa    1080
tattttgatc ttgatttcc atgaaatacg cctcctaata tattgtgtaa ctctatcata   1140
ttatattatt tttctaaaat caataaatat aaacggaaat gtcaggttaa acatatttac   1200
ttttataatg ataagtggta aaattaattt attaaggatt ccttagatt atttactaag   1260
ggcgcactta tacgcagtaa cttcgttact tcgtatttat gctataaaac ttaactgtta   1320
gttagtttta tcgtcaagcg tgtttgttaa aattcgctac gctcatgttt gaaaagaaag   1380
agaggtgata caattggcaa tcttccattt atcaatgaca atagcaaaaa gagaaaacgg   1440
aaaaagaagt ttaatcgcaa tggcttctta tcgaagtggt gaaaaattgt atagtgaact   1500
atatgaaaaa actaatctat acaaccatag aactgttaaa ccagaagctt ttattttaaa   1560
acctgattat gtacctaatg agtttttaga tagacagaca ttatggaata aaatggaatt   1620
agcagaaaaa agtccaaacg ctcaactttg tcgagaggta aatgtagcat tgccaattga   1680
attaaataat tcagaccaaa gaatgttgat tgaagatttt gttaaagata attttgtcaa   1740
tgaaggaatg attgcagacg tagccattca tagagatgat gaaaacaatc ctcatgctca   1800
cattatgcta acaatgagag aagtagatag tgaaggcaat atcttaaaca aagtcatag    1860
aatacctaaa ctagatgaaa atggcaatca gattttaat gaaaagggc aaagagtaac   1920
cgtttcaatt aaaacaaatg attggggtag aaaatctctt gtttctgaaa ttcgtaaaga   1980
ttgggcagac aaagttaatc aatatttaaa agatagaaat atcgatcaac aaataacaga   2040
aaaatcgcat gcggaacttg gaaaaaaaga actaccaaca attcatgaag gttttttactc   2100
aaaaaaatta gaagacaaag gagttataag cgagttaaaa agaaaaatt tagaaattca   2160
aagttacaat gatattctag ccgaacttga taaacttgaa aatcaagaaa agtattaaa    2220
```

-continued

```
acaagaccaa aactttactt taaaatttga aaaactttc tcacctttag aaaaaggaga      2280
actgaaaaat ctttcaaaag aattgaaatt atttattaat gatgaaaaca ttgataaacg      2340
attaggtgaa ttaaaacgat gggaaaattc acttatcttt aataataaaa tggaaattca      2400
aaaacaacgt ttgatgttaa gtaaaattag tagtgaacga gatatgctta caaaggcaaa      2460
tgaaatttta gacaaacaag cagaaagatt cttcaaaaaa tcttatccaa gtttgaatat      2520
tgacaaattt tcaaatcacg aagttagagc aatggttaat gaaaccatat ttagaaaaca      2580
gttattgaat aaagaccagt tagcagaggt catttacaat gaaagagtag tagaaaaaga      2640
agaaagtaaa aagattttta aagaaaaacc atttcaaact agccgttatc ttgattcaaa      2700
aattaaacaa attgaagata gtataacaaa agaaataaac cctgaaagaa aagaaatttt      2760
atcaattaaa aaagaaaaac taataggaat aaaacaagga ttgatagaat atgttcaatc      2820
agaagttgaa agaaaatttg ataaaaatgt ttcaatagat tcagtcatag aaggtgaaat      2880
gttacttgca aaagctgact attacaaaac aactgatttt tctaaagtcg aaggagttgc      2940
tagattcagc agtgaggaaa ttaattccat gttggaacaa tcaaaaggct tcttaactaa      3000
cattcagacg gtgaaaattc ctaatgattg tcaaggtgta tttttttgttc aagatagcat      3060
gaaacatatt gatgaactaa gcccattagc aaaacaaaat ctgaaaaagg ttgttaatcg      3120
caatgcttat ttacctgatt ctgataagat agaattaagt aaagaaattg aaaataccaa      3180
taaagatcaa tcccaagaat tggataaaga cgtaccagaa aaaatgaag tgactgtaaa       3240
aatgttccaa tttgcgaagt caattaatcg tttgttgagt ggtaaccaac tacagaaaaa      3300
acgaaaccta gacaaattga ttaagcaaac aaaagcaaaa aaaatcaat cattacaaag       3360
gaatattcct ttgcgataaa ataaaaacaa gaggtgtata aaatgaaaaa atttatcaaa      3420
gatacaaagt ttaagcttgg aagtgcggtt gttgcgttgg gtacattgtt tattactgat      3480
ccagtgtttg cagccactga tccacaagcg aaattagttc aagcgggtaa cactataaaa      3540
ggtgttttaa cagccttaat tgttgtagtt ggtgggattg cttgtgcgaa gattgttatt      3600
aaatacttgc cgtctattga tgacccacaa gaaaaaaata ccatgtataa agccttggga      3660
acagccttgc ttgttacggc attaggtggg gcgttggttt ggttagtacc ttgggcgtat      3720
ggcttacttg cttaatagag aagggagtta gttatgaata gcgatcaagt gaaacaagcc      3780
ctattagatt tgttaaatgc agacactgaa aaagggcgga cttggttttt tccgtctaat      3840
gtatctgatc ggtacacagt catttaggg ctagatttaa aacaatcagc aaaagcgatc       3900
ggtacgcat taataagcgt gttattgaca attcttattt tccgtagcac agccgttttt       3960
cctttaatta tctatgtcat tgttggtttg gtgtcatttg gtggtgtatg ggcgttttat      4020
acgattaaac caattacaga ccgacctaac atttctatat ctgattttat gaagcaaaga      4080
aaagactttt ctaaaagacc aaaagtctat tacaaaaagc caaagaacg agtgtaaaag       4140
agaggtgatt taattgtttg attttctaaa aaaaagttcc aaaagtaacg ataataaaaa      4200
aagcgatacg atgaaagaaa tgatttattg ggaagatagt tcccgatttc aaggcgtttt      4260
taaagacttt tttgtcgttt atcagccaga aaaaagcaa ttcagccttg tgagtatgct       4320
aaaagttgac ggcttaaacg ttgataacctt gccagtatca gagcaagaag ggttaaacga     4380
agatttggt gtcttctat ctcaaaacgt tctatatgaa ccgcagatca cttctaagaa        4440
tgtaccagta gaaattgacg attttgtaga agcctggggg attacagtag aaaattatcg      4500
caaaatgcca gggcataacg aagctttatt acaattaaag gctagttact attatcatta      4560
```

```
tagaaattta gcaagtaaca tggaaacttc aagaaacaa cattttgtaa ttaattctga   4620
accaatttca aggaaacat atgatagttt agaattgtcc tatcaagtgt tacgtgataa   4680
gacaaggaca atcaggacgg ctttaattgc ttttttaagc aagtatgatt gccaagttga   4740
aatgtgtacg attggcgaga tgaaaaaggt tttgaatagt taggagcgtt aaaatggaga   4800
agataccaaa agagaaaatt gtcttgatac ccgaagttga tacggacgtt gtatctgatt   4860
tagcaccatt taactttaca gtagaacgtg acaaattatt gattgatgat tcatacgcag   4920
ttccctatgt cattacaaaa tacaacaata agccacgtgg gaattggttt aatcgtattc   4980
gtaaaatgag tggagatata accatatctc attactacac taaagcaaac ggtaactcat   5040
tgaatgatta ttacaacaga accattaaga acaagcaagc agagatcgat cgttcgcatg   5100
atccgttgac gattatccgt ttagaacgtg aaatgaaaat tgctcaaacg cagttagaac   5160
aagccgttga cgaaaacact tcttatcttt acttgtacac ctatgttttg attaaaagta   5220
agtcagaaga taaattaaaa aaattgtgtg aagattttga aacacgttgt atcgcaagtg   5280
gagtaaaagc gttaattcca tatactatga ttgataaggc gtattggagt tcattaccgt   5340
tacaatctaa tgaagtacct gaatacacct atacaatcgc taattcaatc agtgcaagca   5400 gtattttcc ttttgatgat aatgaattaa gtgtatttac taaaaatatg attattgagg   5460
gaattaataa agatactgaa aatatcgtta gtattgatta caccaacaga aaattagtag   5520
tcaatcgtaa taaattcgtt tttggtttat ctggtgggg aaagaccact tacttaacgt   5580
cagactattt aaaaaaatat gcttttctg ataactcaac agaattaagg cacagaattg   5640 ttttattga tcccgaagat gaacaaacag agcgtgtacg ttctctaggg ggcgaaataa   5700
tcaatctatc gtctatgtca gatgttcgta tcaatccatt tcaaatttac tcacgcaata   5760
cgctagatgt tgattaaaa gaatcattat ccgattttga agaggacgag cttgtagaaa   5820
atattgaaat aaagcataaa gattatgaaa tgactgacaa tgatattgat aaagaaatca   5880
gtaaacgaat gaatatttta acgccttatt tcctaatggt ggatcattct ttgactgata   5940
gtcaattatc cattattaaa atagaagcta aaaatgcta taccactta tacgagaaga   6000 aaaacttgtc aaaaatggaa aacaccgatt ttccaacatt ttcagactta gaaaatcgat   6060
tgaaagcctt agaagaaact gatccaaaaa gatacaaacg aattgaagat tttatttatt   6120
cattagaaga ttttacaatc ggaagtcgta ccatttttaa cggtcataca aatatagact   6180
taaacaatcc gttaatttgc ttttctttgc gagatttaca gaccgaagaa gggatcagag   6240
atttagcata cctcaacagc tttagttatc tatttgaaga ataaccaac aatccgcaaa   6300 ttgtaacgtc tgtttatgca gatgaatttc acttttatt gaagaataaa attagtgctg   6360 acttttctt ccaagcatat aaacgcttta gaaaatacaa tgctgattgt accgtatcaa   6420
cccaacagat tgatgatgta ttaaaagcac ctgataatat cggtaaagca attattggga   6480
atagctttac aaaagtattc ttcggacttg atgaaacgga agcacaaggt atttcaaatg   6540
agttgaaact taaactcaca aaaaaagaat tatcgttcat tacctcaaaa cgtcaagggg   6600
aagctttgct ttttcatggt acaaagcgag caaagataaa agtagattta acacaggaag   6660
aaatgcgttt gcttaaccca ggcgaatatg aagtatttta cggcgttagt ccgaagaag   6720 agatcaactg gttgttaaga tcgaaaattc aatagaaggg agaaaaaaat gaaatacaaa   6780
atcttgaaaa atttacaatt ctactatcaa gagaatgtca ttgtcgtcca aataaacgaa   6840
aaatatttga cgaatcgaga acatattttt gatgtagaag aaagtgaaca atattttgtt   6900
gatgtcgagg agattttgac caaagacgga aagctagaaa ttgtttataa ccgacctaat   6960
```

```
ggctatacac cactactaga tttaaaagaa tatgctgatt tttataaatt ggatatagtg    7020
aatcgattac ttgaaatgaa tgtactagaa aaaacaaaca cctatctagc aatgcaaaat    7080
atcctactca aagatacacg tgacttgctt tttatttata aagcagatca ctttgataat    7140
ttgccttact caactaaaga agaattagag cagtggaaaa atttttatttg tagtttttttt   7200 ggtaaattca cacttgagaa gtatgagaag aatcgtattg aggttctaac aaaagaaaaa    7260
aattcatttt taaatgatgt agaagcagtt gaaagcttgg aatcattaag agatttaata    7320
aaaaatcgac taaccgaaga acaaaagaat ttcttttctg ctgaattaca ggacaagaaa    7380
gcagacgtcc gaaaaattcg cagaaataaa agcttaaaaa ttgcgttagt tgtaggtgtt    7440
attgcgttat atggcggtac ggttttactt atgaaagtaa atgagaagaa acaagttacg    7500
gctacacagc aaagcgcaga aacagagatc actattttaa ataagattat tgataatgat    7560
agtgagaata tcgaagaaga tatgcaaaag ctcaattatc ctaagaaaaa acaagttgat    7620
atttacgtga aacttggtga ttataccaag gcttatgaac ttgataaaaa gtcagataaa    7680
aaaattattc aaagtctgta caaacaagga gaaaccgaaa aatagaagc ccttgattta     7740 ccaggaagcg actatttagc agacttcaaa aagattttag cgtatgacaa ttcaacagat    7800
attgagtatc tggttcaaac tagtaccgat acaacaattg ttgaagcttt aatcgataaa    7860
tcagtaaaag aaaagacat tccaacagtg aaaaatattc gtcaagtatc aattacacaa    7920
aagaaattag caatcgatcc taaacgtcaa atcagtatga ttgacttatt gattgaaaat    7980
aacagtgaag aattagaaaa tatgtataag gataattctt taaatgagga cttgaagaaa    8040
aaacaaacca atgacttgtt agaagaaaac aacacgttgc ttagtgaaaa gattgaatta    8100
acaaacgctg aaaaagatta ggaaggttgg tgattt                              8136

<210> SEQ ID NO 64
<211> LENGTH: 2053
<212> TYPE: DNA
<213> ORGANISM: Artificial Sequence
<220> FEATURE:
<223> OTHER INFORMATION: pCU1

<400> SEQUENCE: 64
ctgtttccat tctgtttctg aaattctgtt tttctgagcc atctgtgggc ctccgtagtt      60
ttggttacag aaaggatata ctcagaataa ataggggtca atacaagtac gatttttata    120
aactttattt tatttgaggg tgaggcccgg tgcggcacga gcgcggcgtt gatggtgccg    180
cgaaaggtgc ctggcgccat gcttggatta aacatgaac cgtgaagaac tgcgaaactt     240
gttttcgcgg ttctgagggg ttgaccgagc cgcgaagtgg taagcgatga tatgcacata    300
tccacaggca tatttttaaa aggtatttta tagattttt atctttttaa agtcttttag     360
agctatataa ctcattgatt taaaatcata aataagtgtt atctctggga atccgcccac    420
cttgttatgg gaattggccc acctatctat gggaaacacc ccaccttact atgggaatta    480
gcccaccttg ttatgggaat tggcccacct tagacgaaac tgtaaaaaat gtatttactt    540
gtttgaactt tgtggtagtg tggagagtaa tttttaaccc acaaaggcaa ggctcatgga    600
taagttgcta acaaaaaga taaagttaa gcagtctaac gagcttaccg aagctgctta     660
ctacctctcg ctaaaagcaa agcgcgttct ctggttatgt cttatgcaga cgtatttcac    720
agcttcagta agcgaagatg atgatgagat ggctgtactc ggtgactcta ctttcaaagt    780
aaaggtggct gactatcagc aaattttca ggtaagccgt aaccaggcta tcaaggatgt     840
```

```
taaagaaggc gtgtttgagt taagccgttc tgcggtaatc ttttacccga agaagggag    900
ttttgactgc gtcgcgcgcc cctggctaac agaggctggc agccgatcag ctcgtggtat    960
ctgggaaatc gaatttaacc ataaactcct gcggtacatt tacggcctga cgaaccagtt   1020
caccacctac tcgctccgcg attgtggcag tcttcgaaat ccacggacga tccgccttta   1080
tgaaagtctt gctcaattca atcttcagg cttatgggtt actactcatg cttggttaaa   1140
tgaccgtttc cttttgccgg aatcccaaca gaagaacttg gcagagttga aacgatcttt   1200
ccttgatcct gctctcaagc agataaatga gaaaacacct ttacttgcta agtatagtat   1260
tgatgattca ggaaaatttc tgttctcaat aattgataag caaaatcccg tctgacataa   1320
atcagcacac atgagcctgt catttgacaa attttttgtca tgaagatggg cgaatttcca   1380
cacagcaccg gcgcccggca aggtgggcgg attcccacac ggcaccgacg cccggcaagg   1440
tgggcggatt cccacacggc accggcgccc ggcaacggtg ggcggatttc cacacagcac   1500
cggcgcccgg caaggtgggc ggattccccac acgcaccgg cgcccggcaa ggtgggcgga   1560
ttcccacaca gcaccggcgc ccggcaaggt gggcggattt ccacacagca ccggcgcccg   1620
gcaaggtggg cggattccca cacggcaccg gcgcccggca aggtgggcgg attcccacac   1680
ggcaccggcg cccggcaagg tgggcggatt cccacacggc accggcgccc ggcaaggtgg   1740
gcggatttcc acacagcacc ggcgcccggc aaggtgggcg gatttccaca cagcaccggc   1800
gcccggcaag gtgggcggat tccacacgg caccggcgcc cggcaaggtg ggcggatttc   1860
cataactta attataccctt tgtgttattt gtggattgtg cagctcagtg gggcgctggc   1920
cgtgacggtg cggtgtcccc cgtaaccggc cgcgcggccg ctaactcgca gtacggcgcc   1980
gcgacccgca gcgggccgcc gtacccgcgc cgcacggcgc ccactgcgca ccccgtgga   2040
ggacgtgcgg cag                                                       2053
```

<210> SEQ ID NO 65
<211> LENGTH: 1540
<212> TYPE: DNA
<213> ORGANISM: Artificial Sequence
<220> FEATURE:
<223> OTHER INFORMATION: pBAV1K-T5

<400> SEQUENCE: 65

```
tccgccgccc tagacctagt gtcattttat ttcccccgtt tcagcatcaa gaacctttgc     60
ataacttgct ctatatccac actgataatt gccctcaaac cataatctaa aggcgctaga    120
gtttgttgaa acaatatctt ttacatcatt cgtatttaaa attccaaact ccgctcccct    180
aaggcgaata aaagccatta atcttttgt atttaccaaa ttatagtcat ccactatatc    240
taagagtaaa ttcttcaatt ctcttttttg gctttcatca agtgttatat agcggtcaat    300
atcaaaatca ttaatgttca aaatatcttt tttgtcgtat atatgtttat tcttagcaat    360
agcgtccttt gattcatgag tcaaatattc atatgaacct tgatataat caagtatctc    420
aacatgagca actgaactat tccccaattt tcgcttaatc ttgttcctaa cgctttctat    480
tgttacagga tttcgtgcaa tatatataac gtgatagtgt ggtttttat agtgctttcc    540
atttcgtata acatcactac tattccatgt atctttatct ttttttttcgt ccatatcgtg    600
taaaggactg acagccatag atacgcccaa actctctaat ttttccttcc aatcattagg    660
aattgagtca ggatataata aaaatccaaa atttctagct ttagtatttt taatagccat    720
gatataatta ccttatcaaa acaagtagc gaaaactcgt atccttctaa aaacgcgagc    780
tttcgcttat tttttttgtt ctgattcctt tcttgcatat tcttctatag ctaacgccgc    840
```

```
aaccgcagat tttgaaaaac cttttgttt cgccatatct gttaattttt tatcttgctc    900
ttttgtcaga gaaatcataa ctcttttttt cgattctgaa atcaccattt aaaaaactcc    960
aatcaaataa ttttataaag ttagtgtatc actttgtaat cataaaaaca acaataaagc   1020
tacttaaata tagatttata aaaaacgttg gcgaaaacgt tggcgattcg ttggcgattg   1080
aaaaacccct taaacccttg agccagttgg gatagagcgt ttttggcaca aaaattggca   1140
ctcggcactt aatgggggt cgtagtacgg aagcaaaatt cgcttccttt cccccccattt   1200 ttttccaaat tccaaatttt tttcaaaaat tttccagcgc taccgctcgg caaaattgca   1260
agcaattttt aaaatcaaac ccatgaggga atttcattcc ctcatactcc cttgagcctc   1320
ctccaaccga aatagaaggg cgctgcgctt attatttcat tcagtcatcg gctttcataa   1380
tctaacagac aacatcttcg ctgcaaagcc acgctacgct caagggcttt tacgctacga   1440
taacgcctgt tttaacgatt atgccgataa ctaaacgaaa taaacgctaa aacgtctcag   1500
aaacgatttt gagacgtttt aataaaaaat cgcctagtgc                         1540

<210> SEQ ID NO 66
<211> LENGTH: 383
<212> TYPE: DNA
<213> ORGANISM: Artificial Sequence
<220> FEATURE:
<223> OTHER INFORMATION: Cos PAC7 383

<400> SEQUENCE: 66
gaccacatca cacccgtcag ccggggagga ctcaacaccc tcgacaacgg gcaaatcatc     60
tgcagaacat gcaacagaag caaaggcaac agaacacaac caaacatcaa attccaacaa    120
caaaccacaa aaacattgat tccatggtga aaaacccgcc aaccccccacc gggcacaccc    180 cctgcacacc cgtgcaagac ctcgtacggc ttagtgaaat acctcccttt tgttgtttta    240
tcgttttgtc gactttttgt ttggtggtgt gtgtggtgca gcctgagctt cctgatagtc    300
gtgattggtg tggggagacg cgtcggtggt ggtgtgtgtg gggcgaggat ccgcgtgccg    360
ggtttgtgtc tgatgaggag tgg                                            383

<210> SEQ ID NO 67
<211> LENGTH: 511
<212> TYPE: DNA
<213> ORGANISM: Artificial Sequence
<220> FEATURE:
<223> OTHER INFORMATION: phage PAC7 origin of replication

<400> SEQUENCE: 67
cgacatcagt cttaaagtct taaacacttt aagtaacttt aaagcttcaa ggcttagccc     60
ttaaggatct aagttactat aaaagcttta aacacttaaa gtaactataa agctttaaga    120
gcttaacatt taaggatata aataaacatt aaagctttaa agtcttaaag taaatatata    180
accttaacac ttagttaag tataaaacct taaaggctta gcacttaagg atataaactt     240
aacatcagtg tttaagactt aaagagttaa agtaactatt aagacttaaa ggcttataag    300
ctttaatact ttaagtagct ataagacttt aaaaacctga agtacttaaa gttaaccatc    360
agtcttaaac tttaatatta taagtattaa agcttataag ttataaaagt ttttagaaga    420
gttaaagggt taacttcttt acttctcttc tctctttggt tctttctctc ttctcttctt    480
ttcttcatca ggggagaaga ggaaccttta a                                   511

<210> SEQ ID NO 68
```

<211> LENGTH: 29768
<212> TYPE: DNA
<213> ORGANISM: Artificial Sequence
<220> FEATURE:
<223> OTHER INFORMATION: PAC7

<400> SEQUENCE: 68

```
tgcaggtgct gacggtgtga acggcgttga cggcgctgat ggtcgggatg gttctgccgg      60
tgagcgcggc ccgcaaggcc cttcaggtcc tgccggcccg caaggtgcac agggtgaacg     120
gggtgagcgt ggtcccgccg gtgcgaatgg atcggatggc catgatggta aggatgggcg     180
ctcggtggtg tctgtgtact gttccggggg ccgcctggtt gtgaaatata gtgacggtgt     240
ggcttccacg atatcgggtt cggcggcctg ccagggtgtg aaaccgtcgc ctctagtgac     300
tatatcatcc cacaaataga aggagtggc tgtgatggtg gtgtttggtg gtggtgtgtt     360
gtgagatata ttcctgcggc gcatcattct gccggctcga atagtccggt gaatagggtt     420
gtgattcatg cgacgtgccc ggatgtgggg tttccgtccg cctcgcgtaa aggacgggct     480
gtgtccacgg caaactattt cgcttcccca tcgtctggtg gttcggcgca ttatgtgtgt     540
gatattgggg agacggtgca atgcttgtcg gagtctacga ttgggtggca tgccccgccg     600
aatccgcata gtttgggtat agagatttgc gcggatgggg gttcgcacgc ctcgttccgg     660
gtgccggggc atgcttacac tcgtgagcag tggctggatc ctcgcgtgtg gcctgcggtt     720
gagcgtgccg ccatcctgtg tagacgtttg tgtgacaagc atggtgttcc gaaaaggaaa     780
ctgtctgtgg ccgatttgaa ggccggtaaa cggggtgttt gcgggcatgt ggatgttacg     840
gatgcgtggc atcagtcgga tcatgacgat ccggggccgt ggtttccgtg ggacaaattt     900
atggctgtgg ttaatggcca cggcggcggt tcaagtagtg aggagttgag tatggctgat     960
gtacaagcgt tacataatca gattaaacag ttgtcggcac aggtggccca gtcggtgaat    1020
aagctgcatc acgatgttgg tgtggttcag gttcagaatg gtgatttggg taaacgtgtt    1080
gatgccttgt cgtgggtgaa gaatcctgtg acggggaagc tgtggcgcac taaggatgct    1140
ttgtggagtg tctggtatta cgtgttggag tgtcgtagcc gtcttgacag gctcgagtct    1200
gctgtcaacg atttgaaaaa gtgatggtgg tttgttgtgg gtaaacagtt ttggttaggt    1260
ttgctggagc gtgccctgaa aacttttgtt caaacgtttg ttgccgtgtt gggggttact    1320
gcgggtgtca cctatactgc ggagtcgttt cgtggtttgc cgtgggaatc cgcgctgatc    1380
acggcaacgg ttgctgctgt cctgtcggtt gctacctcgt ttggtagccc gtcgtttgtg    1440
gccggcaagc ccggcaagca gccccaggtg gatgcgggtt tggttccacc ggatgatggg    1500
ggcttggttg agccgcatat ggtggatgtg tcggatcctg gcatgatcga gccgacggat    1560
gatgcggatc ttgccggcta tgagcctcgg cgtgcagccg agtcggaggt tggcacggta    1620
gagtctactg ttgcataatt gaatatagat gtgtgcccca gcggtgctgc cacgattgtg    1680
tggtggcggc tgctggggca ctattttgt atatgcggtg tggctatgat tcgttgctgt    1740
cgatggtgtc ttcgagcatc tgatacaggt ggaggcaggt agagatagtt tcgctggcct    1800
gatcgagaac gttccggccg ataacgtttt tgtggttgtc gcggtggcgg atgatagccc    1860
acatgatctc gtcggctgcc gcctgtaata gttggcctg gtatgcgatt ccggcgagcc    1920
agtctagtgc ttcctggctt gtatagggc tctggtcctc gctgttgccg cgggtgttgc    1980
tgttgtttgt ggggtgtcct gcactgtcgc atagccacag gatttcgctg cactcgtcta    2040
gcgtgtcttg gtcgatagcg agatcgtcga ggctgacatt gttgacggta aggttcacgt    2100
tgtcgaggga gatgggtaca ccgtactggt tttcgacact gtcaacaatg ttttccagct    2160
```

```
gttgcatgtt ggtgggctgt tgttggacga tacggtgtat cgctgtgttg agggtggtgt       2220
aggtgatgtt gtgtgtgttg tccatggttt ttatgccatt ccttcgttat cgtctggcat       2280
gtagtatgtg ctgtttgcgt actcggttaa cgtcatcagt gtttggtctg cccactgttt       2340
cacggtttgc cgggtgactc cgagtcgttg ggcggctgtg gcgtaggttt gatcataccc       2400
gtatacttcc cggaatgctg ccaacctagc taggtgtttc ctctgtttgg atggttcaca       2460
ggtgagggtg tagtcgtcga tggctagctg tagatcgatc atggagacga tgttgttgcc       2520
gtggtgttgt ggcgcggttg gtggggtgg cattcctggc tccacggagg gtttccaggg        2580
gccgccgttc cagatccatt gggcagcttg gatgatgtcg gcggtggtgt aggttcggtt       2640
cactggtcac cccctgaaca ggtcgttggt gttgttggtg tcgaatcgtc cgacgcagtg       2700
gcagtagtcg tacatgagtt taataatgtg ttggtggtct cccaaatagg tgtttccgct       2760
gatgctgtat gtggctgtgc cgtctttcgc gatggtgtat ttggcggtga tggtttcggg       2820
gttttcggtg tcggtgatga ttgctgtggt ggtggcgcct actgtttgga gtatggtggt       2880
ttgggttccg tcgtcgatgg tggttttaac catggtgtgt gttttcctt tgttagttg         2940 cttgttttggt tgtcggctag atgaataata tcgggtaaag gtttcggctg gtctaggtgt     3000
tgtatggttt tgttggctag ccgtttggct accctgtaac acattttggt gtagtgtttg      3060
ttgtctaggt tgtggtattg ttcccgcacc gcaatatata gcaggagtc ttggtacagg       3120 tcgtctgcac tgattgcggg gtagtgtcg gctgtttgg tgcatgcccg gttgagtgtg       3180
cgaagatgat ggtctgtggc ccacacccac gatgcgtgg tggccaggtc ggcttttgtt      3240
ggtcgtctgc tcatggcact atttcatctc gctatctgat agttgtttgg tgttttgttg    3300
tggatagtgt agcacactag tcctgggtgg ccggtggtgc ctgtgcggtg acggaaccat      3360
gtggattcgc cttccatgga tgggcattgg atgaaggtgc gttgtccttg ctcggagatt      3420
tctaggtggt gccggtgccc ggccatgaga atattagata cggtgccgtt gtggaattct      3480
tggccgcgcc accaatcata gtgtttaccg gtgcgccatt ggtgcccgtg ggcgtgcagt      3540
atccgtgtgc ctgccacatc aacggtggtg gtcatttcgt ctcggctggg gaagtggaag      3600
tgtaggttgg ggtattggtt attgagctgg taggcttctg cgatggcccg gcagcagtcc      3660
acgtcgaatg agtcatcgta ggtggtgact cctttaccga agcgcacggc ttcaccatgg      3720
ttgccgggga tggatgtgat ggtcacattt ttgcagtggt cgaattggtg gatgagttgc      3780
atcatggcca tgcgggtgag cctgatttgt tcggtgaggg gtgtttgtgt tcgccaggcg      3840
ttgttgcctc cttgtgacac gtatccttcg atcatgtcgc cgaggaaggc gatgtggact      3900
cgttcgggtt tgcctgcttg ttgccagcag tgttttgcga ctatgaggga gtgtaggtag      3960
ttgtcggcga agtgtgctgt ttctccgccg gggatgcctt tgccgatttg gaagtctcct     4020
gccccgatga cgaaggctgc ggtgctgtag tcggtgtggg tgtcttgttc gggttttggg      4080
ggtgtccatt cggctagttt atcgacgagt tcgtctaccg ggtaggggtt tgttgcgggt     4140
tggtggtcga tgatttttg tatggatcgg cctgtttctc cgttggggag tgtccattcg      4200
gagatgcgtg tgcggcgcac ggtgccgttg gctagattgt cgtcgatggt gtcgatggcg      4260
ttgtcgtggt tggctagctg tgtgagtagc cggtcaatat tgtctatcac tgggtatcct     4320
cctcttgcgg ggtggtgctg gcttgtttgc ggcgatagtc tttaataacg gtggcggaga     4380
tggggtatcc tgcctgggtg agctgttttg ctagccatga ggcggggata gacctgtcgg     4440
cgagcacgtc ggcggctttg ttgccgtagc gttgaataag ggtttcagtt ttggttgcca    4500
```

```
tgatgtccta tcggttgtgt ggtgggctgc catcctgtgc ggcagtcgcc gtcgtgtcct   4560
ggtttgcgtg tgcaccacga tacggttccg tctgtgtggt tgagtgtttt accgcacatg   4620
acgtttcgga gatgctccgg cagctggtca tcctggttgc tggtttgtgt gtcgaagagt   4680
gttttctggt tggtgaaatg ttctgacacg gtgccgttat gcacgggtag tatccatgtt   4740
ttccattgtt gttgtagcct ggtgttccag tggaattgtt tggcggcgtt ttcggcctgt   4800
tttaaggttt tgtggtagcc gactagtatg cgttgatgct gctggtctgg agggtttggg   4860
cctcgccagt attgtgccgc cacggcgtag cggttgctgt ctgtgaaggc gtcccagcag   4920
tattcgataa tgtgttgcaa catactgtct ggcaggctgt cagggttgat gttgatgttt   4980
tgggtgataa tgtcacggat ggcttgccgg ttttggtgg tgggtttgaa cgagatgctc     5040
acgatagtac cggctggtcg tcttgcatga actggttgaa ggtgttgttc ccggcgtgtt   5100
gggcttgtgt tatttgttgg tcggtccagt ctgggtgttg ctgtttcaga tagtgccagt   5160
ggcacgcatt gtaggtttcg tcttgtagcc gtgtgagatg ttttcggtg atgatttgtt    5220
tccacatggc ccatgacacg tcgagccggt cgaggatttc gagggctggg atgttgaatt   5280
ggttcaggaa gaggatttcg tgggtgtagt agttttctc gtaggcgtcc catccgcttc    5340
ggtgcctgtt gggctggttt ttggggtagg cttcccggca tactttgtgt aaacgcttgg   5400
ccatgtcgtc gggtagtttta atgtcggggt tggcgcggat catggatcgc atcccatcat   5460
aggtggtgcc ccaggtgtgc atgatgtagg tggggtcttc tccgtcggcc catttttctg   5520
cacagatggc gaggcggata cgcctcctgg cagcttggct ggtgttgcgc cggttgggga   5580
ttgggcacgt gtcgagggga tccatgatgt tttagtgtac ctttctggtt tcgtgttgtt   5640
gacaggtttt actgtagcac agtgtctagt gcgtgtgtca accctgttt tccggcttga    5700
aggtaggtgt ctgtgacatc ccctaggatg aggggcacgt gcacagcttg ggggagtgcc   5760
gcctggaggg tttgggccat ctggtcgcct gcggggtctg ggtctgacca gatgtagatg   5820
tggtcgtagc cttcaaaaaa tttggtccaa aaaatttgcc acgaggttgc gccgggtagg   5880
gcgacggccg accatccgca ttgttcgagg atcatggagt cgaattcgcc ttcgcaaatg   5940
tgcatttcgg ctgccgggtt ggccatggcg gccatgttgt agatggagcc tgtgtctcct   6000
gccggggtta ggtatttggg gtggttgtgg gttttgcagt cgtgcgggag tgagcagcgg   6060
aaacgcattt tcttatttc ggctgggccg ccccaaacgg ggtacatgta tgggatggtg    6120
atgcactggt tgtagttttc gtggcctggg atggggtcat tgtcgatgta tccaaggtgg   6180
tggtagcggg ctgtttcttc gctgatgcct cttgctgaga gcaggtcgag tatgttttcg   6240
aggtgggttt cgtagcgggc tgaggctttc tggattcggc ggcgttccgc aatgttgtat   6300
gggcgtatgc tgtcgtacat ttgggttttc ttcttctaat cgttgttgta gcttggcgag   6360
tccgcctccg acaccgcatg tgtggcagta ccagacgccc ttgtcgaggt tgatgctcat   6420
ggagggctgg tggtcgtcgt ggaacgggca gagtatgtgt tgctcgttcc tggacggatt   6480
gtaccgtatc tgataatggt cgaggaggcg gcaggtgtca gaggtgtggg aggagctcgt   6540
tgagggttga taccacatag gcttcactcc atggcttgtt gcgctgtttc atcactacga   6600
gtccgatggt ggaattgttt tgtttgtttc ggtgtgtttc gtagttgcgt gcctcccggc   6660
tggcttgttt cacgaattgg gctaggtgtg gttgcccggc tttcgcctcg ataatgtagg   6720
ttttatggcc ggttgtgagg atgaggtcgc cttcgtcttc gcggccgttg aggtggaggc   6780
gttcgatatt gtgtccggtg tcgcgtagct ggtggaggag tcttgtttcc cattcggctc   6840
cggcccgccg gttgcgtgcc tgctgtgtgg ccatagtttt ttagagtcct tgtgtgttg    6900
```

```
tggtcatgtt ccagggctgt ttttcggcga gtggcccgaa gaatgtgtat tcggggtatg   6960
ctctgagtcg ttcgtatcgg gtgccgtcgg ggctggattt gcctgtgcgc tgtttgagta   7020
cggcgatgcg tgcctctgcc ggtatcgata gcccgttgcc gttatcctcg ccaccataca   7080
atgagactcc gaggatgagt tgtggttttt cggagaggcc gttttgatt tctcgccgtg    7140 ctggcgggtg ttcgatgtcg gttccggttt tgtcggttgc gtggtgtgtg acaataatgg   7200
tggagccagt atccctgccc aatgctgtga tccattgcat ggcttcttgc tgtgcctggt   7260
agtcggattc gcagtcttga atgtccatca ggttgtcgat aacaatgagt ggtgggaagg   7320
tgttccacat ttccatgtag gcttgtaact ccatggtgat gtctgtccat gtgatgggtg   7380
actggaatga gaatgtgatg tgttggccgt ggtggatgct gtctcgatag tattctggcc   7440
cgtagtcgtc gatgttttgt tgtatttgtt gggtggtgtg ttgtgtgttg agggagatga   7500
ttcgtgtgga ggcctcccag ggtgtcatgt cccctgatat gtagagggcg ggctggttga   7560
gcatcgctgt gatgaacatg gctagccctg attttggct gccggaccgc cccgcgatca    7620
tcaccaagtc gcccttatgg atgtgcaaat cttggttatc atatagtggt gcgagttgtg   7680
gtatgcgggg tagttcggct gcggtttggg aggctctctc gaaggatcgt tgtagagaga   7740
gcatcgggac cttaatctat ctgtctgttg gttgtgtggc tggtcagatg gagtcgatat   7800
cgatatcagc atcagcagag gctgaagtgt catctagctg accattatcg cgcttgtcta   7860
cgtattcggc aaccttatcg tagatggcgt cgtccaatgt tttgagcacg accgcgttga   7920
aaccgttttt ggtgcgcacg gtggctagtt tgaaggcctg ctcctcgcca aggtatgcct   7980
ctagttcgcg gatcatggag tgtgggcggt cgttattgcc gcgggctttc tcaataatag   8040
cgttggggat ggtttctggg gtgccgttgt tgagatcgtc tagggtgtgg aagatggtga   8100
catcagcgta gatgcggtct gcgacctgtc caccgtagcc ttcagtgttg tgctggacgt   8160
cgtgcacttt gaaggcgatg gccgtggcgt cctggtttcg ggaggggttg aagaaggtgc   8220
tgttgctgtt gttgcggtag tttgcgagtc ccataactat tgtttccttt tactgttgtg   8280 tctgttttg ttggcttata ttggtttatc gggtgaggct gtttcgctta gtgcggaaag    8340
cgtcggaaac atcactgtta ctggtgatga tcttcttgta ctgttttaga aggtctgcta   8400
gctgtgcctt gcttgttgca ttgttgattt tgttgatgac gatggtgttt tctttggatg   8460
cgattttgtt gacgtagtct ttggctgcct ggttgtatcg gtcttggagg atgattgatg   8520
cgctcgctac gagtgttgct agatcccagt cttggacac gtcatcgttt ttgagtccgc     8580
ctagcaggtc gatgatggcc tgttttgtct gctctgctgt gtctcctcgg atgaccgccc   8640
atggtgcagc atagtctcca ccatatttga gtgtgatcgt gagtcgatca ttgtcgatct   8700
tgtctttatc tgtcatttgg tgtccttttc tttattgtct gtttctggtg gctgtacggt   8760
ggattctacc gggtatctgt acgagttttt gccgttgacg gcccagcagg cgtctcgtac   8820
ggggcatcct ttacagagtg ttgtgacgtg ggggacgaag atgccttcgc tgattccttt   8880
cattgcttga ctgtacatgg atgatacatg ccggtaggtg ttgttgtcaa ggtcgtagag   8940
ttcggtggat gtgccttgtg tcggggactt gtcgtcgttg cggctggtgg ctggcgtcca   9000
aaacatgcct ttcgtgacat ggatgtcgtg ttggttgagc atgtaccggt atgtgtgcag   9060
ctgcatactg tcggcgggta ggcgtccggt tttgaggtcg aggatgaagg tttcgccggt   9120
gtcggtgtcg gtgaaaacac ggtcgatgta gccgactatt tttgtgtcat cgtcgaggat   9180
ggtttctacc gggtattcga tgcctggttt accgtccagg attgcggtga tgtattctgg   9240
```

```
gtggttgcgc ctccatgttt tccagcggtc cacaaaggtg gggccgtaaa ccatccacca    9300
gtcgtagtct ttcttgtgtg gtccgcctga ctcgcacatg tttttgcata ttctgccgga    9360
gggtttgatt tctgtgcctt cggattcggc gagggctacc tgggtgtcga aaatgttttt    9420
gaaggatgag agtttgtctg gcagtgcagg gtattcggcg ggattgtaca ggtgtaggtc    9480
gtattgttcg gtgatgtggt gtatggcgct tccggcgatg gtggcgtacc aggtgtggtg    9540
ttgggcgtga tagccgtggg ataggcgcca ttttctccg cattcggccc actgggtgag     9600
tgaactgtag gagatgtgtc ctgggtggct gatggttttc gggtattgtg ctagaggcat    9660
tacttgtcgc ttgtgttcca tgtgttgcgg gtgtcttggc cggcgtggtg ttgctggtag    9720
gcgaggagtg cgaggcagtg ccaggctgcg tgtgctagat ggggtagccc ggattcgtgg    9780
tcgaggttgt tgccttgctg ccatgatagt agatgcctgt agagggcgtc gacactgtgg    9840
ctccacgggt atcctccggt ccagttgttg tcgccatatt tggtggcacc gtatccggct    9900
acttcgccta gggcgtgaag ggatgctggg tcgatgaggg agagcctgca gagtttcaat    9960
tcttttcggg caccgctgtt ggggtcgtg tacatgcggg tgggctcatc catggggtgt    10020
gtgctcctta agggtgggtt actggttgtt gttgtgggct agggcggcgg cgagaataat    10080
gatggcgagg gtttcggcta tcagtatggg tgttgtgatc atttggtgtc tcggggattg    10140
ttggtgagtg ttgaggcacc caggagggtg gcgagggcgc atgcggcaat aatggcgagg    10200
gctgccttgt gtggggtgcc ggttgcgtac atccatgtga tgatggcacc ttggatccag    10260
gctaggctgg tgaagaaggt ttcgtagctg tgcagctcaa tgttgttgtt gggtgtgttc    10320
atgcttgctc ctgaagaatg gtgttgatgg ttttataaat gttgtacagg tcggtttcga    10380
tagataacag ttggttgatt tggtggtcga gatcaatgtc tgggttgagt gtgttgatgc    10440
gggaggcaat atcggtggct gtgcgtagtg tgccgccggt gtggtgaata atgtgtgccg    10500
tgtcggcgag tccggtggtg acggcgtagt gggataggag aggcatagcg gggatgctcc    10560
ttggcgggtt actgttgcgg gttgatgttg aggtcggtga cgtgcggtga gttttctgtt    10620
ccggtgacga ggcagtggac ggtgacgggt agtttggatg ctcccggctg gcggacggtg    10680
gcgccgtaga cgatgctgaa tgtgtcttta ccgatggttt tgtggagttg gaggtcgatg    10740
tcggggttgc cgttccagtt gacaccttgc gctgcggcct gttgttcggc tttgtggttg    10800
caggtgtgtg ctgccgtgat catggtgagt ccggtggcgg tttcttcacc ccttgcttgg    10860
gcttgcttgt gggctttggc ctgctcggct tgtagggatc gggtggcggc tgcctgccgt    10920
gccgctttct cggctttgcg ctgttgggta gtcttgggg tccatgtggt gttggctgtg    10980
gttgcctgtg gggctggctg tgaggtgagt ggcgggttgt cgtctggtgc tggcatgaat    11040
gaggcggcgg caatgatggc ggctgtgatg cctgcgatgg tgtagccgtt tttcttgttc    11100
atgttttgtg tccccttttcc ggggtgttgt tcgttgctga catggttaat actttcagcg    11160
gctgggccca ctgtcaaggc tgcgctcagt ttgtgtgagc gtttggtgtg tggctagggg    11220
ttttgtcatg taagcgtgac atgtcactac cttgcgtcca gtatccatgg cggttgcgag    11280
ccatcccttt ggcgagcatc tcgtccacag tgaggcacct gcggcgattg gggccttcct    11340
tgaccccgta atcgcctatg cggtgcatgt ccccggcata agtgccatta aatgtttcgt    11400
ggcagactgt gcagtgttct ggtcggtatc cgatgattgt gctatcgcac ttgtggcatg    11460
tccattgcat gattggtcct tctttcgtgt tttaagcttg tgctctgagg attagagcga    11520 cttttcagccc ttggggtag gattatatag gtcaggtatt tctaggcgat tctaggctca    11580
ttgtgtgtgg ttggggtttt atcgggcgca tagggttagc aggtggccca cattggtgcg    11640
```

```
gctcacattc cagtagagtt gcgtggcttc cttactggtg agcggcttcc actcgtcatg   11700
gctgaacacg gtgccatcgg atgcgatgaa cgtgttgggg cgtagcttgt gaagctcggc   11760
ttccacatgc tgccggtagg cttcggcgag gctctcaaaa tccatgtggt cgcaggagag   11820
gttttcgagg cgtgtcaggt cgaaaggctc cgggcagtcg tagctggctg gagtgtagag   11880
ctgggtgaag tggtcggcga tcttctgcat ggcgggttcc tttctggtgt gtggatggtt   11940
tttatcgtgt ggatgcgaca aggatggcgt ctacgtcgat catgtcgatc atgtcgttga   12000
gttcctcggc ctcattctcg gagaggtggc gccagtcggg tggcccgtat acggcgccgt   12060
cgagggtgac agtccacagg ggccggatga gtcgtatggc ttcttcgact ttggcgtggt   12120
acatgcggcg caccatatcc agatcgatgt cgtctgaatg gtttccggtg aggctgtgga   12180
ggctgagcgg gtcgatttct gtctgcctgt agaggctggt gaatgatggt gtgatgagtg   12240
tgccatccat gagtgtgctc cttttctaggg gttgttgtgg tttctagagt gtgtgggctg   12300 tgacccaca gtcaaggcta cgctcatttg gattgagcgt ttcatatggg tgtggcatgg   12360
aatctacacc ctcatactgt gtgagatgta tcacatcccc ctggcttggt gtgcacccct   12420
caagactact ctgccgacct ggcgtggagg gtgtagccca gaaatgccgt ttaaagcttc   12480
aggggtacgc ctaggagcgc cttacagggt gggggctagg tatttatacc cccagcatat   12540
tctgatcgat tctagacgac tcccagagcc cgatacacga tcaaccatct cgacatagac   12600
catcagcccc tatcctggtt agctaagcct caactatgtg gacagtgtgg gacactgtgg   12660
gggaagaagg acacggtaca agaaagaggg gggagcatca gccttaaagc cttaagatct   12720
tagcgcttag caccgatggt cttagcagtt agcaccgagc ccttgagggg gctcggcatc   12780
agcctcatcg ggctcagctc atcaggcaca gccctgaaaa gggtacacgc catcagggaa   12840
ggcttgagag tacgaggagc cctagcgacg agtactcgaa agcctgaggg aacaccctca   12900
gtactgatga gcctagcgta ttcggaaagg acgcaagagt aaagtgtgac agctatccgg   12960
gagtgaaacc cgttccgact agggggtttca gccttaacca ccctcaaagg ttacaagact   13020
ctaagaaaat ttaagaaact tcttaggaag aaagttgtgt tcatatcccc ctaaaaacac   13080
ccaaaatagt cctcaaaccc gcctatagag ccaaacagtc aagtttgact cgtctagacg   13140
gcgtatgata ggctggacag gtagccagct ggacgcaagg ccagaaagtg ctgacgcact   13200
tcccgacctc gcttaccatc agtctaccaa acactttaaa gcttcaaggc ttagcgctaa   13260
gcccttaaga tcttaacgct tagcaccgag ccccctcaa gggctcgaca tcagtcttaa   13320
agtcttaaac actttaagta actttaaagc ttcaaggctt agcccttaag gatctaagtt   13380
actataaaag cttttaaacac ttaaagtaac tataaagctt taagagctta acatttaagg   13440
atataaataa acattaaagc tttaaagtct taaagtaaat atataacctt aacacttaag   13500
ttaagtataa aaccttaaag gcttagcact taaggatata aacttaacat cagtgtttaa   13560
gacttaaaga gttaaagtaa ctattaagac ttaaaggctt ataagcttta atactttaag   13620
tagctataag acttttaaaaa cctgaagtac ttaaagttaa ccatcagtct taaactttaa   13680
tattataagt attaaagctt ataagttata aagtttttta gaagagttaa agggttaact   13740
tctttacttc tcttctctct ttggttcttt ctctcttctc ttcttttctt catcagggga   13800
gaagaggaac ctttaaccgt caacgctgat ggacttttca ccgtgtgact cgtgtgcttc   13860
tggtcgcaag ctcccatcgc acactcccca cactcttttca cccgtgcccc tttacggctt   13920
agcgtgttcg tcggaaggcg tacggcgtgt cacgcttaaa cccttaacac caggtaagac   13980
```

```
ttaaagtgca tattataagt agaagacttt aaaacctata aggtgttccc gcttagcccg   14040
tgttccttta acgctaggcg ctcagcgcta agatgtgaaa cgtgaacacc catccacccc   14100
cattttctct ccgtgtcctt ctccttttga caccgctggg gggcgatgtg atatttctca   14160
catgccaggg ggtagtggag aaaacaacca ccccggaacg tttaagacac ccctcaaac    14220 gaacaaaaca gggcctagaa tcgatcagca gggcaccggt agggtattcc taccccaga    14280 cgattcaagg ccattacagg agcaatgaga ggctcacagg ggccatggga gattgggggg   14340
cgtgatggca cacaccaacc gcacagccag ccaagcccac cggcgctggc gggcaaggct   14400
catcacccaa gcccgacaac aaggccaaac cgaatgccca ctctgcggag tcaccatcac   14460
ctggaacacc cacgacctgc caaccagccc gaagccgac cacatcacac ccgtcagccg    14520
gggaggactc aacaccctcg acaacgggca aatcatctgc agaacatgca acagaagcaa   14580
aggcaacaga acacaaccaa acatcaaatt ccaacaacaa accacaaaaa cattgattcc   14640
atggtgaaaa acccgccaac ccccaccggg cacacccct gcacaccgt gcaagacctc     14700 gtacggctta gtgaaatacc tcccttttgt tgttttatcg ttttgtcgac ttttttgtttg   14760 gtggtgtgtg tggtgcagcc tgagcttcct gatagtcgtg attggtgtgg ggagacgcgt   14820
cggtggtggt gtgtgtgggg cgaggatccg cgtgccgggt ttgtgtctga tgaggagtgg   14880
ttgtttctca tggatgctgc ggtgattcat gatgtggtgt ggcgtgaggg tcgcgcggat   14940
ttggtggctt cgttgcgtgc tcatgtgaag gcttttatgg gtatgttgga taggtattcg   15000
gttgatgtgg cgtctggtgg ccgtggtggg ggttctgcgg tagcgatgat tgaccggtat   15060
aggaagcgta gggggggcttg agtaggtgtc tggtgttgtt gggtctcagg ttcctcgtca   15120
ccgggtggct gtggcgtatt cggtgtctgc tggcggggat gctggggagc ttggtagggc   15180
ttatgggttg acgcctgatc cgtggcagca gcaggtgttg gatgattggc ttgctgtggg   15240
tggtaatggc aggcttgctt cgggtgtgtg tggggtgttt gttccgcggc agaatggcaa   15300
gaatgctatt ttggagattg tggagttgtt taaggcgact attcagggtc gccgtatttt   15360
gcatacggct cacgagttga agtcggctcg taaggcgttt atgcggttgc ggtcgttttt   15420
tgagaatgag cggcagtttc ctgacttgta tcgtatggtg aagtcgattc gtgcgacgaa   15480
tggccaggag gctattgtgt tgcatcatcc ggattgtgcc acgtttgaga agaagtgtgg   15540
ttgtccgggt tggggttcgg ttgagtttgt ggctcgtagc cggggttctg ctcgcgggtt   15600
tacggttgat gatttggtgt gtgatgaggc tcaggagttg tcggatgagc agttggaggc   15660
tttgcttcct accgtgagcg ctgccccgtc tggtgatcct cagcagattt ttttgggtac   15720
gccgccgggg ccgttggctg acgggtctgt ggtgttgcgt cttcgcgggc aggctttgtc   15780
gggtggtaaa cggtttgcgt ggacggagtt ttcgattcct gacgagtctg atccggatga   15840
tgtgtcgcgg cagtggcgga agttggcggg tgacactaat ccggcgttgg ggcgccgcct   15900
gaatttcggg acagtctcgg atgagcatga gtcgatgtct gctgccgggt ttgctcggga   15960
gcggcttggc tggtgggatc gtggccagtc tgcttcgtct gtgattccgg cggataagtg   16020
ggttcagtcg gctgtggttg aggcggctct ggttggcggg aaggtttttg gtgtctcgtt   16080
ttctcgctcg gggatcgtg tcgcgttggc tggtgctggt aaaacggatt ctggtgtgca    16140
tgttgaggtt attgatggcc tgtctgggac gattgttgat ggtgtgggcc agctggctga   16200
ttggttggcg ttgcgttggg gtgacactga aaaggttatg gttgcagggt ctggtgcggt   16260
gttgttgcag aaggctttga cggatcgtgg tgttccgggt cgtggcgtga ttgtggctga   16320
tactggggtg tatgtggagg cgtgtcaagc cttcctggag ggtgtcaggt ctgggagcgt   16380
```

```
gtctcatcct cgtgccgatt cgaggcgtga catgttggat attgctgtga ggtcggctgt    16440
gcagaagaag aagggttctg cgtggggttg gggttcctcg tttaaggatg gttctgaggt    16500
tcctttggag gctgtgtctt tggcgtatct tggtgcgaag atggcgaaag cgaagcggcg    16560
tgaacggtct ggtaggaagc gggtgtctgt ggtatgaact cggatgagtt ggctctgatt    16620
gagggcatgt acgatcgtat tcaagggttg tcttcgtggc attgccgtat tgagggctac    16680
tatgagggct ctaatcgggt gcgtgatttg ggggttgcta ttccttcgga gttgcagcgg    16740
gtgcagacgg tggtgtcatg gcctgggatt gcggtggatg cttggagga cgtctggat    16800 tggcttggct ggactaatgg tgacggctac ggttttgatg gtgtgtatgc tgcgaatcgg    16860
cttgctacgg cgtcgtgtga tgttcacctt gatgcactga ttttgggtt gtcgtttgtg    16920 gcgatcattc cccaagagga tgggtcggtg ttggttcgtc ctcagtcgcc gaagaattgt    16980
actggccggt tttctgccga tgggtcttgt ttggatgctg gccttgtggt gcagcagacg    17040
tgtgatcctg aggttgttga gcggagttg ttgcttcctg atgtgattgt tcaggtggag    17100
cggcggggtt cgcgtgagtg ggttgagacg ggccgtatcg agaatgtgtt gggtgcggtt    17160
ccgttggtgc ctgttgtgaa tcgtcgccgt acttctagga ttgatggccg ttcggagatt    17220
acgaggtcta ttagggctta cacggatgag gctgttcgca cactgttggg gcagtctgtg    17280
aatcgtgatt tttatgcgta tcctcagcgt tgggtgactg gcgtgagcgc ggatgagttt    17340
tcgcagccgg gttgggttct gtcgatggct tctgtgtggg ctgtggataa ggatgatgat    17400
ggtgacactc cgaatgtggg gtcgtttcct gtgaattctc ctacaccgta ttctgatcag    17460
atgcgtttgt tggcgcagtt gactgcgggt gaggcggctg ttccggaacg ctatttcggg    17520
tttatcactt ctaacccgcc ttctggggag gctttggctg cggaggagtc tcggcttgtg    17580
aagcgtgctg aacgcaggca gacgtcgttt ggtcagggct ggctgtcggt tggtttcctg    17640
gctgcccggg cgttggattc gagtgttgat gaggccgcgt ttttggtga tgttggtttg    17700 cgttggcgtg atgcgtcgac gccgactcgg gcggctacgg ctgatgctgt gacgaagctt    17760
gtgggtgctg gtattttgcc tgctgattct cggacggtgt tggagatgtt gggtttggat    17820
gatgtgcagg ttgaggctgt gatgcgtcat cgtgccgagt cttcggatcc gttggcggca    17880
ctggctgggg ctatttcccg tcaaactaac gaggtttgat aggcgatggc ttcgggtgct    17940
gtgtcgaggc ttgctgcgac tgagtatcag cgtgaggctg tcaggtttgc tgggaagtat    18000
gcgggctatt atgccgagtt gggtcgtttg tggcgtgccg gcaggatgag tgacacgcag    18060
tatgtgcgtt tgtgtgtgga gttggagcgt gccggccatg acggttcagc agctatggcg    18120
ggcaaattcg tttcagattt tcgccggttg aatggtgtcg atcctggttt gatcgtgtat    18180
gacgagtttg atgctgcggc ggcttttggct aggtcgtttt cgactatgaa gattatgaat    18240
agtgacccgg ataggcgaa tgatacgatt gatgcgatgg ctgcgggtgt taatcgggct    18300
gttatgaatg ctggtcgtga cacggttgag tggtcggcgg gtgcgcaggg taggtcgtgg    18360
cgtcgggtga ctgatggtga tccgtgtgct ttttgtgcca tgttggctac gaggtcggat    18420
tatacgacta aagagcgggc gcttactact ggtcatacgc ggcgtcataa gcgtgccggt    18480
aggcgtccgt ttggttcgaa gtatcatgat cattgtggtt gtacggtggt tgaggttgtt    18540
ggtccttggg aaccgaatag ggctgatgcc gagtatcaga ggacgtatga gaaggctcgt    18600
gagtgggttg atgatcatgg gttgcagcag tcgtctggca atattttgaa ggctatgcgt    18660
actgttggtg gcatgagata atttgatgtg gtttccggtt gtgtgccgcc ggttatcggt    18720
```

```
gcacagggtt gtctcccgca cggggtcaa caatgttgtg ttgttttccg caaggagtgt   18780
agggttaggc tatggccgat cagagtattg aggaacagaa tgttgacaat gatgttgtgg   18840
agtccggaaa ggataacggc attgttgata cagtaaaaga cgatggcggg caggaggtag   18900
ccgacaatca gttgaagaat gaaggcgagg gtaaatcgcc ggggactgat tggaaggcgg   18960
aggcccgtaa gtgggagtct cgtgctaaaa gtaatttcgc cgagttggag aagcttcgta   19020
catcgagtga cgattctgga tctactattg atgagcttcg ccgcaagaat gaggaactcg   19080
aagaccggat taacgggttt gttcttgagg gtgtgaagcg cgaggtggct gccgagtgtg   19140
gcctgtcggg tgatgcgatc gcttttcttc acggtagcga taaggagtcg cttgccgagt   19200
ctgctaaggc tttgaagggt ttgatcgacc atagtagtgg tggtggcgcg ggtgtgcgcc   19260
gtcttgcggg gagtgccccc gttgatgatg ttaaacgacg tgagggtgtc gcgtttgtgg   19320
atgctcttgt caataattct aggagatgat ttatcatggc tgacgatttt ctttctgcag   19380
ggaagcttga gcttcctggt tctatgattg gtgcggttcg tgaccgtgct atcgattctg   19440
gtgttcttgc taaactgtca ccggagcagc cgactatttt cgggcctgtt aagggcgccg   19500
tttttagtgg tgttccgcgc gctaagattg ttggcgaggg cgatgttaag ccttccgcta   19560
gcgttgatgt ttctgcgttt actgcgcagc ctatcaaggt tgtgactcag cagcgtgtct   19620
cggacgagtt tatgtgggct gacgccgatt accgtctggg tgtgcttcag gatctgattt   19680
ccccggccct gggtgcttct attggtcgcg ccgttgatct tattgctttc catggtattg   19740
atcctgctac gggtaagcct gctgcggctg tcaaggtgtc gctggataag acgaataaga   19800
cggttgatgc caccgattcc gctacggctg atcttgttaa ggctgttggt ctgattgctg   19860
gtgctggttt gcaggttcct aacggtgttg ctttggatcc ggcgttctcg tttgctctgt   19920
caactgaggt gtatccgaag ggttcgccgc ttgccggtca gccaatgtat cctgccgccg   19980
ggttcgccgg cctggataat tggcgcggcc taaatgttgg ttcttcttcg actgtttctg   20040
gtgccccgga gatgtcgcct gcttctggtg ttaaggctat tgttggtgat ttctctcgtg   20100
tccattgggg gttccagcgt aacttcccga ttgagctgat cgagtatggt gacccggatc   20160
agacggggcg tgacttgaag ggccataatg aggttatggt tcgtgccgag gctgtgctgt   20220
atgttgcgat tgagtcgctt gattcgtttg ctgtcgtgaa ggagaaggct gccccgaagc   20280
ctaatccgcc ggccggtaac tgattcattt gttgcgataa tgtttatgct gtgtgcaggg   20340
ggtggtgttg atgggtatca ttttgaagcc tgaggatatt gagccttttg ccgatattcc   20400
tagagagaag cttgaggcga tgattgccga tgtggaggct gtggctgtca gtgtcgcccc   20460
ctgtatcgct aaaccggatt tcaaatatag ggatgccgct aaggctattc tgcgtagggc   20520
tttgttgcgc tggaatgata ctggcgtgtc gggtcaggtg cagtatgagt ctgcgggccc   20580
gtttgctcag actacacggt cgaatactcc tacgaatttg ttgtggcctt ctgagattgc   20640
cgcgttgaag aagttgtgtg agggtgatag tgggcgtggt aaggcgttca ctattacacc   20700
gaccatgagg agtagtgtga atcattctga ggtgtgttcc acggtgtggg gtgagggttg   20760
ctcgtgcggg tcgaatatta acggctatgc tggcccgttg tgggagatat gatatgaccg   20820 gttttccttta cggtgaaacg gttgtgatgc ttcagccgac tgttcgtgtc gatgatcttg   20880
gtgacaaggt ggaggattgg tctaagcctg tcgagactgt gtaccataac gtggccatct   20940
atgcttccgt ttcgcaggag gatgaggccg cggggcgtga ctcggattat gagcattgga   21000
cactgctgtt caagcagcct gtcaaggctg ctggttatcg gtgtcgttgg cgtattcggg   21060
gtgttgtgtg ggaggctgac gggtctccta tggtgtggca tcatccgatg tctggctggg   21120
```

-continued

```
atgctggtac gcaggttaat gtgaagcgta agaagggctg atgggttgtg gcacgtgatg    21180
ttgatgtgaa gctgaacttg ccgggtattc gtgaggtgtt gaagtcttct ggggtgcagg    21240
gcatgttggc tgagcgtggt gagcgtgtca agcgtgcggc ctcggcgaat gtgggcggta    21300
acgcttacga tagggcccag tatcgtgccg ggttgtcgtc tgaggtgcag gttcaccgtg    21360
ttgaggctgt ggcgcgtatt ggcaccacct ataagggtgg taaaaggatt gaggctaagc    21420
atggcacgtt ggcgaggtcg attggggctg cgtcgtgatc gtttacggtg atcctcgaat    21480
atgggctaaa cgtgtgttgg cggatgatgg ttggctgtct gatgtaccgt gcacgggtac    21540
tgtgccggat acatttgagg gtgatctgat ttggttggcg ttggatggtg gcccggagtt    21600
gcatgttcgt gagcgtgttt ttttgcgtgt gaatgtgttt tcggatacgc cggatcgtgc    21660
tatgtctttg gctcgccggg ttgaggctgt gctggctgat ggtgtggatg gtgatccggt    21720
ggtgttttgc aggcgttcga ctgggcctga tttgctggtg gatggtgcac gttttgatgt    21780
gtattcgctt tttgagctga tatgtaggcc tgcggagtct gaataagctt attgttttg     21840
ttttaatgta attgtttgat atttaatggg ggttgtgatg gctgctacac gtaaagcgtc    21900
taatgttcgt tcagcggtta ctggcgacgt ttatattggt gacgcgcacg cgggtgattc    21960
tattaagggt gtggaggcgg ttccttccgg gcttacagct ttggggtatc tgtctgatga    22020
cgggtttaag attaagcctg agcgtaaaac ggatgatttg aaggcttggc agaatgcgga    22080
tgttgttcgc actgtggcta cggagtcgtc tatcgagatt tctttccagc tgattgagtc    22140
gaagaaggag gttatcgaac tgttttggca gtcgaaggtt actgccggat ctgattcggg    22200
ttcgttcgat atttctcctg gtgccacaac aggtgttcac gccctgttga tggatattgt    22260
tgatggcgat caggttattc gctactattt ccctgaggtt gagctcattg atcgtgacga    22320
gattaagggc aagaatggcg aagtgtacgg gtatggtgtg acgttgaagg cgtatcctgc    22380
ccagattaat aagactggta atgcggtgtc gggtcggggg tggatgacgg ctttaaaagc    22440
tgatactcct ccgactcctc cgccggcccc ggttcctccg aagcctcagc cggatccgaa    22500
tccgccgtcc ggtaactgat acacgatttt aggggattgt taatagatga gtgacactgg    22560
tttcacgttg aagattggtg atcgtagctg ggtgttggcg gatgcggagg agacggctca    22620
ggctgttcct gcccgcgttt tccgtcgtgc cgccaggatt gcccagtcgg gggagtctgc    22680
ggatttcgcc caggttgagg tgatgttttc tatgttggag gctgccgccc cagctgacgc    22740
ggtggaggcc ctggaggggc ttcctatggt tcgtgtggcg gaggttttcc gtgagtggat    22800
ggaatacaag cctgacggta agggtgcctc gctgggggaa tagtttggct ccacggcctg    22860
attgatgatt atcgtggggc catcgaatac gatttccgca ccaagtttgg tgtttctgtt    22920
tatagtgttg gtgcccgca gatgtgttgg ggtgaggctg tccggctggc tggcgtgttg    22980
tgtaccgata cgtctagcca gttggcggcc caccttaatg gttggcagcg cccgtttgag    23040
tggtgcgagt gggctgtgtt ggacatgttg gatcattaca ggtctgctaa tagtgagggg    23100
cagccggagc ctgtggcgag gccgactgat gagcgtcggg caaggtttac gtctgggcag    23160
gtggacgata ttttggcgcg tgttcgtgcc ggtggcgggg tgtctcgcga gattgatatt    23220
atgggtgaa tagtgtatgt ctggtgagat tgcttccgca tatgtgtcgt tgtatacgaa    23280
gatgcctggc cttaaaagtg atgttggtaa acagttgtcg ggtgttatgc ctgctgaggg    23340
gcagcgttcg ggtagcctgt ttgctaaagg catgaagttg gcgcttggtg gtgcggcgat    23400
gatgggtgcc atcaatgttg ctaagaaggg cctcaagtct atctatgatg tgactattgg    23460
```

```
tggcggtatt gctcgcgcta tggctattga tgaggctcag gctaaactga ctggtttggg   23520
tcacacgtct tctgatacgt cttcgattat gaattcggct attgaggctg tgactggtac   23580
gtcgtatgcg ttgggggatg cggcgtctac ggcggcggcg ttgtctgctt cgggtgtgaa   23640
gtctggcggt cagatgacgg atgtgttgaa gactgtcgcg gatgtgtctt atatttcggg   23700
taagtcgttt caggatacgg gcgctatttt tacgtctgtg atggctcgcg gtaagttgca   23760
gggcgatgac atgttgcagc ttacgatggc tggtgttcct gtgctgtctt tgcttgccag   23820
gcagacgggt aaaacctcgg ctgaggtttc gcagatggtg tcgaaggggc agattgattt   23880
tgccacgttt gcggctgcga tgaagcttgg catgggtggt gctgcgcagg cgtctggtaa   23940
gacgtttgag ggcgctatga agaatgttaa gggcgctttg ggctatttgg gtgctacggc   24000
tatggcgccg tttcttaacg gcctgcggca gattttgtt gcgttgaatc cggttattaa   24060
gtctatcacg gattctgtga agccgatgtt tgctgccgtc gatgctggta ccagcggat   24120 gatgccgtct attttggcgt ggattaaccg tatgccggct atgatcacga gaatgaatgc   24180
acagatgcgc gccaaggtgg agcagttgaa gggcattttt gcgagaatgc atttgcctgt   24240
tcctaaagtg aatttgggtg ccatgtttgc tggcggcacc gcagtgtttg gtattgttgc   24300
tgcgggtgtg gggaagcttg ttgcagggtt tgctccgttg gcggttgcgt tgaagaatct   24360
gttgccgtcg tttggtgctt tgaggggtgc cgccggggggg cttggtggcg tgtttcgcgc   24420
cctgggtggc cctgtcggga ttgtgatcgg cttgtttgcg gcaatgtttg ccacgaacg   24480 ccagttccgt gccgctgtta tgcagctggt ggctgtggtt ggtcaggcgt tgggccagat   24540
tatggcagct gtgcagccgc tgtttggttt ggttgctggc gtggttgcca ggttggcgcc   24600
ggtgttcggc cagattatcg gtatggttgc tggtttggct gccggctgg tgcctgttat   24660 tggtatgctt attgcccggc tggttcctgt tatcacccag attattggta tggtaacccca   24720 ggttgctgcc atgttgttgc ctatgctgat gccggttatt caggctgttg ttgctgtgat   24780
acggcaggtt attggtgtca ttatgcagtt gataacctgtt ttgatgccgg ttgtgcagca   24840
gattttgggt gctgtcatgt ctgttttgcc gccgattgtt ggtttgatac ggtcgctgat   24900
accggtgatc atgtcgatta tgcgtgtggt ggtgcaggtt gttggtgctg tgctacaggt   24960
ggtggcccgt attattccgg ttgttatgcc gatttatgtt tcggtgattg gattcattgc   25020
caagatttat gctgcggtta tcgttttttga ggctaaggtt attggcgcta ttcttcgtac   25080
tattacgtgg attgtgaatc attcagtgtc tggcgtgagg tctatgggca cggccatcca   25140
gaatggctgg aatcatatta aatcgtttac gtctgcgttt attaacggtt ttaagtcgat   25200
catttctggc ggcgtgaacg cggttgtggg gtttttttacg cggcttggtt tgtcggttgc   25260
ttcccatgtg aggtccggtt taacgctgc gaggggtgct gtttcttccg ccatgaatgc   25320
tattcggagt gttgtgtctt cggtggcgtc tgctgttggc gggttttca gttcgatggc   25380 gtctcgtgtt cggaatggtg ctgtgcgcgg gtttaatggt gcccggagtg cggcttcttc   25440
tgctatgcat gctatggggt ccgctgtgtc tagtggtgtg catggtgtgc tgggttttttt   25500 ccggaatttg cctgacaata ttcggcgtgc gcttggtaat atggggtccc tgttggtgtc   25560
ggctggccgt gatgtggtgt ccggtttagg taatggtatc aagaatgctt tgagtggcct   25620
gttggatacg gtgcgtaata tgggttctca ggttgctaat gcggcgaagt cggtgttggg   25680
tattcattcc ccgtctcggg tgtttcgtga cgaggttggc cggcaggttg ttgccggttt   25740
ggctgagggt attactggta atgctggttt ggcgttggat gcgatgtcgg gtgtggctgg   25800
gaggctgcct gatgcggttg atgcccggtt tggtgtgcga tcgtctgtgg gttcgtttac   25860
```

```
cccgtatggc aggtatcagc gcatgaatga taagagtgtt gtggtgaatg tgaatgggcc  25920
tacttatggg gatcctgccg agtttgcgaa gcggattgag cggcagcagc gtgacgcttc  25980
gaacgcgttg gcttacgtgt gattttgggg gtgtggtgca tgtttattcc tgacccgtct  26040
gatcgttctg gtttgactgt gacttggtct atgttgccgt tgattggtaa tgatccggag  26100
cgtgtgcttc atttgacgga ttatacgggg tcgtctccga taatgttgtt gaatgattcg  26160
ttgcgcggtt tgggtgttcc tgaggtggag cattttctc aaactcatgt tggggtgcat  26220
ggctcggagt ggcgcgggtt taatgtgaag cctcgcgagg tgacgctacc ggtgttggtg  26280
tcgggtgttg gcccggatcc ggtgggcggt tttcgtgacg ttttttgaa ggcgtatgac  26340
gagttgtggt ctgcttttcc tcctggcgag gtgggggagt tgtctgtgaa gactcctgcc  26400
ggtcgtgagc gtgtgttgaa gtgccggttt gattcggtgg atgacacgtt tacggtggat  26460
ccggtgaaca ggggttatgc gcgttatctg ttgcatttga cggcttatga cccgttttgg  26520
tatgggatg agcagaagtt tcgtttcagt aacgctaagt tgcaggattg gttgggtggc  26580
ggccctgtcg acggtaaggg taccgcgttt ccggtggtgt tgacgcctgg tgttggttcg  26640
ggttgggata atctgtctaa taagggtgat gtgcctgcgt ggcctgtgat tcgtgttgag  26700
gggccgttgt cgtcgtggtc tgtgcagatt gatggtttgc gtgtgtcctc ggattggccg  26760
gtggaggagt atgattggat cactattgat acggatcctc gtaagcagtc tgcgttgttg  26820
gacgggtttg aggatgtgat ggatcgtttg aaggagtggg agtttgcgcc tatcccgcct  26880
ggcggttctc ggagtgtgaa tattgagatg gttggtttgg gtgccattgt tgtgtcggtg  26940
cagtacaggt ttttgagggc ttggtgaata gttgatggct ggttttgttc cgcatgtaac  27000
attgtttaca ccggattatc gccgtgtggc gcctatcaat tttttgagt cgttgaagtt  27060
gtcgttgaag tggaatggtt tgtccacttt ggagttggtg gtgtctggtg atcattctag  27120
gcttgacggg ttgactaggc cgggtgcgcg gcttgtggtt gattatgctg gtggccagat  27180
tttttctggg cctgtgcgtc gggtgcatgg tgtgggtccg tggcgttctt cgcgtgtgac  27240
tatcacgtgt gaggatgata ttcgtctgtt gtggcgtatg ttgatgtggc ctgtgaatta  27300
tcgtcctggt atggttggta tggagtggcg tgcggatcgg gattatgccc attattcggg  27360
tgcggcggag tcgtggccta agcgggtgtt ggggataat gcttggcgtt ttccgtctgg  27420
tttgtttatg aacgatgatg agagtcgtgg ccgctatatt aaggattttc aggtgcggtt  27480
tcacgtgttt gccgataagt tgttgccggt gttgtcgtgg gctcggatga ctgtcacggt  27540
gaaccagttt gagaatgcga agtttgatca gcgtggtttg gtgtttgatt gtgtgcctgc  27600
tgtgacccgg aaacatgtgt tgactgccga gtcgggttcg attgtgtcgt gggagtatgt  27660
gcgtgacgcc ccgaaggcga catctgtggt ggttggtggc cgtggcgagg gtaaggatcg  27720
gctgtttttgt gaggatgttg attcggcggc cgaggatgat tggtttgatc gtgtcgaggt  27780
gtttaaggat gcccgtaaca cggattccga gaaggtgtct ctcttcgatg aggctgagcg  27840
ggtgttgtcc gagtcggggg ctacgtcggg gtttaagatt gagttggctg agtcggatgt  27900
gttgcggttt ggtcccggca atctgatgcc tggggatttg atctatgtgg atgtgggttc  27960
tgggcctatt gcggagattg tgcggcagat tgatgtggag tgtgtatcgc ctggtgatgg  28020
ttggacgaag gtgactccgg ttgcgggga ttatgaggat aatccgtcgg ccctgttggc  28080
tcgccgtgtg gctggtttgg ctgcgggtgt gcgggatttg caaaagtttt agtaagtgat  28140
tggggtttgt tgtgggtatt gtgtgtaaag ggtttgatgg tgtgttgacc gagtatgatt  28200
```

```
gggctcaaat gtctggtctg atgggtaata tgccgtctgt gaaggggcct gacgattttc    28260
gtgtcggcac gacgattcag ggttctacgg tgttgtgtga gatcctgccg gggcaggctt    28320
gggctcacgg ggtgatgtgc acgtcgaata tgttgagac ggtgacgggt cagcttccgg    28380
gcccgggtga gactcgatac gactatgtgg tgttgtctcg ggattggcag gagaatacgg    28440
ccaagttgga gattgttccc ggtgggcgtg cggagcgtgc cagggatgtg ttgagggctg    28500
agcctggcgt gtttcatcag cagctactgg cgactttggt gttgtcgtct aacgggttgc    28560
agcagcagtt ggataggcgt gctgtggcgg ctagggttgc gtttggggag tctgctgcgt    28620
gtgatcctac ccctgtggag ggtgaccgtg tgatggttcc ttcggggct gtgtgggcta    28680 accatgccgg cgagtggatg ttgttgtctc ccaggattga gacgggttcg aagtcgatca    28740
tgtttggtgg ttctgctgtg tatgcttaca cgatcccgtt tgagcgccag ttcagtagtc    28800
cgcctgttgt ggtggcgtct atggctacgg cggctggggg cacggcacag attgatgtga    28860
aagcctacaa tgtgactgcc caaaatttta gtttggcgtt tattacgaat gatggttcga    28920
agccgaatgg tgtgcctgcg gtggcgaatt ggattgctgt cggcgtgtga ctgcacgggt    28980
gttgtggcgg atggtgtgat gttgggggc tgtggtgtcg tggtttactc ctgcactggt    29040
ggcctctatt tgtaccgcgt tggccacggt tttgggttct gttcaggctg tcacatcccg    29100
gtctaggaag cgtttacgca ggctgtcggc tcaggtggat gcgatggaag agtatacgtg    29160
gggtgtgcgg cgcgaggtgc gaaggtttaa cgccgggctt cctgatgatg tggagccgat    29220
gcatcttcct gatttgcccg agtttttgaa agatactgtt gatggtggag gtgagtaggg    29280
ttgagggagt tggaggagga gaagcggcag cgccgcaatt ttgagaaggc ttcactggtg    29340
ttgttgtttt tgtcgcttgt gttgttggcg gtggttgctg cgggtgcttt gcgtttcggg    29400
gctgtatcct ctgagcggga ttcggagcag gcgagggccc agtcgaatgg tacgctgcc    29460 aggggtttgg ctgcccgtgt gaagcaggcg tgtgcttcgg gtggggtgga gtctgtgcgt    29520
cttcaccgtt ctggtttgtg tgtggatgct gtgcgtgttg agcagcgtgt tcagggtgtg    29580
ccgggtcctg ccggtgagcg cggcccgcaa ggcccttcag gtcctgccgg ccgggatggt    29640
gttaatggtt cggctgggct ggttggcct gttggtccgc aaggttctcc gggttttgaat    29700 ggtgtgaaag gtcctgacgg cttgcctggc gctaacggtt cggatggccg tgatggtgtt    29760
ccaggtcg                                                           29768
```

<210> SEQ ID NO 69
<211> LENGTH: 29238
<212> TYPE: DNA
<213> ORGANISM: Artificial Sequence
<220> FEATURE:
<223> OTHER INFORMATION: PAC1

<400> SEQUENCE: 69

```
tagcgtacag ggtgtgccag gtcccgccgg tgagcgcggc ccgcaagggc cggctggtgc      60
tgatggtcgg gatggtgtta atggttcgac tgggctggtt ggccctgtgg gtccgcaggg     120
ttctcctggc ttgaatggtg tggctggccc ggacgggttg cctggtgcga acggatcgga     180
tggccatgat ggtgttccag gtcgtgcagg tgctgacggt gtgaacggcg ctgatggtcg     240
ggatggttcg gccggtgagc gcggtgatgt gggcccttca ggtcctgccg gcccgcaagg     300
tgcacagggt gaacgggtc ctattgggcc tcagggtccg cagggttctg ccggtgctga     360
cggcacgaat ggtaaagacg gtaaagatgg gcgctcggtt gtgtctgtgt actgttccga     420
gggccgcctg gttgtgaaat atagtgacgg tgtggcttct acaatatcga gctcggtggc     480
```

```
ctgccagggt gtgaaaccgt cgcctatagt gactatatca tcccacaagt aaaaaagaaa    540
agggaagggt gttactagtg ttgattgtgg tgttaggtgg tgtgtggtga gatacattcc    600
tgcggcgcat cattctgccg gctcgaatag tccggtgaat agggttgtga ttcatgcgac    660
gtgcccggat gtggggtttc cgtctgcctc gcgtaaaggg cgggcggtgt ctacagcaaa    720
ctatttcgcg tccccatcgt cgggtggttc ggcgcattat gtttgcgata ttagtgagac    780
ggtgcagtgc ttgtcggagt ctacgattgg gtggcatgcc cgccgaatc cgcatagttt    840
gggtatcgag atttgcgcgg atgggggttc gcacgcctcg ttccgtgtgc cggggcatgc    900
ttacactcgg gagcagtggc ttgatcctag ggtgtggcct gcggtggaga aggctgccat    960
cctgtgtaga cgtttgtgtg acaaatataa tgttccgaag aggaagctta gtgcagccga   1020
tttgaaggct ggtaggcggg gcatctgcgg gcatactgat gtgacggatg cgtggcacca   1080
gtcggatcat gacgatcctg ggccgtggtt ccgtgggac aggtttatgg ccgtcgtcaa    1140
cggcaaagat gagagtgggg agttaacggt ggctgatgtg aaagccttgc atgatcagat   1200
taaacaattg tctgcccagc ttactggttc ggtgaataag ctgcaccatg atgttggtgt   1260
ggttcaggtt cagaatggtg atttgggtaa gcgtgttgac gccttgtcgt gggtgaagaa   1320
tccggtgacg gggaagctgt ggcgcacaaa ggatgctttg tggagtgtct ggtattacgt   1380
gctggagtgt cgcagccgca tcagtaggct ggagtctact gtcaacgatt taaagaagtg   1440
atctatggtg ggtaaacagt tttggttggg cttgtttgag cgtgccctga aaactttat    1500
tcaaacgttt gttgctgtgt tgggtgtgac tgcgggtgtc acttatactg cggagtcgtt   1560
tcgcggttg ccgtgggagt ctgctctgat tacgccggg gttgctgcaa tactgtcggt     1620
tgctacctcg tttggtagcc cgtcgtttgt ggctggcaaa cctaaaacta cggttgtgga   1680
tgcgggtttg gttccaccgg atgatggggg cttggttgag ccgcacatgg tggatgtgtc   1740
ggatcctggc atgatcgagc ctgcagatga tgcggatctt ggtgtaggct atgtgccgaa   1800
acacgctgcc gagtcggagg ttggcacggt agagtctact gttgcataat tgaatatgtg   1860
tgtgccccag cggtgctgcc acgatcgtgt ggtggttgcc gctggggcac tattttgta    1920
tattgcggtg tggctatgat tcgttgctgt cgatggtgtc ttcgagcatc tgatacaggt   1980
ggaggcaggt agagatagtt tcgctggcct ggtctagaac gttccggccg ataacatttt   2040
tgtgattgtc gcggtggcgg atgatagccc acatgatctc gtcggctgcc gcttgcaata   2100
gttttgactg gtatgcgatt ccggcgagcc agtctatggc ttccgggctt gccggtgtgt   2160
cgtctggaat gccacaggtg ttgctgttgt ttgtgggta tcctgcactg tcgcaaaacc    2220
acaggatttc gctgcactcg tctagcgtgt cctggtcgat agcaagatcg tcgaggctga   2280
cttcgttgac ggtaaggttc acgttgtcga gggagatggg tacaccgtac tggttttcga   2340
cactgtcaac aatgttttcc agctgttgca tgttggtggg ctgttgttgg acgatacggt   2400
gtatcgctgt gttgagggtg gtgtaggtga tattgtgtgt gttgttcatg gtttattcc    2460
atctctgtgc tgtcgtcttg gtcgtatcga ctgtttgcgt agcctgtgag ggtgatgagt   2520
gtttggtctg cccattgttt cactgtttgc cgggtgacac ccaatcgttg ggcggctgtg   2580
gcgtaggttt ggtcgtatcc gtatacttct cggaatgctg ccagccgtgc taaatgtttt   2640
cgctgttttgg atggctggca ggtgagggtg tagtcgtcga tggctagctg tagatcgatc   2700
atggcgacaa tgttgttgcc gtggtgttgt ggcgcggttg gtgggggtgg cattcccggc   2760
tccacggagg gtttccatgg gccgccgttc caaatccatt gggcggcctg aataatatct   2820
```

```
gcggtggtgt aggtcctgtt catgtgtcat ccccctgaaca ggttgtcgaa gtcgtctgtg    2880
ttgctggtgt tggtggtatc gaatcgtccg acgcagtggc agtagtcgta catgagtttg    2940
ataatgtgtt ggtggtctcc caaataggtg ttgccgctga tgctgtaggt ggctgtgccg    3000
tctttgctga tggtgtattt ggcggtgatg gtttcgtggg tttctgtgtt tgtgatgatg    3060
gctgtggtgg tggcgcctac ggtttgtagc ctggtggttt gggttccgtc gtcgagggtg    3120
gtagtaacca tagttggggt tctccttaaa tactggtttg gttgtcggct agatgaataa    3180
tatcggataa aggtttcggc tggtctaggt gttgtatggt tttgttggcg agccgtttgg    3240
ctaccctgta gcacattttg atgtagtgtt tgttgtctag gttgtggtat tgttcccgta    3300
ccgcaatata tagtagggag tcttggtaca ggtcgtctgc gttgattgcg gggtagtgtg    3360
tggctatttt tgtgcatgcc cggttgagtg tgcgtagatg atggtctgtg gcccatcccc    3420
acgatgctgt ggtggccagg tctgatttgg tgggtcgtct gctcatggcg ctatttcatc    3480
tcgctatctg atagttgttt ggtgttttgt tgttgatagt gtagcacact agtccgggat    3540
ggccggtggt gcctgtgcgg tgccggaacc atgtggattc tccttccatg gatgggcatt    3600
ggatgaaggt gcgttgtcct tgctcggaga tttctaggtg gtgccggtgc ccggccatga    3660
gaatattaga tgtggtgccg ttgtggaatt cttggccgcg ccaccattcg tattgtttgc    3720
cggttttcca ttggtgcccg tgtgcgtgca ggatttgtgt gccggctact tcgacggtgg    3780
tggtcatttc gtcccgtgcg gggaagtgga agtgaaggtt gggatattgg ttgtcgagct    3840
ggtaggcttc tgcgatggcg cggcagcagt ccacgtcgaa ggagtcatcg taggtggtga    3900
cgcctttacc gaaacgcacg gcttcaccgt ggttgccggg gatggatgtg atggtcacat    3960
ttttgcagtg gtcgaacatg tggacgagtt gcatcatggc catgcgagtc aaccggattt    4020
gttccgtcaa gggtgtttgt gtgcgccagg cgttgttgcc tccttgtgac acgtatcctt    4080
cgatcatgtc gccgaggaat gcgatgtgga ctcgttgcgg ctgtccggct tgctgccagt    4140
agtgttttgc gactatgagg gagtgcaaat agtcgtctgc gaagtgtgat gtttccccgc    4200
cggggatgcc tttgccgatt tgaaagtctc ccgcccctac cacgaacgca acattgctgt    4260
agtcggtgtg tgtgtcttgg ttgggttttgg ggggtgtcca ttcggctagt ttatcgacga    4320
gttcgtcgac cggatagggg tcggttgcgg gttggtggtc gatgattttt tgtatggatc    4380
ggccggtttc tccgttgggg agtgtccatt cggagatgcg tgtgcgccgt acggtgccgt    4440
ttgcgagatc atcgcggatg gtgtctgctt cgttgtcgtg gttggctagc tgtgtgagga    4500
gccggtctat attgtctatc atcgggtatc ctcctcttgt ggggtggtgt tggcttgttt    4560
gcggcgatag tcttttataa cggtggcgga gatggggtat cctgcctggg tgagctgttt    4620
tgctagccat gaggcgggga tagacctgtc ggcgaggacg tcggcggctt tagcccccgta    4680 gcgttgaata aggtttcag ttttggttgc catgatgtcc taggggttgt gtggtgggct    4740
gccatcctgt gcggcagtcg ccgtcgtgtc ctggtttgcg ggtgcaccac gatacggttc    4800
cgtctgtgtg gttgagtgtt ttaccgcaca tgacgtcacg taggtgctcg ggaaactcat    4860
cgttgttgtt gtccccgtgc atgtcgatca agtgttgggt tttagtaacc atcatgcctc    4920
ctatgtgtga aagagtgtgc aaatactatg caggtgtcat ggatgtttat gcgggtatgg    4980
ttttcatcac cttgctgaac gttacttggt tactgtacat catctgagtg atttcctgat    5040
cagtcttatc ggggtgctgc tttcgcaggt tcgcccactg gcaggcgttg tcggtctcct    5100
gctgtaaacg tgtcaggtgc tgctcgttga tgatgtgttt ccacattgtc catgacacgt    5160
cgagcctgcg gagcatgttc atggctggca cgttgaagga gttgaggaag agtatttctt    5220
```

```
cggtgtagta ctgtttttcg tattggtccc atccgcttcg gtgcctgttg ggctggtttt    5280
tggggtaggc ttcccggcag attttgtgta accgtttggc catgtcgtcg ggtagtttaa    5340
tgtcggggtt ggcgcggatc atggatcgca tcccgtcata ggtggtgccc caggtgtgca    5400
tgatgtggag tgggtcttca ccatcggccc attttcggc gatgatggcg aggcggatgc     5460
gcctcctggc ggctttactg tgttgcgcc ggtgggggat ggggcatgtg tcgaggggat     5520
ccatgatatt ttagtgtacc tttccgtgtt gtggttgttt gtctggtttt attgtagcac    5580
tgtgttgagg gcttgtgtca accctgtttt gccggttttc aggtatgtgt ctgtgacatc    5640
ccccagggtg aggggcacgt gggtggcttg ggggagtgct gcctggaggg tttgggccat    5700
ctggtggcct gcctggtctg ggtcggacca gatgtagatg tggtcgtagc cttcgaagaa    5760
tttggtccag aaggtttgcc acgaggttgc gccgggtagg gcgacggctg gccatccgca    5820
ttgttcgagg atcatggagt cgaattcgcc ttcgcaaatg tgcatttcgg ctgccggggt    5880
ggccatggcg gccatgttgt agatggagcc tgtgtctcct gccggggtga ggtatttggg    5940
gtggttgtgg gttttgcagt cgtgtgggag tgagcagcgg aaacgcattt ttcgtatttc    6000
ggctggccgc ccccaaactg ggtacatgta tgggatggtg atgcactggt tgtagttttc    6060
gtggcctggt atggggtcat tgttgatgta tccaaggtgg tggtagcgag ctgtttcttc    6120
gctgatgcct cttgccgaga ggaggtcgag tatgttttcg aggtgggttt cgtagcgggc    6180
tgaggctttc tggattcggc ggcgttccgc aatgttgtat gggcgtatgc tgtcgtacat    6240
tcgggttttc tttctctaat tgttgttgta gtttggcgag tccgcctccg ataccgcatg    6300
tgtggcagta ccagacgccc ttgtcgaggt tgatgctcat ggagggctgg tggtcgtcgt    6360
ggaacgggca gaggatgtgt tgctcgtttt tggacgggtt gtaccgtatc tggtaggtgt    6420
cgaggaggcg gcaggtgtca gaggtgtggg aggagctcgt tgagggttga taccacatag    6480
gcttcgctcc atggcttgtt gcgctgtttc atcactacga gtccgatggt ggactgactt    6540
tcgcggtttc ggtgggtttc gtagttgcgt gcctcccggc tggcttgttt cacgaattcg    6600
gctaggtggg gctggccggc tttcgcctct atcacatagg ttttgtggcc ggttgtgagg    6660
ataaggtcgc cttcgtcttc acggccgttg aggtggaggc gttctatatc atggccggtg    6720
tcgcgtagtt ggtggaggag tcgtgttttcc cattctgcgc cggccctgcg gtttcttgat    6780
tgttgtgtcg acatgatagt cctttgtgtg ttgtggtcat attccagggc tgttttttcgg   6840 cgaggggccc gaagaaggtg tattcggggt aggctcgtag ccgctcgtat cgggtgccgt    6900
cggggctgga tttgcctgtg cgctgtttga ggacggcgat gcgtgcctct gccgggatcg    6960
atagcccgtt gccgttatcc tcgccaccat acaatgagac tccgaggatg agttgtggtt    7020
tttcggagag gccgttttg atttctcgcc gggcgggcgg gtgttcgatg tcggagccgg     7080
ttttgtcggt tgcgtggtgt gtgacaataa tggtggagcc agtatcgcgg ccgagggctg    7140
tgatccattg catggcttct tgctgggcct gatagtcact ctcgcagtct ggatgtcca     7200 tcaggttgtc gataacgatg atgagtggga aggtgttcca catttccatg taggcttgca    7260
gttccatggt gatatcggtc caggtgatgg gtgactggaa tgagaatgtg atgtgttggc    7320
cgtggtggat gctgtctcga tagtattctg gcccgtaatc gtcgatgttt tgttgtatct    7380
gggcggtggt gtgttgggtg ttgagtgaga tgattcgtgt ggaggcctcc cagggtgtca    7440 tgtccctga tatgtagagg gctggctggt tgagcatcgc tgtgatgaac atggctagcc     7500 ctgattttg gctgccggac cgccccgcga tcatgacgag atcccctttg tggatgtgca     7560
```

```
tatcctggtt gcggtagagg ggttctagtt gtggtatgcg gggcagctcg gctgcggttt    7620
gggaggccct ctcgaaggat cgttggagag agagcatcgg gaccttatct atctatcggt    7680
tacgatttgt atgaatattg gcggttagat ggagtcgatg tctacatcat cactaccagt    7740
ggtgttgggc tgactgtctc gctggtcaac gtaggctgct acaaggtcgt agatggcgtc    7800
gtccaatggt ttgagcacga ccgcgttgaa gccgttttgt gtgcgcacgg tggcgagttt    7860
gaaggcttgc tcttcgccaa ggtaggtttc gaggtcgcgg atcatggagt gtgggcggtc    7920
gttgctgccg cgtacttttt cgatgatggc gttggggatg gtttctgggg tgctgttgtt    7980
gaggtcgtct agggtgtgga agatggtgac atcagcgtag atgcgatcgg cggtctgtcc    8040
accgtagcct tcagtgttgt gctcgacgtc gtggactttg aaggcgatgg cggtggcgtc    8100
ctggtttcgg gaggggttga agaaggtgct gttgctgttg tttcggtagt ttgcgagtcc    8160
cattgttgtt tcctttacta ttttttgttgg tttgtgtcgg tttttatcgg gtgaggctgt    8220
ttcgtttgct gcggaacgcc tcggatacgt cagtgttgct ggtgatgatc ttcttgtact    8280
gtttcagaag gtcggctagc tgtgcttgc ttgttgcatt gttgattttg tcaatgatgg    8340 tgttgttcc ttcactggca atgttgtcta cgtagtcttt gcggcctgg ttgtatcggt    8400 cttgaggat gatggatgcg gaggcgatca gtgttgccag gtcccagttc cttgccgccg    8460
aactgttttt gagtccgcct agcaagtcga tgatagtctt cttacttcg tcggcggtgt    8520 ctccacggat gactgtccat ggggcggcgt agtctccgcc gtatttgagt gtgatggtga    8580
tgcgatcatc agtgctgttg gtgttatcgt tcactggtgc tccttgcttt cttctgttgg    8640
ggctgtgatg gtggtttctg tagggtacct gtaggcgtct ttcccgttga cggcccagca    8700
ggcgtccttg acgggcatc ctttgcagag tgctgtgacg tggggtacga agatgccttg    8760
actgattcct ttcattgctt gactgtacat ggatgataca tgccggtagg tgttgttgtc    8820
aaggtcgtac agttcggtgg atgtgccttg tgtcggggac ttgtcgtcgt tgcggctggt    8880
ggcgggtgtc caaaacatgc cttttcgtcac atgaatgtcg tgttgggcga gcatgtaccg    8940
gtatgtgtgc agctgcatac tgtcggcggg taggcggccg gttttgaggt cgaggatgaa    9000
ggtttcgccg gtgtcggtat ctgtgaaaac acggtcgatg tagccgacaa tctgggtgcc    9060
gtcggggagg gtggtttcta ccgggtattc gatgcctggc tggccgtcaa taacagcggt    9120
gatgtattct gggtggttgc gcctccatgt tttccagcgg tctacaaagg tggggccgta    9180
aaccatccac cagtcgtagt ctttttttgtg tggtccgccc gactcgcaca tgttttttgca    9240 tattctgccg gagggtttga tttctgtgcc ttcggattcg cgagggcta cttgggtgtc    9300 gaaaatgttt ttgaaggatg cgagtttgtc tggcagtgca gggtattcgg cgggattgta    9360
caggtgtagg tcgtattgtt cggtgatgtg atgtatggcg cttccggcga tggtggcgta    9420
ccaggtgtgg tgttgggcgt ggtagccgtg ggataggcgc cattttctc cgcattcggc    9480 ccactgggtg agtgaactgt aggagatgtg gcctggatgg ttgatggttt tcggatattg    9540
tgctaggggc attactggtc gcctttgtgt gtgttccatg ggttgcgggt gtcttggccg    9600
gcgtggtgtt gctggtaggc gaggagtgcg aggcagtgcc aggcagcatg ggctagatgg    9660
ggtagcccgg attcataatc gaggttgttg ccttgctgcc atgatagtag gtgcctgtag    9720
agggcgtcga cgctgtggct ccacgggtag ccgccggtcc agttgttgtc gccgtatttg    9780
gtggcaccgt agcctgccac ggagccgagg gcgtgcaagg ctgtagggtc gatgagggat    9840
agcctgcaaa gtttcaattc tttttttggca ccgctgttgg ggtcggtgta catgcgggtt    9900
ggcttatcca tggggtgtg ctccttaggg gtgggttact ggttggggtt gtgggcgagt    9960
```

```
gctacggcga gaataatgat ggcgagggtt tcagcaataa gtatgggtgt tgtgatcatt    10020
tgctgtctcg gggattgttg gtgagtgtgg aggcgcctag gagggtggcg agggcgcatg    10080
cggcaataat ggcgagggct gccttgtgtg gggtgccggt tgcgtacatc catgtgatga    10140
tggcgccttg gatccaggcg aggctggtga agaacgtttc gtagctgtgt agctcaatgt    10200
tgttgggtgt gttcatgctt gctcctgaag aatggtgttg atggttttat aaatgttgta    10260
caggtcggtt tcgatagata acagttggtg gatttcgtgg tcgagatcaa tgtctgggtt    10320
gagggtgttg atgcgggagg caatatcggt ggctgtgcgt agtgtgccgc cggtgtggtg    10380
aataatgtgt gccgtgtcgg cgagtccggt ggtgacagcg tagtgggaga ggagaggcat    10440 agctggggt gctccttggc gggttactgt tgcgggttga tgttgaggtc ggtgacgtgc     10500
ggtgagcttt ctgttccggt gacgaggcag tggacggtga cgggtagttt ggatgctccc    10560
ggctggcgta cggtggcgcc gtaggcgatg gagaaggtgt ctttgccaat aattttgtgg    10620
agttggaggt cgatgtcggg gttgccgttc catttgacac cgtgtgcggc ggcctgttgt    10680
tcggctttgc ggttgcaggt gtgtgctgcc gtgatcatgg tgagtccggt ggcggtttct    10740
tccccccttg cttgggcttg ccggtggttt ttggcctgct cggctcgcag tgactgttct    10800
gcggctgcct ggcgggcttt cttttcggct ttgcgctgtt ggacggtttt gggggtccac    10860
gcggtgttgg ctgtggtggc ctgtggggct ggctgtgagg caagtggcgg attgtcgtct    10920
ggggctggca tgaatgaggc ggcggcaatg atggcgactg tggcgccggc gatggtgtag    10980
ccttttttct tgttcatgac tgttgtcccc tttccggggt gttgttcgtt gctgacatga    11040
tcaatacttc cagcgaatga acctcgtgtc aaggctgcgc tcaacgattg tgagcgattc    11100
gtgtgtggct aggggtttta tcggctgtac agggtgagga ggtggcctac gttgatgcgg    11160
gtcacattcc agtagagttg cgtggcttca ccccggtga gtggcttcca ctcgttgtgg    11220
ctgaacacgg tgccgtcggt ggcgatgaat gtgttgggc gtagcttgtg gagttcggct    11280
tccacgctct gccggtaggc ttcggcgagg ccctcaaaat ccatgtggtc gcaggagagg    11340
ttttcgaggc gtgtcaggtc gaagggtgtg ggacagtcgt agctggcggg gctgtagagc    11400
tgggtgaagt ggttggcgat cttctgcatc atgattcctt ttctggtgat ggtgtgttga    11460
tggttttatc gtgtggcttc ggcgatgatg gcgtccacat cgattgtgtc gatcatgtcg    11520
tggagttcct cagcctcatc gcggtgagt ggctgccagt cctggggtcc gtatatggca    11580
ccgtcgaggg tgacagtcca caggggccgg atgagtcgta cggcttcttc gactttggca    11640
cggtgcaggc ggcagatgat agacgtgtgg gtgttgccta tgtcacatcc tgccaggtgt    11700
gtggggtgga gtgggttgat ttctgtctgc ccgtagaggt tggtgaagga tggtgtgatg    11760
agtgtgccat ccatgagggt gtgctccttt cggtggtgta tgggttgttg tggtttctag    11820
agtgtgtagg ttgcgatccc atagtcaagg ctgcactcat tcggattgag cgtttcatgg    11880
gatgtggcag gggatgtggc gtatctcact taagccttta tggcctctct cagtgcctca    11940
aatcctctga gggtaggatt atgcagggtt gaccctgctg atcgattcta ggggccttct    12000
agggcgtctc aggggtatgt ctgggttatg gcgggtgtgg cagatgatct agcgagtcaa    12060
ggtgccgagc tgagacataa gatctatcat ctaggtgtgt gagatgcatc acatcctcct    12120
ggcgtggtgt acaccttaa ggctactcgg tcgatctggc gtggagggtg tagtaaagaa    12180
atgccgttta aagccttcgc acggcgccta ggagcgcctt acggggtggg gctaggtat    12240 ttataccccc agcacattct gatcgattct agacgcctcc aggatcctga tacacgatca    12300
```

```
gctatccaga cgcagatcac cagtccctat cctggttagc taagcctcaa ctatgtggac    12360
agtgtgggat actgtggggg aagaaggaca cggtaaaaag aagaggggggg agcatcagcc    12420 ttcacacctt caagccttaa ggttttagcg cttagcaccg atggtcttag cagttagcac    12480
cgagccccct cacgggctcg gcatcagccc gaacaggcac agccctgaaa ggagtacacg    12540
ccatcaggga aggcttgaga gtacgaggag ccctagcgac gagtactcga aagcctgagg    12600
gaacaccctc agcactgatg ggcctagcgt gttcggaaag gacacaagag tgaagtgtga    12660
cagctatccg ggagtgaaac ccgttctgac taggggtttc agccttaacc acctgtaaag    12720
gttacaagac tctaagaaaa tttaaggaaa agtttaggtt taattttgg acctttacta     12780 ccaaaaacac ccgtttacac ccctcaaacc cgcctataga gccaaatcca ccagtttgac    12840
tcatcccagg tggggtatga taggctggac aggtagccag ctggacgcaa ggccgaaatc    12900
cgctgacgcg gctttcaccc ttacatccat cagtctacca aagacttaaa gacctaaggg    12960
cttagcgcta aggtgctgat agcttagcac cgagcccctc aagggctcgg catcagtctt    13020
aaagctttaa acactttaag taaacttaag agcttagcac ttaaagttaa ttaataacct    13080
taaaggctta cacacttagc actgagccct ttaaggctca gcatcagtat aaagatctta    13140
acacctaagt taagtataaa accttaaagg cttagcactt aaggatataa acttaacatc    13200
agtgtttaag actttaaaac ttaaaataac tattaagact aaagacttaa taagctttaa    13260
acacttaaag taactataag actttaaaga ccttaagtat ttaaagttaa ccatcagtct    13320
taaactttaa tattataacc tataagtctt aaagcttata ggtataataa tataatataa    13380
gttataaaag ttttagaaga gctaaggggt taacttcttt acttctctac tctctttggt    13440
actttctctc ttctcttctt ttcttcatca ggggagaaga ggaacccttta accgtcaacg    13500 ctgatggact tttcaccgtg tgactcgtgt gcttctggtc gcacgctccc atcgcacact    13560
ccccacactc tgacacccgt gccccttttca ggcttgacgt gttcggctga aggcgtacgg    13620
cgtgtcacgc ttaaacccctt aacaccaggt aagacttaaa gtgtatatta taagtagaag    13680
actttaaaac cttaaggtgt tcccgcttag cctgtgtcct ttagcgctag gcgccaagcg    13740
ctaagctgtg aaacgcgaac acccatccac cccccattttt cttccgtgtc cttcttcttt    13800
tgacaccgct gggggggcgat gtgatatttc tcacatgcca gggggtagtg gagaaaacaa    13860 acacccccggc acaaacagaa cacccccctca aacgaacaaa acaccccccca gaatcgatca    13920 gcagggcaag ggcaaggtat tcataccccc aacacctttc aggccgttac aggagcaatg    13980
agaggctcac aggggcaagg ggagatcagg ggacgcgatg gcacacacca accgcaccgc    14040
atcatcagcc caccggcgtt ggcggcaacg actcatcacc caagcccaac aacaaggcca    14100
aaccgaatgc ccactctgcg gagcccagat agcctgggac acccatgacc taccaaccag    14160
ccccgaagcc gaccacatca cacccgtcag cagaggagga ctcaacaccc tcgacaacgg    14220
gcaaatcatc tgcagaacat gcaacagaag caaaggcaat cgcagcgaac caaacatcaa    14280
attccaacaa caaaccacaa aaacattgat tccatggtga aaaacctgtc aaccccccacc    14340 ggggacaccc cctgcacagg cgtgcaagac ctcgtacggc ttagtgaaat acctcccttt    14400
tgtggatttg tctgttttgtc gacttttttgt gttggtggtg agtgttgtgc agcctgagct    14460
tcctgatggt cgtgattggt gtggggagac gcgtcgttgg tggcgtgtgt ggggtgagga    14520
ttcgcgtgcc gggttggtgt ctgatgagga gtggctgttt ctcatggatg ctgcggtgat    14580
tcatgatgtg gtgtggcgtg agggtcgcgc ggatttggtg gcttcgcttc gtgctcatgt    14640
gaaggcgttt atgggcatgc tggaggctca ttctggggat gctggcacta ctgtgggtgg    14700
```

```
tgggggttct gcggtggcga tgattgaccg gtataggaag cgcaaggggg cctgattagg    14760
tgtctggtgt tgtgggttct caggttcctc gtcaccgtgt ggctgcggcg tatcaggtga    14820
ctgccggcaa tgatgctggt gctcttgggg ctgcgtatgg gttgactccg gatccgtggc    14880
agcagcaggt gttggatgat tggctggctg tcggtggtaa tggcaggctt gctgcgggtg    14940
tgtgtggggt gtttgtgcct cgccagaacg gcaaaaacgc gatccttgag gttgttgagc    15000
tttttaagat ggtggttcag ggtcggcgta ttttgcatac ggctcacgag ttgaagtcgg    15060
ctcgtaaggc gtttatgcgg ttgagatcgt ttttgagaa tgagcgccgc tatccggatt    15120
tggctcgtat ggtgaaggcg attcgggcga cgaatggtca ggagtcgatc attttgcatc    15180
atcctgattg cagtgtgggt ggtaagaagt gtggctgccc tggttggggt tcggttgagt    15240
ttgtggctcg tagccggggt tcggctcgcg ggtttacggt tgatgatttg gtgtgtgatg    15300
aggctcagga gttgtcggat gagcagttgg aggctttgct tcctacggtg tctgcggctc    15360
cttcgggtga tccgcagcag attttccttg gtaccccgcc ggggcctttg gctgatggtt    15420
ctgtggtgtt gcgtttgcgt gggcaggctt tgtcgggtgg taaaaggttt gcgtggacgg    15480
agttttcgat tcctgacgag tctgatccgg atgatgtgtc gcggcagtgg cggaagttgg    15540
cgggtgacac taatccagcc ttgggtaggc gtctgaattt tgggactgtg tcggatgagc    15600
atgaatcgat gtctgctgcc gggttttgctc gggagcggct tggctggtgg gatcgtggcc    15660
agtctgctac gtctgttgtt ccggcggata agtgggctca gtctgctgtg gatgaggcgg    15720
ctctggttgg cggcaaggtg tttggtgtct cgttttctcg ttctggggat cgggttgctt    15780
tggcgggtgc cggccggact gatgctgggg ttcatgttga ggttattgat gggctgtcgg    15840
ggacgattgt tgatggtgtg ggccggttgg ctgactggtt ggcggttcgt tggggtgata    15900
ctgaccggat catggttgcc gggtctggtg cggtgttgtt gcagaaggcg ttgacggatc    15960
gtggtgttcc gggccgtggc gtggtggttg ctgatactgg cacctatgtg gaggcgtgtc    16020
aggcgttttt ggagggtgtg aggtctggga atgtttctca tcctcgtgct gattctcgcc    16080
gtgacatgtt ggatattgct gtgaggtcgg cggttcagaa gaagaagggt tctgcgtggg    16140 gttgggggttc ctcgtttaag gatggttctg aggttccttt ggaggctgtg tctttggcgt    16200
atcttggtgt gaagatggcg aaggctaggc ggcgtgagag gtctggtagg aagcgggtgt    16260
ctgtggtatg aactcggatg agttggcttt gattgagggc atgtacgatc gtatccaaag    16320
gttgtcttcg tggcattgtc gtattgaggg ctactatgag ggttctagcc gggtgcgtga    16380
tttgggggtg gctattcctc cggagttgca gcgtgtgcag acggtggtgt cgtggcctgg    16440
tatagctgtg gatgctttgg aggagcgtct ggattggctt ggctggacta atggtgacgg    16500
ctacggcctg gatggtgtgt atgctgcgaa tcggcttgct acggcgtcgt gtgatgtgca    16560
tttggatgcg ctgattttg gtttgtcgtt tgtggctgtt atccctcagg gggatgggtc    16620
ggtgttggtt cgtccgcagt caccaaagaa ttgtactggc cggttttcgg ctgacgggtc    16680
tcgtttggat gctggccttg tggtgcagca gacgtgtgat cctgaggttg ttgaggcgga    16740
gttgttgctg cctgatgtga ttgttcaggt ggagcggcgt gggtctcgtg agtgggttga    16800
gacgggccgt atcgtgaata gtcttggtgc ggttccgttg gtgccgattg tgaatcgtcg    16860
ccgtacgtct aggattgatg gccgttcgga gatcactcgg tcgattaggg cttacacgga    16920
tgaggctgtg cgcacactgt tgggcagtc tgtgaatcgt gacttctatg cctaccctca    16980
gcgttgggtg actggcgtgt cggctgacga gttttcgcag cctggctggg tcctgtcgat    17040
```

```
ggcttctgtg tgggctgttg ataaggatga tgacggtgac accccgaatg tggggtcgtt    17100
tcctgtgaat tcgcctacac cgtattcaga tcagatgcgg ctgttggcgc agttgactgc    17160
gggtgaggct gcggttcctg aacgctattt cgggtttatc acgtctaacc cacctagtgg    17220
ggaggctttg gctgcggagg agtctcggct tgtgaagcgt gctgaacgca ggcagacgtc    17280
gtttggtcag ggctggttgt cggttggttt cctggctgcc agggcgcttg attcgagtgt    17340
tgatgaggcc gcgttttttcg gtgatgtggg tttgaggtgg cgtgatgctt cgacgccgac    17400
tcgggcggct acggcggatg ctgtgacgaa gcttgttggt gccggtattt tgcccgcgga    17460
ttctcggacg gtgttggaga tgttgggggct tgatgatgtg caggttgagg ctgtgatgcg    17520
gcatcgtgcc gagtcgtcgg atccgttggc tgcgcttgct ggggctatat cgcgtcaaac    17580
taacgaggtt tgataggcga tggcttcggg ggttgcgtcg aggttggctg ctgccgggta    17640
tcagcggcag gcgattcgtt ttgccgggaa gtatgcgggc tattatgccg agttggggcg    17700
tttgtggcat tccgggaaga tgacagatgc gcagtatgtg cgtttgtgtg tggagttgga    17760
gcgtgccggc catgacggtt ccgcggcgct ggcgggcaag ttcgtgtcgg attttcggaa    17820
gcttaacggt gtggatcctg gtttgatcgt gtatgacgag tttgatgctg ccgccgcgtt    17880
ggctaggtcg ttttcgacta tgaagattat gaatagtgac ccgatagggg cgaatgatac    17940
gattgatgct atggcggcgg gtgttaatcg ggctgtcatg aatgctggcc gtgacacggt    18000
tgagtggtct gctggcgcgc agggtaggtc gtggcgcagg gtgactgatg gtgatccgtg    18060
cgcgttttgt gccatgttgg ctacgaggtc ggattatacg accaaagagc gggcgcttac    18120
tactggtcat acgcggcgtc ataagcgtgc cggtaggcgt ccgtttggtt cgaagtatca    18180
tgatcattgt gggtgtacgg tggttgaggt tgttgggcgt tgggagccaa atagggctga    18240
tgccgagtat cagaggacgt atgagaaggc ccgtgagtgg gttgatgatc atggttttgca    18300 gcagtcgcct ggcaatattt tgaaggctat gcgtactgtt ggcggcatga gataaatttga    18360 tgtggtttcc ggttgtgcgc cgccggttat cggtgcacag ggttgtctcc cgcacggggg    18420
tcaacaatgt tgtgttgttt tccgcaagga gtgtaaggtt aggctatggc cgatcagagt    18480
gttgaggaac agaatgtcga caatgatgct gttgagcccg gaaagggtgg agacattgtt    18540
gatgttgtga aggatgggcg ggctgccggc gatgatcatg ccggtgatgt ttccgtgaag    18600
ggtgaggctt ctgggtcttc gggcacggat tggaaggctg aggctcgtaa gtgggagtct    18660
cgtgctaaaa gtaatttcgc cgagttggag aagcttcgta catcgagtga cgattctgga    18720
tctactattg atgagcttcg ccgcaagaat gaggaactcg aagacaggat caacgggttt    18780
gttcttgagg gtgtgaagcg tgaggtggct gccgagtgtg gcctgtcggg tgatgcggtc    18840
gctttcttgc acggtagcga tcgtgaagca ctggtggagt ctgctaaggc tttgaagggt    18900
ttgattgacc atagtagtgg tggcgcgggt gtgcgccgtc ttgcggggag tgccccgtt    18960 gatgatgtta aacgacgtga gggtgtcgcg tttgtggatg ctcttgtcaa taattctagg    19020
agatgatttg tgatggctga cgattttctt tctgcaggga agcttgagct tcctggttct    19080
atgattggtg cggttcgtga ccgtgctatc gattctggtg ttttggcgaa gctttcgccg    19140
gagcagccga ctattttggg ccctgttaag ggtgccgtgt ttagtggtgt tcctcgcgcc    19200
aagattgttg gtgagggtga ggttaagcct tctgcgtctg ttgatgtttc ggcgtttact    19260
gcgcagccta tcaaggttgt gactcagcag cgtgtctcgg acgagtttat gtgggctgat    19320
gctgattacc gtctggtgtg tttgcaggat ctgatttcgc ctgctcttgg cgcttcgatt    19380
ggtcgcgctg ttgatctgat tgctttccac ggtattgatc cggctacggg taagcctgct    19440
```

| | | | |
|---|---|---|---|
| gcggctgtca | agtcttcgct ggataagacg aagaatattg ttgatgcaac cgatagtgct | 19500 |
| acggctgatc | tgattaaggc ggttgggctg attgctggtg ccggtttgca ggttcctaac | 19560 |
| ggggttgctt | tggatccggc gttctcgttt gccctgtcta ctgaggtgta tccgaagggg | 19620 |
| tctccgcttg | ccggccagcc tatgtatcct gccgccgggt tcgccggttt ggataattgg | 19680 |
| cgtggcttga | atgttggtgc ttcttcgact gtttctggcg ccccggagat gtcgcctgcc | 19740 |
| tctggtgtta | aggctattgt tggtgatttc tctcgtgttc attggggttt ccagcgtaac | 19800 |
| ttcccgatcg | agcttatcga gtatggtgac ccggatcaga ctgggcgtga cctgaagggc | 19860 |
| cataatgagg | ttatggttcg cgccgaggcg gtgctatatg tggctatcga gtcgcttgat | 19920 |
| tcgtttgctg | ttgtgaagga aaggctgccc ccgaagccta atcctccggc cgagaactga | 19980 |
| tttattgttg | cggtgatgtg tcaatgtgca ggggtggtg ttgatgggta tcatttgaa | 20040 |
| gcctgaggat | attgagcctt cgccgatat tcctagagag aagcttgagg cgatgattgc | 20100 |
| cgatgtggag | gctgtggctg tcagtgtcgc ccctgtatc gctaaaccgg atttcaaata | 20160 |
| caaggatgcc | gctaaggcta ttctgcgcag ggctttgttg cgctggaatg ataccggggt | 20220 |
| ttctggtcag | gtgcagtatg agtctgcggg tcctttcgct cagactacac ggtctaatac | 20280 |
| tcccacgaat | ttgttgtggc cttctgagat tgccgcgttg aagaagctgt gtagggtga | 20340 |
| tggtggggct | ggtaaagcgt tcactatcac tccaactatt aattgtcgat atgcacattc | 20400 |
| tgaggtgtgt | tccacggtgt ggggtgaggg ttgctcgtgc gggtcgaata ttaacggcta | 20460 |
| cgctggccct | ttgtgggaga tatgatatga ccagttttcc ttatggtgaa acgattgtga | 20520 |
| tgcttcagcc | gactgttcgt gtcgatgatc ttggtgacaa ggtggaagac tggtctaagc | 20580 |
| ctgtcgagac | tgtgttccat aacgtggcca tctatgcttc gttgtcgcag gaggatgagg | 20640 |
| ccgcggggcg | tgactcggat tatgagcatt ggtcgatgct tttcaagcag cctattgtgg | 20700 |
| gtgctgatta | tcgttgcagg tggcgtatcc ggggtgttgt gtgggaggct gacgggtctc | 20760 |
| ctatcgtgtg | gcatcatccg atgtctggct gggatgcggg cacgcaggtt aatgtgaagc | 20820 |
| gcaagaaggg | ctgataggtt gtggctcagg atgtgaatgt gaagctgaac ttgccgggta | 20880 |
| ttcgtgaggt | gttgaagtct tctggggtgc agtctatgtt ggctgagcgt ggcgaaaggg | 20940 |
| ttaggcgtgc | ggcctcggcg aatgttggcg gtaacgcttt cgatagggcc caatacagta | 21000 |
| atggtttgtc | gtcggaggtg caggttcacc gggttgaggc tgtggcgagg attggtacca | 21060 |
| cctataaggg | tggtaaaagg attgaggcga agcatggcac gttggcgagg tcgattgggg | 21120 |
| ctgcgtcgtg | atcgtttacg gtgatccgcg cgtgtgggct aaacgcgtac tcaaggatga | 21180 |
| tggctggctg | tctgatatac catgtaccgg gacagtgccg gatagctttg agggtgacct | 21240 |
| tatttggttg | gctcttgatg gtgcccaca gttgcatgtg cgtgagcagg ttttttttgcg | 21300 |
| cgtgaatgtg | ttttcggata cgccggatcg tgctatgtcg ttggcgcgtc gtgttgaggc | 21360 |
| tgtgctggct | gatggtgtgg acggtgaccc tgtggtgtac tgtaaacggt ctactggccc | 21420 |
| tgatttgctg | gttgacggtg cacgttttga tgtgtattcg ctttttgagc tgatatgtag | 21480 |
| gcctgcggag | tctgaataag cttattgttt ttgttttaat gtaattgttt gatatttaat | 21540 |
| gggggttgtg | atggctgcaa cacgtaaagc gtctaatgtt cgctctgctg ttacgggtga | 21600 |
| cgtttatatt | ggtgccgctc atgctggtga cgctattgat ggtgtgaaga cggttcctga | 21660 |
| cggtcttacc | gctttagggt acctgtctga tgacgggttt aagattaagc ctgagcgtaa | 21720 |
| aacggatgat | ttgaaggctt ggcagaatgc ggatgttgtt cgcacggttg ctactgagtc | 21780 |

```
gtctatcgag atttctttc agctgatcga gtctaagaag gaggttatcg aactgttttg      21840
gcagtcgaag gttactgccg gatccgattc gggttcgttt gatatttctc cgggtgccac      21900
gacgggtgtt cacgccctgt tgatggatat tgtggatggc gatcaggtta ccgttacta      21960
tttccctgag gttgagcttg tcgatcgtga cgagattaag ggtaagaatg gcgaggtgta      22020
cgggtatggt gtgacgttga aggcgtatcc tgcccagatt aataagaagg gtgatgcggt      22080
gtctggtcgg gggtggatga cggctttaaa agctgatact cctccggttc cgccttctcc      22140
gaagcctcag ccggatccga atccgccgtc cgataattga tacacgagtt tgagggattg      22200
ttgatagatg agtgacacag gttacacgtt gaagatcggt gaccgtagtt gggtgttggc      22260
ggatgcggag gagacggctc aggctgttcc tgcccgcgtg tttcgtcgtg cagctaagat      22320
tgcccagtcg ggggagtctg cggatttcgc ccaggttgag gtgatgtttt ctatgttgga      22380
ggctgccgcc ccggctgacg cggtggaggc tctggagggg cttcctatgg ttcgtgttgc      22440
cgagattttc cgccagtgga tggagtgaa gcctgaaggt aagggtgcct ctttggggga      22500
atagtttggc tccacggcct gattgatgag tatcgtgggg ccatcgaata tgattggcgc      22560
acaaggtttg gtgtgtgcat atacgatata ggtggtcctg caatgggtg gggtgaggct      22620
gtccggctgg ctggcgtgtt gtgtaccgat acgtctagcc agttggcggc ccacctgaat      22680
ggttggcagc gcccgtttga gtggtgcgag tgggctgtgt tggacatgct ggatcattac      22740
aggtctgcta atagtgaggg gcagccgag cctgtggcga ggcctacgga tgagcgtagg      22800
gcccggttta cgtctgggca ggtggacgat attttggcgc gtgttcgtgc cggtggcggg      22860
gtgtctcgcg agattaatat tttggggtga atagtgtatg tctggtgaga ttgcttccgc      22920
atatgtgtcg ttgtatacga agatgccggg tttgaaatca gatgttggta aacagctttc      22980
tggggtgatg ccggctgagg gtcagcgttc gggtagcttg tttgctaaag gcatgaagct      23040
ggctttgggt ggcgccgcaa tggtgggcgc cattaatgtt gctaagaagg gcctcaagtc      23100
gatttatgat gtgactattg gtggcggtat tgctcgcgct atggctattg atgaggctca      23160
ggctaagttg actggtttgg gtcatacgtc ttctgatacg tcttcgatta tgaattcggc      23220
tattgaggct gtgactggta cgtcgtatgc gttgggggat gcggcttcta ctgcggcggc      23280
gttgtctgct tcgggtgtga agtctggcgg gcagatgacg gatgtgttga agactgtcgc      23340
cgatgtgtct tatatttcgg gtaagtcgtt tcaggatacg ggcgctattt ttacgtctgt      23400
gatggctcgc ggtaagttgc agggcgatga catgttgcag cttactatgg cgggtgttcc      23460
tgtcctgtct ttgcttgcca ggcagacggg taaaacgtct gctgaggtgt cgcagatggt      23520
gtcgaagggg cagattgatt tgccacgtt tgcggctgcg atgaagcttg gcatgggtgg      23580
tgctgcgcag gcgtctggta agacgtttga gggcgctatg aagaatgtta agggtgccct      23640
gggctatctt ggtgctacgg ctatggcgcc gtttcttaac gggttgcggc agattttgt      23700
tgcgttgaat ccggttatca agtcggtgac ggattctgtg aagccgatgt tgctgccgt      23760
cgatgctggt attcagcgta tgatgccgtc tattttggcg tggattaacc gtatgccggg      23820
catgatcact cgaatgaatg cacagatgcg cgccaaggtg gagcagttga agagtatttt      23880
tgcaaggttg catttgcctg ttcctaaagt gaatttgggt gccatgtttg cgggtggcac      23940
agccgtgttc ggtattgtgg ctgccggtgt ggggaagctt gttgcagggt ttgccccgtt      24000
ggcggtgtcg ttgaagaatc tgttgccgtc gtttggtgct ttgaagggtg ccgctggtgg      24060
gcttggcggc gtgtttcgcg ccctgggtgg ccctgttggt attgtgatcg gcttgtttgc      24120
ggccatgttt gctacgaacg cccagttccg tgccgctgtt atgcagcttg tggctgtggt      24180
```

```
tggccaggcg ttgggccaga ttatggccgc tgtgcagccg ctgttgggtt tggttgctgg   24240
gctggtggca cggttggctc ccgttttggg ccagattgtt ggtttggtgg ctggtttggc   24300
tgcgcagctt gttcctttga ttagtatgct ggttgcccgg ctagttcctg tgatcaccca   24360
gattattggt gcagtgacgc aggtggcggc catgttgttg ccggcgttga tgccggtgct   24420
tcaggcgatt gttgctgtga tacggcaggt tgttggtgtt gtgatgcaac tggtgcctgt   24480
tttgatgcct gtgattcagc agattttggg tgctgtcatg tctgtgctgc cgcctatcat   24540
cggcctgatc cggtcgttga taccagtcat catgtcggtt atgcgtgtgg tggttcaggt   24600
tgttgcggtt gtgatacagg tggtggcccg tattcttgct gttgtggctc cgatggtggc   24660
tgctgtggtg ggttttgttg cccgtattgt tggtgctgtc gtgtcggctg tggcccgtgt   24720
gattgcggct gtgcccgtg tgatcggatg ggttgtggcc cattttgtgt ctggtttggc   24780
acgcatgggt tcggttattc aggctggctg gaatcatatt agagcgttta cgtcggcgtt   24840
tatgagcggt ttcaagtcga tcatttctgg cggcgtgaac gctgttgtgg ggttttttac   24900
gcggcttggt tcttcggttg cttcccatgt gaggtctggt tttaacgcgg ctcgtggcgc   24960
tgtttcttct gcgatgaatg ctatccggag tgttgtgtct tcggtggcgt ctgctgttgg   25020 cgggttttc agttcgatgg cgtctagggt tcgtagtggg gctgtgcgcg ggtttaatgg   25080
tgcccggagt gcggcttctt ctgctatgca tgctatgggg tccgctgtat ctagcggggt   25140
gcatggtgtg ctgggttttt tccggaattt gcctggtaat attcggcgtg cgcttggtaa   25200 tatgggtcc ttgttggtgt ctgcgggccg tgatgtggtg tctggtttgg gtaatggtat   25260
ccggaatgct atgagtggct tgttggatac ggtgcgtaat atgggttctc aggttgcgaa   25320
tgcggcgaag tcgtgttggg gtattcattc accgtctagg gtgtttcgtg accaggttgg   25380
ccggcaggtt gttgccggtt tggctgaggg gatcacaggg aatgctggtt tggcgttgga   25440
tgcgatgtcg ggtgtggctg gaaggctgcc ggatgctgtt gatgcccggt ttggtgtgcg   25500
atcgtctgtg ggctcgttta cccgtacga ccggtatcgg cgtgcgagcg agaagagtgt   25560
tgtggtgaat gtgaatgggc ctacttatgg ggatccgaac gagtttgcga agcggattga   25620
gcggcagcag cgtgacgctt tgaacgcgtt ggcttacatg tgatcgaggg ggtgttgtgc   25680
atgtttattc ctgacccgtc tgatcgttct ggttttgactg ttacctggtc tatgttgccg   25740
ttgattggta atgatccgga gcgtgtgctt catttgacgg attatacggg tgcgtcgcct   25800
gtcatgttgt tgaatgattc gttgcgcggt ttgggtgttc ctgaggttga gcattttttct  25860 caaactcatg ttggggtgca cggctcggag tggcgcgggt ttaatgtgaa gcctcgcgag   25920
gtgacattac ctgtcctggt gtcgggtgtg gatccggatc cggtgggcgg gtttcgtgac   25980
ggtttcatga aagcctatga cgagttgtgg tcggcgtttc ccccggggcgg ggtggggagg  26040 ttgtctgtga agactcctgc tggtcgtgag cgtgtgttga agtgccggtt tgattcggtg   26100
gatgatacgt ttacggttga tccggtgaat cgtggctatg ctcgctatct gttgcatttg   26160
acagcttatg acccgttttg gtatggggat gagcagaggt ttcgttttag taacgcgaag   26220
ttgcaggatt ggttgggtgg cggccctgtc ggtaaggatg gcacggcgtt tcctgtggtg   26280
ttgacgcctg gtgttggttc gggttgggat aatctgtcga ataagggtga gtgcctgcg   26340 tggcctgtga ttcgtgttga ggggccttg gagtcgtggt ctgtgcagat tgatggtttg   26400
cgtgtgtctt cggattatcc tgttgaggag tatgattgga tcactattga tacggatcct   26460
cgtaagcagt ctgcgttgtt ggatgggttt gaggatgtga tggatcgttt gacagagtgg   26520
```

-continued

```
gagtttgcgc ctatcccgcc tggcggttct cggagtgtga atattgagat ggttggtttg    26580
ggtgccattg ttgtgtcggt gcagtacagg tttttgaggg cttggtgaat agttgatggc    26640
tggtcttgtc ccgcatgtaa cgttgtttac gccggattat cgtcgtgtgg cgcctatcaa    26700
ttttttttgag tcgttgaagt tgtcgttgaa gtggaatggt ttgtctacgc tggagttggt    26760
ggtgtctggg gatcattcta ggcttgacgg gttgactagg ccgggtgcgc ggctggttgt    26820
tgattatggt ggtggccaga ttttttctgg gcctgtgcgt aaggttcatg gtgtgggtcc    26880
gtggcgttct tcgcgggtga ctatcacgtg tgaggatgat atccgcctgt tgtggcgtat    26940
gctaatgtgg cctgtgaatt atcgtcccgg catggttggt tcggagtggc gtgccgacag    27000
ggattatgct cactattcgg gtgcggcgga gtcggtggct aagcaggtgt tgggggataa    27060
tgcttggcgt tttccgcctg gtttgtttat gaacgatgat gagagtcgtg gccgctatat    27120
taaggatttt caggcccggt tccatgtgtt tgccgataag ttgttgccgg tgttgtcgtg    27180
ggctcggatg actgtttcgg tgaaccagtt tgagaatgcg cagtttgatc agcgggtttt    27240
gctgtttgat tgtgtgcctg ctgtgacccg gaagcatgtg ttgactgccg agtctggttc    27300
gattgtgtcg tggagtatgt gcgtgacgc cccgaaggct acgtctgtgg tggttggtgg    27360
ccgcggcgag ggcaaagatc ggctgttttg tgaggatgtt gattcgatgg ccgaggggga    27420
ttggttttgat cgtgtcgagg tgtttaagga tgcccgtaac acggattctg aacatgtgca    27480
tctcatcgat gaggctgagc aggtgctgtc cgagttaggg gccacgtcgg ggtttaagat    27540
cgagttggct gagtcggatg tgttgcggtt tgggccaggc aatctgatgc cgggtgatct    27600
tatctatgtg gatgtgggtt ctggccctat tgccgagatt tgcgcggcaga ttgatgtgga    27660
gtgtgattcg cctggtgatg gttggacgaa ggtgactcct gttgcggggg attatgagga    27720
taatccgtcg gcgttgttgg ctcgccgtgt ggctggtttg gctgcgggtg tgcgggattt    27780
gcaaaagttt tagtaagtga ttgggggtttg ttgtgggtat tgtgtgtaaa gggtttgatg    27840
gtgtgttgac cgagtatgat tgggctcaaa tgtctggtct gatgggtaat atgccgtctg    27900
tgaagggccc ggatgatttt cgtgtcggta cgacggttca gggtgccaca gtgttgtgta    27960
gtgttttgcc ggggcaggcg tgggctcacg gggtgatgtg cacgtcgaat agtgttgaga    28020
cggtgacggg gcagcttccg ggccctggcg agactagata cgactatgtt gtcctgtctc    28080
gggattggga gcagaacacg gccaagttgg agattgttcc tggggggcgt gcggagcgtg    28140
ccagggatgt gttgcgcgcc gagcctggcg tgtttcatca gcaactgttg gcgactttgg    28200
tggtgtcgtc taacgggttg cagcagcagt tggataggcg tgctatagcg gctagggtgg    28260
cgtttggcga gtctgctgcg tgtgatccta cccctgtgga gggtgaccgg gtgatggttc    28320
cttcgggggc tgtgtgggct aatcatgcta acgagtggat gctactgtct ccaggattg    28380
agacgggttc taagtcgatc atgtttggcg ggtctgctgt gtatgcttac acgatcccgt    28440
ttgcccgccc gtttagtagt ccgcctgttg tggtggcgtc tatggctacg gcggctgggg    28500
gcacgcagca gattgatgtg aaagcctaca atgtgactgc caaggatttt ggtttagcgt    28560
ttattacgaa tgacgggtct aagccttctg gtgtgcctgc ggtagctaac tggattgctg    28620
tcggcgtgta atgcgctgct tgtgtgtgcg ggatatgttg tggtggttgt agtggtaggg    28680
ggctgtagtg tcatggttta cacccacact tgtagcctct atttgtaccg ctatcgctac    28740
tgtccttggt tcgattcagg cggttactta caggtcgaag aagaggctta ggcagttgtc    28800
tgcacaggtt gatgcgatgg aagaatacac atggaatatt cgccatattg ttcatcgcta    28860
taacgcgaat ttgcctgaga atgttgagcc tgtaaaaatg cctgatttgc ccgagttttt    28920
```

```
gaaggatact gttgatagtg gtgggggtg aattgtgagg gagttggagg aagagaaacg    28980
gcagcgccgc aattttgaga aggcttcact ggtgttgttg tttttgtcgc ttgtgttgtt    29040
ggctgtggtt gctgtgggtg ctttgcgttt cggggctgta tcctctgagc gggattcgga    29100
gcaggctagg gcccagtcga atggtacggc cgctaagggg ttggctgcga gtgtaaggcg    29160
ggcgtgcgtc tctggtgggc aggagtcggt gcgtcttcac cagtctggct tgtgtgtgga    29220
tgctcagcgt gttgagcg                                                  29238
```

<210> SEQ ID NO 70
<211> LENGTH: 29699
<212> TYPE: DNA
<213> ORGANISM: Artificial Sequence
<220> FEATURE:
<223> OTHER INFORMATION: PAC9

<400> SEQUENCE: 70

```
tgatggtcgg gatggttcgg ccggtgagcg cggtgatgtg ggcccttcag gtcctgccgg      60
cccgcaaggt gcacagggtg aacggggtga gcgcggcccc gccggtgcga acggatccga     120
tggtaaagac ggtaaggatg gtgctgatgg ccgtgatggg cgttcggtga tatcggtgta     180
ctgttccggg ggccgcctgg ttgtgaaata tagtgacggt acggcctcta ccgtgtcggg     240
ttctgcggcc tgcgagagtg tgaaaccatc acctgtggtt actgtatcat cccataggtg     300
aacaagaaga gggaagggtg ttactagtgt tgattgtggt gtttgggggt ggtgtgtggt     360
gagatacatt ccagcggcgc atcactctgc cggttcgaat agtccggtga acagggttgt     420
gattcatgca acatgcccgg atgtgggggtt tccgtccgct tcgcgtaagg gtcgggctgt     480
gtctacagcg aactatttcg cttccccatc atcgggggt tcggcgcatt atgtttgtga     540
tattggggag acggtgcagt gcctgtcaga ggggactata ggtggcatg ccccgccgaa     600 tccgcattct ttgggtatag agatttgcgc ggatgggggt tcgcatgcct cgttccgtgt     660
accggggcat gcttacacga gggagcagtg gcttgatccg caggtgtggc ccgcagtgga     720
gagggccgct atcctgtgtc ggcagttgtg tgacaagcat ggtgttccga aaaggaaact     780
gtctgtggcc gatttgaagg ccggtaaacg gggtgtgtgc gggcatgtgg atgttacgga     840
tgcgtggcat cagtcggatc atgacgatcc ggggccgtgg tttccgtggg acaaatttat     900
ggctgtggtg aatggccacg gcggcggttc aagtagtgag gagttgagta tggctgatgt     960
acaagcgtta cataatcaga ttaaacagtt gtcggcacag gtggcccagt cggtgaataa    1020
gctgcatcac gatgttggtg tggttcaggt tcagaatggt gatttgggta acgtgttga    1080 tgccctgtcg tgggtgaaga atccggtgac cgggaagctg tggcgcacca agacgccct    1140 gtggagcatc tggtattacg tgttggagtg tcgcagccgc atagacaggc ttgagtctgc    1200
tgttaatggt ttgaaaaagt gatggtggtt tgttgtgggt aaacagtttt ggttgggctt    1260
gtttgagcgt gccctgaaaa cttttattca aacgtttgtt gctgtgcttg gggtgacggc    1320
gggtgttact tatactgcgg agtcgtttcg cggtttgccg tgggagtctg ccctgataac    1380
agcaacggtt gctgcggtgc tgtctgttgc tacatcgttt ggtagccgt catttgtggc    1440 cggcaaacct aaaaccacgg ttgtggatgc tgggcttgtt ccacccgacg atgggggcat    1500
ggttgagccg cactcggtgg atgtgtcgga tcctggcatg atcgagccga cagatgatgt    1560
ggatggtttt gctggctatg tgccgaagcg tgcagccgag tcgggggtta gcacggtgga    1620
gtctactgtt gcataattga acatagatgt gtgccccagc ggtgctgcca cgatcgtgtg    1680
```

-continued

```
gtggttgccg ctggggcact cttttgtgt ctataggagt tttacaggtt gtcgtctagt  1740
gtgtcttcga gcatctggtc caggtagagg caggcggaga tagtatcgtt ggcctggtct  1800
agaacgttct ggccgataac attttatga ttgtcgcggt ggctgatgat agaccgcatg  1860
atatcgtcgg ccgccgcctg caatagtttg gcctggtatg cgattcctgc gagccagtct  1920
agtgcttcct ggcttgccag tgtgtcgtct ggaatgccac gggtgttgct gttgtttgtg  1980
gggtgtcctg cactgtcgca gcaccacaag atttcgctgc actcgtctag cgtgtcctgg  2040
tcgatagcaa gatcgtcgag gctgacttct ttgacggtaa ggttcacatt gtcgagggag  2100
atgggtacac cgtattggtt ttcgacactg tcaacaatgt tttccaactg ttgcatgttg  2160
gtgggctgtt gttggatgat acggtgtact actgttttga tggcggtgta ggggatattg  2220
tgtgtgttgt tcatggtttt tatcccaccc ctgtgttgtc gtcgttattg tctggatagt  2280
atctactgtt tgcgtagcct gtgagggtga tgagtgtttg gtctgccac tgtttcactg  2340
tctgccgggt gacacccaat cgttgggcgg ctgtggcgta ggtttgatca tacccgtata  2400
cttcacggaa tgcggctagc ctggctaggt gttttcgctg tttggagggt tcacatgata  2460
gggtgtagtc gtcgatggcg agctgtagat cgatcatggt ggcaatgttg ttgccgtgat  2520
gctggggggc ggttggtggg ggtggcattc ctggctccac actgggtttc catgggccgc  2580
cgttccagat ccattgggcg gcttggatga tgtcggcggt ggtgtaggtt cggttcatgt  2640
gtcaccccct gaacaggtcg ttgctggtgc tggtgttggt ggtgtcgaat cgtccgacgc  2700
agtggcagta gtcgtacatg agtttgataa tgtgttggtg gtctcccaaa taggtgtttc  2760
cgctgatact gtaggtggct gtgccgtctt tactgatggt gtatttggcg gtgatggttt  2820
cggggttttc ggtgtcggtg atgattgctg tggtggtggt gcctactgtt tgtagcacgg  2880
tggtttgggt tccgtcgtcg atagtggttt taaccatggt gtgtgttctc ccttttaga  2940
tgctggtttg gttgtcggct agatgaatga tgtcgggtaa gggtttcggc tggtctaggt  3000
gttgtatggt tttgttggct agccgtttgg ctaccctgta acacattttg gtgtagtgtt  3060
tgttgtctag gttgtggtat tgttcccgca ccgcaatata tagtagagag tcttggtaca  3120
ggtcgtctgc actgattgcg gggtagtgtg cggctgtttt ggtgcatgcc cggttgagtg  3180
tgcgtagatg atggtctgtg gcccacaccc acgatgcggt ggtggctagg tcggcttttg  3240
ttggtcgtct gctcatggca tttctttcat cgggctatct ggtagttgtt tggtgttttg  3300
ttgttgatag tgtagcacac gagtccgggg tttccggtgg tgccagtctt gtgccggtac  3360
catgtggatt cgccttccat ggatgggcat tggatgaagg tgcgttgtcc ttgttcggag  3420
atttctaggt ggtgccggtg cccggccatg aggatgtggg atgtggtgcc gttgtggaat  3480
tcttggccgc gccaccaatc atagtgtttg ccggtcgcc attggtgtcc gtgggcgtgc  3540
aggatttgtg tgccggccac gtcgacggtg gtggtcattt cgtcccgttg ggggaagtgg  3600
aagtgaaggt tggggtattg gttgttgagc tggtaagctt ctgcgatggc gcggcagcag  3660
tccacgtcaa aggagtcgtc gtaggtggtg actccttgc cgaagcgcac ggcttcgccg  3720
tggttgccgg ggatggatgt gatggtcaca ttttgcagt ggtcgaacat gtggacgagt  3780
tgcatcatgg ccatgcgggt gagcctgatt tgttcggtga ggggtgtttg tgtgcgccag  3840
gcgttgttgc ctccttgtga cacgtatcct tcgatcatgt cgccgaggaa tgcgatgtgg  3900
actcgttcgg gtttgcctgc ctgttgccag tagtgttttg cgactatgag ggagtgcaaa  3960
tagtcgtctg cgaatcggct ggtttctccg ccggggatgc ctttgccgat ttggaagtcg  4020
cctgccccga taacgaaggc tgtctcgtca ctgctttggg tgtcttgttc gggtttgggt  4080
```

```
ggctgccatt cggctagttt gttgacgagt tcgtcgacgg ggtagggggtc ggttgcgggt   4140 tggtggtcga tgattttttg tatggatcgg cctgtttctc cgttggggag tgtccattcg   4200
gagatgcgtg tgcggcgtac agtaccgttg gctagattgt cgtcgatggt gtcgatggcg   4260
ttgtcgtggt tggctagctg tgtgagtagc cggtctatat tgtctatcac tggttttcct   4320
cctctggcgg ggtggtgttg gcttgtttgc ggcggtagtc ttttataacg gtggcggaga   4380
tggggtatcc tgcctgggtg agctgttttg ctagccacga ggcgggtata gacctgtcgg   4440
cgaggacgtc tgcagccttg ttgccgtagc gttgaataag ggtttcagtt ttggttgcca   4500
tgatgtccta tcggttgtgt ggcgggctgc catcctgtgc ggcagtcgcc gtcgtggcct   4560
ggtttgcgtg tgcaccacga tacggttccg tctgtgtggt tgagtgtttt gccgcacatg   4620
acgttttgta gatgctcggg cagggcgccg tcaccctggt tgctggtttg tgtgtcgaag   4680
agtgttttct ggttggtgaa atgctctgac acggtgccgt tgtgtacggg tagtatccat   4740
gttttccatt gttgttgtag ccgggtgttc cagtggaatt gtttggccgc gttcgtggct   4800
tgtttgatgg ttttgtagta gccgacgagg atgcgctggt gttcactgtc gggtgggttt   4860
tggcctcgcc agtattgtgc cgcgacggca tacctgttgt tgtctgtgaa ggcgtcccag   4920
cagtattcga taatgtgttg tagtacacta tcgggaatgt ctcgtacttg gttttcgtcg   4980
agccacgcgt cgacaatgat gttgcgtatg gcgtgtttgt ctttggtggt gggtttgaac   5040
gagatactca ccatgctggc ctgtcgtctt gcatgaaatc gttaaaggat gattcgcttg   5100
tgcggcgtgc ctgggtgatt tgctggtcag tccagtcggg gtgttgctgt ttcagatagt   5160
accagcggca ggcatcatat gtttcgttct gcaagcgggt gagatggttt tcggtgatga   5220 tttgttttcca cattgtccac gaaacgtcga gcctgcggag catgtccatg gccggcacat   5280
taaacgagtc aaggaagagt atttcgtggg tgtagtagtt tttctcgtag gcgtaccatc   5340
cgcttcggtg cctgtgggggc tggttttttgg ggtaggcttc ccggcatact ttgtgtaaac   5400
gtttggccat gtcgtcgggt agttcaatgt cggggttggc gcggatcatg gatcgcatcc   5460
cgtcgtaggt ggtgccccag gtgtgcatga tgtgtagtgg gttgtctcca tcggcccatt   5520
tttctgcaca gatggcgagg cggatgcgcc tcctggctgt ttggctggtg ttgcgccggt   5580
tggggattgg gcacgtgtcg agggatcca ttatgtttta gtgtaccttt ctggtttcgt   5640
gttgttgacg tgttttactg tagcacagtg tctagtgctt tgtgtcaaccc tgttttttccg   5700 gcctgcaggt aggtgtctgt gacatctccg accgtgaggg gcacatgggt ggcttggggg   5760
agtgctgcct ggatggtttg tgccatctgg tcgcctgcgg ggtctgggtc tgaccagatg   5820
tagatgtggt cgtagccttc gaagaatttg gtccagaagt tttgccacga ggttgcgccg   5880
ggtagggcta cggccggcca tccgcattgt tcgaggatca tggagtcgaa ttcgccttcg   5940
caaatgtgca tttcggctgc cgggttggcc atggcggcca tgttgtagat ggagcctgtg   6000
tccccggctg gggtcaagta tttggggtgg ttgtgggttt tgcagtcgtg tgggagtgag   6060
cagcggaaac gcattttttcg tatttcggct ggccgctccc aaacggggta catgtatggg   6120
atggtgatgc actggttgta gttttcgtgg cctggtatgg ggtcattgtc gatgtatcca   6180
aggtggtggt agcgggctgt ttcttcgctg atgcctcttg ctgagagcag gtcgagtatg   6240
ttttcgaggt gggtttcgta gcgggctgag gctttctgga ttcggcggcg ttccgcaatg   6300
ttgtagggtt gtatgctgtc gtacattcgg gttttcttct tctagtcgtt gttgtagttt   6360
gtggagtcct cctccgacac cgcatgtgtg gcagtaccag acgcccttgt cgaggttgat   6420
```

```
gctcatggag ggctggtggt cgtcgtggag cgggcagagt atgtgttgct cgttttttgga    6480
cgggttgtag cgtatctggt agatgtcgag gatgcggcgg gtgtcagagg tgtgggagga    6540
gctcgttgag ggttgatacc acataggctt cgctccaggg tttgttgcgt tgtttcatca    6600
ctacgagtcc gatggtggaa ttgttttcgc ggtttcggtg tgtttcgtag ttgcgtgcct    6660
cccggctggc ttgtttcacg aattcggcta ggtgggggctg gccggctttc gcctcgataa    6720
tgtaggtttt gttgctggtt gtgaggatga ggtcgcccttc gtcttcgcgg ccgttgaggt    6780
ggaggcgttc gatatcgtgt ccggtgtcgc gtagctggtg caataatcgt gtttcccatt    6840
cggctccggc ccgccggttg cgtgcctgct gtgtggccat agttttaga gtcctttgtg    6900
tgttgtggtc atgttccagg gctgttttt ggcgagggg ccgaagaatg tgtattcggg    6960
gtaggctcgt agtcgttcat atcgggtgcc gtcggggctg gatttgccgg tgcgctgttt    7020
caatactgcg atgcgtgcct cggccggtat cgtgagaccg ttgccgttat cctcgccacc    7080
atacaatgag actcccaata tgagttgtgg ttttcggag aggccgtttt tgatttctcg    7140
ccgtgccggg gggtgttcga tgtcggttcc ggttttgtcg gtggcgtggt gtgtgacaat    7200
aatggtggat ccggtgtcgc ggcctaatgc tgtgatccat tgcatggctt cttgctgtgc    7260
ctgatagtca ctctcgcagt cttggatgtc catcaggttg tcgataacaa tgagtggcgg    7320
gaaggtgttc cacatttcca tgtaggcttg cagctccatg gtgatgtctg tccatgtgat    7380
gggtgactgg aatgagaatg tgatgtgttg gccgtggtgg atgctgtctc gatagtattc    7440
tggtccgtag tcgtcgatgt tttgttgtat ctgtgtggtg gtgtgttggg tgttgagtga    7500
gatgattcgt gtgtgaggcct cccagggtgt catgtcccct gatatgtaga gggcgggctg    7560
gttgagcatg gcggtgatga acatggctag cccggatttt tggctgcctg agcgccccgc    7620
aatcatgacg agatcccctt tgtggatgtg catgtcctgg ttgcggtaga ggggttctag    7680
ttgtggtatg cggggcagct cggctgcggt ttgggaggct ctctcgaagg atcgttggag    7740
agagagcatc gggaccttat ctatctatcg gttgggtgtg ttttggtggt cagatggagt    7800
cgatgtcgat gtcagcatcg gcggggggctg tggtgtcgtc tagctggccg ttatcgcgct    7860
tgtctacgta ttcggcaacc ttatcgtaga tggcgtcatc gagggggtgg tgtcgtctag    7920
ctggccgtta tcgcgcttgt ctacgtattc ggcaacctta tcgtagatgg cgtcatcgag    7980
gggtttgagc acgaccgcat tgaacccgtt tttggtgcgc acggtggcga gtttgaaggc    8040
ctgctcctcg ccaaggtagg cttcgaggtc gcggatcatg aatgtgggc ggtcgttgtt    8100
gccgcgcgct ttctcaataa tagcgttggg aatgatttct ggggtgccgt tgttgagatc    8160
gtctagggtg tggaagattg tgacatcagc gtagatgcga tcggctgtct gtccaccgta    8220
gccttcggtg ttgtgttcta cgtcgcggat tttgaaggcg atggcggtgg cgtcctggtt    8280
tcgggagggg ttgaagaagg tgctgttgct gttgttgcgg tagttggcga gtcccatggt    8340
tgtttccttt actgtttgtg ttggtttgtg tcggttttat cgggtgaggc tgtttcgttt    8400
gctgcggaaa gcctcggaca cgtcactgtt actggtgatg attttcttgt actgtttcag    8460
aaggtcggct agctgtgcct tgcttgttgc attgttgatt tgtcgatga taatctcgtt    8520
ttcgtttgat gcgatgttgt ctacgtagtc tttggctgcc tggttgtagc ggtcttggag    8580
gatgatggat gcgcttgcta cgagtgttgc tagatcccag tctttggaca cgtcaccgtt    8640
tttgaggccg cctagcagat caataatgga ttgtttgatg tcttctgcgg tgtctccgcg    8700
gatgactgtc catgggggctg cgtagtctcc accgtatttg agtgtgatag ttagctttcc    8760
gctgtctgtg gtgtgctcgt cggtcacgtg ttttcctttt cgttgttttc ggcttctggt    8820
```

-continued

```
ggctgtacgg tggtttctac cgggtatctg tacgagtttt tcccgttgac ggcccagcag   8880
gcgtccttga cggggcatcc tttgcagagt gctgtgacgt ggggtacgaa gatgccttgg   8940
ctgattcctt tcattgcttg actgtacatg gatgatacat gccggtaggt gttgttgtca   9000
agatcaatga gttcggtgga tgtgccctgc tcaaccgatt gctcgtctcc cttggtggta   9060
gcgggtgtcc aaaacattcc tttcgtcaca tggatgccgt gttggttgag catgtaacgg   9120
taggtgtgca gctgcatact gtcggcgggt aggcgtccgg ttttgaggtc caaaatgaag   9180
gtttcacccg tattcgtatc tgtgaatacc cggtcgatgt agccaacgat ctgggtgccg   9240
tcggggaggg tggtttctac cgggtattcg atgcccggct cgccgtcaat aacagcggta   9300
gcatattctg ggtggttgcg cctccatgtt ttccaccggt ccacaaaggt ggggccgtaa   9360
atcatccacc aattgtagtc tttcttgtgt gtcccgcccg actcgcacat gttttttgcat  9420
attctgccgg agggtttgat ttctgtgcct tcggattcgg cgagggcgac ttgggtgtcg   9480
aaaatgtttt tgaaggatga gagtttgtct ggcagtgcag ggtattcggc gggattgtac   9540
aggtgtaggt cgtattgttc ggtgatgtgg tgtatggcgc ttccggcgat ggtggcatac   9600
caggtgtggt gttgggcgtg gtagccgtgg gataggcgcc attttttcacc gcattcggcc  9660
cactgtgaca gtgatgagta ggagatgtgg cctggatggt caatggtgga cggttttttgt  9720
gctaggggca ttacttgtcg cttttgtggg tgttccatgg gtttcgggtg tcttggccgg   9780
cattgtgttg ctggtatgcg aggagtgcga ggcagtgcca ggcagcatgg gccagatggg   9840
gtagcccgga ttcatcatcg aggttgttgc cttgctgcca tgataacagg tgccggtaga   9900
gggcgtcaac actgtggctc cacggatagc cgccggtcca gttgttgtcg ccgtatttgg   9960
tggcgccgta tccggccaca gagccgaggg cgtgtaaggc tgtagggtcg atgagggata  10020
gcctgcaaag tttcaattct ttcttggcgc cagtatcagg gtcggtgtac atgctggtgg  10080
gctcatccat ggtgtgtgtg ctccttaagt atggggttac tggttggggt tgtgggcgag  10140
tgctacggcg agaataatga tggcgagggt ttcagcgatc agtatgggtg ttgtgatcat  10200
ttgtggtcgc ggggattgtt ggtgagggtt gaggcgccca ggaggatagt gagggcgcat  10260
gcggcgatga tggcgagggc tgccttgtgt ggggtgccgg tggcgtacat ccatgtgatg  10320
atgccgcctt ggatccaggc gaggctggtg aagaacgttt cgtagctgtg tagctcaatg  10380
ttgttgttgg gtgtgttcat gcttgctcct gaagaatggt gttgatggtt gtgtaaatgt  10440
tgtacaggtc ggtttcgata gataacagtt ggtggatttg gtggtcgaga tcaatgtcgg  10500
ggttgagggt gttgatgcgg gaggcgatgt cggtggctgt gcgtagtgtg ccgccggtgt  10560
ggtgaatgat gtgtgccgtg tcggcgagtc cggtggtgac agtgtagtgg gagaggagag  10620
gcatagctgg gggtgctcct tgacgggggtt actgttgcgg gttgatgttg aggtcggtga  10680
cgttggggtg gtcttctgtt ccggtgacga ggcagtggac ggtgactggg agtttggatg  10740
cgccgggctg tttcgcggtt gcgccgtaga cgatggagaa ggtgtctttg ccaataattt  10800
tgtggagttg gaggtcgatg tcggggttgc cgttccattt gacgccttgt gtggcggcct  10860
gttgttcggc tttgcggttg caggtgtgtg ctgcggtgat catggtgagt ccggtggcgg  10920
tttcttcacc ccttgcttgg gcttgcttgt gggttttctg ctgttcggct cgcagtgact  10980
gttctgctgc tgcctgccgt gctttctttt cggctttgcg ctgttgggta gtcttggggg  11040
tccattcggt gttggctgtg gtggcttgcg gtgcggggttg tgatgcgagt ggcggattgt  11100
cgtctggggc tggcatgaag gatgctgcgg cgatgatggc ggctgtgatt ccggcgatgg  11160
```

```
tgtagccgtt tttcttgttc atgattttgt gttccccttt ccggggtgtt gttcgttgct   11220
gacatgatta atactttcag cggctgggcc cactgtcaag gctgcgctca acgattgtga   11280
gcgatacttg tgtggctagg ggttttgtcc ttgaggtggg agatgtcttt cccttgcgtc   11340
cagtatccat ggcggttgcg agtcatccct tggcgagca tctcgtccac ggtgagacac    11400
ctgcgacgat ctggaccctc cttgactccc tgatcgcctg tgcggtgcat gtcaccggca   11460
caagtaccat taaatgtctc gtggcagatt gtgcaatgct ctggtcggta tccgatgatt   11520
gtgctatcgc acttgtggca tgtccattgc atgattggtc cttctttcgt gttttaagct   11580
tgtactctga ggattagagc gactttcagc ccttgggggg tatgattata taggtcaggt   11640
atttctaggc gattctaggc tcattgtgtg tggctggggg ttatcgggca cacagggtga   11700
ggagttggcc aacattgatg cgggtcacat tccagtagag ttgcgtggct tccccaccgg   11760
tgagtggctt ccactcgtca tggctgaaca cggtgccgtc ggttgcgatg aatgtgttgg   11820
ggcgtagctt gtgaagctca gtctctacac gctgccggta ggcttcggcg aggccctcga   11880
aatccatgtg gtcgcagggg aggttttcga ggcgtgtcag gtcgaagggt gtggggcagt   11940
cgtagctggc ggggctgtag agctgggtga atggttggc gatcttctgc atgacgggtt    12000 cctttctcg tatggtgagt tgatagtttt atcgggtgga tgcgacaagg atggcgtcta    12060
catcgatcat gtcgatgaga tcgtggagtt cctcggcctc attctcggag aggtggcgcc   12120
agccatagtc gccgtatacg gcgccgtcga gggtgacagt ccacaggggc cggatgagtc   12180
gtatggcttc ttgtacttta gcgtggtaca tgcggcgcac catatccaga tcgatgtcgt   12240
ctgaatggtt tccagtgagg ctgtagaggc tgagcgggtc gatttctgtc tgcctgtaga   12300
gggatgtgaa tgatggtgtg atgagtgtgc catccatgag agtgtgctcc tttcggtggt   12360
ggaggggttg ttgtggtttc tagagtgtgt aggctgcgac ccatagtcaa ggctgcgctc   12420
attcggattg agcgtttcat atgggtgtgg catggaatct acaccccat actgtgtgag    12480 ataggccaca tcctcctggc ttggtgtgaa ccctcgagac tactctgcct atctggcgtg   12540
gagggtgtag cccagaaata ccgtttaaag ccttcatacg gcgcctagga gcgccttaca   12600
gggtgggggc taggtatta taccccccaag caattctgat cgattctaga cgcctcccag    12660
gagcccgata cacgatccgc tatccagaca cagatcatca gcccctatcc tggttagcta   12720
agcctcaact atgtggacag tgttgattac tgtggggtaa gaaggacacg gtaaaagaaa   12780
gaggggggag catcggcttt caagccttaa ggtcttagca gttagcaccg agcccctcaa   12840
gggctcgtcg tcagcccatc aggcacggcc ctgaacgggg tacacgccat cagggaaggc   12900
ttgagagtac gaggagcctt agcgacgagt actcgaaagc ctgagggaac accctcagca   12960
ctgatgggtc tagcgtgttc ggaaaggaca caggagtaaa gcgtgacagc tgtccgggag   13020
tgaaacccgt tctgactagg ggtttcagcc ttaaccaccc tcaaaggtta caagactcta   13080
agaaaattta aggaaaagtt taggtttaat ttttggacct ttactaccaa aaacacccgt   13140
ttacacccct caaacccgcc tatagagcca aatccaccag tttgactcat cccaggtggc   13200
atatgatagg ctggacaggt agccagctgg acgcaaggcc gaaatccgct gacgcggctt   13260
tcacccttac atccatcagt ctaccaaaga cttaaagacc taagggctta cgctaaggt    13320 gctgatagct tagcaccgag cccttgaggg gctcggcatc agccctaaag ccttaaacac   13380
ttaaagtaca tataaaactt taaaagctta acacttaagg ttataaataa acattaaagc   13440
tttaaagtct taaagtacat atataacctt aacacctaag ttaagtataa aaccttaaag   13500
gcttagcact gaaggatata aacttcacat cagttttttaa gactttaaaa cttaaaataa   13560
```

```
ctattaagac ttaaagactt ataagttta aacacttaaa gtaactataa gactttaaag     13620
accttaagta cttaaagtta accatcagtc ttaaacttta atattataac ctataagtct     13680
taaagcttat aagttataaa agttttagaa gagctaagag gttaacttct ttacttctct     13740
tctctctttg gttctttctc tcttctcttc ttttcttcat caggggagaa gaggaacctt     13800
ttaccatcag cgccgatgga ctgtcaccgt gtgactcgtg taccaccggt cgcacgctcc     13860
cggtttcaca ctccccacac tctgacaccc gtgtcccttt caggcttagc gtgttcggct     13920
gaaggcgtac ggcgtgtcgc gccaacaccc ttaacaccag gtaagactta aagtgtatat     13980
tatatgtaga agacttttaaa acctataagg tgttcccgct tagcctgtgt cctacaccgc     14040
taggcgccaa gcgttaagtc ttgaaacgcg aacacacacc cacccccatt tttctttcgt     14100
gtccttctct tttgacaccg ctgggggggcg atgtgatctt tctcactacc catgggggta     14160
gtggagaaca caccacccc accatcaaca gaacaccccc tcaaacgaac aaaacagggc     14220
ctagaatcga tcggcagggc aagggcaagg tattcatacc cccaacacat tccaggccgt     14280
cagagaggca aataagaccc gtacagggct agtcgaggat cggagacgtg atggcacaca     14340
ccaatcgcac cgcatccgcc gcacaccgac actggcggca acgactcatc acccaagccc     14400
gacagcaagg ccaaaccgaa tgcccactct gcggagcaac catcacctgg gacacctacc     14460
agctgccaac tagccccgaa gccgaccaca tcacacccgt cagcagggga ggactcaaca     14520
ccctcgacaa cgggcaaatc atctgcagaa catgcaacag aagcaaaggc aacagaacac     14580
aaccaaacat caaattccaa caacaaacca caaaaaacct tgttccatgg tgacaaaacc     14640
cgccaacccc caccggggac accccctgca cacccgtgca agacctcgta cggcttagtg     14700
aaatacctcc cttttgtgga tttgtctgtt tgtcgacttt ttgtgttggt ggtgagtgtt     14760
gtgcagcctg agcttcctga gggacacgag tggtgtgggg agacgcgtcg ttggtggcgt     14820
gtgtggggtg aggatagccg cgcgcagtac cgtgtctgatg aggagtggct gttttcttatg     14880 gatgctgcgg tgattcatga ttgtgtgtgg cgtgagggtc gcgcggattt ggtggcttcg     14940
cttcgtgctc atgtgaaggc ttttatgggt atgttggatc gttattcggt tgatgtggcg     15000
tctggtggcc gtggtggggg ttctgcggtg gcgatgattg accggtatag gaagcgtagg     15060
ggggcctgat taggtgtctg gtgttgttgg gtctcaggtt cctcgtcatc gtgtggctgc     15120
ggcgtattcg gtgtctgctg gcggtgatgc tggggagttg ggtcgtgcgt atgggttgac     15180
gcctgatccg tggcagcagc aggtgttgga tgattggcta gctgtgggtg gtaatggcag     15240
gcttgcttcg ggtgtgtgtg gggtgttgt gcctcgccag aatggcaaga atgctatttt     15300
ggaggttgtg gagttgttta aggcgactat tcagggtcgc cgtatttgc atacggctca     15360 cgagttgaag tcggctcgta aggcgtttat gcggttgagg tcgttttttg agaatgagcg     15420
gcagtttcct gacttgtatc gtatggtgaa gtcgattcgt gcgacgaatg ccaggaggc     15480 tattgtgttg catcatccgg attgtgccac gtttgagcgt aagtgtggtt gtccgggttg     15540
gggttcggtt gagtttgtgg cccgttctcg tggttctgct cgcgggttta cggttgatga     15600
tttggtgtgt gatgaggctc aggagttgtc ggatgagcag ttggaggcgt tgcttcctac     15660
ggtgtctgcg gctccttcgg gtgatcctca gcagattttc ttgggtacgc cgcctgggcc     15720
gttggctgac gggtctgtgg tgttgcgttt gcgcgggcag gctttgtcgg gtggtaaaag     15780
gtttgcgtgg acggagtttt ctatcccgga tgagtctgat ccggatgatg tgtcgcggca     15840
gtggcggaag cttgctggtg agacgaatcc tgcgctgggt aggcgtctga atttcgggac     15900
```

```
ggtgagcgat gagcatgagt cgatgtctgc tgccgggttt gctcgggagc ggcttggctg   15960
gtgggatcgt ggccagtctg cttcttcggt gattccggcg gataagtggg ttcagtcggc   16020
tgtggatgag gcggctctgg ttggcgggaa agtgtttggt gtctcgtttt ctcgttcggg   16080
ggatcgtgtc gctttggctg gtgctggccg gactgatgct ggtgttcatg ttgaggtgat   16140
tgatgggctg tcggggacga ttgttgatgg tgtgggccgg ttggctgact ggttggcggt   16200 tcgttgggt gatactgacc ggatcatggt tgccgggtct ggtgcggtgt tgttgcagaa   16260
ggcgttgacg gatcgtggtg ttccgggccg tggcgtgatt gtggctgata ctggggtgta   16320
tgtggaggcg tgtcaggcgt ttttggaggg tgtcaggtcg ggtgtggttt ctcatcctcg   16380
tgccgattcg aggcgtgaca tgttggatat tgctgtgagg tcggctgtgc agaagaagaa   16440
gggttctgcg tggggttggg gttcctcgtt taaggatggt tctgaggttc ctttggaggc   16500
tgtgtctttg gcgtatcttg gtgcgaagat ggcgaaggct aggcggcgtg aacggtctgg   16560
taggaagcgg gtgtctgtgg tatgaattcg gatgagttgg ctctgattga gggcatgtac   16620
gatcgtatcc gaaggttgtc ttcgtggcat tgccgtattg agggctacta tgaggctct   16680 agccgggtgc gtgatttggg ggttgctatt cctccggagt tgcagcgtgt gcagacggtg   16740
gtgtcgtggc ctggtattgc ggtggatgct ttggaggagc gtctggattg gcttggctgg   16800
actaatggtg acggctacgg tctggatggt gtgtatgctg cgaatcggct tgctacggcg   16860
tcgtgtgatg tgcatttgga tgcgctgatt tttgggttgt cgtttgtggc tgttattccc   16920
cagggtgatg ggtcggtgtt ggttcgtccg cagtcgccga agaattgcac gggccggttt   16980
tcggctgacg ggtctcgtct ggatgctggc cttgtggtgc agcagacgtg tgatcctgag   17040
gttgttgagg ctgagctttt gttgcctgat gtgattgttc aggtggagcg gcgaggtagc   17100
cgtgagtggg ttgagacggg ccgtataccg aatgtgcttg gggctgttcc gttggtgcct   17160
gttgtgaatc gtcgccgtac gtctaggatt gatgggcgtt cggagatcac tcggtcgatt   17220
agggcttaca cggatgaggc tgttcgcaca ctgttggggc agtctgtgaa tcgtgacttt   17280
tatgcctatc ctcagcgttg ggtgacgggt gtgtcggctg acgagttttc gcagcctggc   17340
tgggtcctgt cgatggcttc tgtgtgggct gtggataagg atgacgacgg tgacactccg   17400
aatgtggggt cgtttcctgt gaattctcct acaccgtatt cggatcagat gcgtttgttg   17460
gctcagctga cggcgggtga ggctgcggtt ccggagcgct atttcgggtt tatcacgtct   17520
aacccgcctt ctggggaggc tttggctgcg gaggagtcga ggcttgtgaa gcgtgccgag   17580
cggcgtcaga cgtcgtttgg tcagggctgg ctgtcggttg gtttcctggc tgccagggcg   17640
cttgattcga gtgttgatga ggccgcgttt ttcggcgatg tgggtttgcg ttggcgtgac   17700
gcttcaaccc cgactcgggc ggctacggct gatgctgtga cgaagcttgt gggtgccggt   17760
attcttccgg cggattctcg tacggtgttg gagatgctgg ggcttgatga tgtgcaggtt   17820
gaggctgtga tgcgtcatcg tgccgagtct tcggatccgt tggcggcact ggctggggct   17880
atatcgcgtc aaactagcga ggtttgatag gcgatggctt cgggtgttgc gtcaaggttg   17940
gctgctgccg ggtatcagcg tgaggcggtc aggtttgccg ggaagtatgc gggctattat   18000
gccgagcttg gtcgtttgtg gcattccggg aagatgacag atgcgcagta tgtgcgtttg   18060
tgtgtggagt tggagcgtgc cggccatgac ggttcagcgg cgttggcggg taagttcgtg   18120
tcggattttc ggaagcttaa cggtgtggat cctggtttga tcgtgtatga cgagtttgat   18180
gctgccgccg cgttggctag gtcgttttcg actattaaga tgatgaatag tgacccggat   18240
agggctaagg atacggttga tgcgatggcg gcgggtgtta atcgggctgt catgaatgct   18300
```

```
ggccgtgaca cggttgagtg gtctgcgggt gcgcagggta ggtcgtggcg ccgggtgacg    18360
gatggtgatc cgtgcgcgtt ttgtgccatg ttggctacga ggtcggatta tacgaccaaa    18420
gagcgggcgc ttactactgg tcatactcgg cgtcataagc gtggcggtag gcgtccgttt    18480
ggttcgaagt atcatgatca ttgtggttgt acggtggttg aggttgttgg cccttgggag    18540 ccaaatagggt ctgatgccgc atatcagagg acgtatgaga aggctcgtga gtgggttgat    18600
gatcatgggt tgcagcagtc gcctggcaat attttgaagg ctatgcgtac tgttggtggc    18660
atgagataat ttgatgtggt ttccggttgt gtgccgccgg ttatcggtgc acagggttgt    18720
ctcccgcacg ggggtcaaca atgttgtgtt gttttccgca aggagtatag ggttaggcta    18780
tggccgatca aaagttgaa gaacagaatg ttgacaatga tgctgttgag cccggaaagg    18840
gtggagacgt tgttgatgtt gtgaaggatg ggcaggctgc cggcgatgat catgccggtg    18900
atgtttccgt gaaggaggag tcttcttctg gcacggattg gaaggctgag gctcgtaagt    18960
gggagtctcg tgctaaaagt aatttcgccg agttggagaa gcttcgcgcc tcggatggtg    19020
atgcggggtc tgtgattgat gagcttcgcc gcaagaatga ggaactcgaa gaccggatta    19080
atgggtttgt tcttgagggt gtgaagcgcg aggtggctgc cgagtgtggc ctgtcgggtg    19140
atgctgtcgc ttttttgcac ggtggcgatc gtgaagcact ggtggagtct gctaaggctt    19200
tgaagggttt gatcgaccat agtagtggtg gcgcgggtgt gcgccgtctt gcggggagtg    19260
cccccgttga tgatgttaaa cgacgtgagg gtgtcgcgtt tgtggatgct cttgtcaata    19320
attctaggag atgatttgtg atggctacg attttctttc tgcagggaag cttgagcttc    19380
ctggttctat gattggtgcg gttcgtgacc gtgctatcga ttctggtgtt ttggcgaagc    19440
tttcgccgga gcagccgact attttttggcc ctgttaaggg tgccgtgttt agtggtgttc    19500
ctcgcgctaa gattgttggt gagggcgagg ttaagccttc cgcgtctgtt gatgtttcgg    19560
cgtttactgc gcagcctatc aaggttgtga ctcagcagcg tgtctcggac gagtttatgt    19620
gggctgatgc tgattaccgt ctgggtgttt tgcaggatct gatttccccg gctcttggtg    19680
cttcgattgg tcgcgccgtg gatctgattg cttttccatgg tattgatcct gccactggta    19740
aagcggctgc cgctgtgcat acttcgctgg ataagacgac gcatattgtt gatgccacgg    19800
attctgctac ggctgatctt gttaaggctg tcggcctgat tgctggtgct ggtttgcagg    19860
ttcctaacgg ggttgctttg gatcccgcgt tctcgtttgc cctgtctact gaggtgtatc    19920
cgaaggggtc tccgcttgcc ggccagccta tgtatcctgc cgccgggttt gccggtttgg    19980
ataattggcg cggcctgaat gttggtgctt cttcgactgt ttctggcgcc ccggagatgt    20040
cgcctgactc gggtgttaag gctattgtgg gtgatttctc tcgtgttcat tggggtttcc    20100
agcgtaactt cccgatcgag cttatcgagt atggcgatcc ggatcagact ggccgcgatt    20160
tgaagggcca taatgaggtt atggttcgtg ccgaggctgt gctgtatgtg gctatcgagt    20220
cgcttgattc gtttgctgtt gtgaaggaga aggctgcccc gaagcctaat ccgccggccg    20280
agaactgatt tattgttgcg gtgatgtgtc aatgtgcagg gggtggtgtt gatgggtatc    20340
attttgaagc ctgaggatat tgagcctttc gccgatattc ctagagagaa gcttgaggcg    20400
atgattgccg atgtggaggc tgtggctgtc agtgtcgccc cctgtatcgc taaaccggat    20460
ttcaaataca aggatgccgc taaggctatt ctgcgcaggg cttttgttgcg ctggaatgat    20520 actggcgtgt cgggtcaggt gcagtacgag tctgcgggtc ctttcgctca gactacacgg    20580
tctagtactc ccacgaattt gttgtggcct tctgagattg tcgcgttgaa gaagctgtgt    20640
```

```
gagggtgatg gtggggctgg taaagcgttc actattacac cgaccatgag gagtagtgtg    20700
aatcattctg aggtgtgttc cacggtgtgg ggtgagggtt gctcgtgcgg gtcgaatatt    20760
aacggctacg ctggccccctt gtgggagata tgatatgacc agttttcctt atggtgaaac    20820
ggttgtgatg cttcaaccga ctgttcgtgt cgatgatctt ggcgacaagg tggaagactg    20880
gtctaagcct gtcgagactg tgtaccataa cgtggccata tatgcttccg tttcgcagga    20940
ggatgaggct gcggggcgtg actcggatta tgagcattgg tcgatgctgt tcaagcagcc    21000
tgttgtgggc gctgattatc gttgtaggtg gcgtattcgg ggtgttgtgt gggaggctga    21060
cgggtctcct atggtgtggc atcaccccat gtccggttgg gatgctggta cgcaggttaa    21120
tgtgaagcgt aagaagggct gatgggtagt ggctcaggat gtgaatgtga agctgaactt    21180
gccgggtatt cgtgaggtgt tgaagtcttc tggagtgcat ggcatgttgg ctgagcgtgg    21240
cgagcgtgtc aagcgtgccg cagcggcgaa tgtgggtggt aacgcgtttg atagggccca    21300
ataccgtaat ggtttgtcgt cggaggtgca ggttcaccgt gttgaggctg tggcgaggat    21360
tggcaccacc tataagggtg ggaagcgtat tgaggcgaag catggcacgt tggcgaggtc    21420
gattggggct gcgtcgtgat cgtttacggt gatccgcgtg tgtgggctaa acgcgtgctc    21480
aaggatgatg gctggctgtc tgggataccg tgtacgggga cggtgcctga ggatttcagc    21540
ggtgacctga tctggttggc gttggatggt ggcccacagt tgcatgttcg tgagcgtgtt    21600
tttttgcgcg tgaacgtgtt ttcggatacg ccggatcgtg ctatgtcgtt ggcgcgtcgt    21660
gtcgaggctg tgctggctga tagtgtggac ggtgaccctg tggtgtactg taaacggtct    21720
actgcccctg atttgctggt tgatggtgca cgttttgatg tgtattcgct ttttgagctg    21780
atatgtaggc ctgcggagtc tgaataagct tattgttttt gttttaatgt aattgtttga    21840
tatttaatgg gggttatgat ggctgcaaca cgtaaagcgt ctaatgttcg ctcagcggtt    21900
actggcgacg tttatattgg tgacgcgcac gcgggtgata ctattaaggg tgtggaggcg    21960
gttccttccg ggcttaccgc tttagggtat ctgtctgatg acgggtttaa gattaagcct    22020
gagcgtaaaa cggatgattt gaaggcttgg cagaatgcgg atgttgttcg cactgtggct    22080
acggagtctt ctatcgagat ttcttttccag ctgatcgaat ccaaaaaaga ggttatcgaa    22140
ctgttttggc agtcgaaggt tactgccgga tccgattcgg gttctttttga tatttctcct    22200
ggtgccacga cgggtgttca cgctctgttg atggatattg ttgatggtga tcaggttatt    22260
cgctactatt tccctgaggt tgagctcatt gatcgtgacg agatcaaggg taagaatggt    22320
gaagtgtacg ggtatggtgt gacgttgaag gcgtatcctg cccagattgg taagactggt    22380
aatgcggtgt ctggtcgggg gtggatgacg gctttaaaag ctgatactcc tccttctccg    22440
aagcctcagc cggatccgaa tccgccggcc gagaactgat acacgatttt agggattgt    22500
tgatagatga gtgacactgg tttcacgttg aagattggtg atcgtagctg ggtgttggcg    22560
gatgctgagg agacggcgca ggctgttcct gcccgcgttt tccgtcgtgc cgccaggatt    22620
gcccagtcgg gggagtctgc ggatttcgcc caggttgagg tgatgttttc tatgttggag    22680
gctgccgccc cggctgacgc tgtggaggcc ctggaggggc ttcctatggt tcgtgtggcg    22740
gaggttttcc gtgagtggat ggaatataag cctgacggta agggtgcctc gctgggggaa    22800
tagtttggct ccacggcctg attgatgatt atcgtggggc catcgaatac gatttccgca    22860
ctaaatttgg tgtttctgtt tatagtgttg gtgcccgca gatgtgttgg ggtgaggctg    22920
tccggctggc tggcgtgttg tgtactgata cgtctagcca gttggcggcc cacctgaatg    22980
gttggcagcg cccgtttgag tggtgtgagt gggctgtgtt ggacatgttg gatcattaca    23040
```

```
ggtctgctaa tagtgagggg cagccggagc ctgtggcgag gccgacggat gagcgtaggg   23100
cccggtttac gtctgggcag gtggacgata ttttggcgcg tgttcgtgcc ggtggcgggg   23160
tgtctcgcga gattaatatt atggggtgaa tagtgtatgt ctggtgagat tgcttccgcg   23220
tatgtgtcgt tgtatacgaa gatgcctggc cttaaaagtg atgttggtaa acagctttct   23280
ggggtgatgc ctgcggaggg tcagcgttcg ggtagcttgt ttgctagcgg gatgaagttg   23340
gcgcttggtg gtgcggcgat gatgggtgcc atcaatgttg ctaagaaggg cctcaagtct   23400
atctatgatg tgactattgg tggcggtatt gctagggcga tggctattga tgaggctcag   23460
gctaaactga ctggtttggg tcatacgtcg tctgacacgt cttcgattat gaattcggct   23520
attgaggctg ttactggtac gtcgtacgcg ttgggggatg cggcgtctac ggctgcggcg   23580
ttgtctgctt cgggtgtgaa gtctggcggg cagatgacgg atgtgttgaa gactgtcgcc   23640
gatgtgtctt atatttcggg taagtcgttt caggatacgg gcgctatttt tacgtccgtg   23700
atggctcgcg gtaagttgca gggcgatgac atgttgcagc ttactatggc gggtgttcct   23760
gtgctgtctt tgcttgccag gcagacgggt aaaacgtctg ctgaggtgtc gcagatggtg   23820
tcgaaggggc agattgattt tgccacgttt gcggctgcga tgaagcttgg catgggtggt   23880
gctgcgcagg cgtctggtaa gacgtttgag ggcgctatga agaatgttaa gggtgccctg   23940
ggttatttgg gtgctacggc tatggcgccg tttcttaacg ggttgcggca gattttgtt    24000 gcgttgaatc cggttattaa gtctatcacg gattctgtga agcctatgtt tgcgtcggtg   24060
gatcagggga ttcagcgggt gatgccgtct attttggcgt ggattaaccg tatgccgggc   24120
atgattacga gaatgaatgc acagatgcgc gccaaggttg agcagttgaa gggcgttttt   24180
gcgaggctgc atttgcctgt tcctaaggtg aattttggtg ccatgtttgc tggcggcacc   24240
gcagtgttcg gtattgttgc tgcgggtgtt gggaagcttg ttgcgggggtt tgccccgttg   24300 gcggtgtctt tgaagaatct gttgccgtcg tttggtgctt tgaggggtgc cgctggggggg   24360 cttggtggcg tgtttcgcgc cctggtggcc cctgttggta ttgtgatcgg gctgtttgct   24420
gccatgtttg ctacgaacgc ccagttccgt gccgctgtta tgcagcttgt gggggttgtt   24480
ggccgggctt tggggcagat tatggtcgct gtgcagccac tgttcgggat tgttgctggc   24540
gtggttgcca ggttggcgcc agtgttcggc cagattatcg gtatggttgc tggtttggct   24600
gcccggctgg tgcctgttat tggtatgctt attgcccggc tggttcctgt tatcacccag   24660
attattggta tggtaaccca ggttgctgcc atgttgttgc ctatgctgat gccggttatt   24720
caggctgttg ttgctgtgat acggcaggtt attggtgtga tcatgcagtt gatacctgtt   24780
ttgatgccgg ttgtgcagca gattttgggt gctgtcatgt ctgttttgcc gccgattgtt   24840
ggtttgatac ggtcgctgat accggtgatc atgtcgatta tgcgtgtggt ggtgcaggtt   24900
gttggtgccg tgttgcaggt ggtggcccgt attattccgg ttgttatgcc gatttatgtt   24960
tcggtgattg gattcattgc caagatttat gctgcggtta tcgttttga ggctaaggtt    25020 attggcgcta ttcttcgtac tattacgtgg attgtgaatc attcagtgtc tggcgtgagg   25080
tctatgggca cggccatcca gaatggctgg aatcatatca aatcgtttac gtcggcgttt   25140
attaacggtt tcaagtcgat catttctgcc ggtgttgccg cggttgtggg gttttttacg   25200
cggcttggtt tgtcggttgc ttctcatgtt cggtctgggt ttaacgcggc ccgtggcgct   25260
gtttcggctg cgatgaatgc tattcggagt gttgtgtctt cggtggcgtc tgctgttggc   25320 gggttttcg ggtcgatggc gtctagggtt cgtagtggtg ctgtgcgcgg gtttaatggt   25380
```

| | | | | |
|---|---|---|---|---|
| gcccggagtg | cggcttcttc | tgctatgcat | gctatgggct | cggctgtgtc tagtggtgtg | 25440 |
| catggtgtgc | taggatttt | ccggaatttg | cctggcaata | ttcggcatgc tctcggcaat | 25500 |
| atgggttct | tgttggtgtc | ggctggccgt | gatgtggtgt | ctggtttggg taacggtatt | 25560 |
| aagaatgcta | tgagtggcct | gttggatacg | gtgcgtaaca | tgggttctca ggttgctaat | 25620 |
| gcggctaagt | ctgtgttggg | tattcattcc | ccgtctcgag | tgtttcgtga ccaggttggc | 25680 |
| cggcaggttg | ttgccggttt | ggccgagggg | atcaccggga | atgcgggttt ggcgttggat | 25740 |
| gcgatgtcgg | gtgtggctgg | acggctgcct | gatgcggttg | atgcccggtt tggtgtgcga | 25800 |
| tcatcggtgg | gctcgtttac | cccgtatgac | aggtatcggc | ggatgggcga aagagtgtt | 25860 |
| gtggtgaatg | tgaatgggcc | tacttatggt | gatcctaacg | agtttgcgaa gcggattgag | 25920 |
| cggcagcagc | gtgacgcttt | gaacgcgttg | gcttacgtgt | gattggggt gttgtgcatg | 25980 |
| tttattcctg | acccgtctga | tcgtgccggt | ttgactgtta | cctggtctat gttgccgttg | 26040 |
| attggtaatg | atccggagcg | tgtgcttcat | ttgacggatt | atacgggtgc gtctcctgtc | 26100 |
| atgttgttga | atgattcgtt | gcgcggtttg | ggtgttcctg | aggtggagca tttttctcaa | 26160 |
| actcatgttg | gggtgcacgg | ctcggagtgg | cgcgggttta | atgtgaagcc tcgcgaggtg | 26220 |
| acattacctg | tcctggtgtc | gggtgttggt | gtggatccgg | ttggcgggtt tcgtgacggt | 26280 |
| tttttgaagg | cgtatgacga | gttgtggtct | gcttttcctc | cgggcgagga ggggagttg | 26340 |
| tctgtgaaga | ccccgtctgg | ccgtgagcgt | gtgctaaaat | gccggtttga ttcggtggat | 26400 |
| gacacgttta | ctgtggatcc | ggtgaacagg | ggttatgcgc | gctatctgtt gcatttgaca | 26460 |
| gcttatgacc | cgttttggta | tggggatgag | cagaagtttc | gttttagtaa tgcgaagttg | 26520 |
| caggattggt | taggtggcgg | ccctgtcggc | aagaagggta | ccgcttttcc ggtggtgttg | 26580 |
| acgcctggtg | ttggttcggg | ttgggataat | ctgtctaata | ggggtgatgt gcctgcgtgg | 26640 |
| cctgtgattc | gtgtggaggg | cccgttggag | tcgtggtctg | tgcagattga tggtttgcgt | 26700 |
| gtgtcttcgg | attacccggt | ggaggagttt | gattggatca | ctattgatac ggatcctcgc | 26760 |
| aaacagtctg | cattgttgaa | cgggtttgag | gatgtgatgg | atcgtttgac agagtgggag | 26820 |
| tttgcccta | tcccgcctgg | cggttctaag | agtgtgaata | ttgagatggt tggtttgggt | 26880 |
| gccattgttg | tgtcggtgca | gtacaggttt | ttgagggctt | ggtgaatagt tgatggctgg | 26940 |
| tcttgttccg | catgtaacat | tgtttacacc | tgattatcgc | cgtgtggcgc ctatcaattt | 27000 |
| ttttgagtcg | ttgaagttgt | cgttaaagtg | gaatggtttg | tccactttgg agttggtggt | 27060 |
| gtctggtgat | cattctaggc | ttgacgggt | gactaggccg | ggtgcacggc tggttgttga | 27120 |
| ttatggtggt | ggccagattt | tttctgggcc | tgtgcgtcgg | gttcatggtg tgggtccgtg | 27180 |
| gcgttcttcc | catgtgacta | tcacgtgtga | ggatgatatt | cgtctgttgt ggcgtatgtt | 27240 |
| gatgtggcct | gtggattatc | gtcctggttt | ggttggtatg | gagtggcgtg ctgaccggga | 27300 |
| ttatgcccac | tattcgggtg | cggctgagtc | ggtggctaag | caggtgttgg gggataatgc | 27360 |
| ttggcgtttt | ccgcctggtt | tgtttatgaa | cgatgatgag | agtcgtggac ggttcattaa | 27420 |
| ggattttcag | gtgcggtttc | acgtgtttgc | cgataagttg | ttgccggtgt tgtcgtgggc | 27480 |
| tcggatgact | gtcacggtga | accagtttga | gaatgcgaag | tttgatcagc gtggtttggt | 27540 |
| gtttgattgt | gtgcctgctg | tgacgcgtaa | gcatgtgttg | actgccgagt ctggttcgat | 27600 |
| tgtgtcgtgg | gagtatgtgc | gtgacgcccc | gaaggcgaca | tcggtggtgg ttggtggccg | 27660 |
| cggcgagggc | aaagatcggc | tgttttgtga | ggatgttgat | tcgatggccg aggatgactg | 27720 |
| gtttgatcgt | gtcgaggtgt | ttaaggatgc | ccgtaacacg | gattctgagc atgtgcatct | 27780 |

```
cattgatgag gctgagcagg tgttgtccga gttgggggcc acgtcggggt ttaagatcga    27840
gttggctgag tcggatgtgt tgcggtttgg gcccggcaat ctgatgcccg gggatttgat    27900
ctatgtggat gtgggttctg gccctatcgc agagattgtg cggcagattg atgtggagtg    27960
tgagtcgccg ggtgacgggt ggacgaaggt gactcctgtt gcaggggatt atgagaataa    28020
tccgtcggcc ctgttggcgc ggcgtgttgc tggtttggct gcgggtgtgc gggatttgca    28080
aaaattctag aaaagattag gggtttgttg tgggtattgt gtgtaaaggg tttgatggtg    28140
tgttgaccga gtatgattgg gctcaaatgt ctggtctgat gggtaatatg ccgtccgtga    28200
aagggccgga cgattttcgt gtcggcacta ctgttcaggg tgccacagtg ttgtgtgagg    28260
tcctgccggg gcaggcttgg gcccacgggg tgatgtgcac gtcgaatagt gttgagacgg    28320
tgaccggcca gcttccgggc ccgggtgaga cccgatacga ctatgtggtg ttgtctcggg    28380
attgggaggc gaatacggcc aagttggaga ttgttcctgg ggggcgtgcg gagcgtgccc    28440
gtgacgtgtt gagggccgag cctggcgtgt accatcagca gttgttggct actttggtgg    28500
tgtcgtctaa cggttgcag cagcagctgg ataggcgtgc tatagcggct agggtggcgt    28560
ttggcgagtc tgctgcgtgt gatcctaccc cagtggaggg tgaccgtgtg atggttccct    28620
ctggggctgt gtgggctaat catgccggcg agtggatgct gttgtccccc aggattgaga    28680
cgggttctaa gtcgatcatg tttggcgggt ctgctgtgta tgcttacacg attccgtttg    28740
agcggccgtt tagtagtgcg cctgttgtgg tggcgtctat ggctacggcg gctgggggca    28800
cgcagcagat caatgtgaaa gcctacaatg tgactgtcca aaattttagt ttggcgttta    28860
ttacgaatga tggttcgaag ccgaatggtg tgcctgcggc ggctaattgg attgctgtcg    28920
gcgtgtgact gtacaggtgt tgtggcggat ggtgtgatgt tggggggctg tggtgtcgtg    28980
gtttactcct gcactggtgg cctctatttg taccgcgttg gccacggttt tgggttctgt    29040
tcaggctgtc acatcccggt ctaggcgcg tttacgcagg ctgtctgcgc aggtggatgc    29100
gatggaagag tatacgtggg gtgtgcggcg cgaggtgcga aggtttaacg ccgggcttcc    29160
tgatgatgtg gagccgatgc atcttcctga tgtgcccgag tttttgaagg atactgttga    29220
tggtggaggt gagtagggtt gagggagttg gaggaggaga agcggcagcg ccgcaatttt    29280
gagaaggctt ccctgatact gttattttg tcgcttgtgt tgttggcggt ggttgccggg    29340
ggtgctttgc ggtacgggtc tgtggcttct caaagggatt cggagcaggc gagggcccag    29400
tcgaatggta cagccgctaa agggttggct gcccgtgtga agcaggcgtg tacccagggt    29460
ggcgtggagt ctgtgaagct gcacaggtct ggtttgtgtg tggatgctgt gcgtgttgag    29520
cagcgtgttc agggtgtgca gggtcctgcc ggtgagcgtg gcccgcaagg gcccgctggt    29580
gttgatggcc gggatggtag caatggttct gctgggctgg ttggccctgt tgggccgcag    29640
ggttcccctg gtttgaatgg tgttccaggt cgtgcaggtg tcgatggtgt gaacggcgc    29699
```

<210> SEQ ID NO 71
<211> LENGTH: 29596
<212> TYPE: DNA
<213> ORGANISM: Artificial Sequence
<220> FEATURE:
<223> OTHER INFORMATION: PAC2

<400> SEQUENCE: 71

```
ctggtttgaa tggtgtgaaa ggtcctgacg ggttgcctgg cgctaacggt tcggatggcc      60
gtgatggtgt tccaggtcgt gcaggtgtcg atggtgtgaa cggcgctgat ggtcgggatg     120
```

```
gttcggccgg tgagcgcggt gatgtgggcc cttcaggtcc tgccggcccg caaggtgcac    180
agggtgaacg gggtgagcgc ggccccgccg gtgcgaacgg atccgatggt aaagacggta    240
aggatggtgc tgatggccgt gatgggcgtt cggtgatatc ggtgtactgt tccgggggcc    300
gcctggttgt gaaatatagt gacggtacgg cctctaccgt gtcgggttct gcggcctgcg    360
agagtgtgaa accatcacct gtggttactg tatcatccca taggtgaaca agaagaggga    420
agggtgttac tagtgttgat tgtggtgttt ggggtggtg tgtggtgaga tacattccag    480
cggcgcatca ctctgccggt tcgaatagtc cggtgaacag ggttgtgatt catgcaacat    540
gcccggatgt ggggtttccg tccgcttcgc gtaagggtcg ggctgtgtct acagcgaact    600
atttcgcttc cccatcatcg ggggttcgg cgcattatgt ttgtgatatt ggggagacgg    660
tgcagtgcct gtcagagggg actatagggt ggcatgcccc gccgaatccg cattctttgg    720
gtatagagat ttgcgcggat gggggttcgc atgcctcgtt ccgtgtaccg gggcatgctt    780
acacgaggga gcagtggctt gatccgcagg tgtggcccgc agtggagagg ccgctatcc    840
tgtgtcggca gttgtgtgac aagcatggtg ttccgaaaag gaaactgtct gtggccgatt    900
tgaaggccgg taaacggggt gtgtgcgggc atgtggatgt tacgatgcg tggcatcagt    960
cggatcatga cgatccgggg ccgtggtttc cgtgggacaa atttatggct gtggtgaatg   1020
gccacggcgg cggttcaagt agtgaggagt tgagtatggc tgatgtacaa gcgttacata   1080
atcagattaa acagttgtcg gcacaggtgg cccagtcgt gaataagctg catcacgatg   1140
ttggtgtggt tcaggttcag aatggtgatt tgggtaaacg tgttgatgcc ctgtcgtggg   1200
tgaagaatcc ggtgaccggg aagctgtggc gcaccaaaga cgccctgtgg agcatctggt   1260
attacgtgtt ggagtgtcgc agccgcatag acaggcttga gtctgctgtt aatggtttga   1320
aaaagtgatg gtggtttgtt gtgggtaaac agttttggtt gggcttgttt gagcgtgccc   1380
tgaaaacttt tattcaaacg tttgttgctg tgcttggggt gacggcgggt gttacttata   1440
ctgcggagtc gtttcgcggt ttgccgtggg agtctgccct gataacagca acggttgctg   1500
cggtgctgtc tgttgctaca tcgtttggta gcccgtcatt tgtggccggc aaacctaaaa   1560
ccacggttgt ggatgctggg cttgttccac ccgacgatgg gggcatggtt gagccgcact   1620
cggtggatgt gtcggatcct ggcatgatcg agccgacaga tgatgtggat ggttttgctg   1680
gctatgtgcc gaagcgtgca gccgagtcgg aggttagcac ggtggagtct actgttgcat   1740
aattgaacat agatgtgtgc cccagcggtg ctgccacgat cgtgtggtgg ttgccgctgg   1800
ggcacacttt ttgtgtctat aggagtttta caggttgtcg tctagtgtgt cttcgagcat   1860
ctggtccagg tagaggcagg cggagatagt atcgttggcc tggtctagaa cgttctggcc   1920
gataacattt ttatgattgt cgcggtggct gatgatagac cgcatgatat cgtcggccgc   1980
cgcctgcaat agtttggcct ggtatgcgat tcctgcgagc cagtctagtg cttcctggct   2040
tgccagtgtg tcgtctggaa tgccacgggt gttgctgttg tttgtggggt gtcctgcact   2100
gtcgcagcac cacaagattt cgctgcactc gtctagcgtg tcctggtcga tagcaagatc   2160
gtcgaggctg acttctttga cggtaaggtt cacattgtcg agggagatgg gtacaccgta   2220
ttggttttcg acactgtcaa caatgttttc caactgttgc atgttggtgg gctgttgttg   2280
gatgatacgg tgtactactg ttttgatggc ggtgtagggg atattgtgtg tgttgttcat   2340
ggttttatc ccaccctgt gttgtcgtcg ttattgtctg gatagtatct actgtttgcg   2400
tagcctgtga gggtgatgag tgtttggtct gcccactgtt tcactgtctg ccgggtgaca   2460
cccaatcgtt gggcggctgt ggcgtaggtt tgatcatacc cgtatacttc acggaatgcg   2520
```

| | |
|---|---|
| gctagcctgg ctaggtgttt tcgctgtttg gagggttcac atgatagggt gtagtcgtcg | 2580 |
| atggcgagct gtagatcgat catggtggca atgttgttgc cgtgatgctg ggggcggtt | 2640 |
| ggtggggtg gcattcctgg ctccacactg ggttcccatg ggccgccgtt ccagatccat | 2700 |
| tgggcggctt ggatgatgtc ggcggtggtg taggttcggt tcatgtgtca ccccctgaac | 2760 |
| aggtcgttgc tggtgctggt gttggtggtg tcgaatcgtc cgacgcagtg gcagtagtcg | 2820 |
| tacatgagtt tgataatgtg ttggtggtct cccaaatagg tgtttccgct gatactgtag | 2880 |
| gtggctgtgc cgtcttact gatggtgtat ttggcggtga tggtttcggg gttttcggtg | 2940 |
| tcggtgatga ttgctgtggt ggtggtgcct actgtttgta gcacggtggt ttgggttccg | 3000 |
| tcgtcgatag tggttttaac catggtgtgt gttctcccct tttagatgct ggtttggttg | 3060 |
| tcggctagat gaatgatgtc gggtaagggt tccggctggt ctaggtgttg tatggttttg | 3120 |
| ttggctagcc gtttggctac cctgtaacac attttggtgt agtgtttgtt gtctaggttg | 3180 |
| tggtattgtt cccgcaccgc aatatatagt agagagtctt ggtacaggtc gtctgcactg | 3240 |
| attgcgggt agtgtgcggc tgttttggtg catgcccggt tgagtgtgcg tagatgatgg | 3300 |
| tctgtggccc acacccacga tgcggtggtg gctaggtcgg cttttgttgg tcgtctgctc | 3360 |
| atggcatttc tttcatcggg ctatctggta gttgtttggt gttttgttgt tgatagtgta | 3420 |
| gcacacgagt ccgggtttc cggtggtgcc agtcttgtgc cggtaccatg tggattcgcc | 3480 |
| ttccatggat gggcattgga tgaaggtgcg ttgtccttgt tcggagattt ctaggtggtg | 3540 |
| ccggtgcccg gccatgagga tgtgggatgt ggtgccgttg tggaattctt ggccgcgcca | 3600 |
| ccaatcatag tgtttgccgg tgcgccattg tgtccgtgg gcgtgcagga tttgtgtgcc | 3660 |
| ggccacgtcg acggtggtgg tcatttcgtc ccgttgggg aagtggaagt gaaggttggg | 3720 |
| gtattggttg ttgagctggt aagcttctgc gatggcgcgg cagcagtcca cgtcgaagga | 3780 |
| gtcgtcgtag gtggtgactc ctttgccgaa gcgcacggct tcgccgtggt tgccggggat | 3840 |
| ggatgtgatg gtcacatttt tgcagtggtc gaacatgtgg acgagttgca tcatggccat | 3900 |
| gcgggtgagc ctgatttgtt cggtgagggg tgtttgtgtg cgccaggcgt tgttgcctcc | 3960 |
| ttgtgacacg tatccttcga tcatgtcgcc gaggaatgcg atgtggactc gttcgggttt | 4020 |
| gcctgcctgt tgccagtagt gttttgcgac tatgagggag tgcaaatagt cgtctgcgaa | 4080 |
| tcggctggtt tctccgccgg ggatgccttt gccgatttgg aagtcgcctg ccccgataac | 4140 |
| gaaggctgtc tcgtcactgc tttgggtgtc ttgttcgggt ttgggtggct gccattcggc | 4200 |
| tagtttgttg acgagttcgt cgacggggta ggggtcggtt gcgggttggt ggtcgatgat | 4260 |
| tttttgtatg gatcggcctg tttctccgtt ggggagtgtc cattcggaga tgcgtgtgcg | 4320 |
| gcgtacagta ccgttggcta gattgtcgtc gatggtgtcg atggcgttgt cgtggttggc | 4380 |
| tagctgtgtg agtagccggt ctatattgtc tatcactggt tttcctcctc tggcggggtg | 4440 |
| gtgttggctt gtttgcggcg gtagtctttt ataacggtgg cggagatggg gtatcctgcc | 4500 |
| tgggtgagct gttttgctag ccacgaggcg ggtatagacc tgtcggcgag gacgtctgca | 4560 |
| gccttgttgc cgtagcgttg aataagggtt tcagttttgg ttgccatgat gtcctatcgg | 4620 |
| ttgtgtggcg ggctgccatc ctgtgcggca gtcgccgtcg tggcctggtt tgcgtgtgca | 4680 |
| ccacgatacg gttccgtctg tgtggttgag tgttttgccg cacatgacgt tttgtagatg | 4740 |
| ctcgggcagg gcgccgtcac cctgttgct ggtttgtgtg tcgaagagtg ttttctggtt | 4800 |
| ggtgaaatgc tctgacacgg tgccgttgtg tacgggtagt atccatgttt tccattgttg | 4860 |

```
ttgtagccgg gtgttccagt ggaattgttt ggccgcgttc gtggcttgtt tgatggtttt    4920
gtagtagccg acgaggatgc gctggtgttc actgtcgggt gggttttggc ctcgccagta    4980
ttgtgccgcg acggcatacc tgttgttgtc tgtgaaggcg tcccagcagt attcgataat    5040
gtgttgtagt acactatcgg gaatgtctcg tacttggttt tcgtcgagcc acgcgtcgac    5100
aatgatgttg cgtatggcgt gttttgtcttt ggtggtgggt ttgaacgaga tactcaccat    5160
gctggcctgt cgtcttgcat gaaatcgtta aaggatgatt cgcttgtgcg gcgtgcctgg    5220
gtgatttgct ggtcagtcca gtcggggtgt tgctgtttca gatagtacca gcggcaggca    5280
tcatatgttt cgttctgcaa gcgggtgaga tggttttcgg tgatgatttg tttccacatt    5340
gtccacgaga cgtcgagcct gcggagcatg tccatggccg gcacattaaa cgagtcaagg    5400
aagagtattt cgtgggtgta gtagtttttc tcgtaggcgt accatccgct tcggtgcctg    5460
tggggctggt ttttggggta ggcttcccgg catactttgt gtaaacgttt ggccatgtcg    5520
tcgggtagtt caatgtcggg gttggcgcgg atcatggatc gcatcccgtc gtaggtggtg    5580
ccccaggtgt gcatgatgtg tagtgggttg tctccatcgg cccattttc tgcacagatg    5640
gcgaggcgga tgcgcctcct ggctgtttgg ctggtgttgc gccggttggg gattgggcac    5700
gtgtcgaggg gatccattat gttttagtgt acctttctgg tttcgtgttg ttgacgtgtt    5760
ttactgtagc acagtgtcta gtgcttgtgt caaccctgtt tttccggcct gcaggtaggt    5820
gtctgtgaca tctccgaccg tgaggggcac atgggtggct tgggggagtg ctgcctggat    5880
ggtttgtgcc atctggtcgc ctgcggggtc tgggtctgac cagatgtaga tgtggtcgta    5940
gccttcgaag aatttggtcc agaagttttg ccacgaggtt gcgccgggta gggctacggc    6000
cggccatccg cattgttcga ggatcatgga gtcgaattcg ccttcgcaaa tgtgcatttc    6060
ggctgccggg ttggccatgg cggccatgtt gtagatggag cctgtgtccc cggctggggt    6120
caagtatttg gggtggttgt gggttttgca gtcgtgtggg agtgagcagc ggaaacgcat    6180
ttttcgtatt tcggctggcc gctcccaaac ggggtacatg tatgggatgg tgatgcactg    6240
gttgtagttt tcgtggcctg gtatggggtc attgtcgatg tatccaaggt ggtggtagcg    6300
ggctgtttct tcgctgatgc ctcttgctga gagcaggtcg agtatgtttt cgaggtgggt    6360
ttcgtagcgg gctgaggctt tctggattcg gcggcgttcc gcaatgttgt agggttgtat    6420
gctgtcgtac attcgggttt tcttcttcta gtcgttgttg tagtttgtgg agtcctcctc    6480
cgacaccgca tgtgtggcag taccagacgc ccttgtcgag gttgatgctc atggagggct    6540
ggtggtcgtc gtgagcgggc cagagtatgt gttgctcgtt tttggacggg ttgtagcgta    6600
tctggtagat gtcgaggatg cggcgggtgt cagaggtgtg ggaggagctc gttgagggtt    6660
gataccacat aggcttcgct ccagggtttg ttgcgttgtt tcatcactac gagtccgatg    6720
gtggaattgt tttcgcggtt tcggtgtgtt tcgtagttgc gtgcctcccg gctggcttgt    6780
ttcacgaatt cggctaggtg gggctggccg gctttcgcct cgataatgta ggttttgttg    6840
ctggttgtga ggatgaggtc gccttcgtct tcgcggccgt tgaggtggag gcgttcgata    6900
tcgtgtccgg tgtcgcgtag ctggtgcaat aatcgtgttt cccattcggc tccggcccgc    6960
cggttgcgtg cctgctgtgt ggccatagtt tttagagtcc tttgtgtgtt gtggtcatgt    7020
tccagggctg ttttcggcg aggggcccga agaatgtgta ttcggggtag gctcgtagtc    7080
gttcatatcg ggtgccgtcg gggctggatt tgccggtgcg ctgtttcaat actgcgatgc    7140
gtgcctcggc cggtatcgtg agaccgttgc cgttatcctc gccaccatac aatgagactc    7200
ccaatatgag ttgtggtttt tcggagaggc cgttttttgat ttctcgccgt gccgggggt    7260
```

```
gttcgatgtc ggttccggtt ttgtcggtgg cgtggtgtgt gacaataatg gtggatccgg    7320
tgtcgcggcc taatgctgtg atccattgca tggcttcttg ctgtgcctga tagtcactct    7380
cgcagtcttg gatgtccatc aggttgtcga taacaatgag tggcgggaag gtgttccaca    7440
tttccatgta ggcttgcagc tccatggtga tgtctgtcca tgtgatgggt gactggaatg    7500
agaatgtgat gtgttggccg tggtggatgc tgtctcgata gtattctggt ccgtagtcgt    7560
cgatgttttg ttgtatctgt gtggtggtgt gttgggtgtt gagtgagatg attcgtgtgg    7620
aggcctccca gggtgtcatg tccctgata tgtagagggc gggctggttg agcatggcgg    7680
tgatgaacat ggctagcccg gattttggc tgcctgagcg ccccgcaatc atgacgagat    7740
cccctttgtg gatgtgcatg tcctggttgc ggtagagggg ttctagttgt ggtatgcggg    7800
gcagctcggc tgcggtttgg gaggctctct cgaaggatcg ttggagagag agcatcggga    7860
ccttatctat ctatcggttg ggtgtgtttt ggtggtcaga tggagtcgat gtcgatgtca    7920
gcatcggcgg gggttgagca cgaccgcatt gaacccgttt ttggtgcgca cggtggcgag    7980
tttgaaggcc tgctcctcgc caaggtaggc ttcgaggtcg cggatcatgg aatgtgggcg    8040
gtcgttgttg ccgcgcgctt tctcaataat agcgttggga atgatttctg gggtgccgtt    8100
gttgagatcg tctagggtgt ggaagattgt gacatcagcg tagatgcgat cggctgtctg    8160
tccaccgtag ccttcggtgt tgtgttctac gtcgcggatt ttgaaggcga tggcggtggc    8220
gtcctggttt cgggaggggt tgaagaaggt gctgttgctg ttgttgcggt agttggcgag    8280
tcccatggtt gttttccttta ctgtttgtgt tggtttgtgt cggttttatc gggtgaggct    8340
gtttcgtttg ctgcggaaag cctcggacac gtcactgtta ctggtgatga ttttcttgta    8400
ctgtttcaga aggtcggcta gctgtgcctt gcttgttgca ttgttgattt tgtcgatgat    8460
aatctcgttt tcgtttgatg cgatgttgtc tacgtagtct ttggctgcct ggttgtagcg    8520
gtcttggagg atgatggatg cgcttgctac gagtgttgct agatcccagt ctttggacac    8580
gtcaccgttt ttgaggccgc ctagcagatc aataatggat tgtttgatgt cttctgcggt    8640
gtctccgcgg atgactgtcc atggggctgc gtagtctcca ccgtatttga gtgtgatagt    8700 tagcttccg ctgtctgtgg tgtgctcgtc ggtcacgtgt tttcctttc gttgttttcg    8760 gcttctggtg gctgtacggt ggtttctacc gggtatctgt acgagttttt cccgttgacg    8820
gcccagcagg cgtccttgac ggggcatcct ttgcagagtg ctgtgacgtg gggtacgaag    8880
atgccttggc tgattccttt cattgcttga ctgtacatgg atgatacatg ccggtaggtg    8940
ttgttgtcaa gatcaatgag ttcggtggat gtgccctgct caaccgattg ctcgtctccc    9000
ttggtggtag cgggtgtcca aaacattcct ttcgtcacat ggatgccgtg ttggttgagc    9060
atgtaacggt aggtgtgcag ctgcatactg tcggcgggta ggcgtccggt tttgaggtcc    9120
aaaatgaagg tttcacccgt attcgtatct gtgaataccc ggtcgatgta gccaacgatc    9180
tgggtgccgt cggggagggt ggtttctacc gggtattcga tgcccggctc gccgtcaata    9240
acagcggtag catattctgg gtggttgcgc ctccatgttt tccaccggtc cacaaaggtg    9300
gggccgtaaa tcatccacca attgtagtct ttcttgtgtg tcccgcccga ctcgcacatg    9360 ttttttgcata ttctgccgga gggtttgatt tctgtgcctt cggattcggc gagggcgact    9420
tgggtgtcga aaatgttttt gaaggatgag agtttgtctg gcagtgcagg gtattcggcg    9480
ggattgtaca ggtgtaggtc gtattgttcg gtgatgtggt gtatggcgct tccggcgatg    9540
gtggcatacc aggtgtggtg ttgggcgtgg tagccgtggg ataggcgcca tttttcaccg    9600
```

```
cattcggccc actgtgacag tgatgagtag gagatgtggc ctggatggtc aatggtggac    9660 ggttttttgtg ctagggggcat tacttgtcgc ttttgtgggt gttccatggg tttcgggtgt    9720
cttggccggc attgtgttgc tggtatgcga ggagtgcgag gcagtgccag gcagcatggg    9780
ccagatgggg tagcccggat tcatcatcga ggttgttgcc ttgctgccat gataacaggt    9840
gccggtagag ggcgtcaaca ctgtggctcc acggatagcc gccggtccag ttgttgtcgc    9900
cgtatttggt ggcgccgtat ccggccacag agccgagggc gtgtaaggct gtagggtcga    9960
tgagggatag cctgcaaagt ttcaattctt tcttggcgcc agtatcaggg tcggtgtaca   10020
tgctggtggg ctcatccatg gtgtgtgtgc tccttaagta tggggttact ggttggggtt   10080
gtgggcgagt gctacggcaa gaataatgat ggcgaggggtt tcagcgatca gtatgggtgt   10140
tgtgatcatt tgtggtcgcg gggattgttg gtgagggttg aggcgcccag gaggatagtg   10200
agggcgcatg cggcgatgat ggcgagggct gccttgtgtg gggtgccggt ggcgtacatc   10260
catgtgatga tgccgccttg gatccaggcg aggctggtga agaacgtttc gtagctgtgt   10320
agctcaatgt tgttgttggg tgtgttcatg cttgctcctg aagaatggtg ttgatggttg   10380
tgtaaatgtt gtacaggtcg gtttcgatag ataacagttg gtggatttgg tggtcgagat   10440
caatgtcggg gttgagggtg ttgatgcggg aggcgatgtc ggtggctgtg cgtagtgtgc   10500
cgccggtgtg gtgaatgatg tgtgccgtgt cggcgagtcc ggtggtgaca gtgtagtggg   10560
agaggagagg catagctggg ggtgctcctt gacggggtta ctgttgcggg ttgatgttga   10620
ggtcggtgac gttgggggtgg tcttctgttc cggtgacaag gcagtggacg gtgactggga   10680
gtttggatgc gccgggctgt ttcgcggttg cgccgtagac gatggagaag gtgtctttgc   10740
caataatttt gtggagttgg aggtcgatgt cggggttgcc gttccatttg acgccttgtg   10800
tggcggcctg ttgttcggct ttgcggttgc aggtgtgtgc tgcggtgatc atggtgagtc   10860
cggtggcggt ttcttcaccc cttgcttggg cttgcttgtg ggttttctgc tgttcggctc   10920
gcagtgactg ttctgctgct gcctgccgtg cttttcttttc ggctttgcgc tgttgggtag   10980 tcttggggggt ccattcggtg ttggctgtgg tggcttgcgg tgcgggttgt gatgcgagtg   11040
gcggattgtc gtctggggct ggcatgaagg atgctgcggc gatgatgcg gctgtgattc   11100 cggcgatggt gtagccgttt ttcttgttca tgattttgtg ttccccttc cggggtgttg   11160 ttcgttgctg acatgattaa tacttttcagc ggctgggccc actgtcaagg ctgcgctcaa   11220
cgattgtgag cgatacttgt gtggctaggg gttttgtcct tgaggtggga gatgtctttc   11280
ccttgcgtcc agtatccatg gcggttgcga gtcatcccctt tggcgagcat ctcgtccacg   11340
gtgagacacc tgcgacgatc tggacccctcc ttgactccct gatcgcctgt gcggtgcatg   11400
tcaccggcac aagtaccatt aaatgtctcg tggcggatgg tgtgatgctc tggtcggtat   11460
ccgatgattg tgctatcgca cttgtggcat gtccattgca tgattggtcc ttctttcgtg   11520
ttttaagctt gtactctgag gattagagcg actttcagcc cttgggggggt atgattatat   11580 aggtcaggta tttctaggcg attctaggct cattgtgtgt ggctgggggt tatcgggcac   11640
acagggtgag gagttggcca acattgatgc gggtcacatt ccagtagagt tgcgtggctt   11700
ccccaccggt gagtggcttc cactcgtcat ggctgaacac ggtgccgtcg gttgcgatga   11760
atgtgttggg gcgtagcttg tgaagctcag tctctacacg ctgccggtag gcttcggcga   11820
ggccctcgaa atccatgtgg tcgcagggga ggttttcgag gcgtgtcagg tcgaagggtg   11880
tggggcagtc gtagctggcg gggctgtaga gctgggtgaa atggttggcg atcttctgca   11940
tgacgggttc cttttctcgt atggtgagtt gatagttttta tcgggtggat gcgacaagga   12000
```

```
tggcgtctac atcgatcatg tcgatgagat cgtggagttc ctcggcctca ttctcggaga    12060
ggtggcgcca gccatagtcg ccgtatacgg cgccgtcgag ggtgacagtc cacaggggcc    12120
ggatgagtcg tatggcttct tgtactttag cgtggtacat gcggcgcacc atatccagat    12180
cgatgtcgtc tgaatggttt ccggtgaggc tgtagaggct gagcgggtcg atttctgtct    12240
gcctgtagag ggatgtgaat gatggtgtga tgagtgtgcc atccatgaga gtgtgctcct    12300
ttcggtggtg gaggggttgt tgtggttct  agagtgtgta ggctgcgacc catagtcaag    12360
gctgcgctca ttcggattga gcgtttcata tgggtgtggc atggaatcta caccccata    12420 ctgtgtgaga taggccacat cctcctggct tggtgtgaac cctcgagact actctgccta    12480
tctggcgtgg agggtgtagc ccagaaatac cgtttaaagc cttcatacgg cgcctaggag    12540
cgccttacag ggtgggggct aggtatttat accccaagc  aattctgatc gattctagac    12600
gcctcccagg agcccgatac acgatccgct atccagacac agatcatcag cccctatcct    12660
ggttagctaa gcctcaacta tgtggacagt gttgattact gtggggtaag aaggacacgg    12720
taaaagaaag agggggagc  atcggccttc aagccttaag gtcttagcag ttagcaccga    12780 gccctcaag  ggctcgtcgt cagcccatca ggcacggccc tgaacggggt acacgccatc    12840
agggaaggct tgagagtacg aggagcctta gcgacgagta ctcgaaagcc tgagggaaca    12900
ccctcagcac tgatgggtct agcgtgttcg gaaaggacac aggagtaaag cgtgacagct    12960
gtccgggagt gaaacccgtt ctgactaggg gtttcagcct taaccaccct caaaggttac    13020
aagactctaa gaaaatttaa ggaaaagttt aggtttaatt tttggacctt tactaccaaa    13080
aacacccgtt tacacccctc aaacccgcct atagagccaa atccaccagt ttgactcatc    13140
ccaggtggca tatgataggc tggacaggta gccagctgga cgcaaggccg aaatccgctg    13200
acgcggcttt caccttaca  tccatcagtc taccaaagac ttaaagacct aagggcttag    13260
cgctaaggtg ctgatagctt agcaccgagc ccttgagggg ctcggcatca gcccctaaagc    13320 cttaaacact taaagtacat ataaaacttt aaaagcttaa cacttaaggt tataaataaa    13380
cattaaagct ttaaagtctt aaagtacata tataaccttta acacctaagt taagtataaa    13440
accttaaagg cttagcactg aaggatataa acttcacatc agttttaag  actttaaaac    13500 ttaaaataac tattaagact taagactta  taagttttaa acacttaaag taactataag    13560
actttaaaga ccttaagtac ttaaagttaa ccatcagtct taaactttaa tattataacc    13620
tataagtctt aaagcttata agttataaaa gttttagaag agctaagagg ttaacttctt    13680
tacttctctt ctctctttgg ttcttctct  cttctcttct tttcttcatc aggggagaag    13740 aggaacctt  taccatcagc gccgatggac tgtcaccgtg tgactcgtgt accaccggtc    13800
gcacgctccc ggtttcacac tccccacact ctgacacccg tgtccctttc aggcttagcg    13860
tgttcggctg aaggcgtacg gcgtgtcgcg ccaacaccct taacaccagg taagacttaa    13920
agtgtatatt atatgtagaa gactttaaaa cctataaggt gttccccgctt agcctgtgtc    13980 ctacaccgct aggcgccaag cgttaagtct tgaaacgcga acacacaccc accccccattt    14040 ttctttcgtg tccttctctt ttgacaccgc tgggggggcga tgtgatcttt ctcactaccc    14100
ccatgggtag tggagaacac acccaccca  ccatcaacag aacacccct  caaacgaaca    14160 aaacagggcc tagaatcgat cggcagggca agggcaaggt attcataccc ccaacacatt    14220
ccaggccgtc agagaggcaa ataagacccg tacagggcta gtcgaggatc ggagacgtga    14280
tggcacacac caatcgcacc gcatccgccg cacaccgaca ctggcggcaa cgactcatca    14340
```

```
cccaagcccg acagcaaggc caaaccgaat gcccactctg cggagcaacc atcacctggg   14400
acacctacca gctgccaact agccccgaag ccgaccacat cacacccgtc agcaggggag   14460
gactcaacac cctcgacaac gggcaaatca tctgcagaac atgcaacaga agcaaaggca   14520
acagaacaca accaaacatc aaattccaac aacaaaccac aaaaaacctt gttccatggt   14580
gacaaaaccc gccaaccccc accggggaca cccctgcac acccgtgcaa gacctcgtac     14640
ggcttagtga ataccctccc ttttgtggat ttgtctgttt gtcgacttt tgtgttggtg     14700 gtgagtgttg tgcagcctga gcttcctgag ggacacgagt ggtgtgggga gacgcgtcgt   14760
tggtggcgtg tgtggggtga ggatagccgc gcgcagtacg tgtctgatga ggagtggctg   14820
tttcttatgg atgctgcggt gattcatgat tgtgtgtggc gtgagggtcg cgcggatttg   14880
gtggcttcgc ttcgtgctca tgtgaaggct tttatgggta tgttggatcg ttattcggtt   14940
gatgtggcgt ctggtggccg tggtgggggt tctgcggtgg cgatgattga ccggtatagg   15000
aagcgtaggg gggcctgatt aggtgtctgg tgttgttggg tctcaggttc ctcgtcatcg   15060
tgtggctgcg gcgtattcgg tgtctgctgg cggtgatgct ggggagttgg gtcgtgcgta   15120
tgggttgacg cctgatccgt ggcagcagca ggtgttggat gattggctag ctgtgggtgg   15180
taatggcagg cttgcttcgg gtgtgtgtgg ggtgtttgtg cctcgccaga atggcaagaa   15240
tgctattttg gaggttgtgg agttgtttaa ggcgactatt cagggtcgcc gtattttgca   15300
tacggctcac gagttgaagt cggctcgtaa ggcgtttatg cggttgaggt cgttttttga   15360
gaatgagcgg cagtttcctg acttgtatcg tatggtgaag tcgattcgtg cgacgaatgg   15420
ccaggaggct attgtgttgc atcatccgga ttgtgccacg tttgagcgta agtgtggttg   15480
tccgggttgg ggttcggttg agtttgtggc ccgttctcgt ggttctgctc gcgggtttac   15540
ggttgatgat ttggtgtgtg atgaggctca ggagttgtcg gatgagcagt tggaggcgtt   15600
gcttcctacg gtgtctgcgg ctccttcggg tgatcctcag cagattttct tgggtacgcc   15660
gcctgggccg ttggctgacg ggtctgtggt gttgcgtttg cgcgggcagg ctttgtcggg   15720
tggtaaaagg tttgcgtgga cggagttttc tatcccggat gagtctgatc cggatgatgt   15780
gtcgcggcag tggcggaagc ttgctggtga gacgaatcct gcgctgggta ggcgtctgaa   15840
tttcgggacg gtgagcgatg agcatgagtc gatgtctgct gccgggtttg ctcgggagcg   15900
gcttggctgg tgggatcgtg gccagtctgc ttcttcggtg attccggcgg ataagtgggt   15960
tcagtcggct gtggatgagg cggctctggt tggcgggaaa gtgtttggtg tctcgttttc   16020
tcgttcgggg gatcgtgtcg ctttggctgg tgctggccgg actgatgctg gtgttcatgt   16080
tgaggtgatt gatgggctgt cggggacgat tgttgatggt gtgggccggt tggctgactg   16140
gttggcggtt cgttggggtg atactgaccg gatcatggtt gccgggtctg gtgcggtgtt   16200
gttgcagaag gcgttgacgg atcgtggtgt tccgggccgt ggcgtgattg tggctgatac   16260
tggggtgtat gtggaggcgt gtcaggcgtt tttgagggt gtcaggtcgg gtgtggtttc   16320
tcatcctcgt gccgattcga ggcgtgacat gttggatatt gctgtgaggt cggctgtgca   16380
gaagaagaag ggttctgcgt ggggttgggg ttcctcgttt aaggatggtt ctgaggttcc   16440 tttgaggct gtgtctttgg cgtatcttgg tgcgaagatg gcgaaggcta ggcggcgtga   16500
acggtctggt aggaagcggg tgtctgtggt atgaattcgg atgagttggc tctgattgag   16560
ggcatgtacg atcgtatccg aaggttgtct tcgtggcatt gccgtattga gggctactat   16620
gagggctcta gccgggtgcg tgatttgggg gttgctattc ctccggagtt gcagcgtgtg   16680
cagacggtgg tgtcgtggcc tggtattgcg gtggatgctt tggaggagcg tctggattgg   16740
```

```
cttggctgga ctaatggtga cggctacggt ctggatggtg tgtatgctgc gaatcggctt    16800
gctacggcgt cgtgtgatgt gcatttggat gcgctgattt ttgggttgtc gtttgtggct    16860
gttattcccc agggtgatgg gtcggtgttg gttcgtccgc agtcgccgaa gaattgcacg    16920
ggccggtttt cggctgacgg gtctcgtctg gatgctggcc ttgtggtgca gcagacgtgt    16980
gatcctgagg ttgttgaggc tgagcttttg ttgcctgatg tgattgttca ggtggagcgg    17040
cgaggtagcc gtgagtgggt tgagacgggc cgtataccga atgtgcttgg ggctgttccg    17100
ttggtgcctg ttgtgaatcg tcgccgtacg tctaggattg atgggcgttc ggagatcact    17160
cggtcgatta gggcttacac ggatgaggct gttcgcacac tgttggggca gtctgtgaat    17220
cgtgactttt atgcctatcc tcagcgttgg gtgacgggtg tgtcggctga cgagttttcg    17280
cagcctggct gggtcctgtc gatggcttct gtgtgggctg tggataagga tgacgacggt    17340
gacactccga atgtggggtc gtttcctgtg aattctccta caccgtattc ggatcagatg    17400
cgtttgttgg ctcagctgac ggcgggtgag gctgcggttc cggagcgcta tttcgggttt    17460
atcacgtcta acccgccttc tggggaggct ttggctgcgg aggagtcgag gcttgtgaag    17520
cgtgccgagc ggcgtcagac gtcgtttggt cagggctggc tgtcggttgg tttcctggct    17580
gccagggcgc ttgattcgag tgttgatgag gccgcgtttt tcggcgatgt gggtttgcgt    17640
tggcgtgacg cttcaacccc gactcgggcg gctacggctg atgctgtgac gaagcttgtg    17700
ggtgccggta ttcttccggc ggattctcgt acggtgttgg agatgctggg gcttgatgat    17760
gtgcaggttg aggctgtgat gcgtcatcgt gccgagtctt cggatccgtt ggcggcactg    17820 gctgggggcta tatcgcgtca aactagcgag gtttgatagg cgatggcttc gggtgttgcg    17880
tcaaggttgg ctgctgccgg gtatcagcgt gaggcggtca ggtttgccgg gaagtatgcg    17940
ggctattatg ccgagcttgg tcgtttgtgg cattccggga agatgacaga tgcgcagtat    18000
gtgcgtttgt gtgtggagtt ggagcgtgcc ggccatgacg gttcagcggc gttggcgggt    18060
aagttcgtgt cggattttcg gaagcttaac ggtgtggatc ctggtttgat cgtgtatgac    18120
gagtttgatg ctgccgccgc gttggctagg tcgttttcga ctattaagat gatgaatagt    18180
gacccggata gggctaagga tacggttgat gcgatggcgg cgggtgttaa tcgggctgtc    18240
atgaatgctg gccgtgacac ggttgagtgg tctgcgggtg cgcagggtag gtcgtggcgc    18300
cgggtgacgg atggtgatcc gtgcgcgttt tgtgccatgt tggctacgag gtcggattat    18360
acgaccaaag agcgggcgct tactactggt catactcggc gtcataagcg tggcggtagg    18420
cgtccgtttg gttcgaagta tcatgatcat tgtggttgta cggtggttga ggttgttggc    18480
ccttgggagc caaatagggc tgatgccgca tatcagagga cgtatgagaa ggctcgtgag    18540
tgggttgatg atcatgggtt gcagcagtcg cctggcaata tttttgaaggc tatgcgtact    18600 gttggtggca tgagataatt tgatgtggtt ccggttgtg tgccgccggt tatcggtgca    18660
cagggttgtc tcccgcacgg gggtcaacaa tgttgtgttg ttttccgcaa ggagtatagg    18720
gttaggctat ggccgatcaa aaagttgaag aacagaatgt tgacaatgat gctgttgagc    18780
ccggaaaggg tggagacgtt gttgatgttg tgaaggatgg gcaggctgcc ggcgatgatc    18840
atgccggtga tgtttccgtg aaggaggagt cttcttctgg cacggattgg aaggctgagg    18900
ctcgtaagtg ggagtctcgt gctaaaagta atttcgccga gttggagaag cttcgcgcct    18960
cggatggtga tgcgggggtct gtgattgatg agcttcgccg caagaatgag gaactcgaag    19020
accggattaa tgggtttgtt cttgagggtg tgaagcgcga ggtggctgcc gagtgtggcc    19080
```

```
tgtcgggtga tgctgtcgct tttttgcacg gtggcgatcg tgaagcactg gtggagtctg   19140
ctaaggcttt gaagggtttg atcgaccata gtagtggtgg cgcgggtgtg cgccgtcttg   19200
cggggagtgc ccccgttgat gatgttaaac gacgtgaggg tgtcgcgttt gtggatgctc   19260
ttgtcaataa ttctaggaga tgatttgtga tggctgacga ttttctttct gcagggaagc   19320
ttgagcttcc tggttctatg attggtgcgg ttcgtgaccg tgctatcgat tctggtgttt   19380
tggcgaagct ttcgccggag cagccgacta ttttggccc tgttaagggt gccgtgttta   19440
gtggtgttcc tcgcgctaag attgttggtg agggcgaggt taagccttcc gcgtctgttg   19500
atgtttcggc gtttactgcg cagcctatca aggttgtgac tcagcagcgt gtctcggacg   19560
agtttatgtg ggctgatgct gattaccgtc tgggtgtttt gcaggatctg atttccccgg   19620
ctcttggtgc ttcgattggt cgcgccgtgg atctgattgc tttccatggt attgatcctg   19680
ccactggtaa agcggctgcc gctgtgcata cttcgctgga taagacgacg catattgttg   19740
atgccacgga ttctgctacg gctgatcttg ttaaggctgt cggcctgatt gctggtgctg   19800
gtttgcaggt tcctaacggg gttgcttgg atcccgcgtt ctcgtttgcc ctgtctactg   19860
aggtgtatcc gaaggggtct ccgcttgccg gccagcctat gtatcctgcc gccgggtttg   19920
ccggtttgga taattggcgc ggcctgaatg ttggtgcttc ttcgactgtt tctggcgccc   19980
cggagatgtc gcctgactcg ggtgttaagg ctattgtggg tgatttctct cgtgttcatt   20040
ggggtttcca gcgtaacttc ccgatcgagc ttatcgagta tggcgatccg gatcagactg   20100
gccgcgattt gaagggccat aatgaggtta tggttcgtgc cgaggctgtg ctgtatgtgg   20160
ctatcgagtc gcttgattcg tttgctgttg tgaaggagaa ggctgccccg aagcctaatc   20220
cgccggccga gaactgattt attgttgcgg tgatgtgtca atgtgcaggg ggtggtgttg   20280
atgggtatca ttttgaagcc tgaggatatt gagcctttcg ccgatattcc tagagagaag   20340
cttgaggcga tgattgccga tgtggaggct gtggctgtca gtgtcgcccc ctgtatcgct   20400
aaaccggatt tcaaatacaa ggatgccgct aaggctattc tgcgcagggc tttgttgcgc   20460
tggaatgata ctggcgtgtc gggtcaggtg cagtacgagt ctgcgggtcc tttcgctcag   20520
actacacggt ctagtactcc cacgaatttg ttgtggcctt ctgagattgt cgcgttgaag   20580
aagctgtgtg agggtgatgg tggggctggt aaagcgttca ctattacacc gaccatgagg   20640
agtagtgtga atcattctga ggtgtgttcc acggtgtggg gtgaggggttg ctcgtgcggg   20700
tcgaatatta acggctacgc tggcccccttg tgggagatat gatatgacca gttttcctta   20760
tggtgaaacg gttgtgatgc ttcaaccgac tgttcgtgtc gatgatcttg gcgacaaggt   20820
ggaagactgg tctaagcctg tcgagactgt gtaccataac gtggccatat atgcttccgt   20880
ttcgcaggag gatgaggctg cggggcgtga ctcggattat gagcattggt cgatgctgtt   20940
caagcagcct gttgtgggcg ctgattatcg ttgtaggtgg cgtattcggg gtgttgtgtg   21000
ggaggctgac gggtctccta tggtgtggca tcaccccatg tccggttggg atgctggtac   21060
gcaggttaat gtgaagcgta agaagggctg atgggtagtg gctcaggatg tgaatgtgaa   21120
gctgaacttg ccgggtattc gtgaggtgtt gaagtcttct ggagtgcatg gcatgttggc   21180
tgagcgtggc gagcgtgtca agcgtgccgc agcggcgaat gtgggtggta acgcgtttga   21240
tagggcccaa taccgtaatg gtttgtcgtc ggaggtgcag gttcaccgtg ttgaggctgt   21300
ggcgaggatt ggcaccacct ataagggtgg gaagcgtatt gaggcgaagc atggcacgtt   21360
ggcgaggtcg attggggctg cgtcgtgatc gtttacggtg atccgcgtgt gtgggctaaa   21420
cgcgtgctca aggatgatgg ctggctgtct gggataccgt gtacggggac ggtgcctgag   21480
```

```
gatttcagcg gtgacctgat ctggttggcg ttggatggtg gcccacagtt gcatgttcgt    21540
gagcgtgttt ttttgcgcgt gaacgtgttt tcggatacgc cggatcgtgc tatgtcgttg    21600
gcgcgtcgtg tcgaggctgt gctggctgat agtgtggacg gtgaccctgt ggtgtactgt    21660
aaacggtcta ctggccctga tttgctggtt gatggtgcac gttttgatgt gtattcgctt    21720
tttgagctga tatgtaggcc tgcggagtct gaataagctt attgttttg ttttaatgta     21780 attgtttgat atttaatggg ggttatgatg gctgcaacac gtaaagcgtc taatgttcgc    21840
tcagcggtta ctggcgacgt ttatattggt gacgcgcacg cgggtgatac tattaagggt    21900
gtggaggcgg ttccttccgg gcttaccgct ttagggtatc tgtctgatga cgggtttaag    21960
attaagcctg agcgtaaaac ggatgatttg aaggcttggc agaatgcgga tgttgttcgc    22020
actgtggcta cggagtcttc tatcgagatt tctttccagc tgatcgaatc caaaaaagag    22080
gttatcgaac tgttttggca gtcgaaggtt actgccggat ccgattcggg ttcttttgat    22140
atttctcctg gtgccacgac gggtgttcac gctctgttga tggatattgt tgatggtgat    22200
caggttattc gctactattt ccctgaggtt gagctcattg atcgtgacga gatcaagggt    22260
aagaatggta agtgtacgg gtatggtgtg acgttgaagg cgtatcctgc ccagattggt    22320
aagactggta atgcggtgtc tggtcggggg tggatgacgg cttaaaagc tgatactcct    22380 ccttctccga agcctcagcc ggatccgaat ccgccggccg agaactgata cacgatttta    22440
ggggattgtt gatagatgag tgacactggt ttcacgttga agattggtga tcgtagctgg    22500
gtgttggcgg atgctgagga gacggcgcag gctgttcctg cccgcgtttt ccgtcgtgcc    22560
gccaggattg cccagtcggg ggagtctgcg gatttcgccc aggttgaggt gatgttttct    22620
atgttgaagg ctgccgcccc ggctgacgct gtggaggccc tggaggggct tcctatggtt    22680
cgtgtggcgg aggttttccg tgagtggatg gaatataagc ctgacggtaa gggtgcctcg    22740
ctgggggaat agtttggctc cacggcctga ttgatgatta tcgtggggcc atcgaatacg    22800
atttccgcac taaatttggt gtttctgttt atagtgttgg tggcccgcag atgtgttggg    22860
gtgaggctgt ccggctggct ggcgtgttgt gtactgatac gtctagccag ttggcggccc    22920
acctgaatgg ttgcagcgc ccgtttgagt ggtgtgagtg ggctgtgttg gacatgttgg    22980
atcattacag gtctgctaat agtgaggggc agccggagcc tgtggcgagg ccgacggatg    23040
agcgtagggc ccggtttacg tctgggcagg tggacgatat tttggcgcgt gttcgtgccg    23100
gtggcggggt gtctcgcgag attaatatta tggggtgaat agtgtatgtc tggtgagatt    23160
gcttccgcgt atgtgtcgtt gtatacgaag atgcctggcc ttaaaagtga tgttggtaaa    23220
cagctttctg gggtgatgcc tgcggagggt cagcgttcgg gtagcttgtt tgctagcggg    23280
atgaagttgg cgcttggtgg tgcggcgatg atgggtgcca tcaatgttgc taagaagggc    23340
ctcaagtcta tctatgatgt gactattggt ggcggtattg ctagggcgat ggctattgat    23400
gaggctcagg ctaaactgac tggtttgggt catacgtcgt ctgacacgtc ttcgattatg    23460
aattcggcta ttgaggctgt tactggtacg tcgtacgcgt tgggggatgc ggcgtctacg    23520
gctgcggcgt tgtctgcttc gggtgtgaag tctggcgggc agatgacgga tgtgttgaag    23580
actgtcgccg atgtgtctta tatttcgggt aagtcgtttc aggatacggg cgctatttt    23640 acgtccgtga tggctcgcgg taagttgcag ggcgatgaca tgttgcagct tactatggcg    23700
ggtgttcctg tgctgtcttt gcttgccagg cagacgggta aaacgtctgc tgaggtgtcg    23760
cagatggtgt cgaaggggca gattgatttt gccacgtttg cggctgcgat gaagcttggc    23820
```

```
atgggtggtg ctgcgcaggc gtctggtaag acgtttgagg gcgctatgaa gaatgttaag    23880
ggtgccctgg gttatttggg tgctacggct atggcgccgt ttcttaacgg gttgcggcag    23940
attttttgttg cgttgaatcc ggttattaag tctatcacgg attctgtgaa gcctatgttt   24000
gcgtcggtgg atcagggat tcagcgggtg atgccgtcta ttttggcgtg gattaaccgt     24060
atgccgggca tgattacgag aatgaatgca cagatgcgcg ccaaggttga gcagttgaag    24120
ggcgttttg cgaggctgca tttgcctgtt cctaaggtga attttggtgc catgtttgct     24180
ggcggcaccg cagtgttcgg tattgttgct gcgggtgttg ggaagcttgt tgcggggttt    24240
gccccgttgg cggtgtcttt gaagaatctg ttgccgtcgt ttggtgcttt gaggggtgcc    24300
gctgggggc ttggtggcgt gtttcgcgcc ctgggtggcc ctgttggtat tgtgatcggg     24360
ctgtttgctg ccatgtttgc tacgaacgcc cagttccgtg ccgctgttat gcagcttgtg    24420
ggggttgttg gccgggcttt ggggcagatt atggtcgctg tgcagccact gttcgggatt    24480
gttgctggcg tggttgccag gttggcgcca gtgttcggcc agattatcgg tatggttgct    24540
ggtttggctg cccggctggt gcctgttatt ggtatgctta ttgcccggct ggttcctgtt    24600
atcacccaga ttattggtat ggtaacccag gttgctgcca tgttgttgcc tatgctgatg    24660
ccggttattc aggctgttgt tgctgtgata cggcaggtta ttggtgtgat catgcagttg    24720
atacctgttt tgatgccggt tgtgcagcag attttgggtg ctgtcatgtc tgttttgccg    24780
ccgattgttg gtttgatacg gtcgctgata ccggtgatca tgtcgattat gcgtgtggtg    24840
gtgcaggttg ttggtgccgt gttgcaggtg gtgcccgta ttattccggt tgttatgccg     24900
attattgttt cggtgattgg attcattgcc aagatttatg ctgcggttat cgtttttgag    24960
gctaaggtta ttggcgctat tcttcgtact attacgtgga ttgtgaatca ttcagtgtct    25020
ggcgtgaggt ctatgggcac ggccatccag aatggctgga atcatatcaa atcgtttacg    25080
tcggcgttta ttaacggttt caagtcgatc atttctgccg gtgttgccgc ggttgtgggg    25140
ttttttacgc ggcttggttt gtcggttgct tctcatgttc ggtctgggtt taacgcggcc    25200
cgtggcgctg tttcggctgc gatgaatgct attcggagtg ttgtgtcttc ggtggcgtct    25260
gctgttggcg ggttttcgg gtcgatggcg tctagggttc gtagtggtgc tgtgcgcggg    25320
tttaatggtg cccggagtgc ggcttcttct gctatgcatg ctatgggctc ggctgtgtct    25380
agtggtgtgc atggtgtgct agggtttttc cggaatttgc ctggcaatat tcggcatgct    25440
ctcggcaata tggggttctt gttggtgtcg gctggccgtg atgtggtgtc tggtttgggt    25500
aacggtatta agaatgctat gagtggcctg ttggatacgg tgcgtaacat gggttctcag    25560
gttgctaatg cggctaagtc tgtgttgggt attcattccc cgtctcgagt gtttcgtgac    25620
caggttggcc ggcaggttgt tgccggtttg gccgagggga tcaccgggaa tgcgggtttg    25680
gcgttggatg cgatgtcggg tgtggctgga cggctgcctg atgcggttga tgcccggttt    25740
ggtgtgcgat catcggtggg ctcgtttacc ccgtatgaca ggtatcggcg gatgggcgag    25800
aagagtgttg tggtgaatgt gaatgggcct acttatggtg atcctaacga gtttgcgaag    25860
cggattgagc ggcagcagcg tgacgctttg aacgcgttgg cttacgtgtg attggggtg    25920
ttgtgcatgt ttattcctga cccgtctgat cgtgccggtt tgactgttac ctggtctatg    25980
ttgccgttga ttggtaatga tccggagcgt gtgcttcatt tgacggatta tacgggtgcg    26040
tctcctgtca tgttgttgaa tgattcgttg cgcggtttgg gtgttcctga ggtggagcat    26100
ttttctcaaa ctcatgttgg ggtgcacggc tcggagtggc gcgggtttaa tgtgaagcct    26160
cgcgaggtga cattacctgt cctggtgtcg ggtgttggtg tggatccggt tggcgggttt    26220
```

```
cgtgacggtt ttttgaaggc gtatgacgag ttgtggtctg cttttcctcc gggcgaggag    26280
ggggagttgt ctgtgaagac cccgtctggc cgtgagcgtg tgctaaaatg ccggtttgat    26340
tcggtggatg acacgtttac tgtggatccg gtgaacaggg gttatgcgcg ctatctgttg    26400
catttgacag cttatgaccc gttttggtat ggggatgagc agaagtttcg ttttagtaat    26460
gcgaagttgc aggattggtt aggtggcggc cctgtcggca agaagggtac cgcttttccg    26520
gtggtgttga cgcctggtgt tggttcgggt tgggataatc tgtctaatag gggtgatgtg    26580
cctgcgtggc ctgtgattcg tgtggagggc ccgttggagt cgtggtctgt gcagattgat    26640
ggtttgcgtg tgtcttcgga ttacccggtg gaggagtttg attggatcac tattgatacg    26700
gatcctcgca aacagtctgc attgttgaac gggtttgagg atgtgatgga tcgtttgaca    26760
gagtgggagt ttgcccctat cccgcctggc ggttctaaga gtgtgaatat tgagatggtt    26820
ggtttgggtg ccattgttgt gtcggtgcag tacaggtttt tgagggcttg gtgaatagtt    26880
gatggctggt cttgttccgc atgtaacatt gtttacacct gattatcgcc gtgtggcgcc    26940
tatcaatttt tttgagtcgt tgaagttgtc gttaaagtgg aatggtttgt ccactttgga    27000
gttggtggtg tctggtgatc attctaggct tgacgggttg actaggccgg gtgcacggct    27060
ggttgttgat tatggtggtg gccagatttt ttctgggcct gtgcgtcggg ttcatggtgt    27120
gggtccgtgg cgttcttccc atgtgactat cacgtgtgag gatgatattc gtctgttgtg    27180
gcgtatgttg atgtggcctg tggattatcg tcctggtttg gttggtatgg agtggcgtgc    27240
tgaccgggat tatgcccact attcgggtgc ggctgagtcg gtggctaagc aggtgttggg    27300
ggataatgct tggcgttttc cgcctggttt gtttatgaac gatgatgaga gtcgtggacg    27360
gttcattaag gattttcagg tgcggtttca cgtgtttgcc gataagttgt tgccggtgtt    27420
gtcgtgggct cggatgactg tcacggtgaa ccagtttgag aatgcgaagt tgatcagcg    27480 tggtttggtg tttgattgtg tgcctgctgt gacgcgtaag catgtgttga ctgccgagtc    27540
tggttcgatt gtgtcgtggg agtatgtgcg tgacgccccg aaggcgacat cggtggtggt    27600
tggtggccgc ggcgagggca aagatcggct gttttgtgag gatgttgatt cgatggccga    27660
ggatgactgg tttgatcgtg tcgaggtgtt taaggatgcc cgtaacacgg attctgagca    27720
tgtgcatctc attgatgagg ctgagcaggt gttgtccgag ttgggggcca cgtcggggtt    27780
taagatcgag ttggctgagt cggatgtgtt gcggtttggg cccggcaatc tgatgcccgg    27840
ggatttgatc tatgtggatg tgggttctgg ccctatcgca gagattgtgc ggcagattga    27900
tgtggagtgt gagtcgccgg gtgacgggtg gacgaaggtg actcctgttg caggggatta    27960
tgagaataat ccgtcggccc tgttggcgcg gcgtgttgct ggtttggctg cgggtgtgcg    28020
ggatttgcaa aaattctaga aaagattagg ggtttgttgt gggtattgtg tgtaaagggt    28080
ttgatggtgt gttgaccgag tatgattggg ctcaaatgtc tggtctgatg ggtaatatgc    28140
cgtccgtgaa agggccggac gatttcgtg tcggcactac tgttcagggt gccacagtgt    28200
tgtgtgaggt cctgccgggg caggcttggg cccacgggt gatgtgcacg tcgaatagtg    28260
ttgagacggt gaccggccag cttccggcc cgggtgagac ccgatacgac tatgtggtgt    28320
tgtctcggga ttgggaggcg aatacggcca agttggagat tgttcctggg gggcgtgcgg    28380
agcgtgcccg tgacgtgttg agggccgagc ctggcgtgta ccatcagcag ttgttggcta    28440 cttttggtggt gtcgtctaac gggttgcagc agcagctgga taggcgtgct atagcggcta    28500
gggtggcgtt tggcgagtct gctgcgtgtg atcctacccc agtggagggt gaccgtgtga    28560
```

| | |
|---|---|
| tggttccctc tggggctgtg tgggctaatc atgccggcga gtggatgctg ttgtccccca | 28620 |
| ggattgagac gggttctaag tcgatcatgt ttggcgggtc tgctgtgtat gcttacacga | 28680 |
| ttccgtttga gcggccgttt agtagtgcgc ctgttgtggt ggcgtctatg gctacggcgg | 28740 |
| ctggggcac gcagcagatc aatgtgaaag cctacaatgt gactgtccaa aattttagtt | 28800 |
| tggcgtttat tacgaatgat ggttcgaagc cgaatggtgt gcctgcggcg gctaattgga | 28860 |
| ttgctgtcgg cgtgtgactg tacaggtgtt gtggcggatg gtgtgatgtt gggggggctgt | 28920 |
| ggtgtcgtgg tttactcctg cactggtggc ctctatttgt accgcgttgg ccacggtttt | 28980 |
| gggttctgtt caggctgtca catcccggtc taggcggcgc ttacgcaggc tgtctgcgca | 29040 |
| ggtggatgcg atggaagagt atacgtgggg tgtgcggcgc gaggtgcgaa ggtttaacgc | 29100 |
| cgggcttcct gatgatgtgg agccgatgca tcttcctgat gtgcccgagt ttttgaagga | 29160 |
| tactgttgat ggtggaggtg agtaggggttg agggagttgg aggaggagaa gcggcagcgc | 29220 |
| cgcaattttg agaaggcttc cctgatactg ttgtttttgt cgcttgtgtt gttggcggtg | 29280 |
| gttgccgggg gtgctttgcg gtacgggtct gtggcttctc aaagggattc ggagcaggcg | 29340 |
| agggcccagt cgaatggtac agccgctaaa gggttggctg cccgtgtgaa gcaggcgtgt | 29400 |
| acccaggggtg gcgtggagtc tgtgaagctg cacaggtctg gtttgtgtgt ggatgctgtg | 29460 |
| cgtgttgagc agcgtgttca gggtgtgcag ggtcctgccg gtgagcgtgg cccgcaaggg | 29520 |
| cccgctggtg ttgatggccg ggatggtagc aatggttctg ctgggctggt tggccctgtt | 29580 |
| gggccgcagg gttccc | 29596 |

<210> SEQ ID NO 72
<211> LENGTH: 29124
<212> TYPE: DNA
<213> ORGANISM: Artificial Sequence
<220> FEATURE:
<223> OTHER INFORMATION: PAC10

<400> SEQUENCE: 72

| | |
|---|---|
| gggtttagcc agccgtgtgc ggcaggcgtg tgcttcgggt ggggtggagt ctgcgcggct | 60 |
| tcaccggtct ggtttgtgtg tggatgctgt gcgtgttgag cgtagcgtgc agggtgtgcc | 120 |
| gggtcctgcc ggtgtacggg gcccgcaagg ccctgcaggt gctgacggca gggatggtgt | 180 |
| taatggttcg gctgggctgg ttggcccgtgt tggtccgcaa ggttcccctg gcttgaatgg | 240 |
| tgtgaaaggt cctgacgggt tgcctggtgc gaatggatcg gatggccatg atggtgttcc | 300 |
| aggtcgtgca ggtgctgacg gtatgaacgg cgttgacggc agggatggtg ttaatggttc | 360 |
| ggctggtgag cgcggtgatg tgggcccttc aggtcctgcc ggcccgcaag gtgcacaggg | 420 |
| tgaacggggt gagcgcggcc ccgccggtac gaacggatac gatggtaagg atggtaagga | 480 |
| tggccgttct gttgtgtccg tgtactgttc cggggggcagc ctggttgtga aatatagtga | 540 |
| cggtgtggtt tctaccgtat cggactcggc ggcctgccag ggtgtgaaac cgtcgcctat | 600 |
| agtgactata tcatcccaca aatagaaagg agtggctgtg atggtagtgt ttggtggtgt | 660 |
| gtggtgaggt ttattcctgc ggcgcatcac tcaagcggtt cgaatagtcc ggtgaatagg | 720 |
| gttgtgattc atgcgacatg cccggatgtg gggtttccgt ctgcctcgcg taaggggcgg | 780 |
| gcggtgtcta cagcaaacta ttttgcttcc ccgtcttcgg gtggttcggc gcattatgtg | 840 |
| tgtgatattg gggagacggt gcagtgcttg tctgagtcta cgattgggtg gcatgccccg | 900 |
| ccgaatccgc atagtttggg tatagagatt tgcgcggatg ggggttcgca cgcctcattc | 960 |
| cgggtgccgg ggcatgctta cactcgtgag cagtggctgg atcctagggt gtggcctgcg | 1020 |

```
gtggagaagg ctgccatcct gtgtagacgt ttgtgtgaca atataatgt tccgaaaagg    1080 aagcttagtg cagccgattt gaaggctggt aaacgtggtg tttgcgggca tgtggatgtt   1140
acggatgcgt ggcatcagtc ggatcatgat gatcctgggc cgtggtttcc gtgggacagg   1200
tttatggccg tcgtcaacgg cggcagtgga gatagtgggg agttaactgt ggctgatgtg   1260
aaagccttgc atgatcagat taaacaattg tctgctcagc ttactggttc ggtgaataag   1320
ctgcaccacg atgtgggtgt ggttcaggtt cagaatggtg atttgggtaa acgtgttgat   1380
gccctgtcgt gggtgaagaa tccggtgacg gggaagctgt ggcgcgccaa ggatgctttg   1440
tggagtgtct ggtattacgt gctggagtgt cgtagccgta ttgacaggct tgagtcgact   1500
gttaatggtt tgaaaaagtg atggtggtgt gttgtgggta acagttttg gttgggcctg    1560 ttggagcgtc ccctgaaaac ttttattcaa acgtttgttg ctgtgcttgg ggtgacggcg   1620
ggtgtcacgt atactgcgga gtcgtttcgc ggtttgccgt gggagtctgc actgattacg   1680
gctacggttg ctgctgtgtt gtcggtggct acttcgtttg gtagcccgtc gtttgtggcc   1740
ggcaagccta aaccacggt tgtggatgcg ggtttggttc caccggatga tgggggcttg    1800
gttgagccgc atatggttga tgtgtcggat cctggcatga tcgagcctgc agatgatgcg   1860
gatcttggtg taggctatgt gccgaaacac gctgccgagt cggaggttgg gacggtagag   1920
tctactgttg cataattgaa catagatgcg tgccccagcg gtgctgccac gatcgtgtgg   1980
tggttgccgc tggggcacta tttctgttta tgcggtgtgg ctatgattcg ttgcggtcga   2040
tggtgtcttc gagcatctga tacaggtgga ggcaggtaga gatcgtatcg ctggcctggt   2100
ctagaacgtt ccggccgata acgttttgt ggttgtcgcg gtggcggatg atagcccaca    2160
tgatctcgtc ggcctccgct tgtaatagtt ttgcctggta tgcgattccg gcgagccagt   2220
ctagtgcttc ctggcttgca tagggctct ggtcctcgct gttgtcacgg gtgttgctgt    2280
tgtttgtggg gtgtcctgca ctgtcgcata accacaggat ttcgctgcac tcgtctagcg   2340
tgtcctggtc gatagcgaga tcgtcgaggc tgacttcgtt gacggtaagg ttcacgttgt   2400
cgagtgagat gggtacaccg tactggtttt cgacactgtc aacaatgttt tccagctgtt   2460
gcatgttggt gggctgttgt tggacgatac ggtgtatcgc tgtgttgagg gtggtgtagg   2520
tgatattgtg tgtgttgttc atggttttat cccatccctg tgctgtcgtc gttttcgtct   2580
ggatagtatc tactgtttgc gtagcctgtt agggtgatga gtgtttggtc tgcccactgt   2640
ttcacggttt gtcttgtcac cccgagtcgt tgggctgcca ccgaataggt ttgatcatac   2700
ccgtatactt ctctgaatgc tgccagccgt gccaaatgtt ttcgctgttt ggatggctgg   2760
caggtgaggg tgtagtcgtc gatggctagc tgcaaatcga tcatggtgac aatgttgttg   2820
ccgtggtgtt gtggcgcggt tggtggtggt ggcattcctg gttcgacact cggttttccat  2880 gggcctccgt tccagatcca ttgggcggct tggatgatgt cggcggtggt gtaggttcgg   2940
ttcactggta atccttaaac aagtcgttca tgttgctggt gttgctggtg ttgctggtgt   3000
cgaatcgtcc cacacagtgg cagtagtcgt acatgagttt aataatgtgt tggtggtctc   3060
ccaaataggt gttgccgctg atgctgtagg tggctgtgcc gtctttactg atggtgtatt   3120
tggcggtgat ggtttcgggg ttttcggtgt cggtgatgat ggctgtggtg gtggtgccta   3180
cggtttgtag cacggtggtt tgggttccgt cgtcgatggt ggttttaacc atgaggggtt   3240
ctccttttaa atgcttgttt ggttgtcggc tagatgaata atatcggata aaggtttcgg   3300
ctggtctagg tgttgtatgg ttttgttggc tagccgtttg gctaccctgt agcacatttt   3360
```

```
ggtatagtgt tgttgtcta ggttgtggta ttgttcccgc accgcaatat atagtaggga    3420
gtcttgatag aggtcgtctg cactgattgc ggggtagtgt gtggctgttt tggtgcatgc    3480
ccggttgagt gtgcgtagat gatggtttgt ggcccatccc cacgatgcgg tggtggctat    3540
gtctgctttt gttggtcgtc tgctcatggc atctctttca tctggctatc tggtagttgt    3600
ttggtgtttt gttgttgata gtgtagcaca cgagtccggg gtttccggtg gcgcctgtgc    3660
ggtgccggaa ccatgtggat tcgccttcca tggatgggca ttggatgaag gtgcgttggc    3720
cttgctcgga gatttctagg tggtgccggt gcccggccat aggatgtgg gatgtggtgc    3780
cgttgtggaa ttcttggccg cgccaccatt cgtagtgttg gttgttgcgc cattggtggc    3840
cgtgggcgtg caggatttgt gtgccggcca ccccaacggt ggtggtcatt tcgtcccggc    3900
tggggaagtg gaagtgaaga ttgggggtagt tgttgttgag ctggtaggct tctgcgatgg    3960
cccggcagca gtccacgtcg aaggagtcgt cgtaggtggt gactcctttg ccgaagcgta    4020
cggcttctcc gtggttgccg gggattgagg tgatggtgac gttttggcag tggtcgaaca    4080
tgtggatgag ttgcatcatg gccatgcggg tgagcctgat ttgttccgtc aagggtgttt    4140
gggtgcgcca ggcgttgttg cctccttgtg acacgtatcc ttcgatcatg tcgccgagga    4200
aggcgatgtg gactcgttgc ggctgtcctg cctgttgcca gtagtgtttt gctgctgtga    4260
gggagtgcaa atagtcgtcg gcgaagtgtg ctgtttctcc gttggggatg cctttgccga    4320
tttggaagtc tcccgcccct accacgaacg caaccttgtt gttgctgcgg gtgtgggtgt    4380
ctggttttgg gggtgtccat tcggctagtt tatcaacgag ttcgtccacg gggtagggt    4440
ctgttgcggg ttggtggtcg atgatttttt gtatggatcg gcctgtttct ccgttgggga    4500
gtgtccattc ggagatgcgt gtgcggcgta cggtgccgtt ggctagattg tcgcagatgg    4560
tgtctgcttc gctatcgtgg ttggctagct gtgtgaggag ccggtctata ttgtctatca    4620
ctggttttcc tcctcttgcg gggtggtgtt ggcttgtttg cggcgatagt ctttaataac    4680
ggtggcggag atggggtatc ctgcctgggt gagctgtttt gctagccatg aggcggggat    4740
ggttttgtcg gcgagcacgt ctgcagcttt gttgccgtag cgttgaataa gggtttcagt    4800
tttggttgcc atgatgtggt tttgtcggcg agcacgtctg cagctttgtt gccgtagcgt    4860
tgaataaggg tttcagtttt ggttgccatg atgtcctagg ggttgtgtgg tgggctgcca    4920
tcctgtgcgg cagtcgccgt cgtgtcctgg tttgcgtgtg caccacgata cgttgccggc    4980
attgtggatg atggcacggc cgcatatgac gtcacgtaga tgctcgggaa acttgtcgtt    5040
gttgtttccg ttcgtgtcga tcaagtgttg ggttttagta accatcatgt ctcctatgtg    5100
tgaaagagtg tgcaaatact atgcaggtgt catggatgtt tatgcgggta tggttttcat    5160
caccttgctg aatgtgactt ggttactgta catcatctgg gtgatttcct gatcggtctt    5220
gtcggggtgc tgctttcgca ggttcgccca ttggcaggcg ttgtcggtct cttgctggag    5280
ccgggtcagg tgctgctcgt tgatgatgtg tttccacatt gtccacgaca cgtcgagcct    5340
gcggagcatg ttcatggctg gcacgttaaa cgagtcgagg aagagtattt cttcggtgta    5400
gtactgtttt tcgtattggt cccatccgct tcggtgcctg ttgggctggt ttttgggta    5460
ggcttcccgg catactttgt gtaaccgttt ggccatgtcg tcgggtagtt taatgtcggg    5520
gttggcgcgg atcatggatc gcatcccatc gtaggtggtg ccccagcggt gcatgatgct    5580
gagtgggtct tcaccatcgg cccatttttc tgcacagatg gcgaggcgta tgcgcctcct    5640
ggcggctttg ctggtgtcgc ggcggccggg gatgggcac gtgtcgagag gatccatgat    5700
gttttatatg cctttctttg tttggtttgc ttgtgtggtt ttattgtagc actgtgtcta    5760
```

```
gtgcttgtgt caaccctgtt tttccggcct gcaggtaggt gtctgtgaca tcgcccaggg    5820 tgagggcac gtgtatggct tgggggagtg ctgcctggag ggtttgtgcc atctggtggc     5880
ctgccttgtc tgggtcggac cagatgtaga tgtggtcgta gccttcgaag aatttggtcc    5940
aaaagttttg ccacgaggtt gcgccgggta gggcgacggc cgaccatccg cattgttcga    6000
ggatcatgga gtcgaattca ccttcgcaaa tgtgcatttc tgctgccggg ttggccatgg    6060
cggccatgtt gtagatggag cctgtgtcac cggccggggt taggtatttg ggtggttgt     6120 gggttttgca gtcgtgcggg agtgagcagc ggaaacgcat ttttcttatt tcggctggcc    6180
gcccccaaac gggtacatg tatgggatgg tgatgcactg gttgtagttt tcgtggccgg     6240 gtatgggtc attgtcgatg tatccaaggt ggtggttgcg ggctgtttct tcgctgatgc     6300
ctcttgctga gagcaggtcg agtatgtttt cgaggtggg ttcgtagagg gccgaggctt     6360
tctggattcg gcggcgttcc gcaatgttgt atgggcgtat gctgtcgtac attcgggttt    6420
tctttctcta gttgttgttt cagttgggcg agtccgcctc cgataccgca tgtgtggcag    6480
taccagacgc ccttgtcgag gttgatgctc atggagggct ggtggtcgtc gtggaatggg    6540
cagaggatgt gttgctcgtt cctggatggg ttgtaacgga tgcggtaggt gtcgaggagg    6600
cggcaggtgt cagaggtgtg ggaggagctc gttgagggtt gataccacat aggcttcgct    6660 ccaggggtttg ttgcgctgtt tcatcactac gagtccgatg gtggactggc tttctcggtt   6720
tcggtgggtt tcgtagttgc gtgcctccag gctggcttgt ttcacgaatt cggctaggtg    6780
gggctgcccg gctttcgcct cgataatgta ggttttatgg ccggttgtga ggatgaggtc    6840
gccttcatcc tctttaccgt tgaggtggag gcgttctata tcatagccgg tgtcgcgtag    6900
ctggtggagg agtcttgttt cccattcggc cccggcccgc cggttgcgtg cctgctgtgt    6960
aaccatcata gtcctttgtg tgttgtggtc atgttccagg gatgttttc ggcgagtggc     7020 ccgaagaatg tgtattcggg gtaggctcgt agccgctcat attttgttcc gtctgggctg    7080
gatttgccgg tgcgctgttt caacactgcg atgcgcgcct cggctggtat cgtgagcccg    7140
ttgccgttat cctcgccacc ataaagtgag actcccaata tgagtgtgg ttttcggag      7200 aggccgttt taatttcccg tctagctggc gggtgttcga tgtcggagcc ggttttgtcg     7260
gttgcgtggt gtgtgacaat aatggtggag ccagtatccc tgcccaatgc tgtgatccat    7320
tgcatggctt cttgctgtgc ctggtagtcg gattcgcagt cttgaatgtc catcaggttg    7380
tcgataacaa tgagtggtgg gaaagtgttc cacatttcca tgtaggcttg tagctccatg    7440
gtgatgtcgg tccaggtgat gggtgactgg aatgagaagg tgatgtgttg gccgtggtgg    7500
atgctgtctc gatagtattc tggcccgtag tcgtcgatgt tgtgttgtat ctgtgtggtg    7560
gtgtgttggg tgttgagtga gatgattcgt gtggaggcct cccagggtgt catgtcccct    7620
gatatgtaga gggcgggctg gttgagcatg gcggtgatga acatggctag cccggatttt    7680
tggctgccgg agcgccccgc gatcatgacc aaatccccctt tgtggatgtg catgtcctgg    7740
ttgcggtaga ggggttctag ttggggtatg cggggcagct cggctgcggt ttgggaggct    7800
ctcgcaaagg atctttggag agagagcatc ggagccttta tctatcgatc ggttggatgt    7860
gttgtggtgg tcagatggag tcgatgtcta catcatcact atcagtggtg ttgggctggc    7920
tgtctcgccg atcaacgtag gctgctacaa ggtcgtagat ggcgtcgtcc aatggtttga    7980
gcacgaccgc gttgaacccg tttttagtgc gcacctgatc gagtttgaag gcctgctcct    8040
cgccaagata tgcctctaaa tcgcggatca tggagtgtgg gcggtcgttg ttgcctcgca    8100
```

```
cttttttcgat aatggcgttg gggatggttt ctggggtgcc gttgttgagg tcgtctaggg    8160
tgtggaagat ggtgacatca gcgtagatac gatcggcgac ctgtccaccg tagccttcag    8220
tgttgtgctg aacgtcgtgg actttgaagg cgatggcggt ggcgtcctgg tttcgggagg    8280
ggttgaagaa ggtgctgttg ctgttgttgc ggtagtttgc gagtcccatt attgtttcct    8340
ttactgtttt gttggtttgt gtcggttttt atcgggtgag gctgtttcgt ttgctgcgga    8400
aagcctcgga aacgtcactg ttactagtga tgatcttttt gtactgtttc agtagatcgg    8460
ctagctgtgc tttgcttgtt gcattgttga ttttgtcgat gatggtgttg tttccttctg    8520
aggcgatgtt gtctacgtag tctttggcgg cctggttgta tcggtcttgg aggatgatgg    8580
atgctgtggc gatcagtgtt gccaggtccc agttccttgc cgcggagctg tttttgagtc    8640
cgcctaacag gtcgatgatg gctttcttta cctggtcggc ggtgtctcct cggatgacgg    8700
tccatggggc ggcgtagtct ccgccgtatt tgagggtgac ggtgaatcgg tcgtcgtctg    8760
tgttgtcggt cactggtgct ccttgtcttc ttgtgttggg gctgtgatgg tggtttctat    8820
agggtacctg taggcgtctt tcccgttgac ggcccagcag gcgtctctga cggggcatcc    8880
tttacagagt gctgtgacgt gtgggacgaa gatgccttgg ctgattccttt tcattgcttg    8940
actgtacatg gatgatacat gccggtaggt gttgttgtca aggtcgtaca gttcggtggc    9000
cgttccctgc ttggcggact gttttgtctgt tttggttgat gcgggtgtcc aaaacatgcc    9060
ttttgtcaca tcgttgccgt gttgggcgag catgtaccgg taggtgtgca gctgcatgct    9120
gtctgctggt aggcggccgg ttttgaggtc gaggatgaag gtttcgccgg tgtcggtgtc    9180
ggtgaagata cggtcgatgt agccaacgat ctgggtgccg tcctggaggg tggtttctac    9240
cgggtattcg atgcctggct ggccgtctag gactgctgtg tggtattgcg gattgtttgt    9300
gcgccagtgt ttccaccggt cgacgaaggt ttgcccgtaa accatccacc agtcgtagtc    9360
tttttgtgt ggcccgcccg actcgcacat gttttttgcac accctgccgg agggtttaat    9420
ctccataccc tctgatcggg tgagggcgac ttgggtgtcg aaaatgtttt tgaaggatga    9480
gagtttgtct ggcagtgcag ggtattcggc ggggttgtac aggtgtaggt cgtattgttc    9540
ggtgatgtgt tgtatggcgc ttccggcgat ggtggcgtac caggtgtggt gttgggcgtg    9600
gtagccgtgg gataggcgcc atttttctcc gcattcggcc cactgtgaca gtgatgagta    9660
ggagatgtgg cctggatggt ggatggtttt cggatattgt gctagaggca ttacttgtcg    9720
cttttgttcc atgggttgcg ggtgtctacc ccggcattgt gttgctggta tgcgaggagt    9780
gctaggcagt gccaggcagc atgtgccagg tggggtagcc cggattcata atcgaggttg    9840
tttccttgct gccaggatag cacatggcgg tagagggcgt caacgctgtg gctccacgga    9900
tagccgccgg tccagttgtt gtcgccgtat ttggtggcac cgtagcctgc aacctcgccg    9960
agggcgtgta aggctgcggg gtcgatgagg gagagcctgc aaagtttgag ttctttcttg    10020
gcgccagtat cagggtcggt gtacatgcgg gtgggctcat ccatggggtg tgtgctcctt    10080
aagggtgggt tactggttgg ggttgtgggc gagtgctact gcgagaataa tgatggcgag    10140
ggtttctgcg atgaggatgg gtgttgtgat catttgttgt ctcgggggatt gctggtgagt    10200
gtggaggcgc ctaggagggt ggtgagggcg catgcggcga tgatggcgag ggctgccttg    10260
tgtggggtgc cggtggcgta catccatgtg atgatggcgc cttggatcca ggcgaggctg    10320
gtgaagaacg tttcgtagct gtgtagctcg ctgttgttgc tggtgatgtc attcatggta    10380
gttttctgct ttgtgtgcga tggttgtgta catgtcgttg agtgtggttt cgatggtgat    10440
gagagtgttg atttcttggt tgaggtcgat gttgtctttg agggtgtcga tgcgggcggc    10500
```

-continued

```
gatgtcggtg gcggtgcgta ggcttactgc tgcaccgtgg atgatgtggc acatgtcggt    10560
gaggccgacc ttggcgatat agtgtgacat gagaggcatg atgggtgtgt cgtctttctg    10620
gtcagcgtga cgggttgatg gacatgtctt ctacctgtgg cttgtcttcg gtgcctgata    10680
cttggcaaaa gactttcacg tgcgccttgg atgctccggg ttgcttggcg gtggcaccgt    10740
aggcgatagt aaaggcgtct ttgtgggcgc cgatgacttt gtgtaggaag aggtcgatgt    10800
cggggtttcc gttccatttg acaccgtttt ctgcggctgc ctgggtggct ttctggttgc    10860
aggcgtgtgc tgccgtaatc atggtgagtc cggtggcggt ttcttcaccc cttgcttggg    10920
cttgcttgtg ggttttgct tgttcggctt gtagggagcg gactgcggct gcctgccgtg    10980 ctttctttc ggctttgcgc tgctgggtag tcttgggggt ccattcggtg ttggctgtgg    11040
tggcctgtgg ggctggctgt gaggcgagtg gcggattgtc gtctggggct ggcatgaatg    11100
aggcggcggc aatgatggcg gctgtgattc cggcgatggt gtagccgttt tcttgttca    11160 tgactgttgt cccctttccg gggtgttgtt cgttgctgac atgattaatc atggtgtgga    11220
cggttcccca tgtcaaggct gcgctcaacg attgtgagcg tttggtgtgt ggctaggggt    11280
tttatcgggc acacagggtg agtagatggc caacattgat gcggctcaca ttccagtaga    11340
gttgtgtggc ttcaccgccg gtgagcggct tccactcgtt gtggctgaac acggtgccat    11400
cggatgcgat gaatgtgtcg gggcgtagct tgtgaagctc ggcttccacg ctctgccggt    11460
aggtttcggc gaggccctca aaatccatgt ggtcgcagga gaggttttcg aggcgtgtca    11520
ggtcgaaggg tgtggggcag tcgtagctgg cggggggtgta gagctgggtg aagtggttgg    11580
cgatcttctg catgatgatg tccttttggt tgctgataac cttgttgagg gtttatcggg    11640
tggatgtgat aaggatggcg tccacgtcga tcatgtcgat gagatcgtgg agttcctcgg    11700
cctcgttttc ggtgagtggc tgccagttgt tgtcgccgta cacggcgccg tcgagggtga    11760
cagtccacag tggccggatg aggcgtacgg cttcttgtac tttagcgtgg tacatgcggc    11820
gcaccatatc cagatccatg tcgtctgaat ggtttccgat gaggttgtgg aggctgagcg    11880
ggtcgatttc tgtctgcctg tagagggatg tgaaggatgg ggtgatgagt gtgccatcca    11940
tgggtgatgt tcctttctgg attgtcttgg ttggttgttg tggtttctag agtgtgcggg    12000
ttgcaaccgg gagtcaaggc tgcgctcatt cggattgagt gtttcatgct ggagtgtcgg    12060
gtgtgacaga tgtcacttaa gcctttattg cctctctcgg cgtctcacat catctggggg    12120
taagattatg cagggttgac cctgctgatc gattctaggg cccttctagg gcgtctcagg    12180
ggtacgtctg ggtgatagcg ggtgtggcag atgatctagc gagtcaaggt accgagctta    12240
gacgtaagat ctatcatcta ggcgtgtgag atgtatcaca tcctcctggc tgggtgtgca    12300
ccctcaaggc tactctgccg atctggcgtg gagggtgtag cccagaaatg ccgttaaag    12360 ccttcacatg gcgcctagaa gcgccttgca gggtgggggc taggtattta tacccccaac    12420
acattctgat cgattctaga cgcctatagg agcctgatac acgatcaacc atctcggcat    12480
agatcatcag cccctatcct agttagctaa gcctgaacta tgtggacagt gtaggatgct    12540
aagagggaag aaggacacgg taaaagaaag agggggggc atcaaccttc acgcccgagg    12600
tacttaagtt aaccttaggg tcttagcacc gagcccctca agggctcggc atcagcatca    12660
tcgggatcag ccgatccggc acagccttag caagtacaca ccatcaggga aggcttgaga    12720
gtacgaggag ccctagcgac gagtactcga aagcctgagg gaacaccctc agcactgatg    12780
ggcctagcgt gttcggaaag tacacagggg tacagtgtga gagctgttcg ggagctaaac    12840
```

```
cccttccggc tagggcaaac accagtccta gactatccca caccctcatc tgttaacctt   12900
ccgttcatta aacgttaagg aaacttttag gtttgatttt tggaccttaa ccaccaaaaa   12960
cacccattta caccctcaa acccgccaat agagccaaac gccggtgttg agggtatctc    13020
tacctagtgt gataggctgg acaggtagcc agctggacgc aaggccagaa agtgctgacg    13080
cacttcccga cctcgcttac catcagtcta ccaaacactt aaaagcttaa cagctaagcg    13140
ctaagccctt aagacctcaa cgcttagcac cgagcccttg aggggctcgg catcagtctt    13200
aggtacttaa agtaacttta aaccttaaag gcttagcact taaggatata aacttaacat    13260
cagtgtttaa gactttaata ctttaagtaa ctataagacc ttaaagcttt aaacacttaa    13320
agttaaccat cagtcttaaa ctttaatatt ataacttata agctttaata cttatattat    13380
attataacct ataagtctta aagcttatag gttataaaag ttttagaaga gctaagaggt    13440
taacttcttt acttctctac tctctttggt tctttctctc ttctcttctt ttcttcatca    13500
ggggagaaga ggaatcttta ccatcagcgc cgatgacctt tcaccgtgtg gatcgtgtgc    13560
ttctggtcgc aagctcccat cgcacactcc ccacactctt acaccgtgt ccctttcggg     13620 cttggcgtgt tcggctaaag gcgtacggcg tgtcacgcta acaccttaa caccgggtaa     13680 gacttaaagt gtatattata tgtagaagac tttaaaacct ataaggtgtt cccgcttagc    13740
ccgtgtccta caccgctagg cgccaagcgc taagccttga aacgcgaaca cacacccacc    13800 ccctttttc ttccgtgtcc ttctcttttg acaccgctgg ggggcgatgt gatctttctc     13860
acacccatgg gggtagtgga gaaaacaaac accccggcac aaacagaaca cccctcaaa    13920 cgaacaaaac agccccccag aatcgaccag cagggcaagg gtagagtatc cataccccca    13980
acggtttcca ggccgttaca gaggcaaata agaccccgtac agggctaggc gaggaacaga    14040
cacatcatgg cacgcaccaa ccgcacagcc gccacggcac accgacgctg gcggcaacga    14100
ctcatcaccc aagcccaaca gcaaggccaa accacctgcc cactctgcgg agtcaccatc    14160
acctgggaca cccaccagct accaaccagc cccgaagccg accacatcac acccgtcagc    14220
cggggaggac tcaacaccct agacaacggg caaatcatct gcagaacatg caacagaagc    14280
aaaggcaatc gcagcgaacc aaacatcaaa ttccaacaac aaaccacaaa aaaccttgtt    14340
tcatggtaga aaacctgcca gcccccaccg gggacacccc ctgcacaggc gtgcaagacc    14400
tcgtacggct tagtgaaata cctccctttt gtggatttgt ctgtttgtcg actttttgtg    14460
ttggtggtga gtgttgtgca gcctgagctt cctgatagtc gtgattggtg tggggagacg    14520
cgtcgttggt ggcgtgtgtg gggtgaggat agccgtgcat cgtacgtgtc tgatgaggag    14580
tggttgtttc tccttgatgc ggctgtgatt catgatgtgg tgtggcgtga gggtcgcgcg    14640
gatttggtgg cttcgcttcg tgctcatgtg aaggctttta tgggtatgtt ggatcggtat    14700
tcggttgatg tggtgtctgg tggccgtgcc ggtggttctg cggtggcgat gattgatcgg    14760
tataggaagc gtaaagggc ctaatgtcga gtgttgttgg ttctcaggtt cctcgtcatc     14820
gtgtggctgc ggcgtattcg gtgtctgctg gtggtgatgc tggggagttg ggtcgtgcgt    14880
atgggttgac gcctgatccg tggcagcagc aggtgttgga tgattggctg gctgtcggta    14940
gcaatggcag gcttgcttcg ggtgtgtgtg gggtgtttgt gcctcgccag aatggcaaga    15000
atgctatttt ggaggttgtg gagttgttta aggcgactat tcagggtcgc cgtattttgc    15060
atacggctca cgagttgaag tcggctcgta aggcgtttat gcggttgagg tcgtttttg     15120 agaatgagcg gcagtttcct gacttgtatc gtatggtgaa gtcgattcgg gcgacgaatg    15180
gtcaggaggc tattgtgttg catcacccgg attgtccgac ttttgagaag aagtgtggct    15240
```

```
gcagcggttg gggttcggtt gagtttgtgg cccgttctcg gggttctgct cgcgggttta   15300
cggttgatga tttggtgtgt gatgaggctc aggagttgtc ggatgagcag ttggaggcgt   15360
tgcttcctac ggtaagtgct gccccgtctg gtgatccgca gcagattttc cttggtacgc   15420
cgcctgggcc gttggctgat ggttctgtgg tgttgcgttt gcgtgggcag gcgcttggtg   15480
gcggtaaaag gtttgcgtgg acggagtttt cgattcctga cgagtctgat ccggatgatg   15540
tgtcgcggca gtggcggaag ttggcggggg atacgaatcc ggcgttgggg cgtcgcctga   15600
attttgggac cgtaagcgat gagcatgagt cgatgtctgc tgccggtttt gctcgggagc   15660
ggcttggctg gtgggatcgt ggccagtctg ctgtgtctgt ggttcctgct gataagtggg   15720
ctcagtctgc ggtggatgag gcgagtctgg ttggcgggaa agtgtttggt gtctcgtttt   15780
ctcgttctgg ggatcgggtt gctttggcgg gtgccggcaa gactgatgct ggggttcatg   15840
ttgaggttat tgatgggctg tcgggaacga ttgttgatgg tgtgggccgg ttggcggact   15900
ggttggcggt tcgttggggt gatactgacc ggatcatggt tgccgggtct ggtgcggtgt   15960
tgttgcagaa ggcgttgacg gatcgtggta ttccgggccg tggcgtggtg gttgctgata   16020
ctggcgttta tgtggaggct tgtcaggcgt ttcttgaggg tgtcaggtcg ggtgtgatca   16080
gtcatcctcg tgctgattct cgccgtgaca tgttggatat tgctgtgagg tcggctgtgc   16140
agaagcgtaa ggggtctgcg tggggttggg gttcctcgtt taaggatggt tctgaggttc   16200
ctttggaggc tgtgtctttg gcgttttggg gggctaaacg tgttcgtcgt ggccgtcggg   16260
agcgtagtgg taggaagcgg gtgtctgtgg tatgaactcg gatgagttgg ctctgattga   16320
gggcatgtac gatcgtatcc aaaggttgtc ttcgtggcat tgtcgtattg agggctacta   16380
tgagggctct aatcgggtgc gtgatttggg ggtggctatt cctccggagt tgcagcgtgt   16440
gcagacggtg gtgtcgtggc ctggtatagc tgtggatgct ttggaggagc gtctggattg   16500
gcttggctgg atgaatggtg acggctacgg cctggatggt gtgtatgctg cgaatcggct   16560
tgctacggcg tcgtgtgatg tgcatttgga tcgctgatt tttgggttgt cgtttgttgc   16620
gataattcct catggtgatg gtacggtgtc ggttcgtccg cagtcaccaa agaattgtac   16680
gggcaagttt tcggctgacg ggtctcgttt ggatgctggt ttggtggtgc agcagacgtg   16740
tgatcctgag gttgttgagg ctgagctttt gcttcctgat gtgattgttc aggtggagcg   16800
gcgtggttcg cgtgaatggg ttgaggtgga tcgtataccg aatgtgttgg gtgcggttcc   16860
gttggtgcct attgtgaatc gtcgccgtac ttctaggatt gatggccgtt cggagattac   16920
gaggtctatt agggcttaca cggatgaggc tgtgcgcaca ctgttggggc agtctgtgaa   16980
tcgtgatttt tatgcgtatc ctcagcgttg ggtgactggc gtgagcgcgg atgagttttc   17040
gcagcctggc tgggtcctgt cgatggcttc tgtgtgggct gtggataagg atgatgacgg   17100
tgacactccg aatgtggggt cgtttcctgt caatagtcct acaccgtatt cggatcagat   17160
gagactgttg gcgcagttga ctgcgggtga ggcggctgtt ccggaacgct atttcggttt   17220
tatcacgtct aacccaccta gtggggaggc tttggctgcc gaggaatctc ggcttgtgaa   17280
gcgtgctgag cggcgtcaaa cgtcgtttgg tcagggttgg ctgtcggttg gttttttggc   17340
tgccaaggcg ttggattctc gtgttgatga ggccgatttt tttggtgatg ttggtttgcg   17400
ttggcgtgat gcttcgacgc ctacccgggc ggctacagct gatgctgtga cgaagcttgt   17460
tggtgccggt attttgcctg ctgattctcg tacggtgttg gagatgttgg ggcttgatga   17520
tgtgcaggtt gaggctgtga tgcgtcatcg tgctgagtcg tctgaccgt tggcggtgct   17580
```

```
tgctggggct atatcgcgtc aaactaacga ggtatgatag gcgatggctt cggggggttga   17640 ggcgaggctt gcggcgactg agtatcagcg tgaggcggtc aggtttgctg ggaagtatgc   17700
gggctattat tctgagcttg gtcgtttgtg gcgtgccggc aggatgagtg acacgcagta   17760
tgtgcgtttg tgtgtggagt tggagcgtgc cggccatgat ggttcggcat cgttggctgc   17820
caggtttgtg tcggattttc gccggttgaa tggtgtggat ccgggtttga ttgtgtatga   17880
cgagtttgat gctgcggcgg ctttggctag gtctatttcg accacgaaga ttcttgagag   17940
tgacccggat agggcgaatg acacgattga tgcgatggcg gcgggttttg atcgggctgt   18000
tatgaatgct ggtcgtgaca cggttgagtg gtctgcgggt gcgcagggta ggtcgtggcg   18060
tcgtgtgacg gatggtgatc cgtgtgcttt ttgtgccatg ttggctacga ggtcggatta   18120
tacgacaaaa gagagggcac ttactactgg acatactcgg cgtcataagc gtggtggtaa   18180
gcgtccgttt ggttcgaagt atcatgatca ttgtggttgt acggtggttg aggttgttgg   18240
cccttgggaa ccaaataggg ctgatgccga gtatcagagg acgtatgaga aggcccgtga   18300
gtgggttgat gatcatgggt tgcagcagtc gcctggcaat attttgaagg ctatgcgtac   18360
tgttggcggc atgagataat ttgatgtggt ttccggttgt gcgccgccgg ttattggtgc   18420 acaggggttgt ctcccgcacg ggggtcaaca atgttgtgtt gttttccgca aggagtgtag   18480
ggttaggcta tggccgatca gagtgttgag gaacagaatg ttgacaatga tgttgtggag   18540
tccgaaaagg ataacggcat tgttgataca gtaaaagacg atggcggaca ggaggtggcc   18600
gacaatcagt tgaagaatga aggcgagggt aaatcgccgg ggactgattg gaaggcggag   18660
gcccgtaagt gggagtctcg tgctaaaagt aatttcgctg agttggagaa gcttcgcgcc   18720
tcggatggtg atgcggggtc tgtgattgat gatcttcgcc gcaagaatga ggaactcgaa   18780
gaccggatta acgggtttgt tcttgagggt gtgaagcgcg aggtggcttc agagtgtggc   18840
ctgtcgggtg atgctgtcgc tttcttgcac ggtagcgatc gtgaagcgct ggtggagtct   18900
gcgaaagctt tgaaggggttt gatcgaccat agtagtggtg gcgcgggtgt gcgccgtctt   18960 gcgggggagtg cccccgttga tgatgttaaa cgacgtgagg gtgtcgcgtt tgtggatgct   19020
cttgtcaata attctaggag atgatttgtg atggctgacg atttctttc tgcagggaag   19080 cttgagcttc ctggttctat gattggtgcg gttcgtgacc gtgctatcga ttctggtgtt   19140
ttggcgaagc tttcgccgga gcagccgact attttggcc ctgttaaggg tgccgtgttt   19200
agtggtgttc ctcgcgctaa gattgttggt gagggcgagg ttaagccttc cgcgtctgtt   19260
gatgtttcgg cgtttactgc gcagcctatc aaggttgtga ctcagcagcg tgtctcggac   19320
gagtttatgt gggctgatgc tgattaccgt ctgggtgttt tgcaggatct gatttccccg   19380
gctcttggtg cttcgattgg tcgcgccgtg gatctgattg cttttccatgg tattgatcct   19440 gccactggta aagcggctgc cgctgtgcat acttcgctgg ataagacgaa gcatattgtt   19500
gatgccacgg attctgctac gaccgatctg gtcaaggctg tcggtcttat cgctggtgct   19560
ggtttgcagg ttcctaacgg ggttgctttg gatccggcgt tctcgtttgc tttgtctact   19620
gaggtgtatc ctaagggttc gcctcttgct ggccagccga tgtatcctgc cgccgggttt   19680
gccggtttgg ataattggcg tggcttgaat gttggttctt cttcgactgt ttctggcgcc   19740
ccggagatgt cgcctgcctc tggtgttaag gctattgtgg gtgatttctc tcgtgttcat   19800
tggggtttcc agcgtaactt cccgatcgag cttatcgagt atggtgaccc ggatcagact   19860
gggcgtgacc tgaagggcca taatgaggtt atggttcgtg ctgaggctgt gctgtatgtg   19920
gctatcgagt cgcttgattc gtttgctgtt gtgaaggaga aggctgcccc gaagcctaat   19980
```

```
ccgccggccg agaactgatt tattgttgcg gtgatgtgtc aatgtgcagg gggtggtgtt    20040
gatgggtatc attttgaagc ctgaggatat tgagcctttc gccgatattc ctagagagaa    20100
gcttgaggcg atgattgccg atgtggaggc tgtggctgtc agtgtcgccc cctgtatcgc    20160
taaaccggat ttcaaataca aggatgctgc taaggctatt ctgcgtaggg ctttgttgcg    20220
ctggaatgat actggcgtgt cgggtcaggt gcagtatgag tctgcgggtc ctttcgctca    20280
gactacacgg tctagtactc ccacgaattt gttgtggcct tctgagattg ccgcgttgaa    20340
gaagctgtgt gagggtgatg gtggggctgg taaagcgttc actattacac cgaccatgag    20400
gagtagggtg aatcattctg aggtgtgttc cacggtgtgg ggtgagggtt gctcgtgtgg    20460
gtcgaatatt aacggctacg ctggccctttt gtgggagata tgatatgacc agttttcctt    20520
atggtgaaac ggttgtgatg cttcaaccga ctgttcgtgt cgatgatctt ggtgacaagg    20580
ttgaggattg ggggcatctt gtagaaacag tgtaccataa cgtggccatc tatgcttccg    20640
tttcgcagga ggatgaggcc gcggggcgtg actctgacta tgagcattgg tcgatgcttt    20700
tcaagcagtc tgttgttggt gctgattatc gttgcaggtg gcgtatccgg ggtgttgtgt    20760
gggaggctga cgggtctcct atggtgtggc atcatccgat gtctggctgg gatgcgggca    20820
cgcagatcaa tgtgaagcgt aagaagggct gatgggtagt ggctcaggat gtgaatgtga    20880
agctgaactt gccgggtatt cgtgaggtgt tgaagtcttc tggggtgcag gctatgttgg    20940
ctgagcgtgg cgagcgtgtc aagcgtgcgg cctcggcgaa tgtgggcggg aacgctttcg    21000
ataaggccca ataccgtaat ggtttgtcgt cggaggtgca ggttcaccgt gttgaggctg    21060
tcgctcgtat aggcaccaca tataagggtg ggaagcgtat tgaggcgaag catggcacgc    21120
tggctcgttc gattgggcgt gcgtcgtgat cgtctacgat gacccaggga agtgggctaa    21180
acgcgtgctc aaggatgatg gctggctgtc tgatataccc tgtgtgggga cggtgcccga    21240
tgattttatg ggtgacctgg tttggttggc gttggatggt ggcccgcagt tgcatgttcg    21300
tgagcgtgtt ttttttgcgcg tgaatgtgtt ttctgatacg cctgatcggg ctatgtcttt    21360
ggcgcgtcgt gttgaggctg tgctggctga cggggttgat ggtgatccgg tggtgtactg    21420
taaacggtct actggtcctg atttgctggt tgatggtgca cgttttgatg tgtattcgct    21480
gttcgagctg atatgtaggc ctgtcgaatc cgagtaaacg tatttgtttt tgttttaatg    21540
taattgtttg atatttaatg ggggttgtga tggctgcaac acgtaaagcg tctaatgttc    21600
gttcagcggt tactggcgac gtttatattg gtgacgcgca cgcgggtgat actattaagg    21660
gtgtggaggc ggttccttcc gggcttacag ctttagggta tctgtcggat gacgggttta    21720
agattaagcc tgagcgtaaa acggatgatt tgaaggcttg gcagaatgcg gatgttgttc    21780
gcacggttgc taccgagtct tctatcgaga tttcttttca gctgatcgag tctaagaagg    21840
aggttatcga actgttttgg cagtcgaagg ttactgccgg agccgattcg ggttcgttcg    21900
atatttctcc tggtgccacc actggcgtgc acgctttact gatggatatt gttgatgggg    21960
atcaggttat tcgctactat ttccctgagg ttgagcttat cgatcgtgac gagattaagg    22020
gtaagaatgg cgaagtgtac gggtatggtg tgacgttgaa ggcttaccct gctcagatta    22080
ataagactgg taatgcggtg tcgggtcgag ggtggatgac ggctttaaaa gctgatactc    22140
cccttctcc gaagcctcag ccggatccga atccgccgtc tgagaactga tacacgattt    22200
tagggattgt tgatagatga gtgacacagg ttacacgttg aagattggtg accgtagctg    22260
ggtgttggcg gatgcggagg agacggctca ggctgttcct gctcgcgttt ttcgtcgtgc    22320
```

```
agctaagatt gcccagtctg gggagtctgc ggatttcgct caggttgagg tgatgttttc    22380
tatgttggag gctgcagccc cggctgacgc ggtggaggcc ctggaggggc ttcctatggt    22440
tcgtgttgcc gagattttcc gccagtggat ggagtggaag cctgaaggta agggtgcctc    22500
tttgggggaa tagtttggct ccacggcctg attgatgagt atcgtgggc catcgaatat     22560
gattggcgca caaggtttgg tgtgtgcata tacgatatag gtggtcctgc gatggggtgg    22620
ggtgaggctg tccggctggc tggcgtgttg tgtggtgata cgtcgagcca gttgcggcc    22680
cacctgaatg gttggcagcg cccgtttgag tggtgcgagt gggctgtgtt ggacatgctg    22740
gatcattaca ggtctgctaa tagtgagggg cagccggagc ctgtggcgag gcctacggat    22800
gagcgtaggg gccggtttac gtctgggcag gtggatgata ttttggcgcg tgttcgtgct    22860
ggtggcgggg tgtctcgcga gattaatatt atggggtgaa tagtgtatgt ctggtgagat    22920
tgcttccgca tatgtgtctt tgtatacgaa gatgcctggt ttgaaggcgg atgttggtaa    22980
acagctttct ggtgtgatgc ctgctgaggg tcagcgttcg ggtagtcttt ttgctaaggg    23040
catgaagttg gcgcttggtg gtgccgcaat ggtgggtgcc atcaatgttg ctaagaaggg    23100
cctcaagtcg atttatgatg tgactattgg tggtggtatt gctagggcga tggctattga    23160
tgaggctcag gctaaactga ctggtttggg tcatacgtct tctgacacgt cttcgattat    23220
gaattcggct attgaggctg tgactggtac gtcgtatgcg ttgggtgatg cggcttctac    23280
tgcggcggcg ttgtctgctt cgggtgtgaa gtctggcggg cagatgacgg atgtgttgaa    23340
gactgtcgcc gatgtgtctt atatttcggg taagtcgttt caggatacgg gcgctatttt    23400
tacgtctgtg atggcccgcg gtaagttgca gggcgatgac atgttgcagc ttacgatggc    23460
gggtgttcct gtgttgtctt tgcttgccag gcagacgggt aaaacgtcgg ctgaggtgtc    23520
gcagatggtg tcgaagggc agattgattt tgccacgttt gcggctgcga tgaagcttgg    23580
catgggtggt gctgcgcagg cgtctggtaa gacgtttgag ggcgctatga agaatgtgaa    23640
gggcgccctg ggttatttgg gtgctacggc tatggcccg tttcttaatg ggttgcggca    23700
gattttgtt gcgttgaatc cggttatcaa gtcggtgacg gattctgtga gccgatgtt    23760
tgctgccgtc gatgctggta ttcagcgtat gatgccgtct atttttggcgt ggattaatcg    23820
tatgccgggc atgatcactc gaatgaatgc acagatgcgc gccaaggttg agcagttgaa    23880
gggcattttt gcgagaatgc atttgcctgt tcctaaagtg aatttgggtg ccatgtttgc    23940
tggcggcacc gcagtgtttg tgttgttgc tgccggtgta gggaagcttg ttgcagggtt    24000
tgccccgttg gcggtgtcgt tgaagaatct gttgccgtcg tttggtgctt gaagggtgt    24060
cgctggcggg cttggtggcg tgtttcgcgc cctgggtggc cctgttggta ttgtgatcgg    24120
cttgtttgct gccatgtttg ctacgaacgc ccagttccgt ggcgcggtga tgcagcttgt    24180
gggggttgtt ggccaggctt tggggcagat tatggccgct gtgcagcctg tgtttggttt    24240
ggttgccggt ttggtggccc ggttggcgcc agtgtttgcc cagattatcg gtttggttgc    24300
aggtttggct gcccagctta tgccggtgat tagtatgctt gttgcccggc tggttcctgt    24360
gatcacccag attattggtg cggtgacaca ggttgctgca atgttgttgc ctgcgttgat    24420
gccggtgttg caggctgttg tggctgtgat tcggcaggtt gttggcgtga tcatgcagtt    24480
ggtgcctgtt ttgatgcctg tgattcaaca gattttgggt gctgtcatgt ctgtgctgcc    24540
acccattatt ggtcttatcc ggtcgttgat gcctgtgatt gcggcggtta tgcgtgtggt    24600
ggtgcaggtt gttgcggttg tgatacaggt ggtggcccgt attcttgcgg ttgtggctcc    24660
gatggtggcg gctgtggtag ggtttgtggc ccgtattgtt ggtgctgtcg tgtcggctgt    24720
```

```
tgcccgtgtt attgctgctg ttgcccgtgt catcgggtgg attgtggccc attttgtgtc    24780
tggtttggca cgtatgggtt cggtggttca ggctggctgg aatcggatta gggcgtttac    24840
gtcagcgttt attaacggtt tcaagtcggt gatttctggc ggcgtgaacg cggttgtggg    24900
gttttttgcc cggctgggtt cttctgttgc ttctcatgtg aggtctggtt ttaacgcggc    24960
ccgtggcgct gtttcttctg cgatgaatgc tatccggagt gtggtgtctt cggtggcgtc    25020
tgctgttggc gggttttttca gttcgatggc gtctagggtt cgtagtggtg ctgtgcgcgg    25080
gtttaatggt gcccggagtg cggcatcttc tgctatgcat gctatggggt ccgctgtgtc    25140
taacggtgtg catggtgtgc tgggttttttt ccggaatttg cctggcaata ttcggcgtgc    25200
gcttggtaat atggggtccc tgttggtgtc ggctggccgt gatgtggtgt ctggtttggg    25260
taatggtatc cggaatgcta tgagtggcct gttggatacg gtgcgtaata tgggttctca    25320
ggttgctaat gcggcgaagt cggtgttggg tattcattcc ccgtctcggg tgtttcgtga    25380
ccaggttggc cgtcaggttg ttgctggttt ggctgagggt attactggta atgctggttt    25440
ggcgttggat gcgatgtcgg gtgtggcggg acggctgcct gatgcggttg atgcccggtt    25500
tggtgtgcga tcgtctgtgg gctcgtttac cccgtatggc aggtatcagc gtatgaatga    25560
taagagtgtt gtggtgaatg tgaatgggcc tacttatggt gatcctaacg agtttgcgaa    25620
gcggattgag cggcagcagc gtgacgcgtt gaatgcgttg gcttacgtgt gattgggggt    25680
gttgtgcatg tttattcctg acccgtctga tcgttcgggt ttgactgtga catggtcgat    25740
ggatccgctg tttggtgggg ggcgtgtgct tcatttgacg gattatacgg gtgcgtctcc    25800
tgctatgttg ttgaatgatt cgttgcgcgg tttgggtgtt cccgaggttg agcattttttc    25860 tcaaacacat gttggggtgc acggctcgga gtggcgcggg tttaatgtga agcctcgcga    25920
ggtgacgcta ccggtgttgg tgtcgggtgt tgactcggat ccggatggcg ggtttcgtga    25980 cggtttttttg aaagcctatg gcgagttgtg gtctgctttt cctcctgcg aggaggggga    26040 gttgtcggtg aagactcctg caggtcgtga gcgtgtgttg aagtgtcggt ttgattcggt    26100
ggatgacacg tttacggttg atcctgtgaa tcgtggctat gcgcgttatg tgattcattt    26160
gacagcttat gacccgtttt ggtatgggga ggagcagaag tttcgtttta gtaacgcgaa    26220
gttgcaggat tggttgggtg gcggccctgt cggcaaggat ggcacggcgt ttcctgtggt    26280
gttgacgcct ggtgttggtt ctggtttggga taatctgtct aataagggtg atgtgcctgt    26340
gtggcctgtg attcgtgttg aggggccttt ggagtcgtgg tctgtgcaga ttgatggttt    26400
gcgtgtgtct tcggattatc ctgtcgagga gtttgattgg atcactattg atacggatcc    26460
tcgtaaacag tctgcgttgt tgaatggggtt tgaggatgtg atggatcgtt gacagagtg    26520 ggagtttgcc ccgattccgc ctggcggttc gaagagtgtg aatattgaga tggttggttt    26580
gggtgccatt gttgtgtcgg tgcagtacag gttttttgagg gcttggtgaa tagttgatgg    26640
ctggtctggt tccgcagata acattgttta cgccggatta tcgccgggtt gcgcctatca    26700 attttttttga gtcgttgaag ttgtcgttga agtggaatgg tttgtcgacg ctggagttgg    26760
tggtgtcggg ggatcattct aggcttgacg ggttgactag gccgggtgca cggctggtgg    26820
ttgattatgg tggtggccag attttttttctg ggcctgtgcg tcgggtgcat ggtgtgggtc    26880
cgtggcgttc ttcgcgggtg actatcacgt gtgaggatga tattcgcctg ttgtggcgta    26940
tgttgatgtg gcctgtgaat tatcgtcctg gtttggttgg tatggagtgg cgtgccgaca    27000
gggattatgc tcactattct ggtgcggcgg agtcggttgc taagcaggtg ttgggggata    27060
```

```
atgcttggcg ttttccgcct ggtttgttta tgaacgatga tgagagtcgt ggccgctata    27120
ttaaggattt tcaggtgcgg tttcacgtgt ttgccgataa gttgttgccg gtgttgtcgt    27180
gggctcggat gactgtttcg gtgaaccagt ttgagaatgc gaagtttgat cagcggggtt    27240
tgctgtttga ttgtgtgcct gctgtgacgc gtagtcatgt gttgactgcc gagtctgggt    27300
ctattgtgtc gtgggagtat gtgcgtgacg ccccgaaggc tacttcggtg gtggttggtg    27360
gccgtggcga gggtaaggat cggctgtttt gtgaggatgt tgattcgatg gccgaggggg    27420
attggtttga tcgtgtagag gtgtttaagg atgcccgtaa cacggattct gaacatgtgc    27480
atctcatcga tgaggctgag caggtgctgt ccgagttagg ggccacgtcg gggtttaaga    27540
tcgagttggc tgagtcggat gtgttgcggt ttgggccagg ccgcctgatg cccggggatt    27600
tgatctatgt ggatgtgggc tcggggccta ttgcggagat tgttcggcag attgatgtgg    27660
agtgtgattc gcctggtgat ggttggacga aggtgacacc ggttgcgggg gattatgagg    27720
ataatccgtc ggcactgttg gctcgccgtg tggctggttt ggctgccggt gtgcgggatt    27780
tgcaaaaatt ttagtaagtg attggggttt gttgtgggta ttgtgtgtaa agggtttgat    27840
ggtgtgttga ccgagtatga ttgggctcaa atgtctggtc tgatgggtaa tatgccgtct    27900
gtgaaagggc cggacgattt tcgtgtcggc acgacgattc agggtgccac agtgttgtgt    27960
gaggtcctgc cggggcaggc ttgggctcac ggggtgatgt gcacgtcgaa tagtgttgag    28020
acggtgacgg ggcagctgcc tggtcctggt gagacccgct acgactatgt ggtgttgtcg    28080
cgggattggg agcagaacac agccaagttg gagattgttc agggtggccg tgcggagcgt    28140
gcccgggatg tgttgcgtgc cgagcctggc gtgtttcatc agcagctact ggcgactttg    28200
gtgttgtcgt ctaacgggtt gcagcagcag ctggataggc gtgctgttgc ggctagggtt    28260
gcgtttggcg agtctgcggc ttgcgatccc accctgtgg agggtgaccg tataatggtg    28320
ccttcggggg ctgtgtgggc taaccatgcc ggcgagtgga tgctgttgtc acccagaatt    28380
gagacgggtt cgaagtcgat catgtttggt ggttctgctg tgtatgctta cacgatcccg    28440
tttgagcgcc agttcagtag tccgcctatt gtggtggcgt ctatggctac ggcggctggg    28500
ggcacgcagc agatcgatgt gaaagcctac aatgtgactg cccaaaattt tagttttggcg    28560 tttattacga atgatggttc gaagccgaat ggtgtgcctg cggttgcgaa ttggattgct    28620
gtcggagtgt gactgcacgg gtgttgtggc ggatggtgtg atgttggggg gctgtagtgt    28680
cgtggtttac tcctgcactg gtggcctcta tctgtaccgc gttggccacg gttttgggtt    28740
ctgttcaggc tgtcacatcc cggtctagga agcgtttacg caggctgtcg gctcaggtgg    28800
atgcgatgga agagtatacg tggggtgtgc ggcgcgaggt gcgaaggttt aacgccgggc    28860
ttcctgacga tgtggagccg atgcatcttc ctgatttgcc cgagttttg aaagatactg    28920 ttgatggtgg aggtgagtag ggttgaggga gttggaggaa gagaaacggc agcgccgcaa    28980
ttttgagaaa gcttcactgt tgctgttgtt tttgtcgctt gtactgttgg cggtggttgc    29040
tgcgggtgct ttgcgtttcg gggctgtatc ctctgagcgg gattcggagc aggcgagggc    29100
ccagtcgaat ggtacggctg ccag                                          29124

<210> SEQ ID NO 73
<211> LENGTH: 30016
<212> TYPE: DNA
<213> ORGANISM: Artificial Sequence
<220> FEATURE:
<223> OTHER INFORMATION: PAC22

<400> SEQUENCE: 73
```

-continued

```
gcgcagggtg agcgtggccc cgccggtgtg aacggatccg atggtaaaga cggtaaagat      60
ggtaaggatg gcgctgatgg gcgttcggtg atatcggtgt actgttccgg gggccgcctg     120
gttgtgaaat atagtgacgg tacagcctcc accgtgtcgg gttctgcggc ctgtgagagt     180
gtgaaaccgt cacctgtggt taccgtatca tcccacaaat agaatatgaa gagggaaggg     240
tgttactagt gttgattgtg gtgtttggtg gtggtgtgtt gtgagataca ttccagcggc     300
gcatcactcg gccggttcga atagtccggt gaacagggtt gtgattcatg cgacatgccc     360
ggatgtgggg tttccgtctg cttcgcgtaa ggggcgggcg gtgtctacgg cgaactattt     420
tgcttcccca tcgtcggtg gttcggcgca ttatgtgtgt gatgttgggg agactgtgca     480
gtgcctgtcg gagtctacga ttggttggca tgccccgccg aatccgcatt ctttgggtat     540
agagatttgc gcggatggcg gttcgcacgc ctcgtttcgt gtgccagggc atgcttacac     600
tcgtgagcag tggcttgatc cgcaggtgtg gcccgcggtg gagagggcgg ctgtcctgtg     660
tcggcagttg tgtgacaagc atggtgttcc gaaaagaaaa ctgtctgtgg ccgatttgaa     720
ggccggtaaa cggggcatct gcgggcacac tgatgtgacg gatgcgtggc atcagtcgga     780
tcatgacgat ccggggccgt ggtttccgtg ggacaaattt atggctgtgg tgaatggcca     840
cggctgcggt tcaagtagtg aggagttaac ggtggctgat gtgaaagcgt tacatgatca     900
gattaaacaa ttgtctgccc agcttactgg ttcggtgaat aagctgcatc acgatgttgg     960
tgtggttcag gttcagaatg gtgacctggc gcgccgcgtg gaggctttgt cgtgggtgaa    1020
gaatccggtg acggggaagc tgtggcgcag caaggatgcc ctgtggagtg tctggtatta    1080
cgtgttggag tgtcgtagcc gtattgacag gcttgagtct gctgtcaacg atttgaaaaa    1140
gtgatggtgg tttgttgtgg gtaaacagtt ttggttgggc ctgctggagc gggcgttgaa    1200
gacttttgtg caaacgtttg ttgctgtgtt gggggtgacg gcgggtgtca cgtatactgc    1260
ggagtcgttt cgtggtttgc cgtgggagtc ggcgctgatt acggctacgg ttgctgcggt    1320
tttgtcggtt gctacctcgt ttggtagccc gtcgtttgtg gctggtaagc caagcaagcc    1380
tcaggtggat gcgggtttgg ttgagcctca catggtggat gtgtcggatc ctggcatgat    1440
cgagccgacg gatgatgctg atcttggtgt gggctatgtg ccgaaacacg ctgccgagtc    1500
ggaggttggc acggtagagt cgactgttgc ataagtgaat atagatgtgt gccccagcgg    1560
tgctgccacg gttgtgtggt ggttgccgct ggggcactat tttgtgtct atagtatttt     1620 atgattcgtt gctgtcgatg gtgtcttcga gcatctggta caggtggagg caggtgcaga    1680
tggtttcgct ggcctggtct agaacggttc ggccgataac gttttgtgg ttgtcgcggt     1740 ggcggatgat agcccacatg atctcgtcgg ctgccgcctg taatagtttt gcctggtatg    1800
cgattccggc gagccagtct agtgcttcct ggcttgcgta ggggctctgg tcctcgctgt    1860
tgccgcgggt gttgctgttg tttgtggggt gtccttcact gtcgcatagc cataggattt    1920
cgctgcactc gtctagcgtg tcttggtcga tagcgagatc gtcgaggctg acattgttga    1980
cggtaaggtt cacgttgtcg atggagatgg gtacaccgta ctggttttca acactgtcaa    2040
caatgttttg tagttgttgc atgttggtgg gctgttgttg gacgatgcgg tgtatcgctg    2100
tgttgagggt ggtgtaagtg atgttgtgtg tgttgttcat ggttttttatg ccattccttc    2160 gttatcgtct ggcatgtagt atgtgctgtt tgcgtactcg gtgagggtga tgagtgtttg    2220
gtctgcccac tgtttcacgg tttgccgggt gactccgagt agttgggcgg ctgtggcgta    2280
ggtttggtcg tatccgtata cttcccggaa tgctgccaac ctagctaaat gttttcgctg    2340
```

-continued

```
tttggagggt tcacaggcga gggtgtagtc gtcgatggcg agttgtagat cgatcatggt    2400
aacaaggttg ttgccgtgat gctgggggc ggttggtggg ggtggcatgc ccggctccac    2460
actgggtttc catggtccgc cgttccagat ccattgtgcg gcttggatga tgtcggcggt    2520
agtgtaggtt cggttcatgt gtcaccccct gaacaggtcg ttggtgttgc tggtgcgggt    2580
ggtgtcgaat cgtccgacgc agtggcagta gtcgtacatg agtttgataa tgtgttggtg    2640
gtctcccaaa taggtgttgc cgctgatgct gtaggtggct gtgccgtctt tgctgatggt    2700
gtatttggcg gtgatggttt cggggttttc ggtgtcggtg atgattgctg tggtggtggt    2760
gcctactgtt tggagcacgg tggtttgggt tccgtcgtcg atggtggttt taaccatggt    2820
gtgtgttctc ccctttgtgt tagttgctgg tttggttgtc ggctagatga atgatgtcgg    2880
gtaagggttt cggctggtct aggtgttgtg tggttttgtt ggctaaacgt ttggctaccc    2940
tgtagcacat tttggtgtag tgtttgttgt cgaggttgtg gtattgttcc cgcaccgcaa    3000
tatatagcag ggagtcttgg tataggtcgt ctgcactgat tgcggggtag tgtgcggctg    3060
ttttggtgca tgcccggttg agtgtgcgta gatgatggtt tgtggcccac acccacgatg    3120
cggtggtggc taggtcggct tttgttggtc gtcggctcat ggcatctctt tcatctggct    3180
atctggtagt tgtttggtgt tttgttgttg atagtgtagc acacgagtcc ggggttgccg    3240
gtggtgcctg ttttgtgccg gaaccatgtg gattctcctt ccatggaggg gcattggatg    3300
aaggtgcgtt gtccttgctc ggagatttct aggtggtgcc ggtgcccggc catgagaatg    3360
tgggatgtgg tgccgttgtg gaattcttgt ccgcgccacc attcgtagtg tttgccggtg    3420
cgccattggt ggccgtgggc gtgcagtatc cgtgtgcctg ccacatcaac ggtggtggtc    3480
atttcgtcgc gttgggggaa gtggaagtgt aggttggggt attggttgtt gagctggtag    3540
gcttctgcga tggcgcggca gcagtccacg tcgaaggagt cgtcgtaggt ggtgactcct    3600
ttgccgaagc gtacggcttc tccgtggttg ccggggatgg atgtgatggt gacgttttg    3660
cagtggtcga attggtggat gagttgcatc atggccatgc gtgtcaaccg gatttgttcc    3720
gtcaaggggg tttgtgtgcg ccaggcgttg ttgccgcctt gtgacacgta tccttcgatc    3780
atgtcgccga ggaatgcgat gtggactcgt tgcggttttc cggcttgttg ccagtagtgt    3840
ttagctgatg tgagggtgtg taggtagtcg tcggcgaagt gtgatgtttc tcctccgggg    3900
atgcctttgc cgatttggaa gtctcctgcc ccgatgacga aggccgcggt gctgtagtcg    3960
gtgcgggtgt cttgttcggg ttttgggggt gtccattcgg ctagcttgtc gacgagttcg    4020
tctaccgggt aggggttggt tgcgggttgg tggtcaataa ttttttgtat ggatcggcct    4080
gtttctccgt tcggtaaggt ccattcggag atgcgtgtgc ggcgcacggt gccgttggct    4140
agattgtcgt cgatggtgtc gatggcgttg tcgtggttgg cgagctgtgt gaggagccgg    4200
tctatgttgt ctatcatcgg gtatcctcct cttctgtttg tggtgtggtg gcttgtttgc    4260
ggcggtagtc tttgatgacg gtggcggaga tggggggta tcctcctctt ctgtttgtgg    4320
tgtggtggct tgtttgcggc ggtagtcttt gatgacggtg gcggagatgg ggtatccggc    4380
ttcagtgagc attcgggcta gctgtgtggc ggggatcgtc ttgtcggcga ggacgtctgc    4440
agccttatca ccgtagcgtt ggatgagggt ttcagttttg gttgccatgg tgtcctatcg    4500
gttgtgtggt gggctgccat cctgtgcggc agtcgccgtc gtgtcctggt ttgcgtgtgc    4560
accacgatac ggttccgtct gtggtggtga gtgttttgcc gcacatgacg ttttgtagat    4620
gctcgggcag tgcgccgtta ctctggttgc tggtttgtgt gtcgaagagt gttttctggt    4680
tggtgaaatg ctcggatacg gtgccgttgt ggactgggag tatccatgtt ttccattgtt    4740
```

```
gttgcatccg ggtgttccag tggaattgtt tagccgcgtt ttctgcctgt ttggcggttt    4800
tgtagtagcc tacaatgatt cgctggtggt tgttgtctgg ctggtgtggc cctttccagt    4860
attgtgccgc cacggcgtag cggttgctgg ctgtgaagcg ctcccagcag tattcaataa    4920
tgtgttgcag tacactatcg ggaatgtctt gtgcttggtt ttcgttaagc cattcttcaa    4980
caatgatgtc gcgtatggcg cgtttgtctt tagtggtggg tttgaacgag atgctcacga    5040
tagcaccggc tggtcgtctt gcatgaactg gttgaaggtg ttgttcccgg cgtgttgggc    5100
ttgtgtgatt tgctggtcgg tccagtctgg gtgttgctgt ttcagatagt gccagtggca    5160
cgcattgtag gtttcgtctt gtagccgtgt gagatggttt tcggtgatga tttgtttcca    5220
catagtccac gagacgtcga gcctgttgag gatttcgagg gctgggatgt tgaattggtt    5280
gaggaacagg atttcgtggg tgtagtattc cttctcgtag gcgtcccatc cgcttcggtg    5340
cctgttgggc tggttttttgg ggtaggcttc ccggcagatt ttgtgcaaat gtttggccat    5400
gtcgtcgggt agtttaatgt cagggttggc gcggatcatg gatcgcatcc catcataggt    5460
ggtgccccag gtgtgcatga tgtaggtggg gtcttcacca tcagtccatt tttctgcaca    5520
gatggcgagg cggatacgcc tcctggcggc ttggctggtg ttgcgccggt tggggattgg    5580
gcacgtgtcg aggggatcca tgatgctttt tatgcctttc tttgtttggg ttgtttgtct    5640
agttttactg tagcacagtg tctagtgctt gtgtcaaccc tgttttttccg gcctgcaggt    5700 aggtgtctgt gacgtcgccg agggtgaggg gcacatgggt ggcttggggg agtgctgcct    5760
ggagggtgtg ggccatctgg tcgcctgctt tgtctgggtc tgaccatatg tagatgtggt    5820
cgtagccttc aaaaaatttg gtccaaaagt tttgccacga ggtggcgccg ggtagggcga    5880
cggccgacca tccgcattgt tcgaggatca tggagtcgaa ttcgccttcg caaatgtgca    5940
tttcggctgc ctggttggcc atggcggcca tgttgtagat ggagcctgtg tccctgccg     6000 gtgtcaagta tttggggtgg ttgtgggttt tgcaatcatg ggggagtgag cagcggaaac    6060
gcatttttcg tatttcggct ggcccttccc agacggggta catgtagggg atggtgatgc    6120
actggttgta gttttcgtgg cctgggatgg ggtcattgtc gatgtatcca aggtggtggt    6180
agcgggctgt ttcttcgctg attcctcttg ccgagagcag gtcgagtatg ttttcgaggt    6240
gggtttcgta tagggccgag gctttctgga ttcggcggcg ttccgcaatg ttgtaggggc    6300
gtatgctgtc gtacattcgg gttttcttcc tctaatcgtt gtttcagttt gtggagtcca    6360
cctccgatac cgcatgtgtg gcagtaccag acgcccttgt cgaggttgat gctcatggag    6420
ggctggtggt cgtcgtggaa cgggcagagg atgtgttgct cgttcctgga cgggttgtag    6480
cgtatctggt gggcgtcgag gaggcggcag gtgtcagagg tgtgggagga gctcgttgag    6540
ggttgatacc acataggctt cgctccaggg tttgttgcgc tgtttcatga tgacgagtcc    6600
gatggtggac tggttttctc ggtttcggtg ggtttcatag ttgcgtgcct cccggctggc    6660
ttgtttcacg aattcggcga gatgtggttg cccggctttc gcctcgataa tgtaggtttt    6720
gtggccggtt gtgaggatga ggtcgccttc gtcttcgcgg ccgttgaggt ggaggcgttc    6780
gatatcatgt ccgatgtcgc gtagctggtg gaggagtctt gtttcccatt cggccccagc    6840
tcgcctattc ctggattgct gtgtagccat catagtcctt tgtgtgttgg ggtcatgttc    6900
cagggctgtt tttctactag gggtccgaag aatgtgtatt cggggtaggc tcgtagtcgt    6960
tcgtatcggt tgccgtctgg gctggatttg ccggttctct gtttgagtac ggcgatgcgc    7020
gcctcggcgg ggatggtgag cccgttgccg ttgtcttcgc caccgtagag tgagactccc    7080
```

```
aggattagtt gtggtttttc ggagaggccg tttttgattt cccgcctagc tggggggtgt    7140
tcgatgtcgg tgccggtttt gtcggttgcg tggtgggtga caataatggt ggagccagtg    7200
tcgcggccta gtgctgtgat ccattgcatg gcttcttgct gtgcctgata gtcactttcg    7260
cagtcttgga tgtccatcag gttgtcgatg acgatgatgg gtgggaaggt gttccacatt    7320
tccatgtagg cttggagttc catggtgatg tctgtccatg tgatgggtga ctggaatgag    7380
aatgtgatgt gtccgccgtg gtggatgctg tctcgatagt attctggccc gtagttgtcg    7440
atgttgtgtt gtatctgttg ggtggtgtgt tgggtgttga gtgagatgat tcgtgtggag    7500
gcctcccagg gtgtcatgtc ccctgatatg tagagggctg gctggttgag catcgcggtg    7560
atgaacattg ctagccctga tttttggctg ccggaccgcc ccgcgatcat gactaggtcc    7620
cctttgtgga tgtgcatgtc ctggttgtca tacaagggtg ctagttgggg tatgcggggc    7680
agttcggcgg cggtttggga ggccctctcg aaggatcttt ggagagagag catcggagcc    7740
ttaatctatc tgtctgttgg ttgggtgttg gtggtcagat ggagtcgatg tcgatgtcag    7800
catcggcggg ggctgtggtg tcgtctagct ggccggtgtc gcgcttgtct acgtattcgg    7860
caaccttatc gtagatggcg tcgtccaatg gtttgaggac gaccgcgttg aacccgtttt    7920
tggtgcgaac ggtggcgagt ttgaaggcct gctcttcgcc gagataggct tctaggtcgc    7980
ggatcatgga gtgtgggcgg tcgttgttgc ctcgcgcttt ctcgatgata gcgttgggga    8040
tagtttctgg ggtgccattg ttgagatcct ggagtgtgtg gaagatggtg acatcggcgt    8100
aaatacggtc ggcgacctgt ccgccgtagc cttcggtgtt gtgctggacg tcgcggattt    8160
tgaaggcgat ggcggtggcg tcctggtttc gggaggggtt gaagaaggtg ctgttgctgt    8220
tgttgcggta gttggcgagt cccattgttg tttcctttac tatttgtgtt ggttttttgtt    8280 gtcttatatt ggtttatcgg gtgaggctgt ttcgttact gcggaacgcc tcagacacgt     8340
cactgttact ggtgatgatc ttcttgtact gtttgaggag gtctgctagt tgtgtcttgc    8400
tggtggcttt gttgatccgg tcgatgatga tgtcgttttc ctggttggcg attttgttga    8460
cgtagtcttt ggcggcttta tcgtatcgat cttgaagcag gattgctgcg ctagcgatca    8520
aggtggctaa atcccagtct ttggatacgg tttcgtcttt caatcctcct agcaggtcaa    8580
tgatggattg tttgatgtct tctgcggtgt ctccgcggat gactgtccat ggggcggcat    8640
agtctccacc gtatttgagt gtgatagtta gttttccgtt gtctgtggtg tgctcgtcgg    8700
tcacgtgttt tcctttttcgt tactgtcggt ttggggtggc tgtacggtgg tttctatcgg    8760
gtatctgtac gagttttttgc cgttgacggc ccagcaggcg tccttgacgg ggcatccttt    8820
gcagagtgct gtgacgtggg gtacgaagat gccttggctg attcctttca ttgcttgact    8880
gtacatggat gatacatgcc ggtaggtgtt gttgtcaagg tcgtagagtt cggttgctgt    8940
gccctgctcg actgattgct cgtctccctt ggtggtggcg ggtgtccaaa acatgccttt    9000
cgtcacatgg atgccgtgtt ggttgagcat gtaccggtat gtgtgcagct gcatactgtc    9060
ggcgggtagg cggccggttt tgaggtcgag gatgaaggtt tcgccggtgt tggtgtcggt    9120
gaatacccgg tcaatatatc cgacaatctg ggtgccgtct tggagggtgg tttctaccgg    9180
gtattcgatg cctggctggc cgtcaataac agcggtagcg tattctgggt ggttgcgcct    9240
ccatgttttc caccggtcca caaaggtggg gccgtatatc atccaccaat tgtagtcttt    9300
cttgttgggg ccccgctttt cgcacatgtt tttgcacact cggccggagg gtttgatgtt    9360
tgtgccttcg gattcggcga gggcgatttg ggtgtcgaaa atgtttgtga aggatgcgag    9420
tttgtctggt agtgcagggt attcggcggg attgtacagg tgtaagtcgt attgttcggt    9480
```

```
gatgtggtgt atggcgcttc cggcgatggt ggcgtaccag gtgtggtgtt gggtgtggta   9540
gccgtgggat aggcgccatt tttctccgca ttcggcccac tgtgacagtg aactgtagga   9600
gatgtggcct ggatggtgga tggttttcgg gtattgtgct aggggcatta cttgtcgcct   9660
ttgtgggtgt tccatgggtt gcgggtgtct accccggcat cgtgttgctg gtaggcgagg   9720
agtgccaagc agtgccaggc agcatgtgcc agatgcggca aatgtgattc gtggtcgagg   9780
ttgtttcctt gctgccatga tagcaggtgc ctgtagaggg cgtcgacact gtggctccac   9840
gggtagccgc cggtccagtt gttgtcgccg tatttggtgg caccgtagcc tgccacttcg   9900
ccgagggcgt gcaaggcggt agggtcgatg agggatagcc tgcaaagttt caattctttc   9960
ttggcacccg tatcagggtc ggtgtacatg ctggttggct catccatggt gtgtgtgctc  10020
cttacgtgtg gggttactgg ttggggttgt ggcgagtgc tacggcgaga ataatgatgg  10080
cgagggtttc tgcgatcagt attggtgttg tgatcatttg ctgtcgcggg gattgttggt  10140
gagggtggat gcgcctagca gggtggtgag ggcgcatgcg gcgatgatgg cgagggcggc  10200
tttgtggctg gtgccggtgg cgtacatcca tgtgatgatg gcgccctgta tccatgccag  10260
tgtggtgaag aacgtttcgt agctgtgcag ctcgatactg ttgggtgtgt tcatgcttgc  10320
tcctgaagaa tggtgttgat ggttgtgtaa atgttgtaca ggtcggcttc gatggtttgt  10380
agctgtttga tttggtggtc gaggtcaatg tttgggttga gggtgttgat gcggatgcg  10440 atgtcggtgg ctgtgcgtag tgtgccgccg gtgtggtgaa tgatgtgtgc cgtgtcggcg  10500
agtccggtgg tgacagcgta gcgggagagg agaggcatga ctgggggtg ctccttgacg  10560 gggttactgt tgcgggttga tgttgaggtc ggtgacgtgc ggtgagcttt ctgttcctgt  10620
gacgaggcag tggacggtga cggggagttt ggatgctccc ggctgccgga cggtggcgcc  10680
gtagacgatg ctgaacgtgt ctttgccaat aattttgtgg agttggaggt cgatgtcggg  10740
gttgccgttc catttgacac cctgtgctgc agctgcctgt tcagccttgt cattgcaggc  10800
gtgtgccgcg gtgatcatgg tgagacctgt ggaggtttct tcaccccgtg tttgggcttg  10860
ccggtgggcg cgctgctgtt cggcttggag ggagcggact gctgcagcct gcttggcggc  10920
tttctcggct ttgcgctgtt ggacggtttc aggtgtccat cggtgttgg ctgtggtggc  10980 ttgtggggct ggctgtgagg cgagtggcgg attatcatcg ggtgccggga ggaaggatgc  11040
tgcggcgatg atggcgatgg tggcgccggc gatggtgtag cctgttttct tgttcatgat  11100
tttgtgttcc cctttccggg gtgttgttcg ttgctgacat gatcaatact ttcagcggct  11160
ggaccctgtg tcaaggtgtc gctcagtatt cttgagcgaa tgtggtttga ctgggggtga  11220
tggcttcttt cgcccaatag gatgtgccac cgctggtcca gtatccgagt tgttgcgct   11280 gcatgccctt ggcttccatc tcatccacgg tgaggcacct cgcgcgattg ggccttcct   11340 tgaccccgtg gtcgcctacc cggtgcatgt cgcctgaggt ggtactcgtg aatgtttcgt  11400
ggcagattgt gcagtgctct ggtcggtatc cgatgattgt gctatcgcac ttgtggcatg  11460
tccattgcat gattgctcct attttccatt ataagacttc ctgtagtgcc attttagcgc  11520
cttgcgggtc ttgggggtac aactatatag gtcaggtatt tctaggcgat tctaggctca  11580
ttgtgtgcga ctggtggtta tcgggcgcac agagtgagca ggtggccaac attgatgcgg  11640
gtcacattcc agtagagttg cgtggcttcc tcactggtga gcggcttcca ctcgttgtgg  11700
ctgaacacgg tgccatcgga tgctatgaac gtgttgggc gtagcttgtg gagttcagtc  11760
tctacatgcc gacggtaggt ttcggcgagg ccctcgaaat cgaggtggtc gcaggagagg  11820
```

```
tttccgaggc gtgtcaggtc gaaaggctca gggcagtcgt agctggcggg gctgtagagc  11880
tgggtgaagt ggttggcaat cttctgcatc atgattcctt ttctggtgat ggtgtgttga  11940
tggttttatc gggtggatgc tttgaggatg gcgtctacat cgatcatgtc gatcatgtcg  12000
ttgagttcct cggcctcatt ctcggagagg tggcgccagc cgggtggccc gtatagggcg  12060
ccgtcgaggg tgacagtcca caggggccgg atgagtcgta tggcttcttc gactttggcg  12120
tggtacatgc ggcgcaccat atccagatcg atgtcgtctg aatggttttcc ggtgaggctg  12180
tggaggctga gtgggtcgat ttctgtctgc ccgtagaggc tggtgaatga tggtgtgatg  12240
agtgtgccat ccatgagggt gctcccttct gaactgtttg ggttggttgt tgtggtttct  12300
agagtgtgta ggttgcaacc ccatagtcaa ggctacgctc attcggattg agcgtttcat  12360
gctggagtgt gtcgggtgtg acagatgtca ctgaatcctt gatggcctct ctcagcgcct  12420
gaaatatgtc cggggtggga ttatgcaggg ttgaccctgc tgatcgattc tagggcccct  12480
acagggcgtc tcaggggtat gtctgggtga tagcaggttc ggtagatgat ctagcgagtc  12540
aaggtgccaa gctgagacag aagatctacc atctaggtgt gtgagatgta tcacactcgc  12600
ctggcttagt gtgcaccctc aagaccacct agtcgatctg gcgtggaggg tgcagcccag  12660
aaataccgtt taaagccttc gcgcggagcc taggagcgcc ttacagggtg ggggctaggt  12720
attcataccc ccaagcaatt ctgatcgatt ctagacgcct ccaggggccc gatacacgat  12780
cagtagtcca gacacagatc atcaacccct atcctggtta gctaagcctc aactatgtgg  12840
acagtgtggg atgctaagag ggaagaagga cacggtaaaa gaaagagggg ggagcatcag  12900
ccttcaagcc tgaaggtctt agcgcttagc accgagcccc ctcaagggct cggcatcagc  12960
ccgaacaggc tcagctcatc aggcacagcc ctgaaaaggg tacacgccat cagggaaggc  13020
ttgagagtac gaggagccct agcgacgagt actcgaaagc ctgaggaaac accctcagca  13080
ctgatgggcc tagcgtgttc ggaaaggaca caagagtaaa gtgtgacagc tgtccgggag  13140
tgaaacccgt tccggctagg ggtttcagcc ttaaccaccc tcaaaggtta caagactcta  13200
agaaaattta agaaaactct taggaagaaa gttgtgttca tatcccccta aaaacaccca  13260
aaatagccct caaacccgcc tatagagcca aaaccaccag tttgactcat cccaggtggg  13320
gtatgatagg ctggacaggt agccagctgg acgcgaggcc agaaagtgct gacgcacttc  13380
ccgacctcgc ttaccatcag tctaccaaac actttaaagc ttcaaggctt agcgctaagc  13440
ccttaagacc ttaacactga acaccgagcc ccctcaaggg ctcggcatca gccttaaagc  13500
cttaaacact ttaagtaact ttaaaacctt aacagcttaa cacttaaggt tataaataaa  13560
cattaaagct ttaaagtctt aaagtaaata tataacctta acacttaagt taagtataaa  13620
accttaaaag ctaagcactt aaagatataa acttaacatc agtgtttaag acttaaagag  13680
ttaaagtaac tattaagact taaaggctta taagctttaa acacttaaag taactataag  13740
actttaaaaa ccttaagtac ttaaagttaa ccatcagtct taaactttaa tactataacc  13800
tataagtctt aaagcttata ggtataataa tataatataa gtattaaagc ttataagtta  13860
taaaagtttt agaagagtta aagggttaac ttctttactt ctcttctctc tttggttctt  13920
tctctcttct cttcttttct tcatcagggg agaagaggaa cctttaaccg tcaacgctga  13980
tggactttca accgtgtgac tcgtgtacca ccggtcgcac gctcccgatg gcacactccc  14040
cacatgctac ctgtgtccct ttcaggctta gcgtgttcgg ctgaaggcgt acggcgtgtc  14100
acgcttaaac ccttaacacc aggtaagact taaagtgtat attataagta gaagactttta  14160
aaacctttaa ggtgttcccg ctgagcctgt gttcttcacc gctaggcgct aagcgctaag  14220
```

```
ccttgaaacg cgaacaccca tccacccttt tcttttaccg tgtccttctt cttttgacac   14280
cgctgggggg cgatgtgatc tttttcacat gccaggggt aggagaagaa acaaccacc    14340
ccggcacaaa cagaacaccc ccctaaacga acaaaacagg cccaggatc gaacagcagg   14400
gcaccggtag agtattccta cccccagaca attccaggcc gttacaggag caatgagagg  14460
ctcacagggg ccataggaga tcaggggacg tgatggcaca caccaaccgc acagccagcc  14520
aagcccaccg gcgctggcgg caacgactca tcacccaagc caaacagcaa ggccaaaccg  14580
aatgcccact ctgcggagcc accatcacct ggggcacaca tgacctgcca accagccccg  14640
aagccgacca catcacaccc gtcagcaggg gaggactcaa caccctcgac aacgggcaaa  14700
tcatctgcag aacatgcaac agaagcaaag gcaatcgcag cgaaccaaac attcaattcc  14760
aacaacaaac cacaaaaacg ttgatcccat ggtgaaaaaa cagccaaccc ccacgggaac  14820
cacccctgc acaccgtgc aagacctcgt acggcttagt gaaataccct ccttttgtgg    14880
ttttgtctgt ctgtcgactt tttgtgttgg tggtgagtgt tgtgcagcct gagcttcctg  14940
atagtcgtgg atggtgtggg gagacgcgtc gttggtggcg tgtgtggggt gaggatagtc  15000
gcgcgcagta cgtgtctgat gaggagtggc tgtttctcat ggatgctgcg gtgattcatg  15060
attgtgtgtg gcgtgagggt cgcgcggatt tggtggcttc gcttcgtgct catgtgaagg  15120
cttttatggg catgttggat cggtattcgg ttgatgtggt gtctggtggc cgtggtgggg  15180
gttctgctgt ggcgatgatt gaccggtatc ggaagcgtaa aggggcctaa tgtcgagcgt  15240
tgttggttct caggttcctc gtcaccgggt ggctgcggct tattcggtgt ctgctggcgg  15300
tgatgcgggt gagcttggta gggcttacgg gttgacgcct gatccgtggc agcagcaggt  15360
gttggatgat tggctggctg tgggtggtaa tggcaggctt gcttcgggtg tgtgtggggt  15420
gtttgtgcct cgccagaatg gcaagaatgc tattttggag attgtggagt tgtttaaggc  15480
gactattcag ggtcgccgta ttttgcatac ggctcacgag ttgaagtcgg ctcgtaaggc  15540
gtttatgcgg ttgaggtcgt tttttgagaa tgagcggcag tttcctgact tgtatcgtat  15600
ggtgaagtcg attcgggcga cgaatggcca ggaggctatt tgttgcatc atccggattg   15660
tgccacgttt gagaagaagt gtggctgtcc gggttgggggt tcggttgagt ttgtggcccg   15720
tagccggggt tcggctcgcg ggtttactgt tgatgatttg gtgtgtgatg aggctcagga  15780
gttgtcggat gagcagttgg aggctttgct tcctacagtg agcgctgccc cgtctggtga  15840
tccgcagcag attttccttg gcacgccgcc tgggccgttg gctgacgggt ctgtggtgtt  15900
gcgtcttcgc gggcaggcgc ttggtggcgg taagcggatt gcgtggacgg agttttcgat  15960
tcctgacgag tctgatccgg atgatgtgtc gcggcagtgg cggaagcttg ctggtgacac  16020
taatccggcg ttgggtcgtc gtctgaattt tgggactgtg tcggatgagc atgagtcgat  16080
gtctgctgcc ggttttgctc gggagcggct tggctggtgg atcgtggcc agtctgcttc  16140
gtcggtgatt ccggcggata agtgggttca gtctgctgtg ggtgaggcga tcttgttgg   16200
cggtaaagtg tttggtgtct cgttttctcg ctcgggggat cgtgtcgcgt tggcgggtgc  16260
tggccggact gatgctgggg ttcatgttga ggttattgat ggcctgtctg gcacgattgt  16320
tgatggtgtg ggcagctgg ctgactggtt ggcgttgcgt tggggtgaca ctgaaaagat    16380
tatggttgcc gggtcgggtg cggtgttgtt gcagaaggcg ttgacggatc gtggtgttcc  16440
gggccgtggc gtgattgtgg ccgatactgg ggtgtatgtg gaggcgtgtc aagccttcct  16500
ggagggtgtc aggtcgggtg tgatcagtca ccctagggct gattcgaggc gtgacatgtt  16560
```

```
ggatattgct gtgaggtcgg ctgtgcagaa gaagaagggt tctgcgtggg gttggggttc    16620
ctcgtttaag gatggttctg aggttccttt ggaggctgtg tctttggcgt atcttggtgc    16680
gaagatggcg aaagcgaagc ggcgtgaacg gtctggtagg aagcgggtgt ctgtggtatg    16740
aactcggatg agttggctct gattgagggc atgtttgatc gtatccgaag gttgtcttcg    16800
tggcattgtc gtattgaggg ctactatgag ggttctgccc gggtgcgtga tttgggggtg    16860
gctattcctc cggagttgca gcgtgtgcag acggtggtgt cgtggcctgg gattgcggtg    16920
gatgctttgg aggagcgtct ggattggctt ggctggacga atggtgacgg ctacggcctg    16980
gatggtgtgt atgctgcgaa tcggcttgct acggcgtcgt gtgatgtcca ccttgatgcg    17040 ctgattttg ggttgtcgtt tgttgcgatc attccccaag aggatgggtc ggtgttggtt    17100
cgtccgcagt cgccgaagaa ttgtacgggc cggttttctg ccgatgggtc tcgtttggat    17160
gctggccttg tggtgcagca gacgtgtgat cctgaggttg ttgaggcgga gttgttgctt    17220
cctgatgtga ttgttcaggt ggagcggcga ggtagccgtg agtgggttga gacgggccgt    17280
atcgagaatg tgttgggtgc ggttccgttg gtgcctgttg tgaatcgtcg ccgtacttcg    17340
aggattgatg gccgttcgga gatcactcgg tcgattcgtg cttacacgga tgaggctgtt    17400
cgcacactgt tgggggcagtc tgtgaatcgt gatttttatg cctatccgca aaggtgggtt    17460
acgggtgtgt cggctgacga gttttcgcag cctggctggg ttctgtcgat ggcttctgtg    17520
tgggctgttg ataaggatga tgacggcgat accccgaatg tggggtcgtt tcctgtgaat    17580
tctcctacac cgtattcgga tcagatgcgt ttgttggcgc agttgactgc gggtgaggcg    17640
gctgttccgg aacgctattt cgggtttatc acgtctaacc cgccttcggg tgaggctttg    17700
gctgcggagg agtctcggct tgtgaagcgt gctgagcgga ggcagacgtc gtttggtcag    17760
ggctggttgt cggttggttt cttggctgcc agggcgttgg attcgagtgt tgatgaggcc    17820 gcgtttttg gtgatgtggg tttgcgttgg cgtgatgctt cgacgccgac tcgggcggct    17880
acggcggatg ctgtgacgaa gcttgtgggt gtcggtattt gccggcgga ttctcggacg    17940 gtgttggaga tgttggggct tgatgatgtg caggttgagg ctgtgatgcg gcatcgtgcc    18000
gagtcgtcga atccgttggc ggcgctggct ggggctattt ctcgtcaaac taacgaggtt    18060
tgataggcga tggcttcggg ggttgtgtcg aggcttgctg cgactgagta tcagcgtgag    18120
gcggtcaggt ttgccgggaa gtatgcgggc tattatgccg agctgggtcg tttgtggcat    18180
tccgggaaga tgacagatgc gcagtatgtg cgtttgtgtg tggagttgga gcgtgccggc    18240
catgacggtt ccgcggcgtt ggcgggcaaa ttcgtgtccg attttcgccg gttgaatggt    18300
gtggatccgg gtttgatcgt gtatgacgag tttgatgctg cggcggcgtt ggctaggtcg    18360
ttttcgacta tgaagattct taagagtgac ccggataggg cgaatgatac gattggtgcg    18420
atggctgcgg gttttgatcg ggctgtgatg aatgctggcc gtgacacggt tgagtggtct    18480
gcgggtgtgc agggtaggtc gtggcgcagg gtgactgatg gtgatccgtg tgcttttttgt   18540 gccatgttgg ctacgaggtc ggattatacg actaaagagc gggcgcttac tacgggtcat    18600
actcggcgtc ataagcgtgc cggtaggcgt ccgtttggtt cgaagtatca tgatcattgt    18660
ggttgtacgg tggttgaggt tgttggcccct tgggagccga ataggctga tgccgcatat    18720 cagaggacgt atgagaaggc tcgtgagtgg gttgatgatc atgggttgca gcagtcgcct    18780
ggcaatattt tgaaggctat gcgtactgtt ggcgatatga gatgatggtt ccggttgtg    18840 tgccgccggt tattggtgca cagggttgtc tcccgcacgg gggtcaacaa tgttgtgttg    18900
ttttccgcaa ggagtgtagg ttaggctatg gccgatcaga gtgttgaaga acagaatgtt    18960
```

```
gacaatgatg ctgttgagcc cggaaagggt ggagacgttg ttgatgttgt gaaggatggg   19020
caggctgccg gcgatgatca tgccggtgat gtttccgtga aggaggagtc ttcttctggc   19080
acggattgga aggctgaggc ccgtaagtgg gagtctcgtg ctaaaagtaa ttttgccgag   19140
ttggagaagc ttcgcgcctc ggatggtgat gcggggtctg tgattgatga gcttcgccgc   19200
aagaatgagg aactcgaaga ccggattaat gggtttgttc ttgagggtgt gaagcgtgag   19260
gtggctgccg agtgtggcct gtcgggtgat gcggtcgctt tcttgcacgg tggcgatcgt   19320
gaagcactgg tggagtctgc taaggctttg aagggtttga tcgaccagag tggtggtggc   19380
gcgggtgtgc gccgtcttgc ggggagtgcc cccgttgatg atgttaaacg acgtgagggt   19440
gtcgcgtttg tggatgctct tgtcaataat tctaggagat gatttataat ggctgacgat   19500
tttctttctg cagggaagct tgagcttcct ggttctatga ttggtgcggt tcgtgaccgt   19560
gctatcgatt ctggtgtttt ggcgaagctt tcgccggagc agccgactat tttcggcccg   19620
gtgaagggtg ccgtgtttag tggtgttcct cgcgcgaaga ttgttggtga gggcgaggtt   19680
aagccttccg cgtctgttga tgtttcggcg tttactgcgc agcctatcaa ggttgtgact   19740
cagcagcgtg tgagcgacga gtttatgtgg gctgacgcgg attaccgtct gggtgttttg   19800
caggatctga tttcgcctgc tctgggtgcc tcgattggtc gcgccgtgga tttgattgct   19860
ttccacggta ttgatcctgc cactggtaag cctgccgcgg ctgtcaaggt gtcgctggat   19920
aagacgaagc atattgttga tgccacggat tccgctacga ctgatcttgt gaaggctgtc   19980
ggcctgatcg ctggtgctgg tttgcaggtt cctagcgggg ttgctttgga tccggcgttc   20040
tcgtttgctc tgtctactga ggtgtatccg aagggctctc cgcttgccgg tcagccgatg   20100
tatcctgccg ccgggtttgc cggttttggat aattggcgtg ggctgaatgt tggtgcttct   20160
tcgactgttt cgggtgcccc ggagatgtcg cctgcctctg tgttaaggc tattgttggt   20220 gatttctctc gtgttcattg ggggttccag cgtaacttcc cgatcgagct gatcgagtat   20280
ggtgacccgg atcagactgg gcgtgatctg aagggccata atgaggttat ggttcgtgcc   20340
gaggctgtgc tgtatgtggc tatcgagtcg cttgattcgt ttgctgttgt gaaggagaag   20400
gctgcaccga ctcctcctcc ggctggtaac tgatacaaga taagcgaatg tgtactatgt   20460
gcagggggtg tgttgatgg gtatcatttt gaagcctgag gatattgagc ctttcgctga   20520
tattcctaga gagaagcttg aggcgatgat cgctgatgtg gaggctgtgg ctgtcagtgt   20580 cgcccctgt atcgctaaac cggatttcaa atacaaggat gccgctaagg ctattctgcg   20640
cagggctttg ttgcgctgga atgataccgg ggtttcgggt caggtgcagt atgagtctgc   20700
gggcccgttt gctcagacta cacggtctaa tactcccacg aatttgttgt ggccttccga   20760
gattgctgcg ttgaagaagt tgtgtgaggg tgatggtggg gctggtaaag cgttcactat   20820
cacacccact attaatagta gatatgcaca ttctgaggtg tgttccacgg tgtggggtga   20880
gggttgctcg tgcgggtcga atattaacgg ctacgctggc cctttgtggg agatatgata   20940
tgaccagttt tccttatggt gaaacggttg tgatgcttca gccgactgtt cgtgtcgatg   21000
atcttggcga caaggtggaa gactggtcta agcctgtcga gactgtgtac cataacgtgg   21060
ccatttatgt ctctgtttcg caggaggatg aggctgccgg ccgtgactct gattatgagc   21120
attggtcgat gcttttcaag cagcctgttg tgggtgccgg ttatcgttgc cggtggcgta   21180
ttcggggtgt tgtgtgggag gctgacgggt ctcctatcgt gtggcatcac cccatgtccg   21240
gttgggatgc tggtacgcag gttaatgtga agcgtaagaa gggctgatgg gttgtggctc   21300
```

-continued

```
aggatgtgaa tgtgaagctg aacttgccgg gtattcgtga ggtgttgaag tcttctgggg    21360
tgcagtcgat gttggctgag cgtggcgagc gtgtcaagcg tgcggcctcg gcgaatgtgg    21420
gcggtaatgc ttttgataag gcccaatacc gtagcggttt gtcgtcggag gtgcaggttc    21480
accgtgttga ggctgtggcc cgtattggca ccacctataa gggtgggaag cgtattgagg    21540
cgaagcatgg cacgctggcc cggtcgattg gggctgcgtc gtgatcgttt atggtgatcc    21600
gcgtgtgtgg gctaaacgtg tgctcaagga tgatggctgg ctgtccgata taccttgtgt    21660
ggggacggtg cctgaggatt ttagcggtga cttgatttgg ttggctcttg atggtggccc    21720
gcagttgcat gttcgtgagc gtgtttttt gcgtgtgaat gtgttttctg atatgccgga    21780
tcgtgctatg tcgttagcta ggcgtgttga ggctgtgctg gctgatggtg tggacggtga    21840
cccggtggtg ttttgtcggc gttctactgg ccctgatttg ctggttgatg gtgcacgttt    21900
tgatgtgtat tcgcttttg agctggtgtg tcggcctgtc gaatccgagt aagcgtatcg    21960 ttgttttta gtttgattgt tttgtagttt gattgttttt tggggttat gatggctgaa    22020 acacgtaaag cgtctaatgt tcgctctgct gttactggcg acgtttatat tggtaaagcg    22080
cacgcgggtg attctattaa gggtgtggag gcggttcctt ccgggcttac agctttaggg    22140
tatctgtctg atgacgggtt taagattaag cctgagcgta aaacggatga tttgaaggct    22200
tggcagaatg cggatgttgt tcgcactgta gctacggagt cgtctatcga gatttctttc    22260
cagctgatcg agtctaagaa agaggttatc gaactgtttt ggcagtcgaa ggttactgcc    22320
ggatccgatt cgggttcgtt cgatatttca ccaggcgcca ccactggcgt gcatgcttta    22380
ctgatggata ttgttgatgg tgatcaggtt attcgctact atttccctga ggtcgagttg    22440
atcgatcgtg acgagattaa gggcaagaat ggcgaggtgt atgggtatgg tgtgacgttg    22500
aaggcgtatc ctgcccagat taataagact ggtgatgcgg tgtctggtcg ggggtggatg    22560
acggctttaa aagctgatac tcctccgact cctcctccag ccccggttcc tccgaagcct    22620
cagccggatc cgaatccgcc gtccgataac tgatacacga ttttagggga ttgttgatag    22680
atgagtgaca ctggttacac gttgaagatt ggtgaccgta gctgggtgtt ggcggatgcg    22740
gaggagacgg ctcaggctgt tcctgcccgc gtgtttcgcc gtgccgccag gattgcccag    22800
tcgggtgagt ctgcggattt cgcccaggtt gaggtgatgt tttcgatgtt ggaggctgcc    22860
gcaccggctg acgcggtgga tgctttggag gggcttccta tggttcgtgt tgccgagatt    22920
ttccgcgagt ggatggaata taagcctgac ggtaagggtg cctcgctggg ggaatagttt    22980
ggctccacgg cctgattgat gattatcgtg gggccatcga atacgatttc cgcaccaagt    23040
ttggtgtttc tgtttatagt gttggtggcc cgcagatgtg ttggggtgag gctgtccggc    23100
tggctggcgt gttgtgtacc gatacgtcta gccagttggc ggcccatctg aatggttggc    23160
agcgcccgtt tgagtggtgt gagtgggctg tgttggacat gttggatcat tacaggtctg    23220
ctaatagtga ggggcagccg gagcctgtgg tgaggccgac ggatgagcgt agggcccggt    23280
ttacgtctgg gcaggtggac gatattttgg cgcgtgttcg tgctggtggc ggggtgtctc    23340
gcgagattaa tattatgggg tgaatagtgt atgtctggtg agattgcttc cgcgtatgtg    23400
tcgttgtata cgaagatgcc tggccttaaa agtgatgttg gtaaacagct ttctggggtg    23460
atgcctgcgg agggtcagcg ttcgggtagc ttgtttgctg gcgggatgaa gttggcgctt    23520
ggtggtgcgg cgatgatggg tgccatcaat gttgctaaga agggcctcaa gtcgattat    23580 gatgtgacta ttggtggcgg tatagctagg gctatggcta ttgatgaggc tcaggctaaa    23640
ctgactggtt tgggtcatac gtcgtctgac acgtcttcga ttatgaattc ggctattgag    23700
```

```
gctgtgactg gtacgtcgta tgcgttgggt gatgcggcgt ctacggcggc ggcgttgtct    23760
gcttcgggtg tgaagtctgg cgggcagatg acgatgtgt tgaagactgt cgccgatgtg    23820
tcttatattt cgggtaagtc gtttcaggat acgggtgcta tttttacgtc tgtgatggct    23880
cgcggtaagt tgcagggcga tgacatgttg cagcttacga tggcgggtgt tcctgtgctg    23940
tctttgcttg ccaggcagac tggtaaaacg tctgctgagg tgtcgcagat ggtgtcgaag    24000
gggcagattg atttaacac gtttgcggct gcgatgaagc ttggcatggg tggtgctgcg    24060
caggcgtctg gtaagacgtt tgagggcgct atgaagaatg ttaagggtgc cctgggttat    24120
cttggtgcta cggctatggc gccgtttctt aacgggttgc ggcagatttt tgttgcgttg    24180
aatccggtta tcaagtcggt gacggattct gtgaagcccc tgtttgcatc ggtggatcag    24240
gggattcagc ggatgatgcc gtctattttg gcgtggatta accggatgcc gggcatgatc    24300
actcgaatga atgcacagat gcgcgccaag gtggagcagt tgaagggcgt ttttgcgagg    24360
ctgcatttgc ctgtccctaa agtgaatttg ggtgccatgt ttgctggcgg caccgcagtg    24420
tttggtattg ttgccgccgg tgtggggaag cttgttgcag ggtttgcccc gttggcggtg    24480
tcgttgaaga atttgttgcc gtcttttggt gctttgaggg gtgccgctgg ggggcttggt    24540
ggcgtgtttc gcgccttggg tggccctgtt ggtattgtga tcggcttgtt tgctgccatg    24600
tttgctacga atgcccagtt ccgtgccgct gttatgcagc ttgtgggggt tgttggccgg    24660
gctttggggc agattatggt cgccttgcag ccactgttcg ggattgttgc tggcgtggtt    24720
gccaggttgg ctcccgtttt tggccagatt attggtatgg ttgctggttt ggcggcccgg    24780
ctggtgcctg ttattggtat gcttattgcc aggctggttc ctgttatcac ccagattatt    24840
ggtatggtaa cccaggttgc tgccatgttg ttgcctatgc tgatgccggt tattcaggct    24900
gttgttgctg tgatacggca ggttattggt gtggtcatgc agttgatacc tgttttgatg    24960
ccggttgtgc agcagatttt gggtgctgtc atgtctgttt tgccgccgat tgttggtttg    25020
atacggtcgc tgataccggt gatcatgtcg attatgcgtg tggtggtgca ggttgttggt    25080
gccgtgctac aggtggtggc ccgtattatt ccggttatta tgccgattta tgtttcggtg    25140
attggattca ttgccaagat ttatgctgcg gttatcgttt ttgaggctaa ggttattggc    25200
gctattcttc gtactattac gtggattgtg aatcattcag tgtctggcgt gaggtctatg    25260
ggcacggcca tccagaatgg ctggaatcat atcaaatcgt ttacgtctgc gtttattaac    25320
ggtttcaagt cgatcatttc tgccggtgtt gccgcggttg tggggttttt tacgcggctt    25380
ggtttgtcgg ttgcctccca tgtgaggtct ggttttaatg cggcccgtgg agctgtttct    25440
tccgctatgg gtgcgattcg gagtgttgtg tcttcggtgg cgtctgctgt tggcgggttt    25500
ttcgggtcga tggcttctcg ggtccggaat ggtgctgtgc gcgggtttaa cggggccagg    25560
agtgcggctt cttctgctat gcatgctatg gggtccgcgg tgtctaacgg tgtgcatagt    25620
gtgctggggt ttttccggaa tctgcccagc aatattaggg gcgccttggg tagtatgggg    25680
tctttgttgg tgtctgctgg ccgtgatgtg gtggccggtt tgggtaacgg tattaagaat    25740
gctttgagtg gcctgttgga tacggtgcgt aatatgggtt ctcaggttgc gaacgcggcg    25800
aagtctgtgt gggtattca ttctccgtct cgggtgtttc gtgacgaggt tggccgtcag    25860
gttgttgccg gtttggctga gggtattact gggaatgctg gtttggcgtt ggatgctatg    25920
tcgggtgtgg ctggtcggct gccggatgtt gtggatgccc ggtttggtgt gcgatcgtct    25980
gtgggctcgt ttacccgta tgaccggtat cggagtgcga gcgagaagag tgttgtggtg    26040
```

```
aatgtgaatg ggcctactta tggtgatcct aatgagtttg cgaagcggat tgagcggcag   26100
cagcgtgacg cttttgaacgc gttggcttac gtgtgattgg gggtgttgtg catgtttatt   26160
cctgacccct ctgatcgtgc cggtttgact gttacttggt ctatgttgcc gttgattggt   26220
aatgatcctg agcgtgtgct tcatttgacg gattatacgg gtgcgtctcc tgtcatgttg   26280
ttgaatgatt cgttgcgtgg ccttggtgtt cctgaggttg agcattttc tcaaactcat   26340 gttggggtgc atggctcgga gtggcgcggg tttaatgtga agcctcgcga ggtgacgttg   26400
ccggtgttgg tgtcgggtgt cgacgaggat ccggtgggcg ggtttcgtga cggttttttg   26460
aaagcctatg atgcgttgtg gtctgctttt cctcccggcg aggaggggga actgtcggtg   26520
aagactcctg ccggcaaaga gcgtgtgttg aagtgccggt tgattcggc tgatgacacg   26580 tttacggtgg atccggtgaa caggggttat gcccgctatc tgttgcattt gacagcttat   26640
gacccgtttt ggtatgggga tgagcaaaag tttcgtttca gtaacgcgaa gttgcaggat   26700
tggttgggtg gcggccctgt cggcaagaag ggtaccgcgt ttcctgtggt gttaacaccg   26760
ggtgtgggct ctgctgggga taacctgtct aacaggggtg atgtgccggc gtggcctgtg   26820
attcgtgttg agggccccct ggagtcgtgg tctgtgcaga ttgatggttt gcgtgtgtct   26880
tcggactatc cggtggagga gtatgattgg attactattg atacggatcc tcgtaagcag   26940
tctgcgttgt tggacgggtt tgaggatgtg atggatcgtt tgacggagtg ggagtttgct   27000
cctattcctc cgggtggttc gaagagtgtg aatattgaga tggttggttt gggtgccatt   27060
gttgtgtcgg tgcagtacag ttttttgagg gcttggtgaa tggttgatgg ctggtcttgt   27120
tccgcatgtc acattgttta cacctgatta tcgccgggta gccctatca attttttga   27180 gtcgctaaaa ctgtcgttga agtggaatgg tttgtccact ttggagttgg tggtgtcggg   27240
ggatcattcc aggcttgacg ggttgacgaa gcctggggct cggctggttg ttgattatgg   27300
tggtggccag attttttctg ggcctgtgcg taaagtgcat ggtgtgggtc cttggcgttc   27360
ttcccgtgtg actatcacgt gtgaggatga tatccgcctg ttgtggcgta tgctgatgtg   27420
gcctgtgaat tatcgtcctg gtttggtggg ttcggagtgg cgtgcggacc gggattatgc   27480
ccactattcg ggtgcggctg agtcggttgc taagcaggtg ttgggggata atgcttggcg   27540 tttttccgcct ggtttgttta tgaacgatga tgagagtcgt ggccgctata ttaaggattt   27600
tcaggcccgg tttcacttgt ttgccgataa actgttgccg gtgttgtcgt gggctcggat   27660
gactgtcacg gtgaaccagt ttgaggatgc gaagtttgat cagcgtggtt tgctgtttga   27720
ttgtgttccg gctgtgactc gtgagcatgt gttgactgcc gagtcgggtt cgattgtgtc   27780
gtgggagtat gtgcgtgacg caccgaaggc tacgtcggtg gttgtgggtg gccgcggcga   27840
gggccgggac aggctgtttt gtgaggatgt tgattcggcg gccgaggagg actggtttga   27900
tcgtgtagag gtgtttaagg atgcccgtaa cacggattct gagaaggtgt ctctcttcga   27960
tgaggctgag caggtgctgc aagagtcggg ggccacgtcg gggtttaaga tcgagttggc   28020
cgagtcggat gtgttacggt ttgggcccgg caatctgatg cccggtgatc ttatctatgt   28080
ggatgtgggc tcggggccta ttgcggagat tgttcggcag attgatgtgg agtgcgattc   28140
gccgggtgac gggtggacga aggtgactcc tgttgctggg gattatgagg ataatccgtc   28200
ggcgctgttg gctcgccgtg tggctggttt ggctgcgggt gtgcgggatt tacaaaaatt   28260
ctaattgttg ggggtttgtt gtgggtattg tgtgtaaagg gtttgatggt gtgttgaccg   28320
agtatgattg ggctcaaatg tctgtgtctga tgggtaatat gccgtccgtt catgcccgg   28380 atgattttcg tgtcggcacg acgattcagg gttccacggt gttgtgtgag gtcctgccgg   28440
```

```
ggcaggcttg ggctcacggg gtgatgtgca cgtcgaatgc tgttgagacg gtgacaggtc    28500
agcttccggg cccgggtgag acccgctatg actatgtggt gttgtcgcgg gattgggagc    28560
agaatacggc gaagttggag attgttcctg gtgggcgtgc tgagcgtgct agggatgtgt    28620
tgcgtgcgga gcctggcgtg ttccatcagc agttgttggc tactttggtg gtgtcgtcta    28680 acggggttgca gcagcagctt gacaggcgtg ctatagctgc ccgtgtggcg tttggggagt    28740
ctgctgcgtg tgaccctacc cctgtggagg gtgaccgtgt gatggttcct tcggggctg    28800 tgtgggctaa ccatgctaac gagtggatgc tcctgtctcc tcgggttgag acgggttcta    28860
agcagatcca gtttggcggg tctgctgtgt atgcttacac gatcccgttt gcccggccgt    28920
ttagtagccc gcctatcgtg gtggcgtcta tggctacggc ggctgggggc acgacacaga    28980
ttgatgtgaa agcctacaat attactagca aggattttag tttggcgttt attacgaatg    29040
atggttcgaa gccgaatggt gtgcctgcgg cggctaattg gattgctgtc ggcgtgtaat    29100
gtacggcttg cgtgtgcggg acgtgttgtg gtggttgtag tggtaggggg ctgtagtgtc    29160
atggtttaca cctacgcttg tggcctctct ttgtaccgct atcgctactg ttcttggttc    29220
gattcaggcg gctatgtaca ggtcgaagaa gaggcttagg cagttgtctg cgcaggttga    29280
tgcgatggaa gagtacacgt ggaatattcg ccatattgtt caccgctata acgcgaattt    29340
gccggatgat gttgagccgg tgaagatgcc tgatttgccc gagttttga aggatactgt    29400 tgatggtggt gggggggtgaa ttgtgaggga gttagaggag gagaagcggc agcgccgctc    29460
gtttgagaag gcttccctga tattgttgtt cttgtcgctt gtcctgttgg cggtggttgc    29520 cggggggtgct ttacgtttcg gggctgtatc ctctgagcgg gattcggagc aggctaaagc    29580
ccagtctaat ggtacagccg ccaggggttt ggctgcccgt gtgtggcagg tgtgtgcttc    29640
tggtggatgg gagtctgtgc ggcttcacca gtctggtttg tgtgtggatg ctgtgcgtgt    29700
tgagcggagt gtgcagggtg ttccgggtcc ggctggtgtg cgtggcccgc aggggccggc    29760
tggtgttgat ggccgggatg gtagcaatgg ttctgctggg ctggttgggc ctgttggtcc    29820
gcagggttcc cctggcttga atggcgtgaa gggtcctgac gggctgcccg gcagtgacgg    29880
ccaggatggc cgtgatggtg ttccgggccg tgcaggagtc gacggtgtga acggatccga    29940
tggcaaggat ggtcgtgatg gttcggctgg tgagcgcggc gatgtggggc cttcgggtcc    30000
tgccggaccc cctggc                                                    30016
```

<210> SEQ ID NO 74
<211> LENGTH: 29913
<212> TYPE: DNA
<213> ORGANISM: Artificial Sequence
<220> FEATURE:
<223> OTHER INFORMATION: PAC13

<400> SEQUENCE: 74

```
tgagcgtggc cccgccggtg tgaatggatc cgatggtaaa gatggtaagg atggccgctc      60
ggtggtgtct gtgtactgtt ctgatggtcg cctggttgtg aaatatagtg acggtgtggc     120
ttctaccata tcgggttcgg tggcctgcca gggtgtgaaa ccgtcgccta tagtgactat     180
atcatcccaa aaatagaaag gagtggctgt gatggtagtg tttggtggtg gtgtgtggtg     240
agatacattc ctgcagcgca tcactcggcc ggttcgaata gtccggtgaa cagggttgtg     300
attcatgcga catgcccgga tgtgggggttt ccgtccgcct cgcgtaaggg tcgggcggtg     360
tctacagcaa actattttgc ttccccatcg tcgggtggtt ctgctcatta tgtttgcgat     420
```

-continued

| | |
|---|---|
| attagtgaga cagtgcaatg tttgagtgag tctacgattg gttggcatgc cccgccgaat | 480 |
| ccgcattctt tgggtataga gatttgcggc gatgggggtt cgcacgcctc gttccgtgtg | 540 |
| ccggggcatg cttacacgag ggagcagtgg ctggatccta gggtgtggcc tgcggtggag | 600 |
| aaggctgcca tcctgtgtag acgtttgtgt gacaaatata atgttccgaa aaggaaactg | 660 |
| tcggctgccg atttgaaggc cggtaaacgt ggtgtttgcg gcatgtgga tgttacggat | 720 |
| gcgtggcatc agtcggatca tgacgatccg gggccgtggt ttccgtggga caaatttatg | 780 |
| gctgtggtga atggccacgg cggcggttca agtagtgagg agttgagtat ggctgatgta | 840 |
| caagcgttac atgatcagat taaacagttg tcggcacagg tggcccagtc ggtgaataag | 900 |
| ctgcatcacg atgttggtgt ggttcaggtt cagaatggtg atttgggtaa gcgtgttgat | 960 |
| gccttgtcgt gggtgaagaa tcctgtgacg gggaagctgt ggcgcactaa ggatgctttg | 1020 |
| tggagtgtct ggtattacgt gttggagtgt cgtagccgta ttgacaggct cgagtctgct | 1080 |
| gtcaacgatg tgaaaaagtg atggtggttt gtggtgggta aacagttttg gttgggcctg | 1140 |
| ctggagcggg cgttaaagac ttttgtgcaa acgtttgtgg ctgtgttggg ggtgacggcg | 1200 |
| ggtgtcacgt atacggcgga gtcgtttcgt ggtttgccgt gggaatcggc cctgatcaca | 1260 |
| gccggggttg ctgcggtttt gtcggttgct acctcgtttg gtagcccgtc gtttgtggcc | 1320 |
| ggcaaacctg gcaagcagcc cctggtggat gagggtttgg ttccaccgga tgatcctgga | 1380 |
| atagtggagt ctcactcggt ggatgtgtcg gatcctggca tgatcgagcc gacggatgat | 1440 |
| gcggatcttg gtgtaggcta tgtgccgaaa catgctgccg agtcggaggt tggcatgata | 1500 |
| gagtctactg ttgcataagt gaatatagat gtgtgcccca gcggtgctgc cacggttgtg | 1560 |
| tggtggttgc cgctggggca ctctttttat gttctatagt attctatgat tcgttgctgt | 1620 |
| cgatggtgtc ttcgagcatc tggtacaggt ggaggcaggt agagatagtt tcgctggcct | 1680 |
| ggtcgagaac ggttcggccg ataacgtttt tgtgattgtc gcggtggcgg atgatagccc | 1740 |
| acatgatctc gtcggccgcc gcctgcaata gtttggcctg gtatgcgatc ccggcgagcc | 1800 |
| agtctagtgc ttccgggctt gcatgggggc tctggtcctc gctgttgccg cgggtgttgc | 1860 |
| tgttgtttgt ggggtgtcct gcactgtcgc ataaccacag gatttcgctg cactcgtcta | 1920 |
| gcgtgtcctg gtcgatagcg agatcgtcga ggctgacatt gttgacggta aggttcacgt | 1980 |
| tgtcgaggga gatgggtaca ccgtactggt tttcgacact gtcaacaatg ttttgtagtt | 2040 |
| gttgcatgtt ggtgggctgt tgttggacga tgcggtgtat cgctgtgttg agggtggtgt | 2100 |
| aggtgatgtt gtgtgtgttg tccatggttt ttatgccatt ccttcgttat cgtctggcat | 2160 |
| gtagtatgtg ctgtttgcgt actcggttaa cgtcatcagt gtttggtctg cccactgttt | 2220 |
| cacagtctgc cttgtcactc cgagtcgttg gcggcagac gcatatgttt ggtcataccc | 2280 |
| gtatacttcc ctgaatgctg ccaaccgtgc caaatgtttt cgctgtttgg atggctggca | 2340 |
| ggtgagggta tagtcgtcga tggctagctg tagatcgatc atggtaacga tgttgttgcc | 2400 |
| gtggtgttgt ggcgcggttg gtgggggtgg catgcctggc tccacactgg gtttccatgg | 2460 |
| tccgccgttc cagatccatt gggcggcttg aataatgtcg gcggtagtat aggttcggct | 2520 |
| cacttggtca cccctgaac aggtcgttgc tggtggtggt gtcgaatcgt ccgacgcagt | 2580 |
| ggcagtagtc gtacatgagt ttaataatgt gttggtggtc tcccaaatag gtgtttccgc | 2640 |
| tgatactgta ggtggctgtg ccgtctttac tgatggtgta tttggcggtg atggtttcgg | 2700 |
| ggttttcggt gtcggtgatg atggctgtgg tggtggcacc tactgtttgg agcacggtgg | 2760 |
| tttgggttcc gtcgtcgatg gtggttttaa ccatgaggtg ttctccccttt gtgttagttg | 2820 |

```
ctggtttggt tgtcggctag atgaatgatg tcgggtaagg gtttcggctg gtcgaggtgt    2880
tgtatggttt tgttggctag ccgtttggct accctgtaac acattttggt gtagtgtttg    2940
ttgtctaggt tgtggtattg ttcccgcacc gcaatatata gcagggagtc ttggtatagg    3000
tcgtctgcac tgattgcggg gtagtgtgcg gctactttgg tacatgcccg gttgagtgtg    3060
cgtagatgat ggtctgtggc ccacacccac gatgcggtgg tggctaggtc ggcttttgtt    3120
ggtcgtctac tcatggcatc tctttcatct ggctatctgg tagttgtttg gtgttttgtt    3180
gttgatagtg tagcacacga gcccggggtt tccggtggtg cccgtcttgt gccggtacca    3240
tgtggattcg ccttccatgg atgggcattg gatgaaggtg cgttgtcctt gctcggagat    3300
ttctaggtgg tgccggtgcc ctgccatgag aatatgggat gtggtgccgt tgtggaattc    3360
ttggccgcgc caccaatcat agtgtttgcc ggtgcgccat tggtgccgt gggcgtgcag    3420 tatccgtgtg cctgccacat caacggtggt ggtcatttcg tctcggctgg ggaaatggaa    3480
gtgtaggttg gggtattggt tgttgagctg gtaggcttct gcgatggcgc ggcagcagtc    3540
tacgtcgaag gagtcgtcgt aggtggtgac gcctttgccg aagcgtacgg cttctccgtg    3600
gttgccgggg atggatgtga tggtgacgtt tttgcagtgg tcgaattggt ggatgagttg    3660
catcatggcc atgcgggtga gcctgatttg ttctgtcagg ggtgtttggg tgcgccaggc    3720
gttgttgcct ccttgtgaca cgtatccttc gatcatgtcg ccgaggaagg cgatgtggac    3780
tcgttgcggt ttgcctgcct gttgccagta gtgttttgcg actatgaggg agcgtaggta    3840
gttgtcggcg aagtgtgctg tttctcctcc ggggatgcct ttgccgattt ggaagtctcc    3900
cgccccgatg acgaaggccg cggtgctgta gtcggtgtgg gtgtcttgtt cgggttttgg    3960
gggtgtccat tcggctagtt tatcaacgag ttcgtctacc gggtaggggt tggttgctgg    4020
ttggtggtca ataatttttt gtatggatcg gccggtttct ccgttcggta aggtccattc    4080
ggagatgcgt gtgcggcgca cggtgccgtt ggctagattg tcgtcgatgg tgtcgatggc    4140
gttgtcgtgg ttggctagct gtgtgagtag ccggtctatg ttgtctatca ctgggtatcc    4200
tcctcgtgtg tggtggtggc ttgtttgcgg cggtagtctt tgataacggt ggcggagatg    4260
gggtatccgg cttgggtgag ttgttttgct agccacgagg cggggatggt tttgtcggcg    4320
agcacgtctg cagccttatc accgtagcgt tggatcaatg tttcagtttt ggttgccatg    4380
atgtcctatc ggctgtgtgg cgggctgcca tcctgtgcgg cagtcgccgt cgtgtcctgg    4440
tttgcgggtg caccacgata cggttccgtc tgtgtggtgg agtgttttgc cgcacaggac    4500
gttttggaga tgctccggca gctggtcatt ctggttgctg gtttgtgtgt cgaagagtgt    4560
tttctggttg gtgaaatgct cggacacggt gccattatgc acgggtagta tccatgtttt    4620
ccattgttgt tgcatccggg tgttccagtg gaattgtttg gcagctgtct cggcttgttt    4680
ggcggttttg tagtagccga ctagtatgcg ctggtgttca ctgtcgggcg ggttttggcc    4740
tcgccagtat tgtgccgcaa ccgcgtacct gttgttgtcg gtgaagcgct gccagcagta    4800
ttcgatgatg tgttgcagta cactatcggg aattttttgt gtttggtttt cgttgagcca    4860
ttcggcttcg atgatgccgt gtatggcgcg tttgtctttg gtggtgggtt tgaacgagat    4920
gctcacgata gtaccggctg atcgtcttgc atgaactggt tgaaggtgtt gttcccggcg    4980
tgttgggctt gtgtgatttg ctggtcggtc cagtctgggt gttgctgttt cagatagtgc    5040
cagtggcacg cattgtaggt ttcgtcttgt agccgtgtga gatggttttc ggtgatgatt    5100
tgtttccaca tagtccatga cacgtcgagc ctgttgagga tttctatggc tgggatgttg    5160
```

```
aattggtcga ggaagaggat ttcgtgggtg tagtagtttt tctcgtaggc gtcccatccg    5220
cttcggtgcc tgttgggctg gttttgggg taggcttccc ggcatacttt tgtgtaaccgt    5280 ttggccatgt cgtcgggtag tttaatgtcg gggttggcgc ggatcatgga tcgcatccca    5340
tcataggtgg tgccccaggt gtgcatgatg taggtgggg cttcaccatc ggcccatttt     5400
tctgcacaga tggcgaggcg gatgcgcctc ctggctgttt ggctgatgtt gcgccggttg    5460
gggatggggc acgtgtcgag gggatccatg atgttttta tgcctttctt ggtttcgtgt     5520
tgttgacggg ttttactgta gcacagtgtc tagtgcttgt gtcaaccctg tttttccggc    5580
ctgcaggtag gtgtctgtga catccccag ggtgagggc acgtgggtgg cttgggggag     5640
tgctgcctgg agggtttgtg ccatctggtc gcctgctttg tctgggtcgg accagatgta    5700
gatgtggtcg tagccttcga agaatttggt ccaaaagttt tgccacgagg tggcgccggg    5760
tagtgctacg gccgaccatc cgcattgttc gaggatcatg gagtcgaatt cgccttcgca    5820
aatgtgcatt tcggctgccg ggttggccat ggcggccatg ttgtagatgg agcctgtgtc    5880
ccctgccggg gtcaaatatt tggggtggtt gtgggttttg cagtcgtgcg ggagtgagca    5940
gcggaaacgc attttcgta tttcggctgg ctgtccccaa acgggtaca tgtatgggat      6000 ggtgatgcac tggttgtagt tttcgtggcc tgggatgggg tcattgtcga tgtatccaag    6060
gtggtggtag cgggctgttt cttcgctgat gcctcttgcc gagagcaggt cgagtatgtt    6120
ttcgaggtgg gtttcgtagc gggctgaggc tttctggatt cggcggcgtt ccgcaatgtt    6180 gtagggcgt atgctgtcgt acattcgggt ttttttctc tagtcgttgt tgtagtttgg     6240
cgagtcctcc tccgataccg catgtgtggc agtaccagac gcccttgtcg aggttgatgc    6300
tcatggaggg ctggtggtcg tcgtggaacg ggcagaggat gtgttgctca ttcctagacg    6360
gattgtaccg tatctggtag gtgtcgagga ggcggcaggt gtcagaggtg tgggaggagc    6420
tcgttgaggg ttgataccac ataggcttcg ctccatggct tgttgcgttg tttcatgacg    6480
acgagtccga tggtggactg gttttcgcgg tttcggtgtg tttcgtagtt gcgtgcctcc    6540
cggctggctt gtttcacgaa ttgggctagg tggggttgtc ctgctttcgc ctcgataatg    6600
taggttttat ggccggttgt gaggatgagg tcgccttcgt cctctttacc gttgaggtgg    6660
aggcgttcta tatcatggcc ggtgtcgcgt agctggtgca ataatcgtgt ttcccattct    6720
gcgcctgccc tgcggttgcg tgactgttgt gtcgacatga tagtcctttg tgtgttgtgg    6780
tcatgttcca tggctgtttt tcggcgagtg gcccgaagaa tgtgtattcc gggtatgccc    6840
tgagccgctc atattttgtt ccgtctgggc tggatttgcc tgtgcgctgt ttcaacactg    6900
agatgcgtgc ctcggcgggg atcgtgagcc cgttgccgtt atcctcgcca ccataaagtg    6960
agactcccaa tatgagttgt ggttttcgg agaggccgtt tttgatttcc cgcctagccg     7020 ggggtgttc gatgtcggtg ccggttttgt cggtggcgtg gtgggtgaca atgatggtgg    7080
agccagtatc tctacctaat gctgtgatcc attgcatggc ttcctgctgg gcctggtagt    7140
cgctctcgca gtcttggatg tccatcaggt tgtcgataac gatgatgggt gggaaggtgt    7200
tccacatttc catgtaggct tgcagttcca tggtgatgtc tgtccatgtg atgggtgact    7260
ggaatgagaa tgtgatgtgt tggccgtggt ggatgctgtc tcgatagtat tctgccccgt    7320
agtcgtcgat gttttgttgt atctgtgtgg tggtgtgttg ggtgttgagt gagatgattc    7380
gcgtggaggc ctcccagggt gtcatgtccc ctgatatgta gagggcgggc tggttgagca    7440
tggcggtgat gaacattgct agcccggatt tttggctgcc ggaccgcccc gcgatcatga    7500
ctaggtcccc tttgtggatg tgcatgtcca ggttgtcata caagggtgct agttgtggta    7560
```

```
tgcggggcag ttcggcggct gtttgggagg ctctctcgaa ggatcgttgg agagagagca    7620
tcggagcctt aatctatctg tctatcggtt ggatgatgtt ttggtggtca gatggagtcg    7680
atgtcgatgt cagcatcagc aggggctgtg gtgtcgtcta gctgaccgtt atcgcgtttg    7740
tctacgtatt cggcaacctt atcgtagatg gcgtcatcga ggggtttgag cacgaccgcg    7800
ttgaagccgt ttttggtgcg cacggtggcg agtttgaagg cctgctcctc gccaaggtag    7860
gcttcgaggt cgcggatcat ggagtgtggg cggtcgttgt tgccgcgggc tttctcaatg    7920
atagcgttgg ggatggtttc tggggtgccg ttgttgagat cctcgagggt gtggaagata    7980
gtcacatcag cgtaaatacg atcggcggtc tgtccaccgt agccttcggt gttgtgttcc    8040
acgtcgcgga ttttgaaggc gatggcggtg gcgtcctggt ttcgggaggg gttgaagaag    8100
gtgctgttgc tgttgttgcg gtagtttgcg agtcccattg ttgtttcctt tactgtttgt    8160
gttgttttgt ttgttggttt gtgtcggttt ttatcgggtg aggctgtttc gtttgctgcg    8220
gaaagcctca gacacgtcac tgttactagt gatggtcttc ttgtactgtt tgaggaggtc    8280
ggctagctgt gccttgcttg ttgcattgtt gattttgtcg atgacgatgc tgttttcttt    8340
ggatgcgatg ttgtccacgt agtctttggc ggcctggttg tatcggtctt ggaggatgat    8400
ggatgctgtg gcgatcaggg ttgccaggtc ccagttcctt gccgcggagc tgttttttgag    8460 tccgcctagc aggtcgatga tagtcttctt tacctggtcg gcggtgtctc cgcggatgac    8520
ggtccatggg gcggcgtagt cgcctccgta tttgagtgtg acggtgaatc ggtcgtcgtc    8580
tgtgttgtcg gtcactggtg ctccttgcct tcttttgttg gggctgtgat ggtggtttct    8640
atagggtacc tgtaggcgtc tttcccgtta acagcccagc aggcgtcctt gacggggcat    8700 ccttacaga gtgctgtgac gtggggtacg aagatgcctt gactgattcc tttcattgct    8760
tgactgtaca tggatgatac atgccggtag gtgttgttgt caagatcgta cagttcggtg    8820
gatgtgccct gttcgaccga ttgctcgtcc cccttggtgg tggcgggtgt ccaaaacatg    8880
cctttcgtca catcgttgcc gtgttgggcg agcatgtacc ggtaggtgtg cagctgcata    8940
ctgtcggcgg gtaggcgtcc tgttttgagg tcgagaatga aggtttcgcc agtgtcggtg    9000
tcggtgaaaa cgcggtcgat gtagccaacg atctgggtgc cgtcctggag ggtggtttct    9060
accgggtatt cgatgcctgg ctggccgtct aggattgcgg tgatgtattc tgggtggttg    9120
cgcctccatg ttttccagcg gtccacaaag gtggggccgt acatcatcca ccagtcgtag    9180
tctttcttgt gtggcccgcc cgactcgcac atgtttttgc atattctgcc ggagggtttg    9240
atttctgtgc cttcggattc ggcgagggcg acttgggtgt cgaaaatgtt tttgaaggat    9300
gagagtttgt ttggtagtgc agggtattcg gtggggttgt acaggtgtag gtcgtattgt    9360
tcggtgatgt ggtgtatggc gcttccgcg atggtggcat accaggtgtg gtgttgggca    9420
tggtagccgt gggataggcg ccatttttca ccacattcgg cccactgtga cagtgatgag    9480
taggagatgt ggcctggatg gtggatggtt ttcgggtatt gtgctagggg cattactggt    9540
cgcctttgtg ggtgttccat gggtttcggg tgtcttggcc ggcattgtgt tgctggtagg    9600
cgaggagtgc gaggcagtgc caggcagcat gggctagatg gggtagcccg gattcgtggt    9660
cgaggttgtt gccttgctgc catgatagta ggtgcctgta gagggcgtcg acgctgtggc    9720
tccacgggta tccgccggtc cagttgttgt cgccgtattt ggtggcaccg tagcctgcga    9780
cttcgccgag ggcgtgtaag gctgcggggt cgatgaggga gagtcggcat agtttgagtt    9840
cttttttggc gcctgtgtct gggttggtgt acatgcgggt gggcttatcc atggggtgtg    9900
```

```
tgctccttag gggtgggtta ctggttgggg ttgtgggcga gtgctacggc gaggatgatg    9960
atggcgaggg tttctgcgat gatgatgggg gttgtgatca tttggtgtct cggggattgt   10020
tggtgagggt tgaggcgcct aggagggtgg tgagggcgca tgcggcgatg atggcgaggg   10080
ctgccttgtg tggggtgccg gttgcgtaca tccatgtgat gatggcgcct ggatccatg    10140 ccagtgtggt gaagaatgtt tcgtagctgt gtagctcgct tttgttgctg gtgatgtcat   10200
tcatggtagt tttctgcttt gtgtgcgatg gttgtgtaca tgtcgttgag tgtggtttcg   10260
atggtgatga gagtgttgat tcttggttg aggtcgatgt tgtctttgag ggtgtcgatg    10320
cgggcggcga tgtcggtggc ggtgcgtagg cttactgctg caccgtggat gatgtggcat   10380
atgtcggtga ggccgacttt ggcgatgtag tgtgacatga gaggcatagc ggggatgctc   10440
cttggcgggt tactgttgcg ggttgatgtt gaggtcggtg acgttggggt ggtcttctgt   10500
tccggtgacg aggcagtgga cggtgactgg gagtttggat gcgccgggct gtttcgcggt   10560
tgcgccgtag acgatggaga aggtgtcttt accaataatt ttgtggagtt ggaggtcgat   10620
gtcggggttg ccgttccagt tgacaccgtg tgctgcggcc tgctgttcgg cttttgcggtt   10680 gcaggtgtgt gctgcggtga tcatggtgag accctgtgag gtttcttcac cccttgcttg   10740
ggcttgccgg tgggttttct gctgttcggc tcgcagtgac tgttctgcgg cggcctggcg   10800
tgctttcttt tcggctttgc gctgttggat agtcttgggt gtccattcgg tgttggctgt   10860
ggtggcttgc ggtgcgggct gtgatgcgag tggcggattg tcgtcgggtg ctggcaggaa   10920
ggatgctgcg gcgatgatgg cggctgtgat tccggcgatg gtgtagcctg ttttcttgtt   10980
catggctttg tgttcccctt tccggggtgt tgttcgttgc tgacatgatt aatactttca   11040
gcggctgggc ccactgtcaa ggctgcgctc agtttgcgtg agcgatactt gtgtggctag   11100
gggtgatggc ttctttcgcc caataggatg tgccaccgct ggtccagtat ccagtttgt    11160 tgcgctgcat gcccttggcg tccatctcgt cgatcgtgag gcacctgcga cgactggggc   11220
ctgtcttgac tccatggtcg cctacccggt gcatgtcgcc tgaggtggta ctcgtgaatg   11280
tttcgtggca gattgtgcag tgctctggct tgtatccgat gatggtgcta tcgcacttgt   11340
ggcatgtcca ttgcatgatt gctcctattt tccattataa gacttcctgt agtgccattt   11400
tagcgccttg cgagtcttgg gggtacaact atataggtcg ggtatttcta ggcgattcta   11460
ggctcgttgt gtgtggttgg gggtttatcg ggcgcacagg gtgagcaggc ttccgatgtt   11520
gatgcgtatc acattccagt agagttgtgt ggcttcaccg tcggtgagtg gcttccactc   11580
gtcatggctg aacacggtgc catcggatgc gatgaacgtg ttggggcgta gcttgtggag   11640
ttcagtctct acacgctgcc ggtaggcttc ggcgaggccc tcaaaatcca tgtggtcgca   11700
ggagaggttt tcgaagcgtg tcaagtcgat gggtgtgggg cagtcgtcgt tggtgggggt   11760
gtagagctgg gtgaagtggt tggcgatctt ctgcatgacg ggttccttt ctcgtgtgat     11820 gggttgatag ttttatcggg ttgcggcggc aataatggca tccacgtcga tcatgtcgat   11880
catgtcgttg agttcctcgg cctcattctc ggagaggtgg cgccagccat agtcgccgta   11940
tacggcgccg tcgagggtga cagtccacag gggccggatg agtcgtacgg cttcttcgac   12000
tttggcgtgg tacatgcggc gcaccatatc cagatcgatg tcgtctgaat ggtttccggt   12060
gaggctgtgg aagctgagcg ggtcgatttc tgtctgcctg tcgaggctgg tgaatgatgg   12120
tgtgatgagt gtgccatcca tagggtgtgt gctcctttcg gtggtggagg ggttgttgtg   12180
gtttctagag tgtgtaggtt gcgacccac  agtcaaggtg gcgctcattc ggattgagcg   12240
tttcatggaa ggtgacggat gtcactgaag ccttgatggc ctctctcatc gcctgaaatc   12300
```

```
ttctagaggt aggattatgc agggtttacc ctgctgatcg attctagggg ccttctaggg    12360
cgtctcaggg gtgtatctgg gtgatagcag gtccggtaga tctatcttgg cttttcatgac   12420 gggggtcgag gtgccagatc tggtcatgga atccacaccc tcatactgtg tgagatgtat   12480
cacatcctcc tggcttggtg tgccctctcg aggctactct gccgatctgg cgtgaagggt   12540
gtagcccaga aatgccgttt aaagcctccc tatggcgcct aggagcgcct tacagagtgg   12600
gggctaggta ttcatacccc caagcaattc tgatcgattc tagacgcctc ccagagcctg   12660
atacacgatc aaccatctcg gcatagacca gcagccccta tcctggttag ctaagcctca   12720
actatgtgga cagtgtggga tactaagggg gaagaaggac acggtaaaag aaagagggg    12780 agcatcagcc ttagggtctt agcacttagc gcttagcacc gagcccctca agggctcggc   12840
atcagcccga cagcccgagc aggctcagcc gatcaggcac agccctgaaa ggggtacacg   12900
ccatcaggga aggcttgaga gtacgaggag ccctagcgac gagtactcga aagcctgagg   12960
gaacacccat cagcactgat gggcctagcg tgttcggaaa ggacacaaga gtacagtgtg   13020
acagctgttc gggagtgaaa cctgttctga ctaggggttt cagccttaac caccctcaaa   13080
ggttacaaga ctctaagaaa atttaaggaa aagtttaggt ttaattttg  gacctttact   13140 accaaaaaca cccgtttaca cccctcaaac ccgcctatag agccaaaacc accagtttga   13200
ctcatcccag gtggggtatg ataggctgga caggtagcca gctggacgca aggccgaaat   13260
ccgctgacgc ggctttcacc cttacatcca tcagtctacc aaagacttaa aagcttaaca   13320
gctaagcgct aagcccttaa gaccttaaca cttagcaccg agcccctcaa gggctcggca   13380
tcagtcttaa agccttaaac acttaaagtt ataataaac  attaaagctt taaagtctta   13440
aagtaaatat ataaccttaa cagttaaacg tttaaagctt taaaccttaa cacctaagtt   13500
aagtataaaa ccttaaaggc ttagcactta aggatataaa cttaacatca gtgtttaaga   13560
ctttaagact ttaaaactta aaataactat taatacttaa aagcttataa gtattaaaca   13620
cttaaagtaa ctataagact ttaaaaacct taagtactta aagttaacca tcagtcttaa   13680
actttaatat tataacctat aagtcttaaa gcttataggt gtaataatat aatataagta   13740
ttaaagctta taagttataa aagtttaga  agagttaaag ggttaacttc tttacttctc   13800
tactctcttt ggtactttct ctcttctctt cttttcttca tcaggggaga agaggaacct   13860
ttaccatcag cgccgatgga cttttcgccg tgtgtctcgt gtaccaccgg tcgcacgctc   13920
ccggtttgta cactccccac actctgacac ctgtgtccct ttacggcttg gcgtgttcgg   13980
ctgaaggcgt acggcgtgtc acgctcacac ccttaacacc aggtaagact taaagtgtat   14040
attataagta gaagacttta aaacctgtaa ggtgttcccg cttagccgt  gtccttccac   14100 gctaggcgcc aagcgctaag ctgtgaaacg cgaacacaca cccaccccct ttttctttc    14160 gtgtccttct cttttgaca  cagctgggg  gcgatgtgat cttttcaca  tgccagggg    14220 tagtggagaa aacaagcacc ccggaatgtt caagacaccc cctcaaacga acaaaacgcc   14280
ccccataatc gatgagcagg gcaagggcaa ggtattcata cccccaacgg ttcccaggct   14340
gttagagagg caaataagac ccctgcaagg gtaggcgagg aacagacaca tcatggcacg   14400
caccaaccgc accgcatcat cagcccaccg ccgctggcgg gcaagactca tcacccagc   14460 acgcaagcaa ggccaaaccg aatgcccact ctgcggagcc accatcacct ggaacacaca   14520
tgacctgcca accagcccg  aagccgacca catcacaccc gtcagcaggg gaggactcaa   14580
caccctcgac aacgggcaaa tcatctgcag aacatgcaac agaagcaaag gcaatcgcag   14640
```

```
cgaaccaaac atccaattcc aacaacaaac cacaaaaacg ctgatcccat ggtgaaaaaa    14700
ctgtcaaccc ccaccgggac cccccctgca cacccgtgca agacctcgta cggcttagtg    14760
aaatacctcc cttttgtggt tttgtctgtt tgtcgacttt ttgtgttggt ggtgagtgtt    14820
gtgcagcctg agcttcctgg tggtcgtgag tggtgtgggg agacgcgtcg ttggtggcgt    14880
gtgtggggtg aggatagccg cgcatcgtat gtgtctgatg aggagtggtt gtttcttatg    14940
gatgctgcgg tgattcatga ttgtgtgtgg cgtgagggca gggcggattt ggtggcttcg    15000
cttcgtgctc atgtgaaggc gtttatgggc atgttggatc gttattcggt tgatgtggtg    15060
tctggtggcc gtggtgggggg ttctgcggtg gcgatgattg accggtatag gaagcgcagg    15120
ggggcttgag taggtgtctg gtgttgtggg ttctcaggtt cctcgtcatc gtgtggctgc    15180
ggcgtattcg gtgtctgctg ggggtgatgc tggggagttg ggtcgtgcgt atgggttgac    15240
gcctgatccg tggcagcagc aggtgttgga tgattggctt gctgtgggtg gtaatggtag    15300
gcttgcttcg ggtgtgtgtg gggtgttttgt tccgcggcag aatggcaaga atgctatttt    15360
ggagattgtg gagttgttta aggcgactat tcagggtcgt cgtatttttgc atacggctca    15420 cgagttgaag tcggctcgta aggcgtttat gcggttgagg tcgttttttg agaatgagcg    15480
gcagtttcct gatttgtatc gtatggtgaa gtcgattcgt gcgacgaatg gccaggaggc    15540
tattgtgttg catcatccgg attgtgccac gtttgagcgt aagtgtggtt gtccgggttg    15600
gggttcggtt gagtttgtgg ctcgtagccg gggttctgct cgcggggttta cggttgatga    15660 tttggtgtgt gatgaggctc aggagttgtc ggatgagcag ttggaggctt tgcttcctac    15720
ggtgagcgct gccccgtctg gtgatccgca gcagattttt ttgggtacgc cgcctggccc    15780
gttggctgac gggtctgtgg tgttgcgttt gcgcgggcaa gccctcggtg gggggaaacg    15840
tatcgcgtgg actgagtttt cgattcctga cgagtctgat ccggatgatg tgtcgcggca    15900
gtggcggaag cttgctggtg atactaatcc ggcgttgggg cgtcgtctga attttgggac    15960
cgtaagcgat gagcatgagt cgatgtctgc tgccggtttt gctcgggagc ggcttggctg    16020
gtgggatcgt ggccagtctg ctgcgtctgt gataccggct gataagtggg ctcattctgc    16080 ggtgatgag gcggctctgg ttggcgggaa ggttttttggt gtctcgtttt ctcgttcggg    16140
ggatcgtgtc gcgttggcgg gtgctggccg gactgatgct ggtgtgcatg ttgaggtgat    16200
tgatggcctg tcggggacga ttgttgatgg tgtgggccag ttggctgatt ggttggcgtt    16260 gcgttgggt gacactgaaa agatcatggt tgccgggtct ggtgcggtgt tgttgcagaa    16320
ggcgttgacg gatcgtggtg ttccgggtcg tggcgtgatt gtggctgata ctggggtgta    16380
tgtggaggcg tgtcaggctt ttctggaggg tgttcgttcg ggtgtgatca gtcatccgcg    16440
tgccgattcg aggcgtgaca tgttggatat tgctgtgagg tcggctgtgc agaagaagaa    16500
gggttctgcg tggggttggg gttcctcgtt taaggatggt tctgaggttc ctttggaggc    16560
tgtgtctttg gcgtatcttg gtgcgaagat ggcgaaggct aggcggcgtg aacggtctgg    16620
taggaagcgg gtgtctgtgg tatgaactcg gatgagttgg ctctgattga gggcatgtac    16680
gatcgtattc aaaggttgtc ttcgtggcat tgtcgcattg agggctacta tgagggttct    16740
gcccgggtgc gtgatttggg ggttgctatt cctccggagt tgcagcgtgt gcagacggtg    16800
gtgtcgtggc ctggtattgc tgtggatgct ttggaggagc gtctggattg gcttggctgg    16860
actaatggtg acggctacgg cctggatggt gtgtatgctg cgaatcgtct atcaaccgcg    16920
tcatgcgacg tccaccttga tgcactgatt tttgggttgt cgtttgttgc gatcattccc    16980 caggggatg gttcggtgtc tgttcgtccg cagtcgccca agaattgtac tggccggttt    17040
```

```
tcggctgacg ggtctcgttt ggatgcgggt ttggtggttc agcagacgtg tgatcctgag   17100
gtggttgagg ctgagttgtt gcttcctgat gtgattgttc aggtggagcg gcgtgggtct   17160
cgtgagtggg ttgagacggg ccgtatcgag aatagtcttg gtgcggttcc gttggtgcct   17220
attgtgaatc gtcgccgtac ttctaggatt gatggccgtt cggagattac gaggtctatt   17280
agggcttaca cggatgaggc tgtgcgcaca ttgttgggcc agtctgtgaa tcgtgacttc   17340
tacgcctacc cgcaaaggtg ggttacgggt gtgtcggctg acgagttttc gcagcctggc   17400
tgggtcctgt cgatggcttc tgtgtgggct gtggataagg atgatgacgg cgacacaccg   17460
aatgtgggat cgtttcctgt gaattctcct acaccgtatt cggatcagat gcgtttgttg   17520
gcgcagttga ctgcgggtga ggcggctgtt ccggaacgct atttcggggt tatcacgtct   17580
aacccgcctt ctggggaggc tttggctgcg gaggagtctc ggcttgtgaa gcgtgctgaa   17640
cgccggcaga cgtcgtttgg tcagggctgg ttgtcggttg gttttttggc tgcccgggcg   17700
ttggattcga gtgttgatga ggctgcgttt tttggtgatg tgggtttgcg ttggcgtgat   17760
gcttcgacgc cgactcgggc ggctacggcg gatgctgtga cgaagcttgt tggtgccggt   17820
attttgcccg cggattctcg gacggtgttg gagatgttgg gtttggatga tgtgcaggtt   17880
gaggctgtga tgcgtcatcg tgctgagtct tcggatccgt tggcggcgct ggctggggct   17940
atatcgcgtc aaactaacga ggtttgatag gcgatggctt cgggtgctat gtcgaggctt   18000
gctgcgactg agtatcagcg tgaggcggtc aggtttgctg ggaagtatgc gggctattat   18060
gccgagcttg gtcgtttgtg gcattccggg aagatgacag atgcgcagta tgtgcgtttg   18120
tgtgtggagt tggagcgtgc cggccatgat ggttcggcat cgttggcggg caggtttgtg   18180
tcggattttc gccggttgaa tggtgtggat cctggtttga ttgtgtatga cgagtttgat   18240
gctgccgccg cgttggctag gtcgttttcg actattaaga ttcttaagag tgatccggat   18300
agggtgaatg acacgattga tgcgatggct gcgggtgtta atcgggctgt catgaatgct   18360
ggccgtgaca cggttgagtg gtctgcgggt gcgcagggta ggtcgtggcg cagggtgacg   18420
gatggtgatc cgtgcgcgtt ttgtgccatg ttggctacga ggtcggatta tacgaccaaa   18480
gaaagggcac tcactactgg tcatacgcgg cgtcataagc gtggtggtaa gcgtccgttt   18540
ggttcgaagt atcatgatca ttgtgggtgt acggtggttg aggttgttgg cccttgggaa   18600
ccaaataggg ctgatgccgc atatcagagg acgtacgaga aggcccgtga gtgggttgat   18660
gatcatgggt tgcagcagtc gcctggcaat attttgaagg ctatgcgtac tgttggcgac   18720
atgagatgat ggtttccggt tgtgtgccgc cggttatcgg tgcacagggt tgtctcccgc   18780 acggggtca caatgttgt gttgttttcc gcaaggagta taggttaggc tatggccgat   18840
cagagtgttg aagaacagaa tgtcgacaat gatgctgttg agcccggaaa gggcgaggac   18900
attgttgctg ttgtgaagga tgggcaggct gccggcgatg atcatgccgg tgatgtttcc   18960
gtgaaggagg agtcttcttc tggcacggat tggaaggctg aggcccgtaa gtgggagtct   19020
cgtgctaaaa gtaatttcgc cgagttggag aagcttcgcg cctcggatgg tgatgcggga   19080
tctactattg atgagcttcg ccgcaagaat gaggaactcg aagacaggat caacgggttt   19140
gttcttgagg gtgtgaagcg cgaggtggct gccgagtgtg gcctgtcggg tgatgcgtc   19200 gctttcttgc acggcgacga tcgtgaagca ctggtggagt ctgctaaggc tttgaagggt   19260
ttgatcgacc atagcagtgg tggcgcgggt gtgcgccgtc ttgcggggag tgcccccgtt   19320
gatgatgtta aacgacgtga gggtgtcgcg tttgtggatg ctcttgtcaa taattctagg   19380
```

```
agatgatttg tgatggctga cgattttctt tctgcaggga agcttgagct tcctggttct   19440
atgattggtg cggttcgtga ccgtgctatc gattctggtg ttttggcgaa gctgtcgccg   19500
gagcagccga ctattttcgg cccggtgaag ggtgccgtgt ttagtggtgt tcctcgcgct   19560
aagattgttg gtgagggtga ggttaagcct tccgcgtctg ttgatgtttc ggcgtttact   19620
gcgcagccta tcaaggttgt gactcagcag cgtgtctcgg acgagtttat gtgggctgac   19680
gctgattacc gtttggtgt tttgcaggat ctgatttccc ctgctcttgg tgcttcgatt   19740
ggtcgcgctg tggatctgat tgcttttccat ggtattgatc ctgctacggg taagcctgct   19800
gcggctgtca aggtgtcgct ggataagact tcgaagacgg ttgatgcaac cgattccgct   19860
acggctgatc ttgttaaggc tgtcggcctg attgctgggg ctggtttgca ggttcctaat   19920
ggtgttgctt tggatccggc gttctcgttt gctctgtcga ctgaggtgta tccgaagggg   19980
tctccgcttg ccggtcagcc gatgtatcct gcggccgggt ttgccggttt ggataattgg   20040
cgtgggctga atgttggtgc ttcttcgact gtttctggtg ccccggagat gtcgcctgcc   20100
tctggtgtta aggctattgt tggtgatttc tctcgtgttc attgggggttt ccagcgtaac   20160 ttcccgatcg agcttatcga gtatggtgac ccggatcaga ctgggcgtga cctgaagggc   20220
cataacgagg ttatggttcg tgccgaggct gtgctgtatg tggctatcga gtcgcttgat   20280
tcgtttgctg ttgtgaagga aaggctgcc ccgaagccta atccgccggc cgagaactga   20340
tttattgttg cggtgatgtg tcaatgtgca ggggtggtg ttgatgggta tcattttgaa   20400
gcctgaggat attgagcctt cgccgatat ccctgagggg aagcttgagg cgatgattgc   20460
tgatgtggag gctgtggctg tcagtgtcgc ccctgtatc gctaaaccgg atttcaaata   20520
caaggatgcc gctaaggcta ttctgcgtag ggctttgttg cgctggaatg ataccggggt   20580
ttcgggtcag gtgcagtatg agtctgcggg cccgtttgct cagactacac ggtcgaatac   20640
tcctacgaat ttgttgtggc cttctgagat tgctgcgttg aagaagttgt gtgagggga   20700 tggtggggct ggtaaagcgt tcactatcac cccaacgatt aatggtcgat atgcacattc   20760
tgaggtgtgt tccacggtgt ggggtgaggg ttgctcgtgc ggatctgata ttaacggcta   20820 cgctggcccct ttgtgggaga tatgatatga ccggttttcc ttacggtgaa acggttgtga   20880
tgcttcagcc gactgttcgt gtcgatgatc ttggtgacaa ggtggaagac tggtctaagc   20940
ctgtcgagac tgtgtactat aacgtggcca tctatgcttc cgtttcgcag gaggatgagg   21000
ccgcgggccg tgactctgac tatgagcatt ggtcgatgct tttcaagcag cctgttgtgg   21060
gtgccggtta tcgttgccgg tggcgtattc gtggtgttgt gtgggaggct gacgggtctc   21120
ctatcgtgtg gcatcacccc atgtccggtt gggatgctgg cacgcaggtt aatgtgaagc   21180
gtaagaaggg ctgataggtt gtggctcagg atgtgaatgt gaagctgaac ttgtctggta   21240
ttcgtgaggt gttgaagtct tctggggtgc agggcatgtt ggctgagcgt ggcgagaggg   21300
tgaggcgtgc ggcctcggcg aatgtgggcg gtaatgcttt cgatagggcc cagtatcgtg   21360
ccgggttgtc gtcggaggtg caggttcacc gtgttgaggc tgtggcccgt attggcacca   21420
cctataaggg tgggaagcgt attgaggcga agcatggcac gctggcccgg tcgattgggg   21480
cggcgtcgtc atcgtctacg gtgacccag gaaatgggc aaacgcgtgc tcaaggatga   21540
tggctggctg tctgatatac cctgtgtggg gacggtgcct gatgatttca gcggtgatct   21600
gatttggttg gctcttgatg gtgcccgca gttgcatgtt cgtgagcgtg ttttttttgcg   21660 ggtgaatgtg ttttctgata tgccggatcg tgctatgtcg ttggcgcgtc gtgttgaggc   21720
tgtgctggct gatggtgtgg acggtgaccc tgtggtgtac tgtaggcgtt ctactggccc   21780
```

```
tgatttgctg gttgatggtg cacgttttga tgtgtattcg cttttttgagc ttatatgtag   21840 gcctgcggag tctgaataag cttattgttt ttgttttaat gtaattgttt gatatttaat   21900
gggggttatg atggctgcaa cacgtaaagc gtctaatgtt cgctctgctg ttactggcga   21960
cgtttatatt ggtgacgcgc acgcgggtga tactattaag ggtgtggagg cggttccttc   22020
cgggcttaca gctttagggt atctgtcgga tgacgggttt aagattaagc ctgagcgtaa   22080 aacgatgat ttgaaggctt ggcagaatgc ggatgttgtt cgcacggttg ctaccgagtc   22140
gtctatcgag atttcttttc agctgatcga gtctaagaag gaggttatcg agctgttttg   22200
gcagtcgaag gttactgctg gcgccgattc gggttcgttt gatatttctc caggcgccac   22260
cactggcgtg cacgctttac tgatggatat tgttgatggg gatcaggtta ttcgctacta   22320
tttccctgag gttgagttga tcgatcgtga cgagattaag ggtaagaatg gcgaggtgta   22380
tgggtatggt gtgacgttga aggcgtatcc tgcccagatt aataagaagg gtgatgcggt   22440
gtctggtcgg gggtggatga cggctttaaa agctgatact cctccgacgc ctcctccggc   22500
cccggttcct ccgaagcctc agccggatcc gaatcctccg gctggtaact gatacacgat   22560 tttaggggatt gttgatagat gagtgacacg ggtttcacgt tgaagattgg tgaccgtagc   22620
tgggtgttgg cggatgcgga ggagacggcg caggctgttc ctgcccgtgt ttttcgccgt   22680
gccgccagga ttgcccagtc gggggagtct gcggatttcg cccaggttga ggtgatgttt   22740
tctatgttgg aggctgccgc cccggctgat gctgtggagg ccttgagggg gcttcctatg   22800
gttcgtgtgg cggaggtttt ccgtcagtgg atggaataca agcctgacgg taagggtgcc   22860
tcgctggggg aatagtttgg ctccacggcc tgattgatga ttatcgtggg gccatcgaat   22920
atgattggag gacccggttc ggttgctcgg tttatgatgt tggtggcccg gtgatgtgtt   22980
ggggtgaggc tgtccggctg gctggcgtgt tgtgtaccga tacgtctagc cagttggcgg   23040
cccacctgaa tggttggcag cgcccgtttg agtggtgtga gtgggcggtg ttggacatgt   23100
tggatcatta caggtctgct aatagtgagg ggcagccgga gcctgtggcg aggcctacgg   23160
atgagcgtag ggcccggttt acgtctgggc aggtggacga tattttggcg cgtgttcgtg   23220
ccggtggcgg ggtgtctcgc gagattaata ttatggggtg aatagtgtat gtctggtgag   23280
attgcttccg catatgtgtc gttgtatacg aagatgcctg gtttgaaggc tgatgttggt   23340
aaacatttgt cgggtgtgat gcctgctgag ggtcagcgtt ctggtagcct gtttgctaag   23400
ggcatgaagt tggctcttgg tggtgcggcg atgatgggcg ctatcaatgt tgctaagaag   23460
ggcctcaagt ctatctatga tgtgactatt ggtggcggta ttgctagggc gatggctatt   23520
gatgaggctc aggctaagtt gactggtttg ggtcatacgt cttctgatac gtcttcgatt   23580
atgaattcgc ctattgaggc tgtgactggt acgtcgtatg cgttgggtga tgcggcgtct   23640
acggctgcgg cgttgtctgc ttcgggtgtg aagtctggcg ggcagatgac ggatgtgttg   23700
aagactgtcg ccgatgtgtc ttatatttcg ggtaagtcgt ttcaggatac gggtgctatt   23760
tttacgtcgg ttatggcgcg cggtaagttg cagggcgatg acatgttgca gcttacgatg   23820
gcgggtgttc ctgtgctgtc tttgcttgcc aggcagactg gtaaaacgtc tgctgaggtg   23880
tcgcagatgg tgtcgaaggg gcagattgat tttaacacgt ttgcggctgc gatgaagctt   23940
ggcatgggtg gtgctgcgca ggcgtctggt aagacgtttg agggcgctat aagaatgtt   24000 aagggcgccc tgggttattt gggtgctacg gctatggccc cgttttttgaa cggtctgcgg   24060 cagatttttg ttgcgttgaa tccggttatc aagtctatca cggattctgt gaagcccctg   24120
```

-continued

```
tttgcgtcgg tggatcaggg gattcagcgg gtgatgccgt ctattttggc gtggattaat    24180
cgtatgccgg ctatgatcac gagaatgaat gcacagatgc gcgccaaggt ggagcagttg    24240
aagggcgttt ttgcgaggct gcatttgcct gttcctaagg tgaatttggg tgccatgttt    24300
gctggcggca ccgcggtgtt tggtattgtt gctgcgggtg tttgggaagct tgttgcgggg    24360 tttgccccgt tggcggtgtc gttgaagaat ctgttgccgt cgtttggtgc tttgaggggt    24420
gccgccgggg ggcttggtgg cgtgtttcgc gccctgggtg gccctgttgg tattgtgatc    24480
ggcttgtttg ctgccatgtt tgctacgaat gcccagttcc gtgccgctgt tatgcagctt    24540 gtggggggttg ttggccgggc tttggggcag atcatggtcg ctattcagcc actgttcggg    24600
attgttgctg gcgtggttgc caggttggcg ccagtgttcg gccagattat cggtatggtt    24660
gctggtttgg ctgcccaatt ggtgcctgtt attggtatgc ttattgcccg gctggttcct    24720
gttatcaccc agattattgg tatggtaacc caggttgctg cgatgatttt gcctatgctg    24780
atgccggtta ttcaggctgt tgttgctgtg atacggcagg ttattggtgt gatcatgcag    24840
ttggtgcctg ttttgatgcc ggttgtgcag cagattttgg gtgctgtcat gtctgttttg    24900
ccgccgattg ttggtttgat acggtcgctg ataccggtga tcatgtcgat tatgcgtgtg    24960
gtggtgcagg ttgttggtgc cgtgctacag gtggtggccc gtattattcc ggttgttatg    25020
ccgatttatg tttcggtgat tggattcatt gccaagattt atgctgcggt tatcgttttt    25080
gaggctaagg ttattggcgc tattcttcgt actattacgt ggattgtgaa tcattcggtg    25140
tctggcgtga ggtctatggg cacagccatc cagaatggct ggaatcatat caaatcgttt    25200
acgtctgcgt ttattaacgg tttcaagtcg atcatttctg gcggcgttgc cgcggttgtg    25260
gggtttttta cgcggcttgg tttgtcggtt gcctcccatg tgaggtccgg tttaaacgcg    25320
gctcgtggcg ctgtttcttc tgcgatgggt gctatccgga gtgttgtgtc ttcggtggcg    25380
tctgctgttg gcgggttttt cgggtcgatg gcttctcggg ttcgtagtgg tgctgtgcgc    25440
gggtttaatg gcgccccggag tgcggcttct tctgctatgc atgctatggg gtccgcggtg    25500
tctaacggcg tgcatggtgt gctagggttt ttccggaatc tgccgggcaa tattcggcgt    25560
gctctcggta atatgggggtc cttgttgtg tctgctggcc gtgatgtggt gtctggtttg    25620
ggtaatggta tccggaatgc tatgagtggc ctgttggata cggtgcgtaa tatgggttct    25680
caggttgcta atgcggcgaa gtcggtgttg ggtattcatt cgccgtcgag ggtgtttcgt    25740
gacgaggttg gccgtcaggt tgttgctggt ttggctgagg gtattactgg taatgctggt    25800
ttggcgttgg atgcgatgtc gggtgttgct tcgcagcttc cggatgctgt tgatgcccgg    25860
tttggtgtgc gatcgtctgt gggctcgttt acccgtacg accggtatcg gcgtgcgagc    25920
gagaagagtg ttgtggtgaa tgttaacggg ccgacgtatg gggatccgaa cgagtttgcg    25980
aagcggattg agcggcagca gcgtgacgct ttgaacgcgt tggcttacgt gtgatagggg    26040
ggtgtggttc atgtttattc ctgacccgtc tgatcgtgcc ggtttgactg tgacctggtc    26100
tatgttgccg ttgattggtg atgctccgga gcgtgtgctt catttgacgg attatacggg    26160
gtcgtctccg gtgatgttgt tgaatgattc gttgcgcggt ttgggtgttc ctgaggttga    26220 gcattttttct cagactcatg ttggggtgca cggctcggag tggcgcgggt ttaatgtgaa    26280
gcctcgcgag gtgactttgc cggtgttggt gtcgggtgtt gaccctgatc cggtgggcgg    26340
gtttcgtgac ggttttttga aagcctatga cgagttgtgg tctgcgtttc ctcctggcga    26400 ggtggggggag ttgtcggtga agaccccgtc tggtcgtgag cgtgtgctgc ggtgccggtt    26460
tgattcggtg gatgacactt ttacggtgga tccggtgaac aggggttatg cgcgttatct    26520
```

```
gttgcatttg acggcttatg acccgttttg gtatggggat gagcaaaagt ttcgttttag   26580
taacgcgaag ttgcaggatt ggttgggtgg cggccctgtt aataagaagg gtaccgcgtt   26640
tcctgtggtg ttaacaccgg gtgtgggctc gggctgggat aacctgtcta ataagggtga   26700
tgtgcctgcg tggcctgtga ttcgtgttga gggtcctttg gagtcgtggt ctgtgcagat   26760
tgatggtttg cgtgtgtctt cggattggcc tgtcgaggag tatgattgga tcactattga   26820
tacggatcct cgtaagcagt ctgcgttgtt ggacgggttt gaggatgtga tggatcgttt   26880
gacggagtgg gagtttgcgc ctattcctcc tggcggttct cggagtgtga atattgagat   26940
ggttggtttg ggtgccattg ttgtgtcggt gcagtacagg tttttgaggg cttggtgaat   27000
agttgatggc tggtcttgtt ccgcatgtaa cattgtttac gccggattat cgccgtgtgg   27060
cgcctatcaa ttttttttgag tcgttgaaac tgtcgttgaa gtggaatggt ttgtccactt   27120
tggagttggt ggtgtcgggg gatcattcta ggcttgacgg gttgacgagg ccgggtgcgc   27180
ggctggttgt tgattatggt ggtggccaga tttttctgg gcctgtgcgt agggtgcatg   27240
gtgtgggtcc gtggcggtct tcccgtgtga ctatcacgtg tgaggatgat attcgtctgt   27300 tgtgcgtat gttgatgtgg cctgtgaatt atcgtcctgg tttggtgggt atggagtggc   27360
gtgcggatag ggattatgct cactattcgg gtgcggcgga gtcggtggct aagcaggtgt   27420
tgggggataa tgcttggcgt tttcctcctg gtttgtttat gaacgatgat gagagtcgtg   27480
gccgctatat taaggatttt caggtgcggt ttcacgtgtt tgccgataaa ttgttgccgg   27540
tgttgtcgtg ggctcggatg actgtcacgg tgaaccagtt tgagaatgcg aagtttgatc   27600
agcgtggttt ggtgtttgat tgtgtgccgg ctgtgacccg gaagcatgtg ttgactgccg   27660
agtcgggttc gattgtgtcg tgggagtatg tgcgtgacgc cccgaaggct acttcggtgg   27720
tggttggtgg ccgcggcgag ggcaaggatc ggctgttttg cgaggatgtt gattcgatgg   27780
ccgaggatga gtggtttgat cgtgtcgagg tgtttaagga tgcccgtaac acggattcag   27840
agcatgtgca tcttattgat gaggctgagc aggtgttgtc cgagttaggg gctacgtcgg   27900
ggtttaagat cgagttggct gagtcggatg tgttgcgttt tgggccaggc aatctgatgc   27960
cgggtgattt gatctatgtg gatgtgggct cggggcctat tgcggagatt gtgcggcaga   28020
ttgatgtgga gtgtgattcg cctggtgatg ggtggacgaa ggtgacacct gttgcggggg   28080
attatgagga taatccgtcg gccctgttgg cgcggcgtgt tgccggtttg gctgcgggtg   28140
tgcgggattt gcaaaaattc tagaaaagat gaggggtttg ttgtgggtat tgtgtgtaaa   28200
gggtttgatg tgtgttgac cgagtatgat tgggctcaaa tgtctggtct gatgggtaat   28260
atgccgtctg tgaagggccc ggatgatttt cgtgtgggca cgactgttca gggtgccaca   28320
gtgttgtgtg aggttttgcc ggggcaggct tgggctcacg gggtgatgtg cacgttgaat   28380
agtgttgaga cggtgacagg gcagctgccg ggccctgggg gggcccgcta cgactatgtg   28440
gtcctgtctc gggattggca ggagaatacg gccaagttgg agattgttcc tgggggcgt   28500 gcggagcgtg cccgtgacgt gttgagggct gagcctggcg tgtttcatca gcagttgttg   28560
gcgactttgg tgttgtcgtc tgacgggttg cagcagcagc tggataggag ggctatagcg   28620
gctagggttg cgtttggcga gtctgctgcg tgtgacccga ccccggtgga gggtgaccgt   28680
gtgatggttc cttcggggggc tgtgtgggct aatcatgcta acgagtggat gttgttgtct   28740
ccgaggattg agacgggttc gaagtcgatc atgtttggcg ttctgctgt gtatgcttac   28800 acgatcccgt tgatcgcca gtttgctagt ccgccggttg tggtggcgtc tatggctacg   28860
```

| | | |
|---|---|---|
| gcggctgggg gcacggcaca gattgatgtg aaagcctaca atattactgc caaagatttt | 28920 | |
| agtttggcgt ttattacgaa tgatggttcg aagccgaatg gtgtgcctgc ggttgcgaat | 28980 | |
| tggattgctg tcggcgtgtg accgggttgt tgttgtggcg gatggtgtga tgttgggggg | 29040 | |
| ctgtggtgtc gtggtttact cctgcactgg tggcctctat ttgtaccgcg ttggccacgg | 29100 | |
| ttttggggttc tgttcaggcg gtcacgtcta aatctcggag gcgtttgcgg cggctgtcgg | 29160 | |
| cgcaggtgga tgcgatggaa gagtatacgt ggggtgtgcg gcgtgaggtt cgccggttta | 29220 | |
| acgctgggct tccggatggg gtggagccga tgcatcttcc tgatgtgcct gagtttttga | 29280 | |
| aggatactgt tgatggtgga ggtgagtagg gttgagggag ttggaggagg agaagcggca | 29340 | |
| gcgccgcaat tttgagaagg cttcactggt gttgttgttt ttgtcgcttg tgttgttggc | 29400 | |
| ggtggttgct gtgggtgctt tgcgtttcgg ggcggtatcc tctgagcggg attcggagca | 29460 | |
| ggcgagggcc cagtcgaatg gtacagcggc tcggggttta gccagcagtg tgaagcaggc | 29520 | |
| gtgtgcttcg agtggggtgg agtcggtgcg gcttcaccgg tctggtttgt gtgtggatgc | 29580 | |
| tgtgcgtgtt gagcggagtg tgcagggtgt gccgggtcct gccggtgagc gcggcccgca | 29640 | |
| aggccctgca ggggttgacg gccgggatgg tgttaatggt tcggctgggc tggttggccc | 29700 | |
| tgttggtccg cagggttctc ctggtttgaa tggtgtgaag gtcctgacg ggttgcctgg | 29760 | |
| tgtgaatgga tcggatggcc atgatggtgt tccaggtcgt gcaggtgctg acggtgtgaa | 29820 | |
| cggcgctgat ggtcggatg gttcgggcgg tgagcgcggc gatgtgggcc cttcaggtcc | 29880 | |
| tgtcggaccc cctggtgcgc agggtgaacg ggg | 29913 | |

<210> SEQ ID NO 75
<211> LENGTH: 29562
<212> TYPE: DNA
<213> ORGANISM: Artificial Sequence
<220> FEATURE:
<223> OTHER INFORMATION: PAC263

<400> SEQUENCE: 75

| | | |
|---|---|---|
| aatggtgtga agggtcctga cggggttgcct ggcgttaacg gttcggatgg ccgtgatggt | 60 | |
| gttccgggtc gtgcaggtgc tgacggtgtg aacggcgttg acggccggga tggtgttaat | 120 | |
| ggttcggctg gtgagcgcgg cgaacagggc ccttcaggtc ctgccggccc ccaaggcgaa | 180 | |
| cggggtgagc gcggccccgc cggtgctaac ggatccgatg gtaaagatgg taaagatggt | 240 | |
| aaagatggcc gttctgtggt gtctgtgtac tgttctgatg gtcgcctggt tgtgaaatat | 300 | |
| agtgacggtg tggcttccac gatatcgggc tcggtagcct gccagggtgt gaaaccgtcg | 360 | |
| cctatagtga ctatatcatc ccacaaataa aagaggaagg gtgttactgt gattgtcatg | 420 | |
| ttttggggtg gtgtgtggtg aggtttattc ctgcggcgca tcattcttcc ggttcgaata | 480 | |
| gtccggtgaa tagggttgtg attcacgcga catgcccgga tgtggggttt ccgtccgcgt | 540 | |
| cccgtaaagg gcggcggtg tccacggcaa actatttcgc gtccccatcg gcgggtgggt | 600 | |
| ggggtttccg tccgcgtccc gtaaagggcg ggcggtgtcc acggcaaact atttcgcgtc | 660 | |
| cccatcggcg ggtggttcgg cgcattatgt gtgtgatatt tcggagactg tgcagtgctt | 720 | |
| gtcggagtct acgattgggt ggcatgcccc gccgaatccg catagtttgg gtatagagat | 780 | |
| ttgcgcggat gggggttcgc atgcctcgtt ccgggtgcca ggccatgctt acacgaggga | 840 | |
| gcagtggctt gatccgcggg tgtgcccgc ggttgagaag gcggctgtcc tgtgccggcg | 900 | |
| tttgtgtgac aaatataatg ttccgaagag gaaactgtct gtggccgatt tgaaggccgg | 960 | |
| taaacggggt gtgtgtggcc atgtggatgt gacggatgcg tggcatcagt cggatcatga | 1020 | |

-continued

```
cgatccgggg ccgtggtttc cgtgggacaa gtttatggcc gtagtcaacg gcaaagatga    1080
gagtggggag ttaactgtgg ctgatgtgaa agccttgcat gatcagatta aacaattgtc    1140
tgctcagctt agtggttcgg tgaataagct gcatcacgat gttggtgtgg ttcaggttca    1200
gaatggtgat ttgggtaaac gtgttgatgc cttgtcgtgg gtgaagaatc ctgtgacggg    1260
gaagctgtgg cgcagcaagg atgctttgtg gagtgtctgg tattacgtgt tggagtgtcg    1320
tagccgtctt gacaggctcg agtctgctgt caacgatttg aaaaagtgat ggtggttttgt   1380 tgtgggtaaa cagttttggt taggtgtgct ggagcgggcg gctaagactt ttgtgcaaac    1440
gtttgttgcg gtgttggggg tgacggcggg tgtcacctat acggcggagt cgtttcgcgg    1500
tttgccgtgg gagtctgccc tgatcacggc tacggtggct gcggtgctgt cggttgctac    1560 atcgttttggt agcccagcgt tgtggccgg taaacctaaa accacgcctg tggatgcggg    1620
tttggttcca ccggatgatg ggggcttggt tgagccgcac tcggtggatg tgtcggatcc    1680
tggcatgatt gagcctgcag atgatgtgga tcttggtgta ggctatgagc tcggcgtgc    1740 tgccgagtcg gaggttggca cggtagagtc tactgttgca taagtgaata tatgtgtgtg    1800
ccccagcggt gctgccacga tcgtgtggtg gttgccgctg gggcactatt tttgtatatt    1860
gcggtgtggc tatgattcgt tgctgtcgat ggtgtcttcg agcatctgat acaggtggag    1920
gcaggtagag atcgtttcgc tggcctggtc gagaacgttc cggccgataa cgttttttgtg   1980 gttgtcgcgg tggcggatga tagaccacat gatctcgtcg gctgccgcct gcaatagttt    2040
tgcctgatat gcgatcccgg cgagccagtc tagtgcttcc tggcttgcat agggggctctg   2100 gtcctcgctg ttgccgcggg tgttgctgtt gtttgtgggg tgtcctgcac tgtcgcagaa    2160
ccataggatt tcgctgcact cgtctagcgt gtcttggtcg atagcgagat cgtcgaggct    2220
gacattgttg acggtaaggt tcacgttgtc gagggagatg ggtacaccgt actggttttc    2280
gacactgtca acaatgtttt gcagctggtt catgttggtg ggctgttgtt ggatgattcg    2340
gtgtaccgct gttttgaggg cggtgtaggg gatattggtt atgttgttca tggttttatc    2400
ccatccctgc gctgtcgtct tggtagtatc gactgtttgc gtaacctgtg agggtgatga    2460
gtgtttggtc tgcccactgt ttcacggttt gccgggtgac tccagtcgt tgggctgcca    2520 ccgaataggt ttggtcatac ccgtatactt ccctgaaggc tgccaggcgt gctagccgtt    2580
tccgctgttt ggatggctgg caggtgaggg tgtagtcgtc tatcgctaat tgtaggtcga    2640
tcatggtgac gatgttgttg ccgtggtgtt gggggcggt tggtgggggt ggcatgcctg    2700
gctccacact gggtttccat gggcctccgt tccagatcca ttgggcggct tggatgatgt    2760
cggcggtggt gtaggttcgg ttcactggtc atcccctgaa taggttgtcg aggttgtctg    2820
ggttgctggt gttggtggtg tcgaatcgtc ccacacagtg gcagtagtcg tacatgagtt    2880
taataatgtg ttggtggtct cccaaatagg tgtttccgct gatactgtag gtggctgtgc    2940
cgtctttact aatagtgtat ttggcggtga tggtttcggg tgtttctgtg ttggtgatga    3000
ttgctgtggt ggtggcgcct acggtttgta gcctggtggt ttgggttccg tcgtcgagga    3060
tggtagtaac catgagggtt gtcctttagt tgctggtttg gttgtcggct agatgaatga    3120
tatcgggtaa aggtttcggc tggtcgaggt gttgtatggt tttgttggct agccgtttgg    3180
ctaccctgta gcacattttg gtgtagtgtt tgttgtctag gttgtggtat tgttccgca    3240 ccgcaatata tagtagggag tcttggtata ggtcgtctgc actgattgcg gggtagtgtg    3300
tggctgtttt ggtgcatgcc cggttgagtg tgcgtagatg atggtctgtg gcccacaccc    3360
```

-continued

```
acgatgcggt ggtggctagg tcggcttttg ttggtcgtct gctcatggca ctattacctg  3420
gctatctggt agttgtttgg tgttttgttg ttgatagtgt agcacacgag tccggggttg  3480
ccggtggtgc ctgtgcggtg cctataccag acggattctc cttccatgga tgggcattgg  3540
atgaaggtgc gttgtccttg ctcggagatt tcgaggtggt gccggtgtcc ggccatgagg  3600
atgtgggatg tggtgccgtt gtggaattct tggccgcgcc accattcgta gtgttggttg  3660
ttgcgccatt ggtgtccgtg ggcgtgcagt atttgtgtgc cggccacatc aacggtggtg  3720
gtcatttcgt ctcgtctggg gaagtggaag tgaaggttgg ggtagttgtt ggtgagttgg  3780
taggcttcgg cgatggcgcg gcagcagtct acatcgaagg agtcgtcgta ggtggtgact  3840
cctttgccga atcgtacggc ttcaccgtgg ttgccgggga tggaggtgat ggtgacgttg  3900
gcgcagtggt cgaacatgtg gacgagttgc atcatggcca tgcgggtgag cctgatttgt  3960
tccgtcaagg gtgtttgtgt gcgccacgcg ttagagccgc cttgtgacac gtatccttcg  4020
atcatgtcgc cgaggaatgc gatgtggacc cgttgcggct ggcctgcctg ttgccagtag  4080
tgttttgcga ctatgaggga gtgcaaatag tcgtcggcga agtgtgctgt ttctccgccg  4140
gggatgcctt tgccgatttg gaagtcgcct gccccgatga cgaaggccgc agtgctgtag  4200
tcggtgtggg tgtcttgttc gggttttgggt ggctgccatt cggctagctt gtcgacgagt  4260
tcgtctatag ggtaggggtt tgttgcgggt tggtggtcga tgatttttg tatggatcgg  4320 cctgtttctc cgttggggag tgtccattcg gagatgcgtg tgcggcgtac ggtgccgttg  4380
gctaggttgt cgtcgatggt gtcgatggcg ttgtcgtggt tggctagttg tgtgagtagc  4440
cggtctatat tgtctatcac tgggtatcct cctcttcctc gtgtgtggtg gtggcttgtt  4500
tgcggcggta gtctttaatg acggtggcgg agatggggta tcctgcctgg gtgagcattt  4560
gggctagctg tgtggcgggg atagacctgt cggcgagcac gtctgcagcc ttgcggccgt  4620
agcgttggat gagggtttca gttttggttg ccatgatgtc ccatcggttg tgtggtgggc  4680
tgccatcctg tgcggcagtc gccgtcgtgt cctggtttgc gtgtgcacca cgatacggtt  4740
ccgtctgtgt ggttgagtgt tttaccgcac atgacgtttt gtagatgctc cggcagctcg  4800
ctattgctat cgtcttgctc gtctagcaaa gttttttgtt gggtgaaaaa ctcggacacg  4860
gtgccgttgt ggactgggag tatccatgtt ttccattgtt gttgtagccg ggtgttccag  4920
tggaattgtt tgctgcgtt cgtggcttgt ttgatggttt tgaagtagcc tacaatgatc  4980
cgttgatggt cactatcggg cttgtgtggc cctttccaat attgggcagc tacagcgtac  5040
ctgttgttgt ctgtgaagcg cccccagcag tattccacca tgtgtgatag taccttgtcg  5100
ggcatgtctc gtacttggtt ttcgtcgagc catgcgtcga caataatgtt gcgtatggct  5160
cgcttgtctt tggtggtggg tttgaatgcg atgctcacaa tgcgggcctg tcgtcttgca  5220
tgaactggtt gaaggtgttg ttcccggcgt gttgggcttg tgtgatttgc tggtcggtcc  5280
agtcggggtg ttgctgtttc agatagtgcc agtggcacgc attgtaggtt tcgtcttgga  5340
gccgtgtgag atggttttcg gtgatgattt gtttccacat ggcccatgac acgtcgagcc  5400
ggttgaggat ttcgagggct gggatgttga attggttcag gaagaggatt tcatgggtgt  5460
agtagttttt ctcgtaggcg tcccatccgc ttcggtgcct gttgggctgg tttttggggt  5520
aggcttcccg gcagattttg tgtaaccgtt tggccatgtc tttgggtagt ttaatgtcgg  5580
ggttggcgcg gatcatggat cgcatcccat cataggtggt gccccaggtg tgcatgatgc  5640
ggagtgggtc ttcaccatcg gcccattttt ctgcacagat ggcgaggcgt atgcgtctcc  5700
tggcggcttt actggtgtcg cggcggccgg ggatggggca ggtgtcgagg ggatccatga  5760
```

```
tgttttagtg tacctttccg tgttgtggtt gtttgtctgg ttttattgta gcactgtgtt    5820
gagggcttgt gtcaaccctg tttttccgac ctgaaggtag gtgtctgtga catcccccag    5880
ggtgagggc  acatgggtgg cttggggag  tgccgtctgg aaggtttggg ccatctggtc    5940
tcctgctttg tctgggtcgg accagatgta gatgtggtcg tagccttcga agaatttggt    6000
ccaaaagttt tgccacgagg ttgcgccggg tagggcgacg gccgaccatc cgcattgttc    6060
gaggatcatg gagtcgaatt cgccttcgca aatgtgtatt tcggctgccg ggttggccat    6120
ggcggccatg ttgtagatgg agcctgtgtc tcctgccggg gttaggtatt tggggtggtt    6180
gtgggttttg cagtcgtgct ggagtgagca gcggaaacgc attttctta  tttcggctgg    6240
cccttcccaa acggggtaca tgtatgggat ggtgatgcac tggttgtagt tttcgtggcc    6300
tgggatgggg tcattgtcga tgtatccaag gtggtggtag cgggctgttt cttcgctgat    6360
gcctcttgct gagaggaggt cgagtatgtt ttcgaggtgg gtttcgtaga gggccgaggc    6420
tttctggatt cggcggcgtt ccgcaatgtt gtatgggcgt atgctgtcgt acattcgggt    6480
tttcttcttc taattgttgt tgtagtttgg cgaggcctcc tccgataccg catgtgtggc    6540
agtaccagac gcccttgtcg aggttgatgc tcatggaggg ctggtggtcg tcgtggaacg    6600
ggcagaggat gtgttgctcg ttcttggacg ggttgtaccg tatgtggtag gtgtcgagga    6660
ggcggcgggt gtcagaggtg tgggaggagc tcgttgaggg ttgataccac ataggcttcg    6720
ctccagggtt tgttgcgctg tttcatcact acgagtccga tagtggactg gttttcgcgg    6780
tttcggtggg tttcgtagtt gcgtgcctcc cggctggctt gtttcacgaa ttcggcgagg    6840
tggggctgcc cggctttggc ttcgataatg taggttttgt tgccggtggt gaggatgagg    6900
tcgccttcat cctctttacc gttgaggtgg aggcgttcta tatcatggcc ggtgtcgcgt    6960
agctggtgga ggagtcgtgt ttcccattcg gctccggctc ggcggtttct tgattgttgt    7020
gtcgacatga tagtcctttg tggtgttcgg tcatgttcca tggctgtttt tcggcgagtg    7080
gcccgaagaa tgtgtattcg gggtaggctc tgagtctttc gtatcgggtt ccgtctgggc    7140
tggatttgcc tgtgcgctgt ttgagtacag cgatgcgtgc ctctgccggt atcgataggc    7200
cgttgccgtt gtcttcgcca ccatacaggg agactcccaa tatgagttgt ggttttcgg    7260
agaggccgtt tttgatttcc cgcctagccg ggggtgttc gatgtcggag ccggttttgt    7320
cggttgcgtg gtgtgtgaca ataatggtgg agcccgtgtc cctacctaat gctgtgatcc    7380
attgcatggc ttcttgctgg gcctgatagt cactctcgca gtcttgtatg tccatcaggt    7440
tgtcgataac gatgatgggt gggaaggtgt tccacatttc catgtaggct tgcagttcca    7500
tggtgatgtc tgtccatgtg atgggtgact ggaatgagaa tgtgatgtgt ccgccgtggt    7560
ggatgctgtc tcgatagtat tctggcccgt agtcgtcgat gttgtgttgt atctgggcgg    7620
tggtgtgttg ggtgttgagt gagatgattc gtgtggaggc ctcccagggg gtcatgtccc    7680
ctgatatgta gagggctggc tggttgagca ttgctgtgat gaacatggct agcccggatt    7740
tttggctgcc ggagcgcccc gcgatcatga cgagatcccc tttgtggatg tgcatgtcca    7800
ggttgcggta gaggggttct agctggggga tgcggggcag ctcggctgcg gtttgggagg    7860
ctctctcgaa ggatcgttgg agagagagca tcggaccctt atctatctgt ctatcggttg    7920
gatgatgttt tggtggtcag atggagtcga tgtcgatgtc agcatcagca ggggctgtgg    7980
tgtcgtctag ctgccgttta tcgcgttgt  ctacgtattc ggcaacctta tcgtagatgg    8040
cgtcgtcgag gggtttgagc acgaccgcgt tgaagccgtt tttggtgcgt acggtggcga    8100
```

-continued

```
gtttgaaggc ttgttcttcg ccaaggtagg cttcgaggtc gcggatcatg gagtgtgggc   8160
ggtcgttgct gccgcgtact ttttcgatga tggcgttggg gatggttcct ggggtgccgt   8220
tgttgaggtc gtctagggtg tggaagatgg tgacatcagc gtagatgcga tcggcggtct   8280
gtccaccgta gccttcggtg ttgtgttcta cgtcgtggat tttgaaggcg atggcggtgg   8340
cgtcctggtt tcgggagggg ttgaagaagg tgctgttgct gttgtttcgg tagtttgcga   8400
gtcccattgt tgtatccttt actgttttgt tggtttgtgt aggttttatc gggtgaggct   8460
gtttcgtttg ctgcggaaag cctcggaaac gtcactgtta ctggtgatga tcttttttgta  8520 ctgtttgaga aggtcggcta gctgtgcttt gctggttgca ttgttgattt tgtcgatgat   8580
ggtgttgttt ccttctgagg cgatgttgtc tacgtagtct ttggcggcct ggttgtagcg   8640
atcttggagg atgatggatg ctgtggcgat cagtgttgcc aggtcccagt tccgtgccgc   8700
cgaactgttt ttgagtccgc ctaacaggtc gatgatggcc tgttttgtct gctctgctgt   8760
gtctcctcgg atgaccgccc atggtgcagc atagtctcca ccgtatttga gtgtgatcgt   8820
gagtcgatca ttgtcgatct tgtctttatc ggtcatttgg tgtccttttc tttattgtct   8880
gtttctggtg gctgtacggt agattctacc gggtacctgt aggcgtcttt cccgttgacg   8940
gcccagcagg cgtcttgtac ggggcagcct ttacagagtg ttgtgacgtg tgggacgaag   9000
atgcctgcgc tgattccttt cattgcttga ctgtacatgg atgatacatg ccggtaggtg   9060
ttgttgtcaa ggtcgtacag ttcggtggat gtgccttgtg tcgggacttt gtcgtcgttg   9120
cggctggtgg ccggcgtcca aaacatgcct tttgttacat cgttgccgtg ttggttgagc   9180
atgtaccggt aggtgtgcag ctgcatactg tcggcgggta ggcgtccggt tttgagatcg   9240
aggatgaagg tttcgccggt gtcggtgtcg gtgaagatac ggtcgatgta gccaacgatc   9300
tgggtgccgt cggggagggt ggtttctacc gggtattcga tgcctggttt accgtccagg   9360
attgcggtga tgtattctgg gtggttgcgt ctccatgttt tccagcggtc cacaaaggtg   9420
gggccgtaca tcatccacca attgtagtct tttttgtgtg gcccgcccga ttcgcacatg   9480
tttttgcata ttctgccgga gggtttgatt tctgtgcctt cggattcggc gagggctact   9540
tgtgtggcga aaatgttttt gaaggatgcg agtttgtctg gtagcgcagg gtattcggcg   9600
gggttgtata ggtgtaggtc gtattgttcg gtgatgtggt gtatggcgct tccggcgatg   9660
gtggcgtacc aggtgtggtg ttgggtgtgg tatccgtgtt ggagacgcca ttttcgccg    9720 cattcggccc attgtgacag tgatgagtag gagatgtggc ctggatggtt gatggttttc   9780
gggtattgtg ctagaggcat tacttgtcgc ttttgttcca tgggtttcgg gtgtcttggc   9840
cggcatcgtg ttgctggtat gcgaggagtg cgaggcagtg ccaggcagca tgggctagat   9900
gcggtagccc ggattcataa tcgaggttgt tgccttgctg ccatgataac aggtgccggt   9960
agagggcatc aacgctgtgg ctccacgggt atcctccggt ccagttgttg tcgccgtatt  10020
tggtggcacc gtagcctgct acgtcgccga gagcgtgaag ggatgctggg tcgatgaggg  10080
agagcctgca aagtttgagt tcttttcggg caccgctgtt ggggtcggtg tacatgcggg  10140
ttggctcatc catgagatat gtgctcctta agcgtgggtt actggttagg gttgtgggcg  10200
agtgctacgg cgagaataat gatggcgagg gtttcagcga tgatgatggg tgttgtgatc  10260
atttgctgtc tcggggattg ttggtgagtg ttgatgcgcc taggagggtg gtgagggcgc  10320
atgcggcaat gatggcgagg gctgccttgt gtgggtgcc ggttgcgtac atccatgtga   10380
tgatgccgcc ttggatccag gctaggctgg tgaagaacgt ttcgtagctg tgtagctcaa  10440
tgttgttgtt gggtgtgttc atgcttgctc ctgaagaatg gtgttgatgg ttttataaat  10500
```

```
gttgtacagg tcggcttcga tggttttgtag ctgtttgatt tggtggtcga gattaatgtc   10560
tgggttgagg gtgttgatgc gggaggcaat atctgtggct gtgcgtagtg ttccgccggt   10620
gtggtgaata atgtgtgccg tgtcggcgag tccggtgatg acagcgtagt gggataggag   10680
aggcatagct gggggtgct ccttggcggg ttactgttgc gggttgatgt tgaggtcggt    10740
gacgtgcggg tggtcttctg ttccggtgac gaggcagtgg acggtgacgg gtagtttgga   10800
tgcgccggga tgtttcgcgg ttgcgccgta gacgatggga aggtgtctt taccaataat    10860 tttgtggagt tggaggtcga tgtcggggtt gccgttccag ttgaggccgt gtgcggcggc   10920
ctgttgttcg gctttgcggt tgcaggtgtg tgctgccgtg atcatggtga gtccggtggc   10980
ggtttcttca ccccgtgttt gggcttgctt gtgggctttc tgctgttctg cttgtaggga   11040
gcggactgcg gctgcctgct tggctgtttt ctcggctttg cgctgttgga cggttttggg   11100
ggtccattcg gtgttggctg tggtggcttg tggggctggt tgtgaggcga gtggcggatt   11160
gtcgtcgggt gctgggagga aagagcatgc ggcgatgatg gcggctgtga ttccggcgat   11220
ggtgtagccg ttttcttgt tcatggctgt tgtcccctttt ccggggtgtt gttcgttgct    11280
gacatgatca atacttccag cgaatggacc tcgtgtcaag actgcgctca aatgttctga   11340
gcgatccttg tgtggctagg ggttttatcg ggcgcatagg gtgagtaggt ggcctacgtt   11400
gatgcggctc acattccagt agagttgtgt ggcttcaccg ccggtgagcg gcttccactc   11460
gtcgtggctg aacacggtgc catcggatgc gatgaacgtg tcgggcgta gcttgtgaag    11520 ttcggcttcc acgctctgcc ggtaggtttc ggcgaggccc tcaaaatcca tgtggtcgca   11580
ggagaggttt tcgaggcgtg tcaggtcgaa gggtgtgggg cagtcgtagc tggcggggt    11640 gtagagctgg gtgaagtggt cggcgatctt ctgcatgacg ggttccttttt ctcgtgtggt  11700 gggttgatgg ttttatcgt gtggcttcgg cgatgatggc gtctacatag atcatgtcga   11760
tgagatcgtg gagttcctcg gcctcattct cggagaggtg gcgccagtcg ggtgcccat    11820 atactgcgcc gtcgagggtg acagtccaca gtggccggat gagtcgtatg gcttcttgta   11880
ctttagcgtg gtacatgcgg cgcaccatat cgagatcgat gtcgtctgaa tggtttccgg   11940
tgaggctgtg gaggctaagc gggtcgattt ctgtctgcct gtagagggat gtgaaggatg   12000
gtgtgatgag tgtgccatcc atgatggtg tgctcctttc ggtggtgtag gggttgttgt    12060 ggttttatg gtgtgaggt tgtgatccat agtcaaggct gcgctcaatc ggattgagcg     12120
tttcatggag tgtgtcgggt gtgacagatg tcactgaagc ctttattgcc tctctcagcg   12180
tctcaaatct tctaggggta gaaatatact agggcagccc tataaatcga ttctaggccc   12240
ctttctgtga ctctgagggg catatgtgag tggagggtgg tatgacaggt ggcatggact   12300
tggaggaagg tgtccagtcg ggagcgctcg atgatccggc tgcacgggtg tctggaaggc   12360
ttatggtctg cgtgagatat gtcacatcac ctagactcta ggaacactac ccacacctgt   12420
agagtctatt ctgcagatgg caccagagcc aagaatgcct ctctaaggca cgtaaaggcc   12480
cctctgaggc tcttacaccc tcaactctag gtatttgtac ccccagcata ttctgatcga   12540
ttctagggcc cttttttgagg cttacgcgag aacagcaccc aaagactagc ccatcaaccc   12600
ttactctggt tagctaagcc tgcactatgt ggacagtgtg ggatgctaag agggaagaag   12660
gacacggtaa agaaaaaag ggggagtacc agccttcacg ccttcaagcc ttaaggtctt    12720
agcactaagc acttagcacc gagcccctc aagggctcgg catcagcccg agcaggctca    12780
gccctgaaag gggtacacgc catcagggaa ggcttgagag tacgaggagc cttagcgacg   12840
```

```
agtactcgaa agcctgagga acaccatca gcactgatgg gcctagcgcg ttcggaaagg   12900
acacaagagt aaagtgtgac agctatccgg gagtgaaacc cgttctggct aggggtttca   12960
gccttaacca cctgtaaagg ttacaagact ctaagaaaat ttaagaaact tcttaggaag   13020
aaagttgtgt tgatgtcacc ccaaaaacac ctaaaatagc cctcaaaccc gcctatagag   13080
ccaaacagtc aagtttgact cgtcttgacg gcgtatgcta ggctggacag gtagccagct   13140
ggacgcaagg ccagaaagtg ctgacgcact tcccgacctt gcttaccatc agtctaccaa   13200
agacttaaaa gtttaacagc taagcgctaa gcccttaaga cctaaacgct tagcaccgag   13260 cccccctcaag ggctcggcat cagtcctaag agcttagccc ttaaggatct aaggttacta   13320 taaagctttta aacactttaa gtaaacttaa gagcttagca cttaaagtta attaataacc   13380
ttaaaggctt acacacttag cactgagccc ttcaaggctc agcatcagta taaagacctt   13440
aacacctaag ttaagtataa aactttaaag gcttagcgct taaggatata aacttaacat   13500
cagtgtttaa gacttaaaga gttaaacact taaagtaact ataatacttt aaaaatctta   13560
agtacttaaa gttaaccatc agtccttaaac tttaatatta taacctataa gtattaaagc   13620
ttataagtta taaagttttt agaagagcta aggggttaaac ttctttactt ctcttctctc   13680
tttggttctt tctctcttct ctccttttct tcatcagggg agaagaggaa cctttaccat   13740
cagcgccgat gggcttttca tcgtgtgact cgtgtgcttc tggtcgcaag ctcccatcgc   13800
acactcccca cactcttaca cccgtgcccc tttcaggctt agcgtgttcg gctgaaggcg   13860
tacggcgtgt cacgctcaca cccttaacac cgggtgagac ttaaagtgta tattatatgt   13920
agaagacttt aaaacctata gagtgttttct gctgagcctg tgtcctacac cgctaggcgc   13980
caagcgctaa gccttgaaac gcgaacacac acccacccc ttttctcttt cgtgtccttc   14040
tcttttgaca ccgctggggg gcgatgtgat ctttctcaca tgccagggg tagtggagaa   14100 aacaaacacc ccggcacaaa cagaacaccc cctcaaacga caaaacagc ccccaggatc   14160 gactagcagg gcaagggtag agtattcata cccccagacg attccaggcc gttagagagg   14220
caatgagagg ctcacagggg tcatgggaga tcggggaacg cgatggcaca caccaaccgc   14280
acagccagcc aagcccaccg acgctggcgg caacgactca tcacccaagc ccgacaacaa   14340
ggccaaaccg aatgcccact ctgcggagca accatcacct gggacacaca ccagctgcca   14400
accagccccg aagccgacca catcacaccc gtcagcaggg gaggactcaa caccctcgac   14460
aacgggcaaa tcatctgcag aacatgcaac agaagcaaag gcaatcgcag cgaaccaaac   14520
atcaaattcc aacaacaaac cacaaaaaca cttgtttcat ggtgacaaac ccgccaaccc   14580
ccaccgggca caccccctgc acacccgtgc aagacctcgt acggcttagt gaaataccctc   14640 ccttttgtgg atttgtctgt ttgtcgactt tttgtgttgg tggtgagtgt ggtgcagcct   14700
gagcttcctg atggtcgtga gtggtgtggg gagacgcgtc gttggtggcg tgtgtggggt   14760
gaggatagtc gcgcgcagta cgtgtctgat gaggagtggc tgtttctcat ggatgctgcg   14820
gtgattcatg attgtgtgtg gcgtgagggt cgcgcggatt tggtggcttc gcttcgtgct   14880
catgtgaagg ctttatggg tatgttggat cggtattcgg ttgatgtggc gtctggtggc   14940
cgtggtgggg gttctgcggt ggcgatgatt gaccggtata ggaagcgcaa gggggcctga   15000
ttaggtgtct ggtgttgttg ggtctcaggt tcctcgtcat cgtgtggctg cggcgtattc   15060
ggtgtctgct ggcggtgatg cgggtgagct tggtagggcg tatggggttga cgcctgatcc   15120 gtggcagcag caggtgttgg atgattggct ggctgtcggt ggtaatgca ggcttgcttc   15180 gggtgtgtgt ggtgtgttttg tgcctcgcca gaatggcaag aatgcgatcc ttgaggttgt   15240
```

```
ggagttgttt aaggcgacta ttcagggtcg ccgtatttg  catacggctc acgagttgaa   15300
gtcggctcgt aaggcgttta tgcggttgag gtcgttttt  gagaatgagc ggcagtttcc   15360
tgacttgtat cgtatggtga agtcgattcg tgcgacgaat ggtcaggagg ctattgtgtt   15420
gcatcatccg gattgtgcca cttttgagaa gaagtgtggc tgtccgggtt ggggttcggt   15480
tgagtttgtg gcccgttctc gtggttctgc tcgcgggttt acggttgatg atttggtgtg   15540
tgatgaggct caggagttgt cggatgagca gttggaggct ttgcttccta cggtgagcgc   15600
tgccccgtct ggtgatccgc agcagatttt cctgggtacg ccgcctgggc cgttggcgga   15660
cgggtctgtg gtgttgcgtt tgcgtggtca ggctttgtcg ggtggtaaaa ggtttgcgtg   15720
gacggagttt tcgattcctg acgagtctga tccggatgat gtgtcgcggc agtggcggaa   15780
gttggcgggg gatacgaatc ctgcgttggg tcgtcgcctg aatttcggga ccgtaagcga   15840
tgagcatgag tcgatgtctg ctgccggttt tgctcgggag cggcttggct ggtgggatcg   15900
tggccagtct gctacgtcgg tgattccggc tgataagtgg gctcagtcgg ctgtggatga   15960
ggcgagtctg gttggcggga aagtgtttgg tgtctcgttt tctcgttctg gggatcgggt   16020
tgctttggct ggtgccggcc ggactgatgc tggggttcat gttgaggtta ttgatgggct   16080
gtctggcacg attgttgatg gtgtgggccg gttggctgac tggttggcgg ttcgttgggg   16140
tgatactgac cggatcatgg ttgccgggtc tggtgcggtg ttgttgcaga aggcgttgac   16200
ggatcgtggt attccgggcc gtggcgtggt ggttgccgat actggcgtgt atgtggaggc   16260
gtgtcaagcc ttcctggaag gtgtaaggtc tgggaatgtt tctcatcctc gtgctgattc   16320
tcgccgtgac atgttggata ttgctgtgag gtcggctgtg cagaagcgta aggggtctgc   16380
gtggggttgg ggttcctcgt ttaaggatgg cagtgaggtg cctttggagg ctgtgtcttt   16440
ggcgtatctt ggtgcgaaga tggcgaaagc gaagcggcgt gaacggtctg gtaggaagcg   16500
ggtgtctgtg gtatgaactc ggatgagttg gctctaattg agggcatgta cgatcgtatc   16560
caaaggttgt cttcgtggca ttgtcgcatt gagggctact atgagggctc gaatcgggtg   16620
cgtgaccttg gtgtggctat tccgccggag ttgcagcgtg tgcagactgt ggtgtcgtgg   16680
cctggtatag ccgtggatgc tttggaggag cgtctggatt ggcttggctg gactaatggt   16740
gacggctacg gcctggatgg tgtgtatgct gcgaatcggc ttgctacggc gtcgtgtgat   16800
gtgcatttgg atgcactaat ttttgggttg tcgtttgttg cgattattcc tcatggtgat   16860
gggtcggttt tggttcgtcc gcagtcacca aagaattgca caggtaagtt ttcggctgac   16920
ggttctcgtc tggaggctgg ccttgtggtg cagcagacgt tgatcctga  ggtggttgag   16980
gctgagcttt tgttgcctga tgtgattgtt caggtggagc ggcggggttc gcgtgaatgg   17040
gtcgagacgg gccgtattga gaatgtgttg ggtgcggttc cgttggtgcc tattgtgaat   17100
cgtcgtcgta cttctaggat tgatggccgt tctgagatta cgaggtctat tagggcttac   17160
acggatgagg ctgttcgcac actgttgggg cagtctgtga atcgtgattt ttatgcgtat   17220
cctcaacgtt gggtgactgg cgtgtcggct gacgagtttt cgcagccggg ttgggtcctg   17280
tcgatggctt ctgtgtgggc tgtggataag gatgatgacg gtgacactcc gaatgtgggg   17340
tcgtttcctg tcaattcgcc tacaccgtat tcggatcaga tgagactgtt ggcgcagttg   17400
actgcgggtg aggcggctgt tccggaacgc tatttcgggt ttatcacgtc taacccacct   17460
agtggggagg ctttgctgc  cgaggaatct cggcttgtga agcgtgctga acgcaggcag   17520
acgtcgtttg gtcagggctg gttgtcggtt ggtttttggg ctgccaaggc gttggattct   17580
```

-continued

```
cgtgttgatg aggccgattt ttttggtgat gttggtttgc gttggcgtga tgcttcaacc    17640
ccgactcggg cggctacggc tgatgctgtg acgaagcttg ttggtgccgg tattttgcct    17700
gctgattctc gtacggtgtt ggagatgctg gggcttgatg atgtgcaggt tgaggctgtg    17760
atgcgtcatc gtgccgaatc tgcggatccg ttggcggcac tggctggggc tatatcgcgt    17820
caaactaacg aggcatgata ggcgatggct tcggtgcta tgtcgaggct tgctgcgact     17880
gagtatcagc gtgaggcggt caggtttgct gggaagtatg cgggctatta tgccgagctg    17940
ggtcgtttgt ggcgtgccgg aagatgaca gacgcgcagt atgtgcgttt gtgtgtggag     18000
ttggagcgtg ccggccatga tggttcggca tcgttggctg ccaggtttgt gtcggatttt    18060
cgccggttga atggtgtgga tccgggtttg attgtgtatg acgagtttga tgctgccgcc    18120
gcgttggcta ggtcgttttc gactatgaag attcttgaga gtgacccgga tagggcgaat    18180
gacacgattg atgcgatggc tgcgggtgtt aatcgggctg tcatgaatgc tggccgtgac    18240
acggttgagt ggtctgcggg tgcgcagggt aggtcgtggc gtagggttac tgatggtgat    18300
ccgtgtgctt tttgtgccat gttggctacg aggtcggatt atacgacaaa agaaagggca    18360
ctcactaccg gtcatacgcg gcgtcataag cgtggtggta agcgtccgtt tggttcgaag    18420
tatcatgatc attgtggttg tacggtggtt gaggttgttg gcccttggga gccaaatagg    18480
gctgatgtcg agtatcagag gacgtatgag aaggcccgtg agtgggttga tgatcatggg    18540
ttgcagcagt cgcctggcaa tattttgaag gctatgcgta ctgttggcga tatgagataa    18600
tttgatgtgg tttccggttg tgcgccgccg gttattggtg cacagggttg tctcccgcac    18660
gggggtcaac aatgttgtgt tgttttccgc aaggagtgta gggttaggct atggccgatc    18720
agagtgttga ggaacagaat gttgacaatg atgttgtgga gtccggaaag gataacggca    18780
ttgttgatac agtaaaagac gatggcgggc aggaggtagc cgacaatcag ttgaagaatg    18840
aaggcgaggg taaatcgccg gggactgatt ggaaggcgga ggcccgtaag tgggagtctc    18900
gtgctaaaag taatttcgcc gagttggaga agcttcgcgc ctcggatggt gattctggat    18960
ctactattgc tgagcttcgc cgcaagaatg aggaactcga agacaggatc aacgggtttg    19020
ttcttgaggg tgtgaagcgc gagatggctt cagagtatgg tttgtccagt gatgcgatcg    19080
ttttcttgtc gggtggcgat aaggagtcgc ttgccgagtc tgcgaaagct tgaagggtt    19140 tgatcgacca tagtagtggt ggcgcggtg tgcgccgtct tgcggggagt gccccgttg     19200 atgatgttaa acgacgtgag ggtgtcgcgt ttgtggatgc tcttgtcaat aattctagga    19260
gatgatttgt gatggttgac gattttcttt ctgcagggaa gctggagctt cctggttcta    19320
tgattggtgc ggttcgtgac cgtgctatcg attctggtgt tttggcgaag ctttcgccgg    19380
agcagccgac tattttttggc cctgttaagg gtgccgtgtt tagtggtgtt cctcgtgcta    19440
agattgttgg tgagggcgag gttaagcctt ccgctagcgt tgatgtttcg gcgtttactg    19500
cgcagcctat caaggttgtg actcagcagc gtgtctcgga cgagtttatg tgggctgatg    19560
ctgattaccg tctgggtgtt ttgcaggatc tgatttcccc ggctcttggt gcttcgattg    19620
gtcgcgccgt ggatctgatt gctttccatg gtattgatcc tgccactggt aaagcggctg    19680
ccgctgtgca tacttcgctg gataagacga agcatattgt tgatgccacg gattctgcta    19740
cgaccgatct ggtcaaggct gtcggtctta tcgctggtgc tggtttgcag gttcctaacg    19800
gggttgcttt ggatccggcg ttctcgtttg ccctgtctac tgaggtgtat ccgaaggggt    19860
ctccgcttgc cggccagcct atgtatcctg ccgccgggtt tgctggtttg gataattggc    19920
gtggcttgaa tgttggttct tcttcgactg tttctggcgc cccggagatg tcgcctgcct    19980
```

```
ctggtgttaa ggctattgtt ggtgatttct cgcgtgttca ttggggtttc cagcgtaact   20040
tcccgatcga gcttatcgag tatggtgacc cggatcagac tgggcgtgac ctgaagggcc   20100
ataatgaggt tatggttcgt gccgaggctg tgctgtatgt ggctatcgag tcgcttgatt   20160
cgtttgctgt tgtgaaggag aaggctgccc cgaagcctaa tccgccggcc gagaactgat   20220
ttattgttgc ggtgatgtgt caatgtgcag ggggtggtgt tgatgggtat cattttgaag   20280
cctgaggata ttgagccttt tgccgatatt cctagagaga agcttgaggc gatgattgcc   20340
gatgtggagg ctgtggctgt cagtgtcgcc ccctgtatcg ctaaaccgga tttcaaatac   20400
aaggatgccg ctaaggctat tctgcgcagg gctttgttgc gctggaatga tactggcgtg   20460
tcgggtcagg tgcagtatga gtctgcgggt cctttcgctc agactacacg gtctagtact   20520
cccacgaatt tgttgtggcc ttctgagatt gccgcgttga agaagctgtg tgagggtgat   20580
ggtggggctg gtaaagcgtt cactattaca ccgaccatga ggagtagtgt gaatcattct   20640
gaggtgtgtt ccacggtgtg gggtgagggt tgctcatgcg ggtcgaatat taacggctac   20700 gctggcccctt tgtgggagat atgatatgac cagttttcct tatggtgaaa cggttgtgat   20760
gcttcaaccg actgttcgtg tcgatgatct tggtgacaag gttgaggatt ggggcatcc   20820 tgtagaaacc gtgtaccata acgtggccat ctatgcttcc gtttcgcagg aggatgaggc   20880
cgcggggcgt gactctgact atgagcattg gtcgatgctt ttcaagcagt ctgttgttgg   20940
tgctgattat cgttgccggt ggcgtattcg gggtgttgtg tgggggctg acgggtctcc   21000 tatggtgtgg catcaccca tgtccggttg ggatgcgggc acgcagatca atgtgaagcg   21060
caagaagggc tgatagattg tggctcagga tgtgaatgtg aagctgaact tgccgggtat   21120
tcgtgaggtg ttgaagtctt ctggggtgca ggctatgttg gctgagcgtg gcgagcgtgt   21180
caagcgtgcg gcctcggcga atgtgggcgg taacgctttc gataaggccc aataccgtaa   21240
tggtttgtcg tcggaggtgc aggttcaccg tgttgaggct gtcgctcgta taggtaccac   21300
atataagggt gggaagcgta ttgaggcgaa gcatggcacg ctggctaggt cgattgggc   21360 ggcgtcgtga tcatctacga tgaccccagg aagtgggcta aacgcgtgct caaggatgat   21420
ggctggctgt ctgggatacc atgcaccggg acagtgcccg atgattttac gggtgacctg   21480
atttggttgg cgttggatgg tggcccacag ttgcatgttc gcgagcaagt ttttttgcgc   21540
gtgaatgtgt tttctgatac gccggatcgt gctatgtcgc tagccaggcg ggtggaggct   21600
gtccttgcgg atggggttga tggcaaccct gtggtgtact gtaaacggtc tactggtcct   21660
gatttgctgg ttgatggtgc acgttttgat gtgtattcgc tgttcgagct gatatgtagg   21720
cctgtcgagt ctgagtaaac gtatttgttt ttgttttaat gtaattgttt gatatttaat   21780
gggggttgtg atggctgcaa cacgtaaagc gtcaatgtt cgttcagcgg ttactggcga   21840
cgtttatatt ggtgacgcgc acgcgggtga tactattaag ggtgtggagg cggttcctga   21900
cggtcttacc gctttagggt atctgtcgga tgacggtttt aagattaagc tgagcgtaa   21960 aacggatgat ttgaaggctt ggcagaatgc ggatgttgtt cgcacggttg ctaccgagtc   22020
ttctatcgag atttctttcc agctgatcga gtctaagaag gaggttatcg agctgttttg   22080
gcagtcgaag gttactgccg gatccgattc aggttcgttc gatatttctc cgggtgccac   22140
gacgggtgtt cacgccctgt tgatggatat tgtggatggt gatcaggtta ttcgctacta   22200
tttccctgag gttgagttga tcgatcgtga cgagatcaag ggcaagaatg gcgaggtgta   22260
cgggtatggt gtgacgttga aggcgtatcc tgcccagatt aataagaagg gtgatgcggt   22320
```

-continued

```
gtcgggtcgg gggtggatga cggctttaaa agctgatact cctccggttc cgccttctcc    22380
gaagccgaag ccggatccta atccgccgtc tgagaactga tacacgattt taggggattg    22440
ttgatagatg agtgacacgg gttacacgtt gaagattggt gaccgtagct gggtgttggc    22500
ggatgcggag gagacggctc aagctgtgcc tgcccgcgtg tttcgccgtg cagctaagat    22560
tgcccagtcg ggggagtctg cggatttcgc ccaggttgag gtgatgtttt ctatgttgga    22620
ggctgccgcc ccagtggatg ctgtggaggc cctggagggg cttcctatgg ttcgtgtggc    22680
cgagattttc cgtgagtgga tggaatataa gcctgacggt aagggtgcct cgctggggga    22740
atagtttggc tccacggcct gattgatgat tatcgtgggg ccatcgaata tgattggagg    22800
acccggttcg gttgctcggt ttatgatgtt ggtggcccga taatgtgttg gggtgaggct    22860
gttcggctgg ctggcgtgtt gtgtaccgat acgtctagcc agttggcggc ccacctgaat    22920
ggttggcagc gcccgtttga gtggtctgag tgggcggtgt tggacatgtt ggatcattac    22980
aggtctgcta atagtgaggg gcagccggag cctgtggcga ggcctacgga tgagcgtagg    23040
gcccggttta cgtttgggca ggtggacgat attttggcgc gtgttcgtgc cggtggcggg    23100
gtgtctcgcg agattaatat tatggggtga atagtgtatg tctggtgaga ttgcttccgc    23160
atatgtgtcg ttgtatacga agatgcctgg tttgaaggct gatgttggta aacagttgtc    23220
gggtgttatg cctgctgagg gtcagcgttc gggtagtctt tttgctaagg gtatgaagtt    23280
ggcgcttggt ggtgccgcaa tggtgggtgc catcaatgtt gctaagaagg gcctcaagtc    23340
gatttatgat gtgactattg gtggcggtat tgctcgcgct atggctattg atgaggctca    23400
ggctaagttg actggtttgg gtcatacgtc gtctgacacg tcttcgatta tgaattcggc    23460
tattgaggct gtgactggta cgtcgtatgc gttgggggat gcggcttcta ctgcggcggc    23520
gttgtctgct tcgggtgtga agtctggcgg gcagatgacg gatgtgttga agactgtcgc    23580
cgatgtgtct tatatttcgg gtaagtcgtt tcaggatacg ggcgctattt ttacgtctgt    23640
gatggcccgc ggtaagttgc agggtgatga catgttgcag cttacgatgg cgggtgttcc    23700
tgtactgtct ttgcttgcca ggcagacggg taaaacgtcg gctgaggtgt cgcagatggt    23760
gtcgaagggg cagattgatt ttgccacgtt tgcggctgcg atgaagcttg gcatgggtgg    23820
tgctgcgcag gcgtctggta agacgtttga gggcgctatg aagaatgtta agggcgcttt    23880
gggctatctt ggtgctacgg ctatggcgcc gtttcttaac gggttgcggc agatttttgt    23940
tgcgttgaat ccggttatca agtctatcac ggattctgtg aagccgatgt tgctgccgt    24000 cgatgctggt attcagcgta tgatgccgtc tattttggcg tggattaacc gtatgccggg    24060
catgatcact cgaatgaatg cacagatgcg cgccaaggtg gagcagttga agggcatttt    24120
tgcaaggttg catttgcctg tccctaaagt gaatttgggt gccatgtttg ctggcggcac    24180
cgcagtgttt ggtattgttg ctgccggtgt ggggaagctt gtcgcggggt ttgccccgtt    24240
ggcggtgtcg gtgaagaatc tactgccgtc gtttggtgct ttgaagggtg ccgccggcgg    24300
gcttggcggc gtgtttcgcg ccctgggtgg ccctgtcggg attgtgatcg gcttgtttgc    24360
tgccatgttt gctacgaacg cccagttccg tgccgctgtt atgcagcttg ggctgtggt    24420 tggtcaagcc ctggggcaga ttatggccgc tgtgcagcct gtgtttggtt ggttgcggg    24480 tctggtggcc cggttggcgc cagtgtttgc ccagattatt ggtttggttg ccgggctggc    24540
tgcccagttg atgcctgtga ttggtatgct tgttgcccgg ctggttcctg tgatcaccca    24600
gattattggt gcggtgacgc aggtggcggc catgttgctg ccggcgttga tgccggtgtt    24660
gcaggctgtt gttgctgtga tacggcaggt tgttggcgtg atcatgcagt tggtgccggt    24720
```

```
gttgatgccg gtgattcagc agattttggg tgcggtcatg tctgtgctgc cgccgattat   24780
tggtttgatc cggtcgttga tgcctgtgat tgcggcggtt atgcgtgtgg tggtgcaggt   24840
tgtttcggtt gtgatacagg tggtggcccg tattcttgct gttgtggctc cgatggtggc   24900
tgccgtggta gggtttgttg cccgtattgt tggtgctgtc gtgtcggctg ttgcccgtgt   24960
tattgctgct gttgcccgtg ttatcgggtg gattgttgct cattttgtgt cgggtttggc   25020
gcgtatgggt tcggttattc aggctggctg gaatcatatt agggcgttta cgtctgcgtt   25080
tattaacggt tttaagtcgg tgatttctgg cggcgtgaac gctgttgtgg ggttttttac   25140
gcggcttggt ttgtcggttg cttctcatgt tcggtctggt tttaacgcgg ctcgtggtgc   25200
tgtttcttct gcgatgaatg ctattcggag tgttgtgtct cggtggcgt ctgctgttgg   25260 cgggttttc agttcgatgg cgtctagggt tcgtagtggt gttgtgcgcg gtttaatgg   25320 ggccaggaat gcggcatctt ccgctatgca tgctatgggg tccgctgtgt ctagcggcgt   25380
gcatagtgtg ctagggtttt tccggaatct gcctggcaat attcggcatg ctctcggtaa   25440 tatgggtct ttgttggtgt ctgctggccg tgatgtggtg gccggtttgg gtaacggtat   25500
taagaatgct ttgagtggcc tgttggatac ggtgcgtaat atgggttctc aggttgctaa   25560
tgctgcgaag tcggtgttgg gtattcattc cccgtcgagg gtgtttcgtg acgaggttgg   25620
ccgtcaggtt gttgccggtt tggctgaggg tattactggg aatgcgggtt tggcgttgga   25680
tgcgatgtct ggtgtggctg gtcggctgcc tgatgtggtg gatgcccggt ttggtgtgcg   25740
atcgtctgtg ggctcgttta ccccgtacga ccggtatcgg cgtgcgagtg agaagagtgt   25800
tgtggtgaat gttaacgggc ccacgtatgg tgatcctaac gagtttgcga agcggattga   25860
gcgtcagcag cgtgacgctt tgaacgcttt ggcttacgtg tgataggggg tgtggttcat   25920
gtttcttcct gacccgtctg atcgttctgg tttgactgtt acctggtcta tggatccgct   25980
gtttggcgat gagcgtgtgc ttcatttgac ggattatacg gggtcgtctc cggtgatgtt   26040
gttgaatgat tcgttgcgcg gtttgggtgt tcctgaggtg gagcatttt ctcaaactca   26100 tgttggggtg catggctcgg agtggcgcgg gtttaatgtg aagcctcgcg aggtgacgct   26160
gcctgtcctg gtgtcgggtg ttggtgtgga tcctgtgggc gggtttcgtg acggtttttt   26220
gaaagcctat gacgcgttgt ggtctgcttt tcctcccggg gaggagggtg aactgtcggt   26280
gaagactcct gccggcaaag agcgtgtgct gaagtgccgg tttgattcgg ctgatgacac   26340
gtttacggtg gatccggtga acaggggtta tgcgcgttat ctgttgcatt tgacggctta   26400
tgacccgttt tggtatgggg atgagcagaa gtttcgtttc agtaacgcga agttgcagga   26460
ttggttgggt ggcggccctg tcggcaagaa gggtacagcg tttcctgtgg tgttgacgcc   26520
tggtgttggt tcgggttggg ataacttgtc taatagaggt gatgtgccgg cgtggcctgt   26580
gattcgtgtg gagggccccc tggagtcgtg gtctgtgcag attgatggtt tgcgtgtgtc   26640
ttcggattgg cctgtcgagg agtatgattg gatcactatt gatacggatc ctcgtaaaca   26700
gtctgcgttg ttgaacgggt ttgaggatgt gatggatcgt ttgaaggagt gggagtttgc   26760
gcctatcccg cctggcggtt ctaagagtgt gaatattgag atggttggtt tgggtgccat   26820
tgttgtgtcg gtgcagtaca ggttttttgag ggcttggtga atagttgatg ctggtcttg   26880 ttccgcggat aacattgttt acaccggatt atcaccgtgt ggcgcctatc aatttttttg   26940
aatcgttgaa actgtcgttg aagtggaatg gtttgtccac tttggagttg gtggtgtctg   27000
gtgatcattc taggcttgac gggttgacta agccgggtgc acggctggtt gttgattatg   27060
```

```
gtggtggcca gatttttct gggcctgtgc gtaaggttca tggtgtgggt ccgtggcgtt   27120
cttcgcgggt gactatcacg tgtgaagatg atattcgtct gttgtggcgt atgttgatgt   27180
ggcctgtgaa ttatcgtcct ggtatggttg gtatggagtg gcgtgccgac agggattatg   27240
cccactattc gggtgcggct gagtcggtgg ctaagcaggt gttgggggat aatgcttggc   27300
gttttccgcc tgatatattt atggtggatg ataagagtcg tggccgctat attaaggatt   27360
ttcaggcgcg gtttcacgtg tttgccgata agttgttgcc ggtgttgtcg tgggctcgga   27420
tgactgtcac ggtgaaccag tttgagaatg cgaagcagga tcagcggggt ttgctgtttg   27480
attgtgtgcc tgccgtgacc cgtaagcatg tgttgactgc cgagtctggg tctattgtgt   27540
cgtgggagta tgtgagggat gccccgaagg cgacatctgt ggtggttggt ggccgcggcg   27600
agggtaagga tcggctgttt tgtgaggatg ttgattcggc ggccgaggat gactgggttg   27660
atcgtgtcga ggtgtttaag gatgcccgta acacggattc tgaacatgtg catcttattg   27720
atgaggcgga gcaggtgctg caggagtctg ggccacgtc ggggtttaag atcgagttgg   27780
ccgagtcgga tgtgttgcgg tttgggccag gcaatctgat gccgggtgat ttgatctatg   27840
tggatgtggg ctcgggctct atcgcggaga ttgttcggca gattgatgtg gagtgtgatt   27900
cgccgggtga tggttggacg aaagtgactc ctgttgcggg ggattatgag gataatccgt   27960
cagcattgtt ggctcgccgt gttgccggtt tggctgcggg tgtgcgggat ttgcaaaagt   28020
tttagaagga ttgggttttg ttgtgggtat tgtgtgtaaa gggtttgatg gtgtgttgac   28080
cgagtatgat tgggctcaaa tgtctggtct gatgggtaat atgccgtcgg tgaaagggcc   28140
ggatgatttt cgtgtcggta cgactattca gggtgccaca gtgttgtgtg aggtcctgcc   28200
ggggcaggct tgggctcacg gggtgatgtg cacgtcgaat agtgttgaga cggtgacggg   28260
gccgcttccg ggcctggcg agacccgata cgactatgtg gtgttgtctc gggattggga   28320
gcagaatacg gccaagttgg agattgtttc tggggggcgt gcggagcgtg ccaggggatgt   28380 gttgcgtgcc gagcctggcg tgtttcatca gcagttgttg gcgactttgg tgttgtcgtc   28440
taacgggttg cagcagcagt tggataggcg tgctatagcg gctagggttg cgtttggcga   28500
gtctgctgcg tgtgatccta ccccggtgga gggtgaccgg gtgatggttc cttcgggggc   28560
tgtgtgggct aatcatgcta acgagtggat gctactgtct ccgaggattg agacgggttc   28620
taagcagatc cagtttggcg ggtctgccgt gtatgcttac acgatcccgt ttgatcgcca   28680
gttcactagt gcgcctgtcg tggtggcgtc tatggctacg gcggctgggg gcacggcaca   28740
gatcgatgtg aaagcctaca atgttactgc caaggatttt cggttggcgt ttatcacgaa   28800
tgacgggtct aagccgaatg tgtgcctgc ggtggctaac tggattgctg tcggcgtgtg   28860
actgtacagg tgttgtggcg gatggtgtga tgttgggggg ctgtggtgtc gtggtttact   28920
cctgcactgg tggcctctat ctgtacggcg ttggccacgg ttttgggttc tgttcaggct   28980
gtcacatccc ggtctaggaa gcgtttacgc aggctgtctg cgcaggtgga tgcgatggaa   29040
gagtatacgt ggggtgtgcg gcgcgaggtt cgaaggttta cgccgggct tcctgacgag   29100 gtggagccta tgcatcttcc tgatttgccc gagttttga aagatactgt tgatggtggt   29160 gggggtgaa ttgtgaggga gttggaggaa gaaaaaaggc agcgccgctc gtttgagaag   29220
gcttccctga tactgttgtt cctgtcgctt tgctgttgg cggtggttgc tgcgggtgct   29280
ttacggtacg ggtctgtggc ttcccagcgg gattcggagc aggcgagggc ccagtctaat   29340
ggtacagccg ctaaagggtt ggccagccgt gtgaagcggg tgtgtgcttc gggtgggcag   29400
gagtcggtgc ggcttcacca gtctggcttg tgtgtggatg ctcggcgtgt tgagcggagt   29460
```

```
gtgcagggtg tgccgggtcc tgcaggtgct gatggccggg atggtgttaa tggttcggct    29520
gggctggttg gccctgttgg tccgcagggt tctcctggtt tg                       29562

<210> SEQ ID NO 76
<211> LENGTH: 83
<212> TYPE: DNA
<213> ORGANISM: Artificial Sequence
<220> FEATURE:
<223> OTHER INFORMATION: Cos PAC7 pIC405

<400> SEQUENCE: 76 aaacccgcc aaccccacc gggcacaccc cctgcacacc cgtgcaagac ctcgtacggc      60
ttagtgaaat acctcccttt tgt                                            83

<210> SEQ ID NO 77
<211> LENGTH: 300
<212> TYPE: DNA
<213> ORGANISM: Artificial Sequence
<220> FEATURE:
<223> OTHER INFORMATION: Cos PAC7 pIC400

<400> SEQUENCE: 77
aggcaacaga acacaaccaa acatcaaatt ccaacaacaa accacaaaaa cattgattcc    60
atggtgaaaa acccgccaac ccccaccggg cacacccct gcacaccgt gcaagacctc    120 gtacggctta gtgaaatacc tcccttttgt tgttttatcg ttttgtcgac ttttttgtttg   180 gtggtgtgtg tggtgcagcc tgagcttcct gatagtcgtg attggtgtgg ggagacgcgt   240
cggtggtggt gtgtgtgggg cgaggatccg cgtgccgggt ttgtgtctga tgaggagtgg   300

<210> SEQ ID NO 78
<211> LENGTH: 300
<212> TYPE: DNA
<213> ORGANISM: Artificial Sequence
<220> FEATURE:
<223> OTHER INFORMATION: Cos PAC7 pIC401

<400> SEQUENCE: 78
gaccacatca caccgtcag ccggggagga ctcaacaccc tcgacaacgg gcaaatcatc    60
tgcagaacat gcaacagaag caaaggcaac agaacacaac caaacatcaa attccaacaa   120
caaaccacaa aaacattgat tccatggtga aaaacccgcc aaccccacc gggcacaccc    180 cctgcacacc cgtgcaagac ctcgtacggc ttagtgaaat acctcccttt tgttgtttta   240 tcgtttttgtc gacttttttgt ttggtggtgt gtgtggtgca gcctgagctt cctgatagtc   300

<210> SEQ ID NO 79
<211> LENGTH: 217
<212> TYPE: DNA
<213> ORGANISM: Artificial Sequence
<220> FEATURE:
<223> OTHER INFORMATION: Cos PAC7 pIC402

<400> SEQUENCE: 79
aggcaacaga acacaaccaa acatcaaatt ccaacaacaa accacaaaaa cattgattcc    60
atggtgaaaa acccgccaac ccccaccggg cacacccct gcacaccgt gcaagacctc    120 gtacggctta gtgaaatacc tcccttttgt tgttttatcg ttttgtcgac ttttttgtttg   180 gtggtgtgtg tggtgcagcc tgagcttcct gatagtc                            217

<210> SEQ ID NO 80
```

```
<211> LENGTH: 150
<212> TYPE: DNA
<213> ORGANISM: Artificial Sequence
<220> FEATURE:
<223> OTHER INFORMATION: Cos PAC7 pIC403

<400> SEQUENCE: 80
aaaacccgcc aaccccccacc gggcacaccc cctgcacacc cgtgcaagac ctcgtacggc      60
ttagtgaaat acctcccttt tgttgtttta tcgttttgtc gacttttgt ttggtggtgt      120 gtgtggtgca gcctgagctt cctgatagtc                                       150

<210> SEQ ID NO 81
<211> LENGTH: 150
<212> TYPE: DNA
<213> ORGANISM: Artificial Sequence
<220> FEATURE:
<223> OTHER INFORMATION: Cos PAC7 pIC404

<400> SEQUENCE: 81
aggcaacaga acacaaccaa acatcaaatt ccaacaacaa accacaaaaa cattgattcc      60
atggtgaaaa acccgccaac ccccaccggg cacacccct gcacaccgt gcaagacctc      120 gtacggctta gtgaaatacc tccctttttgt                                      150

<210> SEQ ID NO 82
<211> LENGTH: 25
<212> TYPE: DNA
<213> ORGANISM: Artificial Sequence
<220> FEATURE:
<223> OTHER INFORMATION: IC208 primer

<400> SEQUENCE: 82
gcttccttag cttgcgaaat ctcga                                            25

<210> SEQ ID NO 83
<211> LENGTH: 26
<212> TYPE: DNA
<213> ORGANISM: Artificial Sequence
<220> FEATURE:
<223> OTHER INFORMATION: IC310 primer

<400> SEQUENCE: 83
gttcggctaa acccaaaagt aaaaac                                           26

<210> SEQ ID NO 84
<211> LENGTH: 35
<212> TYPE: DNA
<213> ORGANISM: Artificial Sequence
<220> FEATURE:
<223> OTHER INFORMATION: AD1541 primer

<400> SEQUENCE: 84
gttccagctc ttccgaggac cacatcacac ccgtc                                 35

<210> SEQ ID NO 85
<211> LENGTH: 35
<212> TYPE: DNA
<213> ORGANISM: Artificial Sequence
<220> FEATURE:
<223> OTHER INFORMATION: AD1542 primer

<400> SEQUENCE: 85
gttccagctc ttcctgccca ctcctcatca gacac                                 35
```

```
<210> SEQ ID NO 86
<211> LENGTH: 38
<212> TYPE: DNA
<213> ORGANISM: Artificial Sequence
<220> FEATURE:
<223> OTHER INFORMATION: IC511 primer

<400> SEQUENCE: 86
gttccagctc ttccgagagg caacagaaca caaccaaa                              38

<210> SEQ ID NO 87
<211> LENGTH: 37
<212> TYPE: DNA
<213> ORGANISM: Artificial Sequence
<220> FEATURE:
<223> OTHER INFORMATION: IC512 primer

<400> SEQUENCE: 87
gttccagctc ttcctgcgac tatcaggaag ctcaggc                               37

<210> SEQ ID NO 88
<211> LENGTH: 37
<212> TYPE: DNA
<213> ORGANISM: Artificial Sequence
<220> FEATURE:
<223> OTHER INFORMATION: IC513 primer

<400> SEQUENCE: 88
gttccagctc ttccgagaaa acccgccaac ccccacc                               37

<210> SEQ ID NO 89
<211> LENGTH: 38
<212> TYPE: DNA
<213> ORGANISM: Artificial Sequence
<220> FEATURE:
<223> OTHER INFORMATION: IC514 primer

<400> SEQUENCE: 89
gttccagctc ttcctgcaca aaagggaggt atttcact                              38

<210> SEQ ID NO 90
<211> LENGTH: 21
<212> TYPE: DNA
<213> ORGANISM: Artificial Sequence
<220> FEATURE:
<223> OTHER INFORMATION: AD1261 primer

<400> SEQUENCE: 90
cagcggcgct gctaagaact t                                                21

<210> SEQ ID NO 91
<211> LENGTH: 20
<212> TYPE: DNA
<213> ORGANISM: Artificial Sequence
<220> FEATURE:
<223> OTHER INFORMATION: AD1262 primer

<400> SEQUENCE: 91
ccggctggca aatgaggcat                                                  20
```